US008071768B2

(12) United States Patent
Baindur et al.

(10) Patent No.: US 8,071,768 B2
(45) Date of Patent: Dec. 6, 2011

(54) ALKYLQUINOLINE AND ALKYLQUINAZOLINE KINASE MODULATORS

(75) Inventors: Nand Baindur, Kendall Park, NJ (US); Michael David Gaul, Yardley, PA (US); Kevin Douglas Kreutter, Plainsboro, NJ (US); Christian Andrew Baumann, Exton, PA (US); Alexander J. Kim, Levittown, PA (US); Guozhang Xu, Bensalem, PA (US); Robert W. Tuman, Chalfont, PA (US); Dana L. Johnson, Upper Black Eddy, PA (US)

(73) Assignee: Janssen Pharmaceutica, N.V., Beerse (BE)

( * ) Notice: Subject to any disclaimer, the term of this patent is extended or adjusted under 35 U.S.C. 154(b) by 1430 days.

(21) Appl. No.: 11/422,349

(22) Filed: Jun. 6, 2006

(65) Prior Publication Data
US 2006/0281772 A1 Dec. 14, 2006

Related U.S. Application Data

(60) Provisional application No. 60/689,384, filed on Jun. 10, 2005, provisional application No. 60/730,919, filed on Oct. 27, 2005.

(51) Int. Cl.
C07D 401/00 (2006.01)
C07D 413/00 (2006.01)
(52) U.S. Cl. .................................. 544/284; 544/122
(58) Field of Classification Search ............... 514/234.5, 514/252.17, 266.22; 544/116, 283
See application file for complete search history.

(56) References Cited

U.S. PATENT DOCUMENTS

| | | | |
|---|---|---|---|
| 3,517,005 A | 6/1970 | Cronin et al. | |
| 4,001,422 A | 1/1977 | Danilewicz et al. | |
| 4,542,132 A | 9/1985 | Campbell et al. | |
| 5,300,515 A | 4/1994 | Takano et al. | |
| 5,474,765 A | 12/1995 | Thorpe | |
| 5,762,918 A | 6/1998 | Thorpe | |
| 5,855,866 A | 1/1999 | Thorpe et al. | |
| 5,866,562 A | 2/1999 | Schohe-Loop et al. | |
| 5,948,786 A * | 9/1999 | Fujiwara et al. | 514/274 |
| 6,169,088 B1 * | 1/2001 | Matsuno et al. | 514/252.16 |
| 6,342,219 B1 | 1/2002 | Thorpe et al. | |
| 6,613,772 B1 | 9/2003 | Schindler et al. | |
| 6,776,796 B2 | 8/2004 | Falotico et al. | |
| 7,074,801 B1 | 7/2006 | Yoshida et al. | |
| 2002/0016625 A1 | 2/2002 | Falotico et al. | |
| 2004/0049032 A1 | 3/2004 | Charrier et al. | |

FOREIGN PATENT DOCUMENTS

| | | |
|---|---|---|
| EP | 08/82717 | 12/1998 |
| EP | 1 566 379 A1 | 8/2005 |
| GB | 2295387 | 5/1996 |
| JP | 59076082 | 4/1984 |
| WO | WO 96/09294 | 3/1996 |
| WO | WO 96/32907 | 10/1996 |
| WO | WO 97/28118 | 8/1997 |
| WO | WO 97/38992 | 10/1997 |
| WO | WO 99/31086 | 6/1999 |
| WO | WO 00/13681 | 3/2000 |
| WO | WO 01/32632 | 5/2001 |
| WO | WO 02/16360 A2 | 2/2002 |
| WO | WO 02/16362 | 2/2002 |
| WO | WO 02/32861 | 4/2002 |
| WO | WO 02/48152 | 6/2002 |
| WO | WO 02/069972 | 9/2002 |
| WO | WO 02/088107 | 11/2002 |
| WO | WO 02/092599 | 11/2002 |
| WO | WO 03/024931 | 3/2003 |
| WO | WO 03/024969 | 3/2003 |
| WO | WO 03/035009 | 5/2003 |
| WO | WO 03/037347 | 5/2003 |
| WO | WO 03/057690 | 7/2003 |

(Continued)

OTHER PUBLICATIONS

Nomoto et al., Chemical & Pharmaceutical Bulletin (1990), 38(11), 3014-19.
Ivan, Marius G. et al. Photochemistry and Photobiology (2003), 78(4), 416-419.
Sadykov, T. et al. Khimiya Geterotsiklicheskikh Soedinenii (1985), (4), 563.
Erzhanov, K. B. et al. Zhurnal Organicheskoi Khimii (1989), 25(8), 1729-32.
Fujiwara, Norio et al. Bioorganic & Medicinal Chemistry Letters (2000), 10(12), pp. 1317-1320.

(Continued)

Primary Examiner — James O Wilson
Assistant Examiner — Alexander R Pagano

(57) ABSTRACT

The invention is directed to alkylquinoline and alkylquinazoline compounds of Formula I:

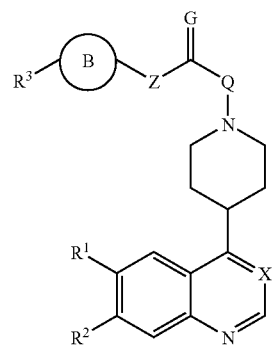

wherein $R_1$, $R_2$, $R_3$, B, Z, G, Q and X are as defined herein, the use of such compounds as protein tyrosine kinase modulators, particularly inhibitors of FLT3 and/or c-kit and/or TrkB, the use of such compounds to reduce or inhibit kinase activity of FLT3 and/or c-kit and/or TrkB in a cell or a subject, and the use of such compounds for preventing or treating in a subject a cell proliferative disorder and/or disorders related to FLT3 and/or c-kit and/or TrkB. The present invention is further directed to pharmaceutical compositions comprising the compounds of the present invention and to methods for treating conditions such as cancers and other cell proliferative disorders.

12 Claims, 6 Drawing Sheets

FOREIGN PATENT DOCUMENTS

| WO | WO 03/064413 | 8/2003 |
|---|---|---|
| WO | WO 03/099771 | 12/2003 |
| WO | WO 2004/002960 | 1/2004 |
| WO | WO 2004/005281 | 1/2004 |
| WO | WO 2004/016597 | 2/2004 |
| WO | WO 2004/018419 | 3/2004 |
| WO | WO 2004/039782 | 5/2004 |
| WO | WO 2004/043389 | 5/2004 |
| WO | WO 2004/046120 | 6/2004 |
| WO | WO 2004/058727 | 7/2004 |
| WO | WO 2004/058749 | 7/2004 |
| WO | WO 2004/071460 | 8/2004 |
| WO | WO 2005/021500 | 3/2005 |
| WO | WO 2005/037825 | 4/2005 |
| WO | WO 2005/051304 | 6/2005 |
| WO | WO 2006/135646 A1 | 12/2006 |
| WO | WO 2006/135721 A1 | 12/2006 |

OTHER PUBLICATIONS

Takai, Haruki et al. Chemical & Pharmaceutical Bulletin (1986), 34(5), 1907-16.
Liotta et al., Nature, Aug. 26, 2004; 430(7003), pp. 973-974.
Jaboin et al., Cancer Lett. Apr. 10, 2003;193(1), pp. 109-114.
Ashman, L., Int J Biochem Cell Biol. (1999);31(10), pp. 1037-1051.
Sattler et al., Leuk Res. (2004), 28 Suppl 1, pp. S11-20.
Advani, A., Curr Hematol Rep. (2005), 4(1), pp. 51-58.
McKenna, Hilary J. et al. Mice lacking flt3 ligand have deficient hematopoiesis affecting hematopoietic progenitor cells, dendritic cells, and natural killer cells. Blood. Jun. 2000; 95(11), pp. 3489-3497.
Drexler, H. G. and H. Quentmeier (2004), "FLT3: receptor and ligand", Growth Factors, 22(2), pp. 71-73.
Stirewalt, D. L. and J. P. Radich,(2003), "The role of FLT3 in haematopoietic malignancies", Nat Rev Cancer, 3(9): 650-65.
Scheijen, B. and J. D. Griffin, (2002), "Tyrosine kinase oncogenes in normal hematopoiesis and hematological disease", Oncogene, 21(21), pp. 3314-3333.
Kottaridis, P. D., R. E. Gale, et al. (2003), "Flt3 mutations and leukaemia", Br J Haematol, 122(4), pp. 523-538.
Ansari Lari, Ali et al., FLT3 mutations in myeloid sarcoma, British Journal of Haematology. (Sep. 2004) 126(6), pp. 785-791.
Gilliliand et al., Blood, (2002), vol. 100, pp. 1532-1542.
Levis, M., K. F. Tse, et al., 2001, "A FLT3 tyrosine kinase inhibitor is selectively cytotoxic to acute myeloid leukemia blasts harboring FLT3 internal tandem duplication mutations." Blood, 98(3), pp. 885-887.
Tse KF, et al. Inhibition of FLT3 mediated transformation by use of a tyrosine kinase inhibitor. Leukemia. Jul. 2001; 15(7), pp. 1001-1010.
Smith, B. Douglas et al., Single agent CEP 701, a novel FLT3 inhibitor, shows biologic and clinical activity in patients with relapsed or refractory acute myeloid leukemia, Blood, May 2004; 103(10), pp. 3669-3676.
Griswold, Ian J. et al. Effects of MLN518, A Dual FLT3 and KIT Inhibitor, on Normal and Malignant Hematopoiesis. Blood, Jul. 2004, 104: 2912-2918.
Yee, Kevin W. H. et al., SU5416 and SU5614 inhibit kinase activity of wild type and mutant FLT3 receptor tyrosine kinase, Blood, Sep. 2002; 100(8), pp. 2941-2949.
O'Farrell, Anne Marie et al., SU11248 is a novel FLT3 tyrosine kinase inhibitor with potent activity in vitro and in vivo, Blood, May 2003; 101(9), pp. 3597-3605.
Stone, R.M. et al., PKC 412 FLT3 inhibitor therapy in AML: results of a phase II trial, Ann Hematol. (2004); 83 Suppl 1, pp. S89-90.
Murata, K. et al., Selective cytotoxic mechanism of GTP 14564, a novel tyrosine kinase inhibitor in leukemia cells expressing a constitutively active Fms like tyrosine kinase 3 (FLT3), J Biol Chem. Aug. 29, 2003; 278(35), pp. 32892-32898.
Levis, Mark et al., Novel FLT3 tyrosine kinase inhibitors, Expert Opin. Investing. Drugs (2003) 12(12), pp. 1951-1962.
Levis, Mark et al., Small Molecule FLT3 Tyrosine Kinase Inhibitors, Current Pharmaceutical Design, (2004), 10, pp. 1183-1193.
Gould, P., International J. Pharm. (1986), 33, pp. 201-217.
Berge et al., J. Pharm. Sci., Jan. 1977, 66(1), pp. 1-19.
Boothroyd et al., Tet Lett (1995), 36(14), pp. 2411-2414.
Sitzmann et al., J. Org Chem, 1985 , 50, pp. 5879-5881.
Tyrrell et al., Synthesis, (2004), 4, pp. 469-483.
Kristensen et al., Organic Letters, (2001), 3(10), pp. 1435-1437.
Stevenson et al., J. Org. Chem., (1986), 51, pp. 616-620.
Hall et al., Inorganic Chemistry (1997), 36(14), pp. 3096-3101.
Bertani et al., Organometallics, (1996), 15(4), pp. 1236-1241.
Quentmeier H, Reinhardt J, Zaborski M, Drexler HG, FLT3 mutations in acute myeloid leukemia cell lines, Leukemia, (2003),17, pp. 120-124.
Sadick, MD et al., Analysis of Heregulin-Induced ErbB2 Phosphorylation with a High-Throughput Kinase Receptor Activation Enzyme-Linked Immunsorbent Assay, Analytical Biochemistry, (1996), 235, pp. 207-214.
Baumann CA et al., Development of a quantitative, high-throughput cell-based enzyme-linked immunosorbent assay for detection of colony-stimulating factor-1 receptor tyrosine kinase inhibitors, J Biochem Biophys Methods, (2004), 60, pp. 69-79.
Libby P, "Vascular biology of atherosclerosis: overview and state of the art", Am J Cardiol (2003), 91(3A), pp. 3A-6A.
Helisch A, Schaper W., Arteriogenesis: the development and growth of collateral arteries. Microcirculation, (2003),10(1), pp. 83-97.
Holz FG et al.,"Pathogenesis of lesions in late age-related macular disease", Am J Ophthalmol. (2004), 137(3), pp. 504-510.
Schiele TM et. Al.,"Vascular restenosis—striving for therapy." Expert Opin Pharmacother, (2004), 5(11), pp. 2221-2232.
Thannickal VJ et al., Idiopathic pulmonary fibrosis: emerging concepts on pharmacotherapy, Expert Opin Pharmacother, (2004), 5(8), pp. 1671-1686.
Cybulsky AV, "Growth factor pathways in proliferative glomerulonephritis", Curr Opin Nephrol Hypertens (2000), 9(3), pp. 217-223.
Harris RC et al, "Molecular basis of injury and progression in focal glomerulosclerosis" Nephron (1999), 82(4), pp. 289-299.
Woolf AS et al., "Evolving concepts in human renal dysplasia", J Am Soc Nephrol, (2004), 15(4), pp. 998-1007.
Grant MB et al.,"The role of growth factors in the pathogenesis of diabetic retinopathy", Expert Opin Investig Drugs (2004), 13(10), pp. 1275-1293.
Sweeney SE, Firestein GS, Rheumatoid arthritis: regulation of synovial inflammation, Int J Biochem Cell Biol. (2004), 36(3), pp. 372-378.
Brodeur GM, "Neuroblastoma: biological insights into a clinical enigma." Nat RevCancer; (2003), 3(3), pp. 203-216.
Eggert A et. al. "Expression of the neurotrophin receptor TrkB is associated with unfavorable outcome in Wilms' tumor" J Clin Oncol. (2001), 19(3), pp. 689-696.
Descamps S et.al., "Nerve growth factor stimulates proliferation and survival of human breast cancer cells through two distinct signaling pathways." J Biol Chem. (2001), 276(21), pp. 17864-17870.
Bardelli A, et. al., "Mutational analysis of the tyrosine kinome in colorectal cancers." Science (2003), 300, p. 949.
Weeraratna AT et. al., "Rational basis for Trk inhibition therapy for prostate cancer." The Prostate (2000), 45(2), pp. 140-148.
Ricci et. al., "Neurotrophins and neurotrophin receptors in human lung cancer." Am J Respir Cell Mol Biol. (2001), 25(4), pp. 439-446.
Simpson WG, The calcium channel blocker verapamil and cancer chemotherapy. Cell Calcium. (1985), 6(6), pp. 449-467.
Ricci A, et. al., "Neurotrophins and neurotrophin receptors in human pulmonary arteries." J Vasc Res. (2000), 37(5), pp. 355-363.
Kim H, et. al., "Paracrine and autocrine functions of brain-derived neurotrophic factor (BDNF) and nerve growth factor (NGF) in brain-derived endothelial cells", J Biol Chem. (2004), 279(32), pp. 33538-33546.
Douma S, et. al., "Suppression of anoikis and induction of metastasis by the neurotrophic receptor TrkB", Nature. (2004), 430(7003), pp. 1034-1040.
Arnon et al., "Monoclonal Antibodies for Immunotargeting of Drugs in Cancer Therapy", in Monoclonal Antibodies and Cancer Therapy, Reisfeld et al. (eds.), pp. 243-256 (Alan R. Liss, Inc. 1985).

Hellstrom et al., "Antibodies for Drug Delivery", in Controlled Drug Delivery (2nd Ed.), Robinson et al. (eds.), pp. 623-653 (Marcel Dekker, Inc. 1987).

Thorpe, "Antibody Carriers of Cytotoxic Agents in Cancer Therapy: A Review", in Monoclonal Antibodies '84: Biological and Clinical Applications, Pinchera et al. (eds.). pp. 475-506 (1985).

Heinrich, Michael C. et al. Review Article: Inhibition of KIT Tyrosine Kinase Activity: A Novel Molecular Approach to the Treatment of KIT Positive Malignancies, Journal of Clin. Oncology, vol. 20, No. 6; 1692-1703 (2002).

International Search Report re: PCT/US2006/022171 dated Oct. 16, 2006.

International Search Report re: PCT/US2006/022414 dated Oct. 24, 2006.

* cited by examiner

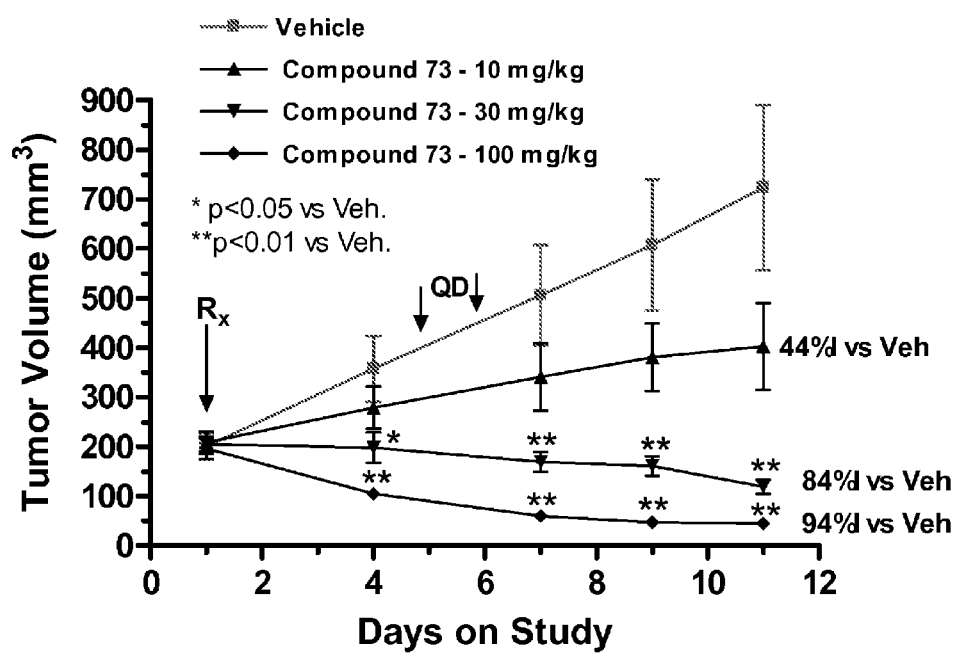
Figure 1a. Effects of orally administered Compound 73 on the growth of MV4-11 tumor xenografts in nude mice.

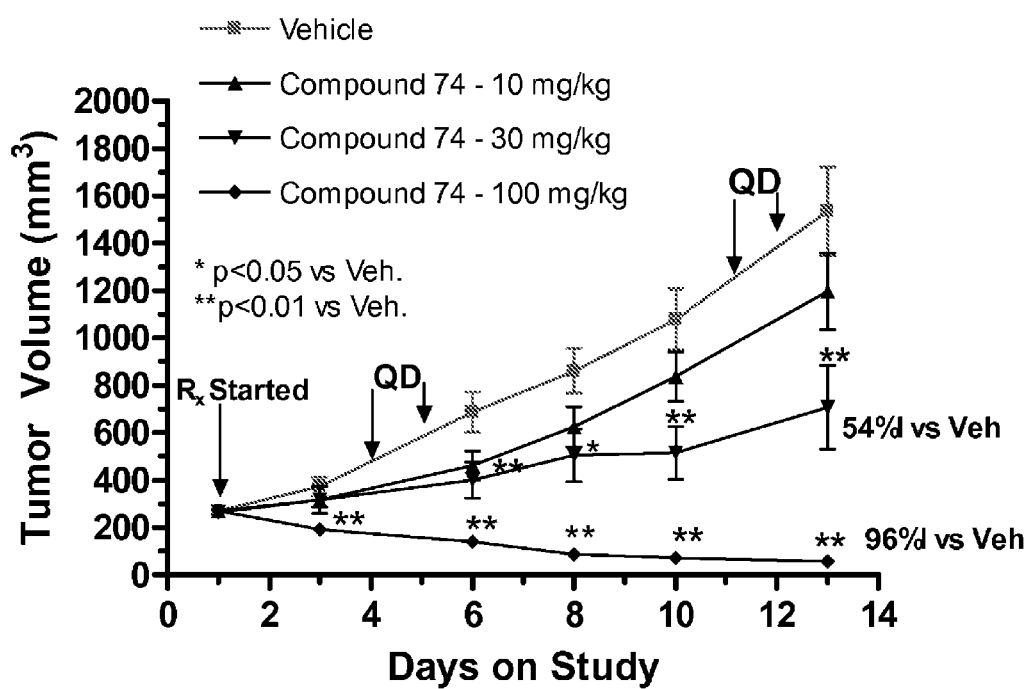
Figure 1b. Effects of orally administered Compound 74 on the growth of MV4-11 tumor xenografts in nude mice.

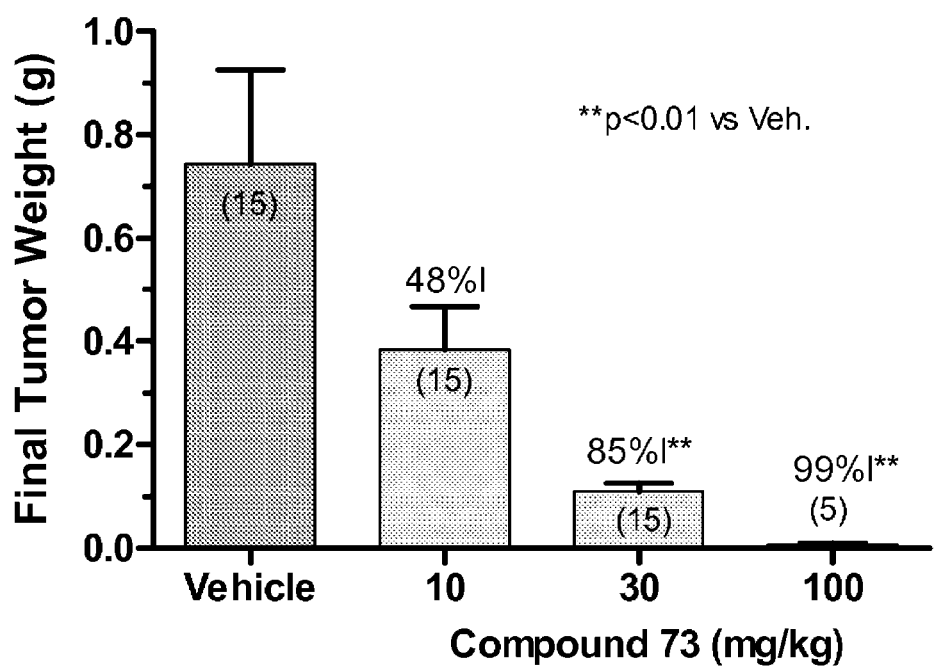
Figure 2a. Effects of orally administered Compound 73 on the final weight of MV4-11 tumor xenografts in nude mice.

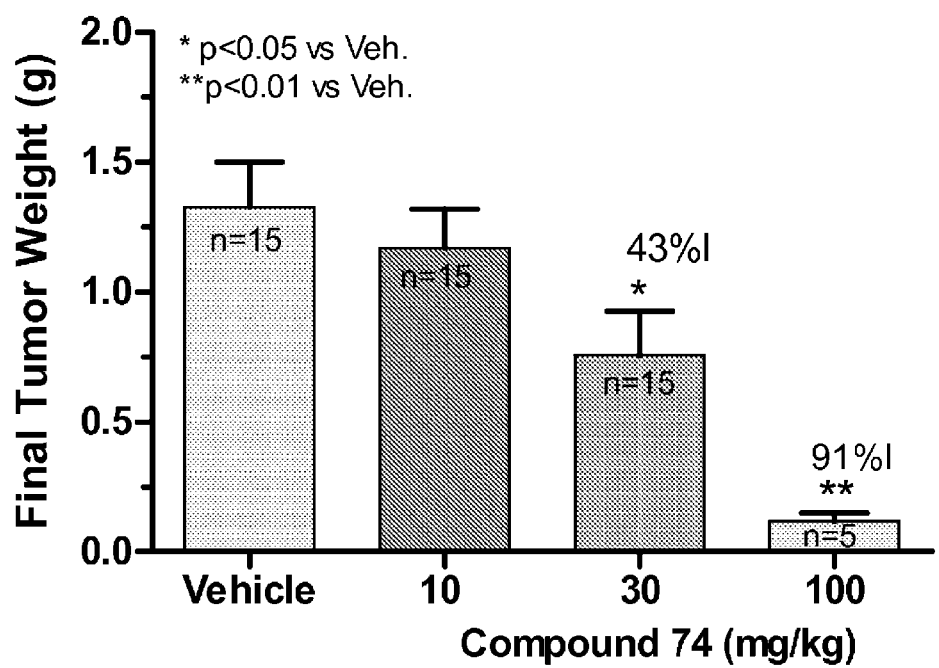
Figure 2b. Effects of orally administered Compound 74 on the final weight of MV4-11 tumor xenografts in nude mice.

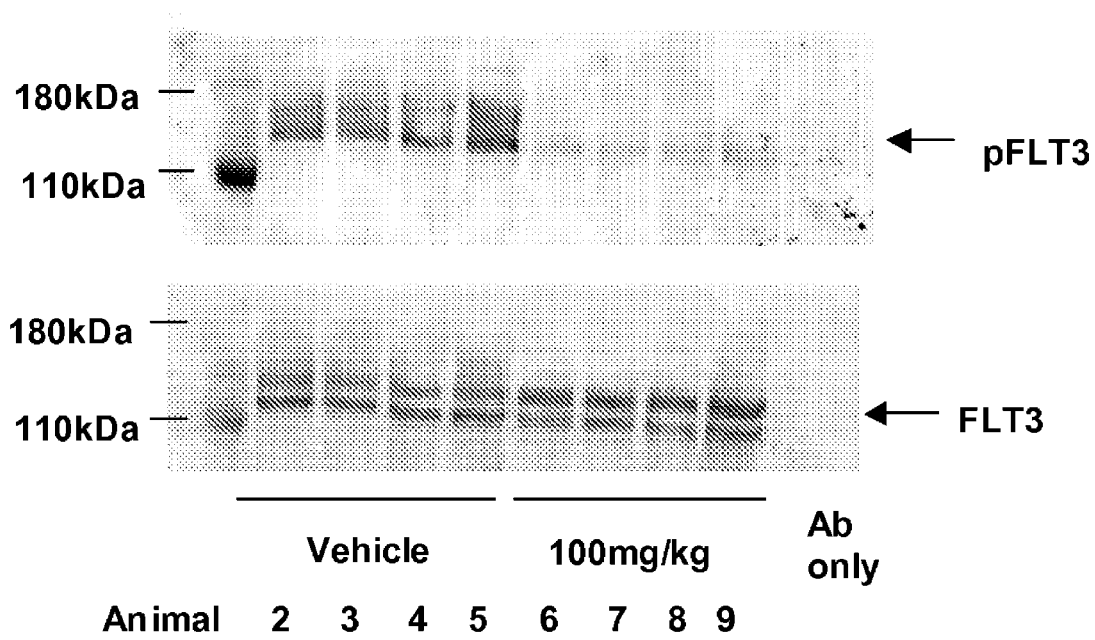
Figure 3. FLT3 phosphorylation in MV4-11 tumors obtained from vehicle- and Compound 73-treated mice.

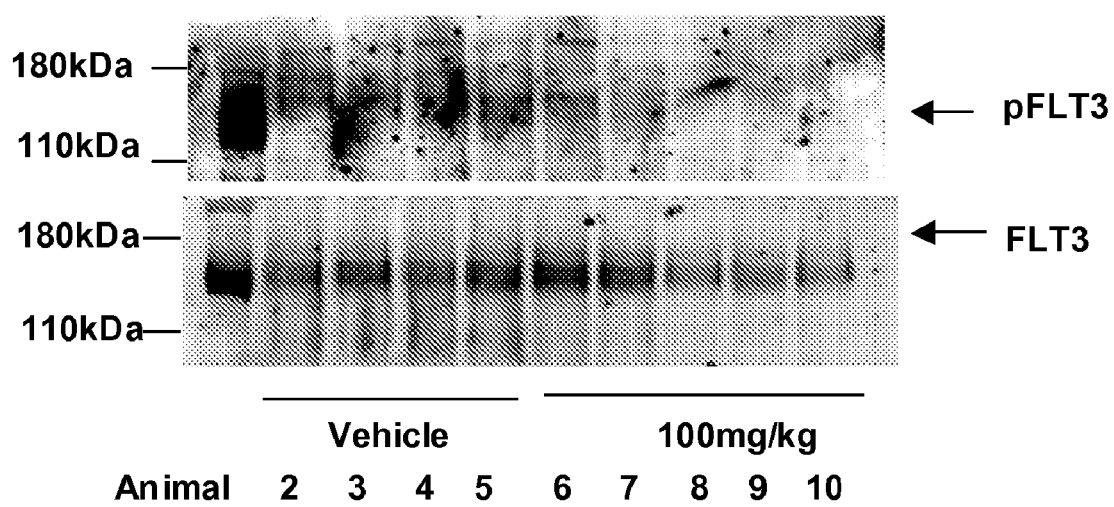
Figure 4. FLT3 phosphorylation in MV4-11 tumors obtained from vehicle- and Compound 74-treated mice.

US 8,071,768 B2

ALKYLQUINOLINE AND ALKYLQUINAZOLINE KINASE MODULATORS

CROSS REFERENCE TO RELATED APPLICATIONS

This application claims priority to U.S. Provisional Application for Patent No. 60/689,384, filed Jun. 10, 2005, and U.S. Provisional Application for Patent No. 60/730,919, filed Oct. 27, 2005, the entire disclosures of which are hereby incorporated in their entirely.

FIELD OF THE INVENTION

The invention relates to novel compounds that function as protein tyrosine kinase modulators. More particularly, the invention relates to novel compounds that function as inhibitors of FLT3 and/or c-kit and/or TrkB.

BACKGROUND OF THE INVENTION

The present invention relates to quinolines and quinazolines as inhibitors of tyrosine kinases, including FLT3, c-kit and TrkB. Quinazolines have been reported with useful therapeutic properties: U.S. Pat. No. 4,001,422 (DE 2530894) and U.S. Pat. No. 4,542,132 (EP 135318) describe quinazolines as cardiac stimulants, and U.S. Pat. No. 3,517,005 discloses quinazolines with hypotensive and bronchodilation activity. Cardiotonic quinazolines have also been reported, see Chemical & Pharmaceutical Bulletin (1990), 38(11), 3014-19. Quinolines have been reported to possess utility for the inhibition of autophosphorylation of FLT3, see PCT International Application WO2004039782, and for the treatment of amnesia and stroke, as well as a variety of other conditions, see U.S. Pat. Nos. 5,300,515 (EP 497303) and 5,866,562; and PCT International Applications WO2004/002960 and WO2002/088107. Also of note are WO2004058727 (substituted 3,5-dihydro-4H-imidazol-4-ones for the treatment of obesity); WO 2000013681 (4-quinolinemethanol derivatives as purine receptor antagonists); DE 19756388 (U.S. Pat. No. 6,613,772) (substituted 2-aryl-4-amino-quinazolines); JP 59076082 (piperidine derivatives); WO 1999031086 (quinolinepiperazine and quinolinepiperidine derivatives and their use as combined 5-HT1A, 5-HT1B, and 5-HT1D receptor antagonists); U.S. Pat. No. 5,948,786 (piperidinylpyrimidines tumor necrosis factor inhibitors); WO 1997038992 (piperidinylpyrimidine derivatives useful as inhibitors of tumor necrosis factor); Ivan, Marius G. et al. Photochemistry and Photobiology (2003), 78(4), 416-419; Sadykov, T. et al. Khimiya Geterotsiklicheskikh Soedinenii (1985), (4), 563; Erzhanov, K. B. et al. Zhurnal Organicheskoi Khimii (1989), 25(8), 1729-32; Fujiwara, Norio et al. Bioorganic & Medicinal Chemistry Letters (2000), 10(12), 1317-1320; Takai, Haruki et al. Chemical & Pharmaceutical Bulletin (1986), 34(5), 1907-16; WO 2002069972 ((triazolylpiperazinyl)isoquinolines for treatment of neurodegenerative diseases, brain injury and cerebral ischemia); and GB 2295387 (quinazoline derivatives as adrenergic 1C receptor antagonists).

Protein kinases are enzymatic components of the signal transduction pathways which catalyze the transfer of the terminal phosphate from ATP to the hydroxy group of tyrosine, serine and/or threonine residues of proteins. Thus, compounds which inhibit protein kinase functions are valuable tools for assessing the physiological consequences of protein kinase activation. The overexpression or inappropriate expression of normal or mutant protein kinases in mammals has been a topic of extensive study and has been demonstrated to play a significant role in the development of many diseases, including diabetes, angiogenesis, psoriasis, restenosis, ocular diseases, schizophrenia, rheumatoid arthritis, atherosclerosis, cardiovascular disease and cancer. The cardiotonic benefits of kinase inhibition has also been studied. In sum, inhibitors of protein kinases have particular utility in the treatment of human and animal disease.

The Trk family receptor tyrosine kinases, TrkA, TrkB, and TrkC, are the signaling receptors that mediate the biological actions of the peptide hormones of the neurotrophin family. This family of growth factors includes nerve growth factor (NGF), brain-derived neurotrophic factor (BDNF), and two neurotrophins (NT), NT-3, and NT-4. TrkB serves as a receptor for both BDNF and NT-4. BDNF promotes the proliferation, differentiation and survival of normal neural components such as retinal cells and glial cells.

It has recently been reported (see, Nature 2004 Aug. 26; 430(7003):973-4; 1034-40) that TrkB activation is a potent and specific suppressor of anchorage independent cell death (anoikis). Anchorage independent cell survival allows tumor cells to migrate through the systemic circulation and grow at distant organs. This metastatic process is often responsible for the failure of cancer treatment and the cause of mortality in cancer. Other studies (see, Cancer Lett. 2003 Apr. 10; 193(1):109-14) have also suggested that BDNF agonism of TrkB is capable of blocking cisplatin induced cell death. Taken together, these results suggest that TrkB modulation is an attractive target for treatment of benign and malignant proliferative diseases, especially tumor diseases.

The receptor tyrosine kinase c-kit and its ligand Stem Cell Factor (SCF) are essential for hemoatpoiesis, melanogenesis and fertility. SCF acts at multiple levels of the hemoatpoietic hierarchy to promote cell survival, proliferation, differentiation, adhesion and functional activation. It is of particular importance in the mast cell and erythroid lineages, but also acts on multipotential stem and progenitor cells, megakaryocytes, and a subset of lymphoid progenitors (see, *Int J Biochem Cell Biol.* 1999 October; 31(10):1037-51). Sporadic mutations of c-kit as well as autocrine/paracrine activation mechanisms of the SCF/c-kit pathway have been implicated in a variety of malignancies. Activation of c-kit contributes to metastases by enhancing tumor growth and reducing apoptosis. Additionally, c-kit is frequently mutated and activated in gastrointestinal stromal tumors (GISTs), and ligand-mediated activation of c-kit is present in some lung cancers (see, Leuk Res. 2004 May; 28 Suppl 1:S11-20). The c-kit receptor also is expressed on more than 10% of blasts in 64% of de novo acute myelogenous leukemias (AMLs) and 95% of relapsed AMLs. C-kit mediates proliferation and anti-apoptotic effects in AML (see, *Curr Hematol Rep.* 2005 January; 4(1):51-8).

C-Kit expression has been documented in a wide variety of human malignancies, including mastocytosis, mast cell leukemia, gastrointestinal stromal tumour, sinonasal natural killer/T-cell lymphoma, seminoma, dysgerminoma, thyroid carcinoma; small-cell lung carcinoma, malignant melanoma, adenoid cystic carcinoma, ovarian carcinoma, acute myelogenous leukemia, anaplastic large cell lymphoma, angiosarcoma, endometrial carcinoma, pediatric T-cell ALL, lymphoma, breast carcinoma and prostate carcinoma. See, Heinrich, Michael C. et al. Review Article: Inhibition of KIT Tyrosine Kinase Activity: A Novel Molecular Approach to the Treatment of KIT-Positive Malignancies.

The fms-like tyrosine kinase 3 (FLT3) ligand (FLT3L) is one of the cytokines that affects the development of multiple hematopoietic lineages. These effects occur through the binding of FLT3L to the FLT3 receptor, also referred to as fetal liver kinase-2 (flk-2) and STK-1, a receptor tyrosine kinase (RTK) expressed on hematopoietic stem and progenitor cells. The FLT3 gene encodes a membrane-bound RTK that plays an important role in proliferation, differentiation and apoptosis of cells during normal hematopoiesis. The FLT3 gene is mainly expressed by early meyloid and lymphoid progenitor cells. See McKenna, Hilary J. et al. Mice lacking flt3 ligand have deficient hematopoiesis affecting hematopoietic progenitor cells, dendritic cells, and natural killer cells. Blood. June 2000; 95: 3489-3497; Drexler, H. G. and H. Quentmeier (2004). "FLT3: receptor and ligand." Growth Factors 22(2): 71-3.

The ligand for FLT3 is expressed by the marrow stromal cells and other cells and synergizes with other growth factors to stimulate proliferation of stem cells, progenitor cells, dendritic cells, and natural killer cells.

Hematopoietic disorders are pre-malignant disorders of these systems and include, for instance, the myeloproliferative disorders, such as thrombocythemia, essential thrombocytosis (ET), angiogenic myeloid metaplasia, myelofibrosis (MF), myelofibrosis with myeloid metaplasia (MMM), chronic idiopathic myelofibrosis (IMF), and polycythemia vera (PV), the cytopenias, and pre-malignant myelodysplastic syndromes. See Stirewalt, D. L. and J. P. Radich (2003). "The role of FLT3 in haematopoietic malignancies." Nat Rev Cancer 3(9): 650-65; Scheijen, B. and J. D. Griffin (2002). "Tyrosine kinase oncogenes in normal hematopoiesis and hematological disease." Oncogene 21(21): 3314-33.

Hematological malignancies are cancers of the body's blood forming and immune systems, the bone marrow and lymphatic tissues. Whereas in normal bone marrow, FLT3 expression is restricted to early progenitor cells, in hematological malignancies, FLT3 is expressed at high levels or FLT3 mutations cause an uncontrolled induction of the FLT3 receptor and downstream molecular pathway, possibly Ras activation. Hematological malignancies include leukemias, lymphomas (non-Hodgkin's lymphoma), Hodgkin's disease (also called Hodgkin's lymphoma), and myeloma—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM) and myeloid sarcoma. See Kottaridis, P. D., R. E. Gale, et al. (2003). "Flt3 mutations and leukaemia." Br J Haematol 122(4): 523-38. Myeloid sarcoma is also associated with FLT3 mutations. See Ansari-Lari, Ali et al. FLT3 mutations in myeloid sarcoma. British Journal of Haematology. 2004 Sep. 126(6):785-91.

Mutations of FLT3 have been detected in about 30% of patients with acute myelogenous leukemia and a small number of patients with acute lymphomatic leukemia or myelodysplastic syndrome. Patients with FLT3 mutations tend to have a poor prognosis, with decreased remission times and disease free survival. There are two known types of activating mutations of FLT3. One is a duplication of 4-40 amino acids in the juxtamembrane region (ITD mutation) of the receptor (25-30% of patients) and the other is a point mutation in the kinase domain (5-7% of patients).

The mutations most often involve small tandem duplications of amino acids within the juxtamembrane domain of the receptor and result in tyrosine kinase activity. Expression of a mutant FLT3 receptor in murine marrow cells results in a lethal myeloproliferative syndrome, and preliminary studies (Blood. 2002; 100: 1532-42) suggest that mutant FLT3 cooperates with other leukemia oncogenes to confer a more aggressive phenotype.

Taken together, these results suggest that specific inhibitors of the individual kinases FLT3 and c-kit, and especially of the group of kinases comprising FLT3 and c-kit, present an attractive target for the treatment of hematopoietic disorders and hematological malignancies.

FLT3 kinase inhibitors known in the art include AG1295 and AG1296; Lestaurtinib (also known as CEP 701, formerly KT-5555, Kyowa Hakko, licensed to Cephalon); CEP-5214 and CEP-7055 (Cephalon); CHIR-258 (Chiron Corp.); EB-10 and IMC-EB10 (ImClone Systems Inc.); GTP 14564 (Merk Biosciences UK). Midostaurin (also known as PKC 412 Novartis AG); MLN 608 (Millennium USA); MLN-518 (formerly CT53518, COR Therapeutics Inc., licensed to Millennium Pharmaceuticals Inc.); MLN-608 (Millennium Pharmaceuticals Inc.); SU-11248 (Pfizer USA); SU-11657 (Pfizer USA); SU-5416 and SU 5614; THRX-165724 (Theravance Inc.); AMI-10706 (Theravance Inc.); VX-528 and VX-680 (Vertex Pharmaceuticals USA, licensed to Novartis (Switzerland), Merck & Co USA); and XL 999 (Exelixis USA). The following PCT International Applications and US patent applications disclose additional kinase modulators, including modulators of FLT3: WO 2002032861, WO 2002092599, WO 2003035009, WO 2003024931, WO 2003037347, WO 2003057690, WO 2003099771, WO 2004005281, WO 2004016597, WO 2004018419, WO 2004039782, WO 2004043389, WO 2004046120, WO 2004058749, WO 2004058749, WO 2003024969 and US Patent Application No. 20040049032.

See also Levis, M., K. F. Tse, et al. 2001 "A FLT3 tyrosine kinase inhibitor is selectively cytotoxic to acute myeloid leukemia blasts harboring FLT3 internal tandem duplication mutations." Blood 98(3): 885-7; Tse K F, et al. Inhibition of FLT3-mediated transformation by use of a tyrosine kinase inhibitor. Leukemia. 2001 July; 15(7): 1001-10; Smith, B. Douglas et al. Single-agent CEP-701, a novel FLT3 inhibitor, shows biologic and clinical activity in patients with relapsed or refractory acute myeloid leukemia Blood, May 2004; 103: 3669-3676; Griswold, Ian J. et al. Effects of MLN518, A Dual FLT3 and KIT Inhibitor, on Normal and Malignant Hematopoiesis. Blood, July 2004; [Epub ahead of print]; Yee, Kevin W. H. et al. SU5416 and SU5614 inhibit kinase activity of wild-type and mutant FLT3 receptor tyrosine kinase. Blood, September 2002; 100: 2941-294; O'Farrell, Anne-Marie et al. SU11248 is a novel FLT3 tyrosine kinase inhibitor with potent activity in vitro and in vivo. Blood, May 2003; 101: 3597-3605; Stone, R. M. et al. PKC 412 FLT3 inhibitor therapy in AML: results of a phase II trial. Ann Hematol. 2004; 83 Suppl 1:S89-90; and Murata, K. et al. Selective cytotoxic mechanism of GTP-14564, a novel tyrosine kinase inhibitor in leukemia cells expressing a constitutively active Fms-like tyrosine kinase 3 (FLT3). J Biol Chem. 2003 Aug. 29; 278(35):32892-8; Levis, Mark et al. Novel FLT3 tyrosine kinase inhibitors. Expert Opin. Investing. Drugs (2003) 12(12) 1951-1962; Levis, Mark et al. Small Molecule FLT3 Tyrosine Kinase Inhibitors. Current Pharmaceutical Design, 2004, 10, 1183-1193.

SUMMARY OF THE INVENTION

The present invention provides novel quinolines and quinazolines (the compounds of Formula 1) as protein tyrosine kinase modulators, particularly inhibitors of FLT3 and/or c-kit and/or TrkB, and the use of such compounds to reduce or inhibit kinase activity of FLT3 and/or c-kit and/or TrkB in a cell or a subject, and the use of such compounds for preventing or treating in a subject a cell proliferative disorder and/or disorders related to FLT3 and/or c-kit and/or TrkB.

Illustrative of the invention is a pharmaceutical composition comprising a compound of Formula I and a pharmaceutically acceptable carrier. Another illustration of the present invention is a pharmaceutical composition prepared by mixing any of the compounds of Formula I and a pharmaceutically acceptable carrier.

Other features and advantages of the invention will be apparent from the following detailed description of the invention and from the claims.

DESCRIPTION OF THE FIGURES

FIG. 1 shows the effects of oral administration of compounds of the present invention on the growth of MV4-11 tumor xenografts in nude mice.

FIG. 2 shows the effects of oral administration of compounds of the present invention on the final weight of MV4-11 tumor xenografts in nude mice.

FIG. 3 and FIG. 4 show FLT3 phosphorylation in MV4-11 tumors obtained from mice treated with compounds of the present invention.

DETAILED DESCRIPTION OF THE INVENTION

Definitions

As used herein, the following terms are intended to have the following meanings (additional definitions are provided where needed throughout the Specification):

The term "alkenyl," whether used alone or as part of a substituent group, for example, "$C_{1-4}$alkenyl(aryl)," refers to a partially unsaturated branched or straight chain monovalent hydrocarbon radical having at least one carbon-carbon double bond, whereby the double bond is derived by the removal of one hydrogen atom from each of two adjacent carbon atoms of a parent alkyl molecule and the radical is derived by the removal of one hydrogen atom from a single carbon atom. Atoms may be oriented about the double bond in either the cis (Z) or trans (E) conformation. Typical alkenyl radicals include, but are not limited to, ethenyl, propenyl, allyl (2-propenyl), butenyl and the like. Examples include $C_{2-8}$alkenyl or $C_{2-4}$alkenyl groups.

The term "$C_{a-b}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{1-4}$ denotes a radical containing 1, 2, 3 or 4 carbon atoms.

The term "alkyl," whether used alone or as part of a substituent group, refers to a saturated branched or straight chain monovalent hydrocarbon radical, wherein the radical is derived by the removal of one hydrogen atom from a single carbon atom. Unless specifically indicated (e.g. by the use of a limiting term such as "terminal carbon atom"), substituent variables may be placed on any carbon chain atom. Typical alkyl radicals include, but are not limited to, methyl, ethyl, propyl, isopropyl and the like. Examples include $C_{1-8}$alkyl, $C_{1-6}$alkyl and $C_{1-4}$alkyl groups.

The term "alkylamino" refers to a radical formed by the removal of one hydrogen atom from the nitrogen of an alkylamine, such as butylamine, and the term "dialkylamino" refers to a radical formed by the removal of one hydrogen atom from the nitrogen of a secondary amine, such as dibutylamine. In both cases it is expected that the point of attachment to the rest of the molecule is the nitrogen atom.

The term "alkynyl," whether used alone or as part of a substituent group, refers to a partially unsaturated branched or straight chain monovalent hydrocarbon radical having at least one carbon-carbon triple bond, whereby the triple bond is derived by the removal of two hydrogen atoms from each of two adjacent carbon atoms of a parent alkyl molecule and the radical is derived by the removal of one hydrogen atom from a single carbon atom. Typical alkynyl radicals include ethynyl, propynyl, butynyl and the like. Examples include $C_{2-8}$alkynyl or $C_{2-4}$alkynyl groups.

The term "alkoxy" refers to a saturated or partially unsaturated branched or straight chain monovalent hydrocarbon alcohol radical derived by the removal of the hydrogen atom from the hydroxide oxygen substituent on a parent alkane, alkene or alkyne. Where specific levels of saturation are intended, the nomenclature "alkoxy", "alkenyloxy" and "alkynyloxy" are used consistent with the definitions of alkyl, alkenyl and alkynyl. Examples include $C_{1-8}$alkoxy or $C_{1-4}$alkoxy groups.

The term "alkoxyether" refers to a saturated branched or straight chain monovalent hydrocarbon alcohol radical derived by the removal of the hydrogen atom from the hydroxide oxygen substituent on a hydroxyether. Examples include 1-hydroxyl-2-methoxy-ethane and 1-(2-hydroxylethoxy)-2-methoxy-ethane groups.

The term "aralkyl" refers to a $C_{1-6}$ alkyl group containing an aryl substituent. Examples include benzyl, phenylethyl or 2-naphthylmethyl. It is intended that the point of attachment to the rest of the molecule be the alkyl group.

The term "aromatic" refers to a cyclic hydrocarbon ring system having an unsaturated, conjugated π electron system.

The term "aryl" refers to an aromatic cyclic hydrocarbon ring radical derived by the removal of one hydrogen atom from a single carbon atom of the ring system. Typical aryl radicals include phenyl, naphthalenyl, fluorenyl, indenyl, azulenyl, anthracenyl and the like.

The term "arylamino" refers to an amino group, such as ammonia, substituted with an aryl group, such as phenyl. It is expected that the point of attachment to the rest of the molecule is through the nitrogen atom.

The term "benzo-fused cycloalkyl" refers to a bicyclic fused ring system radical wherein one of the rings is phenyl and the other is a cycloalkyl or cycloalkenyl ring. Typical benzo-fused cycloalkyl radicals include indanyl, 1,2,3,4-tetrahydro-naphthalenyl, 6,7,8,9-tetrahydro-5H-benzocycloheptenyl, 5,6,7,8,9,10-hexahydro-benzocyclooctenyl and the like. A benzo-fused cycloalkyl ring system is a subset of the aryl group.

The term "benzo-fused heteroaryl" refers to a bicyclic fused ring system radical wherein one of the rings is phenyl and the other is a heteroaryl ring. Typical benzo-fused heteroaryl radicals include indolyl, indolinyl, isoindolyl, benzo[b]furyl, benzo[b]thienyl, indazolyl, benzthiazolyl, quinolinyl, isoquinolinyl, cinnolinyl, phthalazinyl, quinazolinyl, and the like. A benzo-fused heteroaryl ring is a subset of the heteroaryl group.

The term "benzo-fused heterocyclyl" refers to a bicyclic fused ring system radical wherein one of the rings is phenyl and the other is a heterocyclyl ring. Typical benzo-fused heterocyclyl radicals include 1,3-benzodioxolyl (also known as 1,3-methylenedioxyphenyl), 2,3-dihydro-1,4-benzodioxinyl (also known as 1,4-ethylenedioxyphenyl), benzo-dihydro-furyl, benzo-tetrahydro-pyranyl, benzo-dihydro-thienyl and the like.

The term "carboxyalkyl" refers to an alkylated carboxy group such as tert-butoxycarbonyl, in which the point of attachment to the rest of the molecule is the carbonyl group.

The term "cyclic heterodionyl" refers to a heterocyclic compound bearing two oxo substituents. Examples include thiazolidinedionyl, oxazolidinedionyl and pyrrolidinedionyl.

The term "cycloalkenyl" refers to a partially unsaturated cycloalkyl radical derived by the removal of one hydrogen atom from a hydrocarbon ring system that contains at least one carbon-carbon double bond. Examples include cyclohexenyl, cyclopentenyl and 1,2,5,6-cyclooctadienyl.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{3-8}$cycloalkyl, $C_{5-8}$cycloalkyl, $C_{3-12}$cycloalkyl, $C_{3-20}$cycloalkyl, decahydronaphthalenyl, and 2,3,4,5,6,7-hexahydro-1H-indenyl.

The term "fused ring system" refers to a bicyclic molecule in which two adjacent atoms are present in each of the two cyclic moieties. Heteroatoms may optionally be present. Examples include benzothiazole, 1,3-benzodioxole and decahydronaphthalene.

The term "hetero" used as a prefix for a ring system refers to the replacement of at least one ring carbon atom with one or more atoms independently selected from N, S, O or P. Examples include rings wherein 1, 2, 3 or 4 ring members are a nitrogen atom; or, 0, 1, 2 or 3 ring members are nitrogen atoms and 1 member is an oxygen or sulfur atom.

The term "heteroaralkyl" refers to a $C_{1-6}$ alkyl group containing a heteroaryl substituent. Examples include furylmethyl and pyridylpropyl. It is intended that the point of attachment to the rest of the molecule be the alkyl group.

The term "heteroaryl" refers to a radical derived by the removal of one hydrogen atom from a ring carbon atom of a heteroaromatic ring system. Typical heteroaryl radicals include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolizinyl, indolyl, isoindolyl, benzo[b]furyl, benzo[b]thienyl, indazolyl, benzimidazolyl, benzthiazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl and the like.

The term "heteroaryl-fused cycloalkyl" refers to a bicyclic fused ring system radical wherein one of the rings is cycloalkyl and the other is heteroaryl. Typical heteroaryl-fused cycloalkyl radicals include 5,6,7,8-tetrahydro-4H-cyclohepta(b)thienyl, 5,6,7-trihydro-4H-cyclohexa(b)thienyl, 5,6-dihydro-4H-cyclopenta(b)thienyl and the like.

The term "heterocyclyl" refers to a saturated or partially unsaturated monocyclic ring radical derived by the removal of one hydrogen atom from a single carbon or nitrogen ring atom. Typical heterocyclyl radicals include 2H-pyrrolyl, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, piperidinyl, 1,4-dioxanyl, morpholinyl, 1,4-dithianyl, thiomorpholinyl, thiomorpholinyl 1,1 dioxide, piperazinyl, azepanyl, hexahydro-1,4-diazepinyl and the like.

The term "oxo" refers to an oxygen atom radical; said oxygen atom has two open valencies which are bonded to the same atom, most preferably a carbon atom. The oxo group is an appropriate substituent for an alkyl group. For example, propane with an oxo substituent is either acetone or propionaldehyde. Heterocycles can also be substituted with an oxo group. For example, oxazolidine with an oxo substituent is oxazolidinone.

The term "squaryl" refers to a cyclobutenyl 1,2 dione radical.

The term "substituted," refers to a core molecule on which one or more hydrogen atoms have been replaced with one or more functional radical moieties. Substitution is not limited to a core molecule, but may also occur on a substituent radical, whereby the substituent radical becomes a linking group.

The term "independently selected" refers to one or more substituents selected from a group of substituents, wherein the substituents may be the same or different.

The substituent nomenclature used in the disclosure of the present invention was derived by first indicating the atom having the point of attachment, followed by the linking group atoms toward the terminal chain atom from left to right, substantially as in:

$(C_{1-6})$alkylC(O)NH$(C_{1-6})$alkyl(Ph)

or by first indicating the terminal chain atom, followed by the linking group atoms toward the atom having the point of attachment, substantially as in:

Ph$(C_{1-6})$alkylamido$(C_{1-6})$alkyl either of which refers to a radical of the formula:

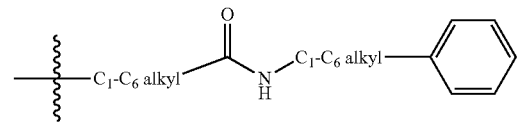

Lines drawn into ring systems from substituents indicate that the bond may be attached to any of the suitable ring atoms.

When any variable (e.g. $R_4$) occurs more than one time in any embodiment of Formula I, each definition is intended to be independent.

The terms "comprising", "including", and "containing" are used herein in their open, non-limited sense.

Nomenclature

Except where indicated, compound names were derived using nomenclature rules well known to those skilled in the art, by either standard IUPAC nomenclature references, such as *Nomenclature of Organic Chemistry, Sections A, B, C, D, E, F and H*, (Pergamon Press, Oxford, 1979, Copyright 1979 IUPAC) and *A Guide to IUPAC Nomenclature of Organic Compounds* (*Recommendations* 1993), (Blackwell Scientific Publications, 1993, Copyright 1993 IUPAC); or commercially available software packages such as Autonom (brand of nomenclature software provided in the ChemDraw Ultra® office suite marketed by CambridgeSoft.com); and ACD/Index Name™ (brand of commercial nomenclature software marketed by Advanced Chemistry Development, Inc., Toronto, Ontario).

Abbreviations

As used herein, the following abbreviations are intended to have the following meanings (additional abbreviations are provided where needed throughout the Specification):

| | |
|---|---|
| ATP | adenosine triphosphate |
| Boc | tert-butoxycarbonyl |
| DCM | dichloromethane |

| | |
|---|---|
| DMF | dimethylformamide |
| DMSO | dimethylsulfoxide |
| DIEA | diisopropylethylamine |
| DTT | dithiothreitol |
| EDC | 1-(3-dimethylaminopropyl)-3-ethylcarbodiimide hydrochloride |
| EDTA | ethylenediaminetetraaceticacid |
| EtOAc | ethyl acetate |
| FBS | fetal bovine serum |
| FP | fluorescence polarization |
| GM-CSF | granulocyte and macrophage colony stimulating factor |
| HBTU | O-benzotriazol-1-yl-N,N,N',N'-tetramethyluronium hexafluorophosphate |
| Hex | hexane |
| HOBT | 1-hydroxybenzotriazole hydrate |
| HPβCD | hydroxypropyl β-cyclodextrin |
| HRP | horseradish peroxidase |
| i-PrOH | isopropyl alcohol |
| LC/MS (ESI) | Liquid chromatography/mass spectrum (electrospray ionization) |
| MeOH | Methyl alcohol |
| NMM | N-methylmorpholine |
| NMR | nuclear magnetic resonance |
| PS | polystyrene |
| PBS | phosphate buffered saline |
| RPMI | Rosewell Park Memorial Institute |
| RT | room temperature |
| RTK | receptor tyrosine kinase |
| NaHMDS | sodium hexamethyldisilazane |
| SDS-PAGE | sodium dodecyl sulfate polyacrylamide gel electrophoreisis |
| TEA | triethylamine |
| TFA | trifluoroacetic acid |
| THF | tetrahydrofuran |
| TLC | thin layer chromatography |

Formula I

The present invention comprises compounds of Formula I:

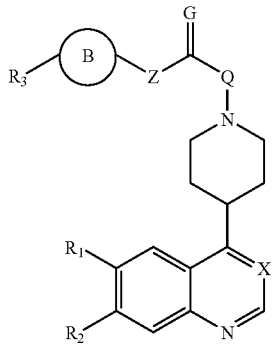

Formula I and N-oxides, pharmaceutically acceptable salts, solvates, and stereochemical isomers thereof, wherein:
Q is $CH_2$ or a direct bond;
G is O or S;
X is N or CH;
Z is NH, N(alkyl), or $CH_2$;
B is phenyl, cycloalkyl (wherein said cycloalkyl is preferably cyclopentanyl, cyclohexanyl, cyclopentenyl or cyclohexenyl), heteroaryl (wherein said heteroaryl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, imidazolyl, or pyrazinyl), a nine to ten membered benzo-fused heteroaryl (wherein said nine to ten membered benzo-fused heteroaryl is preferably benzothiazolyl, benzooxazolyl, benzoimidazolyl, benzofuranyl, indolyl, quinolinyl, isoquinolinyl, or benzo[b]thiophenyl), or a nine to ten membered benzo-fused heterocyclyl (wherein said nine to ten membered benzo-fused heterocyclyl is preferably 2,3-dihydro-benzothiazolyl, 2,3-dihydro-benzooxazolyl, 2,3-dihydro-benzoimidazolyl, 1,2,3,4-tetrahydro-quinolinyl, 1,2,3,4-tetrahydro-isoquinolinyl, isochromanyl, 2,3-dihydro-indolyl, 2,3-dihydro-benzofuranyl or 2,3-dihydro-benzo[b]thiophenyl, and most preferably 2,3-dihydro-indolyl, 2,3-dihydro-benzofuranyl or 2,3-dihydro-benzo[b]thiophenyl);
$R_1$ and $R_2$ are independently selected from:

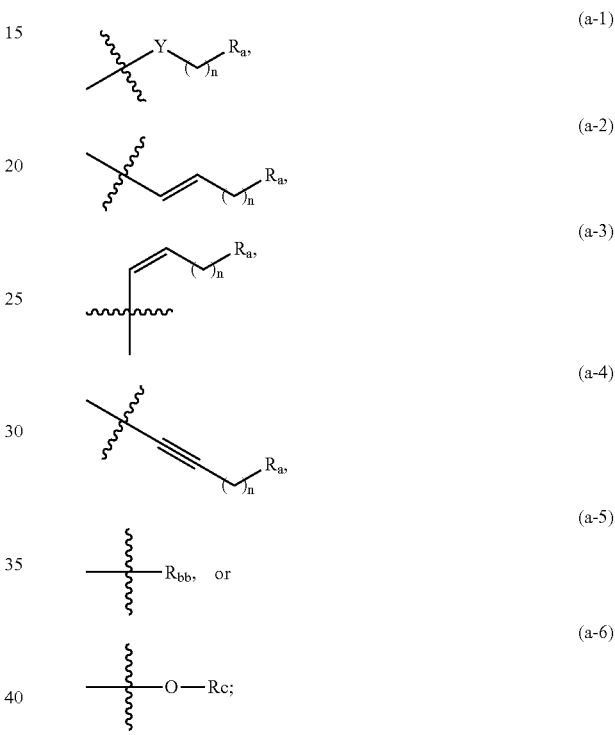

wherein n is 1, 2, 3 or 4;
Y is a direct bond, O, S, NH, or N(alkyl);
$R_a$ is alkoxy, phenoxy, heteroaryl optionally substituted with $R_5$ (wherein said heteroaryl is preferably pyrrolyl, furanyl, thiophenyl, imidazolyl, thiazolyl, oxazolyl, pyranyl, thiopyranyl, pyridinyl, pyrimidinyl, triazolyl, tetrazolyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, triazolyl, tetrazolyl, or pyrazinyl), hydroxyl, alkylamino, dialkylamino, oxazolidinonyl optionally substituted with $R_5$, pyrrolidinonyl optionally substituted with $R_5$, piperidinonyl optionally substituted with $R_5$, piperazinyl-2-one optionally substituted with $R_5$, cyclic heterodionyl optionally substituted with $R_5$, heterocyclyl optionally substituted with $R_5$ (wherein said heterocyclyl is preferably azepanyl, diazepanyl, azetidinyl, pyrrolidinyl, tetrahydrofuranyl, tetrahydrothiophenyl, imidazolidinyl, thiazolidinyl, oxazolidinyl, tetrahydropyranyl, tetrahydrothiopyranyl, piperidinyl, thiomorpholinyl, thiomorpholinyl 1,1-dioxide, morpholinyl, or piperazinyl), squaryl optionally substituted with $R_5$, —$COOR_y$, —$CONR_wR_x$, —$N(R_y)CON(R_w)(R_x)$, —$N(R_w)C(O)OR_x$, —$N(R_w)COR_x$, —$SR_y$, —$SOR_y$, —$SO_2R_y$, —$NR_wSO_2R_y$, —$NR_wSO_2R_x$, —$SO_3R_y$, —$OSO_2NR_wR_x$, or —$SO_2NR_wR_x$;

$R_w$ and $R_x$ are independently selected from: hydrogen, alkyl, alkenyl, aralkyl (wherein the aryl portion of said aralkyl is preferrably phenyl), or heteroaralkyl (wherein the heteroaryl portion of said heteroaralkyl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, or pyrazinyl), or $R_w$ and $R_x$ may optionally be taken together to form a 5 to 7 membered ring, optionally containing a heteromoiety selected from O, NH, N(alkyl), SO, $SO_2$, or S, preferably selected from the group consisting of:

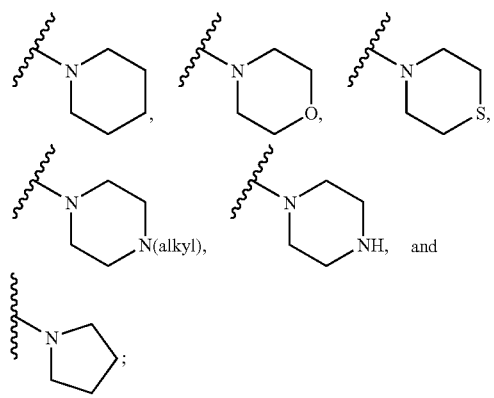

$R_y$ is selected from: hydrogen, alkyl, alkenyl, cycloalkyl (wherein said cycloalkyl is preferably cyclopentanyl or cyclohexanyl), phenyl, aralkyl (wherein the aryl portion of said aralkyl is preferably phenyl), heteroaralkyl (wherein the heteroaryl portion of said heteroaralkyl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, or pyrazinyl), or heteroaryl (wherein said heteroaryl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, or pyrazinyl);

$R_5$ is one, two, or three substituents independently selected from: halogen, cyano, trifluoromethyl, amino, hydroxyl, heteroaryl, alkoxy, —C(O)alkyl, —$SO_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_5$ substituent is not present more than once, unless said $R_5$ substituent is halogen, hydroxyl, alkoxy, or alkyl;

$R_{bb}$ is hydrogen, halogen, alkoxy, dialkylamino, phenyl optionally substituted with $R_6$, heteroaryl optionally substituted with $R_6$ (wherein said heteroaryl is preferably pyrrolyl, furanyl, thiophenyl, imidazolyl, thiazolyl, oxazolyl, pyranyl, thiopyranyl, pyridinyl, pyrimidinyl, triazolyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, triazolyl, or pyrazinyl), piperazinyl-2-one optionally substituted with $R_6$, imidazolidinyl-2-one optionally substituted with $R_6$, oxazolidinyl-2-one optionally substituted with $R_6$, or heterocyclyl optionally substituted with $R_6$ (wherein said heterocyclyl is preferably azepanyl, diazepanyl, azetidinyl, pyrrolidinyl, tetrahydrofuranyl, tetrahydrothiophenyl, imidazolidinyl, thiazolidinyl, oxazolidinyl, tetrahydropyranyl, tetrahydrothiopyranyl, piperidinyl, thiomorpholinyl, thiomorpholinyl 1,1-dioxide, morpholinyl or piperazinyl);

$R_6$ is one, two, or three substituents independently selected from: halogen, cyano, trifluoromethyl, amino, hydroxyl, heteroaryl, alkoxy, —C(O)alkyl, —$SO_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_6$ substituent is not present more than once, unless said $R_6$ substituent is halogen, hydroxyl, alkoxy, or alkyl;

$R_c$ is heterocyclyl optionally substituted with $R_7$ (wherein said heterocyclyl is preferably azepanyl, diazepanyl, azetidinyl, pyrrolidinyl, tetrahydrofuranyl, tetrahydrothiophenyl, imidazolidinyl, thiazolidinyl, oxazolidinyl, tetrahydropyranyl, tetrahydrothiopyranyl, piperidinyl, thiomorpholinyl, thiomorpholinyl 1,1-dioxide, morpholinyl, or piperazinyl), or heteroaryl (wherein said heteroaryl is preferably pyrrolyl, furanyl, thiophenyl, imidazolyl, thiazolyl, oxazolyl, pyridinyl, pyrimidinyl, or pyrazinyl); and $R_7$ is one, two, or three substituents independently selected from: halogen, cyano, trifluoromethyl, amino, hydroxyl, heteroaryl, alkoxy, —C(O)alkyl, —$SO_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_7$ substituent is not present more than once, unless said $R_7$ substituent is halogen, hydroxyl, alkoxy, or alkyl;

$R_3$ is one or more substituents independently selected from: hydrogen provided that $R_{bb}$ is not hydrogen, alkyl, alkoxy, halogen, amino optionally substituted with $R_4$, $C_{1-2}$(alkyl)-OH, nitro, cycloalkyl optionally substituted with $R_4$ (wherein said cycloalkyl is preferably cyclopentanyl or cyclohexanyl), heteroaryl optionally substituted with $R_4$ (wherein said heteroaryl is preferably pyrrolyl, furanyl, thiophenyl, imidazolyl, thiazolyl, oxazolyl, pyranyl, thiopyranyl, pyridinyl, pyrimidinyl, triazolyl, pyrazinyl, pyridinyl-N-oxide, or pyrrolyl-N-oxide; and most preferably pyrrolyl, furanyl, thiophenyl, imidazolyl, thiazolyl, oxazolyl, pyridinyl, pyrimidinyl, triazolyl, or pyrazinyl), alkylamino, heterocyclyl optionally substituted with $R_4$ (wherein said heterocyclyl is preferably tetrahydropyridinyl, tetrahydropyrazinyl, dihydrofuranyl, dihydrooxazinyl, dihydropyrrolyl, dihydroimidazolyl azepenyl, pyrrolidinyl, tetrahydrofuranyl, tetrahydrothiophenyl, imidazolidinyl, thiazolidinyl, oxazolidinyl, tetrahydropyranyl, tetrahydrothiopyranyl, piperidinyl, thiomorpholinyl, morpholinyl or piperazinyl), alkoxyether, —O(cycloalkyl), pyrrolidinonyl optionally substituted with $R_4$, phenoxy optionally substituted with $R_4$, —CN, —OCHF$_2$, —OCF$_3$, —CF$_3$, halogenated alkyl, heteroaryloxy optionally substituted with $R_4$, dialkylamino, —NHSO$_2$alkyl, or —SO$_2$alkyl; wherein $R_4$ is independently selected from: halogen, cyano, trifluoromethyl, amino, hydroxyl, alkoxy, —C(O)alkyl, —CO$_2$alkyl, —SO$_2$alkyl, —C(O)N(alkyl)$_2$, alkyl, or alkylamino.

As used hereafter, the term "compounds of Formula I" is meant to include also N-oxides, pharmaceutically acceptable salts, solvates, and stereochemical isomers thereof.

Embodiments of Formula I

In an embodiment of the present invention: N-oxides are optionally present on one or more of: N-1 or N-3 (when X is N) (see FIG. 1 below for ring numbers).

FIG. 1

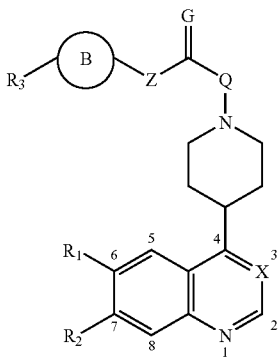

FIG. 1 illustrates ring atoms numbered 1 through 8, as used in the present specification.

Preferred embodiments of the invention are compounds of Formula I wherein one or more of the following limitations are present:
Q is $CH_2$ or a direct bond;
G is O or S;
X is N or CH;
Z is NH or $CH_2$;
B is phenyl, heteroaryl, or a nine to ten membered benzo-fused heteroaryl;
$R_1$ and $R_2$ are independently selected from:

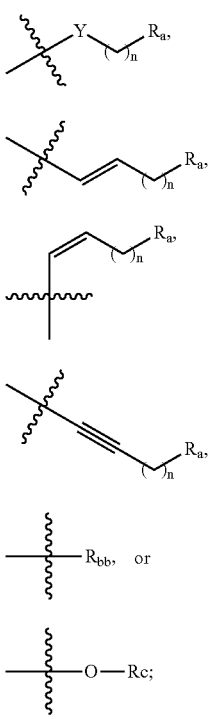

(a-1)
(a-2)
(a-3)
(a-4)
(a-5)
(a-6)

wherein n is 1, 2, 3 or 4;
Y is a direct bond, O, S, NH, or N(alkyl);
$R_a$ is alkoxy, phenoxy, heteroaryl optionally substituted with $R_5$, hydroxyl, alkylamino, dialkylamino, oxazolidinonyl optionally substituted with $R_5$, pyrrolidinonyl optionally substituted with $R_5$, piperidinonyl optionally substituted with $R_5$, piperazinyl-2-one optionally substituted with $R_5$, cyclic heterodionyl optionally substituted with $R_5$, heterocyclyl optionally substituted with $R_5$, squaryl optionally substituted with $R_5$, —COOR$_y$, —CONR$_w$R$_x$, —N(R$_y$)CON(R$_w$)(R$_x$), —N(R$_w$)C(O)OR$_x$, —N(R$_w$)COR$_y$, —SR$_y$, —SOR$_y$, —SO$_2$R$_y$, —NR$_w$SO$_2$R$_y$, —NR$_w$SO$_2$R$_x$, —SO$_3$R$_y$, —OSO$_2$NR$_w$R$_x$, or —SO$_2$NR$_w$R$_x$;

$R_w$ and $R_x$ are independently selected from: hydrogen, alkyl, alkenyl, aralkyl, or heteroaralkyl, or $R_w$ and $R_x$ may optionally be taken together to form a 5 to 7 membered ring, optionally containing a heteromoiety selected from O, NH, N(alkyl), SO, $SO_2$, or S;

$R_y$ is selected from: hydrogen, alkyl, alkenyl, cycloalkyl, phenyl, aralkyl, heteroaralkyl, or heteroaryl;

$R_5$ is one, two, or three substituents independently selected from: halogen, cyano, trifluoromethyl, amino, hydroxyl, heteroaryl, alkoxy, —C(O)alkyl, —SO$_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_5$ substituent is not present more than once, unless said $R_5$ substituent is halogen, hydroxyl, alkoxy, or alkyl;

$R_{bb}$ is hydrogen, halogen, alkoxy, dialkylamino, phenyl optionally substituted with $R_6$, heteroaryl optionally substituted with $R_6$, piperazinyl-2-one optionally substituted with $R_6$, imidazolidinyl-2-one optionally substituted with $R_6$, oxazolidinyl-2-one optionally substituted with $R_6$, or heterocyclyl optionally substituted with $R_6$;

$R_6$ is one, two, or three substituents independently selected from: halogen, cyano, trifluoromethyl, amino, hydroxyl, heteroaryl, alkoxy, —C(O)alkyl, —SO$_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_6$ substituent is not present more than once, unless said $R_6$ substituent is halogen, hydroxyl, alkoxy, or alkyl;

$R_c$ is heterocyclyl optionally substituted with $R_7$, or heteroaryl; and $R_7$ is one, two, or three substituents independently selected from: halogen, cyano, trifluoromethyl, amino, hydroxyl, heteroaryl, alkoxy, —C(O)alkyl, —SO$_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_7$ substituent is not present more than once, unless said $R_7$ substituent is halogen, hydroxyl, alkoxy, or alkyl;

$R_3$ is one or more substituents independently selected from: hydrogen provided that $R_{bb}$ is not hydrogen, alkyl, alkoxy, halogen, amino optionally substituted with $R_4$, $C_{1-2}$(alkyl)-OH, nitro, cycloalkyl optionally substituted with $R_4$, heteroaryl optionally substituted with $R_4$, alkylamino, heterocyclyl optionally substituted with $R_4$, alkoxyether, —O(cycloalkyl), pyrrolidinonyl optionally substituted with $R_4$, phenoxy optionally substituted with $R_4$, —CN, —OCHF$_2$, —OCF$_3$, —CF$_3$, halogenated alkyl, heteroaryloxy optionally substituted with $R_4$, dialkylamino, —NHSO$_2$alkyl, or —SO$_2$alkyl; wherein $R_4$ is independently selected from: halogen, cyano, trifluoromethyl, amino, hydroxyl, alkoxy, —C(O)alkyl, —CO$_2$alkyl, —SO$_2$alkyl, —C(O)N(alkyl)$_2$, alkyl, or alkylamino.

Other preferred embodiments of the invention are compounds of Formula I wherein one or more of the following limitations are present:
Q is $CH_2$ or a direct bond;
G is O;

X is N or CH;
Z is NH or CH$_2$;
B is phenyl or heteroaryl;
R$_1$ and R$_2$ are independently selected from:

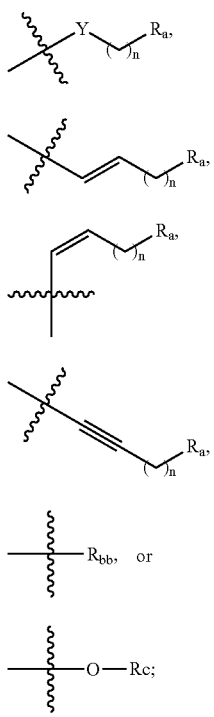

wherein n is 1, 2, 3 or 4;
Y is a direct bond, O, S, NH, or N(alkyl);
R$_a$ is alkoxy, phenoxy, heteroaryl optionally substituted with R$_5$, hydroxyl, alkylamino, dialkylamino, oxazolidinonyl optionally substituted with R$_5$, pyrrolidinonyl optionally substituted with R$_5$, piperidinonyl optionally substituted with R$_5$, piperazinyl-2-one optionally substituted with R$_5$, cyclic heterodionyl optionally substituted with R$_5$, heterocyclyl optionally substituted with R$_5$, squaryl optionally substituted with R$_5$, —COOR$_y$, —CONR$_w$R$_x$, —N(R$_y$)CON(R$_w$)(R$_x$), —N(R$_w$)C(O)OR$_x$, —N(R$_w$)COR$_y$, —SR$_y$, —SOR$_y$, —SO$_2$R$_y$, —NR$_w$SO$_2$R$_y$, —NR$_w$SO$_2$R$_x$, —SO$_3$R$_y$, —OSO$_2$NR$_w$R$_x$, or —SO$_2$NR$_w$R$_x$;
R$_w$ and R$_x$ are independently selected from: hydrogen, alkyl, alkenyl, aralkyl or heteroaralkyl, or R$_w$ and R$_x$ may optionally be taken together to form a 5 to 7 membered ring, optionally containing a heteromoiety selected from O, NH, N(alkyl), SO, SO$_2$, or S;
R$_y$ is selected from: hydrogen, alkyl, alkenyl, cycloalkyl, phenyl, aralkyl, heteroaralkyl, or heteroaryl;
R$_5$ is one, two, or three substituents independently selected from: halogen, cyano, trifluoromethyl, amino, hydroxyl, heteroaryl, alkoxy, —C(O)alkyl, —SO$_2$alkyl, —C(O)NH(alkyl), —C(O)N(alkyl)$_2$, —C(O)C$_{(1-4)}$ alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same R$_5$ substituent is not present more than once, unless said R$_5$ substituent is halogen, hydroxyl, alkoxy, or alkyl;
R$_{bb}$ is hydrogen, halogen, alkoxy, dialkylamino, phenyl, heteroaryl, piperazinyl-2-one optionally substituted with R$_6$, imidazolidinyl-2-one optionally substituted with R$_6$, oxazolidinyl-2-one optionally substituted with R$_6$, or heterocyclyl optionally substituted with R$_6$;
R$_6$ is one, two, or three substituents independently selected from: halogen, cyano, trifluoromethyl, amino, hydroxyl, heteroaryl, alkoxy, —C(O)alkyl, —SO$_2$alkyl, —C(O)NH(alkyl), —C(O)N(alkyl)$_2$, —C(O)C$_{(1-4)}$ alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same R$_6$ substituent is not present more than once, unless said R$_6$ substituent is halogen, hydroxyl, alkoxy, or alkyl;
R$_c$ is heterocyclyl optionally substituted with R$_7$, or heteroaryl; and
R$_7$ is one, two, or three substituents independently selected from: halogen, cyano, trifluoromethyl, amino, hydroxyl, heteroaryl, alkoxy, —C(O)alkyl, —SO$_2$alkyl, —C(O)NH(alkyl), —C(O)N(alkyl)$_2$, —C(O)C$_{(1-4)}$ alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same R$_7$ substituent is not present more than once, unless said R$_7$ substituent is halogen, hydroxyl, alkoxy, or alkyl; and
R$_3$ is one or more substituents independently selected from: hydrogen provided that R$_{bb}$ is not hydrogen, alkyl, alkoxy, halogen, amino optionally substituted with R$_4$, C$_{1-2}$(alkyl)-OH, cycloalkyl optionally substituted with R$_4$, heteroaryl optionally substituted with R$_4$, alkylamino, heterocyclyl optionally substituted with R$_4$, alkoxyether, —O(cycloalkyl), pyrrolidinonyl optionally substituted with R$_4$, phenoxy optionally substituted with R$_4$, —CN, —OCHF$_2$, —OCF$_3$, —CF$_3$, halogenated alkyl, dialkylamino and —SO$_2$alkyl; wherein R$_4$ is independently selected from halogen, cyano, trifluoromethyl, amino, hydroxyl, alkoxy, —C(O)alkyl, —CO$_2$alkyl, —SO$_2$alkyl, —C(O)N(alkyl)$_2$, alkyl, or alkylamino.

Still other preferred embodiments of the invention are compounds of Formula I wherein one or more of the following limitations are present:
Q is CH$_2$ or a direct bond;
G is O;
X is N or CH;
Z is NH or CH$_2$;
B is phenyl or heteroaryl;
R$_1$ and R$_2$ are independently selected from:

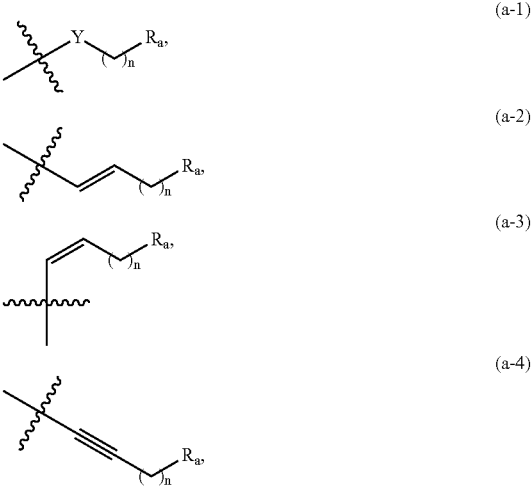

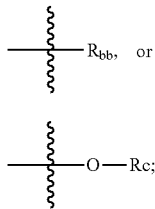

wherein n is 1, 2, 3 or 4;
Y is a direct bond, O, or NH;
$R_a$ is alkoxy, heteroaryl optionally substituted with $R_5$, hydroxyl, alkylamino, dialkylamino, oxazolidinonyl optionally substituted with $R_5$, pyrrolidinonyl optionally substituted with $R_5$, piperidinonyl optionally substituted with $R_5$, piperazinyl-2-one optionally substituted with $R_5$, cyclic heterodionyl optionally substituted with $R_5$, heterocyclyl optionally substituted with $R_5$, squaryl optionally substituted with $R_5$, —$CONR_wR_x$, —$N(R_y)CON(R_w)(R_x)$, —$N(R_w)C(O)OR_x$, —$N(R_w)COR_y$, —$SR_y$, —$SOR_y$, —$SO_2R_y$, or —$NR_wSO_2R_y$;
$R_w$ and $R_x$ are independently selected from: hydrogen, alkyl, alkenyl, aralkyl, or heteroaralkyl, or $R_w$ and $R_x$ may optionally be taken together to form a 5 to 7 membered ring, optionally containing a heteromoiety selected from O, NH, N(alkyl), SO, $SO_2$, or S;
$R_y$ is selected from: hydrogen, alkyl, alkenyl, cycloalkyl, phenyl, aralkyl, heteroaralkyl, or heteroaryl;
$R_5$ is one, two, or three substituents independently selected from: halogen, cyano, trifluoromethyl, amino, hydroxyl, heteroaryl, alkoxy, —C(O)alkyl, —$SO_2$alkyl, —C(O)NH (alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$ alkyl-OH, —C(O)C$_{(1-4)}$alkyl-OCH$_3$, dialkylamino, or alkylamino; provided that the same $R_5$ substituent is not present more than once, unless said $R_5$ substituent is halogen, hydroxyl, alkoxy, or alkyl;
$R_{bb}$ is hydrogen, halogen, alkoxy, piperazinyl-2-one optionally substituted with $R_6$, imidazolidinyl-2-one optionally substituted with $R_6$, oxazolidinyl-2-one optionally substituted with $R_6$, or heterocyclyl optionally substituted with $R_6$;
$R_6$ is one, two, or three substituents independently selected from: halogen, cyano, trifluoromethyl, amino, hydroxyl, heteroaryl, alkoxy, —C(O)alkyl, —$SO_2$alkyl, —C(O)NH (alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$ alkyl-OH, —C(O)C$_{(1-4)}$alkyl-OCH$_3$, dialkylamino, or alkylamino; provided that the same $R_6$ substituent is not present more than once, unless said $R_6$ substituent is halogen, hydroxyl, alkoxy, or alkyl;
$R_c$ is heterocyclyl optionally substituted with $R_7$, or heteroaryl; and
$R_7$ is one, two, or three substituents independently selected from: halogen, cyano, trifluoromethyl, amino, hydroxyl, heteroaryl, alkoxy, —C(O)alkyl, —$SO_2$alkyl, —C(O)NH (alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$ alkyl-OH, —C(O)C$_{(1-4)}$alkyl-OCH$_3$, dialkylamino, or alkylamino; provided that the same $R_7$ substituent is not present more than once, unless said $R_7$ substituent is halogen, hydroxyl, alkoxy, or alkyl; and
$R_3$ is one or more substituents independently selected from: hydrogen provided that $R_{bb}$ is not hydrogen, alkyl, alkoxy, amino optionally substituted with $R_4$, halogen, $C_{1-2}$(alkyl)-OH, cycloalkyl optionally substituted with $R_4$, heteroaryl optionally substituted with $R_4$, alkylamino, heterocyclyl optionally substituted with $R_4$ alkoxyether, —O(cycloalkyl), pyrrolidinonyl optionally substituted with $R_4$, phenoxy optionally substituted with $R_4$, —$OCHF_2$, —$OCF_3$, —$CF_3$, dialkylamino, or —$SO_2$alkyl; wherein $R_4$ is independently selected from halogen, cyano, trifluoromethyl, amino, hydroxyl, alkoxy, —C(O)alkyl, —$CO_2$alkyl, —$SO_2$alkyl, —C(O)N(alkyl)$_2$, alkyl, or alkylamino.

Particularly preferred embodiments of the invention are compounds of Formula I wherein one or more of the following limitations are present:
Q is $CH_2$ or a direct bond;
G is O;
X is N or CH;
Z is NH or $CH_2$;
B is phenyl or heteroaryl;
$R_1$ and $R_2$ are independently selected from:

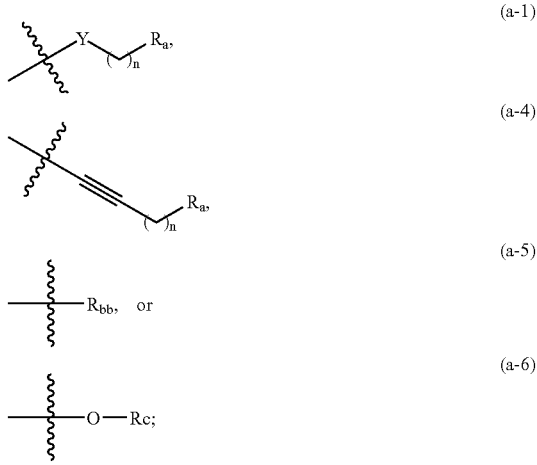

wherein n is 1, 2, 3 or 4;
Y is O or NH;
$R_a$ is alkoxy, heteroaryl optionally substituted with $R_5$, hydroxyl, alkylamino, dialkylamino, oxazolidinonyl optionally substituted with $R_5$, pyrrolidinonyl optionally substituted with $R_5$, piperidinonyl optionally substituted with $R_5$, piperazinyl-2-one optionally substituted with $R_5$, heterocyclyl optionally substituted with $R_5$, squaryl optionally substituted with $R_5$, —$CONR_wR_x$, —$N(R_y)CON(R_w)(R_x)$, —$N(R_w)C(O)OR_x$, —$N(R_w)COR_y$, —$SO_2R_y$, or —$NR_wSO_2R_y$;
$R_w$ and $R_x$ are independently selected from: hydrogen, alkyl, alkenyl, aralkyl, or heteroaralkyl, or $R_w$ and $R_x$ may optionally be taken together to form a 5 to 7 membered ring, optionally containing a heteromoiety selected from O, NH, N(alkyl), SO, $SO_2$, or S;
$R_y$ is selected from: hydrogen, alkyl, alkenyl, cycloalkyl, phenyl, aralkyl, heteroaralkyl, or heteroaryl;
$R_5$ is one or two substituents selected from: —C(O)alkyl, —$SO_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, or —C(O) C$_{(1-4)}$alkyl-OCH$_3$,; provided that the same $R_5$ substituent is not present more than once, unless said $R_5$ substituent is alkyl;
$R_{bb}$ is hydrogen, halogen, alkoxy, piperazinyl-2-one optionally substituted with $R_6$, imidazolidinyl-2-one optionally substituted with $R_6$, oxazolidinyl-2-one optionally substituted with $R_6$, or heterocyclyl optionally substituted with $R_6$;
$R_6$ is one or two substituents independently selected from: halogen, hydroxyl, heteroaryl, alkoxy, —C(O)alkyl, —SO₂alkyl, —C(O)NH(alkyl), —C(O)N(alkyl)₂, —C(O)C₍₁₋₄₎alkyl-N(alkyl)₂, alkyl, —C₍₁₋₄₎alkyl-OH, —C₍₁₋₄₎alkyl-OCH₃, —C(O)C₍₁₋₄₎alkyl-OH, or —C(O)C₍₁₋₄₎alkyl-OCH₃; provided that the same R₆ substituent is not present more than once, unless said R₆ substituent is halogen, hydroxyl, or alkyl;

R_c is heterocyclyl optionally substituted with R₇;

R₇ is one substituent selected from: hydroxyl, —C(O)alkyl, —SO₂alkyl, alkyl, or —C(O)N(alkyl)₂; and R₃ is one or more substituents independently selected from: alkyl, alkoxy, halogen, cycloalkyl optionally substituted with R₄, heteroaryl optionally substituted with R₄, heterocyclyl optionally substituted with R₄, alkoxyether, —O(cycloalkyl), phenoxy optionally substituted with R₄, dialkylamino, or —SO₂alkyl; wherein R₄ is independently selected from: halogen, cyano, trifluoromethyl, amino, hydroxyl, alkoxy, —C(O)alkyl, —CO₂alkyl, —SO₂alkyl, —C(O)N(alkyl)₂, alkyl, or alkylamino.

Most particularly preferred embodiments of the invention are compounds of Formula I wherein one or more of the following limitations are present:

Q is a direct bond;
G is O;
X is N;
Z is NH;
B is phenyl, pyrimidinyl, or pyridinyl;
R₁ and R₂ are independently selected from:

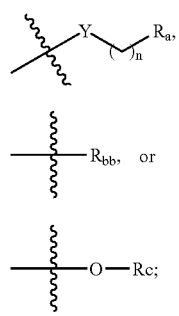

(a-1)

(a-5)

(a-6)

wherein n is 1, 2, 3 or 4;
Y is O;
R_a is alkoxy, heteroaryl optionally substituted with R₅, hydroxyl, alkylamino, dialkylamino, oxazolidinonyl optionally substituted with R₅, pyrrolidinonyl optionally substituted with R₅, piperazinyl-2-one optionally substituted with R₅, heterocyclyl optionally substituted with R₅, —CONR_wR_x, —N(R_y)CON(R_w)(R_x), —SO₂R_y, or —NR_wSO₂R_y;
R_w and R_x are independently selected from: hydrogen, alkyl, alkenyl, aralkyl, or heteroaralkyl, or R_w and R_x may optionally be taken together to form a 5 to 7 membered ring, optionally containing a heteromoiety selected from O, NH, N(alkyl), SO, SO₂, or S;
R_y is selected from: hydrogen, alkyl, alkenyl, cycloalkyl, phenyl, aralkyl, heteroaralkyl, or heteroaryl; and
R₅ is one substituent selected from: —C(O)alkyl, —SO₂alkyl, —C(O)NH(alkyl), —C(O)N(alkyl)₂, —C(O)C₁₋₄alkyl-N(alkyl)₂, alkyl, —C₍₁₋₄₎alkyl-OH, —C₍₁₋₄₎alkyl-OCH₃, —C(O)C₍₁₋₄₎alkyl-OH, or —C(O)C₍₁₋₄₎alkyl-OCH₃;
R_bb is hydrogen, halogen, alkoxy, piperazinyl-2-one optionally substituted with R₆, imidazolidinyl-2-one optionally substituted with R₆, oxazolidinyl-2-one optionally substituted with R₆, or heterocyclyl optionally substituted with R₆; and R₆ is one substituent selected from: hydroxyl, alkoxy, —C(O)alkyl, —SO₂alkyl, —C(O)NH(alkyl), —C(O)N(alkyl)₂, —C(O)C₁₋₄alkyl-N(alkyl)₂, alkyl, —C₍₁₋₄₎alkyl-OH, —C₍₁₋₄₎alkyl-OCH₃, —C(O)C₍₁₋₄₎alkyl-OH, or —C(O)C₍₁₋₄₎alkyl-OCH₃;

R_c is heterocyclyl optionally substituted with R₇;

R₇ is one substituent selected from —C(O)alkyl, —SO₂alkyl, or alkyl; and

R₃ is one substituent independently selected from: alkyl, alkoxy, cycloalkyl, heterocyclyl, —O(cycloalkyl), or dialkylamino.

Pharmaceutically Acceptably Salts

The compounds of the present invention may also be present in the form of pharmaceutically acceptable salts.

For use in medicines, the salts of the compounds of this invention refer to non-toxic "pharmaceutically acceptable salts." FDA approved pharmaceutically acceptable salt forms (Ref. International J. Pharm. 1986, 33, 201-217; J. Pharm. Sci., 1977, January, 66(1), p 1) include pharmaceutically acceptable acidic/anionic or basic/cationic salts.

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, NH₃, NH₄OH, N-methyl-D-glucamine, piperidine, potassium, potassium-t-butoxide, potassium hydroxide (aqueous), procaine, quinine, sodium, sodium carbonate, sodium-2-ethylhexanoate (SEH), sodium hydroxide, triethanolamine (TEA) or zinc.

Prodrugs

The present invention includes within its scope prodrugs of the compounds of the invention. In general, such prodrugs will be functional derivatives of the compounds which are readily convertible in vivo into an active compound. Thus, in the methods of treatment of the present invention, the term "administering" shall encompass the means for treating, ameliorating or preventing a syndrome, disorder or disease described herein with a compound specifically disclosed or a compound, or prodrug thereof, which would obviously be included within the scope of the invention albeit not specifically disclosed for certain of the instant compounds. Conventional procedures for the selection and preparation of suitable prodrug derivatives are described in, for example, "*Design of Prodrugs*", ed. H. Bundgaard, Elsevier, 1985.

Stereochemical Isomers

One skilled in the art will recognize that the compounds of Formula I may have one or more asymmetric carbon atoms in their structure. It is intended that the present invention include within its scope single enantiomer forms of the compounds, racemic mixtures, and mixtures of enantiomers in which an enantiomeric excess is present.

The term "single enantiomer" as used herein defines all the possible homochiral forms which the compounds of Formula I and their N-oxides, addition salts, quaternary amines or physiologically functional derivatives may possess.

Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (enantiomers).

The term "stereoisomer" refers to isomers of identical constitution that differ in the arrangement of their atoms in space. Enantiomers and diastereomers are examples of stereoisomers.

The term "chiral" refers to the structural characteristic of a molecule that makes it impossible to superimpose it on its mirror image.

The term "enantiomer" refers to one of a pair of molecular species that are mirror images of each other and are not superimposable.

The term "diastereomer" refers to stereoisomers that are not mirror images.

The symbols "R" and "S" represent the configuration of substituents around a chiral carbon atom(s).

The term "racemate" or "racemic mixture" refers to a composition composed of equimolar quantities of two enantiomeric species, wherein the composition is devoid of optical activity.

The term "homochiral" refers to a state of enantiomeric purity.

The term "optical activity" refers to the degree to which a homochiral molecule or nonracemic mixture of chiral molecules rotates a plane of polarized light.

The term "geometric isomer" refers to isomers that differ in the orientation of substituent atoms in relationship to a carbon-carbon double bond, to a cycloalkyl ring or to a bridged bicyclic system. Substituent atoms (other than H) on each side of a carbon-carbon double bond may be in an E or Z configuration. In the "E" (opposite sided) configuration, the substituents are on opposite sides in relationship to the carbon-carbon double bond; in the "Z" (same sided) configuration, the substituents are oriented on the same side in relationship to the carbon-carbon double bond. Substituent atoms (other than hydrogen) attached to a carbocyclic ring may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

It is to be understood that the various substituent stereoisomers, geometric isomers and mixtures thereof used to prepare compounds of the present invention are either commercially available, can be prepared synthetically from commercially available starting materials or can be prepared as isomeric mixtures and then obtained as resolved isomers using techniques well-known to those of ordinary skill in the art.

The isomeric descriptors "R," "S," "E," "Z," "cis," and "trans" are used as described herein for indicating atom configuration(s) relative to a core molecule and are intended to be used as defined in the literature (IUPAC Recommendations for Fundamental Stereochemistry (Section E), *Pure Appl. Chem.*, 1976, 45:13-30).

The compounds of the present invention may be prepared as individual isomers by either isomer-specific synthesis or resolved from an isomeric mixture. Conventional resolution techniques include forming the free base of each isomer of an isomeric pair using an optically active salt (followed by fractional crystallization and regeneration of the free base), forming an ester or amide of each of the isomers of an isomeric pair (followed by chromatographic separation and removal of the chiral auxiliary) or resolving an isomeric mixture of either a starting material or a final product using preparative TLC (thin layer chromatography) or a chiral HPLC column.

Polymorphs and Solvates

Furthermore, compounds of the present invention may have one or more polymorph or amorphous crystalline forms and as such are intended to be included in the scope of the invention. In addition, some of the compounds may form solvates, for example with water (i.e., hydrates) or common organic solvents. As used herein, the term "solvate" means a physical association of a compound of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like. It is intended that the present invention include within its scope solvates of the compounds of the present invention. Thus, in the methods of treatment of the present invention, the term "administering" shall encompass the means for treating, ameliorating or preventing a syndrome, disorder or disease described herein with a compound specifically disclosed or a compound, or solvate thereof, which would obviously be included within the scope of the invention albeit not specifically disclosed for certain of the instant compounds.

N-Oxides

The compounds of Formula I may be converted to the corresponding N-oxide forms following art-known procedures for converting a trivalent nitrogen into its N-oxide form. Said N-oxidation reaction may generally be carried out by reacting the starting material of Formula I with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tbutyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Tautomeric Forms

Some of the compounds of Formula I may also exist in their tautomeric forms. Such forms although not explicitly indicated in the present application are intended to be included within the scope of the present invention.

Preparation of Compounds of the Present Invention

During any of the processes for preparation of the compounds of the present invention, it may be necessary and/or desirable to protect sensitive or reactive groups on any of the molecules concerned. This may be achieved by means of conventional protecting groups, such as those described in *Protecting Groups*, P. Kocienski, Thieme Medical Publishers, 2000; and T. W. Greene & P. G. M. Wuts, *Protective Groups in Organic Synthesis*, 3$^{rd}$ ed. Wiley Interscience, 1999. The protecting groups may be removed at a convenient subsequent stage using methods known in the art.

General Reaction Scheme

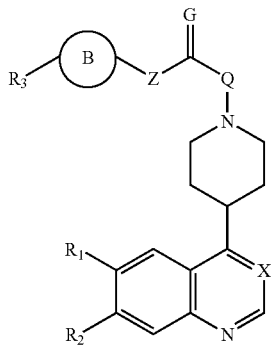

I

Compounds of formula I can be prepared by methods known to those who are skilled in the art. The following reaction schemes are only meant to represent examples of the invention and are in no way meant to be a limit of the invention.

The compounds of formula I, wherein X, B, G, Q, Z, $R_1$, $R_2$, and $R_3$ are as defined in Formula I, may be synthesized as outlined by the general synthetic route illustrated in Scheme 1. In the first step, treatment of a piperidinyl ester II with a strong base such as lithium hexamethyldisilazide in solvent such as tetrahydrofuran (THF) followed by addition of an appropriate chloroquinazoline/quinoline III at a temperature of −78° C. to 25° C. can provide the substituted piperidine IV. Treatment of IV to decarboxylation conditions, such as LiCl in DMSO/$H_2O$ at a temperature of 100° C. to 200° C. or KOH in MeOH at a temperature of 25° C. to 200° C., followed by deprotection of the amine protecting group (PG) under standard conditions known to those skilled in the art can provide piperidine V. The final step can involve reaction of piperidine V with an appropriate acylating/alkylating reagent VI, wherein LG may be an appropriate leaving group such as Br, Cl, I, imidazole, or p-nitrophenoxy, to provide the desired final product I. These reactions are generally performed in the presence of a solvent, such as methylene chloride, and a base, such as diisopropylethylamine, at a temperature of 0° C. to 150° C., preferably from 0° C.-25° C. The 4-chloroquinazolines or quinolines III are either commercially available or can be prepared as outlined in Scheme 5. The acylating reagents VI are either commercially available or, wherein Q is a direct bond and Z is NH or N(alkyl), can be prepared as illustrated in Scheme 1. Treatment of an appropriate $R_3$BZH, wherein Z is NH or N(alkyl), with an appropriate acylating reagent such as carbonyldiimidazole, thiophosgene, or p-nitrophenylchloroformate in the presence of a base such as triethylamine can provide VI. Many $R_3$BZH reagents are either commercially available or can be prepared by a number of known methods (e.g. *Tet Lett* 1995, 36, 2411-2414).

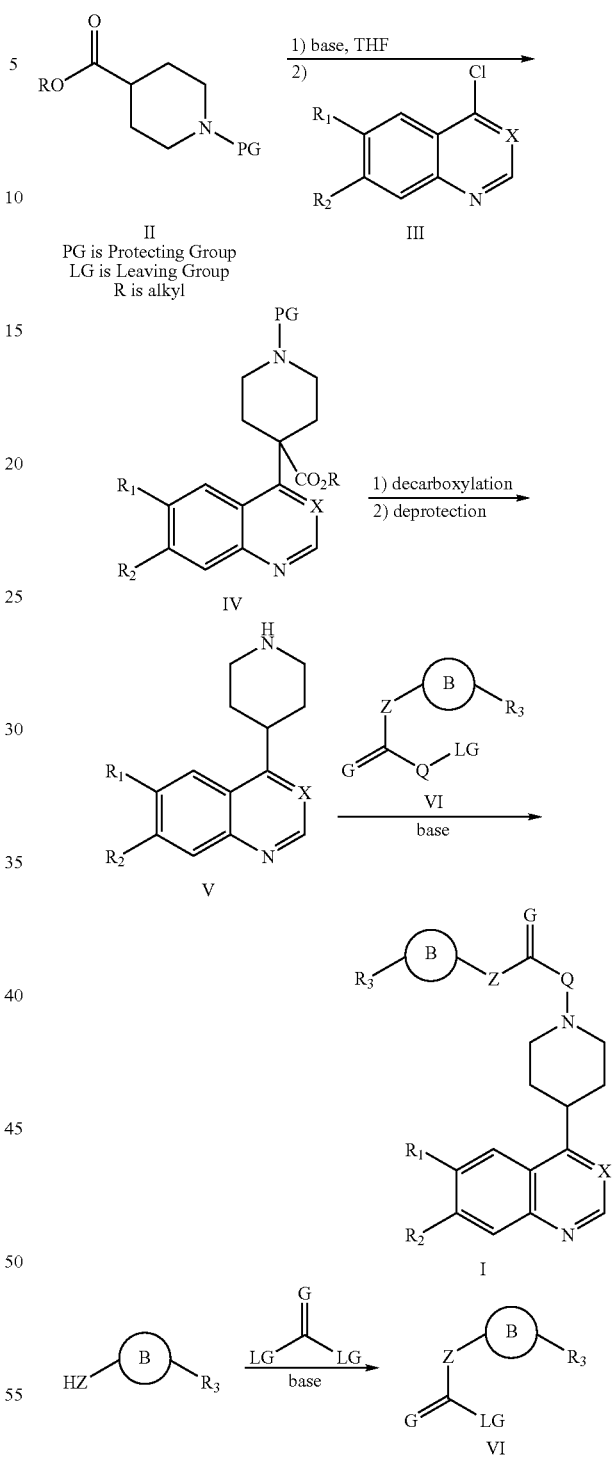

An alternative method to prepare the piperidine intermediate V, wherein X is N and $R_1$ and $R_2$ are defined as in Formula I, is illustrated in Scheme 2. Treatment of isonipecotic acid with an appropriate amino protecting group can provide the N-protected piperidine VII. Transformation of the carboxylic acid to the primary amide and subsequent dehydration under standard conditions can provide the cyano piperidine VIII. Treatment of piperidine VIII with an appropriate aniline IX utilizing a Friedel Crafts reaction with a Lewis acid, such as BF$_3$·Et$_2$O, can provide the substituted aniline X. Formation of the quinazoline ring can be accomplished by treating aniline X with a reagent such as formamide at a temperature of 100° C. to 200° C. and subsequent deprotection of the amino protecting group under standard conditions can provide the desired piperidine V.

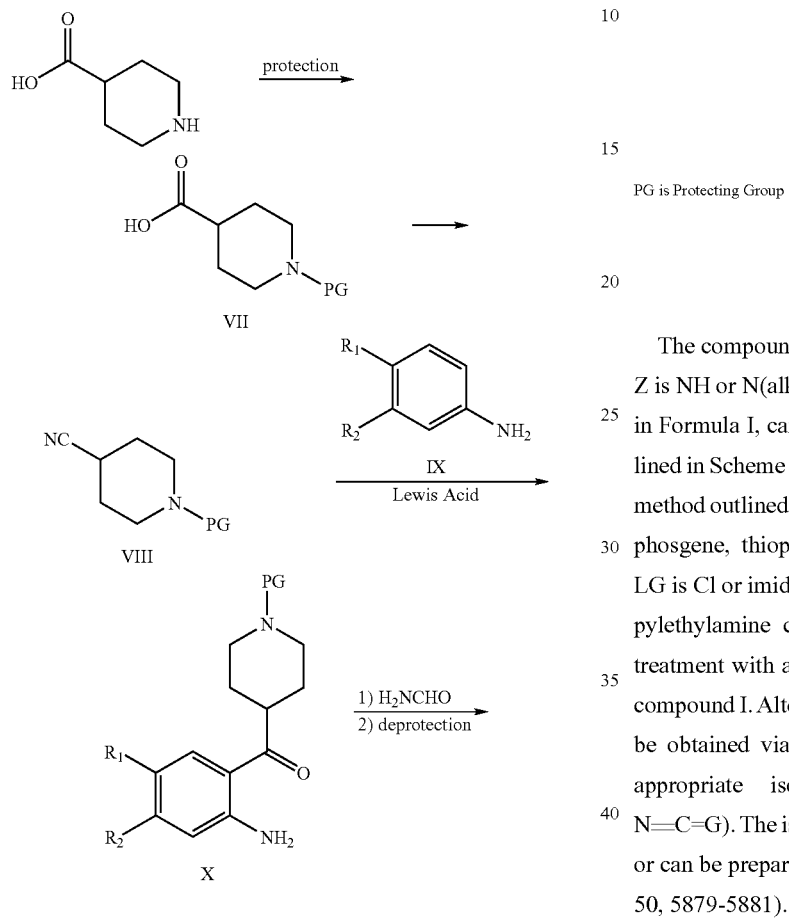

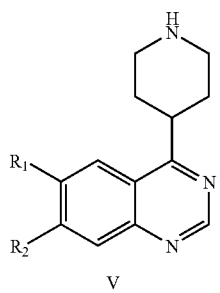

PG is Protecting Group

The compounds of Formula I, wherein Q is a direct bond, Z is NH or N(alkyl), and G, X, R$_1$, R$_2$, and R$_3$ are defined as in Formula I, can be prepared by the reaction sequence outlined in Scheme 3. Treatment of piperidine V, prepared by the method outlined in Scheme 1, with an acylating agent such as phosgene, thiophosgene, or carbonyldiimidazole, wherein LG is Cl or imidazole, and an organic base such as diisopropylethylamine can provide intermediate XI, which upon treatment with an appropriate R$_3$BZH can provide the final compound I. Alternatively compound I, wherein Z is NH, can be obtained via direct treatment of piperidine V with an appropriate isocyanate or isothiocyanate (R$_3$—B—N=C=G). The isocyanates are either commercially available or can be prepared by a known method (*J. Org Chem,* 1985, 50, 5879-5881).

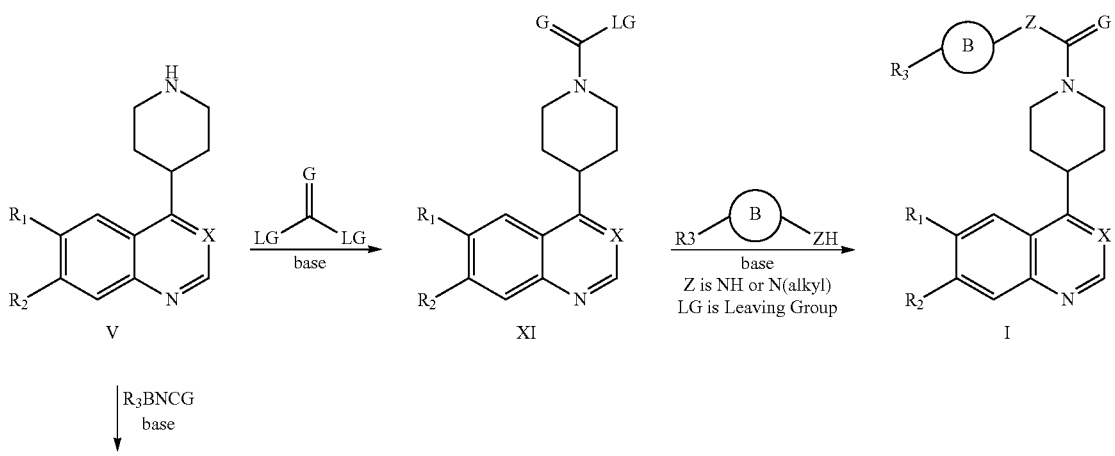

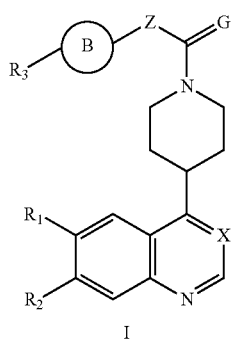

I

The compounds of Formula I, where Q is a direct bond, B is phenyl or heteroaryl, G is O, Z is NH or N(alkyl), $R_3$ is phenyl or heteroaryl, and X, $R_1$, and $R_2$ are defined as in Formula I, can be prepared by the reaction sequence outlined in Scheme 4. Treatment of a piperidine V, which can be prepared as described in Scheme 1, with an appropriate iodoarylamide acylating agent XII, wherein LG is an appropriate leaving group, for instance, bromide, chloride, or p-nitrophenoxide, can provide the iodoaryl XIII. Reaction of iodoaryl XIII with an appropriate aryl boronic acid or aryl boronic ester (R is H or alkyl) in the presence of a palladium catalyst such as bis(triphenylphosphine)palladium dichloride in a solvent such as toluene at a temperature of 50° C. to 200° C. can provide the final product I. The iodoaryl acylating agents are either commercially available or prepared as outlined in Scheme 1 while the boronic acids/boronic esters are either commercially available or prepared by known methods (*Synthesis* 2003, 4, 469-483; *Organic letters* 2001, 3, 1435-1437).

Scheme 4

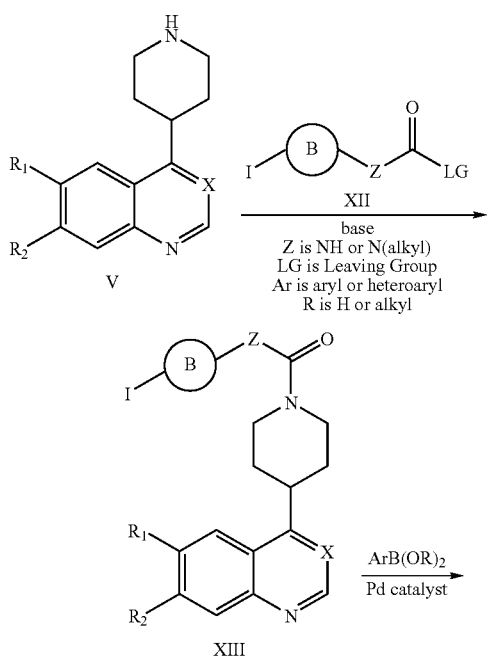

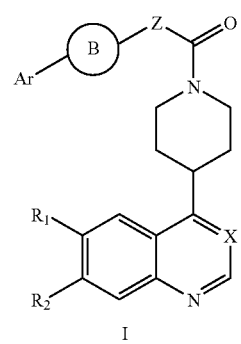

I

Preparation of an appropriate chloroquinazoline III can be accomplished by the reaction sequence illustrated in Scheme 5. Starting from a corresponding anthranilic acid XIV, treatment with a reagent such as formamidine acetate in a solvent such as ethanol can provide quinazolone XV. Subsequent treatment of XV with a chlorinating agent, such as oxalyl chloride in DMF in a solvent such as dichloroethane, can provide the desired chloroquinazoline III. The anthranilic acids are either commercially available or can prepared by known methods (WO9728118).

Scheme 5

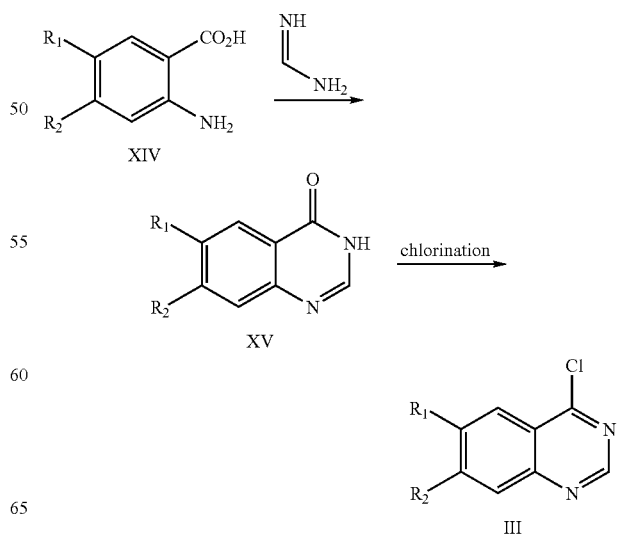

Compounds of Formula I, wherein $R_1$ is —CC(CH$_2$)$_n$R$_a$, G is O, and X, B, Q, Z, R$_a$, R$_2$, and R$_3$ are defined as in Formula I, can be prepared by the sequence outlined in Scheme 6. Treatment of the appropriate iodo substituted piperidine V, which can be prepared as described in Scheme 1, with an appropriate reagent VI can provide the iodoaryl intermediate XVI. Reaction of XVI with an appropriate alkynyl alcohol in the presence of a palladium catalyst such as bis(triphenylphosphine)palladium dichloride, a copper catalyst such as copper(I) iodide, a base such as diethyl amine and a solvent such as dimethylformamide at a temperature of 25° C. to 150° C. can provide the alkynyl alcohol XVII. Conversion of the alcohol XVII to an appropriate leaving group known by those skilled in the art such as a mesylate followed by an SN$_2$ displacement reaction of XVIII with an appropriate nucleophilic heterocycle, heteroaryl, amine, alcohol, sulfonamide, or thiol can provide the final compound I. If R$_a$ nucleophile is a thiol, further oxidation of the thiol can provide the corresponding sulfoxides and sulfones. If R$_a$ nucleophile is an amino, acylation of the nitrogen with an appropriate acylating or sulfonylating agent can provide the corresponding amides, carbamates, ureas, and sulfonamides. If the desired R$_a$ is COOR$_y$ or CONR$_w$R$_x$, these can be derived from the corresponding hydroxyl group. Oxidation of the hydroxyl group to the acid followed by ester or amide formation under conditions known in the art can provide examples wherein R$_a$ is COOR$_y$ or CONR$_w$R$_x$. One could prepare the compounds where R$_2$ is —CC(CH$_2$)$_n$R$_a$ utilizing the same reaction sequence with the appropriate 7-iodoaryl quinazoline or quinoline.

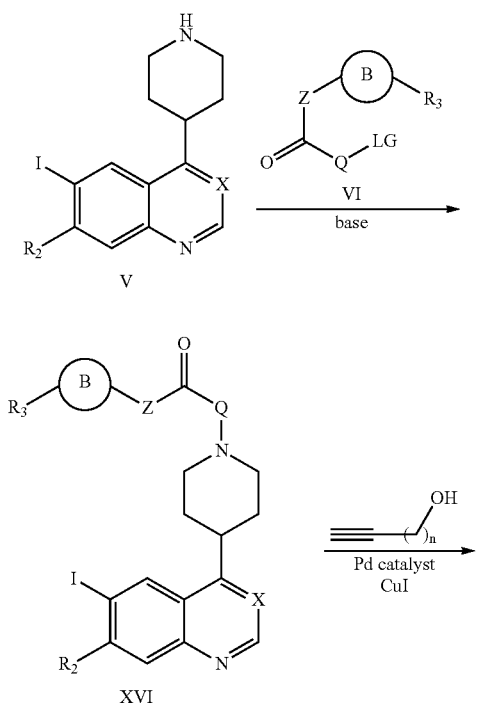

Scheme 6

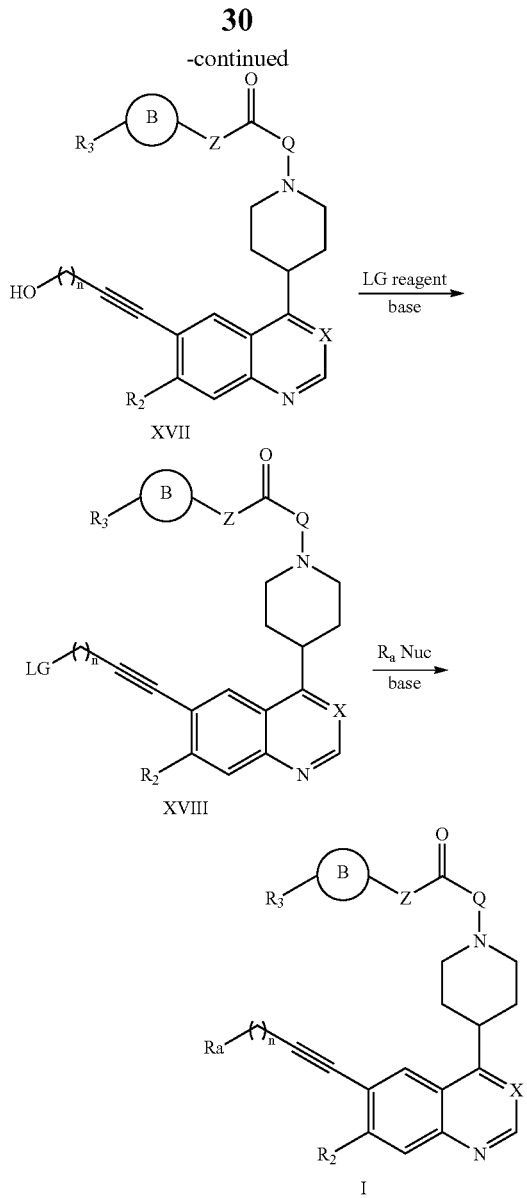

LG is Leaving Group
Nuc is a nucleophile

Compounds of Formula I, wherein $R_1$ is phenyl or heteroaryl, G is O, and X, B, Q, Z, R$_2$, and R$_3$ are defined as in Formula I, can also be prepared as outlined in Scheme 7. Treatment of compound XIX, which can be prepared by decarboxylation of previously described compound IV, with an appropriate aryl boronic acid or aryl boronic ester (R is H or alkyl) in the presence of a palladium catalyst such as bis(triphenylphosphine)palladium dichloride in a solvent such as toluene at a temperature of 50° C. to 200° C. can provide aryl intermediate XX. Deprotection of the amine protecting group known to those skilled in the art under standard conditions can provide the piperidine XXI, which can then be acylated or alkylated using reagent VI to provide the final compound I. The boronic acids/boronic esters are either commercially available or prepared by known methods (*Synthesis* 2003, 4, 469-483; *Organic letters* 2001, 3, 1435-1437). One could prepare the compounds where R$_2$ is phenyl or heteroaryl utilizing the same reaction sequence with the appropriate 7-iodo quinazoline or quinoline.

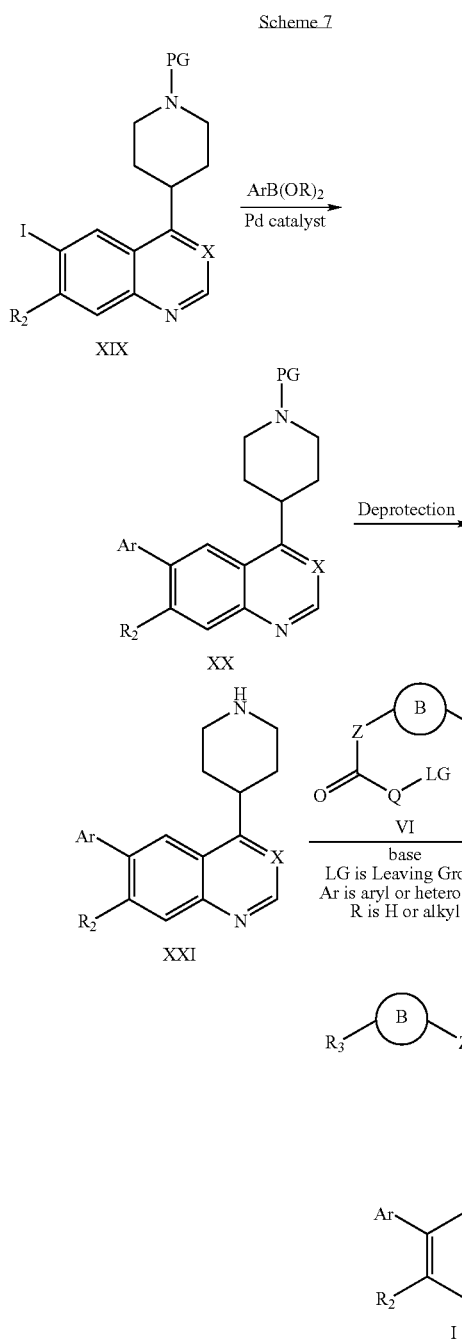

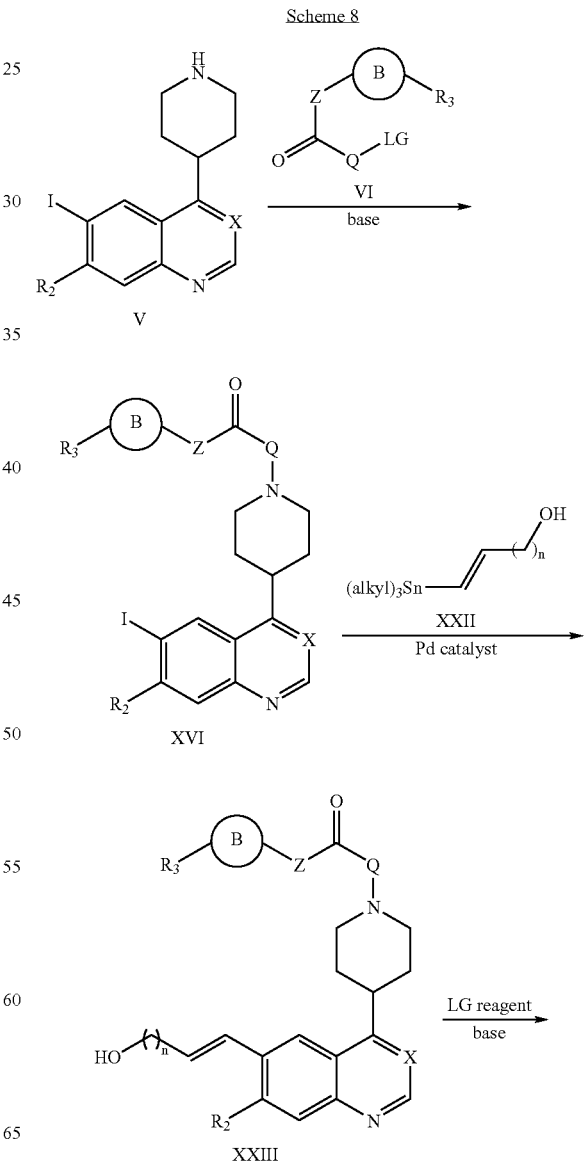

philic heterocycle, heteroaryl, amine, alcohol, sulfonamide, or thiol can provide the final compound I. If $R_a$ nucleophile is a thiol, further oxidation of the thiol can provide the corresponding sulfoxides and sulfones. If $R_a$ nucleophile is an amino, acylation of the nitrogen with an appropriate acylating or sulfonylating agent can provide the corresponding amides, carbamates, ureas, and sulfonamides. If the desired $R_a$ is $COOR_y$ or $CONR_wR_x$, these can be derived from the corresponding hydroxyl group. Oxidation of the hydroxyl group to the acid followed by ester or amide formation under conditions known in the art can provide examples wherein $R_a$ is $COOR_y$ or $CONR_wR_x$. The corresponding cis olefin isomers of Formula I can be prepared by the same method utilizing the appropriate cis vinyl stannane. Reduction of the olefin moiety under known conditions can provide the saturated compounds where $R_1$ is —$CH_2CH_2(CH_2)_nR_a$. One could prepare the compounds where $R_2$ is —$CHCH(CH_2)_nR_a$ utilizing the same reaction sequence with the appropriate 7-iodo quinazoline or quinoline.

Compounds of formula I, wherein $R_1$ is —$CHCH(CH_2)_n$ $R_a$, G is O, and X, B, Q, Z, $R_a$, $R_2$, and $R_3$ are defined as in Formula I, can be prepared by the sequence outlined in Scheme 8. Treatment of the appropriate iodo substituted piperidine V, which can be prepared as described in Scheme 1, with an appropriate reagent VI can provide the iodoaryl intermediate XVI. Reaction of XVI with an appropriate vinylstannane XXII in the presence of a palladium catalyst such as bis(triphenylphosphine)palladium dichloride and a solvent such as dimethylformamide at a temperature of 25° C. to 150° C. can provide the alkenyl alcohol XXIII. Conversion of the alcohol XXIII to an appropriate leaving group known by those skilled in the art such as a mesylate followed by an $SN_2$ displacement reaction of XXIV with an appropriate nucleo-

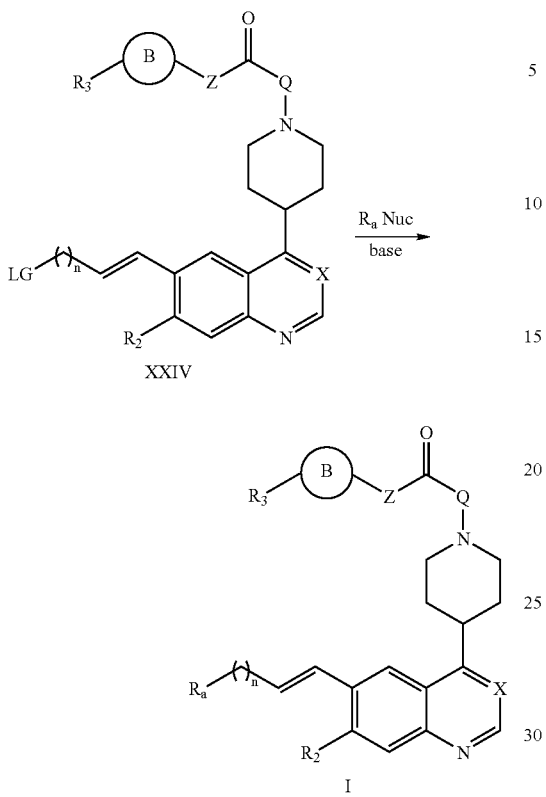

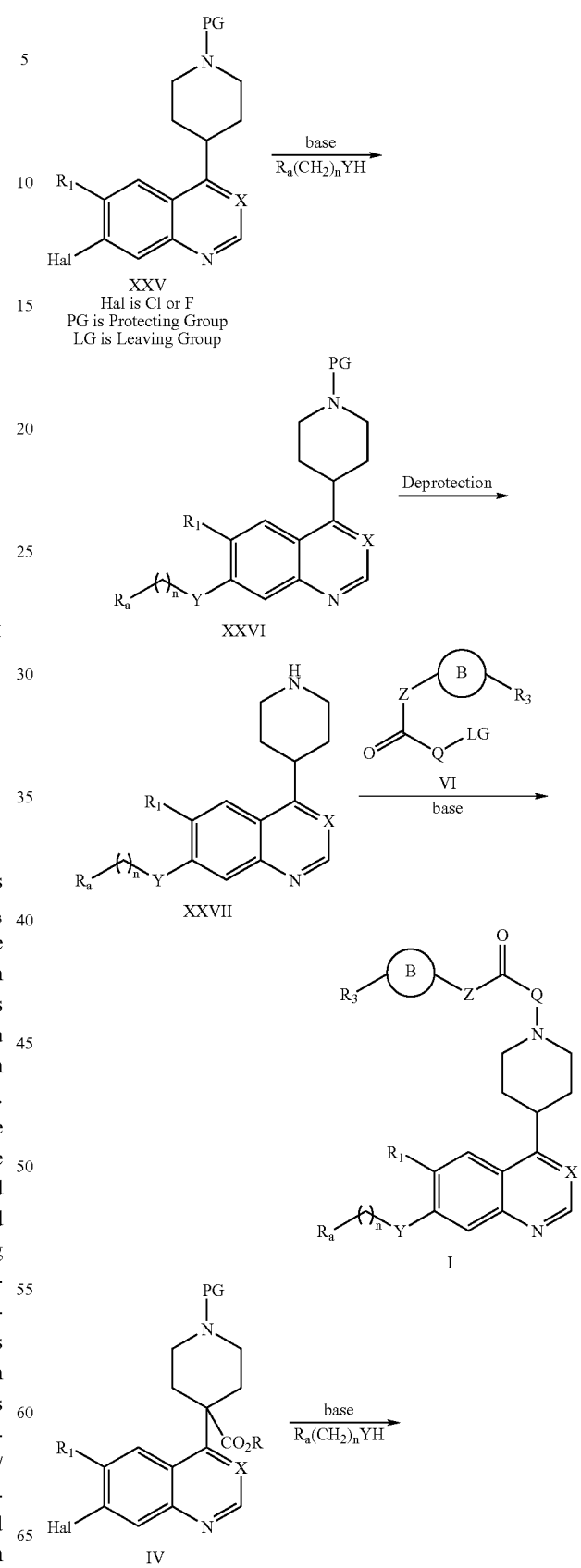

Scheme 9

Hal is Cl or F
PG is Protecting Group
LG is Leaving Group

Compounds of formula I wherein $R_2$ is —Y(CH$_2$)$_n$R$_a$, Y is O, S, NH, or N(alkyl), G is O, and X, B, Q, Z, R$_a$, R$_1$, and R$_3$ are defined as in Formula I, can be prepared by the sequence outlined in Scheme 9. Treatment of compound XXV, which can be prepared as described in Scheme 1, with a base such as hydroxide ion or potassium t-butoxide in the presence of a suitable R$_a$(CH$_2$)$_n$YH at a temperature of 25° C. to 150° C. in a solvent such as THF can provide the substituted XXVI. Deprotection of the amine protecting group known to those skilled in the art under standard conditions can provide the piperidine XXVII, which can then be acylated or alkylated using reagent VI to provide the final compound I. One could prepare the compounds where R$_1$ is —Y(CH$_2$)$_n$R$_a$ utilizing the same reaction sequence with the appropriate 6-halogenated substituted quinazoline or quinoline. A related synthetic route to intermediate quinazoline/quinoline XXVI is also outlined in Scheme 9. Treatment of compound IV, which can be prepared as described in Scheme 1, with a base such as KOH in the presence of a suitable R$_a$(CH$_2$)$_n$YH at a temperature of 25° C. to 150° C. in a solvent mixture such as dioxane/water, can provide the substituted intermediate XXVI. Compounds of formula I where R$_2$ is —OR$_c$ or R$_{bb}$ can be prepared by the same reaction sequence outlined in Scheme 9 using an appropriate —OR$_c$ or R$_{bb}$ in the SnAr step.

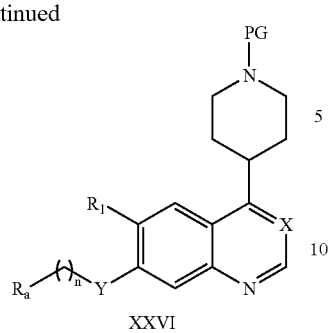

XXVI

An alternative method to prepare compounds of Formula I, wherein $R_2$ is —Y(CH$_2$)$_n$R$_a$, Y is O, S, NH, or N(alkyl), G is O, and X, B, Q, Z, R$_a$, R$_1$, and R$_3$ are defined as in Formula I, can be prepared by the sequence outlined in Scheme 10. Treatment of compound XXV, which can be prepared as described in Scheme 1, with a base such as hydroxide ion or potassium t-butoxide in the presence of a suitable PG$_1$O (CH$_2$)$_n$YH, where PG$_1$ is an appropriate alcohol protecting group, at a temperature of 25° C. to 150° C. in a solvent such as THF can provide the substituted XXVIII. Deprotection of the PG$_1$ group known to those skilled in the art under standard conditions can provide intermediate XXIX. Conversion of the alcohol XXIX to an appropriate leaving group known by those skilled in the art such as a mesylate followed by an SN$_2$ displacement reaction of XXX with an appropriate nucleophilic heterocycle, heteroaryl, amine, alcohol, sulfonamide, or thiol can provide compound XXXI. If R$_a$ nucleophile is a thiol, further oxidation of the thiol can provide the corresponding sulfoxides and sulfones. If R$_a$ nucleophile is an amino, acylation of the nitrogen with an appropriate acylating or sulfonylating agent can provide the corresponding amides, carbamates, ureas, and sulfonamides. If the desired R$_a$ is COOR$_y$ or CONR$_w$R$_x$, these can be derived from the corresponding hydroxyl group. Oxidation of the hydroxyl group to the acid followed by ester or amide formation under conditions known in the art can provide examples wherein R$_a$ is COOR$_y$ or CONR$_w$R$_x$. Deprotection of the amine protecting group known to those skilled in the art under standard conditions can provide the piperidine XXXII, which can then be acylated or alkylated using reagent VI to provide the final compound I. One could prepare the compounds where R$_1$ is —Y(CH$_2$)$_n$R$_a$ utilizing the same reaction sequence with the appropriate 6-halogenated substituted quinazoline or quinoline.

Scheme 10

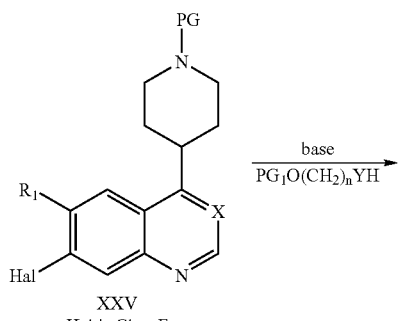

XXV
Hal is Cl or F
PG and PG$_1$ are Protecting Group
LG is Leaving Group

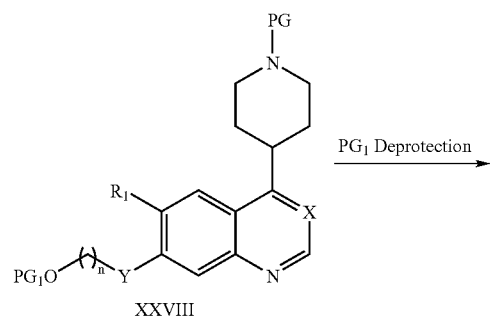

XXVIII

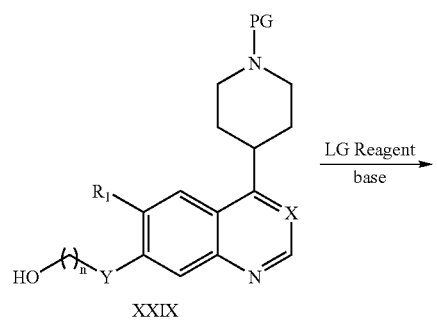

XXIX

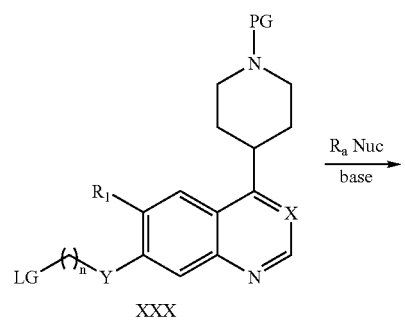

XXX

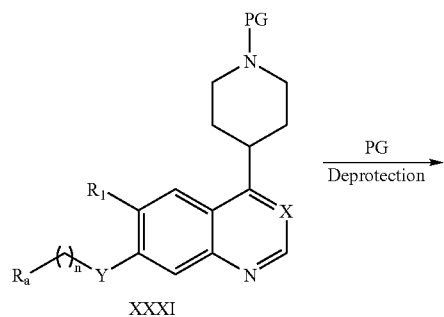

XXXI

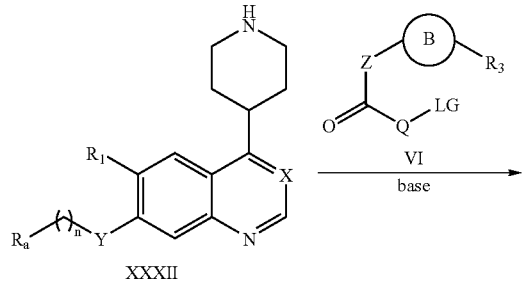

XXXII

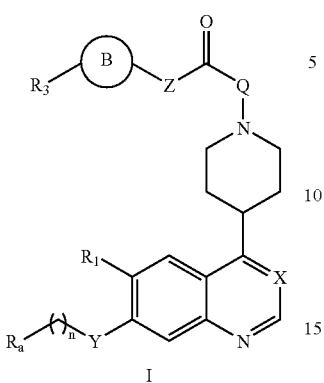

I

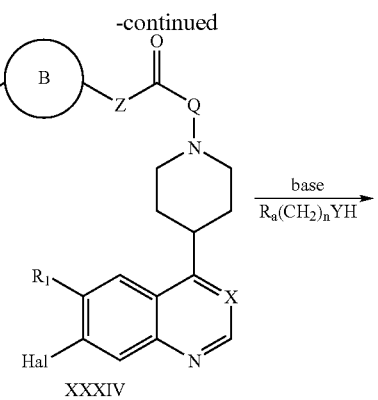

XXXIV

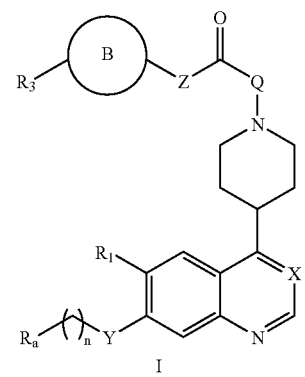

I

Hal is Cl or F
PG is Protecting Group
LG is Leaving Group

An alternative method to prepare compounds of Formula I, wherein $R_2$ is —Y(CH$_2$)$_n$R$_a$, Y is O, S, NH, or N(alkyl), G is O, and X, B, Q, Z, $R_a$, $R_1$, and $R_3$ are defined as in Formula I, can be prepared by the sequence outlined in Scheme 11. Removal of the amine protecting group known to those skilled in the art under standard conditions of compound XXV, which can be prepared as described in Scheme 1, can provide the piperidine XXXIII, which can then be acylated or alkylated using reagent VI to provide compound XXXIV. Treatment of XXXIV with a base such as hydroxide ion or potassium t-butoxide in the presence of a suitable $R_a$(CH$_2$)$_n$YH at a temperature of 25° C. to 150° C. in a solvent such as THF can provide the final compound I. One could prepare the compounds where $R_1$ is —Y(CH$_2$)$_n$R$_a$ utilizing the same reaction sequence with the appropriate 6-halogenated substituted quinazoline or quinoline.

Compounds of formula I wherein $R_1$ and $R_2$ are —Y(CH$_2$)$_n$R$_a$, Y is O, S, NH, or N(alkyl), G is O, and X, B, Q, Z, $R_a$, and $R_3$ are defined as in Formula I, can be prepared by the sequence outlined in Scheme 12. Treatment of compound XXXV, which can be prepared as described in Scheme 1, with a base such as hydroxide ion or potassium t-butoxide in the presence of a suitable $R_a$(CH$_2$)$_n$YH at a temperature of 25° C. to 150° C. in a solvent such as THF can provide the substituted XXXVI. A subsequent SnAr reaction of compound XXXVI with a base such as hydroxide ion or potassium t-butoxide in the presence of another $R_a$(CH$_2$)$_n$YH at a temperature of 25° C. to 150° C. in a solvent such as DMSO can provide the substituted XXXVII. Deprotection of the amine protecting group known to those skilled in the art under standard conditions can provide the piperidine XXXVIII, which can then be acylated or alkylated using reagent VI to provide the final compound I. One could also prepare compounds where $R_1$ is —OR$_c$ or with an appropriate $R_{bb}$ such as alkoxy using the same reaction sequence in Scheme 12.

Scheme 11

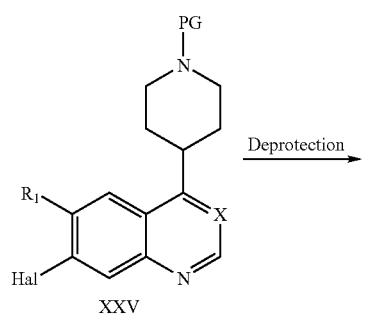

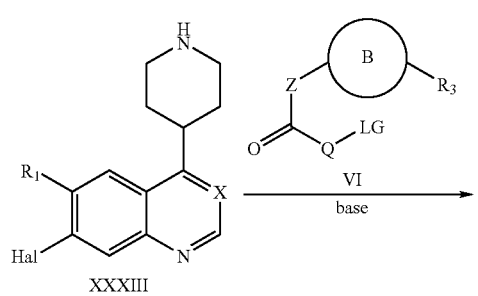

Scheme 12

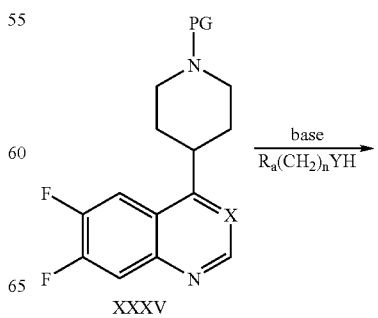

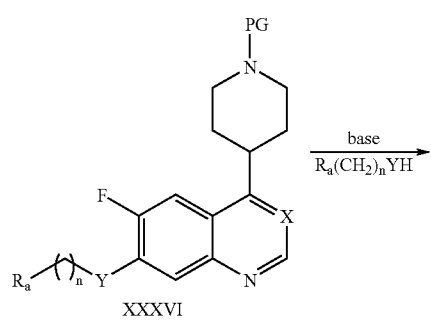

XXXVI

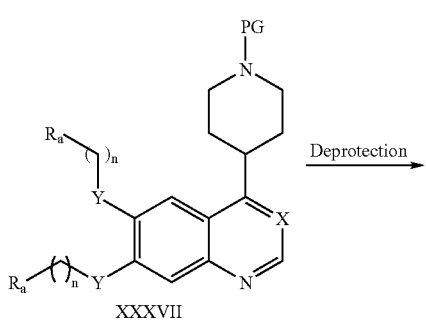

XXXVII

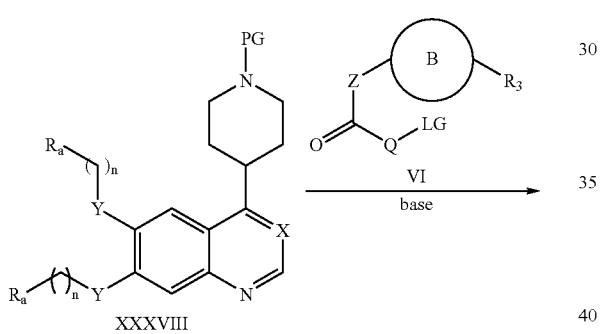

XXXVIII

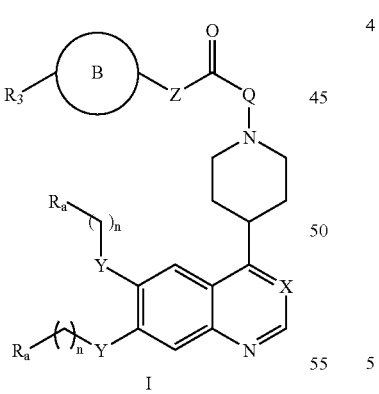

I

PG is Protecting Group

Representative Compounds

Representative compounds of the present invention synthesized by the afore-mentioned methods are presented below. Examples of the synthesis of specific compounds are presented thereafter. Preferred compounds are numbers 73, 74, 85, 152, 157, 158, 163, 178, 183, 197, 207, and 209; particularly preferred are numbers 73, 74, 157, 178, and 207.

| Entry | Compound |
|---|---|
| 1 | |
| 2 | |
| 3 | |
| 4 | |
| 5 | |

-continued
| Entry | Compound |
|---|---|
| 6 | 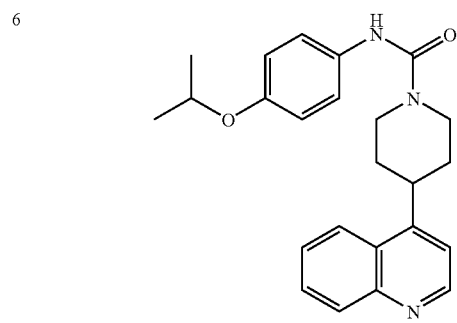 |
| 7 | 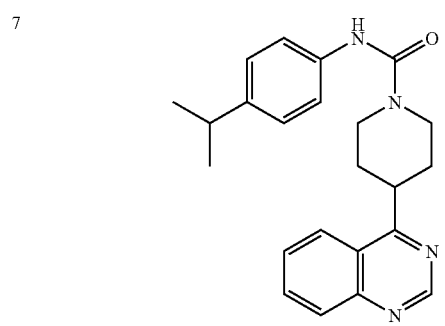 |
| 8 | 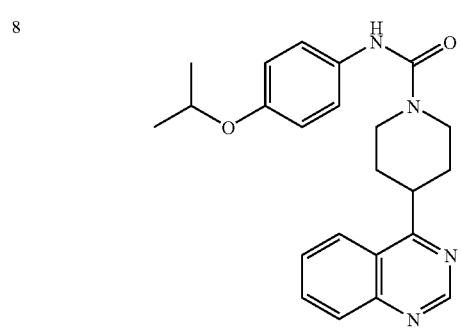 |
| 9 | 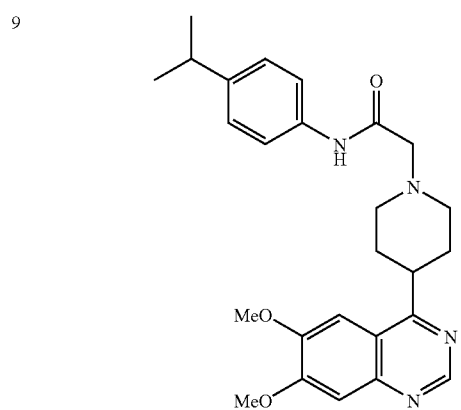 |
-continued
| Entry | Compound |
|---|---|
| 10 | 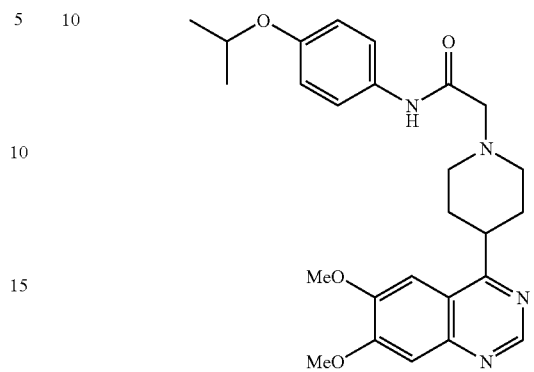 |
| 11 | 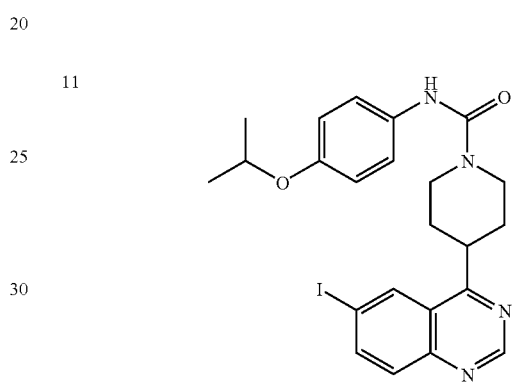 |
| 12 | 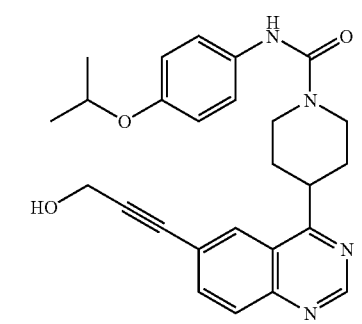 |
| 13 | 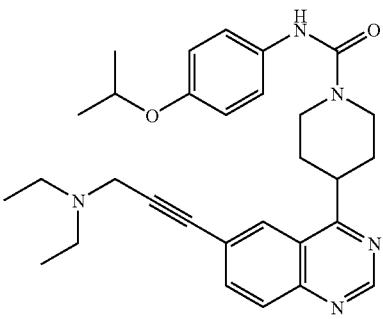 |

-continued

| Entry | Compound |
|---|---|
| 14 | (structure) |
| 15 | (structure) |
| 16 | (structure) |
| 17 | (structure) |

-continued

| Entry | Compound |
|---|---|
| 18 | (structure) |
| 19 | (structure) |
| 20 | (structure) |
| 21 | (structure) |
| 22 | (structure) |

-continued

| Entry | Compound |
|---|---|
| 23 | (structure) |
| 24 | (structure) |
| 25 | (structure) |
| 26 | (structure) |
| 27 | (structure) |
| 28 | (structure) |
| 29 | (structure) |
| 30 | (structure) |
| 31 | (structure) |

-continued
| Entry | Compound |
|---|---|
| 32 | 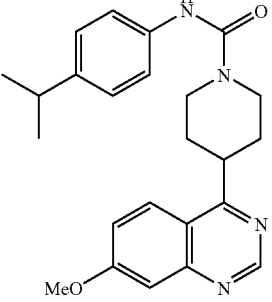 |
| 33 | 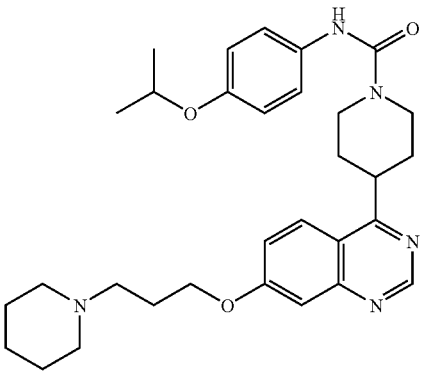 |
| 34 | 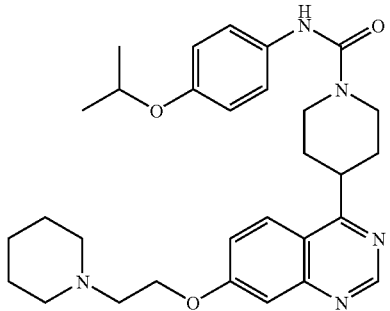 |
| 35 | 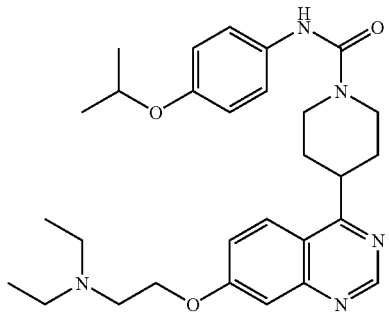 |
-continued
| Entry | Compound |
|---|---|
| 36 | 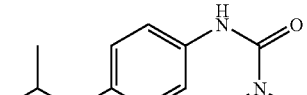 |
| 37 | 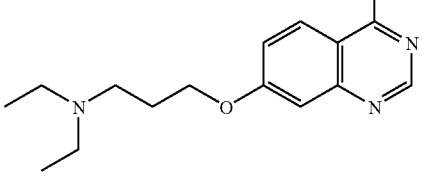 |
| 38 | 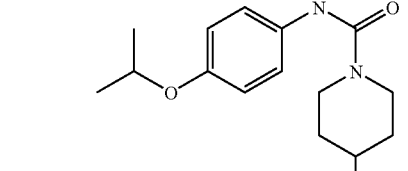 |
| 39 | 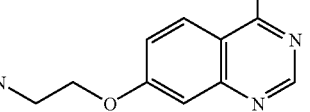 |

| Entry | Compound |
|---|---|
| 40 | 4-(6,7-dimethoxyquinazolin-4-yl)-N-(4-(2-methoxyethoxy)phenyl)piperidine-1-carboxamide |
| 41 | 4-(6,7-dimethoxyquinazolin-4-yl)-N-(4-methoxyphenyl)piperidine-1-carboxamide |
| 42 | N-cyclohexyl-4-(6,7-dimethoxyquinazolin-4-yl)piperidine-1-carboxamide |
| 43 | N-(4-butylphenyl)-4-(6,7-dimethoxyquinazolin-4-yl)piperidine-1-carboxamide |
| 44 | 4-(6,7-dimethoxyquinazolin-4-yl)-N-(4-ethoxyphenyl)piperidine-1-carboxamide |
| 45 | 4-(6,7-dimethoxyquinazolin-4-yl)-N-phenylpiperidine-1-carboxamide |
| 46 | 4-(6,7-dimethoxyquinazolin-4-yl)-N-(4-(trifluoromethyl)phenyl)piperidine-1-carboxamide |
| 47 | 4-(6,7-dimethoxyquinazolin-4-yl)-N-(4-phenoxyphenyl)piperidine-1-carboxamide |
| 48 | 4-(6,7-dimethoxyquinazolin-4-yl)-N-(p-tolyl)piperidine-1-carboxamide |

| Entry | Compound |
|---|---|
| 49 | |
| 50 | |
| 51 | |
| 52 | |
| 53 | |
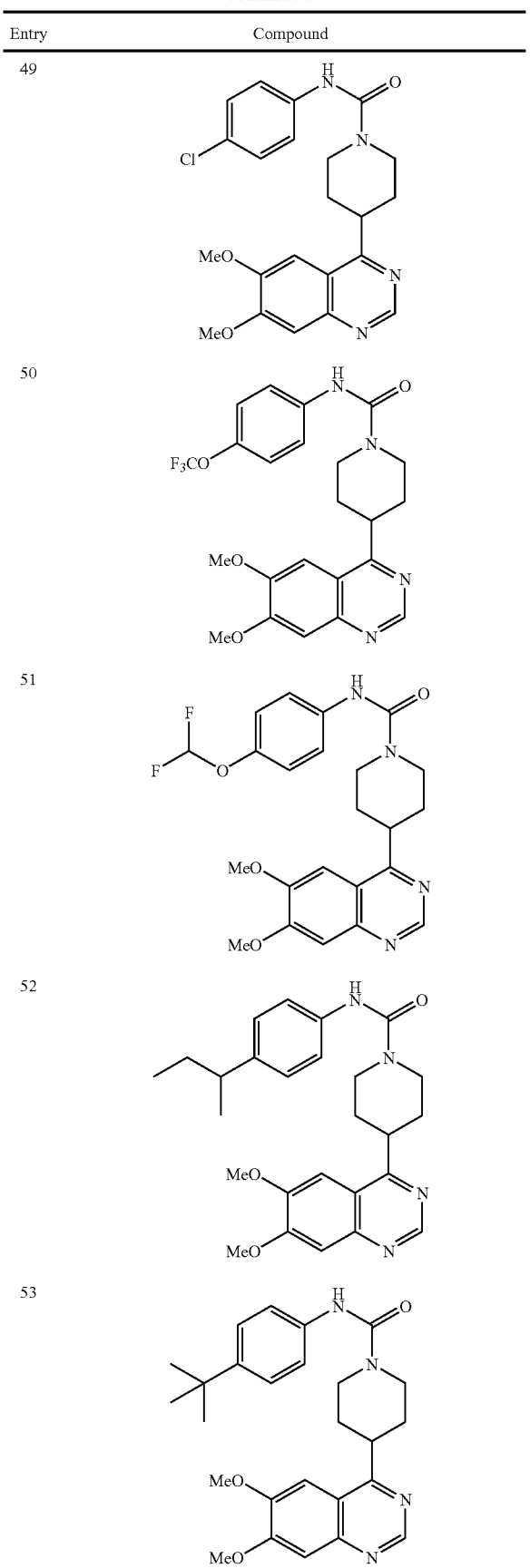
| Entry | Compound |
|---|---|
| 54 | |
| 55 | |
| 56 | |
| 57 | |
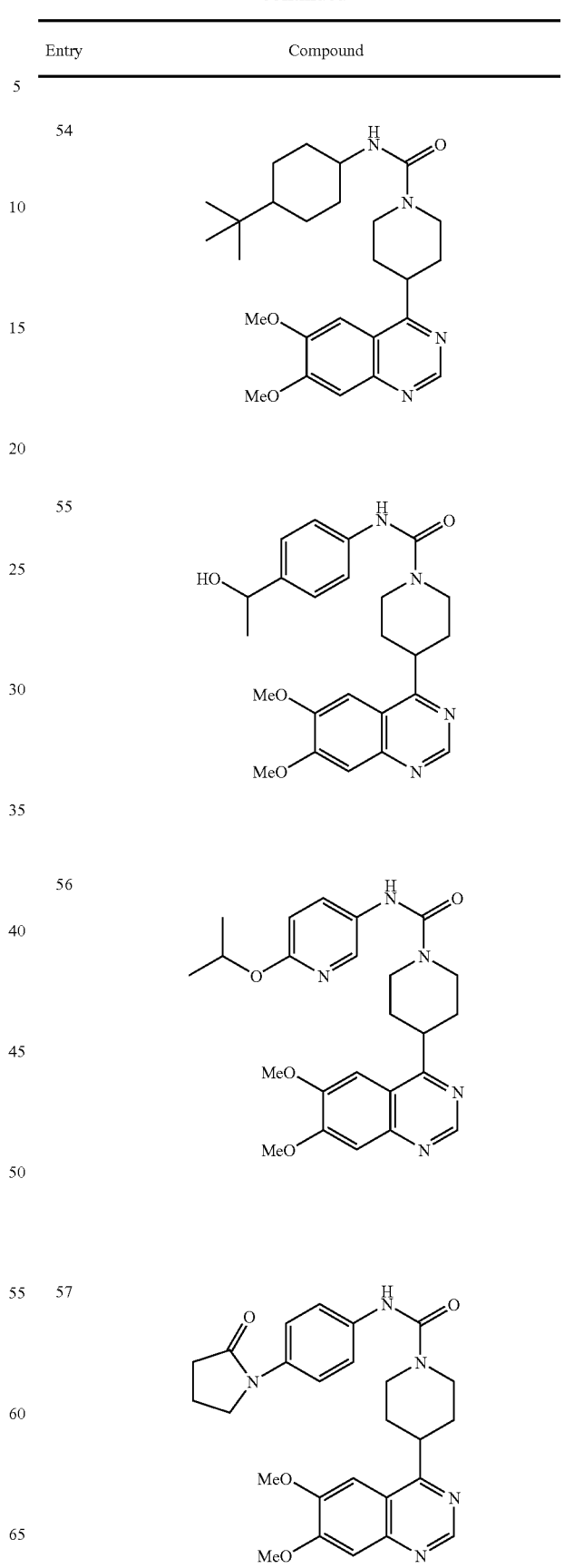

| Entry | Compound |
|---|---|
| 58 | 5-pyrimidinyl-phenyl-carbamoyl-piperidinyl-6,7-dimethoxyquinazoline |
| 59 | 2-furyl-phenyl-carbamoyl-piperidinyl-6,7-dimethoxyquinazoline |
| 60 | 6-chloropyridin-3-yl-phenyl-carbamoyl-piperidinyl-6,7-dimethoxyquinazoline |
| 61 | N-Boc-tetrahydropyridinyl-phenyl-carbamoyl-piperidinyl-6,7-dimethoxyquinazoline |
| 62 | tetrahydropyridinyl-phenyl-carbamoyl-piperidinyl-6,7-dimethoxyquinazoline |

| Entry | Compound |
|---|---|
| 63 | N-Boc-piperidinyl-phenyl-carbamoyl-piperidinyl-6,7-dimethoxyquinazoline |
| 64 | piperidinyl-phenyl-carbamoyl-piperidinyl-6,7-dimethoxyquinazoline |
| 65 | isopropoxyphenyl-carbamoyl-piperidinyl-7-(3-methanesulfonamidopropoxy)quinazoline |
| 66 | morpholinophenyl-carbamoyl-piperidinyl-7-(3-methanesulfonamidopropoxy)quinazoline |

-continued

| Entry | Compound |
|---|---|
| 67 | |
| 68 | |
| 69 | |
| 70 | |

-continued

| Entry | Compound |
|---|---|
| 71 | |
| 72 | |
| 73 | |
| 74 | |

| Entry | Compound |
|---|---|
| 75 | (structure) |
| 76 | (structure) |
| 77 | (structure) |
| 78 | (structure) |
| 79 | (structure) |
| 80 | (structure) |
| 81 | (structure) |
| 82 | (structure) |

| Entry | Compound |
|---|---|
| 83 | 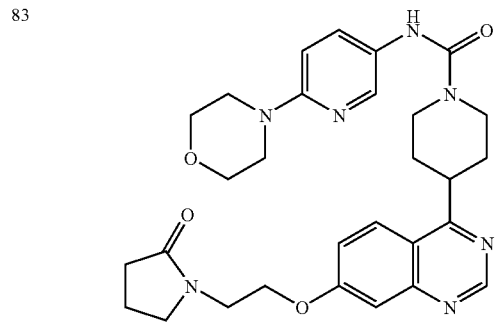 |
| 84 | 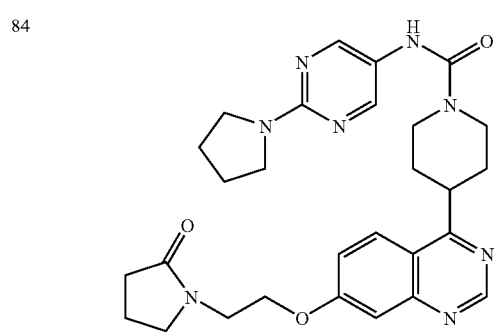 |
| 85 | 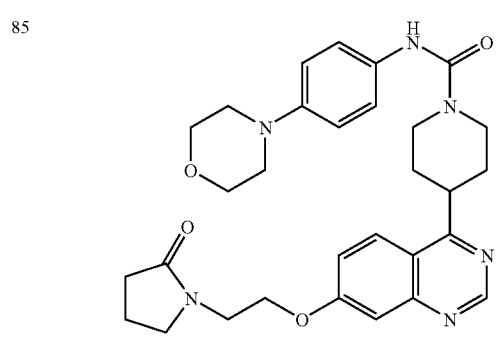 |
| 86 | 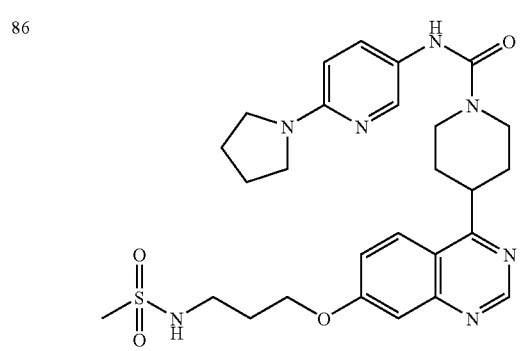 |
| 87 | 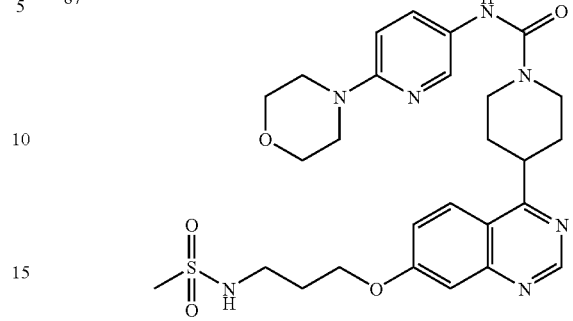 |
| 88 | 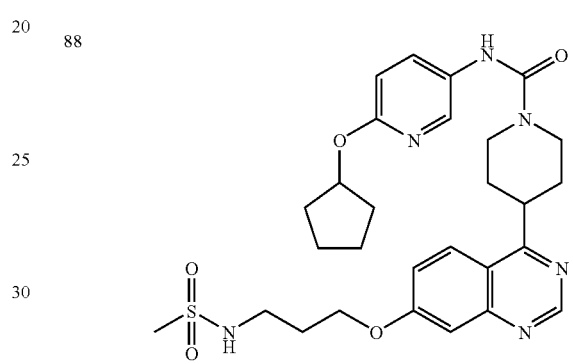 |
| 89 | 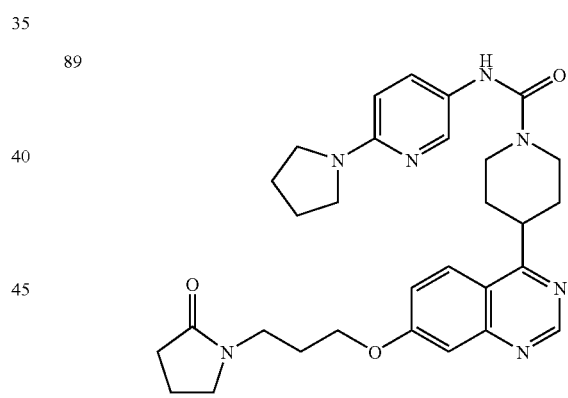 |
| 90 | 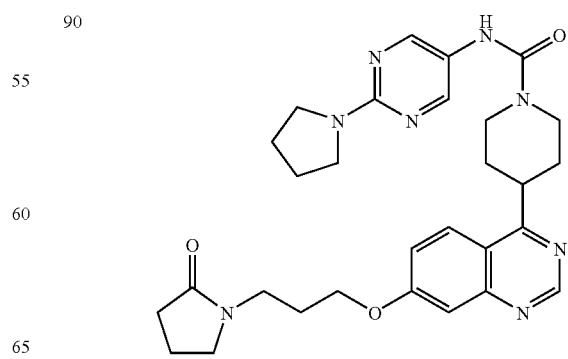 |

| Entry | Compound |
|---|---|
| 91 | |
| 92 | |
| 93 | |
| 94 | |
| 95 | |
| 96 | |
| 97 | |
| 98 | |

| Entry | Compound |
|---|---|
| 99 | |
| 100 | |
| 101 | |
| 102 | |
| 103 | |
| 104 | |
| 105 | |
| 106 | |

-continued

| Entry | Compound |
|---|---|
| 107 | |
| 108 | |
| 109 | |
| 110 | |

-continued

| Entry | Compound |
|---|---|
| 111 | |
| 112 | |
| 113 | |
| 114 | |

-continued

| Entry | Compound |
|---|---|
| 115 | |
| 116 | |
| 117 | |
| 118 | |

-continued

| Entry | Compound |
|---|---|
| 119 | |
| 120 | |
| 121 | |
| 122 | |

US 8,071,768 B2
| Entry | Compound |
|---|---|
| 123 | 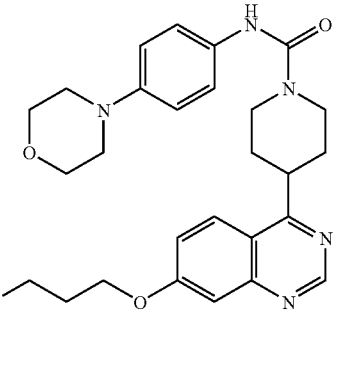 |
| 124 | 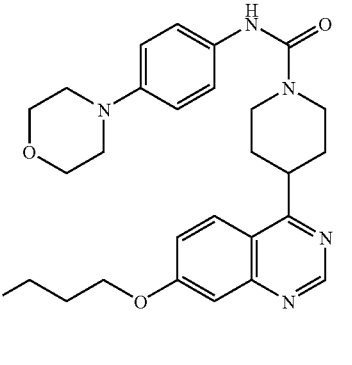 |
| 125 | 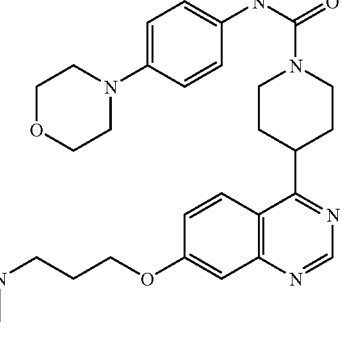 |
| 126 | 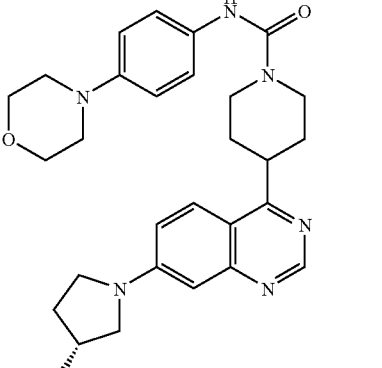 |
| 127 | 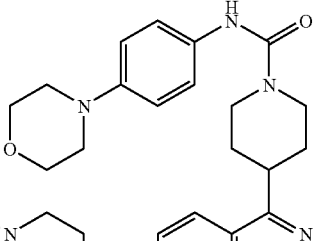 |
| 128 | 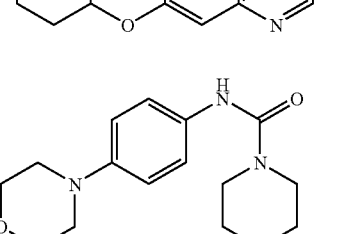 |
| 129 | 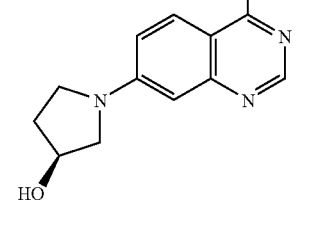 |
| 130 | 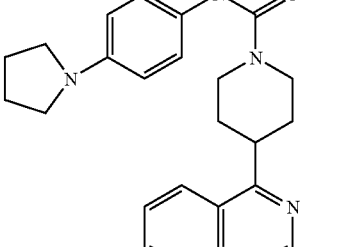 |

-continued

| Entry | Compound |
|---|---|
| 131 | (structure) |
| 132 | (structure) |
| 133 | (structure) |
| 134 | (structure) |

-continued

| Entry | Compound |
|---|---|
| 135 | (structure) |
| 136 | (structure) |
| 137 | (structure) |
| 138 | (structure) |

| Entry | Compound |
|---|---|
| 139 | (structure) |
| 140 | (structure) |
| 141 | (structure) |
| 142 | (structure) |

| Entry | Compound |
|---|---|
| 143 | (structure) |
| 144 | (structure) |
| 145 | (structure) |
| 146 | (structure) |

| Entry | Compound |
|---|---|
| 147 | 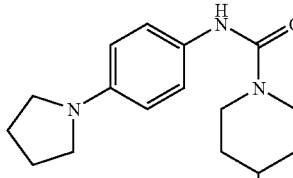 |
| 148 | 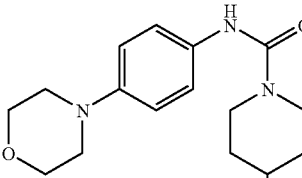 |
| 149 | 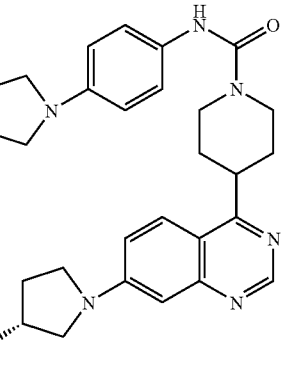 |
| 150 | 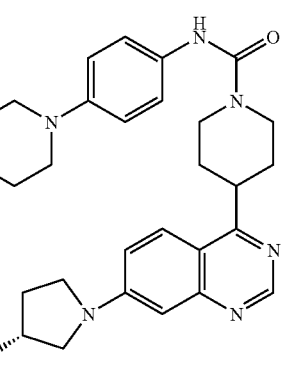 |
| Entry | Compound |
|---|---|
| 151 | 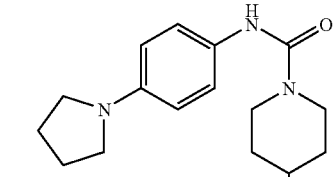 |
| 152 | 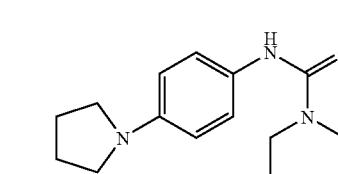 |
| 153 | 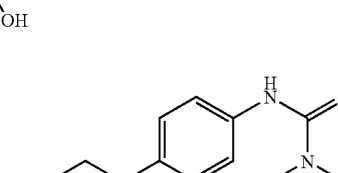 |
| 154 | 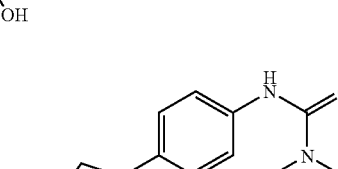 |

| Entry | Compound |
|---|---|
| 155 | |
| 156 | |
| 157 | |
| 158 | |
| 159 | |
| 160 | |
| 161 | |
| 162 | |

| Entry | Compound |
|---|---|
| 163 | (structure) |
| 164 | (structure) |
| 165 | (structure) |

| Entry | Compound |
|---|---|
| 166 | (structure) |
| 167 | (structure) |
| 168 | (structure) |
| 169 | (structure) |

-continued
| Entry | Compound |
|---|---|
| 170 | 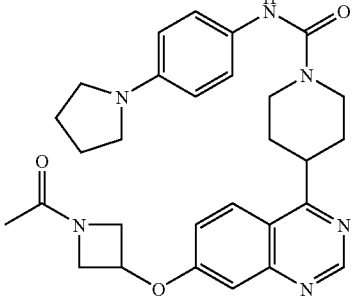 |
| 171 | 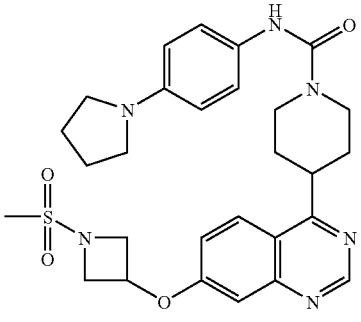 |
| 172 | 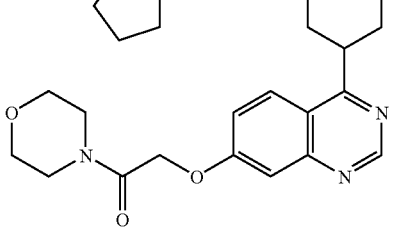 |
| 173 | 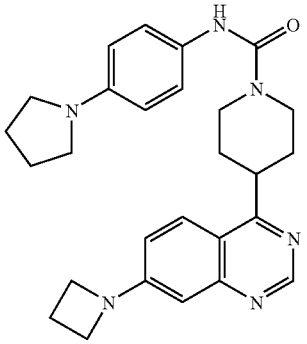 |
-continued
| Entry | Compound |
|---|---|
| 174 | 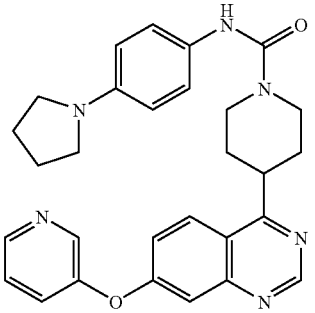 |
| 175 | 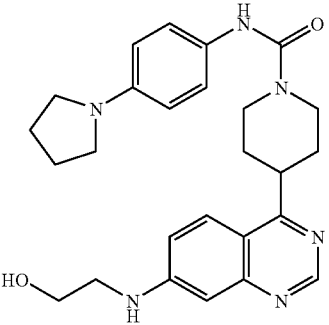 |
| 176 |  |
| 177 | 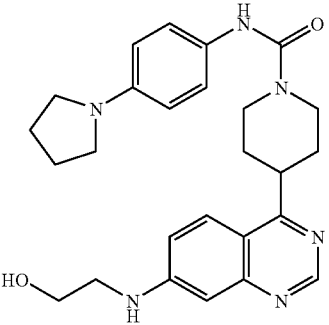 |

| Entry | Compound |
|---|---|
| 178 | 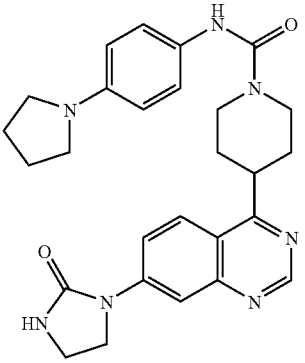 |
| 179 | |
| 180 | |
| 181 | |
| Entry | Compound |
|---|---|
| 182 | 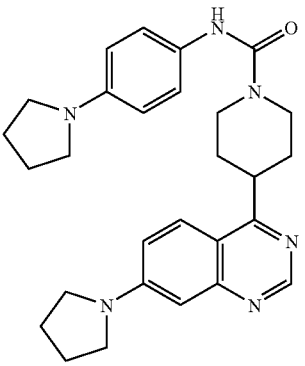 |
| 183 | |
| 184 | |
| 185 | |

| Entry | Compound |
|---|---|
| 186 | |
| 187 | |
| 188 | |
| 189 | |
| 190 | |
| 191 | |
| 192 | |
| 193 | |

-continued
| Entry | Compound |
|---|---|
| 194 | 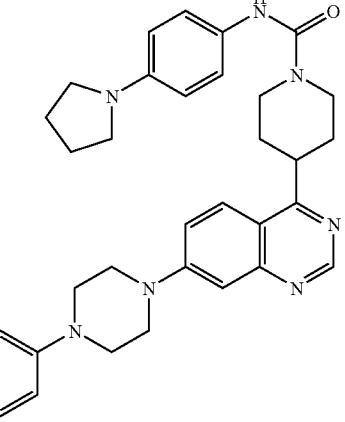 |
| 195 | 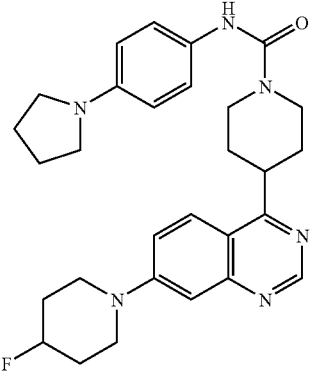 |
| 196 | 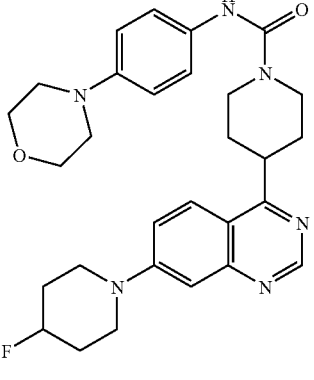 |
| 197 | 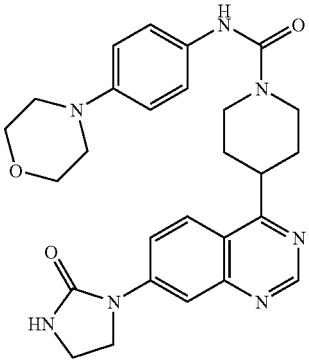 |
-continued
| Entry | Compound |
|---|---|
| 198 | 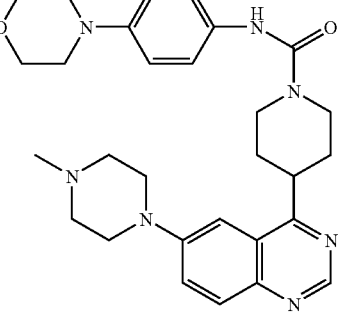 |
| 199 | 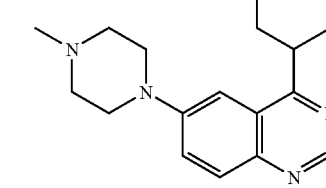 |
| 200 | 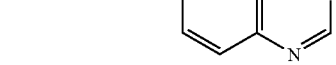 |
| 201 | 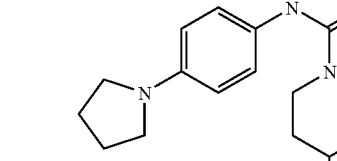 |

| Entry | Compound |
|---|---|
| 202 | |
| 203 | |
| 204 | |
| 205 | |
| 206 | |
| 207 | |
| 208 | |
| 209 | |
| 210 | |

91
-continued

| Entry | Compound |
|---|---|
| 211 | 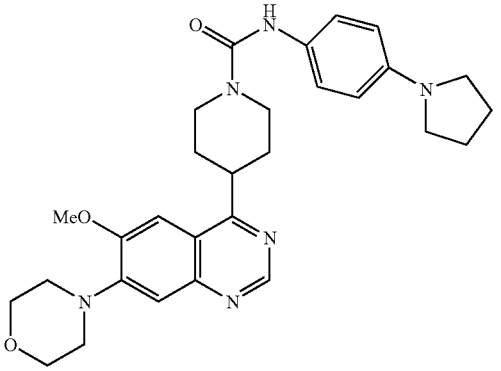 |
| 212 | 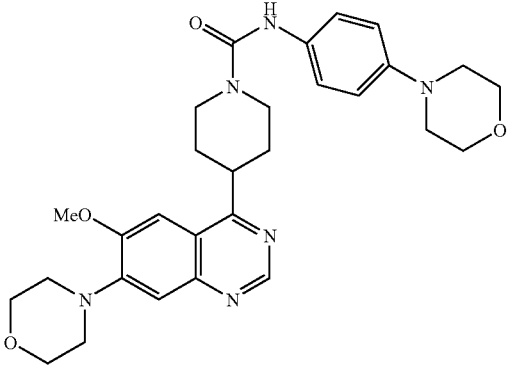 |

Example 1

4-(6,7-Dimethoxy-quinazolin-4-yl)-piperidine-1-carboxylic acid (4-isopropoxy-phenyl)-amide hydrochloride

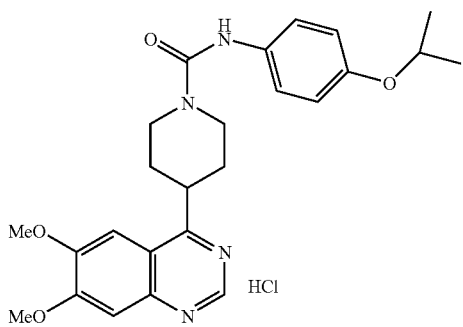

a. (4-Isopropoxy-phenyl)-carbamic acid 4-nitro-phenyl ester

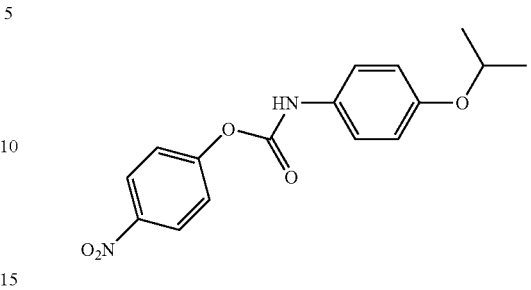

To a solution of 4-isopropoxyaniline (9.06 g, 60.0 mmol) in DCM (120 mL) and pyridine (30 mL) was added 4-nitrophenyl chloroformate (10.9 g, 54.0 mmol) portionwise with stirring over ~1 min with brief ice-bath cooling. After stirring at rt for 1 h, the homogeneous solution was diluted with DCM (300 mL) and washed with 0.6 M HCl (1×750 mL) and 0.025 M HCl (1×1 L). The organic layer was dried (Na$_2$SO$_4$) and concentrated to give the title compound as a light violet-white solid (16.64 g, 98%). $^1$H-NMR (300 MHz, CDCl$_3$) δ 8.26 (m, 2H), 7.40-7.28 (m, 4H), 6.98 (br s, 1H), 6.87 (m, 2H), 4.50 (heptet, J=6.0 Hz, 1H), 1.33 (d, J=6.0 Hz, 6H). LC/MS (ESI): calcd mass 316.1, found 633.2 (2 MH)$^+$.

b. Piperidine-1,4-dicarboxylic acid 1-tert-butyl ester 4-methyl ester

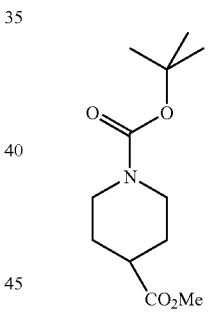

To a mixture of isonipecotic acid (39.0 g, 302 mmol) in MeOH (300 mL) was bubbled HCl gas. The flask was tightly capped and stirred at rt for 1.5 h, at which point the homogeneous solution was concentrated, taken up in DCM (2×125 mL), and repeatedly concentrated under reduced pressure to give a white solid largely free of MeOH. To this was added TEA (43.6 mL, 313 mmol) and DCM (80 mL), and this slurry was stirred on an ice bath while a solution of (Boc)$_2$O (60.9 g, 279 mmol) in DCM (100 mL) was added dropwise with stirring over 10 min at 0° C. After 1 h stirring at 0° C., the ice bath was removed and the slurry was stirred at rt overnight. The slurry was then diluted with ether (700 mL), washed with 0.5M NaH$_2$PO$_4$ (1×400 mL), 4 M NaCl (1×450 mL), dried (Na$_2$SO$_4$), and concentrated under reduced pressure to provide the title compound as a clear light amber oil that crystallized upon standing (65.3 g, 96%). $^1$H-NMR (300 MHz, CDCl$_3$) δ 4.10-3.95 (br m, 2H), 3.69 (s, 3H), 2.92-2.75 (br m, 2H), 2.45 (m, 1H), 1.93-1.82 (m, 2H), 1.70-1.55 (m, 2H), 1.46 (s, 9H).

c. 4-(6,7-Dimethoxy-quinazolin-4-yl)-piperidine-1,4-dicarboxylic acid 1-tert-butyl ester 4-methyl ester

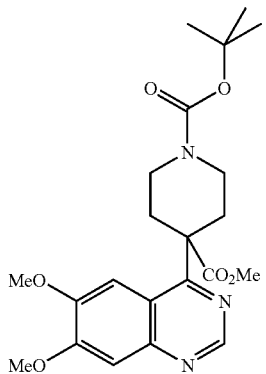

To a mixture of piperidine-1,4-dicarboxylic acid 1-tert-butyl ester 4-methyl ester (17.1 g, 70.5 mmol), as prepared in the previous step, and 4-chloro-6,7-dimethoxyquinazoline (15.0 g, 67.0 mmol) (Oakwood Products, Inc.) immersed in a −78° C. bath was added 1.08 M LiHMDS/THF (71 mL, 77 mmol) in ~20 mL portions under argon via syringe along the sides of the flask (to allow cooling of the hindered base before reaction with the ester). Following completion of LiHMDS/THF addition, the reaction was allowed to sit in the −78° C. bath for 2-3 min before removing the cold bath and allowing the mixture to stir with gradual warming to rt. After 18 h stirring at rt, and an additional 2 d sitting at rt, the mixture was quenched with 0.5 M NaH$_2$PO$_4$ (150 mL) and extracted with DCM (1×150 mL and 1×100 mL). The organic layers were combined, dried (Na$_2$SO$_4$), and concentrated under reduced pressure to provide the crude title compound as a translucent yellow oil that was used in the next step without further purification (33 g, "114%" crude yield). A small sample was purified by flash chromatography (1:1 hex/EtOAc) for characterization. $^1$H-NMR (400 MHz, CDCl$_3$) δ 9.11 (s, 1H), 7.34 (s, 1H), 7.29 (s, 1H), 4.05 (s, 3H), 3.96 (s, 3H), 3.76-3.67 (m, 2H), 3.62-3.49 (m, 2H), 3.61 (s, 3H), 2.50-2.36 (br s, 4H), 1.46 (s, 9H). LC/MS (ESI): calcd mass 431.2, found 432.2 (MH)$^+$.

d. 6,7-Dimethoxy-4-piperidin-4-yl-quinazoline

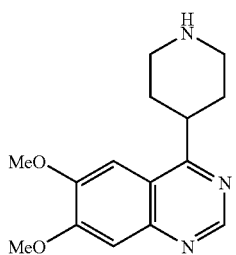

A mixture of crude 4-(6,7-dimethoxy-quinazolin-4-yl)-piperidine-1,4-dicarboxylic acid 1-tert-butyl ester 4-methyl ester (33 g), as prepared in the previous step, MeOH (100 mL), and KOH pellets (26 g, 400 mmol assuming 87% w/w water) was stirred at reflux (100° C. oil bath) for 1 h, at which point the translucent reddish-amber solution was allowed to cool to rt and diluted with water (100 mL) and 6 M HCl (100 mL). The solution was stirred at 100° C. for 10 min (Caution: Initial vigorous bubbling), allowed to cool to rt, diluted with 2.5 M NaOH (90 mL) and extracted with DCM (1×150 mL; 1×50 mL). The organic layers were combined, dried (Na$_2$SO$_4$), and concentrated under reduced pressure to afford the title compound as a beige powder (13.95 g, 76% from 4-chloro-6,7-dimethoxyquinazoline). $^1$H-NMR (300 MHz, DMSO-d$_6$) δ 8.98 (s, 1H), 7.48 (s, 1H), 7.32 (s, 1H), 3.98 (s, 3H), 3.96 (s, 3H), 3.69 (m, 1H), 3.05 (m, 2H), 2.84-2.71 (m, 2H), 1.88-1.65 (m, 4H). LC/MS (ESI): calcd mass 273.2, found 274.2 (MH)$^+$.

e. 4-(6,7-Dimethoxy-quinazolin-4-yl)-piperidine-1-carboxylic acid (4-isopropoxy-phenyl)-amide

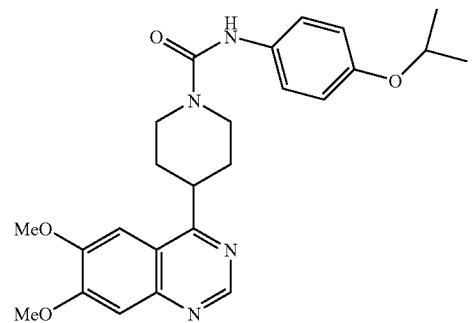

To a mixture of 6,7-dimethoxy-4-piperidin-4-yl-quinazoline (1.86 g, 6.80 mmol), prepared essentially as described in the previous step, and (4-isopropoxy-phenyl)-carbamic acid 4-nitro-phenyl ester (2.28 g, 7.22 mmol), prepared essentially as described in Example 1a, in CH$_3$CN (13 mL) was added DIEA (1.24 mL, 7.50 mmol). The homogeneous solution was refluxed for 4 h, allowed to cool to rt, shaken with 1 M K$_2$CO$_3$, and extracted with EtOAc (2×25 mL). The organic layers were combined, washed with 0.5 M NaH$_2$PO$_4$ (1×50 mL), 4 M NaCl (1×25 mL), dried three times (Na$_2$SO$_4$), and concentrated under reduced pressure to give crude title compound as a beige semisolid (3.5 g). Flash chromatography (3:4→1:2 hex/acetone) afforded the title compound as an off-white foam (2.21 g, 72%). $^1$H-NMR (300 MHz, CDCl$_3$) 9.08 (s, 1H), 7.34 (s, 1H), 7.28-7.22 (m, 3H), 6.83 (m, 2H), 6.46 (br s, 1H), 4.47 (heptet, J=6.1 Hz, 1H), 4.27 (br m, 2H), 4.07 (s, 3H), 4.06 (s, 3H), 3.59 (tt, J=11.0 Hz, 3.7 Hz, 1H), 3.15 (td, J=12.8 Hz, 2.4 Hz, 2H), 2.22-2.06 (m, 2H), 2.04-1.92 (m, 2H), 1.31 (d, J=6.1 Hz, 6H). LC/MS (ESI): calcd mass 450.2, found 451.3 (MH)$^+$. Anal. Calcd for C$_{25}$H$_{30}$N$_4$O$_4$: C, 66.65; H, 6.71; N, 12.44. Found: C, 66.41; H, 6.68; N, 12.22.

95 f. 4-(6,7-Dimethoxy-quinazolin-4-yl)-piperidine-1-carboxylic acid (4-isopropoxy-phenyl)-amide hydrochloride

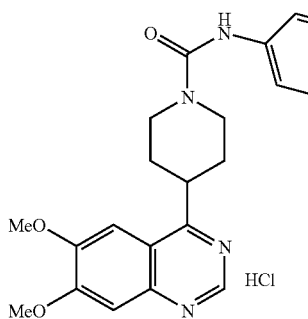

To a solution of 4-(6,7-dimethoxy-quinazolin-4-yl)-piperidine-1-carboxylic acid (4-isopropoxy-phenyl)-amide (1.41 g, 3.14 mmol), as prepared in the preceding step, in dry CH$_3$CN (3.0 mL) was added 1.70 M HCl/CH$_3$CN (2.0 mL, 3.4 mmol) in one portion at rt. The slightly translucent solution was swirled once, allowed to sit at rt for 30 min, and then stored overnight in a desiccator at −30° C. to initiate crystal formation. (The 1.70 M HCl/CH$_3$CN solution was formed by briefly bubbling dry HCl gas into a tared graduated cylinder containing 8.3 mL dry CH$_3$CN.) The vial was then allowed to sit at rt for 1 d. The resulting crystals were washed with CH$_3$CN (3×10 mL), dried under reduced pressure, and powdered to provide, after additional drying at 80° C. under reduced pressure, the title compound as a yellow powder (463 mg, 30%). $^1$H-NMR (300 MHz, DMSO-d$_6$) 9.16 (s, 1H), 8.44 (br s, 1H), 7.72 (s, 1H), 7.49 (s, 1H), 7.35 (m, 2H), 6.80 (m, 2H), 4.50 (heptet, J=6.0 Hz, 1H), 4.29 (br m, 2H), 4.12-4.00 (m, 1H), 4.05 (s, 3H), 4.03 (s, 3H), 3.16-3.01 (m, 2H), 1.97-1.80 (br m, 4H), 1.23 (d, J=6.0 Hz, 6H). LC/MS (ESI): free base calcd mass 450.2, found 451.3 (MH)$^+$. Anal. Calcd for C$_{25}$H$_{30}$N$_4$O$_4$.1.33HCl.0.71 water.0.18CH$_3$CN: C, 58.69; H, 6.46; N, 11.28; Cl, 9.05. Found: C, 58.98; H, 6.41; N, 11.39; Cl, 9.05. Karl Fischer: 2.46% water.

Example 2

4-(6,7-Dimethoxy-quinazolin-4-yl)-piperidine-1-carboxylic acid (4-iodo-phenyl)-amide

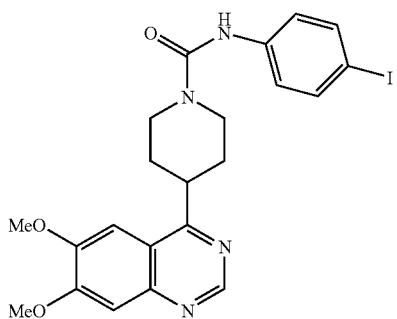

96 a. (4-Iodo-phenyl)-carbamic acid 4-nitro-phenyl ester

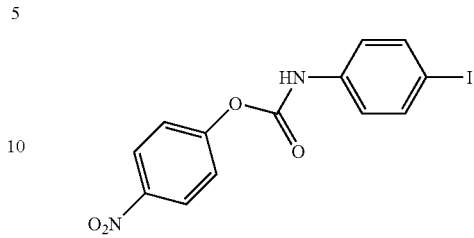

The title compound was prepared from 4-iodoaniline essentially as described in Example 1a, except the reaction was stirred at rt for 3 h. The homogeneous solution was then partitioned with DCM and aq HCl essentially as described in Example 1a, except a heavy precipitate formed in the organic layer. Filtration of the organic layer provided the title compound as an off-white solid (8.50 g, 61%). $^1$H-NMR (400 MHz, CDCl$_3$) 8.30 (m, 2H), 7.68 (m, 2H), 7.39 (m, 2H), 7.30-7.20 (m, 2H), 6.98 (br s, 1H).

b. 4-(6,7-Dimethoxy-quinazolin-4-yl)-piperidine-1-carboxylic acid (4-iodo-phenyl)-amide

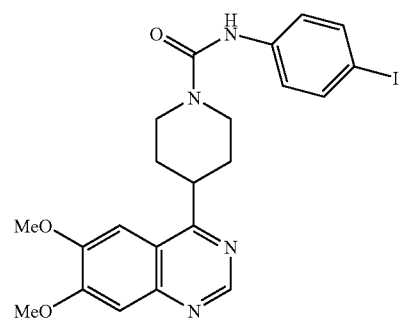

To a mixture of 6,7-dimethoxy-4-piperidin-4-yl-quinazoline (5.18 g, 19.0 mmol), prepared as described in Example 1d, and (4-iodo-phenyl)-carbamic acid 4-nitro-phenyl ester (8.00 g, 20.8 mmol), prepared as described in the preceding step, in DCM (20 mL) was added DIEA (3.44 mL, 20.8 mmol) with stirring at rt. After stirring at rt for 5 min, CHCl$_3$ (20 mL) was added to thin the slurry, and after stirring for 4 h at rt, the greenish mixture was washed with 0.1 M NaOH (208 mL), and the resulting precipitate in the organic layer was filtered. The filter cake was dissolved in 92:8 DCM/MeOH (250 mL) and washed with water (1×50 mL) and 0.1 M NaOH (1×200 mL). The organic layer was then dried (Na$_2$SO$_4$), concentrated under reduced pressure, and the resulting greyish solid was triturated with hot toluene (1×20 mL) and filtered. The filter cake was washed with toluene (2×20 mL) to provide, after drying of the filter cake, the title compound as an off-white solid (7.84 g, 80%). Nmr reveals a single ~15 mol % impurity. A sample was purified to homogeneity by flash chromatography. $^1$H-NMR (300 MHz, CDCl$_3$) 9.07 (s, 1H), 7.58 (m, 2H), 7.35 (s, 1H), 7.25 (s, 1H), 7.17 (m, 2H), 6.49 (br s, 1H), 4.32-4.22 (m, 2H), 4.07 (s, 3H), 4.06 (s, 3H), 3.60 (m, 1H), 3.24-3.11 (m, 2H), 2.23-2.07 (m, 2H), 2.05-1.94 (m, 2H). LC/MS (ESI): calcd mass 518.1, found 519.2 (MH)+.

Example 3

4-(6,7-Dimethoxy-quinazolin-4-yl)-piperidine-1-carboxylic acid (4-imidazol-1-yl-phenyl)-amide

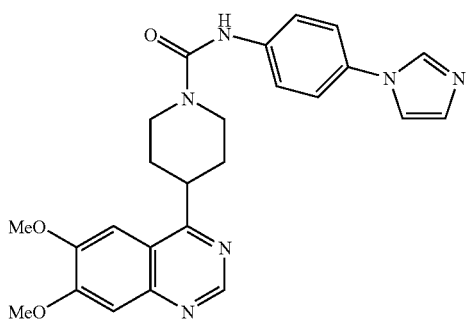

a. 4-(6,7-Dimethoxy-quinazolin-4-yl)-piperidine-1-carbonyl chloride

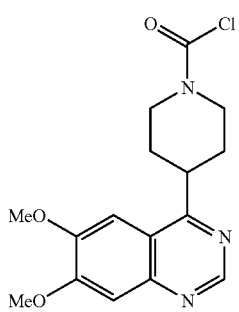

To a −78° C. solution of 1.85 M phosgene in toluene (15.8 mL, 29.3 mmol) and DCM (32 mL) was added 6,7-dimethoxy-4-piperidin-4-yl-quinazoline (4.00 g, 14.6 mmol), prepared as described in Example 1d, in one portion with stirring, followed immediately by the rapid addition of DIEA (2.66 mL, 16.1 mmol) along the walls of the flask over ~5 sec. The flask was sealed and stirred at −78° C. for another 5 min before placing the flask in an ice bath with stirring at 0° C. for 30 min. The opaque easily stirred slurry was then poured into a mixture of DCM (70 mL), 0.5 M trisodium citrate (60 mL), and ice (60 mL), and partitioned. The aqueous layer was extracted with DCM (1×50 mL) and the organic layers combined, dried (Na$_2$SO$_4$), and concentrated under reduced pressure to give the crude title compound as an orange solid. Purification by flash chromatography (7:1→4:1 DCM/acetone) afforded the title compound as a beige solid (2.50 g, 51%). $^1$H-NMR (300 MHz, CDCl$_3$) 9.07 (s, 1H), 7.35 (s, 1H), 7.23 (s, 1H), 4.58-4.47 (m, 2H), 4.072 (s, 3H), 4.068 (s, 3H), 3.65 (tt, J=10.9 Hz, 4.0 Hz, 1H), 3.46-3.33 (m, 1H), 3.28-3.14 (m, 1H), 2.30-2.06 (m, 2H), 2.06-1.95 (m, 2H). LC/MS (ESI): calcd mass 335.1, found 336.1 (MH)+.

b. 4-(6,7-Dimethoxy-quinazolin-4-yl)-piperidine-1-carboxylic acid (4-imidazol-1-yl-phenyl)-amide

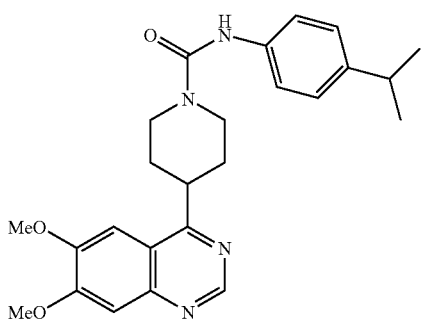

4-(6,7-Dimethoxy-quinazolin-4-yl)-piperidine-1-carbonyl chloride (16.5 mg, 0.05 mmol), prepared as described in Example 3a, was dissolved in anhydrous THF (2 mL) and to it was added 4-imidazol-1-yl-phenylamine (12 mg, 0.075 mmol) followed by DIEA (14 µL, 0.075 mmol) and the mixture was stirred at 65° C. for 3 h. It was then concentrated in vacuo and the residue was purified by Preparative TLC (silica gel, 5% MeOH/DCM) to obtain 2 mg (5%) of pure 4-(6,7-dimethoxy-quinazolin-4-yl)-piperidine-1-carboxylic acid (4-imidazol-1-yl-phenyl)-amide. $^1$H-NMR (300 MHz, CDCl$_3$) δ 9.04 (s, 2H), 7.63 (m, 3H), 7.55-7.40 (m, 5H), 7.33 (s, 1H), 4.37 (m, 2H), 4.07 (s, 6H), 3.76-3.58 (m, 2H), 3.14 (m, 2H), 2.18-1.90 (m, 3H). LC/MS (ESI): calcd mass 458.2, found 459.5 (MH)+.

Example 4

4-(6,7-Dimethoxy-quinazolin-4-yl)-piperidine-1-carboxylic acid (4-isopropyl-phenyl)-amide a. (4-Isopropyl-phenyl)-carbamic acid 4-nitro-phenyl ester

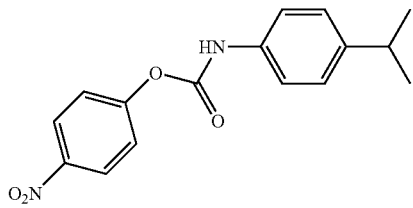

To a solution of 4-isopropylaniline (3.02 g, 22.3 mmol) in DCM (40 mL) and pyridine (10 mL) was added 4-nitrophenyl chloroformate (4.09 g, 20.3 mmol) portionwise with stirring over ~30 sec with brief ice-bath cooling. After stirring at rt for 1 h, the homogeneous solution was diluted with DCM (100 mL) and washed with 0.6 M HCl (1×250 mL), 0.025 M HCl (1×400 mL), water (1×100 mL), and 1 M NaHCO$_3$ (1×100 mL). The organic layer was dried (Na$_2$SO$_4$) and concentrated to give the title compound as a light peach-colored solid (5.80 g, 95%). $^1$H-NMR (300 MHz, CDCl$_3$) δ 8.28 (m, 2H), 7.42-7.32 (m, 4H), 7.22 (m, 2H), 6.93 (br s, 1H), 2.90 (h, J=6.9 Hz, 1H), 1.24 (d, J=6.9 Hz, 6H). LC/MS (ESI): calcd mass 300.1, 601.3 (2MH)$^+$.

b. 4-(6,7-Dimethoxy-quinazolin-4-yl)-piperidine-1-carboxylic acid (4-isopropyl-phenyl)-amide

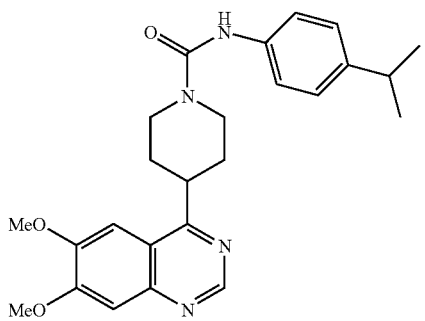

A mixture of 6,7-dimethoxy-4-piperidin-4-yl-quinazoline (18.8 mg, 68.9 μmol), as prepared in Example 1d, and (4-isopropyl-phenyl)-carbamic acid 4-nitro-phenyl ester 21.3 mg, 71.0 μmol), as prepared in the preceding step, was stirred in CH$_3$CN (250 μL) at 80° C. for 4 h. The reaction was then partitioned with DCM (4 mL) and 1 M K$_2$CO$_3$ (4 mL), and the organic layer was dried (Na$_2$SO$_4$) and concentrated under reduced pressure. Flash chromatography of the residue (EtOAc) provided the title compound (21.5 mg, 72%). $^1$H-NMR (300 MHz, CDCl$_3$) δ 9.08 (s, 1H), 7.34 (s, 1H), 7.31-7.25 (m, 3H), 7.16 (m, 2H), 6.37 (br s, 1H), 4.32-4.22 (m, 2H), 4.07 (s, 3H), 4.06 (s, 3H), 3.60 (tt, 1H), 3.18 (td, 2H), 2.87 (heptet, 1H), 2.24-2.08 (m, 2H), 2.04-1.94 (m, 2H), 1.23 (d, 6H). LC/MS (ESI): calcd mass 434.2, found 435.3 (MH)$^+$.

Example 5

4-Quinolin-4-yl-piperidine-1-carboxylic acid (4-isopropyl-phenyl)-amide

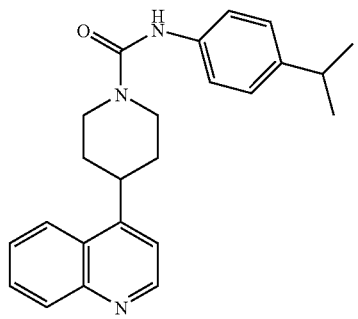

a. 4-Piperidin-4-yl-quinoline

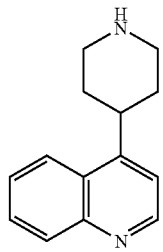

A solution of 1.03 M LiHMDS/THF (11.5 mL, 11.8 mmol) was treated dropwise with a solution of piperidine-1,4-dicarboxylic acid 1-tert-butyl ester 4-ethyl ester (2.79 g, 10.9 mmol) (WO 2003064413) in THF (6 mL) over 5 min at 0° C. with stirring under argon. After stirring 30 min at 0° C., the dark yellow homogeneous solution was treated dropwise with a solution of 4-chloroquinoline (1.615 g, 9.88 mmol) in THF (5 mL) over 1-2 min at 0° C. with stirring. The ice bath was then removed and the reaction was stirred at rt overnight, then refluxed for two hours. After cooling to rt, 1 M KOH (aq) (44 mL, 44 mmol) was added and the reaction refluxed for 30 min. Dioxane (22 mL) was added to the bilayer, and the reaction was refluxed an additional 30 min. After cooling to rt, the bilayer was treated dropwise with 12 N HCl (7.4 mL, 89 mmol HCl) (Caution: exotherm) and then refluxed for 30 min under air. The light amber bilayer was allowed to cool to rt, made basic by the addition of 2.5 M NaOH (50 mL), and extracted with DCM (1×50 mL) and 4:1 DCM/MeOH (1×50 mL). The organic layers were combined, dried (Na$_2$SO$_4$), and concentrated to give a residue that was shown by LC/MS to contain the title compound as a minor component and the ethyl ester intermediate as the major component. The ethyl ester intermediate was stirred with KOH pellets (2.4 g, 37 mmol) in MeOH (10 mL) at 100° C. (oil bath) for 3 h, allowed to cool to rt, treated cautiously with 6 M HCl (aq) (10 mL) and water (10 mL), and stirred at 100° C. for 20 min. After cooling to rt, the homogeneous solution was brought to pH >12 with 2.5 M NaOH and extracted with 9:1 DCM/MeOH (2×50 mL). The organic layers were combined, dried (Na$_2$SO$_4$), and concentrated under reduced pressure. Flash chromatography (85:15 DCM/MeOH saturated with NH3) afforded the title compound as a white semisolid (702 mg, 34%). $^1$H-NMR (300 MHz, CDCl$_3$) δ 8.86 (d, 1H), 8.11 (m, 2H), 7.70 (m, 1H), 7.56 (m, 1H), 7.30 (d, 1H), 3.46 (tt, 1H), 3.27 (m, 2H), 2.91 (td, 2H), 2.02-1.92 (m, 2H), 1.87 (br s, 1H), 1.85-1.69 (m, 2H). LC/MS (ESI): calcd mass 212.1, found 213.1 (MH)$^+$.

b. 4-Quinolin-4-yl-piperidine-1-carboxylic acid (4-isopropyl-phenyl)-amide

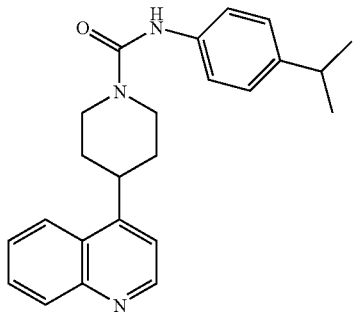

A solution of 4-piperidin-4-yl-quinoline (21.1 mg, 99.5 µmol), as prepared in the previous step, (4-isopropyl-phenyl)-carbamic acid 4-nitro-phenyl ester (33.2 mg, 111 µmol), as prepared in Example 4a, and DIEA (18 µL, 109 µmol) in DMSO (100 µL) was stirred at 100° C. for 14 h. The reaction was then allowed to cool to rt, shaken with 2 M K$_2$CO$_3$ (aq) (2 mL), and extracted with DCM (2×2 mL). The organic layers were combined, dried (Na$_2$SO$_4$), and concentrated under reduced pressure. Flash chromatography of the residue (3:4 hex/acetone) provided the title compound (12 mg, 32%). $^1$H-NMR (300 MHz, CDCl$_3$) δ 8.88 (d, 1H), 8.14 (m, 2H), 7.74 (m, 1H), 7.61 (m, 1H), 7.30 (m, 2H), 7.28 (d, 1H), 7.17 (m, 2H), 6.38 (br s, 1H), 4.36-4.26 (m, 2H), 3.58 (m, 1H), 3.16 (td, 2H), 2.87 (heptet, 1H), 2.13-2.03 (m, 2H), 1.95-1.79 (m, 2H), 1.23 (d, 6H). LC/MS (ESI): calcd mass 373.2, found 374.2 (MH)$^+$.

Example 6

4-Quinolin-4-yl-piperidine-1-carboxylic acid (4-isopropoxy-phenyl)-amide

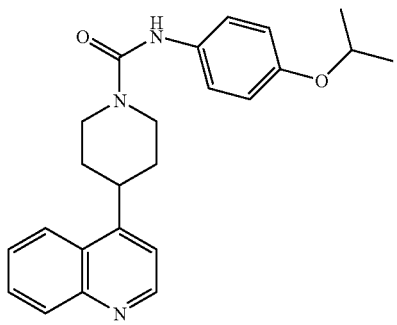

Prepared essentially as described for Example 5b using 1.4 eq (4-isopropoxy-phenyl)-carbamic acid 4-nitro-phenyl ester, as prepared in Example 1a. Flash chromatography (3:4 hex/acetone) provided the title compound (9 mg, 31%). $^1$H-NMR (300 MHz, CDCl$_3$) δ 8.87 (d, 1H), 8.12 (m, 2H), 7.72 (m, 1H), 7.59 (m, 1H), 7.26 (m, 3H), 6.84 (m, 2H), 6.45 (br s, 1H), 4.48 (heptet, 1H), 4.35-4.25 (m, 2H), 3.55 (tt, 1H), 3.12 (td, 2H), 2.10-2.00 (m, 2H), 1.92-1.76 (m, 2H), 1.31 (d, 6H). LC/MS (ESI): calcd mass 389.2, found 390.2 (MH)$^+$.

Example 7

4-Quinazolin-4-yl-piperidine-1-carboxylic acid (4-isopropyl-phenyl)-amide

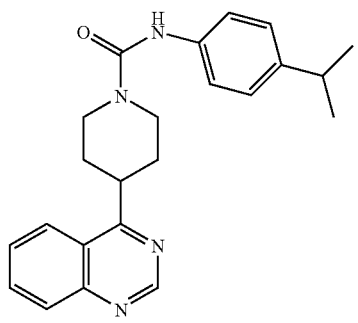

a. 4-chloro-quinazoline

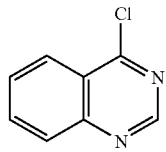

A mixture of 4-hydroxyquinazoline (2.56 g, 17.5 mmol) and POCl$_3$ (8.0 mL, 88 mmol) was stirred at 140° C. (oil bath) for 10 min. The homogeneous light amber solution was then allowed to cool to rt before concentrating under reduced pressure at 70° C. The translucent residue was dissolved in DCM (25 mL), and the homogeneous yellow solution was partitioned with ice and 1 M NaHCO$_3$ to pH ~6 (paper) (~20 mL aq layer). The organic layer was dried twice (Na$_2$SO$_4$), filtered through a 0.22 micron filter, and concentrated under reduced pressure (bath <40° C.) to provide the title compound as a yellow solid (2.53 g, 88%). $^1$H-NMR (300 MHz, CDCl$_3$) δ 9.07 (s, 1H), 8.30 (ddd, 1H), 8.11 (m, 1H), 8.00 (m, 1H), 7.77 (m, 1H).

b. 4-Quinazolin-4-yl-piperidine-1,4-dicarboxylic acid 1-tert-butyl ester 4-methyl ester

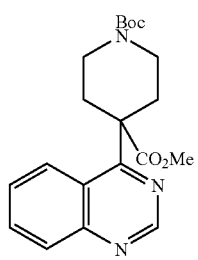

A mixture of 4-chloroquinazoline (2.02 g, 12.3 mmol), prepared as described in the preceding step, and piperidine-1,4-dicarboxylic acid 1-tert-butyl ester 4-methyl ester (3.13 g, 12.8 mmol), as prepared in Example 1b, was treated with 1.08 M LiHMDS/THF in one portion by syringe at 0° C. with stirring under argon. After stirring for an additional 5 min at 0° C., the ice bath was removed and the homogeneous amber solution was stirred at rt for 4.5 h. The reaction was quenched with 1 M NaH$_2$PO$_4$ (30 mL) and extracted with DCM (2×30 mL). The organic layers were combined, dried (Na$_2$SO$_4$), and concentrated under reduced pressure to give the crude title compound as a clear amber syrup (4.98 g). $^1$H-NMR (300 MHz, CDCl$_3$) δ 9.29 (s, 1H), 8.06 (m, 2H), 7.87 (m, 1H), 7.59 (m, 1H), 3.72-3.52 (m, 4H), 3.60 (s, 3H), 2.50-2.40 (br m, 4H), 1.46 (s, 9H). LC/MS (ESI): calcd mass 371.2, found 372.2 (MH)$^+$.

c. 4-piperidin-4-yl-quinazoline

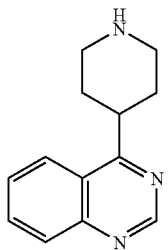

A mixture of crude 4-quinazolin-4-yl-piperidine-1,4-dicarboxylic acid 1-tert-butyl ester 4-methyl ester (4.58 g), as prepared in the previous step, DMSO (7.5 mL), and 10 M KOH (aq) (7.5 mL) was vigorously stirred at 100° C. for 12 h. After cooling to rt, the reaction was cautiously treated with 6 M HCl (18.4 mL) (gas evolution!) and water (19 mL), and the mixture with heavy precipitate was stirred at 100° C. for 10 min. The resulting amber translucent solution was allowed to cool to rt, made basic with 2.5 M NaOH (20 mL) and water (10 mL), shaken to dissolve the DMSO into the aqueous milieu, and extracted with DCM (2×75 mL). The organic layers were combined, dried (Na$_2$SO$_4$), and concentrated under reduced pressure to give the impure title compound as an amber translucent syrup (2.63 g, "100%" crude yield from 4-chloroquinazoline). $^1$H-NMR (300 MHz, CDCl$_3$) δ 9.27 (s, 1H), 8.17 (dd, 1H), 8.06 (m, 1H), 7.89 (m, 1H), 7.65 (m, 1H), 3.75 (m, 1H), 3.45-3.35 (m, 2H), 3.04-2.92 (m, 2H), 2.1-1.8 (m, 5H). LC/MS (ESI): calcd mass 213.1, found 214.0 (MH)$^+$.

d. 4-Quinazolin-4-yl-piperidine-1-carboxylic acid (4-isopropyl-phenyl)-amide

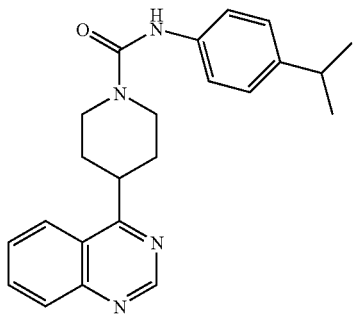

Prepared essentially as described for Example 5b using 4-piperidin-4-yl-quinazoline, as described in the previous step, and stirring at 100° C. for 100 min. Flash chromatography (1:4 hex/EtOAc) afforded the title compound as a beige solid (23.3 mg, 54%). $^1$H-NMR (300 MHz, CDCl$_3$) δ 9.26 (s, 1H), 8.18 (m, 1H), 8.08 (m, 1H), 7.91 (m, 1H), 7.67 (m, 1H), 7.28 (m, 2H), 7.16 (m, 2H), 6.40 (br s, 1H), 4.33-4.24 (m, 2H), 3.78 (tt, 1H), 3.17 (td, 2H), 2.87 (heptet, 1H), 2.23-1.97 (m, 4H), 1.23 (d, 6H). LC/MS (ESI): calcd mass 374.2, found 375.2 (MH)$^+$.

Example 8

4-Quinazolin-4-yl-piperidine-1-carboxylic acid (4-isopropoxy-phenyl)-amide

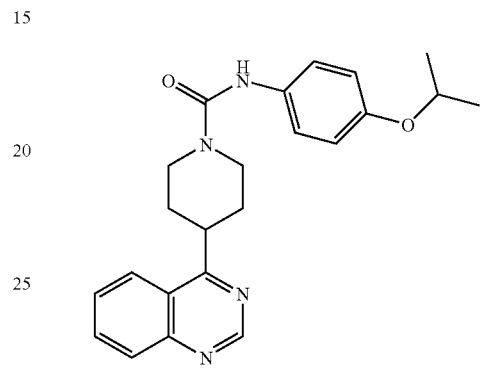

Prepared essentially as described for Example 7d, using (4-isopropoxy-phenyl)-carbamic acid 4-nitro-phenyl ester, as prepared in Example 1a. Flash chromatography (1:4 hex/EtOAc) afforded the title compound as a beige solid (27.6 mg, 55%). $^1$H-NMR (300 MHz, CDCl$_3$) δ 9.26 (s, 1H), 8.18 (m, 1H), 8.08 (m, 1H), 7.91 (m, 1H), 7.67 (m, 1H), 7.25 (m, 2H), 6.84 (m, 2H), 6.36 (br s, 1H), 4.48 (heptet, 1H), 4.32-4.23 (m, 2H), 3.78 (tt, 1H), 3.16 (td, 2H), 2.22-1.96 (m, 4H), 1.32 (d, 6H). LC/MS (ESI): calcd mass 390.2, found 391.2 (MH)$^+$.

Example 9

2-[4-(6,7-Dimethoxy-quinazolin-4-yl)-piperidin-1-yl]-N-(4-isopropyl-phenyl)-acetamide

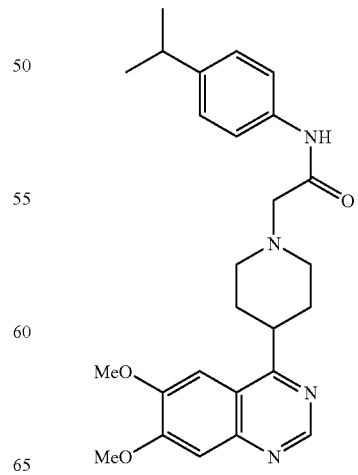

A mixture of 4-isopropylaniline (17.7 mg, 131 μmol), CaCO₃ (33.1 mg, 331 μmol) (10 micron powder), and CH₃CN (240 μL) was stirred in an ice bath for 2-3 min before adding bromoacetyl bromide (10.3 μL, 119 μmol) dropwise over 10-15 s with stirring at 0° C. After an additional 2-3 min stirring at 0° C., the ice bath was removed and the slurry was stirred at rt for 30 min. Then 6,7-dimethoxy-4-piperidin-4-yl-quinazoline (35.1 mg, 129 μmol), as prepared in Example 1d, was added in one portion and the mixture was stirred at 100° C. for 40 min. The reaction was then allowed to cool to rt, quenched with 2 M K₂CO₃ (2 mL), and extracted with DCM (2×2 mL). The organic layers were combined, dried (Na₂SO₄), and concentrated under reduced pressure. Flash chromatography of the residue (1:1 hex/acetone) provided the title compound (30.3 mg, 57%). ¹H-NMR (300 MHz, CDCl₃) δ 9.11 (s, 2H), 7.51 (m, 2H), 7.33 (s, 1H), 7.25 (s, 1H), 7.19 (m, 2H), 4.05 (s, 6H), 3.41 (tt, 1H), 3.21 (s, 2H), 3.18-3.10 (m, 2H), 2.88 (heptet, 1H), 2.51 (td, 2H), 2.24 (qd, 2H), 2.02-1.92 (m, 2H), 1.22 (d, 6H). LC/MS (ESI): calcd mass 448.3, found 449.3 (MH)⁺.

Example 10

2-[4-(6,7-Dimethoxy-quinazolin-4-yl)-piperidin-1-yl]-N-(4-isopropoxy-phenyl)-acetamide

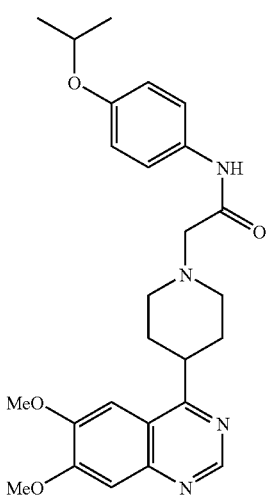

Prepared essentially as described for Example 9, using 4-isopropoxyaniline. Flash chromatography (1:1 hex/acetone) provided the target compound (20.3 mg, 39%). ¹H-NMR (300 MHz, CDCl₃) δ 9.12 (s, 1H), 9.08 (br s, 1H), 7.49 (m, 2H), 7.35 (s, 1H), 7.25 (s, 1H), 6.87 (m, 2H), 4.51 (heptet, 1H), 4.07 (s, 6H), 3.42 (tt, 1H), 3.21 (s, 2H), 3.20-3.11 (m, 2H), 2.53 (td, 2H), 2.25 (qd, 2H), 2.03-1.93 (m, 2H), 1.33 (d, 6H). LC/MS (ESI): calcd mass 464.2, found 465.2 (MH)⁺.

Example 11

4-(6-Iodo-quinazolin-4-yl)-piperidine-1-carboxylic acid (4-isopropoxy-phenyl)-amide

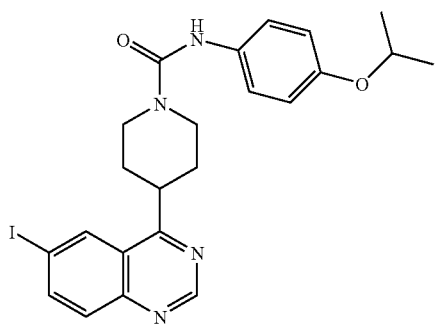

a. 4-Chloro-6-iodo-quinazoline

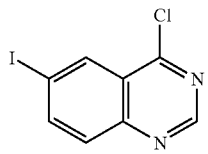

A mixture of 5-iodoanthranilic acid (9.96 g, 37.9 mmol) and formamidine acetate (4.20 g, 40.3 mmol) (adapted from *J. Org. Chem.* 51:616, 1986) in absolute EtOH (80 mL) was refluxed under air for 2 h. The smoky amber solution with heavy white precipitate was then concentrated under reduced pressure at 90° C., and residual protic solvent was removed with toluene rotary evaporation (2×100 mL) at 90° C. The resulting sticky tan solid was treated with a thick white slurry of Vilsmeier-Haack reagent in one portion under air at rt. [The Vilsmeier-Haack reagent was prepared by the addition of a solution of oxalyl chloride (10.9 mL, 125 mmol) in DCE (44 mL) to a solution of DMF (6.7 mL, 87 mmol) in DCE (21 mL) dropwise over 10 min at 0° C. with vigorous stirring. The ice bath was removed immediately following completion of oxalyl chloride addition, and the white slurry was stirred at "rt" for 5 min before transfer to the crude 4-hydroxy-6-iodo-quinazoline intermediate.] The reaction was then refluxed under air (oil bath 110° C.) for 1 h 15 min, and the resulting homogeneous brown solution was allowed to cool to rt, at which point a heavy precipitate formed. The reaction was poured into ice water (300 mL) and extracted with DCM (3×250 mL). The opaque organic layers were combined, dried (Na₂SO₄), and filtered to provide a clear red amber filtrate. Concentration under reduced pressure, followed by toluene rotary evaporation at 90° C. to remove potentially reactive volatiles, afforded the title compound as a tan powder (8.41 g, 94% from iodoanthranilic acid) suitable for treatment with LiHMDS in the next step. ¹H-NMR (300 MHz, CDCl₃) δ 9.07 (s, 1H), 8.67 (dd, 1H), 8.22 (dd, 1H), 7.81 (d, 1H).

b. 4-(6-Iodo-quinazolin-4-yl)-piperidine-1,4-dicarboxylic acid 1-tert-butyl ester 4-methyl ester

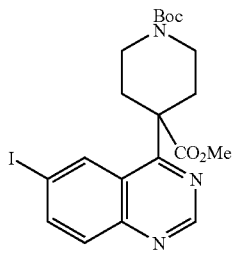

Prepared essentially as described in Example 1c using 4-chloro-6-iodo-quinazoline, as prepared in the preceding step, 1.1 eq LiHMDS/THF and 1.1 eq piperidine-1,4-dicarboxylic acid 1-tert-butyl ester 4-methyl ester, as prepared in Example 1b, and stirring at rt for 14 h following enolate formation at −78° C. The homogeneous brown solution was worked up as described in Example 1c to provide the impure crude title compound as a very dark brown thick oil (14.97 g). $^1$H-NMR (300 MHz, CDCl$_3$) δ 9.28 (s, 1H), 8.41 (d, 1H), 8.10 (dd, 1H), 7.80 (d, 1H), 3.8-3.5 (m, 4H), 3.66 (s, 3H), 2.45-2.35 (m, 4H), 1.46 (s, 9H). LC/MS (ESI): calcd mass 497.1, found 398.0 (MH-Boc)+.

c. 6-Iodo-4-piperidin-4-yl-quinazoline

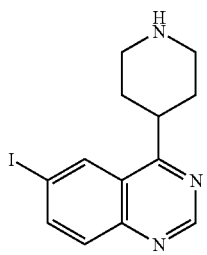

A mixture of 4-(6-iodo-quinazolin-4-yl)-piperidine-1,4-dicarboxylic acid 1-tert-butyl ester 4-methyl ester (14.21 g, 28.6 mmol), prepared as described in the preceding step, LiCl (2.38 g, 56.1 mmol), water (1.54 mL, 85.8 mmol), and DMSO (14 mL) was stirred at 150° C. under air for 3 h in a 500 mL flask fitted with a lightly capped Liebig condenser to minimize loss of reagent water while allowing gas escape. The reaction was then allowed to cool to rt, 2 M HCl (aq) (100 mL) was added, and the mixture was stirred at 100° C. for 10 min (Caution: Gas evolution). The reaction was cooled on an ice bath, 2.5 M NaOH (100 mL) was added, and the reaction was extracted with DCM (1×250 mL and 1×50 mL). The organic layers were combined, dried (Na$_2$SO$_4$), and concentrated to provide a 60:40 mixture of the title compound and its methyl ester, contaminated with DMSO, as a dark green oil (10.5 g). This material was resubjected to Krapchow decarboxylation conditions using LiCl (2.41 g, 63 mmol), water (1.54 mL, 85.8 mmol), and DMSO (4 mL) (~7 mL total DMSO) for an additional 5 h at 150° C. After a total of 8 h at 150° C., the reaction was allowed to cool to rt, and 3 M HCl (100 mL) was added (gas evolution) and the reaction stirred at 100° C. for 15 min. The reaction was then stirred at 0° C. while 2.5 M NaOH (120 mL) was added slowly over ~30 s to pH >12 (paper), and the cream-colored opaque slurry was extracted with 9:1 DCM/MeOH (4×100 mL). The combined organic layers were dried (Na$_2$SO$_4$) and concentrated under reduced pressure to provide the title compound as a clear dark green oil contaminated with DMSO and an aromatic impurity (5.97 g). $^1$H-NMR (300 MHz, CDCl$_3$) δ 9.27 (s, 1H), 8.52 (d, 1H), 8.12 (dd, 1H), 7.78 (d, 1H), 3.68-3.55 (m, 1H), 3.36-3.27 (m, 2H), 2.92 (td, 2H), 2.1-1.8 (m, 5H). LC/MS (ESI): calcd mass 339.0, found 340.1 (MH)$^+$.

d. 4-(6-Iodo-quinazolin-4-yl)-piperidine-1-carboxylic acid (4-isopropoxy-phenyl)-amide

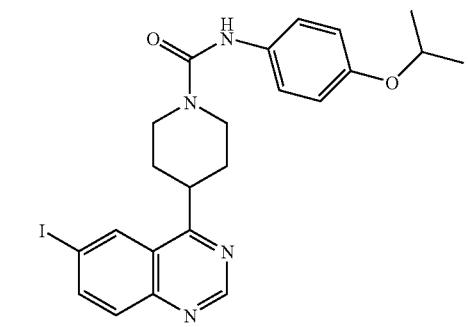

A solution of impure 6-iodo-4-piperidin-4-yl-quinazoline (4.00 g, "11.8 mmol"), as prepared in the preceding step, in CHCl$_3$ (20 mL) was treated with (4-isopropoxy-phenyl)-carbamic acid 4-nitro-phenyl ester (4.10 g, 13.0 mmol), prepared as described in Example 1a, in one portion at rt under air. DIEA (2.15 mL, 13.0 mmol) was then added in one portion, and residual nitrophenyl ester and DIEA was transferred to the reaction with additional CHCl$_3$ (20 mL). After 8 h rt stirring, the reaction was washed in succession with 1 M NaH$_2$PO$_4$ (50 mL) and 2 M K$_2$CO$_3$ (1×50 mL). The organic phase was filtered, the filter cake was washed with DCM (2×10 mL), and the combined filtrates were dried (Na$_2$SO$_4$) and concentrated under reduced pressure. Flash chromatography of the residue (1:2 hex/EtOAc) afforded the title compound as a beige foam (2.58 g, 42%). $^1$H-NMR (300 MHz, CDCl$_3$) δ 9.26 (s, 1H), 8.52 (d, 1H), 8.13 (dd, 1H), 7.80 (d, 1H), 7.25 (m, 2H), 6.83 (m, 2H), 6.33 (br s, 1H), 4.48 (heptet, 1H), 4.32-4.22 (m, 2H), 3.68 (tt, 1H), 3.17 (td, 2H), 2.21-1.92 (m, 4H), 1.32 (d, 6H). LC/MS (ESI): calcd mass 516.1, found 517.2 (MH)$^+$.

Example 12

4-[6-(3-Hydroxy-prop-1-ynyl)-quinazolin-4-yl]-piperidine-1-carboxylic acid (4-isopropoxy-phenyl)-amide

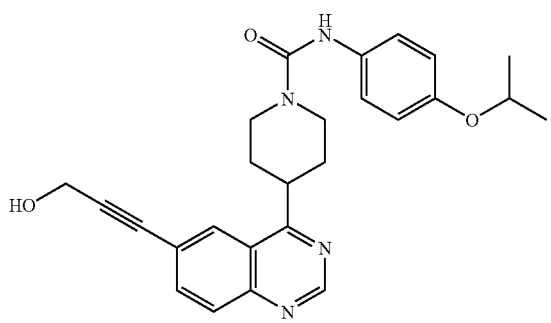

A mixture of 4-(6-iodo-quinazolin-4-yl)-piperidine-1-carboxylic acid (4-isopropoxy-phenyl)-amide (1.056 g, 2.05 mmol), as prepared in Example 11d, CuI (3.9 mg, 20.5 μmol), trans-PdCl$_2$[P(C$_6$H$_5$)$_3$]$_2$ (26.8 mg, 38.2 μmol), propargyl alcohol (139 μL, 2.36 mmol), and diethylamine (3.4 mL) was flushed with a stream of argon for 30 s, and then quickly sealed and vigorously stirred at rt under argon for 5 h. The resulting dark brown bilayer was concentrated under reduced pressure at rt, dissolved in DCM (10 mL), and vigorously shaken with 0.75 M EDTA (tetrasodium salt) (1×2 mL). The light green aqueous layer was extracted with DCM (1×10 mL), the organic layers were combined, dried (Na$_2$SO$_4$), and concentrated to give a beige foam soluble in 9:1 EtOAc/DCM (~5 mL). Flash chromatography (1:9 hex/EtOAc→EtOAc) provided the title compound as a yellow foam (825 mg, 91%). $^1$H-NMR (300 MHz, CDCl$_3$) δ 9.24 (s, 1H), 8.26 (d, 1H), 8.01 (d, 1H), 7.87 (dd, 1H), 7.25 (m, 2H), 6.85 (m, 2H), 6.33 (br s, 1H), 4.59 (d, 2H), 4.48 (heptet, 1H), 4.32-4.23 (m, 2H), 3.71 (m, 1H), 3.22-3.10 (m, 2H), 2.21-1.94 (m, 5H), 1.32 (d, 6H). LC/MS (ESI): calcd mass 444.2, found 445.2 (MH)$^+$.

Example 13

4-[6-(3-Diethylamino-prop-1-ynyl)-quinazolin-4-yl]-piperidine-1-carboxylic acid (4-isopropoxy-phenyl)-amide

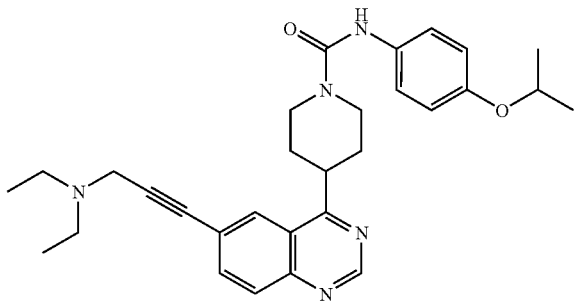

a. Methanesulfonic acid 3-{4-[1-(4-isopropoxy-phenylcarbamoyl)-piperidin-4-yl]-quinazolin-6-yl}-prop-2-ynyl ester

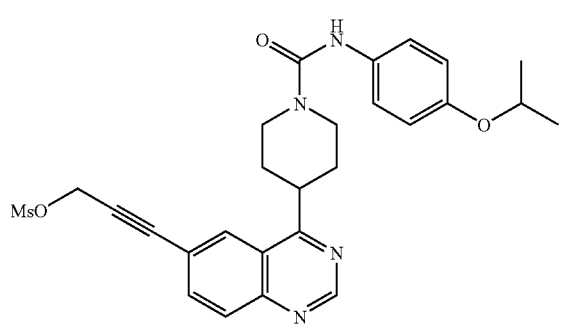

A solution of 4-[6-(3-hydroxy-prop-1-ynyl)-quinazolin-4-yl]-piperidine-1-carboxylic acid (4-isopropoxy-phenyl)-amide (816 mg, 1.84 mmol), as prepared in Example 12, and DIEA (350 μL, 2.12 mmol) in DCM (13 mL) was treated with methanesulfonyl chloride (157 μL, 2.02 mmol) dropwise over 1 min with stirring at 0° C. under positive argon pressure. The ice bath was immediately removed, and the reaction was stirred at rt for 1 h 15 min. Flash chromatographic purification of the crude reaction mixture (1:9 hex/EtOAc→EtOAc) afforded the title compound (896 mg, 93%). $^1$H-NMR (300 MHz, CDCl$_3$) δ 9.27 (s, 1H), 8.31 (d, 1H), 8.04 (d, 1H), 7.89 (dd, 1H), 7.26 (m, 2H), 6.85 (m, 2H), 6.34 (br s, 1H), 5.15 (s, 2H), 4.49 (heptet, 1H), 4.33-4.23 (m, 2H), 3.73 (m, 1H), 3.25-3.11 (m, 2H), 3.18 (s, 3H), 2.22-1.94 (m, 4H), 1.32 (d, 6H). LC/MS (ESI): calcd mass 522.2, found 523.3 (MH)$^+$.

b. 4-[6-(3-Diethylamino-prop-1-ynyl)-quinazolin-4-yl]-piperidine-1-carboxylic acid (4-isopropoxy-phenyl)-amide

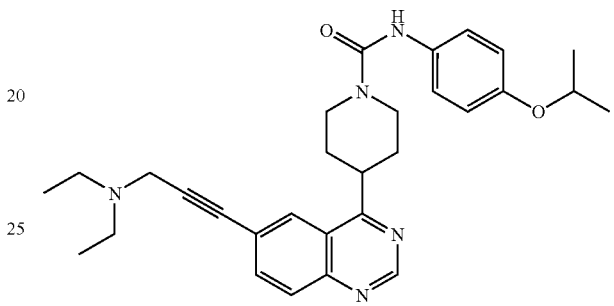

A solution of methanesulfonic acid 3-{4-[1-(4-isopropoxy-phenylcarbamoyl)-piperidin-4-yl]-quinazolin-6-yl}-prop-2-ynyl ester (180.0 mg, 345 μmol), as prepared in the previous step, in CH$_3$CN (0.5 mL) was treated with diethylamine (79 μL, 759 μmol) very rapidly by syringe in 1 portion with stirring at rt, and the pale yellow solution was allowed to stir at rt for 2 h. Purification of the crude reaction with a flash silica column (1:2 hex/acetone) afforded the title compound as an off-white foam (136 mg, 79%). $^1$H-NMR (300 MHz, CDCl$_3$) δ 9.22 (s, 1H), 8.21 (d, 1H), 7.99 (d, 1H), 7.88 (dd, 1H), 7.25 (m, 2H), 6.84 (m, 2H), 6.38 (br s, 1H), 4.48 (heptet, 1H), 4.32-4.22 (m, 2H), 3.78-3.65 (m, 1H), 3.70 (s, 2H), 3.16 (td, 2H), 2.68 (q, 4H), 2.21-1.94 (m, 4H), 1.31 (d, 6H), 1.15 (t, 6H). LC/MS (ESI): calcd mass 499.3, found 500.5 (MH)$^+$. A select fraction of this material was submitted for combustion analysis: Anal. Calcd for C$_{30}$H$_{37}$N$_5$O$_2$.0.18 water: C, 71.65; H, 7.49; N, 13.93. Found: C, 71.7; H, 7.55; N, 13.92.

Example 14

4-[6-(3-Piperidin-1-yl-prop-1-ynyl)-quinazolin-4-yl]-piperidine-1-carboxylic acid (4-isopropoxy-phenyl)-amide

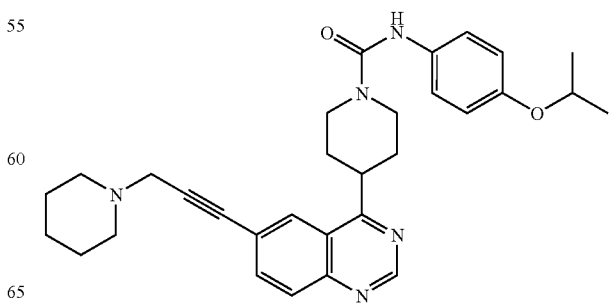

Prepared essentially as described in Example 13b, using piperidine (10.9 mg, 63%). ¹H-NMR (400 MHz, CDCl₃) δ 9.23 (s, 1H), 8.24 (d, 1H), 7.99 (d, 1H), 7.89 (dd, 1H), 7.28-7.23 (m, 2H), 6.88-6.82 (m, 2H), 6.36 (br s, 1H), 4.49 (heptet, 1H), 4.32-4.24 (m, 2H), 3.72 (tt, 1H), 3.52 (s, 2H), 3.16 (td, 2H), 2.62 (br s, 4H), 2.18-2.05 (m, 2H), 2.05-1.95 (m, 2H), 1.68 (m, 4H), 1.49 (br m, 2H), 1.32 (d, 6H). LC/MS (ESI): calcd mass 511.3, found 512.4 (MH)⁺.

Example 15

4-[6-(3-Morpholin-4-yl-prop-1-ynyl)-quinazolin-4-yl]-piperidine-1-carboxylic acid (4-isopropoxy-phenyl)-amide

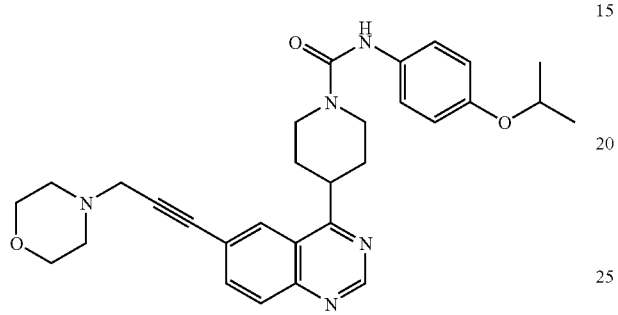

Prepared essentially as described in Example 13b, using morpholine. Flash chromatography (1:2 hex/acetone) afforded the title compound as a white foam (148.9 mg, 87%). ¹H-NMR (300 MHz, CDCl₃) δ 9.23 (s, 1H), 8.23 (d, 1H), 8.00 (d, 1H), 7.88 (dd, 1H), 7.25 (m, 2H), 6.85 (m, 2H), 6.31 (br s, 1H), 4.49 (heptet, 1H), 4.32-4.23 (m, 2H), 3.84-3.66 (m, 5H), 3.58 (s, 2H), 3.18 (td, 2H), 2.69 (m, 4H), 2.22-2.05 (m, 2H), 2.05-1.94 (m, 2H), 1.32 (d, 6H). LC/MS (ESI): calcd mass 513.3, found 514.5 (MH)⁺. A select fraction of this material was submitted for combustion analysis: Anal. Calcd for $C_{30}H_{35}N_5O_3 \cdot 0.20$ water: C, 69.66; H, 6.9; N, 13.54. Found: C, 69.58; H, 6.81; N, 13.49.

Example 16

N-(4-Isopropyl-phenyl)-2-(4-quinazolin-4-yl-piperidin-1-yl)-acetamide

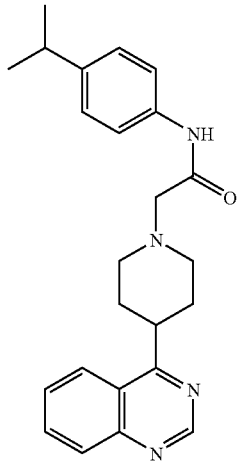

Prepared essentially as described for Example 9 using 4-piperidin-4-yl-quinazoline, prepared as described in Example 7c. Flash chromatography (1:4 hex/EtOAc) provided the title compound (19.3 mg, 34%). ¹H-NMR (300 MHz, CDCl₃) δ 9.30 (s, 1H), 9.12 (br s, 1H), 8.17 (m, 1H), 8.08 (m, 1H), 7.91 (m, 1H), 7.67 (m, 1H), 7.52 (m, 2H), 7.21 (m, 2H), 3.61 (tt, 1H), 3.22 (s, 2H), 3.19-3.10 (m, 2H), 2.89 (heptet, 1H), 2.53 (td, 2H), 2.25 (qd, 2H), 2.00 (m, 2H), 1.24 (d, 6H). LC/MS (ESI): calcd mass 388.2, found 389.4 (MH)⁺.

Example 17

4-(6,7-Dimethoxy-quinazolin-4-yl)-piperidine-1-carboxylic acid (6-cyclobutoxy-pyridin-3-yl)-amide

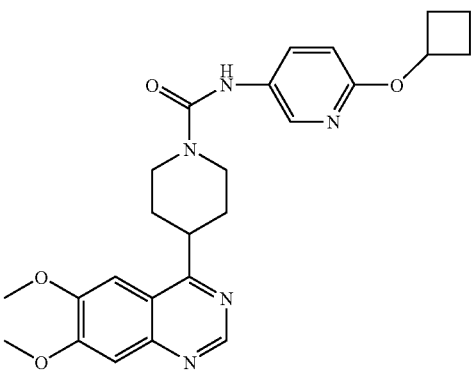

a. 2-Cyclobutoxy-5-nitro-pyridine

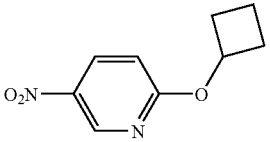

A mixture of 2-chloro-5-nitropyridine (7.12 g, 45.0 mmol) and cyclobutanol (3.40 g, 47.2 mmol) in THF (30 mL) was vigorously stirred at 0° C. while NaH (1.18 g, 46.7 mmol) was added in three portions over ~10-20 s under air (Caution: Extensive gas evolution). Reaction residue was rinsed down with additional THF (5 mL), followed by stirring under positive argon pressure in the ice bath for 1-2 more minutes. The ice bath was then removed and the brown homogeneous solution was stirred at "rt" for 1 h. The reaction was concentrated under reduced pressure at 80° C., taken up in 0.75 M EDTA (tetrasodium salt) (150 mL), and extracted with DCM (1×100 mL, 1×50 mL). The combined organic layers were dried (Na₂SO₄), concentrated, taken up in MeOH (2×100 mL) and concentrated under reduced pressure at 60° C. to provide the title compound as a thick dark amber oil that crystallized upon standing (7.01 g, 80%). ¹H NMR (300 MHz, CDCl₃) δ 9.04 (dd, J=2.84 and 0.40 Hz, 1H), 8.33 (dd, J=9.11 and 2.85 Hz, 1H), 6.77 (dd, J=9.11 and 0.50 Hz, 1H), 5.28 (m, 1H), 2.48 (m, 2H), 2.17 (m, 2H), 1.87 (m, 1H), 1.72 (m, 1H).

b. 6-Cyclobutoxy-pyridin-3-ylamine

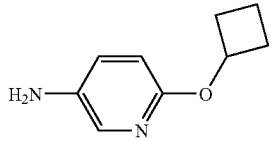

A flask containing 10% w/w Pd/C (485 mg) was gently flushed with argon while slowly adding MeOH (50 mL) along the sides of the flask, followed by the addition in ~5 mL portions of a solution of 2-cyclobutoxy-5-nitro-pyridine (4.85 g, 25 mmol), as prepared in the previous step, in MeOH (30 mL). (Caution: Large scale addition of volatile organics to Pd/C in the presence of air can cause fire.) The flask was then evacuated one time and stirred under H2 balloon pressure for 2 h at rt. The reaction was then filtered, and the clear amber filtrate was concentrated, taken up in toluene (2×50 mL) to remove residual MeOH, and concentrated under reduced pressure to provide the crude title compound as a translucent dark brown oil with a faint toluene smell (4.41 g, "108%" crude yield). $^1$H NMR (300 MHz, CDCl$_3$) δ 7.65 (d, J=3.0 Hz, 1H), 7.04 (dd, J=8.71 and 2.96 Hz, 1H), 6.55 (d, J=8.74 Hz, 1H), 5.04 (m, 1H), 2.42 (m, 2H), 2.10 (m, 2H), 1.80 (m, 1H), 1.66 (m, 1H). LC-MS (ESI): calcd mass 164.1, found 165.2 (MH$^+$).

c. (6-Cyclobutoxy-pyridin-3-yl)-carbamic acid 4-nitro-phenyl ester

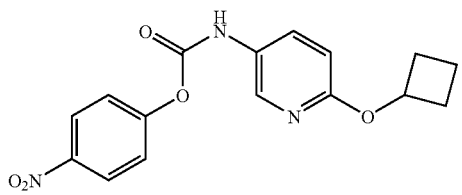

A mixture of 6-cyclobutoxy-pyridin-3-ylamine (4.41 g, assume 25 mmol), as prepared in the previous step, and CaCO$_3$ (3.25 g, 32.5 mmol) (10 micron powder) was treated with a homogeneous solution of 4-nitrophenyl chloroformate (5.54 g, 27.5 mmol) in toluene (28 mL) in one portion at rt, and was stirred at "rt" (reaction warmed spontaneously) for 2 h. The reaction mixture was then directly loaded onto a flash silica column (95:5 DCM/MeOH→9:1 DCM/MeOH) to afford 5.65 g of material, which was further purified by trituration with hot toluene (1×200 mL) to provide the title compound (4.45 g, 54%). $^1$H NMR (400 MHz, CDCl$_3$) δ 8.28 (m, 2H), 8.12 (d, 1H), 7.81 (m, 1H), 7.39 (m, 2H), 6.85 (br s, 1H), 6.72 (d, 1H), 5.14 (m, 1H), 2.45 (m, 2H), 2.13 (m, 2H), 1.84 (m, 1H), 1.68 (m, 1H). LC-MS (ESI): calcd mass 329.1, found 330.1 (MH$^+$).

d. 4-(6,7-Dimethoxy-quinazolin-4-yl)-piperidine-1-carboxylic acid (6-cyclobutoxy-pyridin-3-yl)-amide

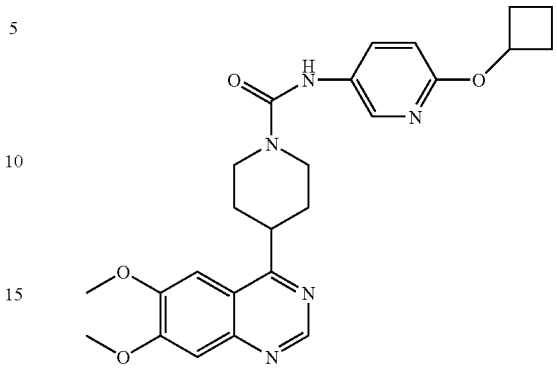

A mixture of 6,7-dimethoxy-4-piperidin-4-yl-quinazoline (114.1 mg, 418 μmol), as prepared in Example 1d, (6-cyclobutoxy-pyridin-3-yl)-carbamic acid 4-nitro-phenyl ester (151 mg, 459 μmol), as prepared in the preceding step, and DCM (818 μL) was treated with TEA (63 μL, 455 μmol) in one portion, and stirred under air at 45° C. for 30 min. The reaction mixture was then directly applied to a flash silica column (3:4 hex/acetone) to provide the title compound as a foam (141.1 mg, 73%). This material was taken up in 2 M K$_2$CO$_3$ (2 mL) and extracted with DCM (2×2 mL). The combined organic layers were dried (Na$_2$SO$_4$), concentrated, and repurified with a silica flash column (9:2 EtOAc/acetone) to provide analytically pure title compound as an off-white foam (84.4 mg, 44%). $^1$H NMR (300 MHz, CDCl$_3$) δ 9.08 (s, 1H), 7.97 (d, 1H), 7.77 (dd, 1H), 7.34 (s, 1H), 7.26 (s, 1H), 6.67 (d, 1H), 6.39 (br s, 1H), 5.11 (m, 1H), 4.32-4.22 (m, 2H), 4.07 (s, 3H), 4.06 (s, 3H), 3.60 (tt, 1H), 3.18 (td, 2H), 2.51-2.37 (m, 2H), 2.24-1.94 (m, 6H), 1.89-1.57 (m, 2H). LC-MS (ESI): calcd mass 463.2, found 464.3 (MH$^+$). Anal. Calcd for C$_{25}$H$_{29}$N$_5$O$_4$: C, 64.78; H, 6.31; N, 15.11. Found: C, 64.64; H, 6.24; N, 15.04.

Alternatively, 4-(6,7-dimethoxy-quinazolin-4-yl)-piperidine-1-carboxylic acid (6-cyclobutoxy-pyridin-3-yl)-amide (Example 17d) can be prepared similarly to the procedure given for Example 51:

$^1$H NMR (300 MHz, CDCl$_3$) δ 9.08 (s, 1H), 8.02 (d, J=2.85 Hz, 1H), 7.82 (dd, J=8.64 and 2.69 Hz, 1H), 7.37 (s, 1H), 7.26 (s, 1H), 6.68 (d, J=8.83 Hz, 1H), 6.49 (s, 1H), 5.10 (m, 1H), 4.29 (m, 2H), 4.08 (s, 3H), 4.07 (s, 3H), 3.61 (m, 1H), 3.18 (td, J=12.87 and 2.88 Hz, 2H), 2.43 (m, 2H), 1.95-2.22 (m, 6H), 1.58-1.87 (m, 2H). LC-MS (ESI): calcd mass 463.2, found 464.4 (MH$^+$).

Example 18

4-(6,7-Dimethoxy-quinazolin-4-yl)-piperidine-1-carboxylic acid (4-morpholin-4-yl-phenyl)-amide

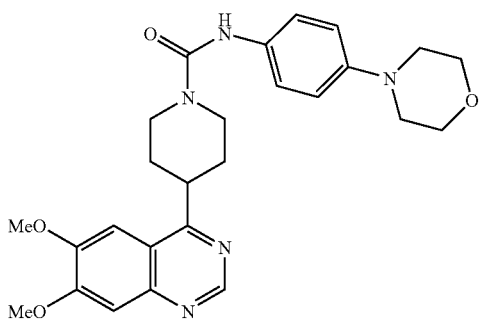

a. (4-Morpholin-4-yl-phenyl)-carbamic acid 4-nitro-phenyl ester

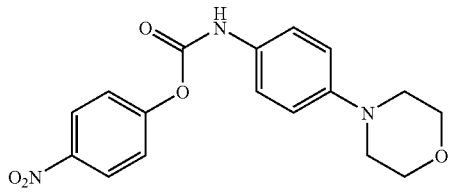

A mixture of 4-morpholinoaniline (1.01 g, 5.68 mmol) and CaCO$_3$ (743 mg, 7.42 mmol) (10 micron powder) was treated with a solution of 4-nitrophenyl chloroformate (1.49 g, 7.39 mmol) in DCM (7.5 mL) in one portion under air on an ice bath. The thick, easily stirred reaction slurry was stirred for 1-2 min on the ice bath before stirring at rt for 1 h. The slurry was then diluted with 9:1 DCM/MeOH (7.5 mL) and directly applied to a flash silica column (95:5 DCM/MeOH) to provide 0.7 g of material. This was further purified by trituration with hot toluene (25 mL) to afford the title compound as a light olive green powder (444 mg, 23%). $^1$H NMR (300 MHz, CDCl$_3$) δ 8.28 (m, 2H), 7.42-7.31 (m, 4H), 6.95-6.85 (m, 3H), 3.86 (m, 4H), 3.13 (m, 4H).

b. 4-(6,7-Dimethoxy-quinazolin-4-yl)-piperidine-1-carboxylic acid (4-morpholin-4-yl-phenyl)-amide

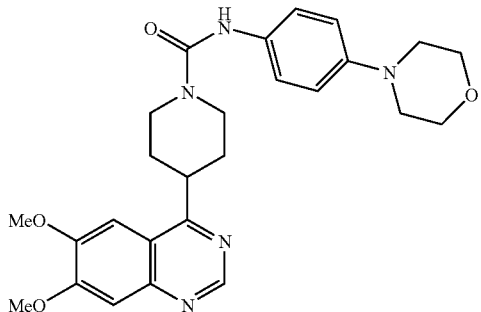

A mixture of 6,7-dimethoxy-4-piperidin-4-yl-quinazoline (111.4 mg, 408 μmol), prepared as described in Example 1d, but with purification by silica flash chromatography (9:1 DCM/MeOH saturated with NH3), (4-morpholin-4-yl-phenyl)-carbamic acid 4-nitro-phenyl ester (147 mg, 429 μmol), prepared as described in the previous step, and DCM (700 μL) was treated with TEA (63 μL, 449 μmol) in one portion at rt. The homogeneous amber solution was stirred at rt for 3.5 h, diluted with DCM (1.3 mL), and washed with 2 M K$_2$CO$_3$ (2 mL). The aqueous layer was extracted with DCM (2×2 mL), the organic layers were combined, dried (Na$_2$SO$_4$), and concentrated, and the residue was purified with silica flash chromatography (1:1 DCM/acetone) to afford the title compound (167.1 mg, 86%). $^1$H-NMR (300 MHz, CDCl$_3$): δ 9.08 (s, 1H), 7.34 (s, 1H), 7.31-7.24 (m, 3H), 6.88 (m, 2H), 6.31 (br s, 1H), 4.32-4.22 (m, 2H), 4.07 (s, 3H), 4.06 (s, 3H), 3.86 (m, 4H), 3.59 (m, 1H), 3.23-3.07 (m, 6H), 2.24-2.07 (m, 2H), 2.05-1.93 (m, 2H). LC/MS (ESI): calcd mass 477.2, found 478.3 (MH$^+$). Select fractions of this material were combined (112.5 mg) and submitted for combustion analysis: Anal. Calcd for C$_{26}$H$_{31}$N$_5$O$_4$: C, 65.39; H, 6.54; N, 14.67. Found: C, 65.26; H, 6.58; N, 14.51.

Alternatively, the following procedure can be used to prepare 4-(6,7-dimethoxy-quinazolin-4-yl)-piperidine-1-carboxylic acid (4-morpholin-4-yl-phenyl)-amide (Example 18b):

Prepared as described in Example 3b except that 4-morpholin-4-yl-phenylamine was used in place of 4-imidazol-1-yl-phenylamine. Purification by Preparative TLC (silica gel, 5% MeOH/DCM) yielded 7.3 mg (31%) of pure 4-(6,7-dimethoxy-quinazolin-4-yl)-piperidine-1-carboxylic acid (4-morpholin-4-yl-phenyl)-amide. LC/MS (ESI): calcd mass 477.2, found 478.5 (MH$^+$).

Example 19

4-(6,7-Dimethoxy-quinazolin-4-yl)-piperidine-1-carboxylic acid (4-piperidin-1-yl-phenyl)-amide

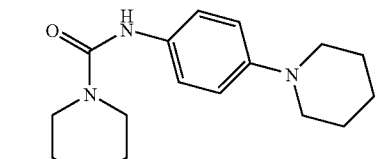

(4-Piperidin-1-yl-phenyl)-carbamic acid 4-nitro-phenyl ester

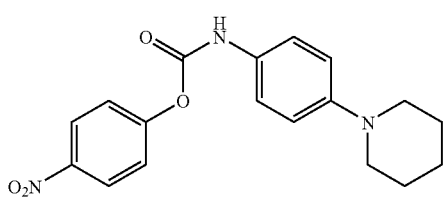

Prepared essentially as described in Example 18a, using 4-piperidinoaniline and toluene solvent. Silica flash chromatography (5:2 hex/EtOAc→EtOAc→9:1 DCM/MeOH) provided the target compound as a grey powder (1.416 g, 73%). $^1$H-NMR (300 MHz, CDCl$_3$): δ 8.28 (m, 2H), 7.39 (m, 2H), 7.31 (m, 2H), 6.93 (m, 2H), 6.82 (br s, 1H), 3.17-3.09 (m, 4H), 1.77-1.66 (m, 4H), 1.63-1.54 (m, 2H). LC/MS (ESI): calcd mass 341.1, found 342.2 (MH$^+$).

b. 4-(6,7-Dimethoxy-quinazolin-4-yl)-piperidine-1-carboxylic acid (4-piperidin-1-yl-phenyl)-amide

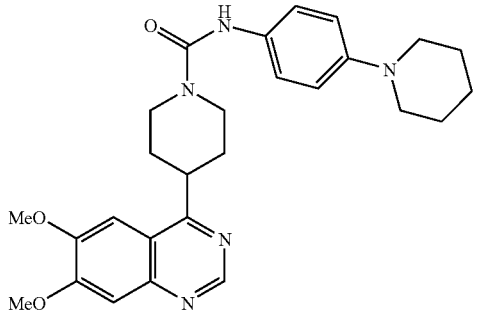

Prepared essentially as described in Example 18b using (4-piperidin-1-yl-phenyl)-carbamic acid 4-nitro-phenyl ester, as prepared in the previous step. Purification of the reaction mixture with silica flash chromatography (12:1 EtOAc/acetone→95:5 EtOAc/MeOH) provided the title compound as a light pink foam (91.3 mg, 46%). $^1$H-NMR (300 MHz, CDCl$_3$): δ 9.08 (s, 1H), 7.34 (s, 1H), 7.27-7.21 (m, 3H), 6.90 (m, 2H), 6.30 (s, 1H), 4.30-4.22 (m, 2H), 4.07 (s, 3H), 4.06 (s, 3H), 3.59 (m, 1H), 3.21-3.04 (m, 6H), 2.21-2.08 (m, 2H), 2.03-1.94 (m, 2H), 1.75-1.66 (m, 4H), 1.60-1.51 (m, 2H). LC/MS (ESI): calcd mass 475.3, found 476.5 (MH)$^+$. Anal. Calcd for C$_{27}$H$_{33}$N$_5$O$_3$: C, 68.19; H, 6.99; N, 14.73. Found: C, 67.96; H, 6.93; N, 14.58.

Alternatively, the following procedure can be used to prepare 4-(6,7-dimethoxy-quinazolin-4-yl)-piperidine-1-carboxylic acid (4-piperidin-1-yl-phenyl)-amide (Example 19b):

Prepared as described in Example 3b except that 4-piperidin-1-yl-phenylamine was used in place of 4-imidazol-1-yl-phenylamine. Purification by Preparative TLC (silica gel, 5% MeOH/DCM) yielded 7.6 mg (32%) of pure 4-(6,7-dimethoxy-quinazolin-4-yl)-piperidine-1-carboxylic acid (4-piperidin-1-yl-phenyl)amide. $^1$H-NMR (300 MHz, CDCl$_3$): 9.07 (s, 1H), 7.34 (s, 1H), 7.31-7.23 (m, 3H), 6.98 (m, 2H), 6.42 (bs, 1H), 4.28 (m, 2H), 4.06 (s, 6H), 3.58 (m, 1H), 3.25-3.00 (m, 6H), 2.23-2.05 (m, 2H), 1.98 (m, 2H), 1.75 (m, 4H), 1.58 (m, 2H). LC/MS (ESI): calcd mass 475.3, found 476.5 (MH)$^+$.

Example 20

4-(6,7-Dimethoxy-quinazolin-4-yl)-piperidine-1-carboxylic acid [4-(4-methyl-piperazin-1-yl-phenyl)]-amide

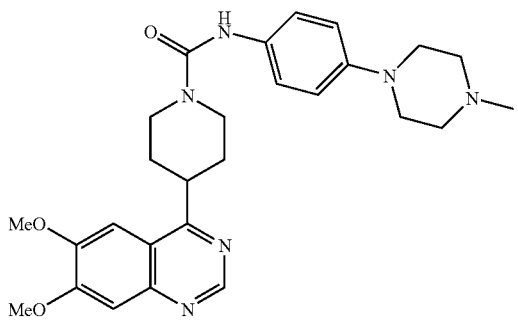

This was prepared as described in Example 3b except that 4-(4-methyl-piperazin-1-yl)-phenylamine was used in place of 4-imidazol-1-yl-phenylamine. Purification by Preparative TLC (silica gel, 5% MeOH/DCM) yielded 14.5 mg (30%) of pure 4-(6,7-dimethoxy-quinazolin-4-yl)-piperidine-1-carboxylic acid [4-(4-methyl-piperazin-1-yl-phenyl)]-amide. $^1$H-NMR (300 MHz, CDCl$_3$): 9.07 (s, 1H), 7.32 (s, 1H), 7.30-7.22 (m, 3H), 6.88 (d, 2H), 6.39 (s, 1H), 4.27 (m, 2H), 4.06 (s, 6H), 3.58 (m, 1H), 3.23-3.13 (m, 4H), 2.63 (m, 4H), 2.38 (s, 3H), 2.25-2.04 (m, 4H), 1.98 (m, 2H). LC/MS (ESI): calcd mass 490.3, found 491.5 (MH)$^+$.

Example 21

4-(6,7-Dimethoxy-quinazolin-4-yl)-piperidine-1-carboxylic acid (4-cyclohexyl-phenyl)-amide

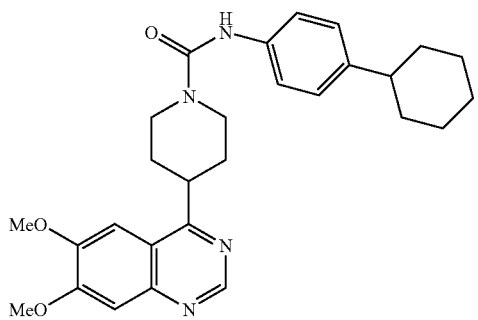

This was prepared as described in Example 3b except that 4-cyclohexyl-phenylamine was used in place of 4-imidazol-1-yl-phenylamine. Purification by Preparative TLC (silica gel, 5% MeOH/DCM) yielded 20.4 mg (43%) of pure 4-(6,7-dimethoxy-quinazolin-4-yl)-piperidine-1-carboxylic acid (4-cyclohexyl-phenyl)-amide. $^1$H-NMR (300 MHz, CDCl$_3$): 9.08 (s, 1H), 7.37 (s, 1H), 7.29 (s, 1H), 7.26 (m, 2H), 7.13 (d, 2H), 6.42 (s, 1H), 4.27 (m, 2H), 4.07 (s, 6H), 3.60 (m, 1H), 3.13 (m, 2H), 2.45 (m, 1H), 2.23-2.05 (m, 2H), 1.98 (m, 2H), 1.89-1.60 (m, 6H), 1.36 (m, 4H). LC/MS (ESI): calcd 474.3, found 475.4 (MH)$^+$.

Example 22

4-(6,7-Dimethoxy-quinazolin-4-yl)-piperidine-1-carboxylic acid (4-hydroxymethyl-phenyl)-amide

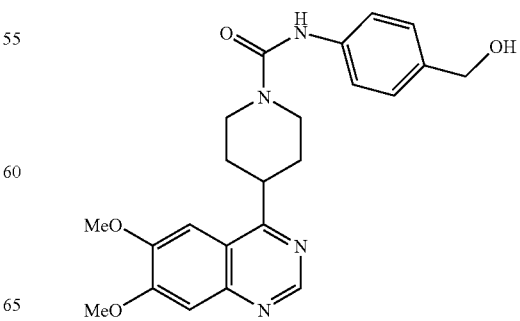

This was prepared as described in Example 3b except that 4-hydroxymethyl-phenylamine was used in place of 4-imidazol-1-yl-phenylamine. Purification by Preparative TLC (silica gel, 5% MeOH/DCM) yielded 11.2 mg (27%) of pure 4-(6,7-dimethoxy-quinazolin-4-yl)-piperidine-1-carboxylic acid (4-hydroxymethyl-phenyl)-amide. $^1$H-NMR (300 MHz, CDCl$_3$): 9.05 (s, 1H), 7.35 (d, 3H), 7.28 (d, 3H), 6.64 (s, 1H), 4.78 (bs, 1H), 4.62 (s, 2H), 4.29 (m, 2H), 4.07 (s, 6H), 3.60 (m, 1H), 3.16 (m, 2H), 2.22-2.04 (m, 2H), 2.04-1.80 (m, 2H). LC/MS (ESI): calcd 422.2, found 423.3 (MH)$^+$.

Example 23

4-(6,7-Dimethoxy-quinazolin-4-yl)-piperidine-1-carboxylic acid (1H-indol-5-yl)-amide

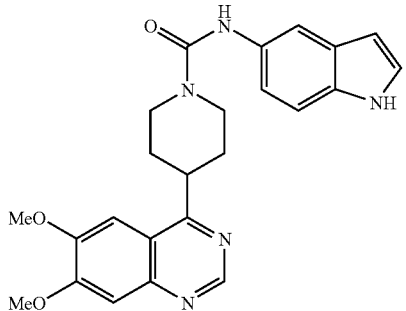

This was prepared as described in Example 3b except that 1H-indol-5-ylamine was used in place of 4-imidazol-1-yl-phenylamine. Purification by Preparative TLC (silica gel, 5% MeOH/DCM) yielded 12.4 mg (29%) of pure 4-(6,7-dimethoxy-quinazolin-4-yl)-piperidine-1-carboxylic acid (1H-indol-5-yl)-amide. $^1$H-NMR (300 MHz, CDCl$_3$): 9.08 (s, 1H), 8.29 (bs, 1H), 7.61 (s, 1H), 7.36 (s, 1H), 7.32-7.25 (m, 2H), 7.19-7.10 (m, 2H), 6.48 (m, 2H), 4.31 (m, 2H), 4.07 (s, 6H), 3.60 (m, 1H), 3.16 (m, 2H), 2.25-2.08 (m, 2H), 2.00 (m, 2H). LC/MS (ESI): calcd 431.2, found 432.3 (MH)$^+$.

Example 24

4-(6,7-Dimethoxy-quinazolin-4-yl)-piperidine-1-carboxylic acid benzothiazol-6-ylamide

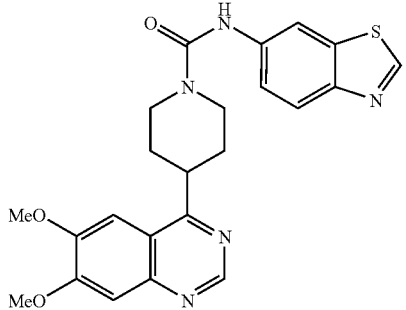

This was prepared as described in Example 3b except that benzothiazol-6-ylamine was used in place of 4-imidazol-1-yl-phenylamine. Purification by Preparative TLC (silica gel, 5% MeOH/DCM) yielded 10.3 mg (23%) of pure 4-(6,7-dimethoxy-quinazolin-4-yl)-piperidine-1-carboxylic acid benzothiazol-6-ylamide. $^1$H-NMR (300 MHz, CDCl$_3$): 9.09 (s, 1H), 8.87 (s, 1H), 8.32 (d, 1H), 8.00 (d, 1H), 7.41 (s, 1H), 7.33-7.24 (m, 2H), 6.82 (s, 1H), 4.34 (m, 2H), 4.08 (s, 6H), 3.64 (m, 1H), 3.22 (m, 2H), 2.30-1.90 (m, 4H). LC/MS (ESI): calcd mass 449.2, found 450.2 (MH)$^+$.

Example 25

4-(6,7-Dimethoxy-quinazolin-4-yl)-piperidine-1-carboxylic acid (4-acetylamino-phenyl)-amide

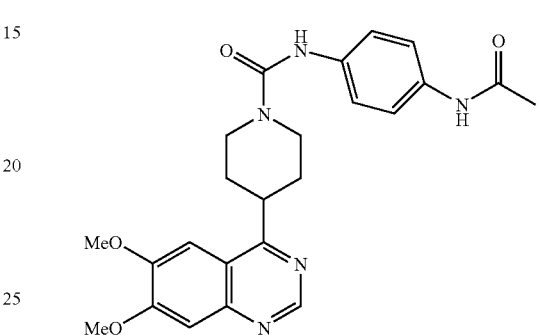

This was prepared as described in Example 3b except that N-(4-amino-phenyl)-acetamide was used in place of 4-imidazol-1-yl-phenylamine. Purification by Preparative TLC (silica gel, 5% MeOH/DCM) yielded 4.2 mg (10%) of pure 4-(6,7-dimethoxy-quinazolin-4-yl)-piperidine-1-carboxylic acid (4-acetylamino-phenyl)-amide. $^1$H-NMR (300 MHz, CDCl$_3$): 9.07 (s, 1H), 7.47-7.35 (m, 3H), 7.33-7.25 (m, 3H), 6.64 (s, 1H), 4.30 (m, 2H), 4.08 (s, 6H), 3.62 (m, 1H), 3.17 (m, 2H), 2.24-2.06 (m, 5H), 1.99 (m, 2H). LC/MS (ESI): calcd 449.2, found 450.4 (MH)$^+$.

Example 26

4-(6,7-Dimethoxy-quinazolin-4-yl)-piperidine-1-carboxylic acid (4-dimethylamino-phenyl)-amide

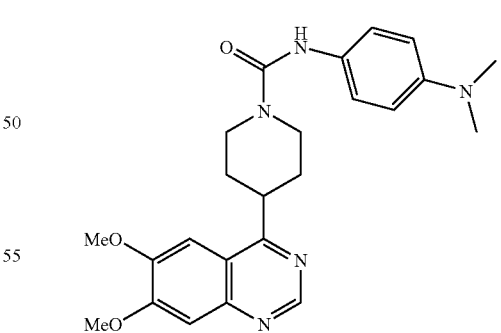

To a solution of 6,7-dimethoxy-4-piperidin-4-yl-quinazoline (27.5 mg, 0.1 mmol), as prepared in Example 1d, in anhydrous DMF, was added 4-dimethylamino-phenylisocyanate (25 mg, 0.15 mmol) and the mixture was stirred at rt overnight. It was then concentrated in vacuo and the residue was purified by Preparative TLC (silica gel, 5% MeOH/DCM) to yield 19 mg (44%) of pure 4-(6,7-Dimethoxy-quinazolin-4-yl)-piperidine-1-carboxylic acid (4-dimethylamino-phenyl)-amide. ¹H-NMR (300 MHz, CDCl₃): 9.07 (s, 1H), 7.33 (s, 1H), 7.28-7.17 (m, 3H), 6.9-6.56 (bs, 2H), 6.50-6.22 (bs, 1H), 4.26 (m, 2H), 4.06 (s, 6H), 3.57 (m, 1H), 3.14 (m, 2H), 3.02-2.76 (m, 6H), 2.22-1.90 (m, 4H). LC/MS (ESI): calcd mass 435.2, found 436.5 (MH)⁺.

Example 27

4-(6,7-Dimethoxy-quinazolin-4-yl)-piperidine-1-carboxylic acid (2,3-dihydro-benzofuran-5-yl)-amide

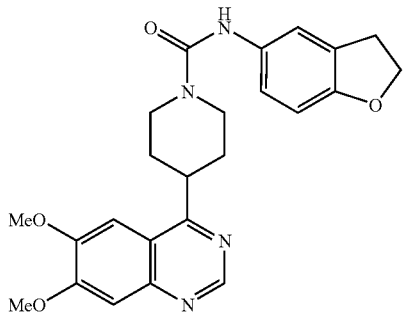

This was prepared as described in Example 26 except that 5-isocyanato-2,3-dihydro-benzofuran was used in place of 4-dimethylamino-phenylisocyanate. Purification by Preparative TLC (silica gel, 5% MeOH/DCM) yielded 15.7 mg (36%) of pure 4-(6,7-Dimethoxy-quinazolin-4-yl)-piperidine-1-carboxylic acid (2,3-dihydro-benzofuran-5-yl)-amide. ¹H-NMR (300 MHz, CDCl₃): 9.08 (s, 1H), 7.39 (s, 1H), 7.34 (s, 1H), 7.28-7.25 (s, 1H), 6.92 (d, 1H), 6.70 (d, 1H), 6.34 (s, 1H), 4.55 (t, 2H), 4.27 (m, 2H), 4.07 (s, 6H), 3.60 (m, 1H), 3.24-3.10 (m, 4H), 2.24-2.06 (m, 2H), 2.04-1.94 (m, 2H). LC/MS (ESI): calcd mass 434.2, found 435.4 (MH)⁺.

Example 28

1-[4-(6,7-Dimethoxy-quinazolin-4-yl)-piperidin-1-yl]-2-(4-isopropyl-phenyl)-ethanone

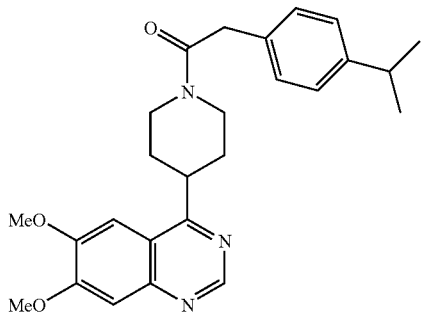

To a solution of 4-isopropylphenylacetic acid (36 mg, 0.2 mmol) in anhydrous DCM (1 mL) was added PS-carbodiimide (100 mg, 0.3 mmol) and the mixture was shaken at rt for 15 min. Then, a solution of 6,7-dimethoxy-4-piperidin-4-yl-quinazoline (27.5 mg, 0.1 mmol), as prepared in Example 1d, in anhydrous DMF (1 mL) was added to the mixture and it was shaken overnight at rt. It was then filtered and the resin was washed with THF/DCM and the combined filtrate and washings were concentrated in vacuo. The crude product was purified by flash column chromatography (silica gel, 1% MeOH/DCM) to yield 13.4 mg (31%) of pure 1-[4-(6,7-dimethoxy-quinazolin-4-yl)-piperidin-1-yl]-2-(4-isopropyl-phenyl)-ethanone. ¹H-NMR (300 MHz, CDCl₃): δ 9.06 (s, 1H), 7.39 (s, 1H), 7.26 (s, 1H), 7.23-7.19 (m, 4H), 4.82 (d, 1H), 4.17-4.00 (m, 7H), 3.76 (m, 2H), 3.57 (m, 1H), 3.23 (m, 1H), 2.96-2.80 (m, 2H), 2.06-1.80 (m, 4H), 1.23 (d, 6H). LC/MS (ESI): calcd mass 433.2, found 434.4 (MH)⁺.

Example 29

4-(7-Chloro-quinazolin-4-yl)-piperidine-1-carboxylic acid (4-isopropoxy-phenyl)-amide

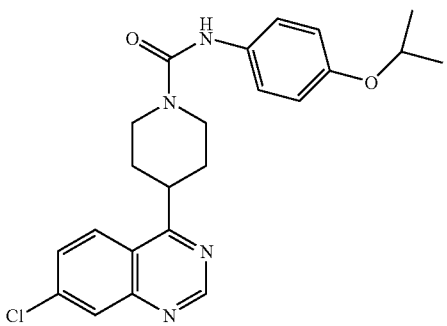

To a stirred mixture of 4,7-Dichloroquinazoline (800 mg, 4 mmol) and piperidine-1,4-dicarboxylic acid 1-tert-butyl ester 4-methyl ester (1.2 g, 5.2 mmol), as prepared in Example 1b, in a sealed vial at rt was added drop-wise a 1 M solution of LiHMDS in THF (6 mL, 6 mmol). The mixture was stirred at rt overnight. It was then quenched with aqueous NaH₂PO₄ and the mixture was extracted with DCM. The DCM layer was drawn off, washed with water, brine, dried over anhydrous MgSO₄, filtered and concentrated in vacuo to obtain 2.2 g (>100%) of crude 4-(7-chloro-quinazolin-4-yl)-piperidine-1,4-dicarboxylic acid 1-tert-butyl ester 4-methyl ester (29a) as a yellow semi-solid which was used as such for the next step.

Solid KOH (224 mg, 4 mmol) was added to a suspension of 4-(7-chloro-quinazolin-4-yl)-piperidine-1,4-dicarboxylic acid 1-tert-butyl ester 4-methyl ester (29a; 41 mg, 0.1 mmol) in a 1:1 mixture of dioxane and water (1 mL). The mixture was stirred at 100° C. for 3 h. It was then cooled to rt and concentrated in vacuo. The residue was dissolved in DCM and washed with water, brine, dried over anhydrous MgSO₄, filtered and concentrated in vacuo to obtain crude 4-(7-chloro-quinazolin-4-yl)-piperidine-1-carboxylic acid tert-butyl ester (29b). This was dissolved in 2 mL of 3M HCl/MeOH was stirred at rt for 1 h and then concentrated in vacuo to obtain crude 4-(7-chloro-quinazolin-4-yl)-piperidine (29c) as a di-HCl salt. To a suspension of (29c) in anhydrous MeOH, was added DIEA (45 µL, 0.25 mmol) followed by (4-isopropoxy-phenyl)-carbamic acid 4-nitro-phenyl ester (48 mg, 0.15 mmol) and the mixture was stirred at rt for 1 h. It was then concentrated in vacuo and the residue was purified by flash column chromatography (silica gel, 1% MeOH/DCM) to obtain 5 mg (12% overall yield from 29a) of pure 4-(7-chloro-quinazolin-4-yl)-piperidine-1-carboxylic acid (4-isopropoxy-phenyl)-amide. ¹H-NMR (300 MHz, CDCl₃): δ 9.25 (s, 1H), 8.15-8.06 (m, 2H), 7.62 (d, 1H), 7.23 (d, 2H), 6.85 (d, 2H), 6.30 (s, 1H), 4.49 (m, 1H), 4.26 (m, 2H), 3.70

(m, 1H), 3.15 (m, 2H), 2.23-2.05 (m, 2H), 2.05-1.92 (m, 2H), 1.32 (d, 6H). LC/MS (ESI): calcd mass 424.2, found 425.4 (MH)⁺.

Example 30

4-(7-Chloro-quinazolin-4-yl)-piperidine-1-carboxylic acid (4-isopropyl-phenyl)-amide

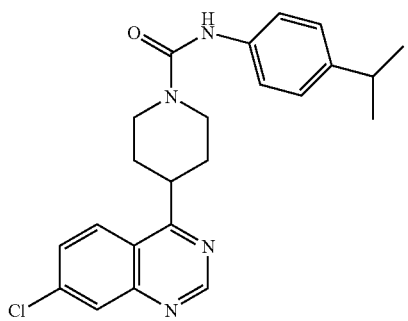

This was prepared as described in Example 29 except that (4-isopropyl-phenyl)-carbamic acid 4-nitro-phenyl ester, as prepared in Example 4a, was used in place of (4-isopropoxy-phenyl)-carbamic acid 4-nitro-phenyl ester. Purification by flash column chromatography (silica gel, 1% MeOH/DCM) yielded 11 mg (27% overall yield from 29a) of pure 4-(7-chloro-quinazolin-4-yl)-piperidine-1-carboxylic acid (4-isopropoxy-phenyl)-amide. ¹H-NMR (300 MHz, CDCl₃): δ 9.24 (s, 1H), 8.15-8.05 (m, 2H), 7.62 (d, 1H), 7.31-7.25 (d, 2H), 7.16 (d, 2H), 6.38 (s, 1H), 4.28 (m, 2H), 3.72 (m, 1H), 3.16 (m, 2H), 2.87 (m, 1H), 2.25-2.05 (m, 2H), 2.05-1.93 (m, 2H), 1.23 (d, 6H). LC/MS (ESI): calcd mass 408.2, found 409.4 (MH)⁺.

Example 31

4-(7-Methoxy-quinazolin-4-yl)-piperidine-1-carboxylic acid (4-isopropoxy-phenyl)-amide

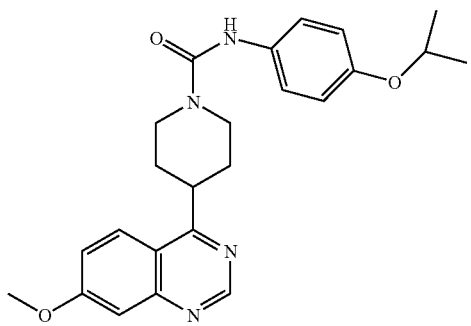

Solid KOH (224 mg, 4 mmol) was added to a solution of 4-(7-chloro-quinazolin-4-yl)-piperidine-1,4-dicarboxylic acid 1-tert-butyl ester 4-methyl ester (29a; 41 mg, 0.1 mmol), prepared as described in Example 29, in anhydrous MeOH (1 mL). The mixture was stirred at 100° C. for 3 h. It was then cooled to rt and concentrated in vacuo. The residue was dissolved in DCM and washed with water, brine, dried over anhydrous MgSO₄, filtered and concentrated in vacuo to obtain crude 4-(7-methoxy-quinazolin-4-yl)-piperidine-1-carboxylic acid tert-butyl ester (31a). This was dissolved in 2 mL of 3M HCl/MeOH was stirred at rt for 1 h and then concentrated in vacuo to obtain crude 4-(7-methoxy-quinazolin-4-yl)-piperidine (31b) as a di-HCl salt. To a suspension of (31b) in anhydrous MeOH (2 mL), was added DIEA (45 μL, 0.25 mmol) followed by (4-isopropoxy-phenyl)-carbamic acid 4-nitro-phenyl ester (48 mg, 0.15 mmol), as prepared in Example 1a, and the mixture was stirred at rt for 1 h. It was then concentrated in vacuo and the residue was purified by flash column chromatography (silica gel, 1% MeOH/DCM) to obtain 5.4 mg (13% overall yield from 29a) of pure 4-(7-methoxy-quinazolin-4-yl)-piperidine-1-carboxylic acid (4-isopropoxy-phenyl)-amide. ¹H-NMR (300 MHz, CDCl₃): δ 9.14 (s, 1H), 8.06 (d, 1H), 7.35 (d, 1H), 7.30-7.25 (m, 3H), 6.84 (d, 2H), 6.30 (s, 1H), 4.48 (m, 1H), 4.26 (m, 2H), 3.99 (s, 3H), 3.69 (m, 1H), 3.14 (m, 2H), 2.23-2.05 (m, 2H), 2.03-1.92 (m, 2H), 1.31 (d, 6H). LC/MS (ESI): calcd mass 420.2, found 421.4 (MH)⁺.

Example 32

4-(7-Methoxy-quinazolin-4-yl)-piperidine-1-carboxylic acid (4-isopropyl-phenyl)-amide

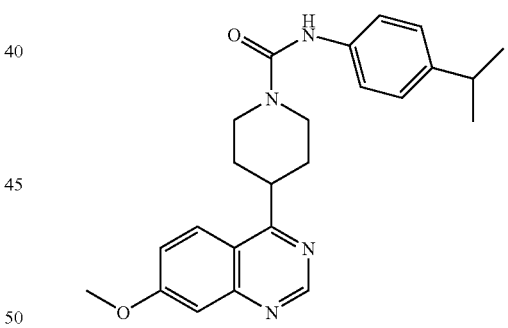

This was prepared as described in Example 31 except that (4-isopropyl-phenyl)-carbamic acid 4-nitro-phenyl ester, as prepared in Example 4a, was used in place of (4-isopropoxy-phenyl)-carbamic acid 4-nitro-phenyl ester. Purification by flash column chromatography (silica gel, 1% MeOH/DCM) yielded 14.1 mg (35% overall yield from 15a) of pure 4-(7-chloro-quinazolin-4-yl)-piperidine-1-carboxylic acid (4-isopropoxy-phenyl)-amide. ¹H-NMR (300 MHz, CDCl₃): δ 9.14 (s, 1H), 8.06 (d, 1H), 7.34 (d, 1H), 7.31-7.24 (m, 3H), 7.16 (d, 2H), 6.39 (s, 1H), 4.27 (m, 2H), 3.98 (s, 3H), 3.69 (m, 1H), 3.14 (m, 2H), 2.87 (m, 1H), 2.23-2.05 (m, 2H), 2.04-1.92 (m, 2H), 1.23 (d, 6H). LC/MS (ESI): calcd mass 404.2, found 405.4 (MH)⁺.

Example 33

4-(7-(3-Piperidin-1-yl-propoxy)-quinazolin-4-yl)-piperidine-1-carboxylic acid (4-isopropoxy-phenyl)-amide

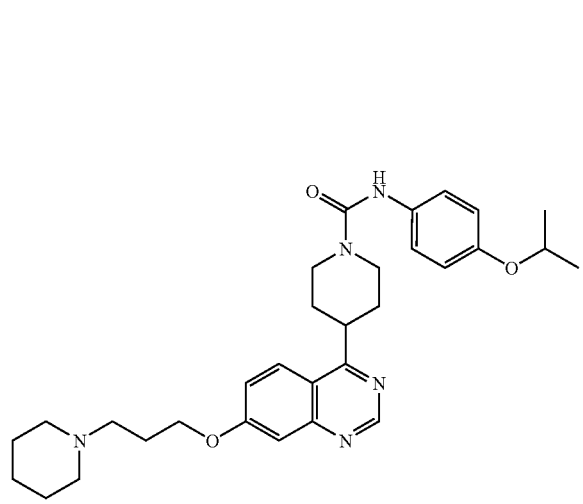

Solid KOH (112 mg, 2 mmol) was added to a mixture of 4-(7-chloro-quinazolin-4-yl)-piperidine-1,4-dicarboxylic acid 1-tert-butyl ester 4-methyl ester (29a; 82 mg, 0.2 mmol), prepared as described in Example 29, and 3-hydroxypropylpiperidine (0.25 mL). The mixture was stirred at 100° C. for 3 h. It was then cooled to rt and diluted with water. The mixture was extracted with DCM and the organic layer was drawn off and washed with water thrice, with brine once, then dried over anhydrous MgSO$_4$, filtered and concentrated in vacuo. To this was added 3 mL of 3M HCl/MeOH and the mixture was stirred at rt for 2 h and then concentrated in vacuo. This was suspended in anhydrous MeOH (3 mL), and to it DIEA (1.75 mL, 0.6 mmol) was added followed by (4-isopropoxy-phenyl)-carbamic acid 4-nitro-phenyl ester (96 mg, 0.3 mmol), as prepared in Example 1a, and the mixture was stirred at rt overnight. It was then concentrated in vacuo and the residue was dissolved in DCM and washed extensively with water thrice and brine once and then dried over anhydrous MgSO$_4$, filtered and concentrated in vacuo. The crude product was purified by flash column chromatography (silica gel, 1% MeOH/DCM followed by 90:9:1 DCM:MeOH:NH$_4$OH) to obtain 14 mg (13% overall yield from 29a) of pure 4-(7-(3-piperidin-1-yl-propoxy)-quinazolin-4-yl)-piperidine-1-carboxylic acid (4-isopropoxy-phenyl)-amide. $^1$H-NMR (300 MHz, CDCl$_3$): δ 9.13 (s, 1H), 8.05 (d, 1H), 7.35-7.21 (m, 4H), 6.84 (d, 2H), 6.33 (s, 1H), 4.48 (m, 1H), 4.32-4.15 (m, 4H), 3.68 (m, 1H), 3.13 (m, 2H), 2.7-2.45 (m, 6H), 2.20-1.90 (m, 8H), 1.75-1.58 (m, 4H), 1.31 (d, 6H). LC/MS (ESI): calcd mass 531.3, found 532.6 (MH)$^+$.

Example 34

4-(7-(2-Piperindin-1-yl-ethoxy)-quinazolin-4-yl)-piperidine-1-carboxylic acid (4-isopropoxy-phenyl)-amide

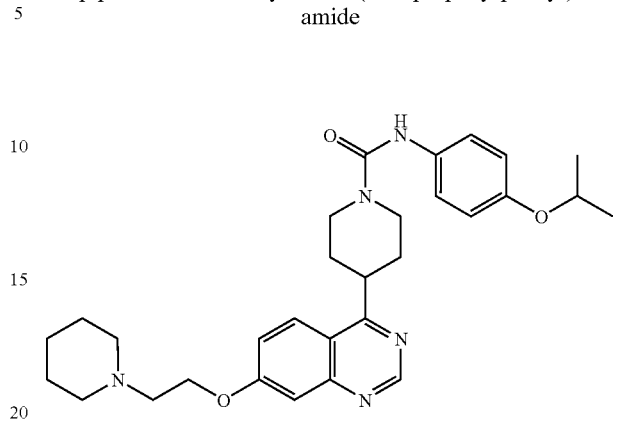

This was prepared as described in Example 33 except that 2-hydroxyethylpiperidine (0.5 mL) was used in place of 3-hydroxypropylpiperidine (0.25 mL). Purification by flash column chromatography (silica gel, 5% MeOH/DCM) yielded 45 mg (43% overall yield from 29a) of pure 4-(7-(2-piperindin-1-yl-ethoxy)-quinazolin-4-yl)-piperidine-1-carboxylic acid (4-isopropoxy-phenyl)-amide. $^1$H-NMR (300 MHz, CDCl$_3$): δ 9.12 (s, 1H), 8.05 (d, 1H), 7.34-7.21 (m, 4H), 6.83 (d, 2H), 6.42 (s, 1H), 4.47 (m, 1H), 4.37 (m, 2H), 4.26 (m, 2H), 3.67 (m, 1H), 3.19-3.02 (m, 2H), 2.98 (m, 2H), 2.68 (m, 4H), 2.21-2.03 (m, 2H), 1.96 (m, 2H), 1.72 (m, 4H), 1.50 (m, 2H), 1.31 (d, 6H). LC/MS (ESI): calcd mass 517.3, found 518.5 (MH)$^+$.

Example 35

4-[7-(2-Diethylamino-ethoxy)-quinazolin-4-yl)-piperidine-1-carboxylic acid (4-isopropoxy-phenyl)-amide

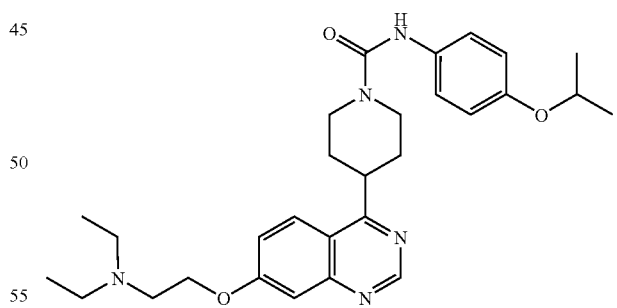

This was prepared as described in Example 33 except that 2-diethylaminoethanol (0.5 mL) was used in place of 3-hydroxypropylpiperidine (0.25 mL). Purification by flash column chromatography (silica gel, 5% MeOH/DCM followed by 90:9:1 DCM:MeOH:NH$_4$OH) yielded 30 mg (30% overall yield from 29a) of pure 4-[7-(2-diethylamino-ethoxy)-quinazolin-4-yl)-piperidine-1-carboxylic acid (4-isopropoxy-phenyl)-amide. $^1$H-NMR (300 MHz, CDCl$_3$): δ 9.13 (s, 1H), 8.05 (d, 1H), 7.35-7.21 (m, 4H), 6.84 (d, 2H), 6.30 (s, 1H), 4.48 (m, 1H), 4.31-4.20 (m, 4H), 3.68 (m, 1H), 3.14 (m, 2H), 3.00 (m, 2H), 2.70 (m, 4H), 2.22-2.04 (m, 2H), 1.97 (m, 2H), 1.31 (d, 6H), 1.12 (d, 6H). LC/MS (ESI): calcd mass 505.3, found 506.6 (MH)+.

Example 36

4-[7-(3-Diethylamino-propoxy)-quinazolin-4-yl)-piperidine-1-carboxylic acid (4-isopropoxy-phenyl)-amide

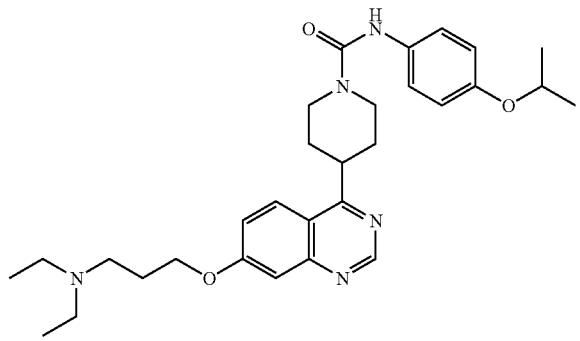

This was prepared as described in Example 33 except that 3-diethylaminopropanol (0.5 mL) was used in place of 3-hydroxypropylpiperidine (0.25 mL). Purification by flash column chromatography (silica gel, 5% MeOH/DCM followed by 90:9:1 DCM:MeOH:NH$_4$OH) yielded 20 mg (19% overall yield from 29a) of pure 4-[7-(3-diethylamino-propoxy)-quinazolin-4-yl)-piperidine-1-carboxylic acid (4-isopropoxy-phenyl)-amide. $^1$H-NMR (300 MHz, CDCl$_3$): δ 9.13 (s, 1H), 8.04 (d, 1H), 7.34-7.21 (m, 4H), 6.84 (d, 2H), 6.33 (s, 1H), 4.48 (m, 1H), 4.32-4.15 (m, 4H), 3.68 (m, 1H), 3.14 (m, 2H), 2.74-2.54 (m, 6H), 2.22-1.90 (m, 6H), 1.31 (d, 6H), 1.07 (t, 6H). LC/MS (ESI): calcd mass 519.3, found 520.6 (MH)+.

Example 37

4-[7-(2-Morpholin-4-yl-ethoxy)-quinazolin-4-yl)]-piperidine-1-carboxylic acid (4-isopropoxy-phenyl)-amide

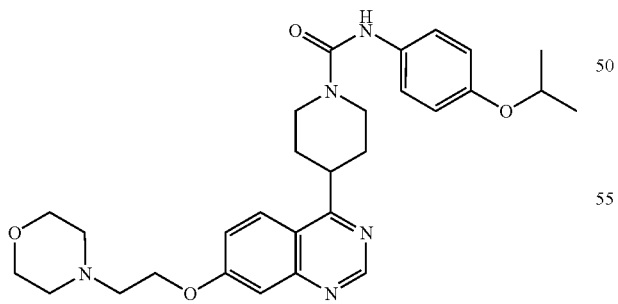

This was prepared as described in Example 33 except that 2-hydroxyethylmorrpholine (0.5 mL) was used in place of 3-hydroxypropylpiperidine (0.25 mL). Purification by flash column chromatography (silica gel, 5% MeOH/DCM followed by 90:9:1 DCM:MeOH:NH$_4$OH) yielded 25 mg (24% overall yield from 29a) of pure 4-[7-(2-morpholin-4-yl-ethoxy)-quinazolin-4-yl)]-piperidine-1-carboxylic acid (4-isopropoxy-phenyl)-amide. $^1$H-NMR (300 MHz, CDCl$_3$): δ 9.14 (s, 1H), 8.05 (d, 1H), 7.33-7.20 (m, 4H), 6.84 (d, 2H), 6.32 (s, 1H), 4.48 (m, 1H), 4.33-4.20 (m, 4H), 3.79-3.61 (m, 5H), 3.13 (m, 2H), 2.90 (m, 2H), 2.26 (m, 4H), 2.22-2.03 (m, 2H), 1.96 (m, 2H), 1.31 (d, 6H). LC/MS (ESI): calcd mass 519.3, found 520.6 (MH)+.

Example 38

4-[7-(3-Morpholin-4-yl-propoxy)-quinazolin-4-yl)]-piperidine-1-carboxylic acid (4-isopropoxy-phenyl)-amide

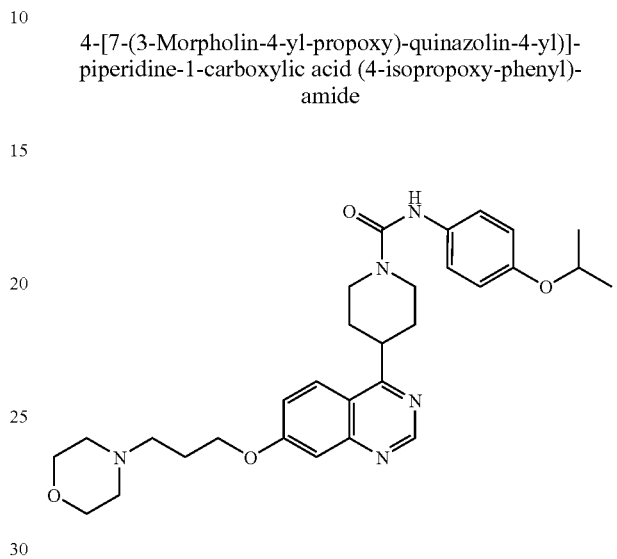

This was prepared as described in Example 33 except that 3-hydroxypropylmorpholine (0.5 mL) was used in place of 3-hydroxypropylpiperidine (0.25 mL). Purification by flash column chromatography (silica gel, 5% MeOH/DCM followed by 90:9:1 DCM:MeOH:NH$_4$OH) yielded 15 mg (14% overall yield from 29a) of pure 4-[7-(3-morpholin-4-yl-propoxy)-quinazolin-4-yl)]-piperidine-1-carboxylic acid (4-isopropoxy-phenyl)-amide. $^1$H-NMR (300 MHz, CDCl$_3$): δ 9.13 (s, 1H), 8.05 (d, 1H), 7.35-7.21 (m, 4H), 6.85 (d, 2H), 6.30 (s, 1H), 4.48 (m, 1H), 4.31-4.17 (m, 4H), 3.76-3.61 (m, 5H), 3.14 (m, 2H), 2.57 (m, 2H), 2.49 (m, 4H), 2.22-1.90 (m, 6H), 1.32 (d, 6H). LC/MS (ESI): calcd mass 533.3, found 534.6 (MH)+.

Example 39

4-{7-[3-(4-Methyl-piperazin-1-yl)-propoxy]-quinazolin-4-yl)}-piperidine-1-carboxylic acid (4-isopropoxy-phenyl)-amide

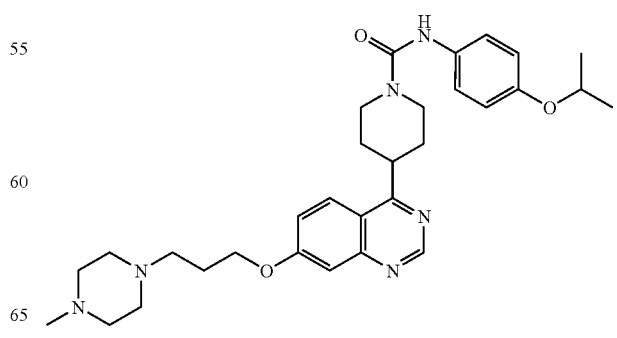

This was prepared as described in Example 33 except that 3-(4-methyl-piperazin-1-yl)-propan-1-ol (0.5 mL) was used in place of 3-hydroxypropylpiperidine (0.25 mL). Purification by flash column chromatography (silica gel, 5% MeOH/DCM followed by 90:9:1 DCM:MeOH:NH$_4$OH) yielded 25 mg (23% overall yield from 29a) of pure 4-{7-[3-(4-methyl-piperazin-1-yl)-propoxy]-quinazolin-4-yl)}-piperidine-1-carboxylic acid (4-isopropoxy-phenyl)-amide. $^1$H-NMR (300 MHz, CDCl$_3$): δ 9.13 (s, 1H), 8.05 (d, 1H), 7.34-7.21 (m, 4H), 6.84 (d, 2H), 6.31 (s, 1H), 4.48 (m, 1H), 4.31-4.15 (m, 4H), 3.68 (m, 1H), 3.13 (m, 2H), 2.70-2.40 (m, 8H), 2.32 (s, 3H), 2.22-1.90 (m, 8H), 1.31 (d, 6H). LC/MS (ESI): calcd mass 546.3, found 547.6 (MH)$^+$.

Example 40

4-(6,7-Dimethoxy-quinazolin-4-yl)-piperidine-1-carboxylic acid [4-(2-methoxy-ethoxy)-phenyl]-amide

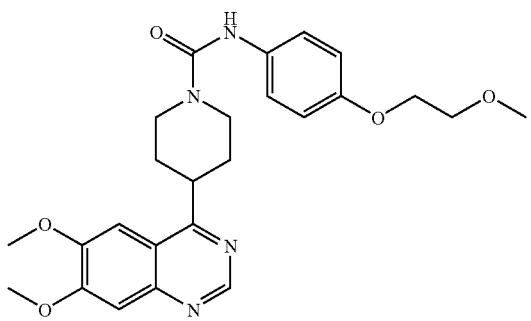

a. 4-(2-Methoxy-ethoxy)-phenylamine

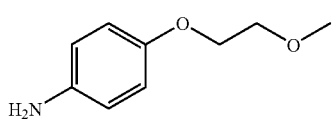

A mixture of 4-iodoaniline (219 mg, 1.0 mmol), 2-methoxyethanol (152 mg, 2.0 mmol), copper iodide (19.0 mg, 0.1 mmol), cesium carbonate (554 mg, 1.7 mmol) and 1,10-phenanthroline (36.0 mg, 0.2 mmol) was stirred in toluene (0.5 mL) at 110° C. overnight. The reaction was then cooled to RT and filtered through silica gel and washed with diethyl ether. The ether was removed in vacuo to obtain a crude solid. Purification by prep tlc (1:9 MeOH/DCM) afforded the title compound as a solid (8.9 mg, 5.3%). $^1$H NMR (300 MHz, CDCl$_3$) δ 6.82-6.72 (m, 4H), 4.06 (t, 2H), 3.72 (t, 2H), 3.45 (s, 3H).

b. 4-(6,7-Dimethoxy-quinazolin-4-yl)-piperidine-1-carboxylic acid [4-(2-methoxy-ethoxy)-phenyl]-amide

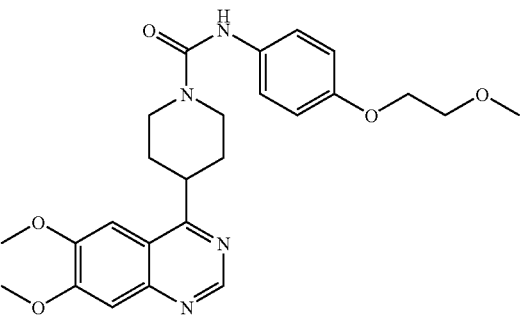

A mixture of 4-(6,7-dimethoxy-quinazolin-4-yl)-piperidine-1-carbonyl chloride (18 mg, 0.0536 mmol), as prepared in Example 3a, 4-(2-methoxy-ethoxy)-phenylamine (8.9 mg, 0.0533 mmol), as prepared in the previous step, and triethylamine (14 μL, 0.1 mmol) was stirred in DMSO (0.5 mL) at 50° C. overnight. The reaction was then cooled to RT, partitioned between EtOAc (10 mL) and H$_2$O (10 mL). The organic phase was dried over Na$_2$SO$_4$ and concentrated in vacuo. Purification by prep tlc (1:9 MeOH/DCM) afforded the title compound as a brown solid (5.7 mg, 23%). $^1$H NMR (300 MHz, CDCl$_3$) δ 9.16 (s, 1H), 7.28-7.25 (m, 4H), 6.89 (m, 2H), 6.33 (br s, NH), 4.29-4.24 (m, 2H), 4.12-4.07 (m, 8H), 3.74 (m, 2H), 3.59 (m, 1H), 3.45 (s, 3H), 3.17 (m, 2H), 2.22-2.08 (m, 2H), 2.05-1.97 (m, 2H); LC/MS (ESI): calcd mass 466.2, found 467.4 [M+1]$^+$.

Example 41

4-(6,7-Dimethoxy-quinazolin-4-yl)-piperidine-1-carboxylic acid (4-methoxy-phenyl)-amide

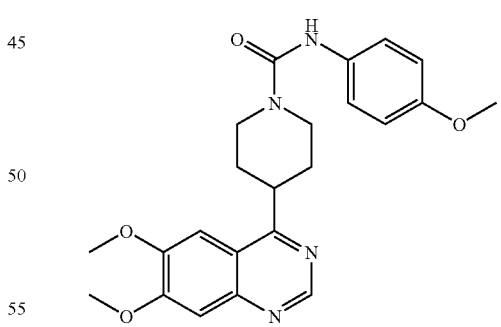

To a solution of 6,7-dimethoxy-4-piperidin-4-yl-quinazoline (30 mg, 0.110 mmol), as prepared in Example 1d, in DMF (1 mL) was treated with 1-isocyanato-4-methoxy-benzene (24.5 mg, 0.164 mmol) at RT overnight. The reaction was then partitioned between EtOAc (10 mL) and H$_2$O (10 mL). The organic phase was dried over Na$_2$SO$_4$ and concentrated in vacuo. Purification by prep tlc (1:9 MeOH/DCM) afforded the title compound as a yellow solid (25.9 mg, 56%). $^1$H NMR (300 MHz, CDCl$_3$) δ 9.10 (s, 1H), 7.29 (m, 4H), 6.88 (m, 2H), 6.30 (br s, NH), 4.30-4.26 (m, 2H), 4.08 (s, 6H), 3.80 (s, 3H), 3.61 (m, 1H), 3.17 (m, 2H), 2.19-2.14 (m, 2H), 2.03-1.97 (m, 2H); LC/MS (ESI): calcd mass 422.2, found 423.3 [M+1]+.

Example 42

4-(6,7-Dimethoxy-quinazolin-4-yl)-piperidine-1-carboxylic acid cyclohexylamide

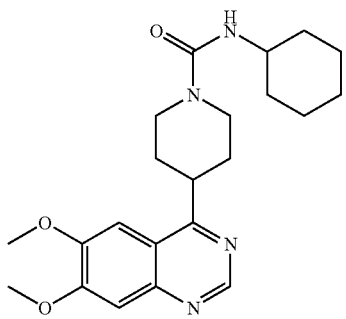

A solution of 6,7-dimethoxy-4-piperidin-4-yl-quinazoline (30 mg, 0.110 mmol), as prepared in Example 1d, in DMF (1 mL) was treated with isocyanato-cyclohexane (20.6 mg, 0.165 mmol) at RT overnight. The reaction was then partitioned between EtOAc (10 mL) and H$_2$O (10 mL). The organic phase was dried over Na$_2$SO$_4$ and concentrated in vacuo. Purification by prep tlc (1:9 MeOH/DCM) afforded the title compound as a light yellow solid (22 mg, 50%). $^1$H NMR (300 MHz, CDCl$_3$) δ 9.08 (s, 1H), 7.38 (s, 1H), 7.26 (s, 1H), 4.35 (d, 1H), 4.14 (d, 1H), 4.07 (s, 6H), 3.68 (m, 1H), 3.53 (m, 1H), 3.03 (m, 2H), 2.12-1.90 (m, 4H), 1.70-1.55 (m, 5H), 1.40-1.09 (m, 5H); LC/MS (ESI): calcd mass 398.2, found 399.3 [M+1]+.

Example 43

4-(6,7-Dimethoxy-quinazolin-4-yl)-piperidine-1-carboxylic acid (4-butyl-phenyl)-amide

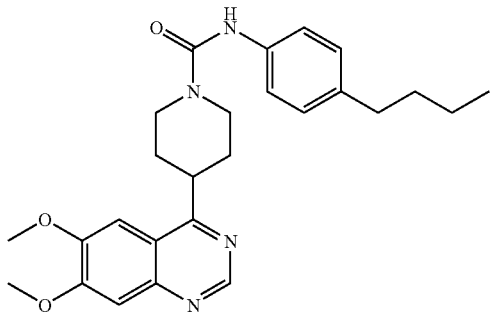

A solution of 6,7-dimethoxy-4-piperidin-4-yl-quinazoline (30 mg, 0.110 mmol), as prepared in Example 1d, in DMF (1 mL) was treated with 1-butyl-4-isocyanato-benzene (28.8 mg, 0.165 mmol) at RT overnight. The reaction was then partitioned between EtOAc (10 mL) and H$_2$O (10 mL). The organic phase was dried over Na$_2$SO$_4$ and concentrated in vacuo. Purification by prep tlc (1:9 MeOH/DCM) afforded the title compound as a light yellow solid (20.3 mg, 41%). $^1$H NMR (300 MHz, CDCl$_3$) δ 9.09 (s, 1H), 7.40 (s, 1H), 7.28 (m, 3H), 7.13-7.10 (m, 2H), 6.36 (br s, NH), 4.30-4.26 (m, 2H), 4.08 (s, 6H), 3.61 (m, 1H), 3.17 (m, 2H), 2.57 (m, 2H), 2.17 (m, 2H), 2.02-1.98 (m, 2H), 1.34 (m, 4H), 0.94-0.80 (m, 3H); LC/MS (ESI): calcd mass 448.3, found 449.3 [M+1]+.

Example 44

4-(6,7-Dimethoxy-quinazolin-4-yl)-piperidine-1-carboxylic acid (4-ethoxy-phenyl)-amide

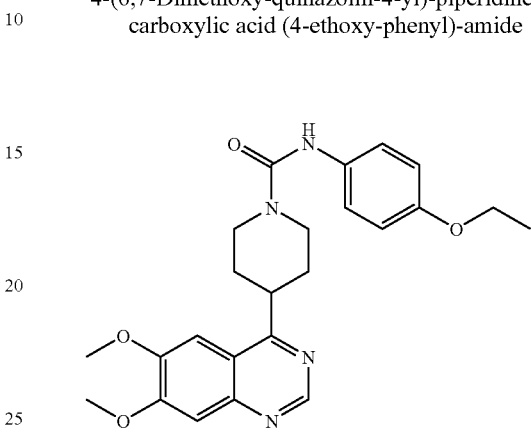

A solution of 6,7-dimethoxy-4-piperidin-4-yl-quinazoline (30 mg, 0.110 mmol), as prepared in Example 1d, in DMF (1 mL) was treated with 1-ethoxy-4-isocyanato-benzene (26.8 mg, 0.164 mmol) at RT overnight. The reaction was then partitioned between EtOAc (10 mL) and H$_2$O (10 mL). The organic phase was dried over Na$_2$SO$_4$ and concentrated in vacuo. Purification by prep tlc (1:9 MeOH/DCM) afforded the title compound as a light brown solid (9.7 mg, 20%). $^1$H NMR (300 MHz, CDCl$_3$) δ 9.09 (s, 1H), 7.41 (m, 1H), 7.26 (m, 3H), 6.87 (m, 2H), 6.29 (br s, NH), 4.30-4.25 (m, 2H), 4.08 (s, 6H), 4.01 (q, 2H), 3.61 (m, 1H), 3.17 (m, 2H), 2.17 (m, 2H), 2.02-2.01 (m, 2H), 1.40 (t, 3H); LC/MS (ESI): calcd mass 436.2, found 437.3 [M+1]+.

Example 45

4-(6,7-Dimethoxy-quinazolin-4-yl)-piperidine-1-carboxylic acid phenylamide

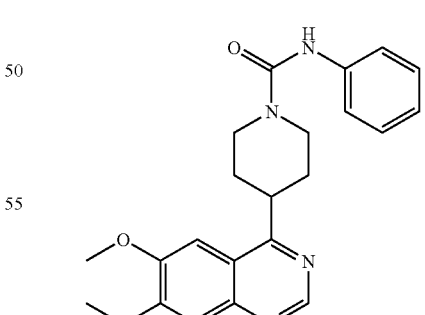

A solution of 6,7-dimethoxy-4-piperidin-4-yl-quinazoline (30 mg, 0.110 mmol), as prepared in Example 1d, in DMF (1 mL) was treated with isocyanato-benzene (19.6 mg, 0.165 mmol) at RT overnight. The reaction was then partitioned between EtOAc (10 mL) and H$_2$O (10 mL). The organic phase was dried over Na$_2$SO$_4$ and concentrated in vacuo. Purification by prep tlc (1:9 MeOH/DCM) afforded the title compound as a yellow solid (11.4 mg, 27%). $^1$H NMR (300 MHz, CDCl$_3$) δ 9.09 (s, 1H), 7.37 (m, 6H), 7.06 (m, 1H), 6.42 (br s, NH), 4.31-4.27 (m, 2H), 4.08 (s, 6H), 3.62 (m, 1H), 3.19 (m, 2H), 2.17 (m, 2H), 2.04-1.98 (m, 2H); LC/MS (ESI): calcd mass 392.2, found 393.3 [M+1]$^+$.

Example 46

4-(6,7-Dimethoxy-quinazolin-4-yl)-piperidine-1-carboxylic acid (4-trifluoromethyl-phenyl)-amide

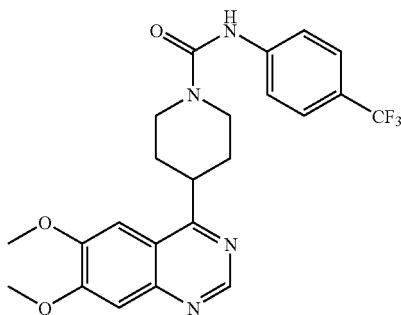

A solution of 6,7-dimethoxy-4-piperidin-4-yl-quinazoline (20 mg, 0.0733 mmol), as prepared in Example 1d, in DMF (1 mL) was treated with 1-isocyanato-4-trifluoromethyl-benzene (20 mg, 0.107 mmol) at RT overnight. The reaction was then partitioned between EtOAc (10 mL) and H$_2$O (10 mL). The organic phase was dried over Na$_2$SO$_4$ and concentrated in vacuo. Purification by prep tlc (1:9 MeOH/DCM) afforded the title compound as a yellow solid (9.0 mg, 27%). $^1$H NMR (300 MHz, CDCl$_3$) δ 9.10 (s, 1H), 7.54 (m, 2H), 7.39 (m, 1H), 7.28 (m, 2H), 6.69 (m, 1H), 6.63 (br s, NH), 4.33-4.29 (m, 2H), 4.09 (s, 6H), 3.65 (m, 1H), 3.22 (m, 2H), 2.17 (m, 2H), 2.06-2.01 (m, 2H); LC/MS (ESI) calcd mass 460.2, found 461.3 [M+1]$^+$.

Example 47

4-(6,7-Dimethoxy-quinazolin-4-yl)-piperidine-1-carboxylic acid (4-phenoxy-phenyl)-amide

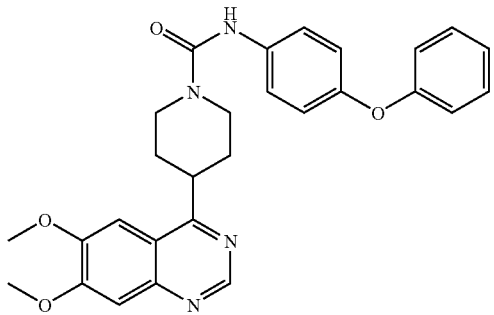

A solution of 6,7-dimethoxy-4-piperidin-4-yl-quinazoline (20 mg, 0.0733 mmol), as prepared in Example 1d, in DMF (1 mL) was treated with 4-phenoxyphenyl isocyanate (23 mg, 0.109 mmol) at RT overnight. The reaction was then partitioned between EtOAc (10 mL) and H$_2$O (10 mL). The organic phase was dried over Na$_2$SO$_4$ and concentrated in vacuo. Purification by prep tlc (1:9 MeOH/DCM) afforded the title compound as a brown solid (15.7 mg, 44%). $^1$H NMR (300 MHz, CDCl$_3$) δ 9.10 (s, 1H), 7.48 (m, 1H), 7.33 (m, 5H), 7.07 (m, 1H), 6.99 (m, 4H), 6.41 (br s, NH), 4.32-4.27 (m, 2H), 4.09 (s, 6H), 3.63 (m, 1H), 3.20 (m, 2H), 2.17 (m, 2H), 2.03-1.99 (m, 2H); LC/MS (ESI) calcd mass 484.2, found 485.3 [M+1]$^+$.

Example 48

4-(6,7-Dimethoxy-quinazolin-4-yl)-piperidine-1-carboxylic acid p-tolylamide

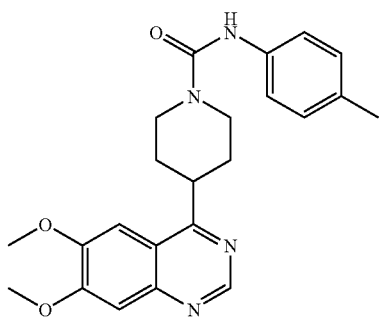

A solution of 6,7-dimethoxy-4-piperidin-4-yl-quinazoline (20 mg, 0.0733 mmol), as prepared in Example 1d, in DMF (1 mL) was treated with 1-isocyanato-4-methyl-benzene (15 mg, 0.113 mmol) at RT overnight. The reaction was then partitioned between EtOAc (10 mL) and H$_2$O (10 mL). The organic phase was dried over Na$_2$SO$_4$ and concentrated in vacuo. Purification by prep tlc (1:9 MeOH/DCM) afforded the title compound as a brown solid (25.1 mg, 84%). $^1$H NMR (300 MHz, CDCl$_3$) δ 9.09 (s, 1H), 7.26-7.21 (m, 3H), 7.12 (m, 3H), 6.37 (br s, NH), 4.30-4.26 (m, 2H), 4.07 (s, 6H), 3.60 (m, 1H), 3.18 (m, 2H), 2.30 (s, 3H), 2.17 (m, 2H), 2.01-1.98 (m, 2H); LC/MS (ESI) calcd mass 406.2, found 407.3 [M+1]$^+$.

Example 49

4-(6,7-Dimethoxy-quinazolin-4-yl)-piperidine-1-carboxylic acid (4-chloro-phenyl)-amide

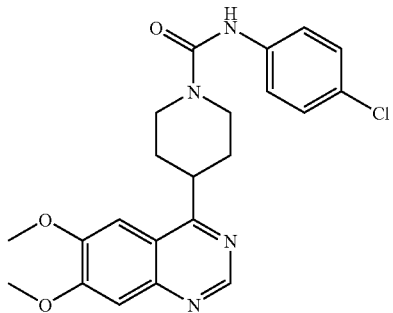

A solution of 6,7-dimethoxy-4-piperidin-4-yl-quinazoline (20 mg, 0.0733 mmol), as prepared in Example 1d, in DMF (1 mL) was treated with 1-chloro-4-isocyanato-benzene (16.8 mg, 0.110 mmol) at RT overnight. The reaction was then partitioned between EtOAc (10 mL) and H₂O (10 mL). The organic phase was dried over Na₂SO₄ and concentrated in vacuo. Purification by prep tlc (1:9 MeOH/DCM) afforded the title compound as a yellow solid (9.2 mg, 29%). ¹H NMR (300 MHz, CDCl₃) δ 9.08 (s, 1H), 7.38-7.33 (m, 4H), 7.26 (m, 2H), 6.44 (br s, NH), 4.29-4.26 (m, 2H), 4.07 (s, 6H), 3.62 (m, 1H), 3.19 (m, 2H), 2.16 (m, 2H), 2.02-1.99 (m, 2H); LC/MS (ESI) calcd mass 426.2, found 427.2 [M+1]⁺.

Example 50

4-(6,7-Dimethoxy-quinazolin-4-yl)-piperidine-1-carboxylic acid (4-trifluoromethoxy-phenyl)-amide

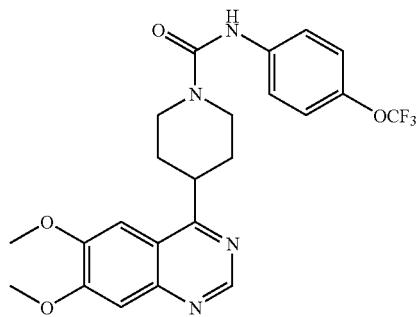

A solution of 6,7-dimethoxy-4-piperidin-4-yl-quinazoline (20 mg, 0.0733 mmol), as prepared in Example 1d, in DMF (1 mL) was treated with 1-isocyanato-4-trifluoromethoxy-benzene (22 mg, 0.108 mmol) at RT overnight. The reaction was then partitioned between EtOAc (10 mL) and H₂O (10 mL). The organic phase was dried over Na₂SO₄ and concentrated in vacuo. Purification by prep tlc (1:9 MeOH/DCM) afforded the title compound as a yellow solid (18.2 mg, 52%). ¹H NMR (300 MHz, CDCl₃) δ 9.08 (s, 1H), 7.39 (m, 3H), 7.16 (m, 2H), 7.00 (m, 1H), 6.52 (br s, NH), 4.30-4.27 (m, 2H), 4.07 (s, 6H), 3.62 (m, 1H), 3.20 (m, 2H), 2.18-2.11 (m, 2H), 2.03-1.99 (m, 2H); LC/MS (ESI) calcd mass 476.2, found 477.3 [M+1]⁺.

Example 51

4-(6,7-Dimethoxy-quinazolin-4-yl)-piperidine-1-carboxylic acid (4-difluoromethoxy-phenyl)-amide

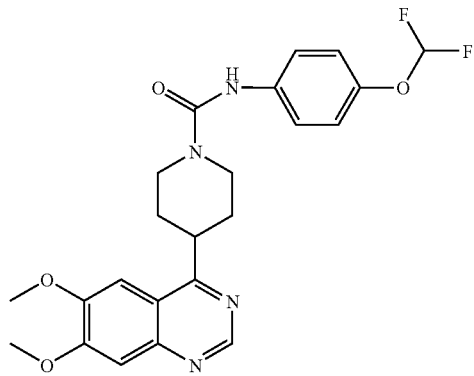

To a solution of 4-(6,7-dimethoxy-quinazolin-4-yl)-piperidine-1-carbonyl chloride (46.9 mg, 0.14 mmol), as prepared in Example 3a, in DMSO (1 mL) was added 4-(difluoromethoxy)aniline (26.6 mg, 0.17 mmol), followed by DIEA (35.9 mg, 0.28 mmol). The mixture was heated at 100° C. with stirring. After 2 h, it was cooled to room temperature and partitioned between EtOAc and water. The combined EtOAc extracts were dried (Na₂SO₄) and concentrated under reduced pressure. The residue was purified by flash column chromatography on silica gel (EtOAc→5% MeOH/EtOAc as eluent) to afford the title compound as a white solid (20.4 mg, 32%). ¹H NMR (300 MHz, CDCl₃) δ 9.09 (s, 1H), 7.40 (s, 1H), 7.38 (d, J=8.99 Hz, 2H), 7.27 (s, 1H), 7.07 (d, J=8.93 Hz, 2H), 6.48 (s, 1H), 6.45 (t, J=74.22 Hz, 1H), 4.28 (m, 2H), 4.08 (s, 3H), 4.07 (s, 3H), 3.62 (m, 1H), 3.20 (td, J=13.02 and 2.64 Hz, 2H), 2.14 (m, 2H), 2.01 (m, 2H). LC-MS (ESI) calcd mass 458.2, found 459.3 (MH⁺).

Similar to the synthesis of Example 51, Examples 52-56 were synthesized by the reactions of 4-(6,7-dimethoxy-quinazolin-4-yl)-piperidine-1-carbonyl chloride with the corresponding aniline or amine in the presence of DIEA.

Example 52

4-(6,7-Dimethoxy-quinazolin-4-yl)-piperidine-1-carboxylic acid (4-sec-butyl-phenyl)-amide

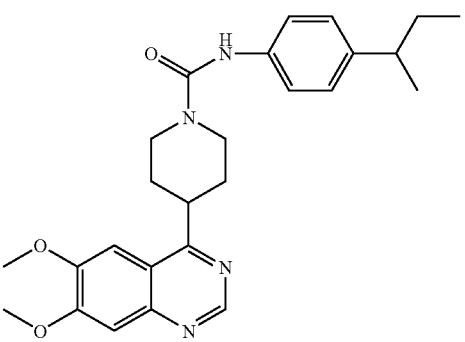

¹H NMR (300 MHz, CDCl₃) δ 9.10 (s, 1H), 7.51 (s, 1H), 7.29 (d, J=8.39 Hz, 2H), 7.28 (s, 1H), 7.11 (d, J=8.58 Hz, 2H), 6.41 (s, 1H), 4.29 (m, 2H), 4.09 (s, 3H), 4.08 (s, 3H), 3.63 (m, 1H), 3.18 (td, J=13.00 and 2.41 Hz, 2H), 2.55 (m, 1H), 2.18 (m, 2H), 1.99 (m, 2H), 1.57 (m, 2H), 1.21 (d, J=6.96 Hz, 3H), 0.81 (t, J=7.35 Hz, 3H). LC-MS (ESI) calcd mass 448.3, found 449.4 (MH⁺).

Example 53

4-(6,7-Dimethoxy-quinazolin-4-yl)-piperidine-1-carboxylic acid (4-tert-butyl-phenyl)-amide

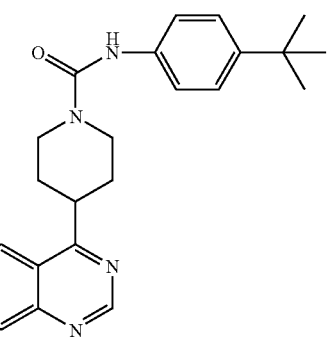

¹H NMR (300 MHz, CDCl₃) δ 9.09 (s, 1H), 7.40 (s, 1H), 7.31 (d, J=3.51 Hz, 2H), 7.26 (d, J=3.42 Hz, 2H), 6.39 (s, 1H), 4.28 (m, 2H), 4.08 (s, 3H), 4.07 (s, 3H), 3.61 (m, 1H), 3.18 (td, J=13.41 and 3.06 Hz, 2H), 2.17 (m, 2H), 1.99 (m, 2H), 1.30 (s, 9H). LC-MS (ESI) calcd mass 448.3, found 449.4 (MH⁺).

Example 54

4-(6,7-Dimethoxy-quinazolin-4-yl)-piperidine-1-carboxylic acid (4-tert-butyl-cyclohexyl)-amide

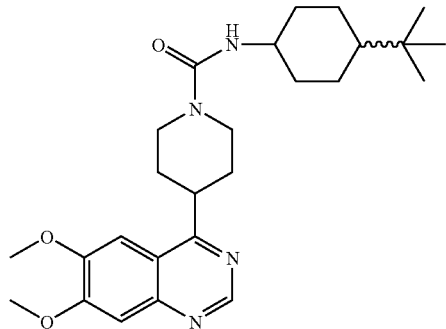

¹H NMR (300 MHz, CDCl₃) δ 9.07 (s, 1H), 7.70 (m, 0.5H), 7.53 (m, 0.5H), 7.35 (s, 1H), 7.25 (s, 1H), 4.28 (m, 1H), 4.12 (m, 2H), 4.05 (s, 6H), 3.53 (m, 1H), 3.02 (td, J=12.78 and 2.39 Hz, 2H), 1.64-2.12 (m, 4H), 0.86-1.32 (m, 9H), 0.85 (s, 9H). LC-MS (ESI) calcd mass 454.3, found 455.4 (MH⁺).

Example 55

4-(6,7-Dimethoxy-quinazolin-4-yl)-piperidine-1-carboxylic acid [4-(1-hydroxy-ethyl)-phenyl]-amide

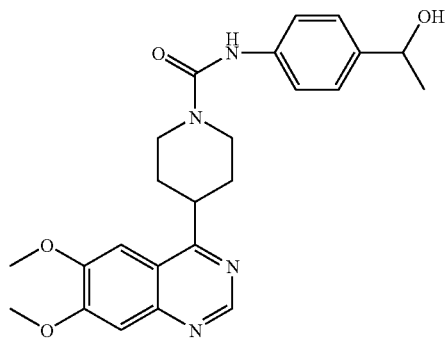

¹H NMR (300 MHz, CDCl₃) δ 9.08 (s, 1H), 7.34 (m, 5H), 6.47 (s, 1H), 4.87 (q, J=6.30 Hz, 1H), 4.28 (m, 2H), 4.07 (s, 3H), 4.06 (s, 3H), 3.61 (m, 1H), 3.18 (td, J=13.00 and 2.60 Hz, 2H), 2.15 (m, 2H), 1.99 (m, 2H), 1.48 (d, J=6.45 Hz, 3H). LC-MS (ESI) calcd mass 436.2, found 437.4 (MH⁺).

Example 56

4-(6,7-Dimethoxy-quinazolin-4-yl)-piperidine-1-carboxylic acid (6-isopropoxy-pyridin-3-yl)-amide

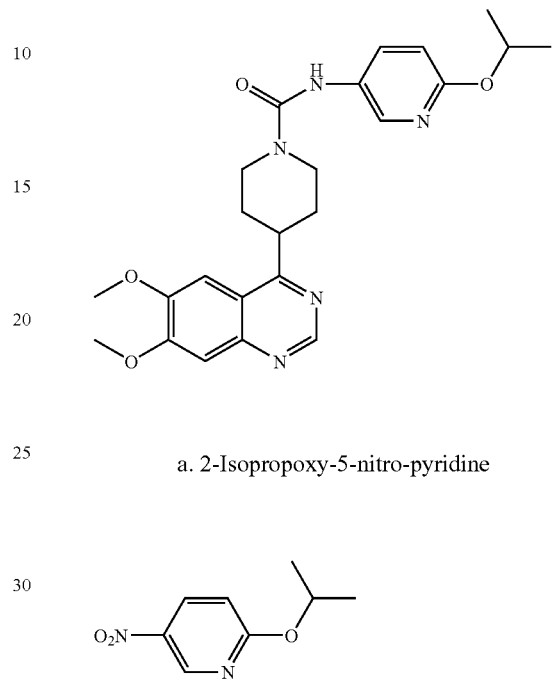

a. 2-Isopropoxy-5-nitro-pyridine

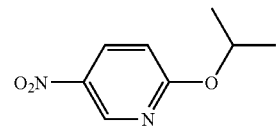

To a solution of 2-chloro-5-nitro-pyridine (450 mg, 2.84 mmol) in isopropanol (10 mL)/DMF (7 mL) was added 60% NaH (57 mg). The mixture was stirred at 80° C. for 4 h and the organic solvents were evaporated under reduced pressure. The residue was partitioned between EtOAc and water. The EtOAc extracts were dried (Na₂SO₄) and evaporated. The crude product was used for the next step reaction without further purification. ¹H NMR (300 MHz, CDCl₃) δ 9.06 (d, J=2.81 Hz, 1H), 8.32 (dd, J=8.79 and 2.53 Hz, 1H), 6.74 (d, J=8.61 Hz, 1H), 5.43 (m, 1H), 1.38 (d, J=6.20 Hz, 6H).

b. 6-Isopropoxy-pyridin-3-ylamine

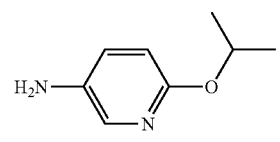

To a solution of 2-isopropoxy-5-nitro-pyridine, as prepared in the previous step, in MeOH (5 mL) was added 20 mg of 10% Pd/C. The mixture was degassed several times and stirred under hydrogen atmosphere for 4 h. It was filtered through a pad of celite and the filtrate was evaporated. The residue was purified by flash column chromatography on silica gel (EtOAc as eluent). ¹H NMR (400 MHz, CDCl₃) δ 7.65 (d, J=2.96 Hz, 1H), 7.02 (dd, J=8.71 and 2.99 Hz, 1H), 6.54 (d, J=8.67 Hz, 1H), 5.14 (m, 1H), 1.31 (d, J=6.17 Hz, 6H). LC-MS (ESI) calcd mass 152.1, found 153.2 (MH⁺).

c. 4-(6,7-Dimethoxy-quinazolin-4-yl)-piperidine-1-carboxylic acid (6-isopropoxy-pyridin-3-yl)-amide

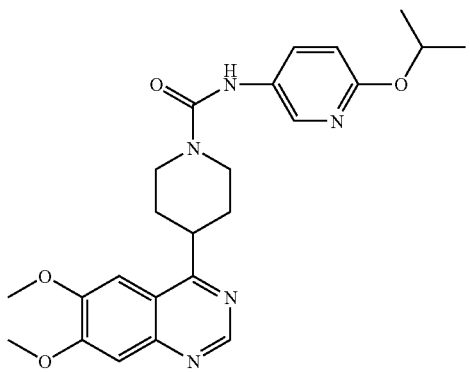

$^1$H NMR (300 MHz, CDCl$_3$) δ 9.09 (s, 1H), 8.04 (d, J=2.69 Hz, 1H), 7.81 (dd, J=8.92 and 2.56 Hz, 1H), 7.39 (s, 1H), 7.27 (s, 1H), 6.68 (d, J=8.86 Hz, 1H), 6.49 (s, 1H), 5.21 (m, 1H), 4.30 (m, 2H), 4.08 (s, 3H), 4.07 (s, 3H), 3.62 (m, 1H), 3.19 (td, J=13.00 and 2.74 Hz, 2H), 2.17 (m, 2H), 2.00 (m, 2H), 1.34 (d, J=6.17 Hz, 6H). LC-MS (ESI) calcd mass 451.2, found 452.4 (MH$^+$).

Example 57

4-(6,7-Dimethoxy-quinazolin-4-yl)-piperidine-1-carboxylic acid [4-(2-oxo-pyrrolidin-1-yl)-phenyl]-amide

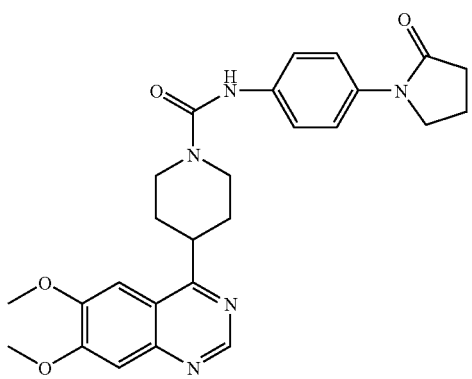

To a mixture of 4-(6,7-dimethoxy-quinazolin-4-yl)-piperidine-1-carboxylic acid (4-iodo-phenyl)-amide (57.9 mg, 0.11 mmol), as prepared in Example 2b, and pyrrolidin-2-one (13.3 mg, 0.16 mmol) in toluene (3 mL) was added CuI (1.5 mg), followed by N,N-dimethylethylenediamine (1.4 mg) and K$_3$PO$_4$ (56.7 mg). The reaction mixture was heated at 105° C. overnight. It was concentrated under reduced pressure and the crude residue was purified by flash column chromatography on silica gel (10% MeOH/EtOAc as eluent) to afford the desired product (8.6 mg, 16.4% yield). $^1$H NMR (300 MHz, CD$_3$OD) δ 8.95 (s, 1H), 7.58 (s, 1H), 7.50 (d, J=9.26 Hz, 2H), 7.41 (d, J=9.27 Hz, 2H), 7.32 (s, 1H), 4.36 (m, 2H), 4.06 (s, 3H), 4.04 (s, 3H), 3.91 (t, J=6.93 Hz, 2H), 3.39 (m, 1H), 3.19 (m, 2H), 2.59 (t, J=8.46 Hz, 2H), 1.94-2.30 (m, 6H). LC-MS (ESI) calcd mass 475.2, found 476.4 (MH$^+$).

Example 58

4-(6,7-Dimethoxy-quinazolin-4-yl)-piperidine-1-carboxylic acid (4-pyrimidin-5-yl-phenyl)-amide

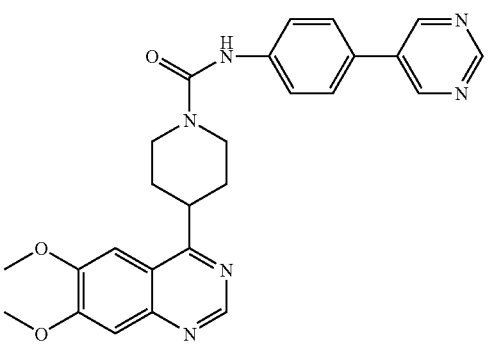

To a suspension of 4-(6,7-dimethoxy-quinazolin-4-yl)-piperidine-1-carboxylic acid (4-iodo-phenyl)-amide (58.2 mg, 0.11 mmol), as prepared in Example 2b, in 1 mL of toluene/EtOH (4:1, v/v) were added pyrimidine-5-boronic acid (15.3 mg, 0.12 mmol), Pd(PPh$_3$)$_4$ (6.5 mg) and 2M K$_2$CO$_3$ solution (0.23 mL). The reaction mixture was heated at 100° C. overnight. It was concentrated under reduced pressure and the black residue was purified by flash column chromatography on silica gel (5% MeOH/EtOAc as eluent) to afford the desired product (18.4 mg, 35.6% yield). $^1$H NMR (300 MHz, CDCl$_3$) δ 9.17 (s, 1H), 9.09 (s, 1H), 8.94 (s, 2H), 7.55 (s, 4H), 7.38 (s, 1H), 7.27 (s, 1H), 6.59 (s, 1H), 4.32 (m, 2H), 4.09 (s, 3H), 4.08 (s, 3H), 3.65 (m, 1H), 3.23 (m, 2H), 2.19 (m, 2H), 2.03 (m, 2H). LC-MS (ESI) calcd mass 470.2, found 471.3 (MH$^+$).

Similar to the synthesis of Example 58, Examples 59-61 were prepared by the reaction of 4-(6,7-dimethoxy-quinazolin-4-yl)-piperidine-1-carboxylic acid (4-iodo-phenyl)-amide with the corresponding boronic acid or borate in the presence of Pd(PPh$_3$)$_4$.

Example 59

4-(6,7-Dimethoxy-quinazolin-4-yl)-piperidine-1-carboxylic acid (4-furan-2-yl-phenyl)-amide

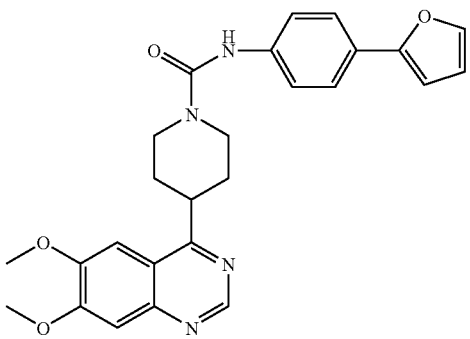

¹H NMR (300 MHz, CDCl₃) δ 9.09 (s, 1H, 7.61 (d, J=8.74 Hz, 2H), 7.44 (m, 1H), 7.42 (d, J=8.78 Hz, 2H), 7.36 (s, 1H), 7.27 (s, 1H), 6.57 (dd, J=3.34 and 0.62 Hz, 1H), 6.50 (s, 1H), 6.45 (dd, J=3.33 and 1.80 Hz, 1H), 4.28 (m, 2H), 4.08 (s, 3H), 4.07 (s, 3H), 3.62 (m, 1H), 3.20 (td, J=12.82 and 2.66 Hz, 2H), 2.16 (m, 2H), 2.01 (m, 2H). LC-MS (ESI) calcd mass 458.2, found 459.4 (MH⁺).

Example 60

4-(6,7-Dimethoxy-quinazolin-4-yl)-piperidine-1-carboxylic acid [4-(6-chloro-pyridin-3-yl)-phenyl]-amide

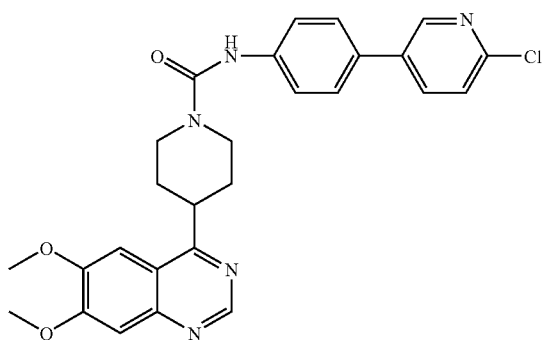

¹H NMR (300 MHz, CDCl₃) δ 9.09 (s, 1H), 8.58 (dd, J=2.58 and 0.63 Hz, 1H), 7.82 (dd, J=8.29 and 2.60 Hz, 1H), 7.51 (s, 4H), 7.37 (dd, J=8.26 and 0.67 Hz, 1H), 7.36 (s, 1H), 7.27 (s, 1H), 6.58 (s, 1H), 4.31 (m, 2H), 4.08 (s, 3H), 4.07 (s, 3H), 3.63 (m, 1H), 3.22 (m, 2H), 2.18 (m, 2H), 2.02 (m, 2H). LC-MS (ESI) calcd mass 503.2, found 504.3 (MH⁺).

Example 61

4-(4-{[4-(6,7-Dimethoxy-quinazolin-4-yl)-piperidine-1-carbonyl]-amino}-phenyl)-3,6-dihydro-2H-pyridine-1-carboxylic acid tert-butyl ester

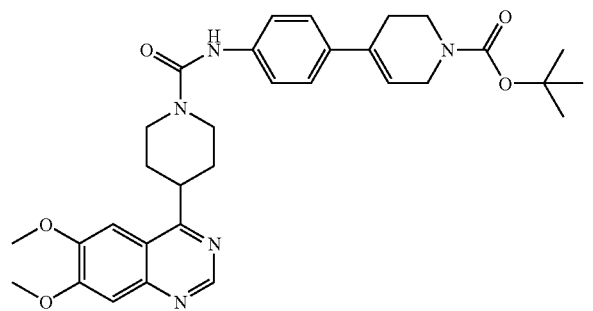

4-(4,4,5,5-Tetramethyl-[1,3,2]dioxaborolan-2-yl)-3,6-dihydro-2H-pyridine-1-carboxylic acid tert-butyl ester was used as starting material. ¹H NMR (300 MHz, CD₃OD) δ 8.94 (s, 1H), 7.56 (s, 1H), 7.36 (m, 4H), 7.31 (s, 1H), 6.03 (m, 1H), 4.36 (m, 2H), 4.06 (s, 3H), 4.04 (m, 2H), 4.03 (s, 3H), 3.90 (m, 1H), 3.62 (m, 2H), 3.22 (td, J=12.97 and 2.74 Hz, 2H), 2.50 (m, 2H), 1.93-2.10 (m, 4H), 1.49 (s, 9H). LC-MS (ESI) calcd mass 573.3, found 574.6 (MH⁺).

Example 62

4-(6,7-Dimethoxy-quinazolin-4-yl)-piperidine-1-carboxylic acid [4-(1,2,3,6-tetrahydro-pyridin-4-yl)-phenyl]-amide

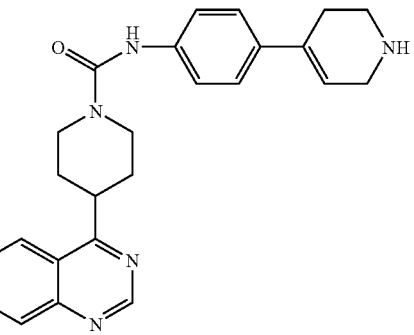

4-(4-{[4-(6,7-Dimethoxy-quinazolin-4-yl)-piperidine-1-carbonyl]-amino}-phenyl)-3,6-dihydro-2H-pyridine-1-carboxylic acid tert-butyl ester (10 mg, 0.017 mmol), as prepared in Example 61, was dissolved in 50% TFA/DCM (5 mL). The solution was stirred at room temperature for 4 h. It was evaporated and the residue was quenched with 2N ammonium in MeOH (6 mL). The solvent was removed and the residue was washed with water, dried in vacuo to afford the title compound as a white solid (8 mg, 100%). ¹H NMR (300 MHz, CD₃OD) δ 8.94 (s, 1H), 7.58 (s, 1H), 7.42 (s, 4H), 7.32 (s, 1H), 6.12 (m, 1H), 4.37 (m, 2H), 4.06 (s, 3H), 4.04 (s, 3H), 3.93 (m, 1H), 3.82 (m, 2H), 3.44 (t, J=6.29 Hz, 2H), 3.22 (m, 2H), 2.78 (m, 2H), 1.93-2.10 (m, 4H). LC-MS (ESI) calcd mass 473.2, found 474.5 (MH⁺).

Example 63

4-(4-{[4-(6,7-Dimethoxy-quinazolin-4-yl)-piperidine-1-carbonyl]-amino}-phenyl)-piperidine-1-carboxylic acid tert-butyl ester

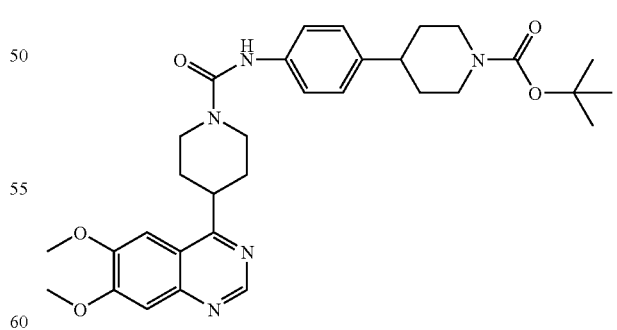

To a solution of 4-(4-{[4-(6,7-dimethoxy-quinazolin-4-yl)-piperidine-1-carbonyl]-amino}-phenyl)-3,6-dihydro-2H-pyridine-1-carboxylic acid tert-butyl ester (5 mg, 0.009 mmol), as prepared in Example 61, in MeOH (5 mL) was added 10% Pd/C (5 mg). The solution was degassed and was kept stirring under hydrogen atmosphere for 2 h. It was filtered through a pad of celite and the filtrate was evaporated to afford the desired product (3.7 mg, 74% yield). $^1$H NMR (300 MHz, CD$_3$OD) δ 8.94 (s, 1H), 7.57 (s, 1H), 7.32 (s, 1H), 7.30 (d, J=8.29 Hz, 2H), 7.15 (d, J=8.51 Hz, 2H), 4.35 (m, 2H), 4.20 (m, 2H), 4.06 (s, 3H), 4.03 (s, 3H), 3.91 (m, 1H), 3.21 (m, 2H), 2.85 (br, 2H), 2.67 (m, 1H), 1.93-2.10 (m, 4H), 1.80 (m, 2H), 1.57 (m, 2H), 1.48 (s, 9H). LC-MS (ESI) calcd mass 575.3, found 576.6 (MH$^+$).

Example 64

4-(6,7-Dimethoxy-quinazolin-4-yl)-piperidine-1-carboxylic acid (4-piperidin-4-yl-phenyl)-amide

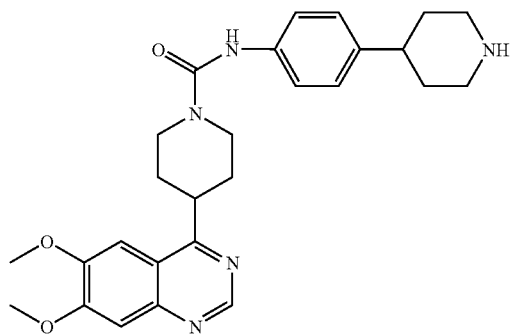

4-(4-{[4-(6,7-Dimethoxy-quinazolin-4-yl)-piperidine-1-carbonyl]-amino}-phenyl)-piperidine-1-carboxylic acid tert-butyl ester, prepared as described in Example 63, was treated essentially as described for Example 62, to afford the title compound. $^1$H NMR (300 MHz, CD$_3$OD) δ 8.94 (s, 1H), 7.57 (s, 1H), 7.36 (d, J=8.62 Hz, 2H), 7.32 (s, 1H), 7.19 (d, J=8.66 Hz, 2H), 4.36 (m, 2H), 4.06 (s, 3H), 4.04 (s, 3H), 3.91 (m, 1H), 3.49 (m, 2H), 3.06-3.28 (m, 4H), 2.87 (m, 1H), 1.79-2.12 (m, 8H). LC-MS (ESI) calcd mass 475.3, found 476.5 (MH$^+$).

Example 65

4-[7-(3-Methanesulfonylamino-propoxy)-quinazolin-4-yl]-piperidine-1-carboxylic acid (4-isopropoxy-phenyl)-amide

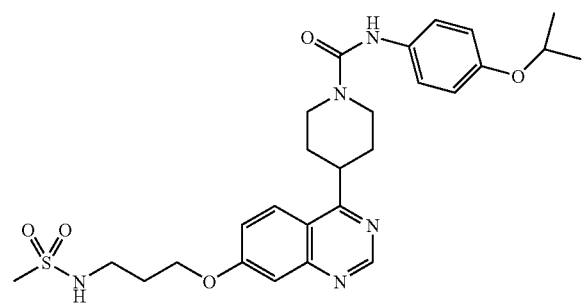

a. 4-(7-Fluoro-quinazolin-4-yl)-piperidine-1,4-dicarboxylic acid 1-tert-butyl ester 4-methyl ester

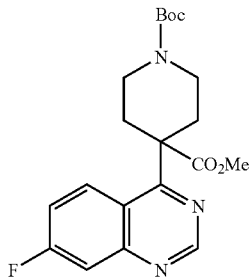

A mixture of 4-chloro-7-fluoro-quinazoline (2.87 g, 15.4 mmol) (WO 9609294 A1) and piperidine-1,4-dicarboxylic acid 1-tert-butyl ester 4-methyl ester (4.15 g, 17.1 mmol), as prepared in Example 1b, was placed in a −78° C. bath for 5 min under argon before adding a 1.08 M LiHMDS/THF solution (17.8 mL, 19.2 mmol) rapidly by syringe along the sides of the flask (to allow cooling and dispersion of the hindered base before reaction with the ester). Following completion of LiHMDS/THF addition, the reaction was manually swirled in the −78° C. bath for 2-3 min before removing the cold bath and allowing the mixture to stir with gradual warming to rt. After 2.5 h stirring at rt, the dark brown homogeneous solution was quenched with 1.0 M NaH$_2$PO$_4$ (38 mL) and extracted with DCM (1×150 mL and 1×25 mL). The organic layers were combined, dried (Na$_2$SO$_4$), and concentrated under reduced pressure, and subject to high vacuum at 90° C. with toluene chasers (3×10 mL) to provide the crude title compound as an opaque thick yellow oil that was used in the next step without further purification (6.83 g, "114%" crude yield). $^1$H-NMR (300 MHz, CDCl$_3$) δ 9.26 (s, 1H), 8.11 (dd, 1H), 7.70 (dd, 1H), 7.36 (ddd, 1H), 3.74-3.64 (m, 2H), 3.62-3.51 (m, 2H), 3.61 (s, 3H), 2.47-2.38 (br m, 4H), 1.46 (s, 9H). LC/MS (ESI): calcd mass 389.2, found 390.1 (MH)$^+$.

b. 4-(7-Fluoro-quinazolin-4-yl)-piperidine-1-carboxylic acid tert-butyl ester

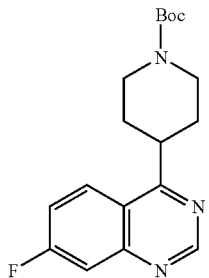

A mixture of 4-(7-fluoro-quinazolin-4-yl)-piperidine-1,4-dicarboxylic acid 1-tert-butyl ester 4-methyl ester ("6.83 g"), as prepared without further purification in the previous step, LiCl (1.32 g, 31.1 mmol), water (832 μL, 46.2 mmol), and DMSO (6.0 mL) was stirred under air at 150° C. (oil bath) with an efficient condenser (to retain reagent water) for 9.5 h. The dark solution was then allowed to cool to rt, shaken with 1.0 M NaHCO$_3$, and extracted with EtOAc (1×60 mL) and 9:1 DCM/MeOH (2×30 mL). The organic layers were combined, dried (Na$_2$SO$_4$), and concentrated to afford a thick clear amber oil. Flash chromatography of this residue (3:2 hexanes/EtOAc) afforded the title compound as a thick clear yellow syrup that was rubbed to a beige solid (2.37 g, 46% from 4-chloro-7-fluoroquinazoline). $^1$H-NMR (300 MHz, CDCl$_3$) δ 9.23 (s, 1H), 8.20 (dd, 1H), 7.67 (dd, 1H), 7.42 (ddd, 1H), 4.42-4.25 (br m, 2H), 3.65 (m, 1H), 2.96 (m, 2H), 2.14-1.83 (m, 4H), 1.49 (s, 1H). LC/MS (ESI): calcd mass 331.2, found 332.1 (MH)+ (weak).

c. 4-[7-(3-Methanesulfonylamino-propoxy)-quinazolin-4-yl]-piperidine-1-carboxylic acid tert-butyl ester

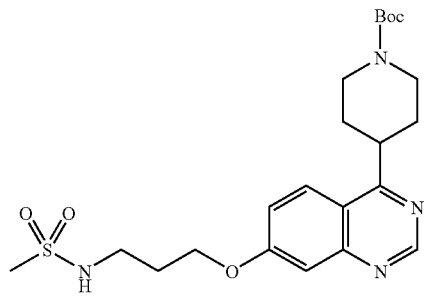

A mixture of 3-amino-propan-1-ol (37.9 mg, 505 μmol), t-BuOK (63.1 mg, 563 μmol), and DME (505 μL) was stirred for 5 min at rt until a homogeneous yellow solution resulted. Solid 4-(7-fluoro-quinazolin-4-yl)-piperidine-1-carboxylic acid tert-butyl ester (170.7 mg, 516 μmol), as prepared in the previous step, was added in one portion under air at "rt" (vial spontaneously warmed), and the resulting homogeneous amber solution was stirred at rt 1 h. The reaction was then diluted with DCM (1.0 mL) and stirred at 0° C. for 5 min before adding MsCl (48 μL, 620 μmol) dropwise with stirring at 0° C. over 1 min. After 1 min additional stirring at 0° C., the ice bath was removed and the hazy yellow solution was stirred at "rt" for 5 min. DIEA (94 μL, 568 μmol) was then added dropwise, and the reaction was stirred rt 2 days. The crude reaction was then loaded directly onto a flash silica column (4:3 DCM/acetone eluent) to provide the title compound as an off-white foam (186 mg, 79%). $^1$H-NMR (400 MHz, CDCl$_3$) δ 9.14 (s, 1H), 8.06 (d, 1H), 7.32 (d, 1H), 7.24 (m, 1H), 4.47 (br t, 1H), 4.32 (br s, 2H), 4.26 (t, 2H), 3.61 (m, 1H), 3.43 (q, 2H), 2.99-2.89 (m, 2H), 2.98 (s, 3H), 2.17 (pentet, 1H), 2.10-1.94 (m, 2H), 1.92-1.83 (m, 2H), 1.49 (s, 9H). LC/MS (ESI): calcd mass 464.2, found 465.2 (MH)+.

d. 4-[7-(3-Methanesulfonylamino-propoxy)-quinazolin-4-yl]-piperidine-1-carboxylic acid (4-isopropoxy-phenyl)-amide

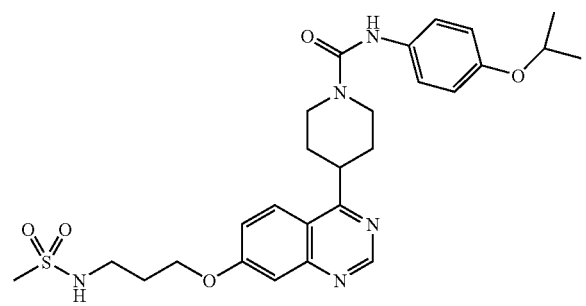

A premixed solution of 1:1 TFA/CHCl$_3$ (80 μL, 539 μmol TFA) was added to 4-[7-(3-ethanesulfonylamino-propoxy)-quinazolin-4-yl]-piperidine-1-carboxylic acid tert-butyl ester (38.7 mg, 83.4 μmol), prepared as described in the previous step, and the tightly capped reaction was stirred under air at 100° C. (aluminum block) for 10 min. After cooling to rt, DIEA (117 μL, 709 μmol) was added dropwise, followed by CHCl$_3$ (0.5 mL), and the resulting homogeneous solution was stirred at rt while (4-isopropoxy-phenyl)-carbamic acid 4-nitro-phenyl ester (32.9 mg, 104 μmol), as prepared in Example 1a, was added in one portion. The resulting homogeneous dark yellow solution was stirred at rt overnight, and then directly loaded onto a flash silica column (5:3 DCM/acetone eluent) to afford impure title compound. This material was taken up in EtOAc (2 mL) and washed with 1.0 M NaHCO$_3$ (3×2 mL), 1.0 M NaH$_2$PO$_4$ (2×2 mL), and again 1.0 M NaHCO$_3$ (2×2 mL). One contaminant was removed (apparently protonated DIEA), but another substantially remained (apparently nitrophenol), so the EtOAc layer was directly loaded onto a flash silica column (5:3 DCM/acetone eluent) to afford the title compound as a white foam (16.0 mg, 35%). $^1$H-NMR (400 MHz, CDCl$_3$) δ 9.13 (s, 1H), 8.06 (d, 1H), 7.32 (d, 1H), 7.27-7.21 (m, 3H), 6.84 (m, 2H), 6.34 (br s, 1H), 4.69 (br t, 1H), 4.48 (heptet, 1H), 4.26 (m, 4H), 3.67 (tt, 1H), 3.42 (q, 2H), 3.13 (td, 2H), 2.97 (s, 3H), 2.21-2.05 (m, 4H), 2.00-1.91 (m, 2H), 1.32 (d, 6H). LC/MS (ESI): calcd mass 541.2, found 542.1 (MH)+. Anal. Calcd for C$_{27}$H$_{35}$N$_5$O$_5$S: C, 59.87; H, 6.51; N, 12.93. Found: C, 60.03; H, 6.51; N, 12.78.

Example 66

4-[7-(3-Methanesulfonylamino-propoxy)-quinazolin-4-yl]-piperidine-1-carboxylic acid (4-morpholin-4-yl-phenyl)-amide

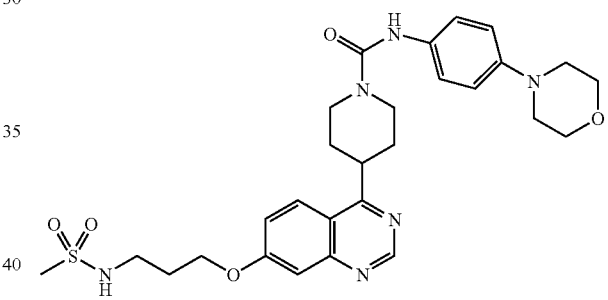

a. (4-Morpholin-4-yl-phenyl)-carbamic acid 4-nitro-phenyl ester; hydrochloride

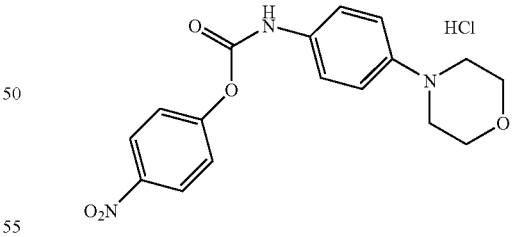

A solution of 4-nitrophenyl chloroformate (798 mg, 3.96 mmol) in THF (2.0 mL) was added rapidly by syringe over ~10 s at rt under air to a stirred solution of 4-morpholin-4-yl-phenylamine (675 mg, 3.79 mmol) in THF (8.8 mL), with a heavy grey precipitate forming "instantly". The reaction was immediately capped and stirred "rt" for 30 min (vial spontaneously warmed), and was then filtered. The grey filter cake was washed with dry THF (2×10 mL), and dried under high vacuum at 80° C. to afford the title compound as a grey powder (1.361 g, 95%). A portion was partitioned with CDCl$_3$ and aqueous 0.5 M trisodium citrate to generate the CDCl₃-soluble free base: ¹H-NMR (300 MHz, CDCl₃) δ 8.28 (m, 2H), 7.42-7.31 (m, 4H), 6.95-6.88 (m, 3H), 3.87 (m, 4H), 3.14 (m, 4H).

b. 4-[7-(3-Methanesulfonylamino-propoxy)-quinazolin-4-yl]-piperidine-1-carboxylic acid (4-morpholin-4-yl-phenyl)-amide

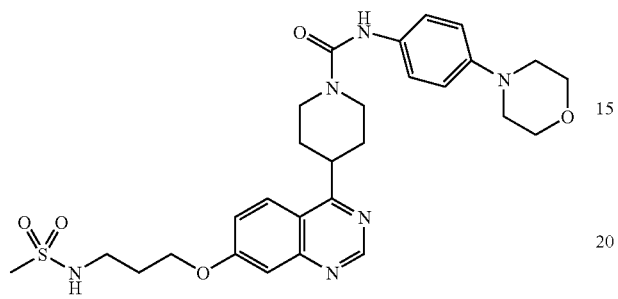

4-[7-(3-methanesulfonylamino-propoxy)-quinazolin-4-yl]-piperidine-1-carboxylic acid tert-butyl ester (7.4 mg, 16 μmol), as prepared in Example 65c, and TFA (100 μL, 1.35 mmol) was capped tightly and stirred at 100° C. (aluminum block) for 5 min. The reaction was then concentrated, and pyridine (100 μL) was added to give a homogeneous solution. (4-Morpholin-4-yl-phenyl)-carbamic acid 4-nitro-phenyl ester hydrochloride (7.5 mg, 20 μmol) was then added in one portion at rt, and the solution was stirred at 80° C. for 10 min, then at rt overnight. The reaction was then concentrated and subjected to silica flash chromatography (4:3→3:5 DCM/acetone) to afford the title compound as an off-white semi-solid (3.5 mg, 39%). ¹H-NMR (400 MHz, 95:5 v/v CDCl₃:CD₃OD) δ 9.10 (s, 1H), 8.09 (d, 1H), 7.33-7.25 (m, 4H), 6.89 (m, 2H), 4.27 (m, 4H), 3.87 (m, 4H), 3.70 (m, 1H), 3.38 (t, 2H), 3.17-3.07 (m, 6H), 2.96 (s, 3H), 2.20-2.05 (m, 4H), 2.01-1.92 (m, 2H). LC/MS (ESI): calcd mass 568.2, found 569.1 (MH)⁺.

Example 67

4-{7-[3-(2-Oxo-pyrrolidin-1-yl)-propoxy]-quinazolin-4-yl}-piperidine-1-carboxylic acid (4-isopropoxy-phenyl)-amide

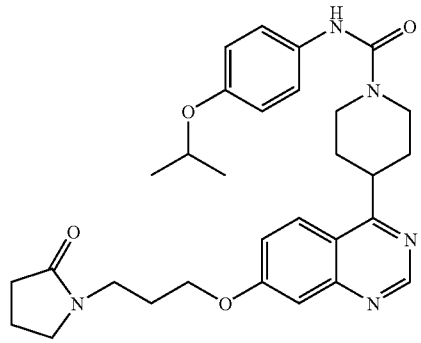

a. 4-{7-[3-(2-Oxo-pyrrolidin-1-yl)-propoxy]-quinazolin-4-yl}-piperidine-1-carboxylic acid tert-butyl ester

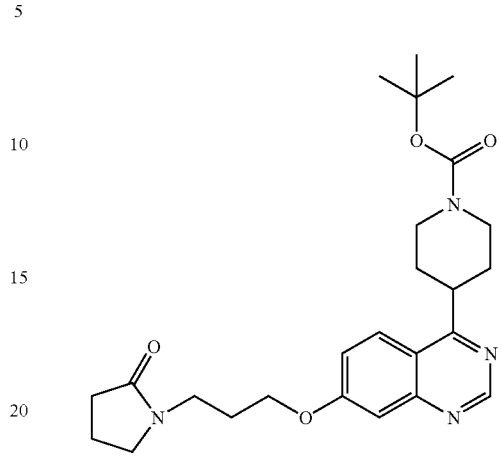

To a mixture of 4-(7-fluoro-quinazolin-4-yl)-piperidine-1-carboxylic acid tert-butyl ester 66.9 mg, 0.20 mmol), as prepared in Example 65b, and tert-BuOK (33.4 mg, 0.30 mmol) was added 1-(3-hydroxypropyl)-2-pyrrolidone (34.7 mg, 0.24 mmol) in anhydrous THF (3 mL). The mixture was stirred at 85° C. for 15 min and the solvent was evaporated under reduced pressure to give a light brown residue, which is used for the next step reaction without purification. ¹H NMR (300 MHz, CDCl₃) δ 9.10 (s, 1H), 8.03 (d, J=9.13 Hz, 1H), 7.26 (m, 1H), 7.23 (dd, J=9.05 and 2.43 Hz, 1H), 4.14 (t, J=6.08 Hz, 2H), 3.58 (m, 1H), 3.50 (t, J=6.60 Hz, 4H), 3.42 (t, J=6.98 Hz, 4H), 2.37 (t, J=8.45 Hz, 2H), 1.80-2.15 (m, 8H), 1.46 (s, 9H). LC-MS (ESI) calcd for C₂₅H₃₅N₄O₄ (MH⁺) 455.3, found 455.2.

b. 4-{7-[3-(2-Oxo-pyrrolidin-1-yl)-propoxy]-quinazolin-4-yl}-piperidine-1-carboxylic acid (4-isopropoxy-phenyl)-amide

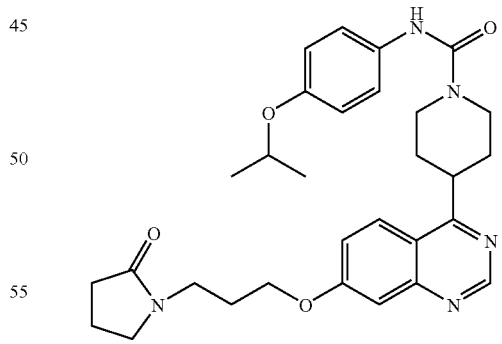

4-{7-[3-(2-Oxo-pyrrolidin-1-yl)-propoxy]-quinazolin-4-yl}-piperidine-1-carboxylic acid tert-butyl ester (as prepared in the previous step, 0.20 mmol) was treated with 50% TFA/CH₂Cl₂ (4 mL) for 2 h and the solvents were evaporated. To the residue was added (4-isopropoxy-phenyl)-carbamic acid 4-nitro-phenyl ester (70.2 mg, 0.22 mmol), as prepared in Example 1a, followed by DIEA (130.5 mg, 1.01 mmol) in CH₃CN (4 mL). The resulting mixture was heated at 95° C. for 1 h and the solvents were evaporated under reduced pressure. The residue was purified by flash column chromatography on silica gel (5% MeOH/EtOAc as eluent) to afford the product as a white solid (95.5 mg, 89% yield). $^1$H NMR (300 MHz, CDCl$_3$) δ 9.14 (s, 1H), 8.06 (d, J=9.33 Hz, 1H), 7.33 (d, J=2.46 Hz, 1H), 7.28 (dd, J=9.30 and 2.65 Hz, 1H), 7.25 (m, 2H), 6.84 (d, J=8.93 Hz, 2H), 6.33 (br, 1H), 4.48 (m, 1H), 4.26 (m, 2H), 4.17 (t, J=6.10 Hz, 2H), 3.69 (m, 1H), 3.53 (t, J=6.99 Hz, 2H), 3.45 (t, J=7.02 Hz, 2H), 3.13 (td, J=12.85 and 2.83 Hz, 2H), 2.40 (t, J=7.78 Hz, 2H), 1.94-2.20 (m, 8H), 1.31 (d, J=6.06 Hz, 6H). LC-MS (ESI) calcd for C$_{30}$H$_{38}$N$_5$O$_4$ (MH$^+$) 532.3, found 532.2. Anal. Calcd for C$_{30}$H$_{37}$N$_5$O$_4$: C, 67.77; H, 7.01; N, 13.17. Found: C, 67.81; H, 6.96; N, 13.16.

Example 68

4-{7-[3-(2-Oxo-pyrrolidin-1-yl)-propoxy]-quinazolin-4-yl}-piperidine-1-carboxylic acid (4-morpholin-4-yl-phenyl)-amide

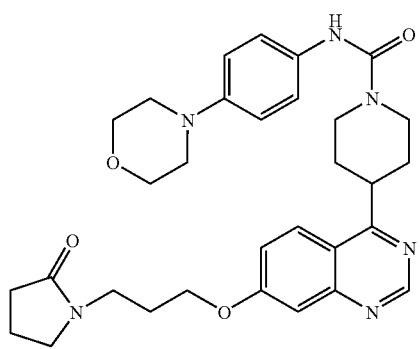

Prepared essentially as described in Example 67b, using (4-morpholin-4-yl-phenyl)-carbamic acid 4-nitro-phenyl ester hydrochloride, as prepared in Example 66a. $^1$H NMR (300 MHz, CD$_3$OD) δ 9.03 (s, 1H), 8.35 (d, J=9.40 Hz, 1H), 7.38 (dd, J=9.34 and 2.50 Hz, 1H), 7.31 (d, J=2.48 Hz, 1H), 7.25 (d, J=9.09 Hz, 2H), 6.93 (d, J=9.14 Hz, 2H), 4.34 (m, 2H), 4.22 (t, J=6.03 Hz, 2H), 3.92 (m, 1H), 3.82 (t, J=4.65 Hz, 4H), 3.53 (t, J=6.88 Hz, 4H), 3.16 (td, J=13.05 and 2.81 Hz, 2H), 3.08 (t, J=4.82 Hz, 4H), 2.37 (t, J=7.74 Hz, 2H), 1.89-2.17 (m, 8H). LC-MS (ESI) calcd for C$_{31}$H$_{39}$N$_6$O$_4$ (MH$^+$) 559.3, found 559.2. Anal. Calcd for C$_{31}$H$_{38}$N$_6$O$_4$: C, 66.65; H, 6.86; N, 15.04. Found: C, 66.34; H, 6.80; N, 14.97.

Example 69

4-(6,7-Dimethoxy-quinazolin-4-yl)-piperidine-1-carboxylic acid (6-cyclopentyloxy-pyridin-3-yl)-amide

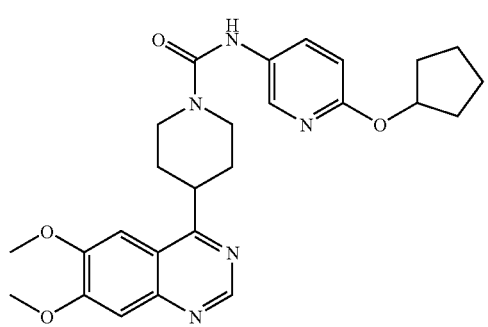

a. 2-Cyclopentyloxy-5-nitro-pyridine

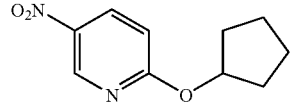

To a solution of 2-chloro-5-nitropyridine (7.01 g, 44.4 mmol) in THF (30 mL) and cyclopentanol (3.9 g, 45.3 mmol) was added sodium hydride (1.3 g, 54.2 mmol) portionwise with stirring over ~30 sec with ice-bath cooling at 0° C. After stirring at 0° C. for 5 min, the ice bath was removed and the reaction was stirred at rt for 3 h. It was then concentrated in vacuo and the residue was dissolved in DCM and washed extensively with 1 M NaHCO$_3$ and then dried over anhydrous Na$_2$SO$_4$, filtered and concentrated in vacuo. The crude product was purified by flash column chromatography (silica gel, 9:1 Hexane:Ethyl Acetate) to obtain pure 2-cyclopentyloxy-5-nitro-pyridine (0.4 g, 4%). $^1$H-NMR (300 MHz, CDCl$_3$): δ 9.07 (s, 1H), 8.32 (m, 1H), 6.74 (d, 1H), 5.53 (m, 1H), 2.00 (m, 2H), 1.81 (m, 4H), 1.66 (m, 2H).

b. 6-Cyclopentyloxy-pyridin-3-ylamine

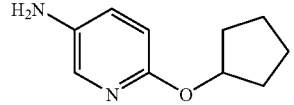

To a solution of 2-cyclopentyloxy-5-nitro-pyridine (0.3099 g, 1.49 mmol), in MeOH (2 mL) was added 10% Pd/C (90 mg). The solution was degassed and was kept stirring under hydrogen atmosphere for overnight. It was filtered through a pad of celite and the filtrate was evaporated to afford the desired product as a brown oil (248 mg, 94% yield). $^1$H-NMR (300 MHz, CDCl$_3$): δ 7.69 (d, 1H), 7.04 (m, 1H), 6.56 (d, 1H), 5.25 (m, 1H), 1.93 (m, 2H), 1.78 (m, 4H), 1.60 (m, 2H). LC/MS (ESI) calcd for C$_{10}$H$_{14}$N$_2$O 178.23, found [M+41+1]$^+$ 220.0.

c. (6-Cyclopentyloxy-pyridin-3-yl)-carbamic acid 4-nitro-phenyl ester

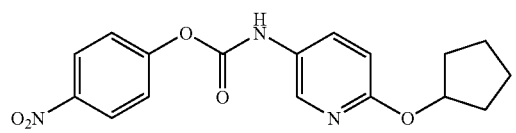

To a solution of 6-cyclopentyloxy-pyridin-3-ylamine (0.248 g, 1.39 mmol) in THF (2 mL) was added 4-nitrophenyl chloroformate (0.280 g, 1.39 mmol) portionwise. After stirring at rt for 1 h, a heavy precipitate formed in the organic layer. Filtration of the organic layer provided the title compound as a light pink solid (0.368 g, 77%). $^1$H-NMR (400 MHz, CDCl$_3$): δ 11.1 (s, 1H), 9.11 (s, 1H), 9.04 (d, 1H), 8.26 (d, 2H), 7.40 (d, 2H), 7.14 (d, 1H), 5.36 (m, 1H), 2.11 (m, 2H), 1.97 (m, 2H), 1.84 (m, 2H), 1.71 (m, 2H).

d. 4-(6,7-Dimethoxy-quinazolin-4-yl)-piperidine-1-carboxylic acid (6-cyclopentyloxy-pyridin-3-yl)-amide

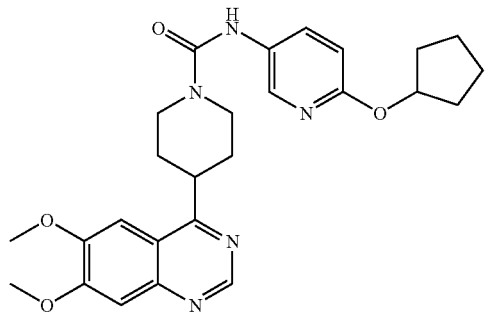

A mixture of 6,7-dimethoxy-4-piperidin-4-yl-quinazoline (12 mg, 0.044 mmol), prepared as described in Example 1d, (6-cyclopentyloxy-pyridin-3-yl)-carbamic acid 4-nitro-phenyl ester (20 mg, 0.058 mmol), prepared as described in the previous step, and DCM (500 uL) was treated with TEA (6 uL, 0.043 mmol) in one portion at rt. The homogeneous amber solution was stirred at rt for 2 h, diluted with DCM (2 mL), and washed with $H_2O$ (2 mL). The aqueous layer was extracted with DCM (2×2 mL), the organic layers were combined, dried ($Na_2SO_4$) and concentrated in vacuo. Purification by prep tlc (1:9 MeOH/DCM) afforded the title compound (6.0 mg, 29%). $^1$H-NMR (300 MHz, $CDCl_3$): δ 9.10 (s, 1H), 8.08 (s, 1H), 7.89 (d, 1H), 7.39 (s, 1H), 7.28 (s, 1H), 6.71 (d, 1H), 6.61 (bs, 1H), 5.30 (m, 1H), 4.32 (d, 2H), 4.08 (s, 6H), 3.62 (m, 1H), 3.20 (m, 2H), 2.16 (m, 2H), 1.98 (m, 4H), 1.79 (m, 4H), 1.62 (m, 2H). LC/MS (ESI) calcd for $C_{26}H_{31}N_5O_4$ 477.56, found $[M+1]^+$ 478.1.

Example 70

4-(6,7-Dimethoxy-quinazolin-4-yl)-piperidine-1-carboxylic acid (4-azepan-1-yl-phenyl)-amide

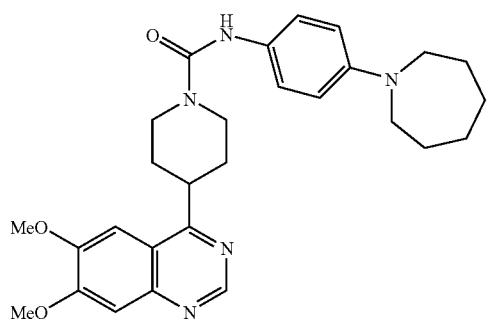

4-(6,7-Dimethoxy-quinazolin-4-yl)-piperidine-1-carbonyl chloride (37 mg, 0.11 mmol), prepared as described in Example 3a, was dissolved in anhydrous dioxane (2 mL) and to it was added 4-azepan-1-yl-phenylamine (19 mg, 0.1 mmol) followed by DIEA (20 uL, 0.11 mmol) and the mixture was stirred at 100° C. for 3 h. It was then concentrated in vacuo and the residue was purified by Preparative TLC (silica gel, 5% MeOH/DCM) to obtain 3 mg (6%) of pure 4-(6,7-dimethoxy-quinazolin-4-yl)-piperidine-1-carboxylic acid (4-azepan-1-yl-phenyl)-amide. $^1$H-NMR (300 MHz, $CDCl_3$) 9.08 (s, 1H), 7.55-7.23 (m, 4H), 7.18 (d, 1H), 6.77 (d, 1H), 6.37 (s, 1H), 4.27 (m, 2H), 4.07 (s, 6H), 3.68-3.32 (m, 3H), 3.30-2.90 (m, 2H), 2.24-1.88 (m, 4H), 1.86-1.38 (m, 10H). LC/MS (ESI): 490.3 $(MH)^+$.

Example 71

4-(6,7-Dimethoxy-quinazolin-4-yl)-piperidine-1-carboxylic acid (3-chloro-4-piperidin-1-yl-phenyl)-amide

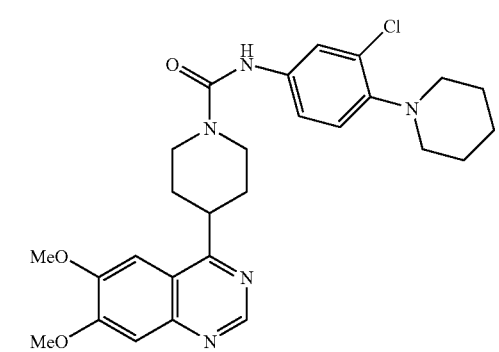

Prepared as described in Example 70, except that 3-chloro-4-piperidin-4-yl-phenylamine was used in place of 4-azepan-1-yl-phenylamine. Purification by Preparative TLC (silica gel, 5% MeOH/DCM) yielded 8.1 mg (16%) of pure 4-(6,7-dimethoxy-quinazolin-4-yl)-piperidine-1-carboxylic acid (3-chloro-4-piperidin-1-yl-phenyl)-amide. $^1$H-NMR (300 MHz, $CDCl_3$): 9.07 (s, 1H), 7.43 (d, 1H), 7.34 (s, 1H), 7.24 (d, 1H), 7.21 (d, 1H), 7.00 (d, 1H), 6.45 (d, 1H), 4.26 (m, 2H), 4.07 (s, 6H), 3.66-3.52 (m, 1H), 3.23-3.10 (m, 2H), 2.93 (m, 4H), 2.23-2.06 (m, 2H), 2.04-1.93 (m, 2H), 1.74 (m, 4H), 1.57 (m, 2H). LC/MS (ESI): 510.3 $(MH)^+$.

Example 72

4-{7-[3-(2-Oxo-pyrrolidin-1-yl)-propoxy]-quinazolin-4-yl}-piperidine-1-carboxylic acid (6-morpholin-4-yl-pyridin-3-yl)-amide

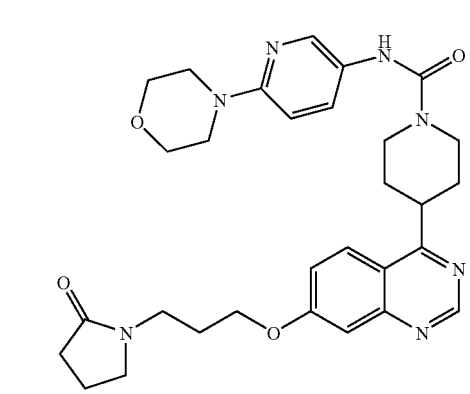

Prepared essentially as described in Example 67b, using (6-morpholin-4-yl-pyridin-3-yl)-carbamic acid 4-nitro-phenyl ester hydrochloride, which was prepared by the method outlined in Example 66a. $^1$H NMR (300 MHz, $CD_3OD$) δ

9.03 (s, 1H), 8.35 (d, J=9.49 Hz, 1H), 8.12 (dd, J=2.72 and 0.62 Hz, 1H), 7.65 (dd, J=9.01 and 2.70 Hz, 1H), 7.39 (dd, J=9.32 and 2.62 Hz, 1H), 7.31 (d, J=2.41 Hz, 1H), 6.82 (d, J=9.03 Hz, 1H), 4.34 (m, 2H), 4.22 (t, J=5.88 Hz, 2H), 3.94 (m, 1H), 3.80 (t, J=4.89 Hz, 4H), 3.53 (t, J=7.09 Hz, 4H), 3.40 (t, J=4.91 Hz, 4H), 3.18 (m, 2H), 2.38 (t, J=8.09 Hz, 2H), 1.90-2.17 (8H). LC-MS (ESI) calcd for $C_{30}H_{38}N_7O_4$ (MH$^+$) 560.3, found 560.2.

Example 73

4-{7-[3-(4-Methyl-piperazin-1-yl)-propoxy]-quinazolin-4-yl}-piperidine-1-carboxylic acid (4-morpholin-4-yl-phenyl)-amide

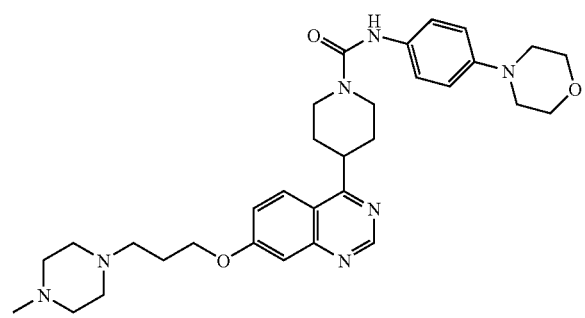

a. 4-(7-Fluoro-quinazolin-4-yl)-piperidine-1-carboxylic acid tert-butyl ester

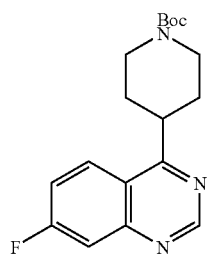

The title compound was prepared essentially as described in Example 65b, except the starting material 4-(7-fluoro-quinazolin-4-yl)-piperidine-1,4-dicarboxylic acid 1-tert-butyl ester 4-methyl ester was purified by silica flash chromatography (3:1→2:1 hexanes/EtOAc) before subjection to LiCl/water/DMSO decarboxylative conditions.

b. 7-[3-(4-Methyl-piperazin-1-yl)-propoxy]-4-piperidin-4-yl-quinazoline

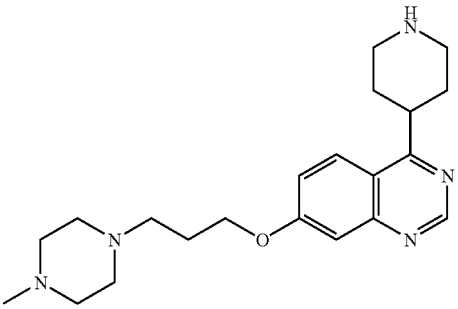

Solid KOtBu (1.36 g, 12.1 mmol) was added in one portion under air to a homogeneous solution of 4-(7-Fluoro-quinazolin-4-yl)-piperidine-1-carboxylic acid tert-butyl ester (3.33 g, 10.1 mmol), as prepared in the preceding step, and commercial 3-(4-methyl-piperazin-1-yl)-propan-1-ol (1.50 g, 9.50 mmol) in dry THF (10 mL), while stirring on an ice bath. Following KOtBu addition, the ice bath was immediately removed, and the resulting homogeneous amber solution was stirred for 6 hr. 6 M aqueous HCl (10 mL, 60 mmol) was then added in one portion, and the reaction was stirred overnight (mild bubbles were seen following HCl addition, but these subsided after 15 min). The reaction was then partitioned with 9:1 DCM/MeOH (50 mL) and 2.5 M NaOH (28 mL, 70 mmol), and the aqueous layer was extracted with 9:1 DCM/MeOH (1×50 mL). The combined organic layers were dried (Na$_2$SO$_4$) and concentrated by rotary evaporation at 90° C. to provide the crude title compound as a clear yellow oil (3.79 g, "102%" crude yield). LC/MS (ESI): calcd mass 369.3, found 370.2 (MH)$^+$.

c. 4-{7-[3-(4-Methyl-piperazin-1-yl)-propoxy]-quinazolin-4-yl}-piperidine-1-carboxylic acid (4-morpholin-4-yl-phenyl)-amide

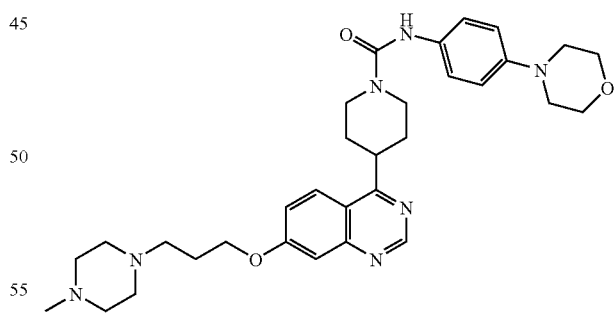

A solution of 7-[3-(4-Methyl-piperazin-1-yl)-propoxy]-4-piperidin-4-yl-quinazoline (3.654 g, 9.9 mmol), as prepared in the previous step, in 98:2 DCM/MeOH (15 mL) was added rapidly dropwise under air in 2 mL portions to an ice bath-chilled stirred mixture of (4-morpholin-4-yl-phenyl)-carbamic acid 4-nitro-phenyl ester hydrochloride (4.13 g, 10.9 mmol), as prepared in Example 66a, and dimethylethylamine (DMEA) (1.4 mL, 13 mmol) in 98:2 DCM/MeOH (20 mL). Residual quinazoline derivative was then transferred to the carbamate reaction mixture with 2×7 mL additional 98:2

DCM/MeOH. The resulting homogeneous dark amber solution was stirred for another 5 min, and the ice bath was then removed and the reaction stirred at "rt" for 1.5 hr. The homogeneous reaction solution was then directly applied to a silica flash column (79 mm diameter×6" length) pre-equilibrated with acetone. The title compound was eluted with 1.5 L acetone→2 L 9:1 acetone/MeOH→2 L 9:1 acetone/MeOH/3% DMEA. The combined fractions were concentrated to afford the title compound contaminated with nitrophenol and DMEA, and this material was partitioned with DCM (100 mL) and 2 M aqueous $K_2CO_3$ (2×20 mL). The organic layer was dried (Na2SO4) and concentrated under high vacuum at 90° C. to afford the title compound as a lavender foam that was crushed to a powder [3.89 g, 70% over three steps from 4-(7-Fluoro-quinazolin-4-yl)-piperidine-1-carboxylic acid tert-butyl ester].

$^1$H-NMR (300 MHz, CDCl$_3$): 9.13 (s, 1H), 8.04 (d, 1H), 7.34-7.22 (m, 4H), 6.88 (m, 2H), 6.32 (s, 1H), 4.31-4.23 (m, 2H), 4.22-4.15 (t, 2H), 3.89-3.82 (m, 4H), 3.75-3.60 (m, 1H), 3.20-3.05 (m, 6H), 2.70-2.45 (m, 10H), 2.35 (s, 3H), 2.22-1.88 (m, 6H). LC/MS (ESI): 574.2 (MH)$^+$. Anal. Calcd for $C_{32}H_{43}N_7O_3 \cdot 0.35H_2O$: C, 66.26; H, 7.59; N, 16.90. Found: C, 66.05; H, 7.47; N, 16.79. Karl Fischer: 1.09% water.

Example 74

4-{7-[2-(2-Oxo-pyrrolidin-1-yl)-ethoxy]-quinazolin-4-yl}-piperidine-1-carboxylic acid (4-pyrrolidin-1-yl-phenyl)-amide

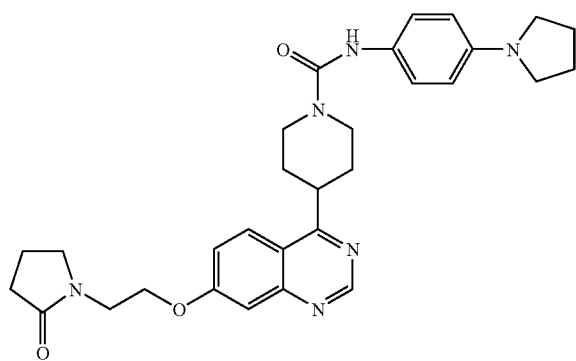

a). (4-Pyrrolidin-1-yl-phenyl)-carbamic acid 4-nitro-phenyl ester hydrochloride

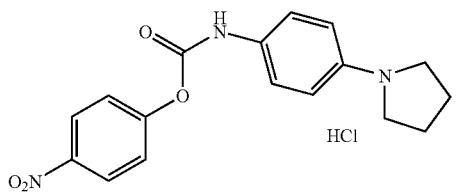

To a stirred solution of 4.9 g (30.4 mmol) of 4-pyrrolidin-1-yl-phenylamine in 70 mL of anhydrous THF at room temperature, was added dropwise a solution of 6.4 g (32 mmol) of 4-nitrophenyl chloroformate in 16 mL of anhydrous THF. After the addition was complete, the mixture was stirred for 1 h and then filtered. The precipitate was washed first with anhydrous THF (2×10 mL) and then with anhydrous DCM (3×10 mL) and dried in vacuo to yield 10 g of an off-white solid. $^1$H-NMR (300 MHz, CD$_3$OD): 10.39 (s, 1H), 8.32 (d, 2H), 7.73 (d, 2H), 7.60 (d, 2H), 7.48 (d, 2H), 3.86-3.68 (bs, 4H), 2.35-2.24 (bs, 4H). LC/MS (ESI): 328 (MH)$^+$.

b). 4-{7-[2-(2-Oxo-pyrrolidin-1-yl)-ethoxy]-quinazolin-4-yl}-piperidine-1-carboxylic acid (4-pyrrolidin-1-yl-phenyl)-amide

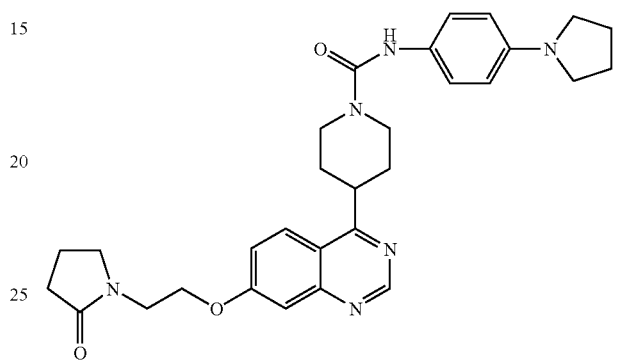

Prepared essentially as described in Example 67b, using 1-(2-hydroxyethyl)-2-pyrrolidone and (4-pyrrolidin-1-yl-phenyl)-carbamic acid 4-nitro-phenyl ester hydrochloride. $^1$H NMR (400 MHz, CDCl$_3$) δ 9.15 (s, 1H), 8.06 (d, J=9.30 Hz, 1H), 7.30 (d, J=2.48 Hz, 1H), 7.25 (dd, J=9.28 and 2.49 Hz, 1H), 7.18 (d, J=8.94 Hz, 2H), 6.52 (d, J=8.89 Hz, 2H), 6.20 (br, 1H), 4.28 (t, J=5.17 Hz, 2H), 4.24 (m, 2H), 3.79 (t, J=5.13 Hz, 2H), 3.66 (m, 1H), 3.60 (t, J=6.95 Hz, 2H), 3.26 (t, J=6.58 Hz, 4H), 3.12 (td, J=12.71 and 2.51 Hz, 2H), 2.42 (t, J=7.80 Hz, 2H), 1.93-2.18 (m, 10H). LC-MS (ESI) calcd for $C_{30}H_{37}N_6O_3$ (MH$^+$) 529.3, found 529.1. Anal. Calcd for $C_{30}H_{36}N_6O_3$: C, 68.16; H, 6.86; N, 15.90. Found: C, 67.97; H, 6.76; N, 15.80.

Example 75

4-[7-(3-piperidin-1-yl)-propoxy)-quinazolin-4-yl]-piperidine-1-carboxylic acid (4-morpholin-4-yl-phenyl)amide

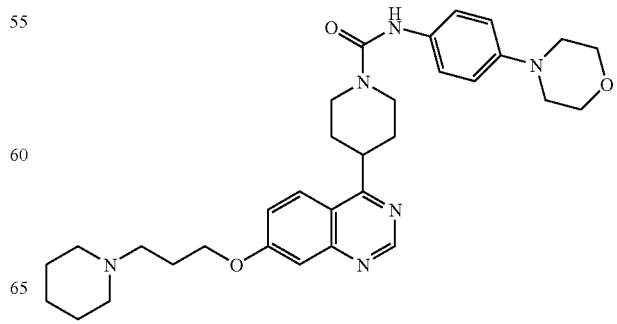

Prepared essentially as described in Example 33 using (4-Morpholino-4-yl-phenyl)-carbamic acid 4-nitrophenyl ester hydrochloride as prepared by the method outlined in Example 66a. $^1$H-NMR (300 MHz, CDCl$_3$): 9.13 (s, 1H), 8.05 (d, 1H), 7.33-7.22 (m, 4H), 6.88 (d, 2H), 6.31 (s, 1H), 4.30-4.23 (m, 2H), 4.22-4.17 (m, 2H), 3.88-3.83 (m, 4H), 3.72-3.63 (m, 1H), 3.18-3.06 (m, 6H), 2.74-2.36 (m, 4H), 2.20-2.05 (m, 4H), 1.97 (d, 2H), 1.76-1.42 (m, 8H). LC/MS (ESI): 559.1 (MH)$^+$.

Example 76

4-{6-[3-(4-Methyl-piperazin-1-yl)-propoxy]-quinazolin-4-yl}-piperidine-1-carboxylic acid (4-isopropoxy-phenyl)-amide

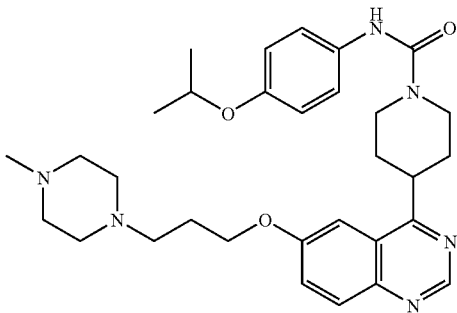

The title compound was prepared from 4-chloro-6-fluoro-quinazoline (WO 2005021500 A1, WO 2004071460 A2, WO 9609294 A1) essentially as described in Example 65, except 3-(4-Methyl-piperazin-1-yl)-propan-1-ol at 100° C. for 1 hr was used in place of 3-amino-propan-1-ol, and the use of methanesulfonyl chloride was omitted. $^1$H-NMR (300 MHz, CDCl$_3$) δ 9.13 (s, 1H), 7.98 (d, 1H), 7.56 (dd, 1H), 7.32 (d, 1H), 7.25 (m, 2H), 6.85 (m, 2H), 6.33 (br s, 1H), 4.49 (heptet, 1H), 4.27 (m, 2H), 4.19 (t, 2H), 3.65 (tt, 1H), 3.18 (td, 2H), 2.65-2.38 (m, 10H), 2.31 (t, 3H), 2.21-1.95 (m, 6H), 1.32 (d, 6H). LC/MS (ESI): calcd mass 546.3, found 547.3 (MH)$^+$.

Example 77

4-[7-(3-Hydroxy-propoxy)-quinazolin-4-yl]-piperidine-1-carboxylic acid (4-morpholin-4-yl-phenyl)-amide

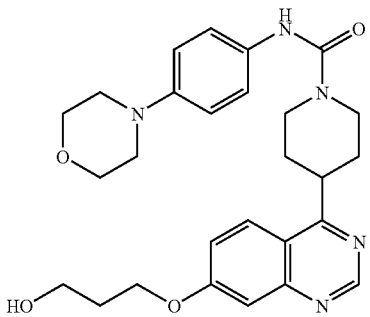

Prepared essentially as described in Example 33 using propane-1,3-diol in place of 3-hydroxypropylpiperidine and (4-morpholin-4-yl-phenyl)-carbamic acid 4-nitrophenyl ester hydrochloride, as prepared by the method outlined in Example 66a, in place of (4-isopropoxy-phenyl)-carbamic acid 4-nitrophenyl ester. $^1$H-NMR (300 MHz, CDCl$_3$): 9.12 (s, 1H), 8.04 (d, 1H), 7.36-7.22 (m, 4H), 6.89 (d, 2H), 6.40 (s, 1H), 4.34-4.21 (m, 4H), 3.95-3.81 (m, 6H), 3.67 (m, 1H), 3.20-3.05 (m, 6H), 2.22-2.02 (m, 4H), 2.02-1.75 (m, 3H). LC/MS (ESI): 492.1 (MH)$^+$.

Example 78

4-[7-(3-Methoxy-propoxy)-quinazolin-4-yl]-piperidine-1-carboxylic acid (4-morpholin-4-yl-phenyl)-amide

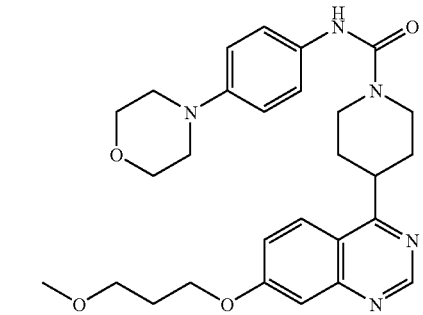

Prepared essentially as described in Example 33 using 3-methoxypropanol in place of 3-hydroxypropylpiperidine and (4-morpholin-4-yl-phenyl)-carbamic acid 4-nitrophenyl ester hydrochloride, as prepared by the method outlined in Example 66a, in place of (4-isopropoxy-phenyl)-carbamic acid 4-nitrophenyl ester. $^1$H-NMR (300 MHz, CDCl$_3$): 9.13 (s, 1H), 8.05 (d, 1H), 7.36-7.23 (m, 4H), 6.90 (d, 2H), 6.36 (s, 1H), 4.31-4.20 (m, 4H), 3.87 (m, 4H), 3.75-3.55 (m, 3H), 3.37 (s, 3H), 3.20-3.05 (m, 6H), 2.22-2.04 (m, 4H), 1.97 (d, 2H). LC/MS (ESI): 506.1 (MH)$^+$.

Example 79

4-{7-[2-(2-Oxo-oxazolidin-3-yl)-ethoxy]-quinazolin-4-yl}-piperidine-1-carboxylic acid (4-isopropoxy-phenyl)-amide

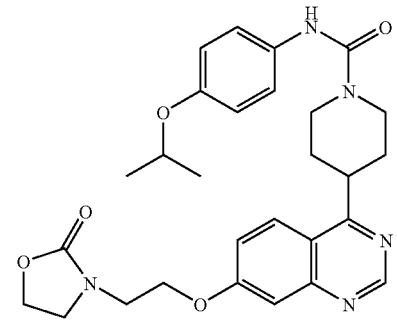

Prepared essentially as described in Example 67 using 3-(2-hydroxyethyl)-oxazolidin-2-one and (4-isopropoxy-phenyl)-carbamic acid 4-nitro-phenyl ester. $^1$H NMR (CDCl$_3$) δ 9.16 (s, 1H), 8.09 (d, J=9.34 Hz, 1H), 7.36 (d, J=2.48 Hz, 1H), 7.28 (m, 1H), 7.25 (d, J=8.48 Hz, 2H), 6.85 (d, J=8.97 Hz, 2H), 6.33 (br, 1H), 4.48 (m, 1H), 4.38 (t, J=7.71 Hz, 2H), 4.33 (t, J=5.13 Hz, 2H), 4.26 (m, 2H), 3.76-3.82

(4H), 3.69 (m, 1H), 3.14 (m, 2H), 1.94-2.21 (4H), 1.31 (d, J=6.06 Hz, 6H). Calcd for $C_{28}H_{34}N_5O_5$ (MH+) 520.3, found 520.1.

Example 80

4-{7-[3-(4-Methyl-piperazin-1-yl)-propoxy]-quinazolin-4-yl}-piperidine-1-carboxylic acid (6-morpholin-4-yl-pyridin-3-yl)-amide

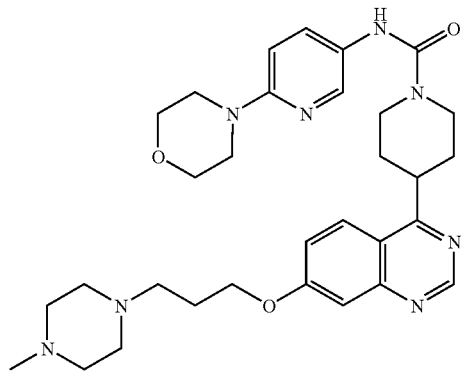

a. (6-Morpholin-4-yl-pyridin-3-yl)-carbamic acid 4-nitrophenyl ester hydrochloride

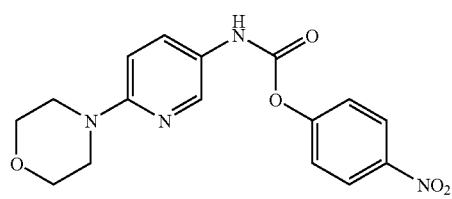

Prepared essentially as described in Example 66a using 6-morpholin-4-yl-pyridin-3-ylamine in place of 4-Morpholino-4-yl-phenylamine. LC/MS (ESI): 345.1 (MH)+.

b. 4-{7-[3-(4-Methyl-piperazin-1-yl)-propoxy]-quinazolin-4-yl}-piperidine-1-carboxylic acid (6-morpholin-4-yl-pyridin-3-yl)-amide

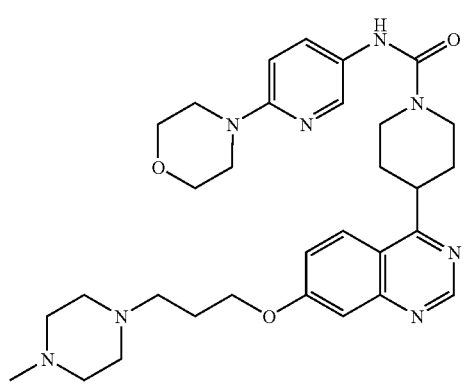

Prepared essentially as described in Example 39 using (6-morpholin-4-yl-pyridin-3-yl)-carbamic acid 4-nitrophenyl ester hydrochloride in place of (4-isopropoxy-phenyl)-carbamic acid 4-nitrophenyl ester. $^1$H-NMR (300 MHz, CDCl$_3$): 9.13 (s, 1H), 8.05 (m, 2H), 7.76 (m, 1H), 7.34-7.22 (m, 2H), 6.65 (d, 1H), 6.33 (s, 1H), 4.33-4.15 (m, 4H), 3.83 (m, 4H), 3.75-3.62 (m, 1H), 3.44 (m, 4H), 3.22-3.06 (m, 2H), 2.95-2.60 (m, 10H), 2.52 (s, 3H), 2.23-1.91 (m, 6H). LC/MS (ESI): 575.2 (MH)+.

Example 81

4-{7-[3-(4-Methyl-piperazin-1-yl)-propoxy]-quinazolin-4-yl}-piperidine-1-carboxylic acid (3-fluoro-4-morpholin-4-yl-phenyl)-amide

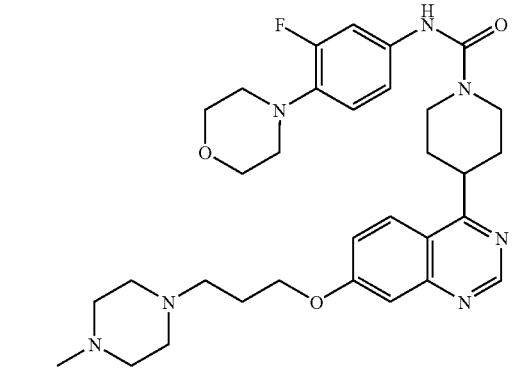

a. (3-Fluoro-4-morpholin-4-yl-phenyl)-carbamic acid 4-nitrophenyl ester hydrochloride

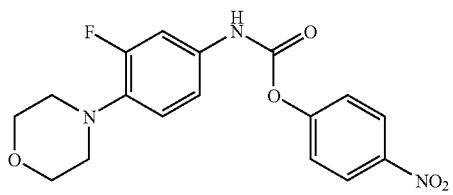

Prepared essentially as described in Example 66a using 3-fluoro-4-morpholino-4-yl-phenylamine in place of 4-morpholin-4-yl-phenylamine. LC/MS (ESI): 362.1 (MH)+.

b. 4-{7-[3-(4-Methyl-piperazin-1-yl)-propoxy]-quinazolin-4-yl}-piperidine-1-carboxylic acid (3-fluoro-4-morpholin-4-yl-phenyl)-amide

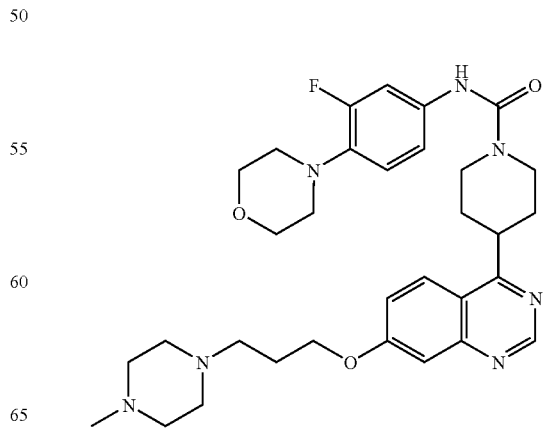

Prepared essentially as described in Example 39 using (3-Fluoro-4-morpholin-4-yl-phenyl)-carbamic acid 4-nitrophenyl ester hydrochloride in place of (4-isopropoxy-phenyl)-carbamic acid 4-nitrophenyl ester. $^1$H-NMR (300 MHz, CDCl$_3$): 9.13 (s, 1H), 8.05 (d, 1H), 7.34-7.22 (m, 3H), 7.00 (d, 1H), 6.86 (t, 1H), 6.41 (s, 1H), 4.31-4.16 (m, 4H), 3.87 (m, 4H), 3.75-3.62 (m, 1H), 3.22-2.98 (m, 8H), 2.71-2.51 (m, 8H), 2.38 (s, 3H), 2.21-1.93 (m, 6H). LC/MS (ESI): 592.2 (MH)$^+$.

Example 82

4-{7-[3-(4-Methyl-piperazin-1-yl)-propoxy]-quinazolin-4-yl}-piperidine-1-carboxylic acid (6-cyclopentyloxy-pyridin-3-yl)-amide

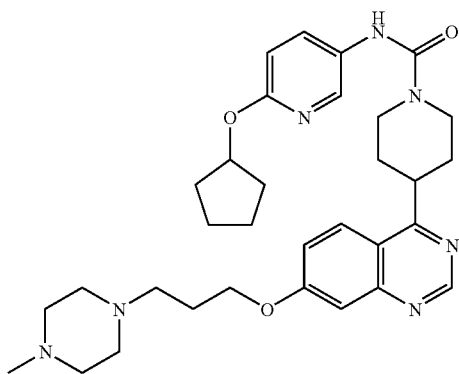

Prepared essentially as described in Example 39 using (6-cyclopentoxy-pyridin-3-yl)-carbamic acid 4-nitrophenyl ester as prepared by the method outlined in Example 69c, in place of (4-isopropoxy-phenyl)-carbamic acid 4-nitrophenyl ester. $^1$H-NMR (300 MHz, CDCl$_3$): 9.13 (s, 1H), 8.07-7.97 (m, 2H), 7.76 (m, 1H), 7.34-7.22 (m, 2H), 6.67 (d, 1H), 6.34 (s, 1H), 5.30 (m, 1H), 4.33-4.15 (m, 3H), 3.75-3.62 (m, 1H), 3.22-3.01 (m, 3H), 2.68-2.47 (m, 8H), 2.37 (s, 3H), 2.24-1.52 (m, 16H). LC/MS (ESI): 574.2 (MH)$^+$.

Example 83

4-{7-[2-(2-Oxo-pyrrolidin-1-yl)-ethoxy]-quinazolin-4-yl}-piperidine-1-carboxylic acid (6-morpholin-4-yl-pyridin-3-yl)-amide

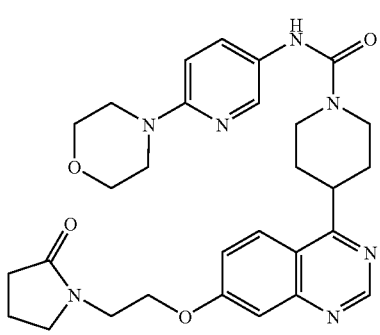

Prepared essentially as described in Example 67 using 1-(2-hydroxy-ethyl)-pyrrolidin-2-one and (6-morpholin-4-yl-pyridin-3-yl)-carbamic acid 4-nitro-phenyl ester hydrochloride, which was prepared as described in Example 80a. $^1$H NMR (CD$_3$OD) δ 9.04 (s, 1H), 8.36 (d, J=9.34 Hz, 1H), 8.27 (m, 1H), 8.12 (m, 1H), 7.65 (dd, J=9.04 and 2.71 Hz, 1H), 7.39 (m, 1H), 6.81 (d, J=8.88 Hz, 1H), 4.36 (t, J=5.15 Hz, 2H), 4.32 (m, 2H), 3.94 (m, 1H), 3.80 (t, J=4.67 Hz, 4H), 3.77 (t, J=4.82 Hz, 2H), 3.64 (t, J=6.81 Hz, 2H), 3.40 (t, J=4.98 Hz, 4H), 3.18 (m, 2H), 2.40 (t, J=7.77 Hz, 2H), 1.90-2.10 (6H). Calcd for C$_{29}$H$_{36}$N$_7$O$_4$ (MH+) 546.3, found 546.1.

Example 84

4-{7-[2-(2-Oxo-pyrrolidin-1-yl)-ethoxy]-quinazolin-4-yl}-piperidine-1-carboxylic acid (2-pyrrolidin-1-yl-pyrimidin-5-yl)-amide

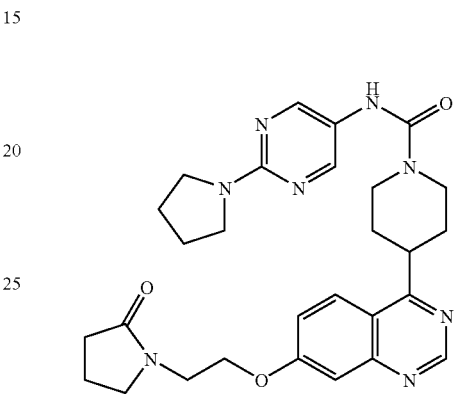

a) 5-Nitro-2-pyrrolidin-1-yl-pyrimidine

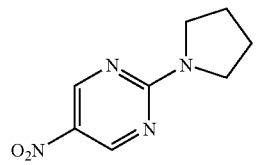

Prepared essentially as described in Example 69a, using 2-chloro-5-nitro-pyrimidine and pyrrolidine. $^1$H NMR (DMSO-d$_6$) δ 9.11 (s, 2H), 3.62 (m, 4H), 1.97 (m, 4H).

b) 2-Pyrrolidin-1-yl-pyrimidin-5-ylamine

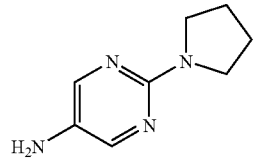

Prepared essentially as described in Example 69b, using 5-nitro-2-pyrrolidin-1-yl-pyrimidine.

$^1$H NMR (CDCl$_3$) δ 7.99 (s, 2H), 3.50 (m, 4H), 3.06 (br, 2H), 1.97 (m, 4H).

c) (2-Pyrrolidin-1-yl-pyrimidin-5-yl)-carbamic acid 4-nitro-phenyl ester

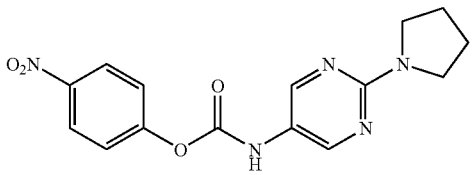

Prepared essentially as described in example 69c. $^1$H NMR (DMSO-d$_6$) δ 10.19 (bs, 1H), 8.45 (s, 2H), 8.30 (d, J=9.23 Hz, 2H), 7.52 (d, J=9.18 Hz, 2 h), 3.45 (m, 4H).

d) 4-{7-[2-(2-Oxo-pyrrolidin-1-yl)-ethoxy]-quinazolin-4-yl}-piperidine-1-carboxylic acid (2-pyrrolidin-1-yl-pyrimidin-5-yl)-amide

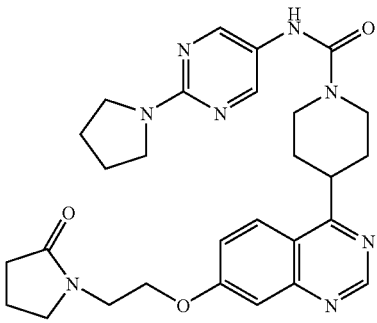

Prepared essentially as described in Example 67 using 1-(2-hydroxy-ethyl)-pyrrolidin-2-one and (2-pyrrolidin-1-yl-pyrimidin-5-yl)-carbamic acid 4-nitro-phenyl ester. $^1$H NMR (CD$_3$OD) δ 9.04 (s, 1H), 8.36 (d, J=9.31 Hz, 1H), 8.31 (s, 2H), 7.39 (dd, J=9.20 and 2.57 Hz, 1H), 7.34 (d, J=2.50 Hz, 1H), 4.36 (t, J=5.23 Hz, 2H), 4.30 (m, 2H), 3.94 (m, 1H), 3.78 (t, J=5.28 Hz, 2H), 3.64 (t, J=7.00 Hz, 2H), 3.53 (t, J=6.74 Hz, 4H), 3.19 (m, 2H), 2.40 (t, J=7.87 Hz, 2H), 1.90-2.12 (10H). Calcd for C$_{28}$H$_{35}$N$_8$O$_3$ (MH+) 531.3, found 531.1.

Example 85

4-{7-[2-(2-Oxo-pyrrolidin-1-yl)-ethoxy]-quinazolin-4-yl}-piperidine-1-carboxylic acid (4-morpholin-4-yl-phenyl)-amide

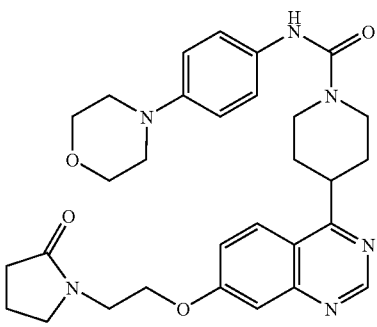

Prepared essentially as described in Example 67 using 1-(2-hydroxy-ethyl)-pyrrolidin-2-one and (4-morpholin-4-yl-phenyl)-carbamic acid 4-nitro-phenyl ester, which was prepared by the method described in Example 74a. $^1$H NMR (CD$_3$OD) δ 9.04 (s, 1H), 8.36 (d, J=9.59 Hz, 1H), 7.39 (dd, J=9.22 and 2.60 Hz, 1H), 7.34 (d, J=2.63 Hz, 1H), 7.25 (d, J=9.01 Hz, 2H), 6.93 (d, J=9.04 Hz, 2H), 4.36 (t, J=5.36 Hz, 2H), 4.32 (m, 2H), 3.93 (m, 1H), 3.83 (t, J=4.78 Hz, 4H), 3.78 (t, J=5.22 Hz, 2H), 3.64 (t, J=7.14 Hz, 2H), 3.16 (m, 2H), 3.08 (t, J=4.83 Hz, 4H), 2.40 (t, J=7.76 Hz, 2H), 1.90-2.12 (6H). Calcd for C$_{30}$H$_{37}$N$_6$O$_4$ (MH+) 545.3, found 545.1.

Example 86

4-[7-(3-Methanesulfonylamino-propoxy)-quinazolin-4-yl]-piperidine-1-carboxylic acid (6-pyrrolidin-1-yl-pyridin-3-yl)-amide

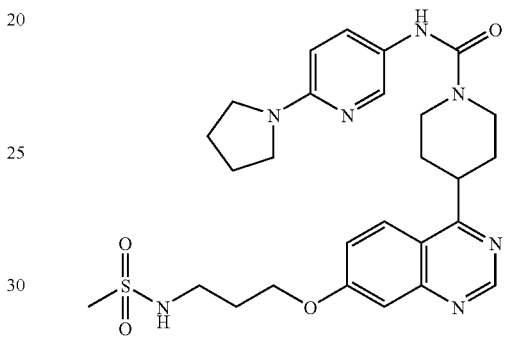

The title compound was prepared essentially as described in Example 65, but using (6-Pyrrolidin-1-yl-pyridin-3-yl)-carbamic acid 4-nitro-phenyl ester hydrochloride, which was prepared from 6-Pyrrolidin-1-yl-pyridin-3-ylamine (WO 2002048152 A2) essentially as described in Example 74a. $^1$H-NMR (400 MHz, CDCl$_3$) δ 9.11 (s, 1H), 8.04 (d, 1H), 7.99 (d, 1H), 7.61 (dd, 1H), 7.31 (d, 1H), 7.24 (dd, 1H), 6.41 (br s, 1H), 6.34 (d, 1H), 5.04 (br t, 1H), 4.30-4.21 (m, 4H), 3.65 (tt, 1H), 3.45-3.37 (m, 6H), 3.11 (td, 2H), 2.96 (s, 3H), 2.19-1.89 (m, 10H). LC/MS (ESI) calcd mass 553.3, found 554.1 (MH)$^+$.

Example 87

4-[7-(3-Methanesulfonylamino-propoxy)-quinazolin-4-yl]-piperidine-1-carboxylic acid (6-morpholin-4-yl-pyridin-3-yl)-amide

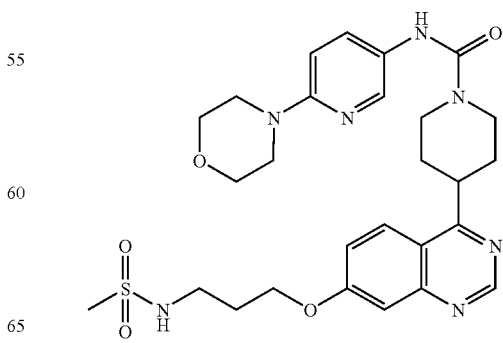

The title compound was prepared essentially as described in Example 65, but using (6-morpholin-4-yl-pyridin-3-yl)-carbamic acid 4-nitro-phenyl ester hydrochloride, which was prepared from commercial 6-morpholin-4-yl-pyridin-3-ylamine essentially as described in Example 66a. ¹H-NMR (400 MHz, CDCl₃) δ 9.11 (s, 1H), 8.06 (s, 1H), 8.05 (d, 1H), 7.74 (dd, 1H), 7.32 (d, 1H), 7.25 (dd, 1H), 6.64 (d, 1H), 6.45 (br s, 1H), 4.93 (br t, 1H), 4.30-4.22 (m, 4H), 3.82 (m, 4H), 3.67 (tt, 1H), 3.42 (m, 6H), 3.13 (td, 2H), 2.97 (s, 3H), 2.20-2.05 (m, 4H), 1.99-1.91 (m, 2H). LC/MS (ESI) calcd mass 569.2, found 570.0 (MH)⁺.

Example 88

4-[7-(3-Methanesulfonylamino-propoxy)-quinazolin-4-yl]-piperidine-1-carboxylic acid (6-cyclopentyloxy-pyridin-3-yl)-amide

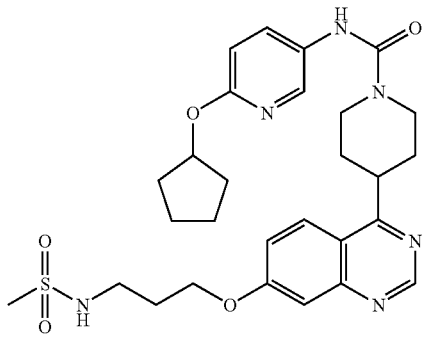

The title compound was prepared essentially as described in Example 65, but using (6-Cyclopentyloxy-pyridin-3-yl)-carbamic acid 4-nitro-phenyl ester hydrochloride, which was prepared as described in Example 69c. ¹H-NMR (400 MHz, CDCl₃) δ 9.10 (s, 1H), 8.04 (d, 1H), 8.01 (d, 1H), 7.74 (dd, 1H), 7.31 (d, 1H), 7.25 (dd, 1H), 6.65 (d, 1H), 6.55 (br s, 1H), 5.30 (m, 1H), 5.05 (br t, 1H), 4.36 (tt, 1H), 4.30-4.22 (m, 4H), 3.41 (q, 2H), 3.13 (m, 2H), 2.97 (s, 3H), 2.20-2.04 (m, 4H), 1.94 (m, 4H), 1.78 (m, 4H), 1.61 (m, 2H). LC/MS (ESI) calcd mass 568.3, found 569.0 (MH)⁺.

Example 89

4-{7-[3-(2-Oxo-pyrrolidin-1-yl)-propoxy]-quinazolin-4-yl}-piperidine-1-carboxylic acid (6-pyrrolidin-1-yl-pyridin-3-yl)-amide

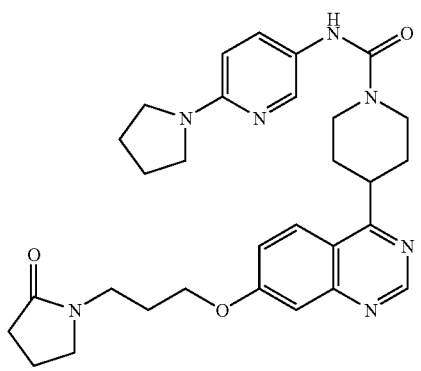

Prepared essentially as described in Example 67b, using (6-pyrrolidin-1-yl-pyridin-3-yl)-carbamic acid 4-nitro-phenyl ester, which was prepared from 6-Pyrrolidin-1-yl-pyridin-3-ylamine (WO 2002048152 A2) essentially as described in Example 74a. ¹H NMR (CD₃OD) δ 9.03 (s, 1H), 8.35 (d, J=9.33 Hz, 1H), 7.99 (d, J=2.60 Hz, 1H), 7.58 (dd, J=9.05 and 2.59 Hz, 1H), 7.39 (dd, J=9.25 and 2.52 Hz, 1H), 7.31 (d, J=2.49 Hz, 1H), 6.54 (d, J=9.24 Hz, 1H), 4.33 (m, 2H), 4.22 (t, J=5.80 Hz, 2H), 3.93 (m, 1H), 3.53 (t, J=6.88 Hz, 4H), 3.43 (t, J=6.72 Hz, 4H), 3.18 (m, 2H), 2.37 (t, J=7.82 Hz, 2H), 1.90-2.17 (12H). Calcd for C₃₀H₃₈N₇O₃ (MH+) 544.3, found 544.1.

Example 90

4-{7-[3-(2-Oxo-pyrrolidin-1-yl)-propoxy]-quinazolin-4-yl}-piperidine-1-carboxylic acid (2-pyrrolidin-1-yl-pyrimidin-5-yl)-amide

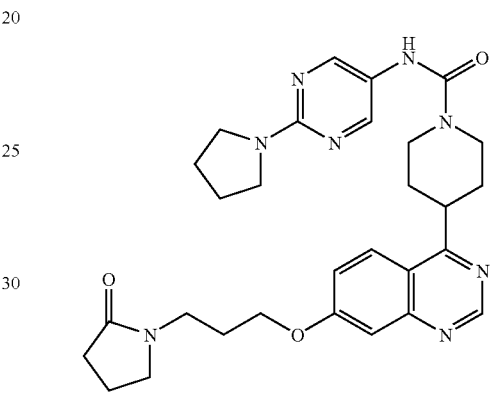

Prepared essentially as described in Example 67b using (2-pyrrolidin-1-yl-pyrimidin-5-yl)-carbamic acid 4-nitro-phenyl ester, which was prepared as described in Example 84c. ¹H NMR (CD₃OD) δ 9.04 (s, 1H), 8.36 (d, J=9.43 Hz, 1H), 8.32 (s, 2H), 7.39 (dd, J=9.26 and 2.52 Hz, 1H), 7.31 (d, J=2.49 Hz, 1H), 4.33 (m, 2H), 4.22 (t, J=5.96 Hz, 2H), 3.95 (m, 1H), 3.53 (t, J=6.61 Hz, 8H), 3.20 (m, 2H), 2.38 (t, J=7.66 Hz, 2H), 1.90-2.17 (12H). Calcd for C₂₉H₃₇N₈O₃ (MH+) 545.3, found 545.1.

Example 91

4-{7-[2-(2-Oxo-oxazolidin-3-yl)-ethoxy]-quinazolin-4-yl}-piperidine-1-carboxylic acid (6-morpholin-4-yl-pyridin-3-yl)-amide

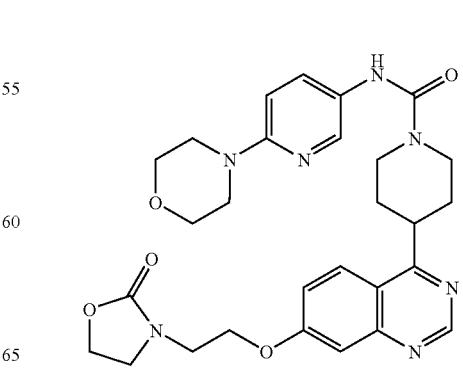

Prepared essentially as described in Example 79 using (6-morpholin-4-yl-pyridin-3-yl)-carbamic acid 4-nitro-phenyl ester, which was prepared as described in Example 80a. $^1$H NMR (CD$_3$OD) δ 9.05 (s, 1H), 8.37 (d, J=9.14 Hz, 1H), 8.13 (dd, J=2.71 and 0.49 Hz, 1H), 7.65 (dd, J=9.04 and 2.69 Hz, 1H), 7.42 (dd, J=9.27 and 2.61 Hz, 1H), 7.37 (d, J=2.49 Hz, 1H), 6.82 (d, J=9.02 and 0.51 Hz, 1H), 4.30-4.41 (6H), 3.94 (m, 1H), 3.74-3.84 (8H), 3.40 (t, J=5.00 Hz, 4H), 3.18 (m, 2H), 1.90-2.08 (4H). Calcd for C$_{28}$H$_{34}$N$_7$O$_5$ (MH+) 548.3, found 548.0.

Example 92

4-{7-[2-(2-Oxo-oxazolidin-3-yl)-ethoxy]-quinazolin-4-yl}-piperidine-1-carboxylic acid (6-pyrrolidin-1-yl-pyridin-3-yl)-amide

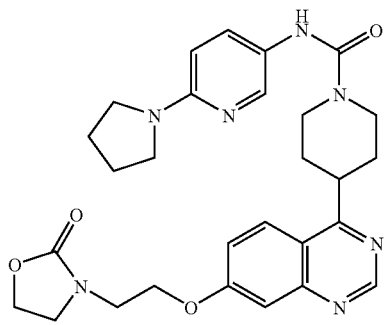

Prepared essentially as described in Example 79 using (6-pyrrolidin-1-yl-pyridin-3-yl)-carbamic acid 4-nitro-phenyl ester, which was prepared from 6-Pyrrolidin-1-yl-pyridin-3-ylamine (WO 2002048152 A2) essentially as described in Example 74a. $^1$H NMR (CD$_3$OD) δ 9.04 (s, 1H), 8.37 (d, J=9.26 Hz, 1H), 7.98 (dd, J=2.65 and 0.62 Hz, 1H), 7.56 (dd, J=9.03 and 2.66 Hz, 1H), 7.41 (dd, J=9.02 and 2.49 Hz, 1H), 7.36 (d, J=2.63 Hz, 1H), 6.50 (d, J=9.02 Hz, 1H), 4.39 (t, J=5.20 Hz, 2H), 4.37 (t, J=8.25 Hz, 2H), 4.33 (m, 2H), 3.94 (m, 1H), 3.73-3.84 (4H), 3.42 (t, J=6.68 Hz, 4H), 3.18 (m, 2H), 1.90-2.07 (8H). Calcd for C$_{28}$H$_{34}$N$_7$O$_4$ (MH+) 532.3, found 532.1.

Example 93

4-[7-(1-Methyl-piperidin-4-ylmethoxy)-quinazolin-4-yl]-piperidine-1-carboxylic acid (4-isopropoxy-phenyl)-amide

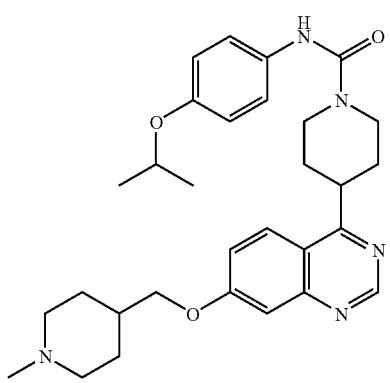

Prepared essentially as described in Example 67 using (1-methyl-piperidin-4-yl)-methanol. $^1$H NMR (CD$_3$OD) δ 9.03 (s, 1H), 8.34 (d, J=9.44 Hz, 1H), 7.37 (dd, J=9.19 and 2.61 Hz, 1H), 7.31 (d, J=2.55 Hz, 1H), 7.23 (d, J=9.06 Hz, 2H), 6.84 (d, J=9.00 Hz, 2H), 4.53 (m, 1H), 4.34 (m, 2H), 4.07 (d, J=5.79 Hz, 2H), 3.92 (m, 1H), 3.32 (m, 2H), 3.16 (m, 2H), 2.95 (m, 2H), 2.30 (s, 3H), 1.87-2.14 (7H), 1.51 (m, 2H), 1.28 (d, J=6.04 Hz, 6H). Calcd for C$_{30}$H$_{40}$N$_5$O$_3$ (MH+) 518.3, found 518.1.

Example 94

4-[7-(1-Methyl-piperidin-4-ylmethoxy)-quinazolin-4-yl]-piperidine-1-carboxylic acid (4-morpholin-4-yl-phenyl)-amide

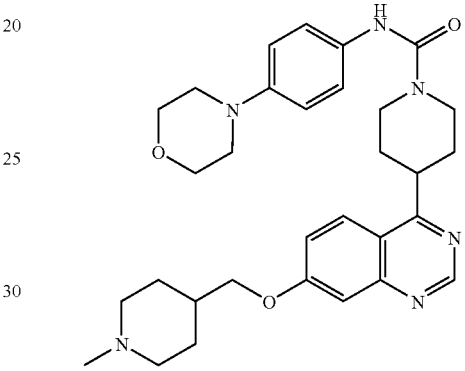

Prepared essentially as described in Example 67 using (1-methyl-piperidin-4-yl)-methanol and (4-morpholin-4-yl-phenyl)-carbamic acid 4-nitro-phenyl ester, which was prepared as described in Example 66a. $^1$H NMR (CDCl$_3$) δ 9.14 (s, 1H), 8.05 (d, J=9.34 Hz, 1H), 7.23-7.30 (4H), 6.88 (d, J=9.02 Hz, 2H), 6.30 (br, 1H), 4.26 (m, 2H), 4.04 (d, J=5.65 Hz, 2H), 3.86 (t, J=4.73 Hz, 4H), 3.68 (m, 1H), 3.20 (m, 2H), 3.16 (m, 2H), 3.10 (t, J=4.78 Hz, 4H), 3.00 (m, 2H), 2.51 (s, 3H), 1.93-2.13 (7H), 1.70 (br, 2H). Calcd for C$_{31}$H$_{41}$N$_6$O$_3$ (MH+) 545.3, found 545.1.

Example 95

4-[7-(2-Morpholin-4-yl-ethoxy)-quinazolin-4-yl]-piperidine-1-carboxylic acid (6-pyrrolidin-1-yl-pyridin-3-yl)-amide

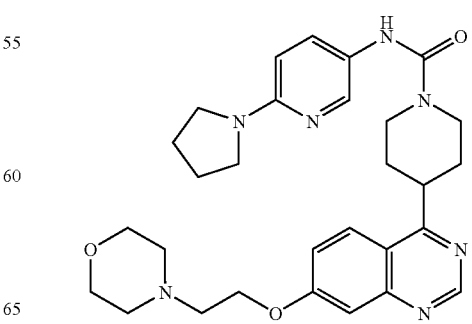

Prepared essentially as described in Example 67 using 2-morpholin-4-yl-ethanol and (6-pyrrolidin-1-yl-pyridin-3-yl)-carbamic acid 4-nitro-phenyl ester, which was prepared from 6-Pyrrolidin-1-yl-pyridin-3-ylamine (WO 2002048152 A2) essentially as described in Example 74a. $^1$H NMR (CDCl$_3$) δ 9.13 (s, 1H), 8.05 (d, J=9.27 Hz, 1H), 7.99 (d, J=2.57 Hz, 1H), 7.67 (dd, J=9.08 and 2.78 Hz, 1H), 7.30 (dd, J=5.33 and 2.39 Hz, 1H), 7.28 (d, J=9.04 Hz, 1H), 6.42 (br, 1H), 6.37 (d, J=9.16 Hz, 1H), 4.29 (t, J=5.58 Hz, 4H), 3.75 (t, J=4.55 Hz, 4H), 3.67 (m, 1H), 3.44 (t, J=6.64 Hz, 4H), 3.13 (td, J=12.96 and 2.42 Hz, 2H), 2.90 (t, J=5.51 Hz, 2H), 2.61 (t, J=4.71 Hz, 4H), 2.13 (m, 2H), 1.92-2.03 (6H). Calcd for C$_{29}$H$_{38}$N$_7$O$_3$ (MH+) 532.3, found 532.1.

Example 96

4-[7-(2-Morpholin-4-yl-ethoxy)-quinazolin-4-yl]-piperidine-1-carboxylic acid (4-morpholin-4-yl-phenyl)-amide

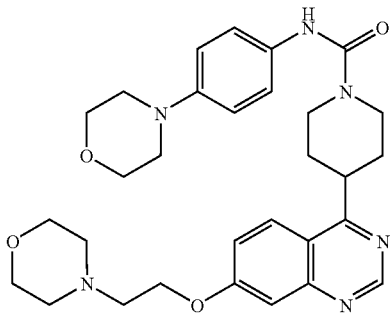

Prepared essentially as described in Example 67 using 2-morpholin-4-yl-ethanol and (4-morpholin-4-yl-phenyl)-carbamic acid 4-nitro-phenyl ester, which was prepared as described in Example 66a. $^1$H NMR (CDCl$_3$) δ 9.14 (s, 1H), 8.05 (d, J=9.22 Hz, 1H), 7.26-7.33 (4H), 6.87 (d, J=9.02 Hz, 2H), 6.33 (br, 1H), 4.22-4.34 (4H), 3.86 (t, J=4.63 Hz, 4H), 3.77 (m, 4H), 3.68 (m, 1H), 3.07-3.18 (6H), 2.93 (m, 2H), 2.64 (m, 4H), 2.13 (m, 2H), 1.97 (m, 2H). Calcd for C$_{30}$H$_{39}$N$_6$O$_4$ (MH+) 547.3, found 547.1.

Example 97

4-{7-[2-(4-Acetyl-piperazin-1-yl)-ethoxy]-quinazolin-4-yl}-piperidine-1-carboxylic acid (4-morpholin-4-yl-phenyl)-amide

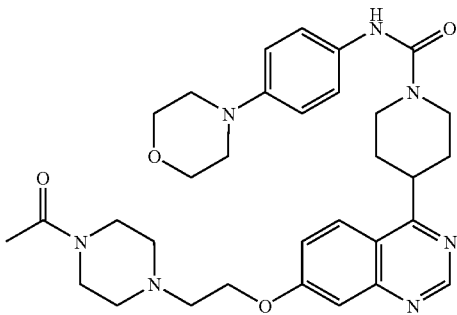

Prepared essentially as described in Example 67 using 1-[4-(2-hydroxy-ethyl)-piperazin-1-yl]-ethanone and (4-morpholin-4-yl-phenyl)-carbamic acid 4-nitro-phenyl ester, which was prepared as described in Example 66a. $^1$H NMR (CD$_3$OD) δ 9.04 (s, 1H), 8.35 (d, J=9.36 Hz, 1H), 7.40 (dd, J=9.22 and 2.45 Hz, 1H), 7.35 (d, J=2.44 Hz, 1H), 7.26 (d, J=9.10 Hz, 2H), 6.92 (d, J=9.12 Hz, 2H), 4.36 (t, J=5.15 Hz, 2H), 4.32 (m, 2H), 3.92 (m, 1H), 3.82 (t, J=4.64 Hz, 4H), 3.62 (t, J=4.71 Hz, 2H), 3.58 (t, J=5.22 Hz, 2H), 3.16 (m, 2H), 3.08 (t, J=4.82 Hz, 4H), 2.94 (t, J=5.46 Hz, 2H), 2.66 (t, J=5.16 Hz, 2H), 2.61 (t, J=5.13 Hz, 2H), 2.10 (s, 3H), 1.89-2.08 (4H). Calcd for C$_{32}$H$_{42}$N$_7$O$_4$ (MH+) 588.3, found 588.1.

Example 98

4-[7-(2-Piperidin-2-yl-ethoxy)-quinazolin-4-yl]-piperidine-1-carboxylic acid (4-morpholin-4-yl-phenyl)-amide

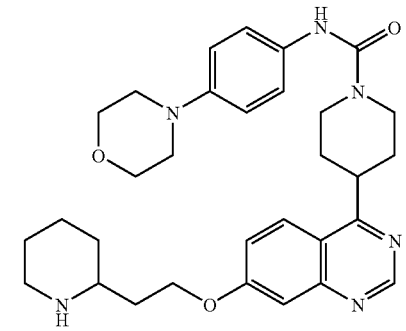

a) 4-(7-Fluoro-quinazolin-4-yl)-piperidine-1-carboxylic acid (4-morpholin-4-yl-phenyl)-amide

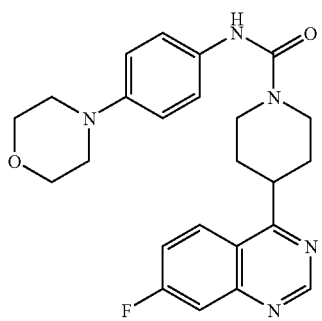

Prepared essentially as described in Example 67 using 4-(7-fluoro-quinazolin-4-yl)-piperidine-1-carboxylic acid tert-butyl ester and (4-morpholin-4-yl-phenyl)-carbamic acid 4-nitro-phenyl ester hydrochloride, which was prepared as described in Example 66a. $^1$H NMR (CDCl$_3$) δ 9.23 (s, 1H), 9.21 (dd, J=9.35 Hz and 5.85 Hz, 1H), 7.69 (dd, J=9.48 and 2.52 Hz, 1H), 7.44 (m, 1H), 7.27 (d, J=8.95 Hz, 2H), 6.89 (d, J=8.95 Hz, 2H), 6.29 (s, 1H), 4.27 (m, 2H), 3.86 (t, J=4.74 Hz, 4H), 3.73 (m, 1H), 3.17 (m, 2H), 3.11 (t, J=4.78 Hz, 4H), 2.15 (m, 2H), 1.99 (m, 2H). Calcd for C$_{24}$H$_{27}$FN$_5$O$_2$ (MH+) 436.2, found 436.1.

b) 4-[7-(2-Piperidin-2-yl-ethoxy)-quinazolin-4-yl]-piperidine-1-carboxylic acid (4-morpholin-4-yl-phenyl)-amide

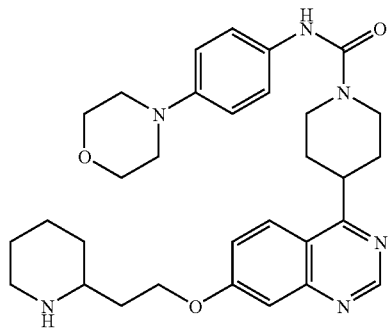

Prepared from 4-(7-Fluoro-quinazolin-4-yl)-piperidine-1-carboxylic acid (4-morpholin-4-yl-phenyl)-amide, synthesized as described in the previous step, and 2-piperidin-2-yl-ethanol using the protocol described in Example 67a. $^1$H NMR (CD$_3$OD) δ 9.03 (s, 1H), 8.34 (d, J=9.31 Hz, 1H), 7.37 (dd, J=9.19 and 2.54 Hz, 1H), 7.33 (d, J=2.47 Hz, 1H), 7.26 (d, J=9.06 Hz, 2H), 6.93 (d, J=9.10 Hz, 2H), 4.34 (m, 2H), 4.28 (m, 2H), 3.94 (m, 1H), 3.82 (t, J=4.69 Hz, 4H), 3.16 (m, 2H), 3.08 (t, J=4.78 Hz, 4H), 3.04 (m, 1H), 2.82 (m, 1H), 2.66 (m, 1H), 1.40-2.10 (12H). Calcd for C$_{31}$H$_{41}$N$_6$O$_3$ (MH+) 545.3, found 545.1.

Example 99

4-[7-(1-Methyl-piperidin-4-ylmethoxy)-quinazolin-4-yl]-piperidine-1-carboxylic acid (6-pyrrolidin-1-yl-pyridin-3-yl)-amide

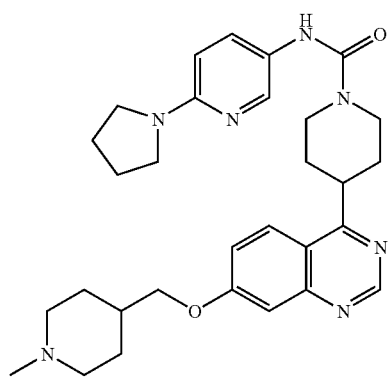

Prepared essentially as described in Example 67 using (1-methyl-piperidin-4-yl)-methanol and (6-pyrrolidin-1-yl-pyridin-3-yl)-carbamic acid 4-nitro-phenyl ester, which was prepared from 6-Pyrrolidin-1-yl-pyridin-3-ylamine (WO 2002048152 A2) essentially as described in Example 74a. $^1$H NMR (CDCl$_3$) δ 9.14 (s, 1H), 8.05 (d, J=9.26 Hz, 1H), 7.97 (d, J=2.61 Hz, 1H), 7.63 (dd, J=8.93 and 2.72 Hz, 1H), 7.28 (dd, J=7.00 and 2.63 Hz, 1H), 7.24 (d, J=2.37 Hz, 1H), 6.36 (d, J=8.87 Hz, 1H), 6.18 (br, 1H), 4.26 (m, 2H), 4.03 (d, J=5.79 Hz, 2H), 3.67 (m, 1H), 3.44 (t, J=6.69 Hz, 4H), 3.14 (td, J=12.22 and 2.65 Hz, 4H), 2.47 (m, 2H), 2.00 (s, 3H), 1.92-2.21 (13H). Calcd for C$_{30}$H$_{40}$N$_7$O$_2$ (MH+) 530.3, found 530.1.

Example 100

4-(7-Dimethylamino-quinazolin-4-yl)-piperidine-1-carboxylic acid (4-isopropoxy-phenyl)-amide

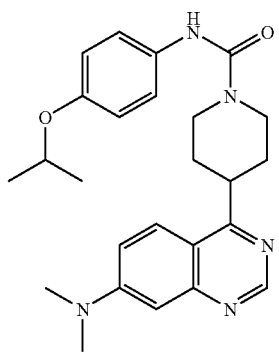

Prepared essentially as described in Example 102 and the title compound was obtained as a major side-product after purification. $^1$H-NMR (300 MHz, CDCl$_3$): 8.98 (s, 1H), 7.97 (d, 1H), 7.30-7.15 (m, 3H), 7.03 (d, 1H), 6.83 (d, 2H), 6.41 (s, 1H), 4.58-4.40 (m, 1H), 4.26 (d, 2H), 3.68-3.55 (m, 1H), 3.18-3.04 (m, 8H), 2.20-1.85 (m, 4H), 1.3 (d, 6H). LC/MS (ESI): 434.1 (MH)$^+$.

Example 101

4-{6-[3-(2-Oxo-pyrrolidin-1-yl)-propoxy]-quinazolin-4-yl}-piperidine-1-carboxylic acid (4-isopropoxy-phenyl)-amide

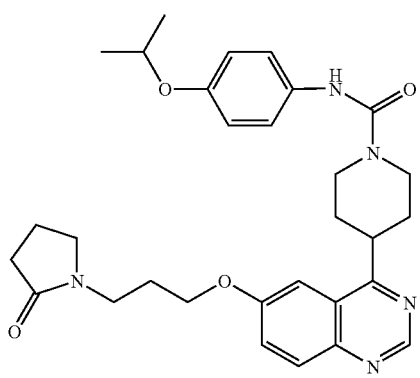

Prepared essentially as described in Example 76, using 1-(3-hydroxy-propyl)-pyrrolidin-2-one. $^1$H NMR (CDCl$_3$) δ

9.13 (s, 1H), 7.98 (d, J=9.22 Hz, 1H), 7.54 (dd, J=9.19 and 2.63 Hz, 1H), 7.34 (d, J=2.52 Hz, 1H), 7.26 (d, J=8.91 Hz, 2H), 6.83 (d, J=8.98 Hz, 2H), 6.43 (br, 1H), 4.47 (m, 1H), 4.26 (m, 2H), 4.16 (t, J=6.11 Hz, 2H), 3.65 (m, 1H), 3.54 (t, J=7.04 Hz, 2h), 3.47 (t, J=7.10 Hz, 2H), 3.18 (m, 2H), 2.39 (t, J=7.88 Hz, 2H), 1.96-2.18 (8H), 1.30 (d, J=6.06 Hz, 6H). Calcd for $C_{30}H_{38}N_5O_4$ (MH+) 532.3, found 532.1.

Example 102

4-{7-[3-(4-Methyl-piperazin-1-yl)-propylamino]-quinazolin-4-yl}-piperidine-1-carboxylic acid (4-iso-propoxy-phenyl)-amide

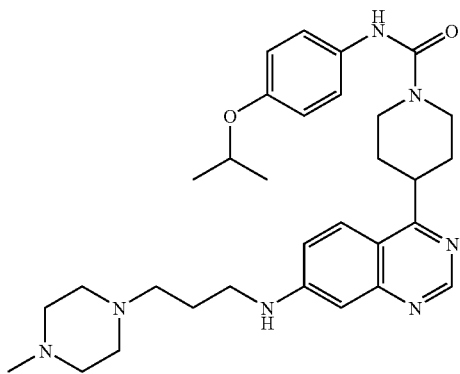

A mixture of 4-(3-aminopropyl)-1-methylpiperazine (0.1 mmol), Et$_3$N (0.1 mmol) and 4-(7-fluoro-quinazolin-4-yl)-piperidine-1-carboxylic acid tert-butyl ester (0.1 mmol), prepared as described in Example 65b, in DMF (1 mL) was stirred at 130° C. for 3 h. It was then diluted with water and extracted with EtOAc. The combined extracts were washed with water, brine, dried (anhydrous MgSO4), filtered and concentrated in vacuo. The crude product was then treated with 3M HCl/MeOH (2 mL) and stirred at rt for 2 h, then concentrated in vacuo. The crude residue was dissolved in a mixture of DCM:MeOH (1:1; 2 mL) and neutralized with excess Et$_3$N and treated with (4-isopropoxy-phenyl)-carbamic acid 4-nitrophenyl ester (0.11 mmol), which was prepared as described in Example 1a, at rt for 1 h. It was then concentrated in vacuo and the crude product was dissolved in DCM and washed with water, brine, dried over anhydrous MgSO4, filtered and concentrated in vacuo. The crude product was then purified by Preparative TLC (silica gel; DCM:MeOH, 9:1) to obtain 3.2 mg (6% overall yield over the three steps) of the title compound. $^1$H-NMR (300 MHz, CDCl$_3$): 8.97 (s, 1H), 7.88 (d, 1H), 7.28-7.22 (m, 3H), 6.97-6.81 (m, 4H), 6.33 (s, 1H), 4.53-4.43 (m, 1H), 4.30-4.20 (d, 2H), 3.66-3.32 (m, 2H), 3.11 (t, 2H), 2.85-2.55 (m, 8H), 2.43 (s, 4H), 2.20-1.85 (m, 8H), 1.31 (d, 6H). LC/MS (ESI): 546.2 (MH)$^+$.

Example 103

4-[7-(4-Methyl-piperazin-1-yl)-quinazolin-4-yl]-piperidine-1-carboxylic acid (4-isopropoxy-phenyl)-amide

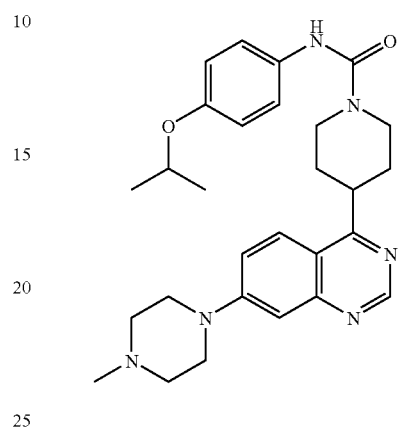

Prepared essentially as described in Example 102 using 1-methyl-piperazine in place of 4-(3-aminopropyl)-1-methylpiperazine. $^1$H-NMR (300 MHz, CDCl$_3$): 9.05 (s, 1H), 7.99 (d, 1H), 7.35-7.20 (m, 4H), 6.84 (d, 2H), 6.33 (s, 1H), 4.54-4.42 (m, 1H), 4.25 (d, 2H), 3.69-3.50 (m, 5H), 3.13 (t, 2H), 2.74 (m, 4H), 2.46 (s, 3H), 2.20-1.88 (m, 4H), 1.31 (d, 6H). LC/MS (ESI): 489.2 (MH)$^+$.

Example 104

4-{7-[3-(4-Methyl-piperazin-1-yl)-propoxy]-quinazolin-4-yl}-piperidine-1-carboxylic acid (6-pyrrolidin-1-yl-pyridin-3-yl)-amide

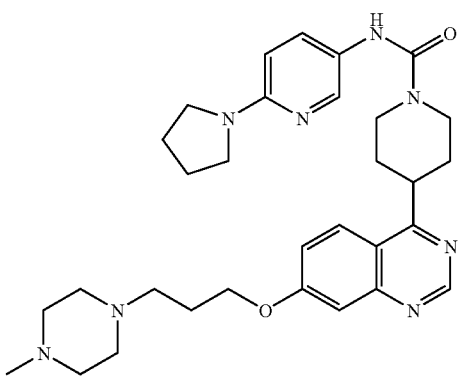

To a solution of 3-(4-methylpiperazin-1-yl)-propan-1-ol (0.22 mmol) in anhydrous THF (2 mL) was added NaH (0.4 mmol) and the mixture was stirred at rt for 5 min. Then, 4-(7-fluoro-quinazolin-4-yl)-piperidine-1-carboxylic acid tert-butyl ester (0.2 mmol), prepared as described in Example 65, was added to it and the mixture was stirred at 60° C. for 2 h. It was then concentrated in vacuo and partitioned between water and DCM. The DCM layer was drawn off, washed with water, brine, dried (anhydrous MgSO4), filtered and concentrated in vacuo. This crude product was then treated with 3M HCl/MeOH (2 mL) and stirred at rt for 2 h and then concentrated in vacuo. A portion of the crude residue (0.05 mmol) was dissolved in a mixture of DCM:MeOH (1:1; 2 mL) and neutralized with excess Et$_3$N (0.3 mmol) and treated with (6-pyrrolidin-1-yl-pyridin-3-yl)-carbamic acid 4-nitrophenyl ester hydrochloride (0.075 mmol), which was prepared from 6-Pyrrolidin-1-yl-pyridin-3-ylamine (WO 2002048152 A2) essentially as described in Example 74a, at rt for 1 h. It was then concentrated in vacuo and the crude product was dissolved in DCM and washed with water thrice, then washed with brine, dried over anhydrous MgSO$_4$, filtered and concentrated in vacuo. The crude product was then purified by Preparative TLC (silica gel; DCM:MeOH:NH$_4$OH, 90:9:1) to obtain 10 mg (35%) of the title compound. $^1$H-NMR (300 MHz, CDCl$_3$): 9.13 (s, 1H), 8.08-7.96 (m, 2H), 7.66-7.60 (m, 1H), 7.34-7.22 (m, 2H), 6.39-6.27 (m, 2H), 4.32-4.14 (m, 4H), 3.74-3.59 (m, 1H), 3.46-3.38 (m, 4H), 3.13 (t, 2H), 2.65-2.50 (m, 10H), 2.37 (s, 3H), 2.22-1.86 (m, 10H). LC/MS (ESI): 559.1 (MH)$^+$.

Example 105

4-{7-[3-(4-Methyl-piperazin-1-yl)-propoxy]-quinazolin-4-yl}-piperidine-1-carboxylic acid (2-pyrrolidin-1-yl-pyrimidin-5-yl)-amide

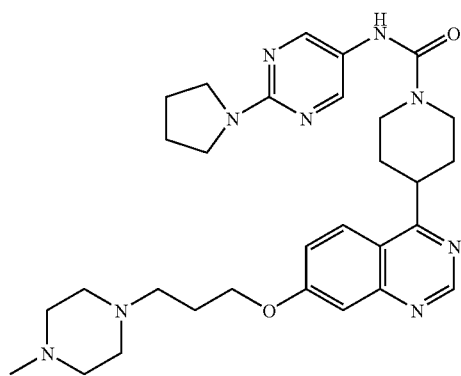

Prepared essentially as described in Example 104 using (2-pyrrolidin-1-yl-pyrimidin-5-yl)-carbamic acid 4-nitrophenyl ester hydrochloride, which was prepared as described in Example 84c, in place of (6-pyrrolidin-1-yl-pyridin-3-yl)-carbamic acid 4-nitrophenyl ester hydrochloride. $^1$H-NMR (300 MHz, CDCl$_3$): 9.12 (s, 1H), 8.32 (m, 2H), 8.04 (d, 1H), 7.34-7.22 (m, 2H), 6.24 (s, 1H), 4.32-4.14 (m, 4H), 3.74-3.61 (m, 1H), 3.60-3.50 (m, 4H), 3.14 (t, 2H), 2.75-2.45 (m, 10H), 2.37 (s, 3H), 2.22-1.88 (m, 10H). LC/MS (ESI): 560.1 (MH)$^+$.

Example 106

4-{7-[3-(4-Methyl-piperazin-1-yl)-propoxy]-quinazolin-4-yl}-piperidine-1-carbothioic acid (6-morpholin-4-yl-pyridin-3-yl)-amide

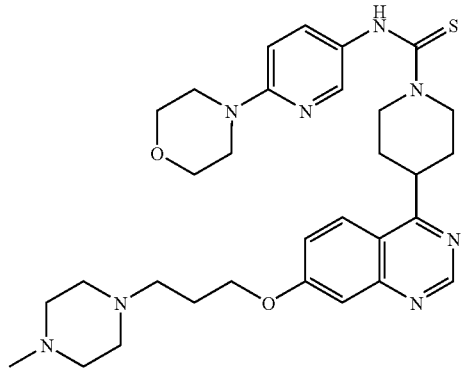

Prepared essentially as described in Example 104 using 4-(5-isothiocyanato-pyridin-2-yl)-morpholine in place of (6-pyrrolidin-1-yl-pyridin-3-yl)-carbamic acid 4-nitrophenyl ester hydrochloride. $^1$H-NMR (300 MHz, CDCl$_3$): 9.11 (s, 1H), 8.08-8.00 (m, 2H), 7.58-7.51 (m, 1H), 7.34-7.22 (m, 3H), 6.64 (d, 1H), 4.86 (d, 2H), 4.19 (t, 2H), 3.86-3.70 (m, 5H), 3.52-3.30 (m, 6H), 2.63-2.40 (m, 10H), 2.34 (s, 3H), 2.30-1.86 (m, 6H). LC/MS (ESI): 591.0 (MH)$^+$.

Example 107

4-[7-(1-Methyl-piperidin-4-ylmethoxy)-quinazolin-4-yl]-piperidine-1-carboxylic acid (6-cyclobutoxy-pyridin-3-yl)-amide

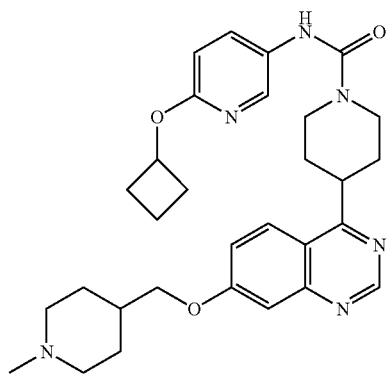

Prepared essentially as described in Example 67 using (1-methyl-piperidin-4-yl)-methanol and (6-cyclobutoxy-pyridin-3-yl)-carbamic acid 4-nitro-phenyl ester, which was prepared as described in Example 17c. $^1$H NMR (CD$_3$OD) δ 9.03 (s, 1H), 8.34 (d, J=9.41 Hz, 1H), 8.07 (dd, J=2.73 and 0.54 Hz, 1H), 7.72 (dd, J=8.87 and 2.77 Hz, 1H), 7.38 (dd, J=9.24 and 2.48 Hz, 1H), 7.31 (d, J=2.48 Hz, 1H), 6.71 (dd, J=8.87 and 0.59 Hz, 1H), 5.05 (m, 1H), 4.34 (m, 2H), 4.06 (d, J=5.77 Hz, 2H), 3.93 (m, 1H), 3.18 (m, 2H), 2.96 (m, 2H), 2.45 (m, 2H), 2.30 (s, 3H), 1.64-2.17 (13H), 1.51 (m, 2H). Calcd for $C_{30}H_{39}N_6O_3$ (MH+) 531.3, found 531.0.

Example 108

4-[7-(1-Methyl-piperidin-4-ylmethoxy)-quinazolin-4-yl]-piperidine-1-carboxylic acid (6-morpholin-4-yl-pyridin-3-yl)-amide

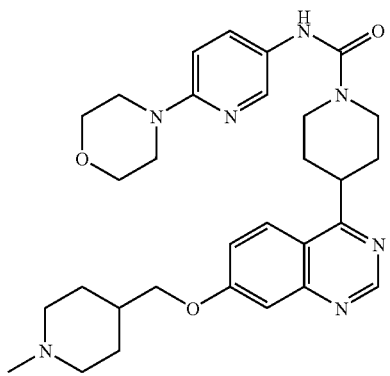

Prepared essentially as described in Example 67 using (1-methyl-piperidin-4-yl)-methanol and (6-morpholin-4-yl-pyridin-3-yl)-carbamic acid 4-nitro-phenyl ester, which was prepared as described in Example 80a. $^1$H NMR (CD$_3$OD) δ 9.04 (s, 1H), 8.36 (d, J=9.31 Hz, 1H), 8.12 (dd, J=2.66 and 0.57 Hz, 1H), 7.65 (dd, J=9.03 and 2.73 Hz, 1H), 7.38 (dd, J=9.14 and 2.61 Hz, 1H), 7.33 (d, J=2.48 Hz, 1H), 6.82 (d, J=9.08 Hz, 1H), 4.34 (m, 2H), 4.12 (d, J=5.75 Hz, 2H), 3.94 (m, 1H), 3.80 (t, J=4.73 Hz, 4H), 3.40 (t, J=4.97 Hz, 4H), 3.31 (m, 2H), 3.18 (m, 2H), 2.70 (m, 2H), 2.65 (s, 3H), 1.90-2.13 (7H), 1.65 (m, 2H). Calcd for $C_{30}H_{40}N_7O_3$ (MH+) 546.3, found 546.0.

Example 109

4-[7-(1-Methyl-piperidin-4-ylmethoxy)-quinazolin-4-yl]-piperidine-1-carboxylic acid (4-pyrrolidin-1-yl-phenyl)-amide

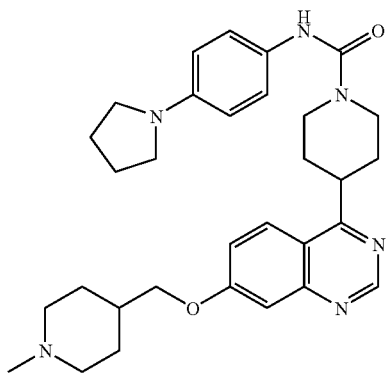

Prepared essentially as described in Example 67 using (1-methyl-piperidin-4-yl)-methanol and (4-pyrrolidin-1-yl-phenyl)-carbamic acid 4-nitro-phenyl ester hydrochloride, which was prepared as described in Example 74a. $^1$H NMR (CD$_3$OD) δ 9.03 (s, 1H), 8.35 (d, J=9.41 Hz, 1H), 7.37 (dd, J=9.20 and 2.61 Hz, 1H), 7.31 (d, J=2.59 Hz, 1H), 7.13 (d, J=8.88 Hz, 2H), 6.54 (d, J=8.98 Hz, 2H), 4.33 (m, 2H), 4.07 (d, J=5.87 Hz, 2H), 3.92 (m, 1H), 3.24 (t, J=6.80 Hz, 4H), 3.16 (m, 4H), 2.97 (m, 2H), 2.33 (s, 3H), 1.88-2.19 (13H). Calcd for $C_{31}H_{41}N_6O_2$ (MH+) 529.3, found 529.1.

Example 110

4-[7-(3-[1,2,4]Triazol-4-yl-propoxy)-quinazolin-4-yl]-piperidine-1-carboxylic acid (6-morpholin-4-yl-pyridin-3-yl)-amide

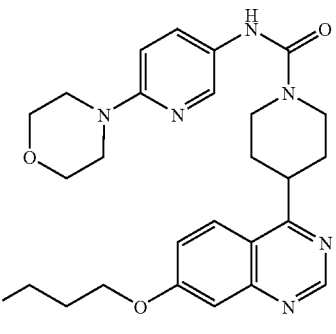

a. 4-[7-(3-[1,2,4]Triazol-4-yl-propoxy)-quinazolin-4-yl]-piperidine-1-carboxylic acid tert-butyl ester

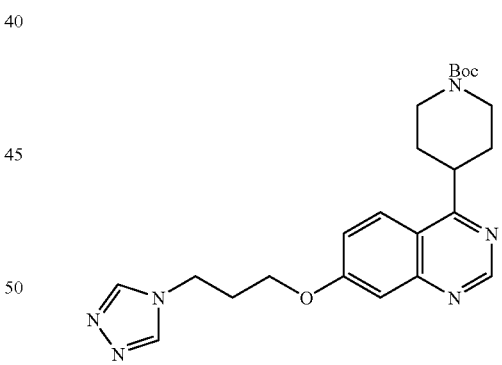

A mixture of 4-(7-fluoro-quinazolin-4-yl)-piperidin-1-carboxylic acid tert-butyl ester (31.6 mg, 95.5 μmol), as prepared in Example 65b, 3-[1,2,4]-triazol-4-yl-propan-1-ol (ChemPacific) (12.0 mg, 94.5 μmol), and KOtBu (11.7 mg, 104 μmol) in DME (100 μL) and DMSO (50 μL) was stirred at rt for 1 hr. The resulting homogeneous amber solution was partitioned with DCM (2 mL) and 0.5M sodium phosphate/pH 7 (2 mL). The organic layer was concentrated to provide the crude title compound that was used immediately for the next step. LC/MS (ESI): calcd mass 438.2, found 439.1 (MH)$^+$.

b. 4-[7-(3-[1,2,4]Triazol-4-yl-propoxy)-quinazolin-4-yl]-piperidine-1-carboxylic acid (6-morpholin-4-yl-pyridin-3-yl)-amide

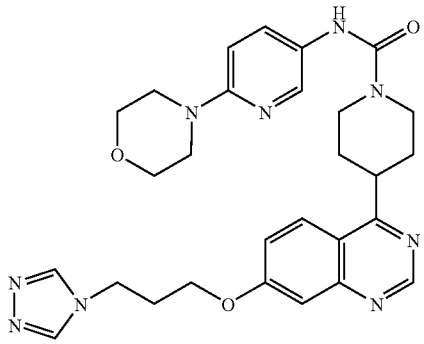

The crude 4-[7-(3-[1,2,4]Triazol-4-yl-propoxy)-quinazolin-4-yl]-piperidine-1-carboxylic acid tert-butyl ester, as prepared in the previous step, was treated with TFA (70 µL) at 100° C. in a sealed vial for 10 min (aluminum block). CHCl₃ (450 µL) and DMEA (140 µL, 1.3 mmol) were added, and one-half of the resulting homogeneous amber solution was treated with (6-morpholin-4-yl-pyridin-3-yl)-carbamic acid-4-nitrophenyl ester hydrochloride (22 mg, 58 µmol), as prepared in Example 80a, and stirred at 40° C. for 1.5 hr. (The other one-half of the homogenous solution was diverted to the synthesis given in Example 114.) The reaction was then partitioned with 2M K₂CO₃ (2 mL) and DCM (2 mL), and the aqueous layer was extracted with 9:1 DCM/MeOH (1×2 mL). The combined organic layers were concentrated and the residue was partially purified with a 5 g silica flash cartridge (97:3 acetone/MeOH eluent with 2% DMEA), and further purified with HPLC (C18 column) to provide the title compound as a powder after lyophilization [2.1 mg, 8.1% overall from 4-(7-fluoro-quinazolin-4-yl)-piperidin-1-carboxylic acid tert-butyl ester.] ¹H-NMR (400 MHz, 95:5 CDCl₃/CD₃OD) δ 9.12 (s, 1H), 8.43 (dd, 1H), 8.30 (br s, 2H), 8.13 (m, 2H), 7.32 (m, 1H), 7.26 (dd, 1H), 6.96 (d, 1H), 4.37 (m, 4H), 4.21 (t, 2H), 3.88 (m, 4H), 3.75 (m, 1H), 3.59 (m, 4H), 3.14 (m, 2H), 2.42 (pentet, 2H), 2.16-1.95 (m, 4H). LC/MS (ESI) calcd mass 543.3, found 544.1 (MH)⁺.

Example 111

4-{7-[3-(2-Dimethylamino-3,4-dioxo-cyclobut-1-enylamino)-propoxy]-quinazolin-4-yl}-piperidine-1-carboxylic acid (6-pyrrolidin-1-yl-pyridin-3-yl)-amide

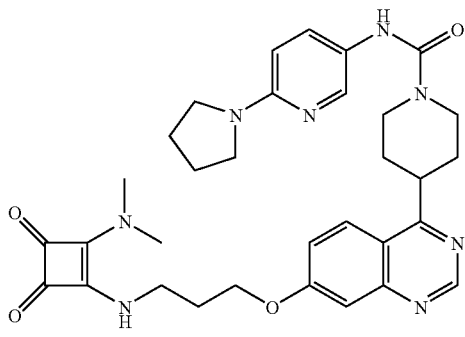

The title compound was prepared essentially as described for Example 65, except 3-Dimethylamino-4-methoxy-cyclobut-3-ene-1,2-dione [*Inorganic Chemistry* (1997), 36(14), 3096-3101] at 80° C. for 1 hr replaced methanesulfonyl chloride at rt, and (6-Pyrrolidin-1-yl-pyridin-3-yl)-carbamic acid 4-nitro-phenyl ester hydrochloride, which was prepared from 6-Pyrrolidin-1-yl-pyridin-3-ylamine (WO 2002048152 A2) essentially as described in Example 74a, was used. Work-up of the crude reaction and HPLC purification was essentially as described in Example 110. ¹H-NMR (400 MHz, 95:5 CDCl₃/CD₃OD) δ 9.08 (s, 1H), 8.35 (dd, 1H), 8.10 (d, 1H), 8.04 (d, 1H), 7.31-7.26 (m, 2H), 6.75 (d, 1H), 4.38 (m, 2H), 4.27 (t, 2H), 3.93 (t, 2H), 3.72 (m, 1H), 3.58 (m, 4H), 3.23 (s, 6H), 3.12 (m, 2H), 2.25-1.92 (m, 10H). LC/MS (ESI) calcd mass 598.3, found 599.0 (MH)⁺.

Example 112

Morpholine-4-carboxylic acid (3-{4-[1-(6-pyrrolidin-1-yl-pyridin-3-ylcarbamoyl)-piperidin-4-yl]-quinazolin-7-yloxy}-propyl)-amide

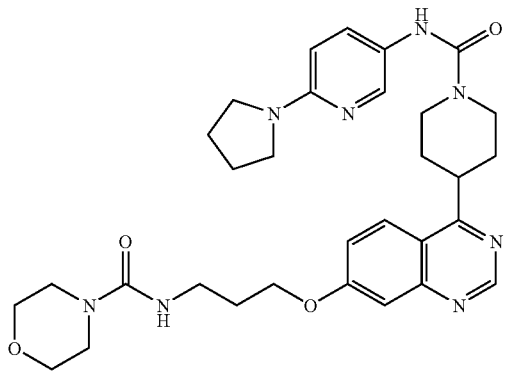

The title compound was prepared essentially as described in Example 111, except commercial 4-morpholinecarbonyl chloride replaced 3-Dimethylamino-4-methoxy-cyclobut-3-ene-1,2-dione. ¹H-NMR (400 MHz, 95:5 CDCl₃/CD₃OD) δ 9.10 (s, 1H), 8.35 (dd, 1H), 8.11 (d, 1H), 8.03 (d, 1H), 7.36 (d, 1H), 7.28 (dd, 1H), 6.75 (d, 1H), 4.39 (m, 2H), 4.24 (t, 2H), 3.80-3.66 (m, 5H), 3.58 (m, 4H), 3.47 (t, 2H), 3.12 (m, 2H), 3.36 (m, 4H), 2.19-1.92 (m, 10H). LC/MS (ESI) calcd mass 588.3, found 589.1 (MH)⁺.

Example 113

Morpholine-4-carboxylic acid (3-{4-[1-(6-morpholin-4-yl-pyridin-3-ylcarbamoyl)-piperidin-4-yl]-quinazolin-7-yloxy}-propyl)-amide

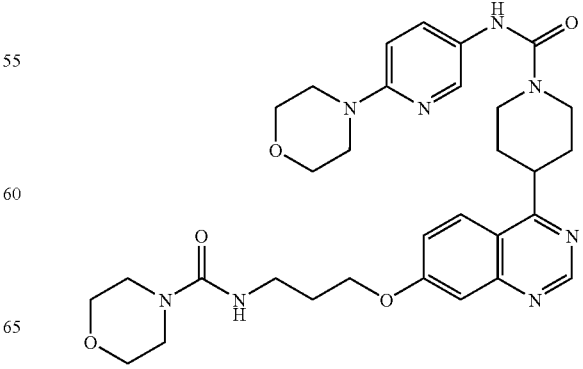

The title compound was prepared essentially as described in Example 112, using (6-morpholin-4-yl-pyridin-3-yl)-carbamic acid 4-nitro-phenyl ester hydrochloride (prepared as described in Example 80a). $^1$H-NMR (400 MHz, 95:5 CDCl$_3$/CD$_3$OD) δ 9.12 (s, 1H), 8.38 (dd, 1H), 8.16 (d, 1H), 8.09 (d, 1H), 7.36 (d, 1H), 7.30-7.25 (m, 1H), 6.90 (d, 1H), 4.37 (m, 2H), 4.24 (m, 2H), 3.87 (m, 4H), 3.70 (m, 4H), 3.58 (m, 4H), 3.48 (m, 2H), 3.36 (m, 4H), 3.13 (m, 2H), 2.20-1.95 (m, 6H). LC/MS (ESI): calcd mass 604.3, found 605.1 (MH)$^+$.

Example 114

4-[7-(3-[1,2,4]Triazol-4-yl-propoxy)-quinazolin-4-yl]-piperidine-1-carboxylic acid (6-pyrrolidin-1-yl-pyridin-3-yl)-amide

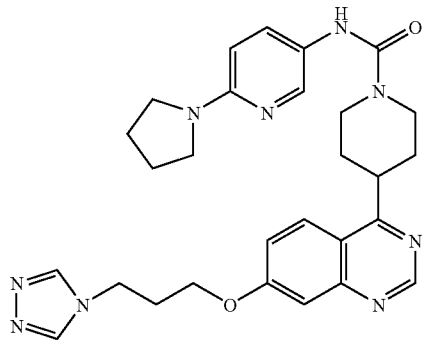

The title compound was prepared essentially as described in Example 110 using (6-Pyrrolidin-1-yl-pyridin-3-yl)-carbamic acid 4-nitro-phenyl ester hydrochloride, which was prepared from 6-Pyrrolidin-1-yl-pyridin-3-ylamine (WO 2002048152 A2) essentially as described in Example 74a. $^1$H-NMR (400 MHz, 9:1 CDCl$_3$/CD$_3$OD) δ 9.14 (s, 1H), 8.43 (dd, 1H), 8.26 (s, 2H), 8.12 (d, 1H), 8.09 (d, 1H), 7.33 (d, 1H), 7.27-7.23 (m, 1H), 6.73 (d, 1H), 4.43-4.32 (m, 4H), 4.20 (t, 2H), 3.72 (tt, 1H), 3.59 (m, 4H), 3.13 (td, 2H), 2.41 (pentet, 2H), 2.18-2.05 (m, 6H), 2.02-1.94 (m, 2H). LC/MS (ESI): calcd mass 527.3, found 528.1 (MH)$^+$.

Example 115

4-{7-[3-(4-Ethyl-piperazin-1-yl)-propoxy]-quinazolin-4-yl}-piperidine-1-carboxylic acid (4-morpholin-4-yl-phenyl)-amide

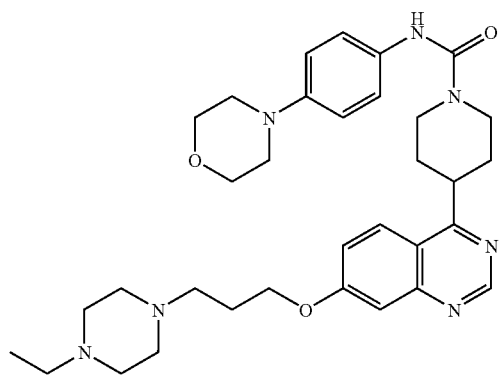

4-[7-(-Hydroxy-propoxy)-quinazolin-4-yl]-piperidine-1-carboxylic acid tert-butyl ester was prepared as described in Example 33 using propane-1,3-diol in place of 3-hydroxypropylpiperidine. To a solution of 4-[7-(-hydroxy-propoxy)-quinazolin-4-yl]-piperidine-1-carboxylic acid tert-butyl ester (0.3 mmol) in anhydrous DCM, was added Et$_3$N (0.6 mmol) and methanesulfonyl chloride (0.6 mmol) and the mixture was stirred at rt for 2 h. It was then washed with water (3×), dried over anhydrous MgSO$_4$, filtered and concentrated in vacuo to obtain 4-[7-(3-methanesulfonyloxy-propoxy)-quinazolin-4-yl]-piperidine-1-carboxylic acid tert-butyl ester. This (0.05 mmol) was dissolved in anhydrous dioxane together with 1-ethyl-piperazine (0.1 mmol) and the mixture was stirred at 100° C. overnight and then concentrated in vacuo, then diluted with water and extracted with DCM. The DCM extract was washed with water (3×), dried over anhydrous MgSO$_4$, filtered and concentrated in vacuo. To this was added 3M HCl/MeOH (1 mL) and the mixture was stirred at rt for 2 h and then concentrated in vacuo and the residue was dissolved in a 1:1 mixture of DCM:MeOH, neutralized with excess Et$_3$N and treated with (4-morpholin-4-yl-phenyl)-carbamic acid 4-nitrophenyl ester hydrochloride (0.06 mmol), which was prepared as described in Example 66a. The mixture was stirred at rt overnight and then concentrated in vacuo and partitioned between water and DCM. DCM layer was drawn off, washed with water thrice, then dried over anhydrous MgSO$_4$, filtered and concentrated in vacuo. The residue was purified by Preparative TLC (silica gel; DCM:MeOH:NH4OH; 90:9:1) to obtain 9.4 mg (32%) of the title compound. $^1$H-NMR (300 MHz, CDCl$_3$): 9.13 (s, 1H), 8.04 (d, 1H), 7.35-7.22 (m, 4H), 6.88 (d, 2H), 6.33 (s, 1H), 4.32-4.15 (m, 4H), 3.89-3.81 (m, 4H), 3.74-3.60 (m, 1H), 3.20-3.04 (m, 7H), 2.66-2.35 (m, 12H), 2.22-1.88 (m, 5H), 1.10 (t, 3H). LC/MS (ESI): 588.1 (MH)$^+$.

Example 116

4-(7-{3-[4-(2-Hydroxy-ethyl)-piperazin-1-yl]-propoxy}-quinazolin-4-yl)-piperidine-1-carboxylic acid (4-morpholin-4-yl-phenyl)-amide

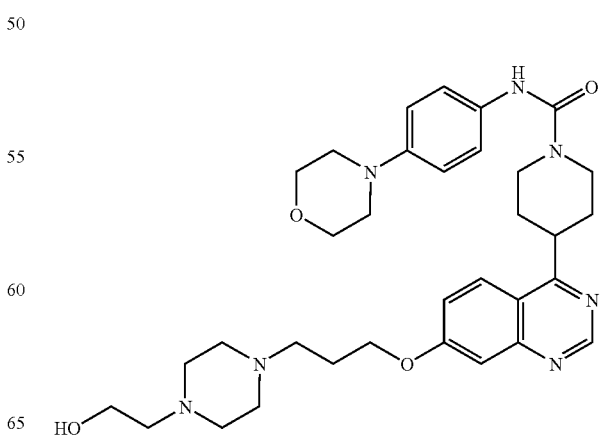

Prepared essentially as described in Example 115 using 2-piperazin-1-yl-ethanol in place of 1-ethyl-piperazine. $^1$H-NMR (300 MHz, CDCl$_3$): 9.12 (s, 1H), 8.05 (d, 1H), 7.36-7.22 (m, 4H), 6.88 (d, 2H), 6.36 (s, 1H), 4.32-4.16 (m, 4H), 3.90-3.81 (m, 4H), 3.74-3.6 (m, 1H), 3.31-3.21 (m, 4H), 3.15-3.05 (m, 7H), 2.79 (s, 3H), 2.67-2.53 (m, 6H), 2.22-1.90 (m, 6H). LC/MS (ESI): 604.1 (MH)$^+$.

Example 117

4-{7-[3-(4-Acetyl-piperazin-1-yl)-propoxy]-quinazolin-4-yl}-piperidine-1-carboxylic acid (4-morpholin-4-yl-phenyl)-amide

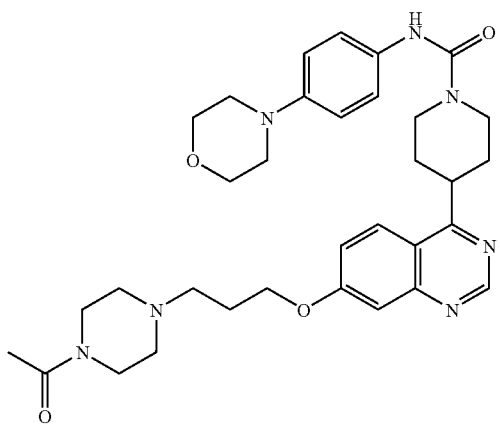

Prepared essentially as described in Example 115 using 1-acetyl-piperazine in place of 1-ethyl-piperazine. $^1$H-NMR (300 MHz, CDCl$_3$): 9.13 (s, 1H), 8.05 (d, 1H), 7.35-7.23 (m, 4H), 6.88 (d, 2H), 6.29 (s, 1H), 4.31-4.18 (m, 4H), 3.89-3.83 (m, 4H), 3.70-3.43 (m, 5H), 3.20-3.07 (m, 6H), 2.64-2.39 (m, 6H), 2.22-1.90 (m, 9H). LC/MS (ESI): 602.1 (MH)$^+$.

Example 118

4-{7-[3-(4-Methanesulfonyl-piperazin-1-yl)-propoxy]-quinazolin-4-yl}-piperidine-1-carboxylic acid (4-morpholin-4-yl-phenyl)-amide

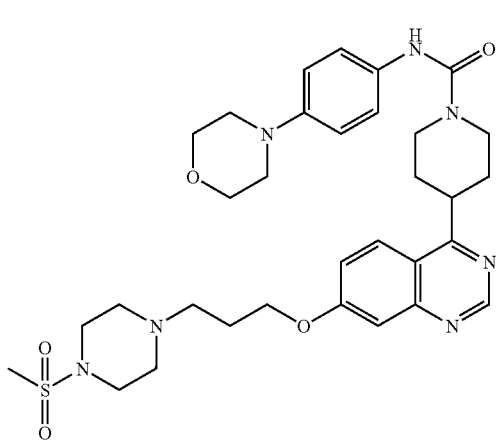

4-[7-(3-Methanesulfonyloxy-propoxy)-quinazolin-4-yl]-piperidine-1-carboxylic acid tert-butyl ester (0.1 mmol), prepared as described in Example 115, was dissolved in anhydrous dioxane together with piperazine (0.5 mmol) and the mixture was stirred at 100° C. overnight and then concentrated in vacuo, then diluted with water and extracted with DCM. The DCM extract was washed with water thrice, dried over anhydrous MgSO$_4$, filtered and concentrated in vacuo to obtain 4-[7-(3-piperazin-1-yl-propoxy)-quinazolin-4-yl]-piperidine-1-carboxylic acid tert-butyl ester. This (0.05 mmol) was dissolved in anhydrous DCM (1 mL) and treated with Et$_3$N (0.1 mmol) followed by methanesulfonyl chloride (0.1 mmol) and the mixture was stirred at rt overnight and then washed with water thrice, then dried over anhydrous MgSO$_4$, filtered and concentrated in vacuo. To this was added 3M HCl/MeOH (1 mL) and the mixture was stirred at rt for 2 h and then concentrated in vacuo and the residue was dissolved in a 1:1 mixture of DCM:MEOH, neutralized with excess Et$_3$N and treated with (4-morpholin-4-yl-phenyl)-carbamic acid 4-nitrophenyl ester hydrochloride (0.06 mmol), which was prepared as described in Example 66a. The mixture was stirred at rt overnight and then concentrated in vacuo and partitioned between water and DCM. DCM layer was drawn off, washed with water thrice, then dried over anhydrous MgSO$_4$, filtered and concentrated in vacuo. The residue was purified by Preparative TLC (silica gel; DCM:MeOH: NH4OH; 90:9:1) to obtain 14.3 mg (45%) of the title compound. $^1$H-NMR (300 MHz, CDCl$_3$): 9.13 (s, 1H), 8.04 (d, 1H), 7.35-7.22 (m, 4H), 6.88 (d, 2H), 6.33 (s, 1H), 4.31-4.13 (m, 4H), 3.89-3.80 (m, 4H), 3.74-3.56 (m, 3H), 3.20-3.03 (m, 6H), 2.61-2.38 (m, 11H), 2.22-1.88 (m, 6H). LC/MS (ESI): 638.1 (MH)$^+$.

Example 119

(S)-4-{7-[3-(2-Hydroxymethyl-pyrrolidin-1-yl)-propoxy]-quinazolin-4-yl}-piperidine-1-carboxylic acid (4-morpholin-4-yl-phenyl)-amide

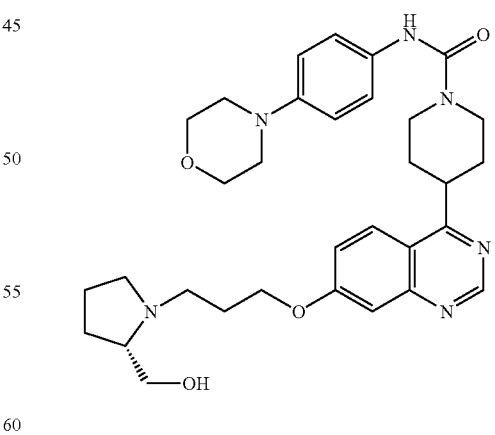

Prepared essentially as described in Example 115 using (S)-prolinol in place of 1-ethyl-piperazine. $^1$H-NMR (300 MHz, CDCl$_3$): 9.13 (s, 1H), 8.05 (d, 1H), 7.35-7.23 (m, 4H), 6.88 (d, 2H), 6.31 (s, 1H), 4.31-4.18 (m, 4H), 3.89-3.81 (m, 4H), 3.72-3.62 (m, 2H), 3.50-3.00 (m, 9H), 2.78-2.26 (m, 4H), 2.22-1.66 (m, 10H). LC/MS (ESI): 575.1 (MH)$^+$.

Example 120

4-(3-{4-[1-(4-Morpholin-4-yl-phenylcarbamoyl)-piperidin-4-yl]-quinazolin-7-yloxy}-propyl)-piperazine-1-carboxylic acid dimethylamide

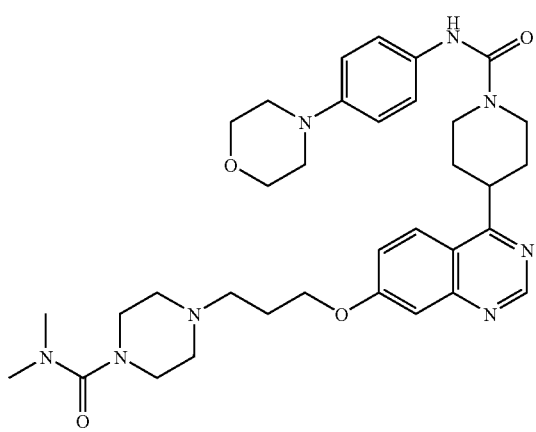

Prepared essentially as described in Example 118 using N,N-dimethylcarbamyl chloride in place of methanesulfonyl chloride. $^1$H-NMR (300 MHz, CDCl$_3$): 9.12 (s, 1H), 8.04 (d, 1H), 7.35-7.21 (m, 4H), 6.87 (d, 2H), 6.38 (s, 1H), 4.32-4.15 (m, 4H), 3.90-3.80 (m, 4H), 3.75-3.60 (m, 1H), 3.32-3.23 (m, 4H), 3.15-3.06 (m, 6H), 2.82 (s, 6H), 2.63-2.43 (m, 6H), 2.22-1.90 (m, 6H). LC/MS (ESI): 631.1 (MH)$^+$.

Example 121

Methanesulfonic acid 3-{4-[1-(4-isopropoxy-phenylcarbamoyl)-piperidin-4-yl]-quinazolin-7-yloxy}-propyl ester

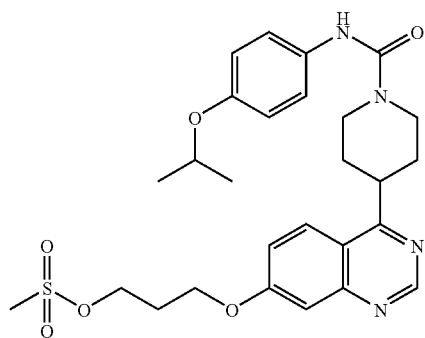

To 4-[7-(3-methanesulfonyloxy-propoxy)-quinazolin-4-yl]-piperidine-1-carboxylic acid tert-butyl ester (0.1 mmol), prepared as described in Example 115, was added 3M HCl/MeOH (2 mL) and the mixture was stirred at rt for 2 h and then concentrated in vacuo and the residue was dissolved in a 1:1 mixture of DCM:MeOH, neutralized with excess Et$_3$N and treated with (4-isopropoxy-phenyl)-carbamic acid 4-nitrophenyl ester (0.11 mmol), which was prepared as described in Example 1a. The mixture was stirred at rt overnight and then concentrated in vacuo and partitioned between water and DCM. DCM layer was drawn off, washed with water thrice, then dried over anhydrous MgSO$_4$, filtered and concentrated in vacuo. The residue was purified by Preparative TLC (silica gel; DCM:MeOH; 9.5:0.5) to obtain 40 mg (75%) of the title compound. $^1$H-NMR (300 MHz, CDCl$_3$): 9.12 (s, 1H), 8.05 (d, 1H), 7.32-7.20 (m, 4H), 6.81 (d, 2H), 6.53 (s, 1H), 4.50-4.40 (m, 3H), 4.25 (t, 4H), 3.72-3.59 (m, 1H), 3.16-3.03 (m, 2H), 3.01 (s, 3H), 2.36-2.26 (m, 2H), 2.18-2.00 (m, 2H), 1.99-1.87 (m, 2H), 1.29 (d, 6H). LC/MS (ESI): 543.1 (MH)$^+$.

Example 122

Methanesulfonic acid 3-{4-[1-(4-morpholin-4-yl-phenylcarbamoyl)-piperidin-4-yl]-quinazolin-7-yloxy}-propyl ester

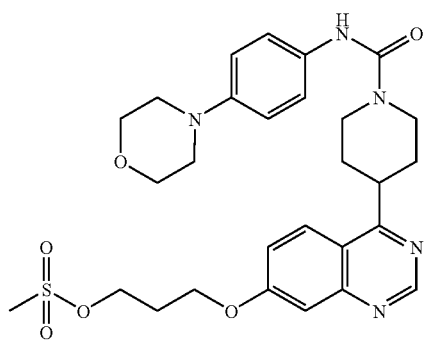

Prepared essentially as described in Example 121 using (4-morpholin-4-yl-phenyl)-carbamic acid 4-nitrophenyl ester hydrochloride, as prepared by the method outlined in Example 66a, in place of (4-isopropoxy-phenyl)-carbamic acid 4-nitrophenyl ester. $^1$H-NMR (300 MHz, CDCl$_3$): 9.13 (s, 1H), 8.06 (d, 1H), 7.35-7.23 (m, 4H), 6.87 (d, 2H), 6.40 (s, 1H), 4.48 (t, 2H), 4.31-4.20 (m, 4H), 3.88-3.80 (m, 4H), 3.73-3.61 (m, 1H), 3.18-3.05 (m, 6H), 3.02 (s, 3H), 2.38-2.27 (m, 2H), 2.20-1.85 (m, 4H). LC/MS (ESI): 570.1 (MH)$^+$.

Example 123

4-[7-(3-piperazin-1-yl-propoxy)-quinazolin-4-yl]-piperidine-1-carboxylic acid (4-morpholin-4-yl-phenyl)-amide

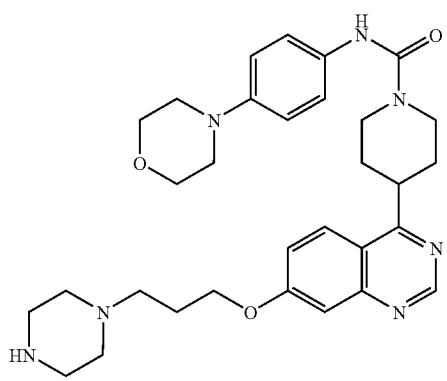

4-[7-(3-piperazin-1-yl-propoxy)-quinazolin-4-yl]-piperidine-1-carboxylic acid tert-butyl ester (0.05 mmol), prepared as described in Example 118, was dissolved in anhydrous DCM (1 mL) and treated with Et$_3$N (0.05 mmol) followed by FMOC-Cl (0.1 mmol) and the mixture was stirred at rt overnight and then washed with water thrice, then dried over anhydrous MgSO₄, filtered and concentrated in vacuo. To this was added 3M HCl/MeOH (1 mL) and the mixture was stirred at rt for 2 h and then concentrated in vacuo and the residue was dissolved in a 1:1 mixture of DCM:MeOH, neutralized with excess Et₃N and treated with (4-morpholin-4-yl-phenyl)-carbamic acid 4-nitrophenyl ester hydrochloride (0.06 mmol), as prepared by the method outlined in Example 66a. The mixture was stirred at rt overnight and then concentrated in vacuo and partitioned between water and DCM. DCM layer was drawn off, washed with water thrice, then dried over anhydrous MgSO₄, filtered and concentrated in vacuo. The residue was purified by Preparative TLC (silica gel; DCM:MeOH:NH4OH; 90:9:1) to obtain the pure product. This was dissolved in anhydrous DCM (1 mL) and diethylamine (0.25 mL) was added and the mixture was stirred at rt overnight. It was then concentrated in vacuo and purified by Preparative TLC (silica gel; DCM:MeOH:NH4OH; 90:9:1) to obtain 2.8 mg (10%) of the title compound. $^{1}$H-NMR (300 MHz, CDCl₃): 9.13 (s, 1H), 8.05 (d, 1H), 7.35-7.23 (m, 4H), 6.88 (d, 2H), 6.35 (s, 1H), 4.32-4.14 (m, 4H), 3.90-3.80 (m, 4H), 3.75-3.60 (m, 1H), 3.20-2.91 (m, 10H), 2.75-2.55 (m, 6H), 2.18-1.85 (m, 7H). LC/MS (ESI): 560.0 (MH)⁺.

Example 124

4-[7-(3-Pyrrolidin-1-yl-propoxy)-quinazolin-4-yl]-piperidine-1-carboxylic acid (4-morpholin-4-yl-phenyl)-amide Prepared essentially as described in Example 115 using pyrrolidine in place of 1-ethyl-piperazine. $^{1}$H-NMR (300 MHz, CDCl₃): 9.13 (s, 1H), 8.05 (d, 1H), 7.34-7.23 (m, 4H), 6.88 (d, 2H), 6.30 (s, 1H), 4.32-4.18 (m, 4H), 3.90-3.83 (m, 4H), 3.75-3.60 (m, 2H), 3.20-3.05 (m, 5H), 2.80-2.55 (m, 6H), 2.22-1.76 (m, 10H). LC/MS (ESI): 545.0 (MH)⁺.

Example 125

4-{7-[3-(4-Methyl-[1,4]diazepan-1-yl)-propoxy]-quinazolin-4-yl}-piperidine-1-carboxylic acid (4-morpholin-4-yl-phenyl)-amide

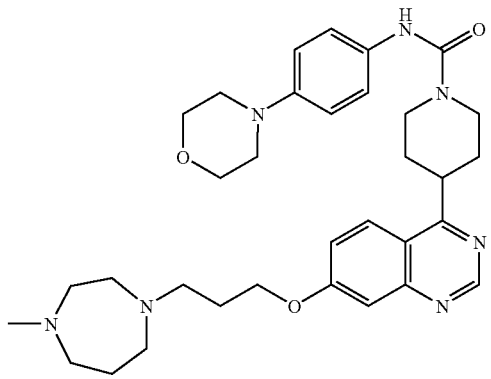

Prepared essentially as described in Example 115 using 1-methyl-[1,4]diazepane in place of 1-ethyl-piperazine. $^{1}$H-NMR (300 MHz, CDCl₃): 9.13 (s, 1H), 8.05 (d, 1H), 7.34-7.23 (m, 4H), 6.88 (d, 2H), 6.30 (s, 1H), 4.31-4.16 (m, 4H), 3.89-3.83 (m, 4H), 3.74-3.63 (m, 2H), 3.20-3.07 (m, 5H), 2.83-2.67 (m, 9H), 2.43 (s, 3H), 2.22-1.84 (m, 9H). LC/MS (ESI): 588.2 (MH)⁺.

Example 126

(R)-4-[7-(3-Hydroxy-pyrrolidin-1-yl)-quinazolin-4-yl]-piperidine-1-carboxylic acid (4-morpholin-4-yl-phenyl)-amide

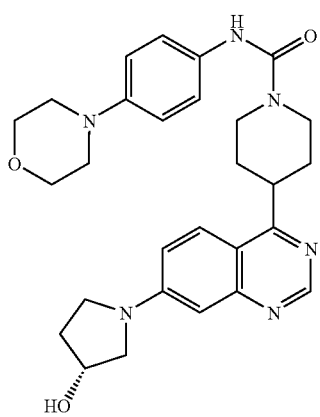

a. 4-[7-(R)-3-Hydroxy-pyrrolidin-1-yl)-quinazolin-4-yl]-piperidine-1-carboxylic acid tert-butyl ester

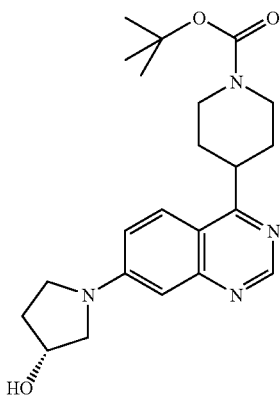

A mixture of 4-(7-fluoro-quinazolin-4-yl)-piperidine-1-carboxylic acid tert-butyl ester (34.9 mg, 0.105 mmol), which was prepared as described in Example 65b, and (R)-(+)-3-pyrrolidinol (32 mg, 0.368 mmol) in DMSO (0.4 mL) was heated at 120° C. with stirring for 40 min. It was partitioned between ethyl acetate and water, the combined organic extracts were washed with brine, dried over Na$_2$SO$_4$ and evaporated to afford almost pure product (40 mg, 95.7%). $^1$H NMR (CDCl$_3$) δ 8.97 (s, 1H), 7.96 (d, J=9.39 Hz, 1H), 7.01 (dd, J=9.33 and 2.45 Hz, 1H), 6.88 (d, J=2.19 Hz, 1H), 4.71 (m, 1H), 4.32 (m, 2H), 3.67 (m, 2H), 3.58 (m, 1H), 3.51 (m, 2H), 2.93 (m, 2H), 1.80-2.28 (6H), 1.49 (s, 9H). Calcd for C$_{22}$H$_{31}$N$_4$O$_3$ (MH+) 399.2, found 399.0.

b. 4-[7-(3-Hydroxy-pyrrolidin-1-yl)-quinazolin-4-yl]-piperidine-1-carboxylic acid (4-morpholin-4-yl-phenyl)-amide

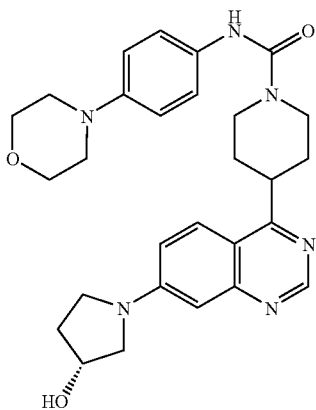

4-[7-(R)-3-Hydroxy-pyrrolidin-1-yl)-quinazolin-4-yl]-piperidine-1-carboxylic acid tert-butyl ester (21 mg, 0.053 mmol) was treated with 2.5 mL of 50% TFA/CH$_2$Cl$_2$ for 2 h, it was evaporated and the dry residue was re-dissolved in CH$_3$CN (1.5 mL). To the CH$_3$CN solution was added DIPEA (64 μL), followed by (4-morpholin-4-yl-phenyl)-carbamic acid 4-nitro-phenyl ester hydrochloride (27.9 mg, 0.074 mmol), which was prepared as described in Example 66a. The resulting mixture was stirred at room temperature for 1 h and the solvents were removed under reduced pressure. The residue was washed with water and purified by flash column chromatography on silica gel (EtOAc→15% MeOH/EtOAc as eluent). $^1$H NMR (CD$_3$OD) δ 8.95 (s, 1H), 7.96 (d, J=9.47 Hz, 1H), 7.29 (d, J=8.96 Hz, 2H), 7.03 (dd, J=9.35 and 2.53 Hz, 1H), 6.92 (d, J=1.94 Hz, 1H), 6.87 (d, J=8.87 Hz, 2H), 4.69 (m, 1H), 4.25 (m, 2H), 3.86 (t, J=4.78 Hz, 4H), 3.46-3.72 (5H), 3.07-3.14 (6H), 2.04-2.24 (4H), 1.92 (m, 2H). Calcd for C$_{28}$H$_{35}$N$_6$O$_3$ (MH+) 503.3, found 503.1.

Example 127

4-[7-(1-Methyl-piperidin-4-yloxy)-quinazolin-4-yl]-piperidine-1-carboxylic acid (4-morpholin-4-yl-phenyl)-amide

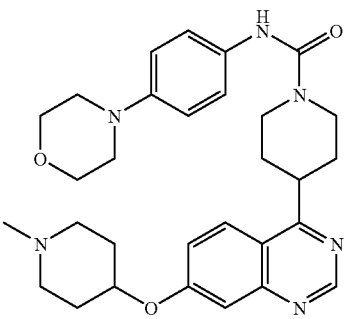

Prepared essentially as described in Example 67 using 1-methyl-piperidin-4-ol and (4-morpholin-4-yl-phenyl)-carbamic acid 4-nitro-phenyl ester, which was prepared as described in Example 66a. $^1$H NMR (CD$_3$OD) δ 9.02 (s, 1H), 8.35 (d, J=9.25 Hz, 1H), 7.37 (dd, J=9.12 and 2.44 Hz, 1H), 7.34 (d, J=2.48 (Hz, 1H), 7.26 (d, J=8.87 Hz, 2H), 6.93 (d, J=8.96 Hz, 2H), 4.72 (m, 1H), 4.34 (m, 2H), 3.92 (m, 1H), 3.82 (t, J=4.66 Hz, 4H), 3.17 (m, 2H), 3.08 (t, J=4.83 Hz, 4H), 2.77 (m, 2H), 2.47 (m, 2H), 2.34 (s, 3H), 1.87-2.18 (8H). Calcd for C$_{30}$H$_{39}$N$_6$O$_3$ (MH+) 531.3, found 531.1.

Example 128

4-[7-(3-Hydroxy-pyrrolidin-1-yl)-quinazolin-4-yl]-piperidine-1-carboxylic acid (4-morpholin-4-yl-phenyl)-amide

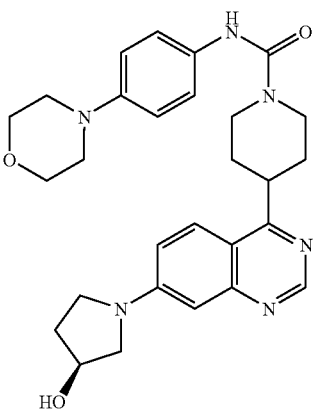

Prepared essentially as described in Example 126b, using (S)-(+)-3-pyrrolidinol. $^1$H NMR (CDCl$_3$) δ 8.95 (s, 1H), 7.96 (d, J=9.48 Hz, 1H), 7.29 (m, 3H), 7.03 (dd, J=9.19 and 2.29 Hz, 1H), 6.91 (d, J=1.78 Hz, 1H), 6.88 (m, 2H), 6.46 (br, 1H), 4.69 (m, 1H), 4.25 (m, 2H), 3.86 (t, J=4.48 Hz, 4H), 3.55-3.72 (4H), 3.48 (m, 1H), 3.09 (m, 6H), 2.04-2.26 (4H), 1.91 (m, 2H). Calcd for C$_{28}$H$_{35}$N$_6$O$_3$ (MH+) 503.3, found 503.1.

Example 129

(S)-4-[7-(3-Hydroxy-pyrrolidin-1-yl)-quinazolin-4-yl]-piperidine-1-carboxylic acid (4-pyrrolidin-1-yl-phenyl)-amide

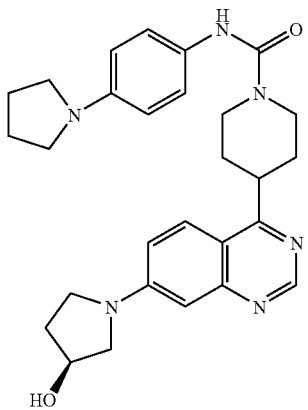

Prepared essentially as described in Example 126 using (S)-(+)-3-pyrrolidinol and (4-pyrrolidin-1-yl-phenyl)-carbamic acid 4-nitro-phenyl ester hydrochloride, which was prepared as described in Example 74a. $^1$H NMR (CD$_3$OD) δ 8.83 (s, 1H), 8.29 (d, J=9.70 Hz, 1H), 7.29 (dd, J=9.34 and 2.62 Hz, 1H), 7.16 (d, J=8.91 Hz, 2H), 6.77 (d, J=2.31 Hz, 1H), 6.59 (m, 2H), 4.62 (m, 1H), 4.34 (m, 2H), 3.89 (m, 1H), 3.63-3.73 (4H), 3.47 (m, 1H), 3.08-3.34 (4H), 1.86-2.26 (10H). Calcd for C$_{27}$H$_{34}$N$_7$O$_2$ (MH+) 487.3, found 487.1.

Example 130

(R)-4-[7-(2-Methoxymethyl-pyrrolidin-1-yl)-quinazolin-4-yl]-piperidine-1-carboxylic acid (4-morpholin-4-yl-phenyl)-amide

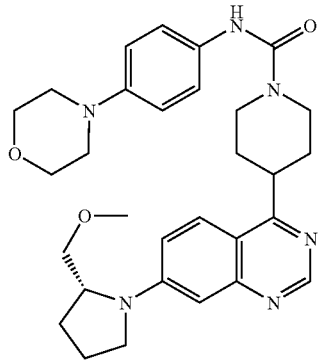

Prepared essentially as described in Example 126 using (R)-2-(methoxymethyl)pyrrolidine. $^1$H NMR (CDCl$_3$) δ 8.98 (s, 1H), 7.95 (d, J=9.47 Hz, 1H), 7.27 (d, J=6.95 Hz, 2H), 7.13 (dd, J=9.42 and 2.52 Hz, 1H), 6.95 (d, J=2.41 Hz, 1H), 6.87 (d, J=9.00 Hz, 2H), 6.31 (br, 1H), 4.25 (m, 2H), 4.11 (m, 1H), 3.86 (t, J=4.65 Hz, 4H), 3.61 (m, 1H), 3.54 (dd, J=9.34 and 3.54 Hz, 2H), 3.38 (s, 3H), 3.32 (m, 2H), 3.08-3.17 (6H), 1.91-2.19 (8H). Calcd for C$_{30}$H$_{39}$N$_6$O$_3$ (MH+) 531.3, found 530.1.

Example 131

4-[6-(4-Methyl-piperazin-1-yl)-quinazolin-4-yl]-piperidine-1-carboxylic acid (4-isopropoxy-phenyl)-amide

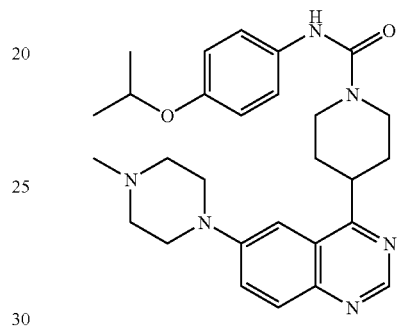

Prepared essentially as described in Example 76, using 1-methyl-piperazine. $^1$H NMR (CDCl$_3$) δ 9.08 (s, 1H), 7.93 (d, J=9.31 Hz, 1H), 7.65 (dd, J=9.32 and 2.57 Hz, 1H), 7.25 (d, J=8.92 Hz, 2H), 7.24 (d, J=4.74 Hz, 1H), 6.84 (d, J=8.93 Hz, 2H), 6.37 (br, 1H), 4.48 (m, 1H), 4.25 (m, 2H), 3.66 (m, 1H), 3.40 (t, J=4.89 Hz, 4H), 3.17 (td, J=12.74 and 3.04 Hz, 2H), 2.73 (m, 4H), 2.45 (s, 3H), 1.96-2.19 (4H), 1.31 (d, J=6.06 Hz, 6H). Calcd for C$_{28}$H$_{37}$N$_6$O$_2$ (MH+) 489.3, found 489.1.

Example 132

(R)-4-[7-(2-Hydroxymethyl-pyrrolidin-1-yl)-quinazolin-4-yl]-piperidine-1-carboxylic acid (4-morpholin-4-yl-phenyl)-amide

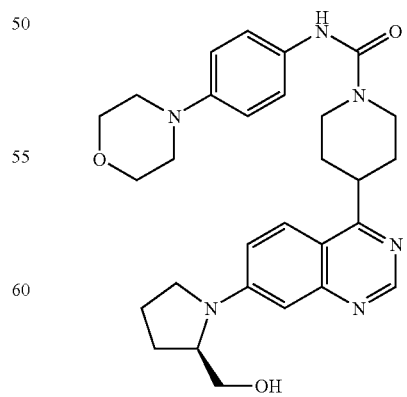

Prepared essentially as described in Example 126 using (R)-2-pyrrolidinemethanol. $^1$H NMR (CDCl$_3$) δ 8.96 (s, 1H), 7.93 (d, J=9.45 Hz, 1H), 7.27 (d, J=9.08 Hz, 2H), 7.14 (dd, J=9.21 and 2.22 Hz, 1H), 6.95 (d, J=2.26 Hz, 1H), 6.86 (d, J=8.99 Hz, 2H), 6.40 (br, 1H), 4.24 (m, 2H), 4.08 (m, 1H), 3.85 (t, J=4.70 Hz, 4H), 3.77 (dd, J=10.77 and 3.67 Hz, 1H), 3.68 (dd, J=10.73 and 7.22 Hz, 1H), 3.60 (m, 2H), 3.50 (m, 1H), 3.06-3.14 (6H), 2.03-2.17 (6H), 1.92 (m, 2H). Calcd for $C_{29}H_{37}N_6O_3$ (MH+) 517.3, found 517.1.

Example 133

4-[7-(3-Morpholin-4-yl-propoxy)-quinazolin-4-yl]-piperidine-1-carboxylic acid (4-morpholin-4-yl-phenyl)-amide

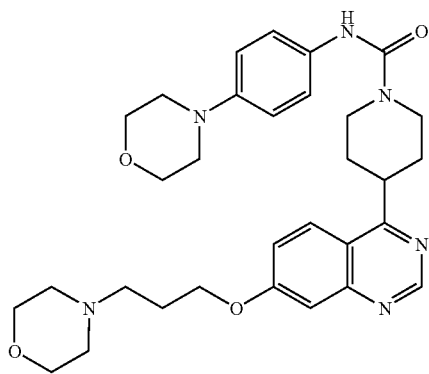

Prepared essentially as described in Example 33 using 3-morpholin-4-yl-propan-1-ol in place of 3-hydroxypropylpiperidine and (4-morpholin-4-yl-phenyl)-carbamic acid 4-nitrophenyl ester hydrochloride, as prepared by the method outlined in Example 66a, in place of (4-isopropoxy-phenyl)-carbamic acid 4-nitrophenyl ester. $^1$H-NMR (300 MHz, CDCl$_3$): 9.13 (s, 1H), 8.04 (d, 1H), 7.35-7.22 (m, 4H), 6.87 (d, 2H), 6.37 (s, 1H), 4.32-4.16 (m, 4H), 3.90-3.60 (m, 9H), 3.20-3.04 (m, 6H), 2.43-2.62 (m, 6H), 2.21-1.90 (m, 6H). LC/MS (ESI): 561.1 (MH)$^+$.

Example 134

4-[7-(3-Diethylamino-propoxy)-quinazolin-4-yl]-piperidine-1-carboxylic acid (4-morpholin-4-yl-phenyl)-amide

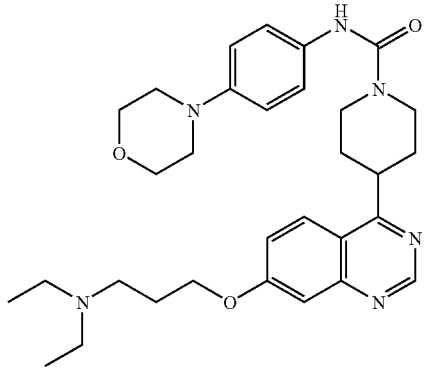

Prepared essentially as described in Example 33 using 3-diethylamino-propan-1-ol in place of 3-hydroxypropylpiperidine and (4-morpholin-4-yl-phenyl)-carbamic acid 4-nitrophenyl ester hydrochloride, as prepared by the method outlined in Example 66a, in place of (4-isopropoxy-phenyl)-carbamic acid 4-nitrophenyl ester. $^1$H-NMR (300 MHz, CDCl$_3$): 9.13 (s, 1H), 8.04 (d, 1H), 7.35-7.23 (m, 4H), 6.88 (d, 2H), 6.33 (s, 1H), 4.32-4.15 (m, 4H), 3.90-3.81 (m, 4H), 3.74-3.60 (m, 1H), 3.20-3.04 (m, 6H), 2.72-2.51 (m, 6H), 2.22-1.89 (m, 6H), 1.06 (t, 6H). LC/MS (ESI): 547.2 (MH)$^+$.

Example 135

4-[7-(4-Methyl-piperazin-1-yl)-quinazolin-4-yl]-piperidine-1-carboxylic acid (4-morpholin-4-yl-phenyl)-amide

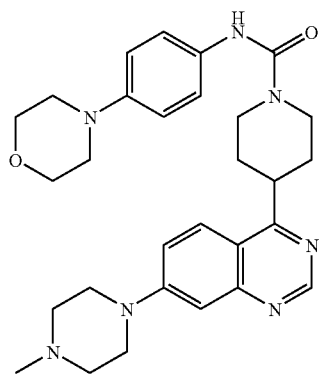

A mixture of 1-methylpiperazine (0.11 mmol) and 4-(7-fluoro-quinazolin-4-yl)-piperidine-1-carboxylic acid tert-butyl ester (0.05 mmol), prepared as described in Example 65, in DMSO (1 mL) was stirred at 120° C. for 1 h. It was then diluted with water and extracted with DCM. The combined extracts were washed with water, brine, dried (anhydrous MgSO4), filtered and concentrated in vacuo. The crude product was then treated with 3M HCl/MeOH (2 mL) and stirred at rt for 2 h and then concentrated in vacuo. The crude residue was dissolved in a mixture of DCM:MeOH (1:1; 2 mL) and neutralized with excess Et$_3$N and treated with (4-morpholin-4-yl-phenyl)-carbamic acid 4-nitrophenyl ester hydrochloride (0.06 mmol), as prepared by the method outlined in Example 66a, at rt overnight. It was then concentrated in vacuo and the crude product was dissolved in DCM and washed with water thrice, then washed with brine, dried over anhydrous MgSO$_4$, filtered and concentrated in vacuo. The crude product was then purified by Preparative TLC (silica gel; DCM:MeOH:NH$_4$OH, 90:9:1) to obtain 5.5 mg (21%) of the title compound. $^1$H-NMR (300 MHz, CDCl$_3$): 9.04 (s, 1H), 7.98 (d, 1H), 7.36-7.18 (m, 4H), 6.88 (d, 2H), 6.32 (s, 1H), 4.25 (m, 2H), 3.89-3.83 (m, 4H), 3.69-3.55 (m, 1H), 3.53-3.43 (m, 4H), 3.19-3.04 (m, 6H), 2.66-2.58 (m, 4H), 2.39 (s, 3H), 2.20-1.90 (m, 4H). LC/MS (ESI): 516.1 (MH)$^+$.

Example 136

4-[7-(4-Ethyl-piperazin-1-yl)-quinazolin-4-yl]-piperidine-1-carboxylic acid (4-morpholin-4-yl-phenyl)-amide

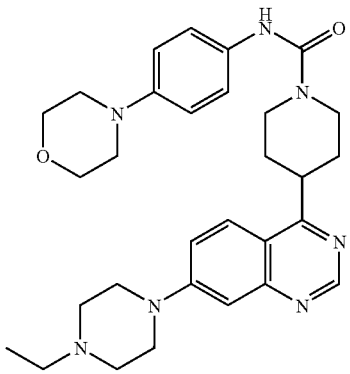

Prepared essentially as described in Example 135 using 1-ethyl-piperazine in place of 1-methyl-piperazine. $^1$H-NMR (300 MHz, CDCl$_3$): 9.04 (s, 1H), 7.98 (d, 1H), 7.38-7.17 (m, 4H), 6.87 (d, 2H), 6.35 (s, 1H), 4.25 (m, 2H), 3.89-3.82 (m, 4H), 3.69-3.56 (m, 1H), 3.53-3.44 (m, 4H), 3.18-3.05 (m, 6H), 2.69-2.60 (m, 4H), 2.55-2.45 (q, 2H), 2.20-1.90 (m, 4H), 1.15 (t, 3H). LC/MS (ESI): 530.1 (MH)$^+$.

Example 137

4-{7-[4-(2-Hydroxy-ethyl)-piperazin-1-yl]-quinazolin-4-yl}-piperidine-1-carboxylic acid (4-morpholin-4-yl-phenyl)-amide

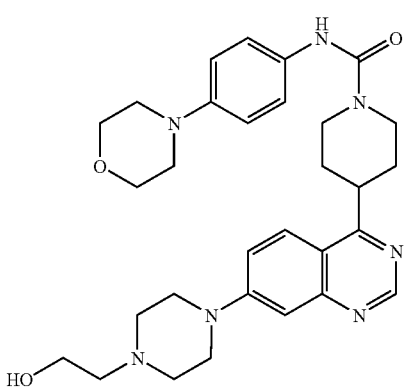

Prepared essentially as described in Example 135 using 1-(2-hydroxyethyl)-piperazine in place of 1-methyl-piperazine. $^1$H-NMR (300 MHz, CDCl$_3$): 9.05 (s, 1H), 7.99 (d, 1H), 7.38-7.19 (m, 4H), 6.88 (d, 2H), 6.34 (s, 1H), 4.25 (m, 2H), 3.89-3.81 (m, 4H), 3.74-3.57 (m, 3H), 3.51-3.43 (m, 4H), 3.19-3.04 (m, 6H), 2.75-2.60 (m, 6H), 2.20-1.90 (m, 5H). LC/MS (ESI): 546.1 (MH)$^+$.

Example 138

4-[7-(4-Methyl-[1,4]diazepan-1-yl)-quinazolin-4-yl]-piperidine-1-carboxylic acid (4-morpholin-4-yl-phenyl)-amide

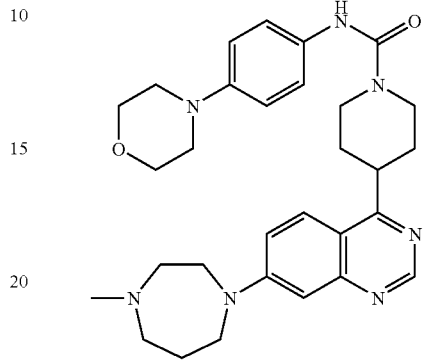

Prepared essentially as described in Example 135 using 1-methyl-[1,4]diazepane in place of 1-methyl-piperazine. $^1$H-NMR (300 MHz, CDCl$_3$): 8.98 (s, 1H), 7.95 (d, 1H), 7.31-7.24 (m, 2H), 7.20-7.10 (m, 1H), 7.01 (d, 1H), 6.88 (d, 2H), 6.33 (s, 1H), 4.25 (m, 2H), 3.90-3.51 (m, 9H), 3.18-3.05 (m, 6H), 2.83-2.75 (m, 2H), 2.65-2.55 (m, 2H), 2.41 (s, 3H), 2.20-1.90 (m, 6H). LC/MS (ESI): 530.1 (MH)$^+$.

Example 139

(S)-4-[7-(2-Hydroxymethyl-pyrrolidin-1-yl)-quinazolin-4-yl]-piperidine-1-carboxylic acid (4-morpholin-4-yl-phenyl)-amide

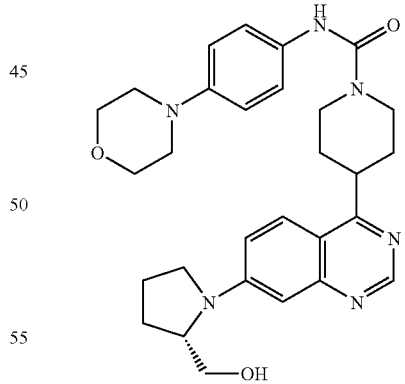

Prepared essentially as described in Example 126 using (S)-2-pyrrolidinemethanol. $^1$H NMR (CDCl$_3$) δ 8.96 (s, 1H), 7.92 (d, J=9.37 Hz, 1H), 7.27 (d, J=9.14 Hz, 2H), 7.14 (dd, J=9.35 and 2.44 Hz, 1H), 6.95 (d, J=2.30 Hz, 1H), 6.86 (d, J=8.97 Hz, 2H), 6.41 (br, 1H), 4.24 (m, 2H), 4.08 (m, 1H), 3.85 (t, J=4.67 Hz, 4H), 3.77 (dd, J=11.02 and 4.00 Hz, 1H), 3.68 (dd, J=10.88 and 6.80 Hz, 1H), 3.54-3.63 (2H), 3.35 (m, 1H), 3.06-3.14 (6H), 2.04-2.18 (6H), 1.92 (m, 2H). Calcd for C$_{29}$H$_{37}$N$_6$O$_3$ (MH+) 517.3, found 517.1.

Example 140

4-(7-piperazin-1-yl-quinazolin-4-yl)-piperidine-1-carboxylic acid (4-morpholin-4-yl-phenyl)-amide

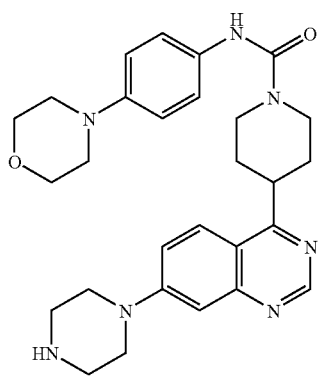

A mixture of piperazine (5 mmol) and 4-(7-fluoro-quinazolin-4-yl)-piperidine-1-carboxylic acid tert-butyl ester (1 mmol) in DMSO (1 mL) was stirred at 120° C. for 1 h. It was then diluted with water and extracted with DCM. The combined extracts were washed with water, brine, dried (anhydrous MgSO4), filtered and concentrated in vacuo to obtain 4-(7-piperazin-1-yl-quinazolin-4-yl)-piperidine-1-carboxylic acid tert-butyl ester. This (0.1 mmol) was dissolved in anhydrous DCM (1 mL) and treated with Et$_3$N (0.2 mmol) followed by 9-fluorenylmethyl chloroformate (FMOC-Cl, 0.2 mmol) and the mixture was stirred at rt overnight and then washed with water thrice, then dried over anhydrous MgSO$_4$, filtered and concentrated in vacuo. To this was then added 3M HCl/MeOH (2 mL) and stirred at rt for 2 h and then concentrated in vacuo. The crude residue was dissolved in a mixture of DCM:MeOH (1:1; 2 mL) and neutralized with excess Et$_3$N and treated with (4-morpholin-4-yl-phenyl)-carbamic acid 4-nitrophenyl ester hydrochloride (0.11 mmol), as prepared by the method outlined in Example 66a, at rt overnight. It was then concentrated in vacuo and the crude product was dissolved in DCM and washed with water thrice, then washed with brine, dried over anhydrous MgSO$_4$, filtered and concentrated in vacuo. The crude product was then purified by Preparative TLC (silica gel; DCM:MeOH:NH$_4$OH, 90:9:1) to obtain 5.6 mg (11%) of the title compound. $^1$H-NMR (300 MHz, CDCl$_3$): 9.04 (s, 1H), 7.97 (d, 1H), 7.36-7.18 (m, 4H), 6.88 (d, 2H), 6.31 (s, 1H), 4.25 (m, 2H), 3.89-3.82 (m, 4H), 3.70-3.56 (m, 1H), 3.46-3.38 (m, 4H), 3.19-3.04 (m, 10H), 2.21-1.90 (m, 5H). LC/MS (ESI): 502.1 (MH)$^+$.

Example 141

4-[7-(4-Acetyl-piperazin-1-yl)-quinazolin-4-yl]-piperidine-1-carboxylic acid (4-morpholin-4-yl-phenyl)-amide

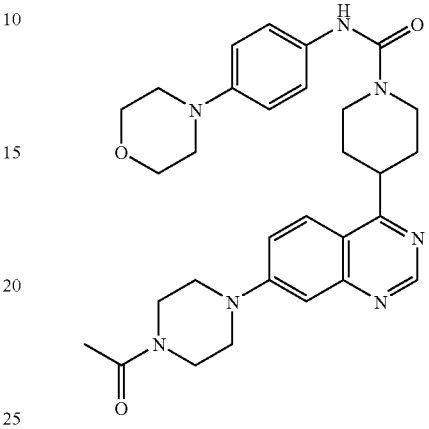

Prepared essentially as described in Example 140 using acetyl chloride in place of FMOC-Cl. $^1$H-NMR (300 MHz, CDCl$_3$): 9.05 (s, 1H), 8.01 (d, 1H), 7.36-7.20 (m, 3H), 6.86 (d, 3H), 6.48 (s, 1H), 4.25 (m, 2H), 3.90-3.76 (m, 6H), 3.74-3.56 (m, 3H), 3.53-3.40 (m, 4H), 3.19-3.00 (m, 6H), 2.20-2.01 (m, 5H), 2.00-1.85 (m, 2H). LC/MS (ESI): 544.1 (MH)$^+$.

Example 142

4-[7-(4-Methanesulfonyl-piperazin-1-yl)-quinazolin-4-yl]-piperidine-1-carboxylic acid (4-morpholin-4-yl-phenyl)-amide

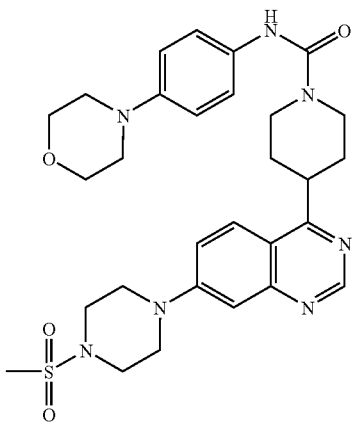

Prepared essentially as described in Example 140 using methanesulfonyl chloride in place of FMOC-Cl. $^1$H-NMR (300 MHz, CDCl$_3$+CD$_3$OD): 8.92 (s, 1H), 7.99 (d, 1H), 7.33-7.12 (m, 4H), 6.81 (d, 2H), 4.21 (m, 2H), 3.82-3.75 (m, 4H), 3.67-3.48 (m, 5H), 3.40-3.32 (m, 4H), 3.09-2.96 (m, 6H), 2.79 (s, 3H), 2.08-1.81 (m, 4H). LC/MS (ESI): 580.1 (MH)$^+$.

Example 143

4-{4-[1-(4-Morpholin-4-yl-phenylcarbamoyl)-piperidin-4-yl]-quinazolin-7-yl}-piperazine-1-carboxylic acid dimethylamide

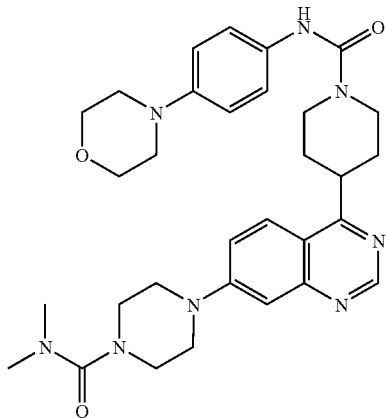

Prepared essentially as described in Example 140 using N,N-dimethylcarbamoyl chloride in place of FMOC-Cl. $^1$H-NMR (300 MHz, CDCl$_3$): 9.04 (s, 1H), 7.99 (d, 1H), 7.35-7.17 (m, 4H), 6.86 (d, 2H), 6.47 (s, 1H), 4.25 (m, 2H), 3.88-3.81 (m, 4H), 3.65-3.56 (m, 1H), 3.49-3.39 (m, 8H), 3.17-3.04 (m, 6H), 2.89 (s, 6H), 2.20-1.85 (m, 4H). LC/MS (ESI): 573.1 (MH)$^+$.

Example 144

4-{7-[4-(2-Dimethylamino-acetyl)-piperazin-1-yl]-quinazolin-4-yl}-piperidine-1-carboxylic acid (4-morpholin-4-yl-phenyl)-amide

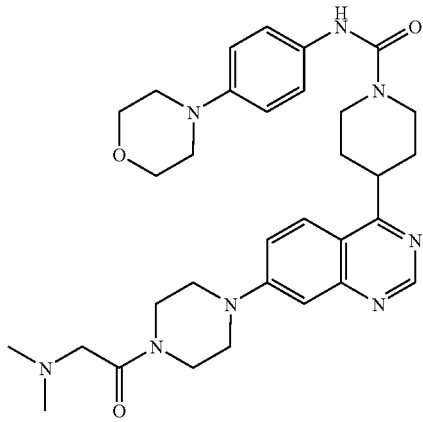

Prepared essentially as described in Example 140 using N,N-dimethylaminoacetyl chloride in place of FMOC-Cl. $^1$H-NMR (300 MHz, CDCl$_3$): 9.05 (s, 1H), 8.01 (d, 1H), 7.35-7.17 (m, 4H), 6.86 (d, 2H), 6.46 (s, 1H), 4.25 (m, 2H), 3.88-3.76 (m, 8H), 3.70-3.55 (m, 1H), 3.50-3.40 (m, 4H), 3.20-3.03 (m, 8H), 2.30 (s, 6H), 2.19-1.87 (m, 4H). LC/MS (ESI): 587.1 (MH)$^+$.

Example 145

4-(7-Morpholin-4-yl-quinazolin-4-yl)-piperidine-1-carboxylic acid (4-morpholin-4-yl-phenyl)-amide

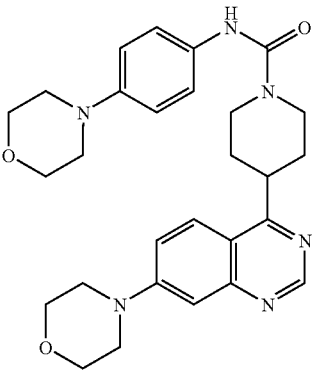

Prepared essentially as described in Example 135 using morpholine in place of 1-methyl-piperazine. $^1$H-NMR (300 MHz, CDCl$_3$): 9.07 (s, 1H), 8.01 (d, 1H), 7.36-7.19 (m, 4H), 6.88 (d, 2H), 6.32 (s, 1H), 4.25 (m, 2H), 3.94-3.81 (m, 8H), 3.70-3.57 (m, 1H), 3.44-3.37 (m, 4H), 3.19-3.05 (m, 6H), 2.20-1.87 (m, 4H). LC/MS (ESI): 503.1 (MH)$^+$.

Example 146

4-[7-(2-Methanesulfonyl-ethylamino)-quinazolin-4-yl]-piperidine-1-carboxylic acid (4-morpholin-4-yl-phenyl)-amide

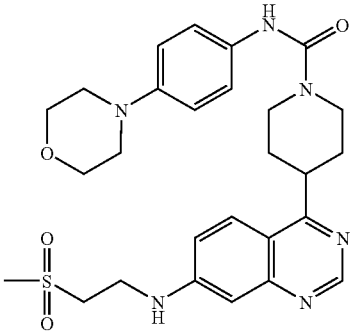

Prepared essentially as described in Example 126 using 2-methanesulfonyl-ethylamine. $^1$H NMR (CDCl$_3$) δ 9.03 (s, 1H), 7.94 (d, J=8.91 Hz, 1H), 7.27 (d, J=9.01 Hz, 2H), 6.96-7.01 (2H), 6.87 (d, J=8.98 Hz, 2H), 5.35 (br, 1H), 5.23 (t, J=5.65 Hz, 1H), 4.26 (m, 2H), 3.83-3.92 (6H), 3.61 (m, 1H), 3.39 (m, 2H), 3.07-3.17 (6H), 2.99 (s, 3H), 2.11 (m, 2H), 1.93 (m, 2H). Calcd for C$_{27}$H$_{35}$N$_6$O$_2$S (MH+) 539.2, found 539.0.

Example 147

4-{7-[2-(2-Oxo-oxazolidin-3-yl)-ethoxy]-quinazolin-4-yl}-piperidine-1-carboxylic acid (4-pyrrolidin-1-yl-phenyl)-amide

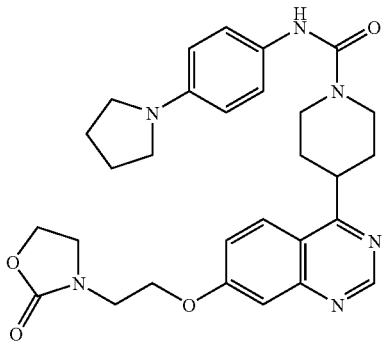

Prepared essentially as described in Example 67 using 3-(2-hydroxy-ethyl)-oxazolidin-2-one and (4-pyrrolidin-1-yl-phenyl)-carbamic acid 4-nitro-phenyl ester hydrochloride, which was prepared as described in Example 74a. $^1$H NMR (CDCl$_3$) δ 9.16 (s, 1H), 8.07 (d, J=9.22 Hz, 1H), 7.31 (d, J=2.61 Hz, 1H), 7.25 (m, 1H), 7.18 (d, J=8.92 Hz, 2H), 6.52 (d, J=8.93 Hz, 2H), 6.19 (br, 1H), 4.38 (t, J=7.90 Hz, 2H), 4.33 (t, J=4.79 Hz, 2H), 4.26 (m, 2H), 3.80 (t, J=8.21 Hz, 2H), 3.78 (t, J=4.75 Hz, 2H), 3.67 (m, 1H), 3.26 (t, J=6.65 Hz, 4H), 3.12 (td, J=12.53 and 2.63 Hz, 2H), 2.13 (m, 2H), 1.93-2.01 (6H). Calcd for C$_{29}$H$_{35}$N$_6$O$_4$ (MH+) 531.3, found 531.1.

Example 148

4-{7-[2-(2-Oxo-oxazolidin-3-yl)-ethoxy]-quinazolin-4-yl}-piperidine-1-carboxylic acid (4-morpholin-4-yl-phenyl)-amide

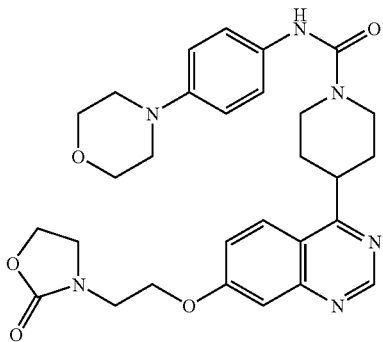

Prepared essentially as described in Example 67 using 3-(2-hydroxy-ethyl)-oxazolidin-2-one and (4-morpholin-4-yl-phenyl)-carbamic acid 4-nitro-phenyl ester hydrochloride, which was prepared as described in Example 66a. $^1$H NMR (CDCl$_3$) δ 9.15 (s, 1H), 8.07 (d, J=9.34 Hz, 1H), 7.32 (d, J=2.44 Hz, 1H), 7.24-7.29 (3H), 6.88 (d, J=8.97 Hz, 2H), 6.29 (br, 1H), 4.38 (t, J=8.04 Hz, 2H), 4.33 (t, J=4.89 Hz, 2H), 4.26 (m, 2H), 3.86 (t, J=4.67 Hz, 4H), 3.80 (t, J=8.04 Hz, 2H), 3.79 (t, J=5.05 Hz, 2H), 3.68 (m, 1H), 3.14 (td, J=13.86 and 3.07 Hz, 2H), 3.10 (t, J=4.80 Hz, 4H), 2.13 (m, 2H), 1.97 (m, 2H). Calcd for C$_{29}$H$_{35}$N$_6$O$_5$ (MH+) 547.3, found 547.0.

Example 149

(R)-4-[7-(3-Dimethylamino-pyrrolidin-1-yl)-quinazolin-4-yl]-piperidine-1-carboxylic acid (4-pyrrolidin-1-yl-phenyl)-amide

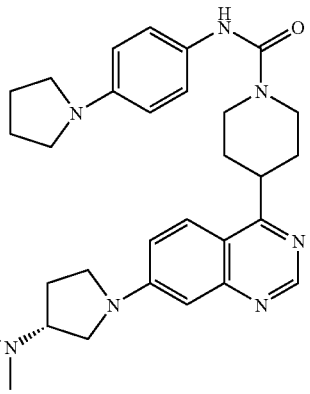

Prepared essentially as described in Example 126 using (3R)-(+)-3-(dimethylaminopyrrolidine) and (4-pyrrolidin-1-yl-phenyl)-carbamic acid 4-nitro-phenyl ester hydrochloride, which was prepared as described in Example 74a. $^1$H NMR (CDCl$_3$) δ 8.98 (s, 1H), 7.95 (d, J=9.34 Hz, 1H), 7.18 (d, J=8.87 Hz, 2H), 6.99 (dd, J=9.29 and 2.46 Hz, 1H), 6.84 (d, J=2.38 Hz, 1H), 6.51 (d, J=8.92 Hz, 2H), 6.20 (br, 1H), 4.24 (m, 2H), 3.65 (m, 2H), 3.58 (m, 1H), 3.47 (m, 1H), 3.30 (t, J=8.68 Hz, 1H), 3.25 (t, J=6.61 Hz, 4H), 3.09 (td, J=12.94 and 2.28 Hz, 2H), 2.90 (m, 1H), 2.34 (s, 6H), 2.28 (m, 1H), 2.11 (m, 2H), 1.90-2.02 (7H). Calcd for C$_{30}$H$_{40}$N$_7$O (MH+) 514.3, found 514.1.

Example 150

(R)-4-[7-(3-Dimethylamino-pyrrolidin-1-yl)-quinazolin-4-yl]-piperidine-1-carboxylic acid (4-morpholin-4-yl-phenyl)-amide

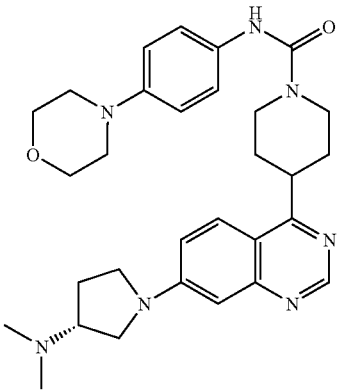

Prepared essentially as described in Example 126 using (3R)-(+)-3-(dimethylaminopyrrolidine). $^1$H NMR (CDCl$_3$) δ 8.98 (s, 1H), 7.95 (d, J=9.32 Hz, 1H), 7.27 (d, J=9.00 Hz, 2H), 7.00 (dd, J=9.19 and 2.38 Hz, 1H), 6.87 (d, J=8.96 Hz, 2H), 6.84 (d, J=2.31 Hz, 1H), 6.31 (br, 1H), 4.24 (m, 2H), 3.86 (t, J=4.65 Hz, 4H), 3.65 (m, 2H), 3.60 (m, 1H), 3.48 (m, 1H), 3.31 (t, J=8.68 HZ, 1H), 3.13 (m, 2H), 3.10 (t, J=4.85 Hz, 4H), 2.92 (m, 1H), 2.35 (s, 6H), 2.29 (m, 1H), 2.11 (m, 2H), 1.97 (m, 3H). Calcd for $C_{30}H_{40}N_7O_2$ (MH+) 530.3, found 530.1.

Example 151

(S)-4-[7-(1-Methyl-pyrrolidin-2-ylmethoxy)-quinazolin-4-yl]-piperidine-4-carboxylic acid (4-pyrrolidin-1-yl-phenyl)-amide

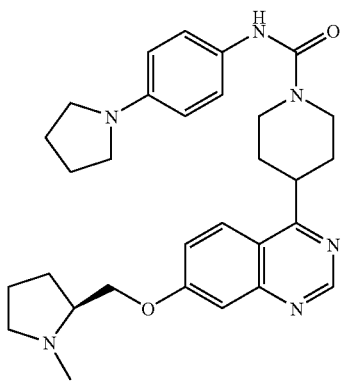

Prepared essentially as described in Example 67 using (S)-(−)-1-methyl-2-pyrrolidinemethanol and (4-pyrrolidin-1-yl-phenyl)-carbamic acid 4-nitro-phenyl ester hydrochloride, which was prepared as described in Example 74a. $^1$H NMR (CDCl$_3$) δ 9.13 (s, 1H), 8.04 (d, J=9.34 Hz, 1H), 7.26-7.34 (2H), 7.18 (d, J=8.47 Hz, 2H), 6.53 (d, J=8.63 Hz, 2H), 6.18 (br, 1H), 4.25 (m, 2H), 4.12 (m, 2H), 3.68 (m, 1H), 3.25 (m, 4H), 3.12 (m, 3H), 2.73 (m, 1H), 2.51 (s, 3H), 2.33 (m, 1 h), 1.78-2.18 (12H). Calcd for $C_{30}H_{49}N_6O_2$ (MH+) 515.3, found 515.3.

Example 152

(S)-4-{7-[2-(2-Hydroxymethyl-pyrrolidin-1-yl)-ethoxy]-quinazolin-4-yl}-piperidine-1-carboxylic acid (4-pyrrolidin-1-yl-phenyl)-amide

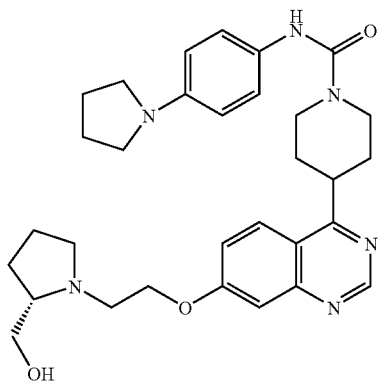

a. 4-[7-(2-Hydroxy-ethoxy)-quinazolin-4-yl]-piperidine-1-carboxylic acid tert-butyl ester

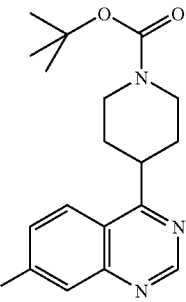

4-(7-Fluoro-quinazolin-4-yl)-piperidine-1-carboxylic acid tert-butyl ester (97.4 mg, 0.294 mmol), which was prepared as described in Example 65b, was added to ethane-1,2-diol (2.98 g, 48.01 mmol) and the suspension was heated to 90° C. to allow the starting material totally dissolved in ethane-1,2-diol. KOH (130.7 mg) was added and the mixture was stirred at 120° C. for 2 h. It was partitioned between ethyl acetate and water and the combined organic extracts were washed with brine, dried over Na$_2$SO$_4$ and evaporated to afford the product as a white solid (90 mg, 82%). $^1$H NMR (CDCl$_3$) δ 9.12 (s, 1H), 8.05 (d, J=9.27 Hz, 1H), 7.32 (d, J=2.46 Hz, 1H), 7.28 (dd, J=9.21 and 2.54 Hz, 1H), 4.31 (br, 1H), 4.26 (t, J=4.01 Hz, 2H), 4.20 (m, 1H), 4.06 (t, J=4.67 Hz, 2H), 3.83 (m, 1H), 3.60 (m, 1H), 2.93 (m, 2H), 1.80-2.11 (4H), 1.47 (s, 9H). Calcd for $C_{20}H_{28}N_3O_4$ (MH+) 374.2, found 374.2.

b. 4-[7-(2-Methanesulfonyloxy-ethoxy)-quinazolin-4-yl]-piperidine-1-carboxylic acid tert-butyl ester

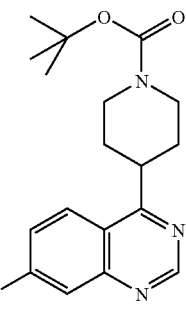

To a mixture of 4-[7-(2-hydroxy-ethoxy)-quinazolin-4-yl]-piperidine-1-carboxylic acid tert-butyl ester (90 mg, 0.24 mmol) and DIPEA (167.2 μL) in CH$_2$Cl$_2$ (5 mL) was added MsCl (37.2 μL). The reaction mixture was stirred for 4 h and the solvents were evaporated. The residue was purified by flash column chromatography on silica gel (EtOAc as eluent) to afford almost pure product. $^1$H NMR (CDCl$_3$) δ 9.15 (s, 1H), 8.09 (d, J=9.33 Hz, 1H), 7.33 (d, J=2.44 Hz, 1H), 7.29 (dd, J=9.18 and 2.59 Hz, 1H), 4.66 (t, J=4.29 Hz, 2H), 4.42 (t, J=4.39 Hz, 2H), 4.33 (m, 2H), 3.61 (m, 1H), 3.11 (s, 3H), 2.94 (m, 2H), 1.83-2.10 (4H), 1.48 (s, 9H). Calcd for $C_{21}H_{30}N_3O_6S$ (MH+) 452.2, found 452.2.

c. 4-{7-[2-(2-Hydroxymethyl-pyrrolidin-1-yl)-ethoxy]-quinazolin-4-yl}-piperidine-1-carboxylic acid (4-pyrrolidin-1-yl-phenyl)-amide

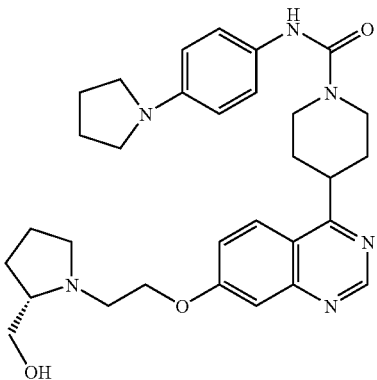

To a solution of 4-[7-(2-methanesulfonyloxy-ethoxy)-quinazolin-4-yl]-piperidine-1-carboxylic acid tert-butyl ester (40.6 mg, 0.09 mmol) in DMSO (0.4 mL) was added (S)-(+)-2-pyrrolidinemethanol (90.9 mg, 0.9 mmol). The mixture was stirred at 120° C. overnight and subsequently partitioned between EtOAc and water. The combined organic extracts were washed with brine, dried over $Na_2SO_4$ and evaporated. The residue was treated with 50% $TFA/CH_2Cl_2$ (8 mL) for 2 h, the solvents ($TFA/CH_2Cl_2$) were removed under reduced pressure and half of the residue was re-dissolved in $CH_2Cl_2$. DIPEA (55 µL) was added to the above solution, followed by (4-pyrrolidin-1-yl-phenyl)-carbamic acid 4-nitro-phenyl ester hydrochloride (19.6 mg, 0.054 mmol), which was prepared as described in Example 74a. The reaction mixture was stirred for 1 h, diluted with water. The organic phase was collected and the solvents were evaporated. The crude residue was purified by flash column chromatography on silica gel (15% MeOH/EtOAc as eluent) to afford a white solid (10 mg, 40.8% overall yield). $^1$H NMR ($CD_3OD$) δ 9.03 (s, 1H), 8.35 (d, J=9.44 Hz, 1H), 7.40 (dd, J=9.25 and 2.54 Hz, 1H), 7.34 (d, J=2.48 Hz, 1H), 7.13 (d, J=8.87 Hz, 2H), 6.54 (d, J=8.96 Hz, 2H), 4.29-4.36 (4H), 3.92 (m, 1H), 3.60 (dd, J=10.98 and 4.81 Hz, 1H), 3.52 (dd, J=11.00 and 5.90 Hz, 1H), 3.40 (m, 1H), 3.27 (m, 1H), 3.24 (t, J=6.61 Hz, 4H), 3.15 (td, J=12.57 and 2.55 Hz, 2H), 2.88 (dt, J=13.67 and 5.50 Hz, 1H), 2.71 (m, 1H), 2.47 (m, 1H), 1.90-2.09 (9H), 1.79 (m, 2H), 1.66 (m, 1H). Calcd for $C_{31}H_{41}N_6O_3$ (MH+) 545.3, found 545.3.

Example 153

(S)-4-{7-[2-(2-Hydroxymethyl-pyrrolidin-1-yl)-ethoxy]-quinazolin-4-yl}-piperidine-1-carboxylic acid (4-morpholin-4-yl-phenyl)-amide

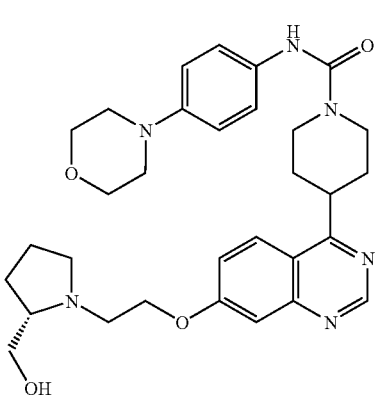

Prepared essentially as described in Example 152 using (4-morpholin-4-yl-phenyl)-carbamic acid 4-nitro-phenyl ester hydrochloride, which was prepared as described in Example 66a. $^1$H NMR ($CD_3OD$) δ 9.08 (s, 1H), 8.41 (d, J=9.42 Hz, 1H), 7.48 (dd, J=9.22 Hz and 2.54 Hz, 1H), 7.41 (d, J=2.49 Hz, 1H), 7.26 (d, J=9.09 Hz, 2H), 6.93 (d, J=9.08 Hz, 2H), 4.56 (m, 2H), 4.34 (m, 2H), 3.87-3.98 (2H), 3.83 (t, J=4.60 Hz, 4H), 3.68-3.76 (4H), 3.60 (m, 1H), 3.24 (m, 1H), 3.17 (m, 2H), 3.08 (t, J=4.77 Hz, 4H), 1.92-2.28 (8H). Calcd for $C_{31}H_{41}N_6O_4$ (MH+) 561.3, found 561.2.

Example 154

(R)-4-[7-(1-Acetyl-pyrrolidin-3-yloxy)-quinazolin-4-yl]-piperidine-1-carboxylic acid (4-pyrrolidin-1-yl-phenyl)-amide

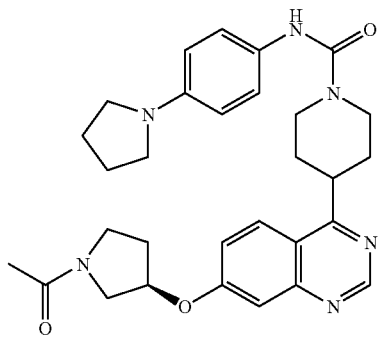

a. 4-[7-(1-Acetyl-pyrrolidin-3-yloxy)-quinazolin-4-yl]-piperidine-1-carboxylic acid tert-butyl ester

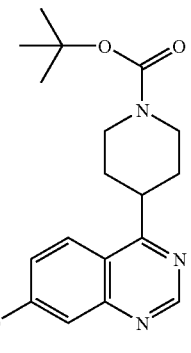

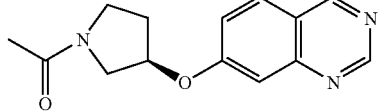

To a solution of KOt-Bu (55.1 mg, 0.47 mmol) in THF (1 mL) was added (R)-hydroxypyrrolidine (37.7 mg, 0.43 mmol), followed by 4-(7-fluoro-quinazolin-4-yl)-piperidine-1-carboxylic acid tert-butyl ester (110.3 mg, 0.33 mmol), which was prepared as described in Example 65b, in THF (1 mL). The mixture was stirred for 1 h at room temperature, quenched with $(CH_3CO)_2O$. The mixture was then partitioned between EtOAc and water. The organic extracts were washed with brine and evaporated and the residue was used for the next step reaction without further purification. LC/MS for $C_{24}H_{33}N_4O_4$ (MH+) 440.2, found 440.5.

b (R)-4-[7-(1-Acetyl-pyrrolidin-3-yloxy)-quinazolin-4-yl]-piperidine-1-carboxylic acid (4-pyrrolidin-1-yl-phenyl)-amide

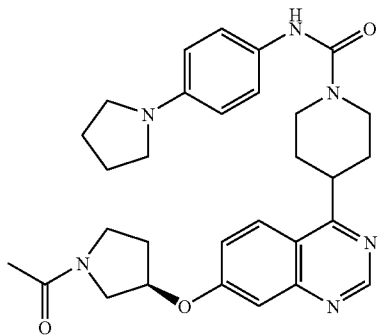

Prepared essentially as described in Example 67b, using (4-pyrrolidin-1-yl-phenyl)-carbamic acid 4-nitro-phenyl ester hydrochloride, which was prepared as described in Example 74a. $^1$H NMR (CDCl$_3$) δ 9.14 (s, 1H), 8.07 (d, J=9.67 Hz, 1H), 7.27 (m, 1H), 7.23 (m, 1H), 7.18 (d, J=8.88 Hz, 2H), 6.52 (d, J=8.87 Hz, 2H), 6.20 (br, 1H), 5.14 (m, 1H), 4.24 (m, 2H), 3.58-3.88 (5H), 3.26 (t, J=6.57 Hz, 4H), 3.12 (m, 2H), 2.11 (s, 3H), 1.92-2.12 (10H). Calcd for C$_{30}$H$_{37}$N$_6$O$_3$ (MH+) 529.3, found 529.1.

Example 155

4-[7-(4-Carboxylic acid methylamide-piperidin-1-yl)-quinazolin-4-yl]-piperidine-1-carboxylic acid (4-pyrrolidin-1-yl-phenyl)-amide

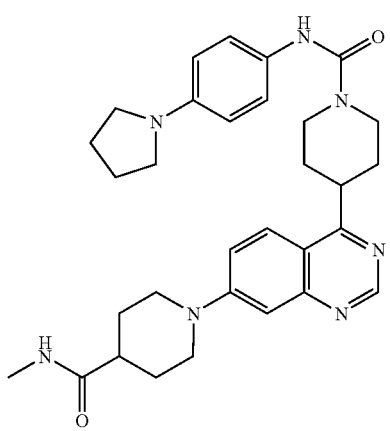

Prepared essentially as described in Example 126 using piperidine-4-carboxylic acid methylamide and (4-pyrrolidin-1-yl-phenyl)-carbamic acid 4-nitro-phenyl ester hydrochloride, which was prepared as described in Example 74a. $^1$H NMR (CDCl$_3$) δ 9.03 (s, 1H), 7.96 (d, J=9.52 Hz, 1H), 7.31 (dd, J=9.48 and 2.47 Hz, 1H), 7.18 (d, J=8.88 Hz, 2H), 7.17 (m, 1H), 6.52 (d, J=8.90 Hz, 2H), 6.19 (br, 1H), 5.54 (m, 1H), 4.25 (m, 2H), 4.03 (m, 2H), 3.60 (m, 1H), 3.26 (t, J=6.64 Hz, 4H), 3.10 (td, J=12.63 and 2.98 Hz, 2H), 3.00 (td, J=12.41 and 2.91 Hz, 2H), 2.83 (d, J=4.82 Hz, 3H), 2.35 (m, 1H), 2.11 (m, 2H), 1.84-2.02 (10H). Calcd for C$_{31}$H$_{40}$N$_7$O$_2$ (MH+) 542.3, found 542.2.

Example 156

4-{7-[2-(4-Methyl-piperazin-1-yl)-ethoxy]-quinazolin-4-yl}-piperidine-1-carboxylic acid (4-morpholin-4-yl-phenyl)-amide

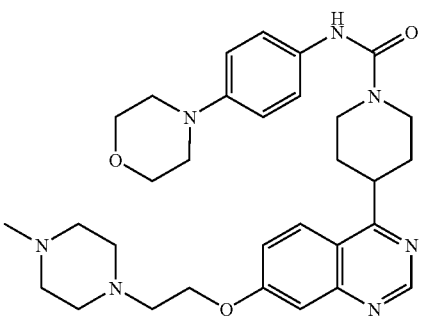

Prepared essentially as described in Example 152 using 1-methyl-piperazine and (4-morpholin-4-yl-phenyl)-carbamic acid 4-nitro-phenyl ester hydrochloride, which was prepared as described in Example 66a. $^1$H NMR (CDCl$_3$) δ 9.12 (s, 1H), 8.02 (d, J=9.23 Hz, 1H), 7.23-7.31 (3H), 6.86 (d, J=9.07 Hz, 2H), 6.28 (br, 1H), 4.27 (t, J=5.84 Hz, 2H), 4.22 (m, 2H), 3.84 (t, J=4.65 Hz, 4H), 3.66 (m, 1H), 3.06-3.18 (6H), 2.90 (t, J=5.54 Hz, 2H), 2.63 (m, 4H), 2.47 (m, 4H), 2.29 (s, 3H), 2.12 (m, 2H), 1.95 (m, 2H). Calcd for C$_{31}$H$_{42}$N$_7$O$_3$ (MH+) 560.3, found 560.1.

Example 157

4-{7-[2-(4-Methyl-piperazin-1-yl)-ethoxy]-quinazolin-4-yl}-piperidine-1-carboxylic acid (4-pyrrolidin-1-yl-phenyl)-amide

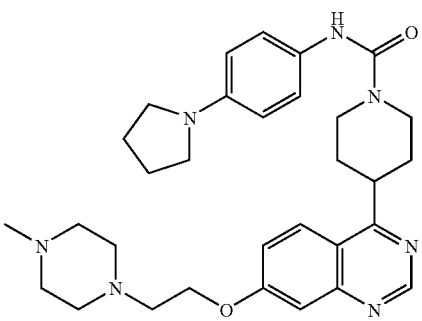

Prepared essentially as described in Example 152 using 1-methyl-piperazine $^1$H NMR (CD$_3$OD) δ 9.04 (s, 1H), 8.36 (d, J=9.34 Hz, 1H), 7.40 (dd, J=9.30 and 2.64 Hz, 1H), 7.35 (d, J=2.48 Hz, 1H), 7.13 (d, J=8.99 Hz, 2H), 6.54 (d, J=9.01 Hz, 2H), 4.35 (t, J=5.32 Hz, 4H), 3.93 (m, 1H), 3.24 (m, 6H), 3.16 (m, 2H), 2.93 (t, J=5.23 Hz, 2H), 2.58 (4H), 2.32 (s, 3H), 1.91-2.05 (10H). Calcd for C$_{31}$H$_{42}$N$_7$O$_2$ (MH+) 544.3, found 544.3.

Example 158

4-{7-[3-(4-Methyl-piperazin-1-yl)-propoxy]-quinazolin-4-yl}-piperidine-1-carboxylic acid (4-pyrrolidin-1-yl-phenyl)-amide

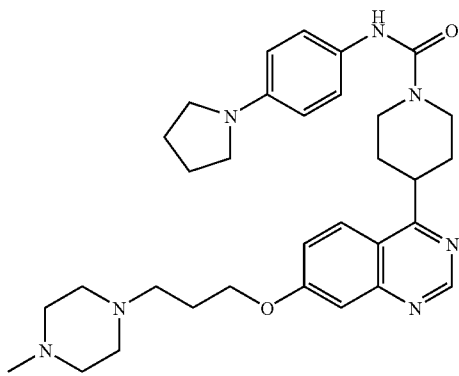

Prepared essentially as described in Example 104 using (4-pyrrolidin-1-yl-phenyl)-carbamic acid 4-nitrophenyl ester hydrochloride, prepared by the method as outlined in Example 74a, in place of (6-pyrrolidin-1-yl-pyridin-3-yl)-carbamic acid 4-nitrophenyl ester hydrochloride. $^1$H-NMR (300 MHz, CDCl$_3$): 9.12 (s, 1H), 8.04 (d, 1H), 7.35-7.12 (m, 4H), 6.52 (d, 2H), 6.26 (s, 1H), 4.31-4.11 (m, 4H), 3.71-3.57 (m, 1H), 3.31-3.00 (m, 6H), 2.74-2.46 (m, 8H), 2.39 (s, 3H), 2.20-1.82 (m, 12H). LC/MS (ESI): 558.1 (MH)$^+$.

Example 159

4-[7-(4-Methyl-piperazin-1-yl)-quinazolin-4-yl]-piperidine-1-carboxylic acid (4-pyrrolidin-1-yl-phenyl)-amide

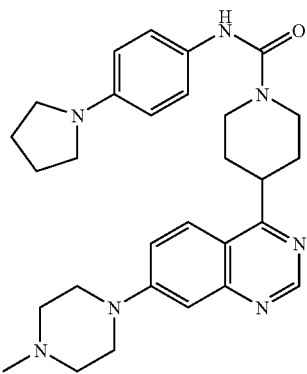

Prepared essentially as described in Example 135 using (4-pyrrolidin-1-yl-phenyl)-carbamic acid 4-nitrophenyl ester hydrochloride, prepared by the method as outlined in Example 74a, in place of (4-morpholin-4-yl-phenyl)-carbamic acid 4-nitrophenyl ester hydrochloride. $^1$H-NMR (300 MHz, CDCl$_3$): 9.03 (s, 1H), 7.97 (d, 1H), 7.36-7.13 (m, 4H), 6.51 (d, 2H), 6.29 (s, 1H), 4.24 (m, 2H), 3.66-3.54 (m, 1H), 3.51-3.41 (m, 4H), 3.30-3.16 (m, 4H), 3.14-3.01 (m, 2H), 2.65-2.55 (m, 4H), 2.37 (s, 3H), 2.18-1.85 (m, 8H). LC/MS (ESI): 500.1 (MH)$^+$.

Example 160

4-[7-(4-Methyl-piperazin-1-yl)-quinazolin-4-yl]-piperidine-1-carboxylic acid (6-pyrrolidin-1-yl-pyridin-3-yl)-amide

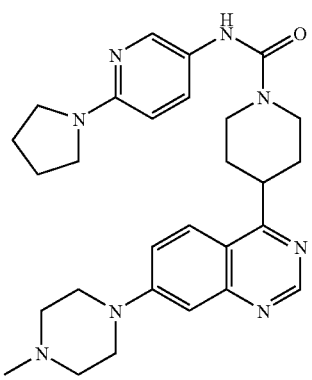

Prepared essentially as described in Example 135 using (6-pyrrolidin-1-yl-pyridin-3-yl)-carbamic acid 4-nitrophenyl ester hydrochloride, which was prepared from 6-Pyrrolidin-1-yl-pyridin-3-ylamine (WO 2002048152 A2) essentially as described in Example 74a, in place of (4-morpholin-4-yl-phenyl)-carbamic acid 4-nitrophenyl ester hydrochloride. $^1$H-NMR (300 MHz, CDCl$_3$): 9.03 (s, 1H), 8.06-7.96 (m, 2H), 7.75 (d, 1H), 7.35-7.18 (m, 2H), 6.76-6.60 (s, 1H), 6.40 (s, 1H), 4.30 (m, 2H), 3.68-3.40 (m, 11H), 2.70-2.51 (m, 4H), 2.41 (s, 3H), 2.18-1.87 (m, 8H). LC/MS (ESI): 501.1 (MH)$^+$.

Example 161

(S)-4-{7-[3-(2-Hydroxymethyl-pyrrolidin-1-yl)-propoxy]-quinazolin-4-yl}-piperidine-1-carboxylic acid (4-pyrrolidin-1-yl-phenyl)-amide

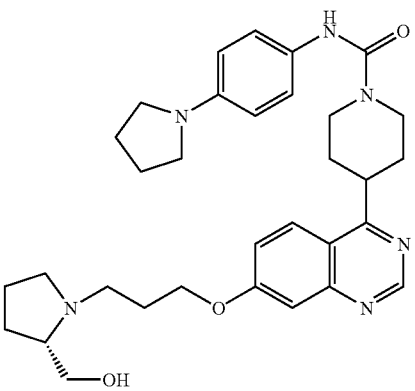

Prepared essentially as described in Example 115 using (S)-prolinol in place of 1-ethyl-piperazine and (4-pyrrolidin-1-yl-phenyl)-carbamic acid 4-nitrophenyl ester hydrochloride, prepared by the method as outlined in Example 74a, in place of (4-morpholin-4-yl-phenyl)-carbamic acid 4-nitrophenyl ester hydrochloride. ¹H-NMR (300 MHz, CDCl₃): 9.04 (s, 1H), 8.06 (d, 1H), 7.43-6.95 (m, 4H), 6.49 (d, 2H), 6.28 (s, 1H), 4.33-4.15 (m, 4H), 3.72-3.57 (m, 4H), 3.36-2.97 (m, 15H), 2.22-1.70 (m, 10H). LC/MS (ESI): 559.2 (MH)⁺.

Example 162

(S)-4-[7-(1-Acetyl-pyrrolidin-2-ylmethoxy)-quinazolin-4-yl]-piperidine-1-carboxylic acid (4-pyrrolidin-1-yl-phenyl)-amide

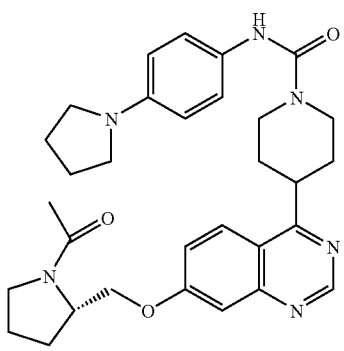

Prepared essentially as described in Example 154, using (S)-(+)-2-pyrrolidinemethanol. ¹H NMR (CDCl₃) δ 9.12 (s, 1H), 8.04 (d, J=9.35 Hz, 1H), 7.37 (d, J=2.54 Hz, 1H), 7.27 (dd, J=9.16 and 2.56 Hz, 1H), 7.18 (d, J=8.91 Hz, 2H), 6.52 (d, J=8.95 Hz, 2H), 6.23 (br, 1H), 4.52 (m, 1H), 4.34 (dd, J=9.38 and 3.09 Hz, 1H), 4.23 (m, 2H), 4.15 (dd, J=9.38 and 7.00 Hz, 1H), 3.64 (m, 1H), 3.43-3.60 (2H), 3.25 (t, J=6.63 Hz, 4H), 3.10 (m, 2H), 2.10-2.18 (2H), 2.09 (s, 3H), 1.92-2.08 (10H). Calcd for C₃₁H₃₉N₆O₃ (MH+) 543.3, found 543.2.

Example 163

4-[7-(1-Acetyl-piperidin-4-ylmethoxy)-quinazolin-4-yl]-piperidine-1-carboxylic acid (4-pyrrolidin-1-yl-phenyl)-amide

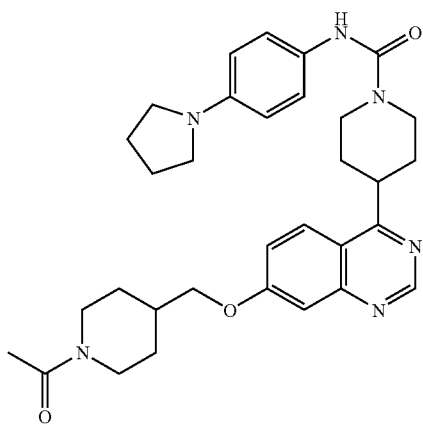

Prepared essentially as described in Example 154, using piperidin-4-yl-methanol. ¹H NMR (CD₃OD) δ 9.03 (s, 1H), 8.34 (d, J=9.42 Hz, 1H), 7.38 (dd, J=9.28 and 2.56 Hz, 1H), 7.32 (d, J=2.51 Hz, 1H), 7.13 (d, J=8.99 Hz, 2H), 6.54 (d, J=9.01 Hz, 2H), 4.59 (m, 1H), 4.33 (m, 2H), 4.08 (d, J=6.21 Hz, 2H), 4.00 (m, 1H), 3.91 (m, 1H), 3.24 (t, J=6.59 Hz, 4H), 3.11-3.20 (3H), 2.70 (td, J=12.73 and 2.58 Hz, 1H), 2.19 (m, 1H), 2.12 (s, 3H), 1.89-2.08 (10H), 1.28-1.48 (2H). Calcd for C₃₂H₄₁N₆O₃ (MH+) 557.3, found 557.3.

Example 164

4-{7-[3-(4-Methanesulfonyl-piperazin-1-yl)-propoxy]-quinazolin-4-yl}-piperidine-1-carboxylic acid (4-pyrrolidin-1-yl-phenyl)-amide

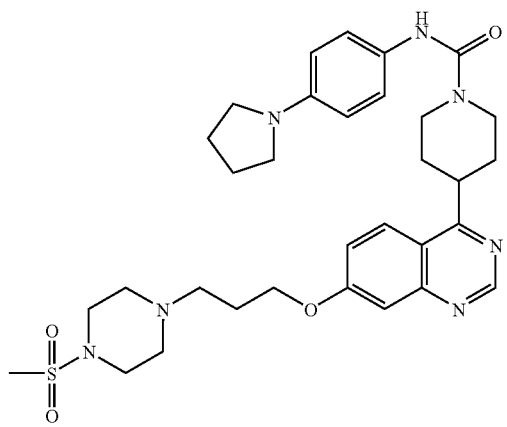

Prepared essentially as described in Example 118 using (4-pyrrolidin-1-yl-phenyl)-carbamic acid 4-nitrophenyl ester hydrochloride, prepared by the method as outlined in Example 74a, in place of (4-morpholin-4-yl-phenyl)-carbamic acid 4-nitrophenyl ester hydrochloride. ¹H-NMR (300 MHz, CDCl₃): 9.13 (s, 1H), 8.05 (d, 1H), 7.35-7.13 (m, 4H), 6.53 (d, 2H), 6.22 (s, 1H), 4.30-4.17 (m, 4H), 3.71-3.61 (m, 1H), 3.38-3.00 (m, 10H), 2.79 (s, 3H), 2.73-2.55 (m, 6H), 2.19-1.90 (m, 10H). LC/MS (ESI): 622.3 (MH)⁺.

Example 165

4-(3-{4-[1-(4-Pyrrolidin-1-yl-phenylcarbamoyl)-piperidin-4-yl]-quinazolin-7-yloxy}-propyl)-piperazine-1-carboxylic acid dimethylamide

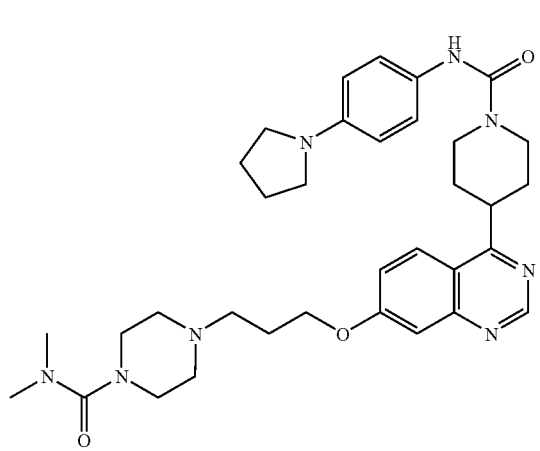

Prepared essentially as described in Example 120 using (4-pyrrolidin-1-yl-phenyl)-carbamic acid 4-nitrophenyl ester hydrochloride, prepared by the method as outlined in Example 74a, in place of (4-morpholin-4-yl-phenyl)-carbamic acid 4-nitrophenyl ester hydrochloride. $^1$H-NMR (300 MHz, CDCl$_3$): 9.12 (s, 1H), 8.05 (d, 1H), 7.37-7.13 (m, 4H), 6.52 (d, 2H), 6.25 (s, 1H), 4.34-4.16 (m, 4H), 3.71-3.59 (m, 1H), 3.40-3.04 (m, 9H), 2.89-2.79 (m, 5H), 2.68-2.41 (m, 6H), 2.21-1.88 (m, 12H). LC/MS (ESI): 615.3 (MH)$^+$.

Example 166

4-[7-(4-Acetyl-piperazin-1-yl)-quinazolin-4-yl]-piperidine-1-carboxylic acid (4-pyrrolidin-1-yl-phenyl)-amide

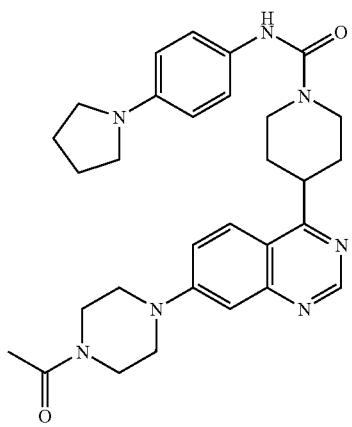

Prepared essentially as described in Example 141 using (4-pyrrolidin-1-yl-phenyl)-carbamic acid 4-nitrophenyl ester hydrochloride, prepared by the method as outlined in Example 74a, in place of (4-morpholin-4-yl-phenyl)-carbamic acid 4-nitrophenyl ester hydrochloride. $^1$H-NMR (300 MHz, CDCl$_3$): 9.05 (s, 1H), 8.02 (d, 1H), 7.35-7.11 (m, 4H), 6.90-6.00 (bm, 3H), 4.25 (d, 2H), 3.86-3.78 (m, 2H), 3.72-3.56 (m, 3H), 3.5-3.40 (m, 4H), 3.20-3.00 (m, 4H), 2.20-2.04 (m, 5H), 2.03-1.77 (m, 8H). LC/MS (ESI): 528.2 (MH)$^+$.

Example 167

4-[7-(4-Methanesulfonyl-piperazin-1-yl)-quinazolin-4-yl]-piperidine-1-carboxylic acid (4-pyrrolidin-1-yl-phenyl)-amide

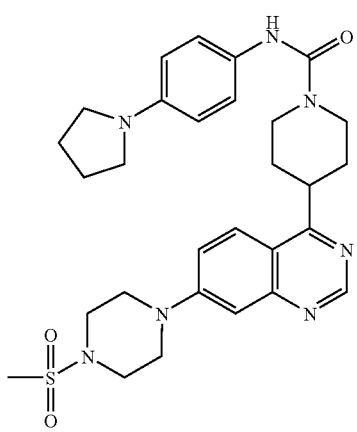

Prepared essentially as described in Example 142 using (4-pyrrolidin-1-yl-phenyl)-carbamic acid 4-nitrophenyl ester hydrochloride, prepared by the method as outlined in Example 74a, in place of (4-morpholin-4-yl-phenyl)-carbamic acid 4-nitrophenyl ester hydrochloride. $^1$H-NMR (300 MHz, CDCl$_3$): 9.08 (s, 1H), 8.02 (d, 1H), 7.37-7.11 (m, 4H), 6.90-6.00 (bm, 3H), 4.25 (d, 2H), 3.68-2.92 (bm, 13H), 2.84 (s, 3H), 2.18-1.87 (m, 10H). LC/MS (ESI): 564.2 (MH)$^+$.

Example 168

4-{4-[1-(4-Pyrrolidin-1-yl-phenylcarbamoyl)-piperidin-4-yl]-quinazolin-7-yl}-piperazine-1-carboxylic acid dimethylamide

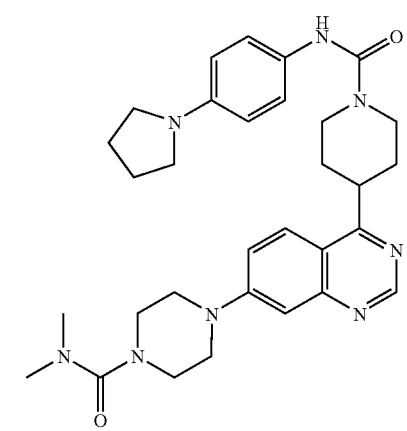

Prepared essentially as described in Example 143 using (4-pyrrolidin-1-yl-phenyl)-carbamic acid 4-nitrophenyl ester hydrochloride, prepared by the method as outlined in Example 74a, in place of (4-morpholin-4-yl-phenyl)-carbamic acid 4-nitrophenyl ester hydrochloride. $^1$H-NMR (300 MHz, CDCl$_3$): 9.04 (s, 1H), 7.99 (d, 1H), 7.35-7.12 (m, 4H), 6.60-6.25 (bm, 3H), 4.24 (d, 2H), 3.65-3.55 (m, 1H), 3.50-3.37 (m, 8H), 3.32-3.01 (m, 4H), 2.88 (s, 6H), 2.16-1.80 (m, 10H). LC/MS (ESI): 557.2 (MH)$^+$.

Example 169

4-[7-(2-Hydroxy-ethoxy)-quinazolin-4-yl]-piperidine-1-carboxylic acid (4-pyrrolidin-1-yl-phenyl)-amide

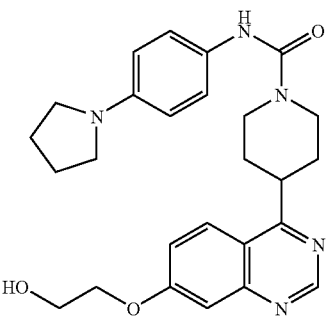

a. 4-[7-(2-Hydroxy-ethoxy)-quinazolin-4-yl]-piperidine-1-carboxylic acid tert-butyl ester

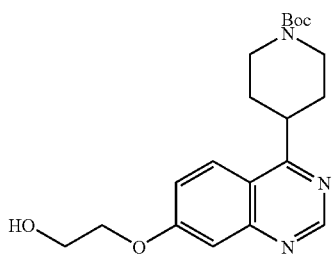

KOtBu (1.17 g, 10.4 mmol) was added to ethylene glycol (10 mL, 179 mmol) to provide a homogeneous solution. 4-(7-fluoro-quinazolin-4-yl)-piperidine-1-carboxylic acid tert-butyl ester (2.61 g, 7.89 mmol), as prepared in Example 65b, was added, and the opaque white slurry was stirred at rt for 3.5 hr. DMSO (5 mL) was then added, and the mixture stirred at 110° C. for 20 min at which point it became a homogeneous solution. The reaction was then stirred at rt overnight, at which point it became a translucent white slurry. The mixture was then diluted with 0.1M NaHCO₃ and extracted with EtOAc (2×50 mL). The combined organic layers were washed with 0.1M NaHCO₃ (1×100 mL), dried (Na₂SO₄), concentrated, and dissolved in ~15 mL toluene. The title compound crystallized upon standing at rt, was filtered, and the crystalline filter cake washed with toluene (1×10 mL). The filter cake was dried under high vacuum at 100° C. to afford the title compound as a white powder (2.38 g, 81%). LC/MS (ESI): calc mass 373.2, found 374.2.

b. 4-[7-(2-Hydroxy-ethoxy)-quinazolin-4-yl]-piperidine-1-carboxylic acid (4-pyrrolidin-1-yl-phenyl)-amide

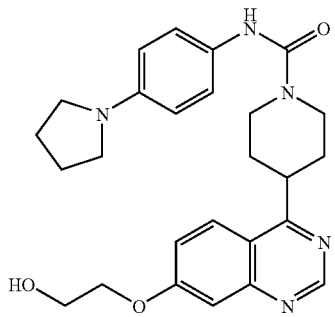

The title compound was prepared essentially as described for Example 10b, using (4-pyrrolidin-1-yl-phenyl)-carbamic acid 4-nitro-phenyl ester hydrochloride, prepared as described in Example 74a. The title compound was purified by filtration of the crude reaction slurry. The resulting filter cake was taken up in 95:5 DCM/MeOH and washed sequentially with 2M K₂CO₃ and water. The hazy organic layer was then diluted with DCM and MeOH until a clear solution resulted, and was then dried (Na₂SO₄) and concentrated to afford the title compound (6.3 mg, 12%). ¹H-NMR (400 MHz, 95:5 CDCl₃/CD₃OD) δ 9.10 (s, 1H), 8.11 (d, 1H), 7.36-7.30 (m, 2H), 7.17 (m, 2H), 6.53 (m, 2H), 4.28 (m, 4H), 4.03 (t, 2H), 3.70 (tt, 1H), 3.26 (m, 4H), 3.11 (td, 2H), 2.16-1.92 (m, 8H). LC/MS (ESI) calcd mass 461.2, found 462.3 (MH)⁺.

Example 170

4-[7-(1-Acetyl-azetidin-3-yloxy)-quinazolin-4-yl]-piperidine-1-carboxylic acid (4-pyrrolidin-1-yl-phenyl)-amide

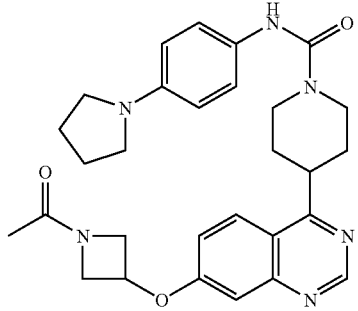

a. 4-[7-(Azetidin-3-yloxy)-quinazolin-4-yl]-piperidine-1-carboxylic acid tert-butyl ester

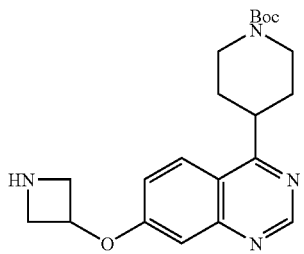

A mixture of Azetidin-3-ol hydrochloride (Oakwood) (461 mg, 4.21 mmol), KOtBu (1.02 g, 9.11 mmol), and dry DMSO (4.2 mL) was stirred at rt for 30 min until a translucent solution resulted. Then 4-(7-fluoro-quinazolin-4-yl)-piperidine-1-carboxylic acid tert-butyl ester (1.46 g, 4.41 mmol), as prepared in Example 65b, was added, and the resulting opaque orange mixture (no visible precipitate) was stirred at rt for 3.5 hr. The reaction was then shaken with water (40 mL) and extracted with DCM (1×20 mL) and 9:1 DCM/MeOH (1×20 mL). The combined organic layers were washed with 0.2 M K₂CO₃ (3×20 mL), dried (Na2SO4), and concentrated to give 1.715 g of the title compound as an off-white solid ("106%" crude yield). LC/MS (ESI): calcd mass 384.2, found 385.3 (MH)⁺.

b. 4-[7-(1-Acetyl-azetidin-3-yloxy)-quinazolin-4-yl]-piperidine-1-carboxylic acid tert-butyl ester

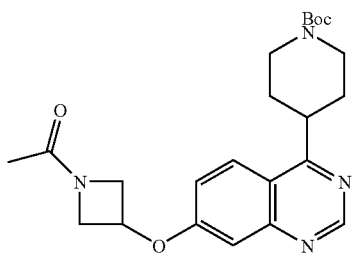

Acetic anhydride (66 µL, 703 µmol) was added dropwise with stirring at rt to a mixture of 4-[7-(Azetidin-3-yloxy)-quinazolin-4-yl]-piperidine-1-carboxylic acid tert-butyl ester (180 mg, 469 µmol), as prepared in the previous step, in DCM (1.0 mL). The resulting homogeneous yellow solution was stirred overnight, and was then partitioned with DCM (3 mL) and 1M NaHCO$_3$ (1×4 mL). The organic layer was dried (Na$_2$SO$_4$), concentrated, and purified by silica flash chromatography (8:2 DCM/acetone/3% DMEA eluent) to afford the title compound as a white crystalline film (88.3 mg, 44% over two steps). LC/MS (ESI): calcd mass 426.2, found 426.9 (MH)$^+$.

c. 4-[7-(1-Acetyl-azetidin-3-yloxy)-quinazolin-4-yl]-piperidine-1-carboxylic acid (4-pyrrolidin-1-yl-phenyl)-amide

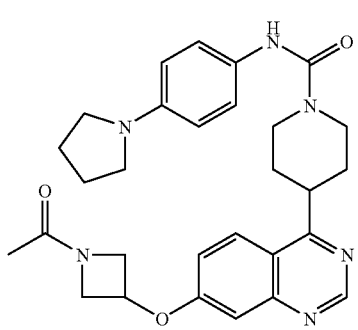

The title compound was prepared from 4-[7-(1-Acetyl-azetidin-3-yloxy)-quinazolin-4-yl]-piperidine-1-carboxylic acid tert-butyl ester (44.1 mg, 103 µmol), as synthesized in the previous step, using (4-pyrrolidin-1-yl-phenyl)-carbamic acid 4-nitro-phenyl ester hydrochloride, prepared in Example 74a, and using essentially the reaction and work-up procedure described in Example 110b. The title compound was purified by silica flash cartridge chromatography (9:1 DCM/acetone/3% DMEA eluent). The combined fractions (10 mL) were washed with 1M NaHCO$_3$ (1×5 mL) to remove a DMEA$^+$ impurity, and were dried (Na$_2$SO$_4$) and concentrated to provide the title compound (13.8 mg, 26%). $^1$H-NMR (400 MHz, 95:5 CDCl$_3$/CD$_3$OD) δ 9.13 (s, 1H), 8.16 (d, 1H), 7.31 (dd, 1H), 7.17 (m, 2H), 7.03 (d, 1H), 6.54 (m, 2H), 5.16 (m, 1H), 4.67 (ddd, 1H), 4.51 (dd, 1H), 4.32-4.23 (m, 3H), 4.15 (dd, 1H), 3.70 (tt, 1H), 3.26 (m, 4H), 3.11 (tt, 2H), 2.17-1.97 (m, 8H), 1.94 (s, 3H). LC/MS (ESI): calcd mass 514.3, found 515.3 (MH)$^+$.

Example 171

4-[7-(1-Methanesulfonyl-azetidin-3-yloxy)-quinazolin-4-yl]-piperidine-1-carboxylic acid (4-pyrrolidin-1-yl-phenyl)-amide

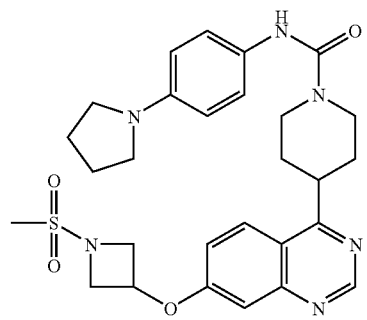

The title compound was prepared essentially as described for Example 170b-c, using methanesulfonyl chloride and 1.5 equivalents of TEA in place of acetic anhydride. $^1$H-NMR (400 MHz, 95:5 CDCl$_3$/CD$_3$OD) δ 9.13 (s, 1H), 8.15 (d, 1H), 7.31 (dd, 1H), 7.17 (m, 2H), 7.04 (d, 1H), 6.53 (m, 2H), 5.15 (m, 1H), 4.43 (m, 2H), 4.27 (m, 2H), 4.15 (m, 2H), 3.70 (tt, 1H), 3.26 (m, 4H), 3.11 (td, 2H), 2.97 (s, 3H), 2.16-2.04 (m, 2H), 2.03-1.93 (m, 6H). LC/MS (ESI): calcd mass 550.2, found 551.2 (MH)$^+$.

Example 172

4-[7-(2-Morpholin-4-yl-2-oxo-ethoxy)-quinazolin-4-yl]-piperidine-1-carboxylic acid (4-pyrrolidin-1-yl-phenyl)-amide

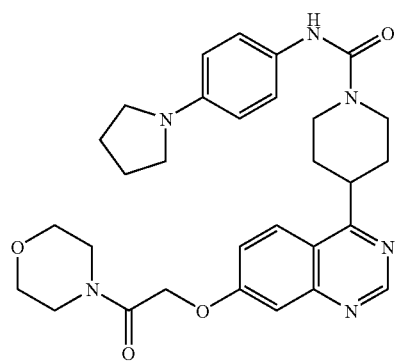

a. 4-[7-(2-Morpholin-4-yl-2-oxo-ethoxy)-quinazolin-4-yl]-piperidine-1-carboxylic acid tert-butyl ester

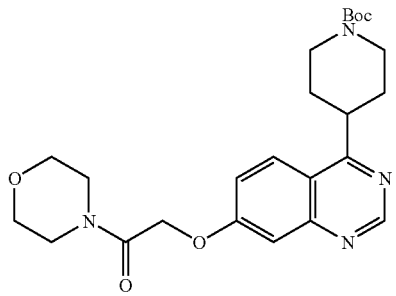

A mixture of morpholine (107.4 mg, 1.23 mmol) and methyl glycolate (77.5 mg, 860 μmol) was stirred at 150° C. for 3 hr. The resulting homogeneous clear amber oil was taken up in toluene (2×2 mL) with repeated rotary evaporation to remove methanol. The residue was taken up in dry THF (860 μL) and KOtBu was added (113 mg, 1.01 mmol). The mixture was stirred at 100° C. for 5-10 min until a brown slurry formed with no visible chunks. The mixture was then allowed to cool to rt, 4-(7-fluoro-quinazolin-4-yl)-piperidine-1-carboxylic acid tert-butyl ester (302 mg, 912 μmol), as prepared in Example 65b, was added, and the resulting nearly homogeneous reddish-brown solution was stirred at rt for 1 hr, at which point the reaction solidified into a paste. The reaction was taken up in DCM (4 mL) and washed with 1M NaHCO$_3$ (1×2 mL) and 1M NaH$_2$PO$_4$ (1×2 mL), and the organic layer was dried (Na$_2$SO$_4$) and concentrated. The residue was purified by silica flash chromatography (9:1 DCM/acetone→8:2→8:2 DCM/acetone/3% DMEA eluent) to provide the title compound as a pale yellow oil (94.8 mg, 24% over two steps). LC/MS (ESI): calcd mass 456.2, found 457.3 (MH)$^+$.

b. 4-[7-(2-Morpholin-4-yl-2-oxo-ethoxy)-quinazolin-4-yl]-piperidine-1-carboxylic acid (4-pyrrolidin-1-yl-phenyl)-amide

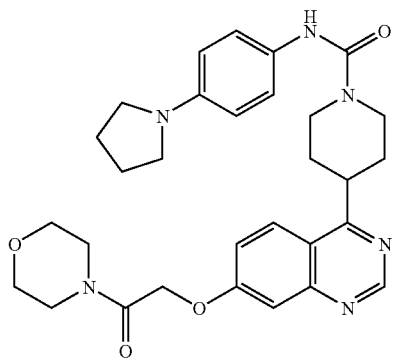

The title compound was prepared from 4-[7-(2-Morpholin-4-yl-2-oxo-ethoxy)-quinazolin-4-yl]-piperidine-1-carboxylic acid tert-butyl ester as synthesized in the previous step, using (4-pyrrolidin-1-yl-phenyl)-carbamic acid 4-nitro-phenyl ester hydrochloride (preparation given in Example 74a), essentially as described in Example 170c. $^1$H-NMR (400 MHz, CDCl$_3$) δ 9.14 (s, 1H), 8.10 (d, 1H), 7.38 (dd, 1H), 7.29 (d, 1H), 7.18 (m, 2H), 6.51 (m, 2H), 6.34 (s, 1H), 4.88 (s, 2H), 4.26 (m, 2H), 3.75-3.61 (m, 7H), 3.55 (m, 2H), 3.25 (m, 4H), 3.10 (td, 2H), 2.16-2.04 (m, 2H), 2.02-1.90 (m, 6H). LC/MS (ESI): calcd mass 544.3, found 545.3 (MH)$^+$.

Example 173

4-(7-Azetidin-1-yl-quinazolin-4-yl)-piperidine-1-carboxylic acid (4-pyrrolidin-1-yl-phenyl)-amide

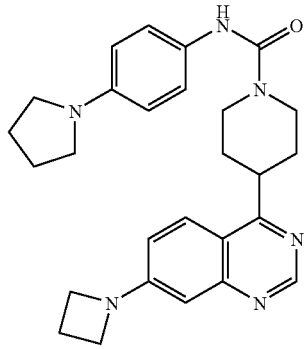

Prepared essentially as Example 126 using azetidine and (4-pyrrolidin-1-yl-phenyl)-carbamic acid 4-nitro-phenyl ester hydrochloride, which was prepared as described in Example 74a. $^1$H NMR (CD$_3$OD) δ 8.80 (s, 1H), 8.20 (d, J=9.30 Hz, 1H), 7.13 (d, J=8.98 Hz, 2H), 6.95 (dd, J=9.20 and 2.36 Hz, 1H), 6.56 (d, J=2.34 Hz, 1H), 6.54 (d, J=9.00 Hz, 2H), 4.32 (m, 2H), 4.13 (t, J=7.41 Hz, 4H), 3.82 (m, 1H), 3.24 (t, J=6.69 Hz, 4H), 3.12 (td, J=13.10 and 2.99 Hz, 2H), 2.50 (m, 2H), 1.96-2.07 (6H), 1.88 (m, 2H). Calcd for C$_{27}$H$_{33}$N$_6$O (MH+) 457.3, found 457.3.

Example 174

4-[7-(Pyridin-3-yloxy)-quinazolin-4-yl]-piperidine-1-carboxylic acid (4-pyrrolidin-1-yl-phenyl)-amide

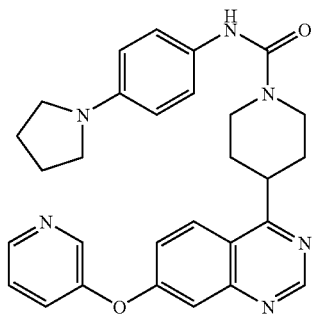

Prepared essentially as Example 67 using pyridin-3-ol and (4-pyrrolidin-1-yl-phenyl)-carbamic acid 4-nitro-phenyl ester hydrochloride, which was prepared as described in Example 74a. $^1$H NMR (CDCl$_3$) δ 9.14 (s, 1H), 8.53-8.54 (2H), 8.19 (d, J=9.22 Hz, 1H), 7.50 (ddd, J=8.34, 2.78, and 1.44 Hz, 1H), 7.44 (dd, J=9.19 and 2.56 Hz, 1H), 7.40 (ddd, J=8.34, 4.73 and 0.64 Hz, 1H), 7.31 (d, J=2.53 Hz, 1H), 7.17 (d, J=8.91 Hz, 2H), 6.51 (d, J=8.95 Hz, 2H), 6.25 (br, 1H), 4.23 (m, 2H), 3.70 (m, 1H), 3.25 (t, J=6.61 Hz, 4H), 3.12 (td, J=13.18 and 2.66 Hz, 2H), 2.13 (m, 2H), 1.94-2.01 (6H). Calcd for C$_{29}$H$_{31}$N$_6$O$_2$ (MH+) 495.2, found 495.2.

Example 175

4-[7-(2-Hydroxy-ethylamino)-quinazolin-4-yl]-piperidine-1-carboxylic acid (4-pyrrolidin-1-yl-phenyl)-amide

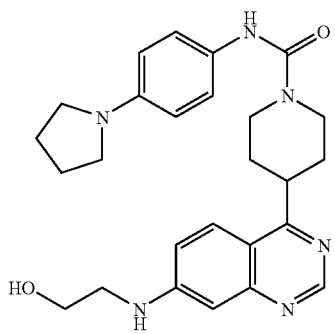

Prepared essentially as Example 126 using 2-amino-ethanol and (4-pyrrolidin-1-yl-phenyl)-carbamic acid 4-nitro-phenyl ester hydrochloride, which was prepared as described in Example 74a. $^1$H NMR (CD$_3$OD) δ 8.78 (s, 1H), 8.10 (d, J=9.42 Hz, 1H), 7.15 (dd, J=9.29 and 2.38 Hz, 1H), 7.13 (d, J=8.97 Hz, 2H), 6.77 (d, J=2.36 Hz, 1H), 4.32 (m, 2H), 3.81 (m, 1H), 3.79 (t, J=5.77 Hz, 2H), 3.40 (t, J=5.77 Hz, 2H), 3.24 (t, J=6.62 Hz, 4H), 3.12 (td, J=13.22 and 2.52 Hz, 2H), 1.95-2.06 (6H), 1.87 9 m, 2H). Calcd for C$_{26}$H$_{33}$N$_6$O$_2$ (MH+) 461.3, found 461.3.

Example 176

4-[7-(2-Oxo-oxazolidin-3-yl)-quinazolin-4-yl]-piperidine-1-carboxylic acid (4-pyrrolidin-1-yl-phenyl)-amide

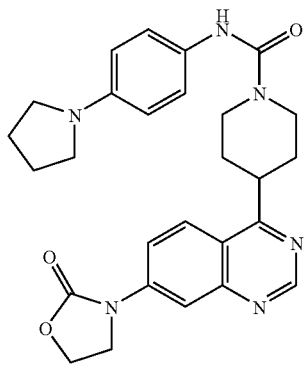

a. 4-[7-(2-Oxo-oxazolidin-3-yl)-quinazolin-4-yl]-piperidine-1-carboxylic acid tert-butyl ester

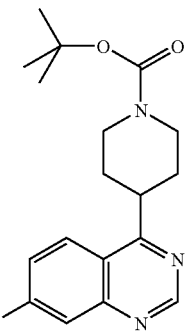

To a solution of 4-(7-fluoro-quinazolin-4-yl)-piperidine-1-carboxylic acid tert-butyl ester (139.6 mg, 0.42 mmol), which was prepared as described in Example 65b, in DMSO (0.8 mL) was added ethanolamine (256.2 mg, 4.2 mmol). The mixture was stirred at 120° C. overnight and subsequently partitioned between EtOAc and water. The combined organic extracts were washed with brine, dried over Na$_2$SO$_4$ and evaporated. The residue was re-dissolved in CH$_2$Cl$_2$ (4 mL), treated with COCl$_2$ (1 mL of 1M solution in toluene) and TEA (200 mg). The mixture was partitioned between CH$_2$Cl$_2$ and water. The CH$_2$Cl$_2$ extracts were evaporated and the residue was purified by flash column chromatography on silica gel (hexanes/EtOAc 1:1, v/v) to afford the desired product. LC/MS for C$_{21}$H$_{27}$N$_4$O$_4$ (MH+) 399.2, found 399.2.

b. 4-[7-(2-Oxo-oxazolidin-3-yl)-quinazolin-4-yl]-piperidine-1-carboxylic acid (4-pyrrolidin-1-yl-phenyl)-amide

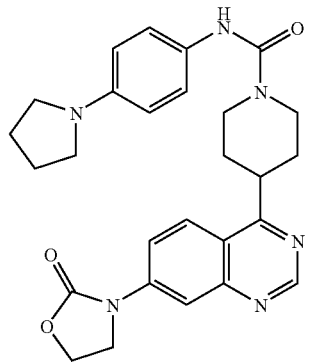

Prepared essentially as Example 67b using (4-pyrrolidin-1-yl-phenyl)-carbamic acid 4-nitro-phenyl ester hydrochloride, which was prepared as described in Example 74a. $^1$H NMR (CDCl$_3$) δ 9.19 (s, 1H), 8.60 (dd, J=9.38 and 2.38 Hz, 1H), 8.17 (d, J=9.45 Hz, 1H), 7.54 (d, J=2.35 Hz, 1H), 7.18 (m, 2H), 6.53 (m, 2H), 6.22 (br, 1H), 4.59 (t, J=7.99 Hz, 2H), 4.26 (m, 2H), 4.21 (t, J=8.01 Hz, 2H), 3.72 (m, 1H), 3.26 (m, 4H), 3.13 (t, J=12.39 Hz, 2H), 2.10 (td, J=12.16 and 3.85 Hz, 2H), 1.99 (m, 6H). Calcd for $C_{27}H_{31}N_6O_3$ (MH+) 487.3, found 487.3.

Example 177

(R)-4-[7-(1-Methanesulfonyl-pyrrolidin-3-yloxy)-quinazolin-4-yl]-piperidine-1-carboxylic acid (4-pyrrolidin-1-yl-phenyl)-amide

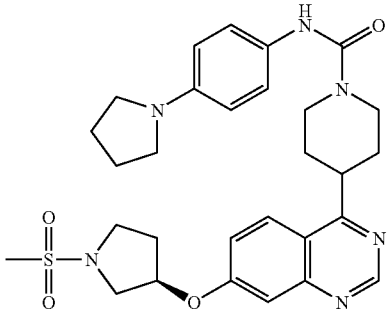

Prepared essentially as Example 154 with the sole exception that the intermediate generated was quenched with MsCl. $^1$H NMR (CDCl$_3$) δ 9.16 (s, 1H), 8.10 (d, J=9.33 Hz, 1H), 7.26 (m, 1H), 7.21 (dd, J=9.15 and 2.60 Hz, 1H), 7.18 (m, 2H), 6.52 (m, 2H), 6.20 (br, 1H), 5.14 (m, 1H), 4.25 (m, 2H), 3.72-3.78 (3H), 3.61-3.72 (2H), 3.52 (td, J=10.45 and 7.09 Hz, 2H), 3.10-3.30 (4H), 2.87 (s, 3H), 2.28-2.46 (2H), 2.13 (m, 2H), 1.98 (m, 6H). Calcd for $C_{29}H_{37}N_6O_4S$ (MH+) 565.3, found 565.3.

Example 178

4-[7-(2-Oxo-imidazolidin-1-yl)-quinazolin-4-yl]-piperidine-1-carboxylic acid (4-pyrrolidin-1-yl-phenyl)-amide

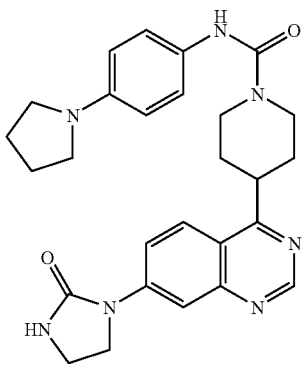

a. 4-[7-(2-Oxo-imidazolidin-1-yl)-quinazolin-4-yl]-piperidine-1-carboxylic acid tert-butyl ester

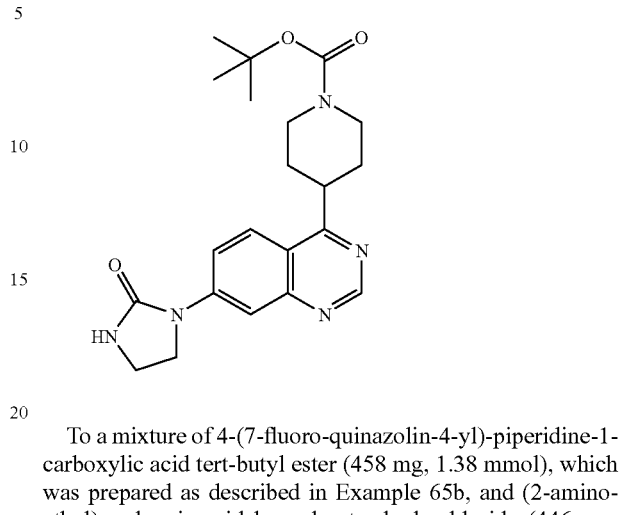

To a mixture of 4-(7-fluoro-quinazolin-4-yl)-piperidine-1-carboxylic acid tert-butyl ester (458 mg, 1.38 mmol), which was prepared as described in Example 65b, and (2-aminoethyl)-carbamic acid benzyl ester hydrochloride (446 mg, 1.93 mmol) in DMSO (1.0 mL) was added K$_2$CO$_3$ (1.52 g, 11.04 mmol). The mixture was stirred at 115° C. overnight and subsequently partitioned between EtOAc and water. The combined organic extracts were washed with brine, dried over Na$_2$SO$_4$ and evaporated. The residue was purified by flash column chromatography on silica gel (EtOAc as eluent) to afford the desired product as a white solid (400 mg, 73%). $^1$H NMR (CDCl$_3$) δ 9.13 (s, 1H), 8.69 (dd, J=9.40 and 2.35 Hz, 1H), 8.08 (d, J=9.53 Hz, 1H), 7.42 (d, J=2.33 Hz, 1H), 5.25 (br, 1H), 4.31 (m, 2H), 4.09 (t, J=8.21 Hz, 2H), 3.69 (t, J=8.14 Hz, 2H), 3.63 (m, 1H), 2.95 (m, 2H), 1.77-2.04 (4H), 1.48 (s, 9H). Calcd for $C_{21}H_{28}N_5O_3$ (MH+) 398.3, found 398.3.

b. 4-[7-(2-Oxo-imidazolidin-1-yl)-quinazolin-4-yl]-piperidine-1-carboxylic acid (4-pyrrolidin-1-yl-phenyl)-amide

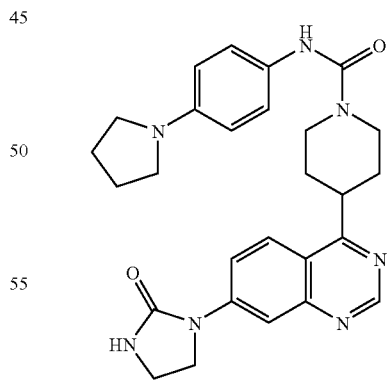

Prepared essentially as Example 67b using (4-pyrrolidin-1-yl-phenyl)-carbamic acid 4-nitro-phenyl ester hydrochloride, which was prepared as described in Example 74a. $^1$H NMR (CDCl$_3$) δ 9.13 (s, 1H), 8.71 (dd, J=9.40 and 2.33 Hz, 1H), 8.09 (d, J=9.53 Hz, 1H), 7.41 (d, J=2.32 Hz, 1H), 7.17 (d, J=8.83 Hz, 2H), 6.51 (d, J=8.47 Hz, 2H), 6.28 (br, 1H), 5.10 (br, 1H), 4.25 (m, 2H), 4.07 (t, J=6.17 Hz, 2H), 3.71 (m, 1H), 3.67 (m, 2H), 3.24 (m, 4H), 3.11 (td, J=12.75 and 2.13 Hz, 2H), 1.93-2.13 (8H). Calcd for C$_{27}$H$_{32}$N$_7$O$_2$ (MH+) 486.3, found 486.3.

Example 179

4-(7-Pyrrolidin-1-yl-quinazolin-4-yl)-piperidine-1-carboxylic acid (4-pyrrolidin-1-yl-phenyl)-amide

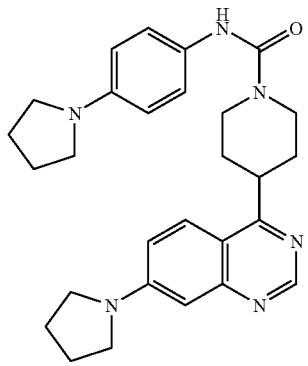

Prepared essentially as described in Example 159 using pyrrolidine in place of 1-methyl-piperazine. $^1$H-NMR (300 MHz, CDCl$_3$): 8.95 (s, 1H), 7.94 (d, 1H), 7.17 (d, 2H), 7.01 (m, 1H), 6.83 (d, 1H), 6.51 (d, 2H), 6.28 (s, 1H), 4.24 (d, 2H), 3.65-3.52 (m, 1H), 3.49-3.39 (m, 4H), 3.28-3.20 (m, 4H), 3.13-3.02 (m, 2H), 2.16-1.78 (m, 12H). LC/MS (ESI): 471.3 (MH)$^+$.

Example 180

4-(7-Imidazol-1-yl-quinazolin-4-yl)-piperidine-1-carboxylic acid (4-pyrrolidin-1-yl-phenyl)-amide

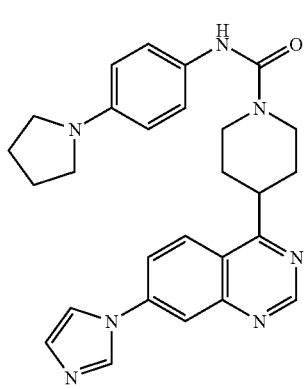

Prepared essentially as described in Example 159 using imidazole in place of 1-methyl-piperazine. $^1$H-NMR (300 MHz, CDCl$_3$): 9.28 (s, 1H), 8.32 (d, 1H), 8.11-8.04 (m, 2H), 7.74 (m, 1H), 7.49 (m, 1H), 7.30 (m, 1H), 7.18 (d, 2H), 6.52 (d, 2H), 6.26 (s, 1H), 4.28 (d, 2H), 3.80-3.69 (m, 1H), 3.29-3.10 (m, 6H), 2.22-1.90 (m, 8H). LC/MS (ESI): 468.3 (MH)$^+$.

Example 181

4-(7-Morpholin-4-yl-quinazolin-4-yl)-piperidine-1-carboxylic acid (4-pyrrolidin-1-yl-phenyl)-amide

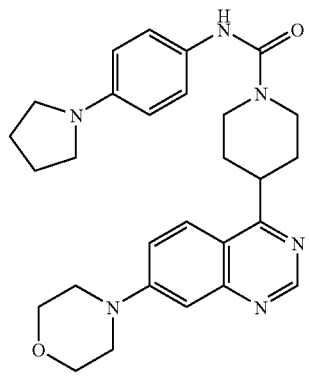

Prepared essentially as described in Example 159 using morpholine in place of 1-methyl-piperazine. $^1$H-NMR (300 MHz, CDCl$_3$): 9.05 (s, 1H), 8.00 (d, 1H), 7.34-7.14 (m, 4H), 6.51 (d, 2H), 6.29 (s, 1H), 4.24 (d, 2H), 3.93-3.87 (m, 4H), 3.66-3.56 (m, 1H), 3.43-3.36 (m, 4H), 3.28-3.19 (m, 4H), 3.14-3.04 (m, 2H), 2.17-1.89 (m, 8H). LC/MS (ESI): 487.3 (MH)$^+$.

Example 182

4-(7-Thiomorpholin-4-yl-quinazolin-4-yl)-piperidine-1-carboxylic acid (4-pyrrolidin-1-yl-phenyl)-amide

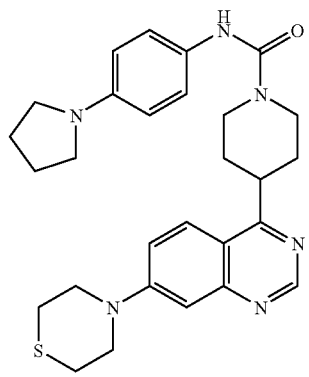

Prepared essentially as described in Example 159 using thiomorpholine in place of 1-methyl-piperazine. $^1$H-NMR (300 MHz, CDCl$_3$): 9.03 (s, 1H), 7.99 (d, 1H), 7.28-7.14 (m, 4H), 6.52 (d, 2H), 6.22 (s, 1H), 4.25 (d, 2H), 3.92-3.85 (m, 4H), 3.65-3.55 (m, 1H), 3.30-3.04 (m, 6H), 2.77-2.72 (m, 4H), 2.18-1.88 (m, 8H). LC/MS (ESI): 503.3 (MH)$^+$.

Example 183

4-[7-(3-Oxo-piperazin-1-yl)-quinazolin-4-yl]-piperidine-1-carboxylic acid (4-pyrrolidin-1-yl-phenyl)-amide

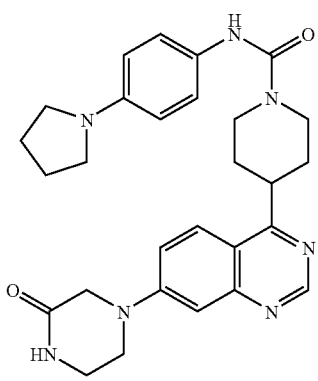

Prepared essentially as described in Example 159 using piperazin-2-one in place of 1-methyl-piperazine. $^1$H-NMR (300 MHz, CDCl$_3$): 9.07 (s, 1H), 8.05 (d, 1H), 7.30-7.15 (m, 4H), 6.55-6.46 (m, 3H), 6.25 (s, 1H), 4.29-4.10 (m, 4H), 3.78-3.55 (m, 5H), 3.29-3.05 (m, 6H), 2.18-1.89 (m, 8H). LC/MS (ESI): 500.2 (MH)$^+$.

Example 184

4-[7-(4-Methyl-3-oxo-piperazin-1-yl)-quinazolin-4-yl]-piperidine-1-carboxylic acid (4-pyrrolidin-1-yl-phenyl)-amide

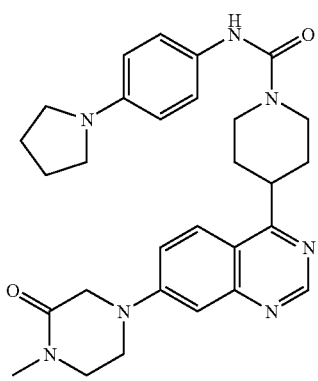

Prepared essentially as described in Example 159 using 1-methyl-piperazin-2-one in place of 1-methyl-piperazine. $^1$H-NMR (300 MHz, CDCl$_3$): 9.07 (s, 1H), 8.05 (d, 1H), 7.27-7.04 (m, 4H), 6.52 (d, 2H), 6.22 (s, 1H), 4.25 (d, 2H), 4.12 (s, 2H), 3.76-3.70 (m, 2H), 3.68-3.53 (m, 4H), 3.31-3.19 (m, 4H), 3.17-3.04 (m, 4H), 2.18-1.89 (m, 8H). LC/MS (ESI): 514.3 (MH)$^+$.

Example 185

4-{7-[4-(2-Hydroxy-ethyl)-piperazin-1-yl]-quinazolin-4-yl}-piperidine-1-carboxylic acid (4-pyrrolidin-1-yl-phenyl)-amide

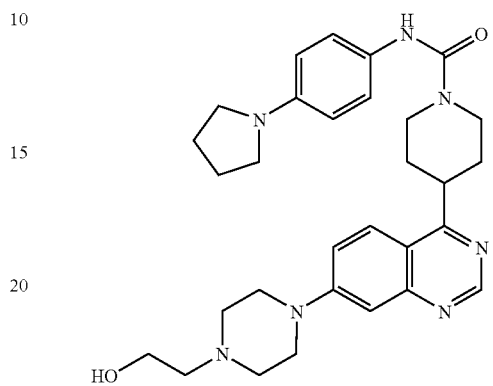

Prepared essentially as described in Example 159 using 1-(2-hydroxyethyl)-piperazine in place of 1-methyl-piperazine. $^1$H-NMR (300 MHz, CDCl$_3$): 9.03 (s, 1H), 7.98 (d, 1H), 7.32 (m, 1H), 7.20-7.14 (m, 3H), 6.51 (d, 2H), 6.31 (s, 1H), 4.24 (d, 2H), 3.71-3.65 (m, 2H), 3.65-3.55 (m, 1H), 3.49-3.42 (m, 4H), 3.28-3.20 (m, 4H), 3.13-3.03 (m, 2H), 2.74-2.65 (m, 4H), 2.65-2.59 (m, 2H), 2.16-1.81 (m, 9H). LC/MS (ESI): 530.3 (MH)$^+$.

Example 186

4-{7-[4-(2-Methoxy-ethyl)-piperazin-1-yl]-quinazolin-4-yl}-piperidine-1-carboxylic acid (4-pyrrolidin-1-yl-phenyl)-amide

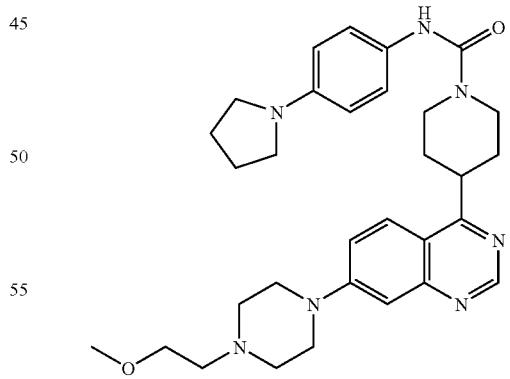

Prepared essentially as described in Example 159 using 1-(2-methoxyethyl)-piperazine in place of 1-methyl-piperazine. $^1$H-NMR (300 MHz, CDCl$_3$): 9.03 (s, 1H), 7.97 (d, 1H), 7.31 (m, 1H), 7.20-7.14 (m, 3H), 6.51 (d, 2H), 6.24 (s, 1H), 4.24 (d, 2H), 3.65-3.53 (m, 3H), 3.51-3.45 (m, 4H), 3.38 (s, 3H), 3.28-3.21 (m, 4H), 3.14-3.04 (m, 2H), 2.72-2.62 (m, 6H), 2.16-1.88 (m, 8H). LC/MS (ESI): 544.3 (MH)$^+$.

Example 187

4-[7-(4-Ethyl-piperazin-1-yl)-quinazolin-4-yl]-piperidine-1-carboxylic acid (4-pyrrolidin-1-yl-phenyl)-amide

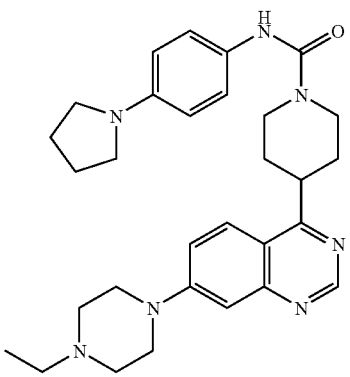

Prepared essentially as described in Example 159 using 1-ethyl-piperazine in place of 1-methyl-piperazine. $^1$H-NMR (300 MHz, CDCl$_3$): 9.03 (s, 1H), 7.97 (d, 1H), 7.32 (m, 1H), 7.21-7.14 (m, 3H), 6.51 (d, 2H), 6.27 (s, 1H), 4.24 (d, 2H), 3.65-3.55 (m, 1H), 3.51-3.44 (m, 4H), 3.28-3.20 (m, 4H), 3.14-3.03 (m, 2H), 2.68-2.58 (m, 4H), 2.53-2.44 (m, 2H), 2.16-1.84 (m, 8H), 1.14 (t, 3H). LC/MS (ESI): 514.3 (MH)$^+$.

Example 188

4-[7-(Tetrahydro-pyran-4-ylmethoxy)-quinazolin-4-yl]-piperidine-1-carboxylic acid (4-pyrrolidin-1-yl-phenyl)-amide

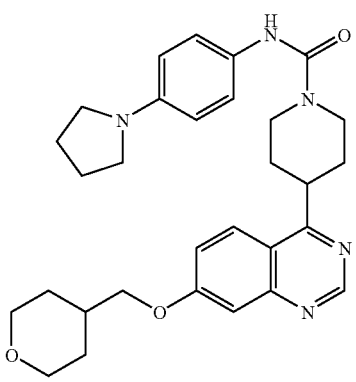

A mixture of (tetrahydro-pyran-4-yl)-methanol (0.2 mmol), KOtBu (0.2 mmol) and 4-(7-fluoro-quinazolin-4-yl)-piperidine-1-carboxylic acid tert-butyl ester (0.1 mmol), prepared as described in Example 65b, in DMSO (1 mL), was stirred at 80° C. for 1 h. It was then diluted with water and extracted with DCM. The combined extracts were washed with water, brine, dried with MgSO4, filtered, and concentrated in vacuo. The crude product was then treated with 3M HCl/MeOH (2 mL) and stirred at rt for 2 h and then concentrated in vacuo. The crude deprotected intermediate was dissolved in a mixture of DCM:MeOH (1:1; 2 mL) and neutralized with excess Et$_3$N and treated with (4-pyrrolidin-1-yl-phenyl)-carbamic acid 4-nitrophenyl ester hydrochloride (0.11 mmol), prepared by the method as outlined in Example 74a, at rt overnight. It was then concentrated in vacuo and the crude product was dissolved in DCM and washed with water thrice, then washed with brine, dried over anhydrous MgSO$_4$, filtered and concentrated in vacuo. The crude product was then purified by Preparative TLC (silica gel; DCM:MeOH, 9.5:0.5) followed by a further purification by Preparative HPLC to obtain 1.5 mg (3%) of the title compound. $^1$H-NMR (300 MHz, CDCl$_3$+CD$_3$OD): 9.05 (s, 1H), 8.09 (m, 1H), 7.52-7.23 (m, 6H), 4.30 (m, 2H), 4.03-3.94 (m, 4H), 3.75-3.50 (m, 8H), 3.48-3.38 (m, 2H), 2.30-2.18 (m, 4H), 2.17-2.00 (m, 2H), 1.97-1.85 (m, 2H), 1.75 (m, 2H), 1.55-1.41 (m, 2H). LC/MS (ESI): 516.2 (MH)$^+$.

Example 189

4-[7-(Tetrahydro-pyran-4-yloxy)-quinazolin-4-yl]-piperidine-1-carboxylic acid (4-pyrrolidin-1-yl-phenyl)-amide

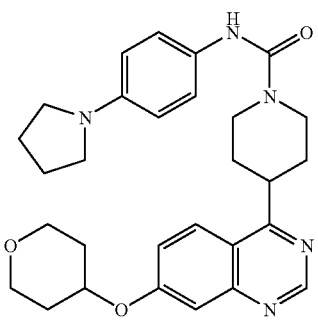

Prepared essentially as described in Example 188 using tetrahydro-pyran-4-ol in place of (tetrahydro-pyran-4-yl)-methanol. $^1$H-NMR (300 MHz, CDCl$_3$): 9.12 (s, 1H), 8.07 (d, 1H), 7.34-7.15 (m, 4H), 6.52 (d, 2H), 6.21 (s, 1H), 4.76-4.68 (m, 1H), 4.26 (d, 2H), 4.06-3.98 (m, 2H), 3.71-3.58 (m, 3H), 3.30-3.19 (m, 4H), 3.16-3.06 (m, 2H), 2.19-2.05 (m, 4H), 2.03-1.82 (m, 8H). LC/MS (ESI): 502.2 (MH)$^+$.

Example 190

(S)-4-[7-(Tetrahydro-furan-3-yloxy)-quinazolin-4-yl]-piperidine-1-carboxylic acid (4-pyrrolidin-1-yl-phenyl)-amide

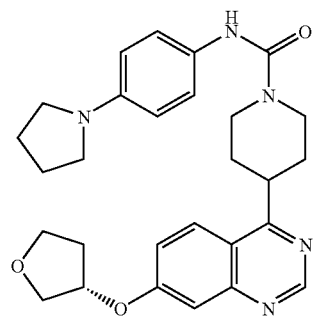

Prepared essentially as described in Example 188 using (S)-tetrahydro-furan-3-ol in place of (tetrahydro-pyran-4-yl)-methanol. $^1$H-NMR (300 MHz, CDCl$_3$): 9.14 (s, 1H), 8.07 (d, 1H), 7.28-7.15 (m, 4H), 6.52 (d, 2H), 6.22 (s, 1H), 5.11 (m, 1H), 4.26 (d, 2H), 4.12-3.99 (m, 3H), 3.98-3.90 (m, 1H), 3.72-3.61 (m, 1H), 3.31-3.18 (m, 4H), 3.16-3.05 (m, 2H), 2.41-2.29 (m, 1H), 2.28-2.04 (m, 3H), 2.03-1.90 (m, 6H). LC/MS (ESI): 488.2 (MH)$^+$.

Example 191

(R)-4-[7-(Tetrahydro-furan-3-yloxy)-quinazolin-4-yl]-piperidine-1-carboxylic acid (4-pyrrolidin-1-yl-phenyl)-amide

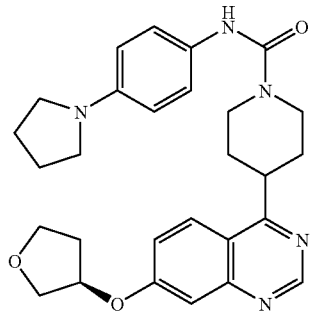

Prepared essentially as described in Example 188 using (R)-tetrahydro-furan-3-ol in place of (tetrahydro-pyran-4-yl)-methanol. $^1$H-NMR (300 MHz, CDCl$_3$): 9.14 (s, 1H), 8.07 (d, 1H), 7.28-7.15 (m, 4H), 6.52 (d, 2H), 6.22 (s, 1H), 5.11 (m, 1H), 4.26 (d, 2H), 4.12-3.99 (m, 3H), 3.98-3.90 (m, 1H), 3.71-3.61 (m, 1H), 3.31-3.18 (m, 4H), 3.16-3.05 (m, 2H), 2.41-2.29 (m, 1H), 2.28-2.05 (m, 3H), 2.03-1.91 (m, 6H). LC/MS (ESI): 488.3 (MH)$^+$.

Example 192

4-[7-(4-Pyridin-2-yl-piperazin-1-yl)-quinazolin-4-yl]-piperidine-1-carboxylic acid (4-pyrrolidin-1-yl-phenyl)-amide

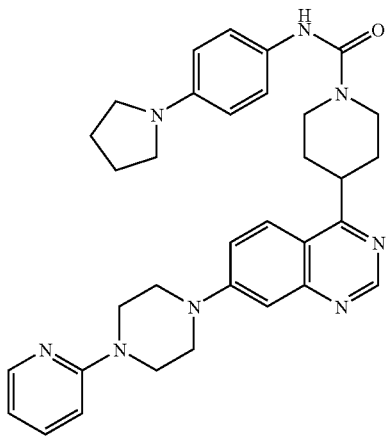

Prepared essentially as described in Example 159 using 1-pyridin-2-yl-piperazine in place of 1-methyl-piperazine.

$^1$H-NMR (300 MHz, CDCl$_3$): 9.05 (s, 1H), 8.22 (d, 1H), 8.01 (d, 1H), 7.53 (m, 1H), 7.36 (m, 1H), 7.24-7.15 (m, 3H), 6.74-6.66 (m, 2H), 6.51 (d, 2H), 6.27 (s, 1H), 4.25 (d, 2H), 3.80-3.72 (m, 4H), 3.67-3.54 (m, 5H), 3.30-3.19 (m, 4H), 3.15-3.04 (m, 2H), 2.17-1.88 (m, 8H). LC/MS (ESI): 563.3 (MH)$^+$.

Example 193

4-[7-(4-Pyrimidin-2-yl-piperazin-1-yl)-quinazolin-4-yl]-piperidine-1-carboxylic acid (4-pyrrolidin-1-yl-phenyl)-amide

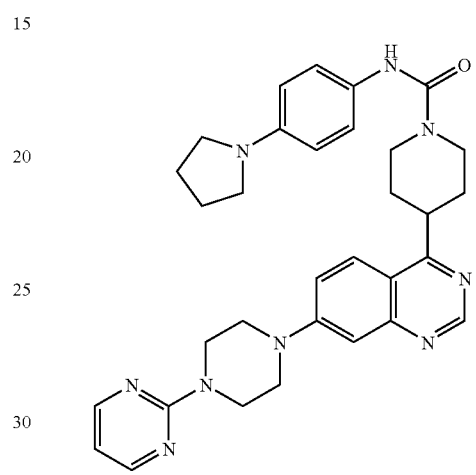

Prepared essentially as described in Example 159 using 1-pyrimidin-2-yl-piperazine in place of 1-methyl-piperazine. $^1$H-NMR (300 MHz, CDCl$_3$): 9.05 (s, 1H), 8.35 (d, 2H), 8.01 (d, 1H), 7.39-7.14 (m, 4H), 6.58-6.47 (m, 3H), 6.28 (s, 1H), 4.25 (d, 2H), 4.07-3.98 (m, 4H), 3.67-3.48 (m, 5H), 3.28-3.18 (m, 4H), 3.15-3.03 (m, 2H), 2.17-1.88 (m, 8H). LC/MS (ESI): 564.3 (MH)$^+$.

Example 194

4-[7-(4-Pyridin-4-yl-piperazin-1-yl)-quinazolin-4-yl]-piperidine-1-carboxylic acid (4-pyrrolidin-1-yl-phenyl)-amide

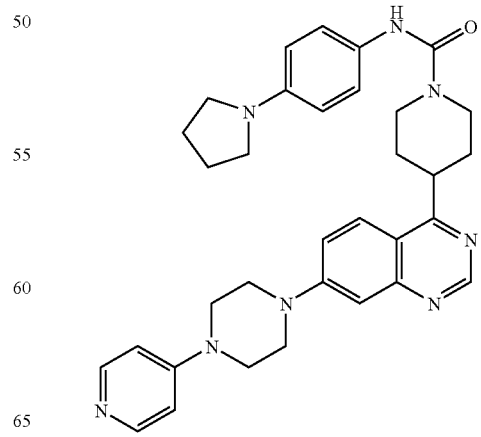

Prepared essentially as described in Example 159 using 1-pyridin-4-yl-piperazine in place of 1-methyl-piperazine. $^1$H-NMR (300 MHz, CDCl$_3$): 9.00 (s, 1H), 8.27 (d, 2H), 7.97 (d, 1H), 7.30-7.09 (m, 4H), 6.65 (d, 2H), 6.46 (d, 2H), 6.14 (s, 1H), 4.19 (d, 2H), 3.61-3.47 (m, 9H), 3.22-3.15 (m, 4H), 3.10-3.00 (m, 2H), 2.12-1.99 (m, 2H), 1.95-1.84 (m, 6H). LC/MS (ESI): 563.3 (MH)$^+$.

Example 195

4-[7-(4-Fluoro-piperidin-1-yl)-quinazolin-4-yl]-piperidine-1-carboxylic acid (4-pyrrolidin-1-yl-phenyl)-amide

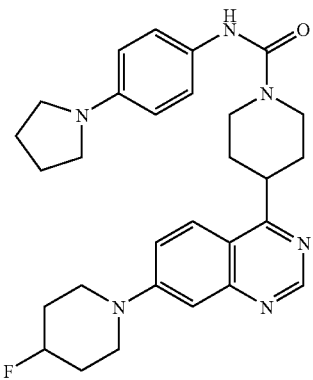

Prepared essentially as Example 126 using 4-fluoro-piperidine and (4-pyrrolidin-1-yl-phenyl)-carbamic acid 4-nitro-phenyl ester hydrochloride, which was prepared as described in Example 74a. $^1$H NMR (CDCl$_3$) δ 8.97 (s, 1H), 7.91 (d, J=9.49 Hz, 1H), 7.25 (dd, J=9.40 and 2.62 Hz, 1H), 7.15 (d, J=2.58 Hz, 1H), 7.11 (d, J=8.88 Hz, 2H), 6.45 (d, J=8.92 Hz, 2H), 4.84 (m, 1H), 4.18 (m, 2H), 3.43-3.60 (5H), 3.19 (t, J=6.60 Hz, 4H), 3.30 (td, J=12.63 and 2.62 Hz, 2H), 1.84-2.10 (12H). Calcd for C$_{29}$H$_{36}$FN$_6$O (MH+) 503.3, found 503.3.

Example 196

4-[7-(4-Fluoro-piperidin-1-yl)-quinazolin-4-yl]-piperidine-1-carboxylic acid (4-morpholin-4-yl-phenyl)-amide

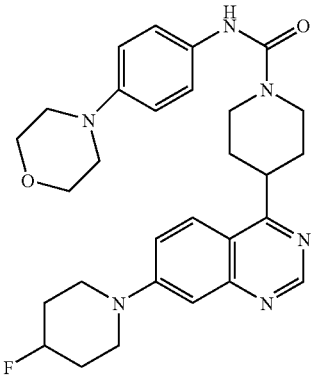

Prepared essentially as Example 126 using 4-fluoro-piperidine. $^1$H NMR (CDCl$_3$) δ 9.04 (s, 1H), 7.98 (d, J=9.49 Hz, 1H), 7.32 (dd, J=9.42 and 2.61 Hz, 1H), 7.27 (d, J=8.91 Hz, 2H), 7.22 (d, J=2.57 Hz, 1H), 6.87 (d, J=9.04 Hz, 2H), 6.31 (br, 1H), 4.90 (m, 1H), 4.25 (m, 2H), 3.86 (t, J=4.71 Hz, 4H), 3.50-3.67 (5H), 3.14 (dd, J=13.15 and 2.72 Hz, 2H), 3.10 (t, J=4.83 Hz, 4H), 1.92-2.17 (8H). Calcd for C$_{29}$H$_{36}$FN$_6$O$_2$ (MH+) 519.3, found 519.3.

Example 197

4-[7-(2-Oxo-imidazolidin-1-yl)-quinazolin-4-yl]-piperidine-1-carboxylic acid (4-morpholin-4-yl-phenyl)-amide

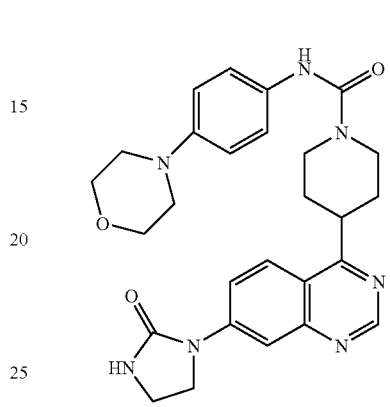

Prepared essentially as Example 178b using (4-morpholin-4-yl-phenyl)-carbamic acid 4-nitro-phenyl ester hydrochloride, which was prepared as described in Example 66a. $^1$H NMR (DMSO-d$_6$) δ 9.04 (s, 1H), 8.39 (dd, J=9.33 and 2.04 Hz, 1H), 8.36 (s, 1H), 8.34 (s, 1H), 7.65 (d, J=2.23 Hz, 1H), 7.38 (s, 1H), 7.30 (d, J=9.10 Hz, 2H), 6.82 (d, J=9.18 Hz, 2H), 4.24 (m, 2H), 3.87 (m, 1H), 3.71 (m, 2H), 3.32-3.45 (8H), 2.99 (m, 4H), 1.78-1.85 (4H). Calcd for C$_{27}$H$_{32}$N$_7$O$_3$ (MH+) 502.3, found 502.3.

Example 198

4-[6-(4-Methyl-piperazin-1-yl)-quinazolin-4-yl]-piperidine-1-carboxylic acid (4-morpholin-4-yl-phenyl)-amide

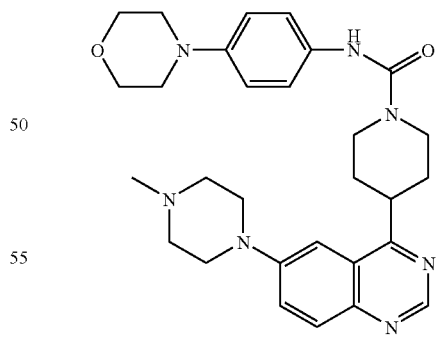

Prepared essentially as described in Example 131 using (4-morpholin-4-yl-phenyl)-carbamic acid 4-nitro-phenyl ester hydrochloride, which was prepared as described in Example 66a. $^1$H NMR (CDCl$_3$) δ 9.08 (s, 1H), 7.94 (d, J=9.27 Hz, 1H), 7.62 (dd, J=9.31 and 2.57 Hz, 1H), 7.30 (d, J=9.00 Hz, 2H), 7.27 (d, J=3.23 Hz, 1H), 6.86 (d, J=9.02 Hz, 2H), 6.53 (br, 1H), 4.28 (m, 2H), 3.84 (t, J=4.66 Hz, 4H), 3.58-3.68 (3H), 3.54 (m, 4H), 3.17 (m, 2H), 3.04-3.10 (4H), 2.96 (m, 2H), 2.61 (s, 3H), 1.93-2.18 (4H). Calcd for C$_{29}$H$_{38}$N$_7$O$_2$(MH+) 516.3, found 516.1.

Example 199

4-{4-[1-(4-Pyrrolidin-1-yl-phenylcarbamoyl)-piperidin-4-yl]-quinazolin-7-yl}-piperazine-1-carboxylic acid ethylamide

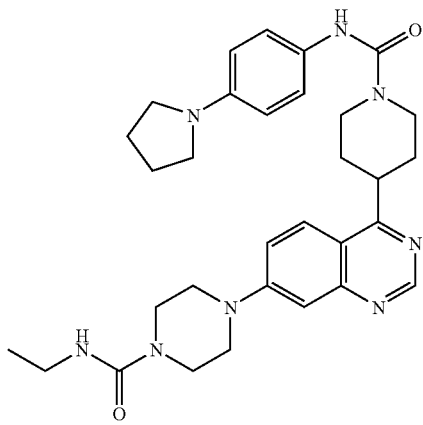

Prepared essentially as described in Example 140 using ethyl isocyanate in place of FMOC-Cl and (6-pyrrolidin-1-yl-pyridin-3-yl)-carbamic acid 4-nitrophenyl ester hydrochloride, as prepared by the method outlined in Example 74a, in place of (4-morpholin-4-yl-phenyl)-carbamic acid 4-nitrophenyl ester hydrochloride. $^1$H-NMR (300 MHz, CDCl$_3$): 9.04 (s, 1H), 8.00 (d, 1H), 7.32-7.14 (m, 4H), 6.51 (d, 2H), 6.30 (s, 1H), 4.58 (m, 1H), 4.25 (m, 2H), 3.66-3.54 (m, 5H), 3.51-3.43 (m, 4H), 3.35-3.17 (m, 6H), 3.15-3.04 (m, 3H), 2.17-2.03 (m, 2H), 2.02-1.88 (m, 5H), 1.16 (t, 3H). LC/MS (ESI): 557.3 (MH)$^+$.

Example 200

4-{7-[4-(2-Methoxy-acetyl)-piperazin-1-yl]-quinazolin-7-yl}-piperidine-1-carboxylic acid (4-pyrrolidin-1-yl-phenyl)-amide

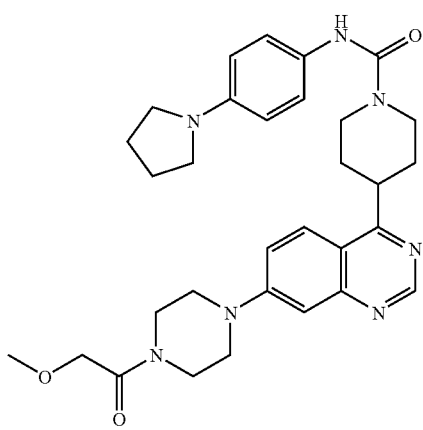

Prepared essentially as described in Example 140 using methoxyacetyl chloride in place of FMOC-Cl and (6-pyrrolidin-1-yl-pyridin-3-yl)-carbamic acid 4-nitrophenyl ester hydrochloride, as prepared by the method outlined in Example 74a, in place of (4-morpholin-4-yl-phenyl)-carbamic acid 4-nitrophenyl ester hydrochloride. $^1$H-NMR (300 MHz, CDCl$_3$): 9.07 (s, 1H), 8.02 (d, 1H), 7.35-7.14 (m, 4H), 6.52 (d, 2H), 6.25 (s, 1H), 4.25 (m, 2H), 4.17 (s, 2H), 3.86-3.56 (m, 6H), 3.49-3.42 (m, 6H), 3.30-3.18 (m, 4H), 3.10 (t, 2H), 2.18-2.04 (m, 2H), 2.02-1.87 (m, 6H). LC/MS (ESI): 558.3 (MH)$^+$.

Example 201

4-{7-[4-(2-Hydroxy-acetyl)-piperazin-1-yl]-quinazolin-7-yl}-piperidine-1-carboxylic acid (4-pyrrolidin-1-yl-phenyl)-amide

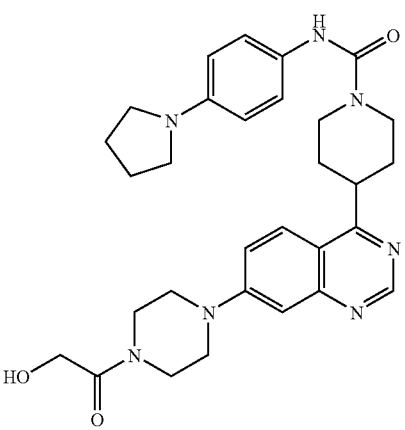

4-(7-piperazin-1-yl-quinazolin-4-yl)-piperidine-1-carboxylic acid tert-butyl ester (0.1 mmol), prepared as described in Example 140, was added to a mixture of t-butoxyacetic acid (0.15 mmol) and PS-carbodiimide (0.2 mmol) in anhydrous DCM (2 mL). The mixture was shaken at rt overnight. It was then filtered and the resin washed with DCM. The combined filtrate and washings were concentrated in vacuo. To this was then added 3M HCl/MeOH (2 mL) and stirred at rt for 2 h and then concentrated in vacuo. The crude residue was dissolved in a mixture of DCM:MeOH (1:1; 2 mL), neutralized with excess Et$_3$N and treated with (6-pyrrolidin-1-yl-pyridin-3-yl)-carbamic acid 4-nitrophenyl ester hydrochloride (0.11 mmol), as prepared by the method outlined in Example 74a, at rt overnight. It was then concentrated in vacuo and the crude product was dissolved in DCM and washed with water thrice, then washed with brine, dried over anhydrous MgSO$_4$, filtered and concentrated in vacuo. The crude product was then purified by Preparative TLC (silica gel; DCM:MeOH, 95:5) followed by a further purification by Preparative HPLC to obtain 1 mg (1%) of the title compound. $^1$H-NMR (300 MHz, CDCl$_3$): 9.08 (s, 1H), 8.04 (d, 1H), 7.34-7.15 (m, 4H), 6.52 (d, 2H), 6.19 (s, 1H), 4.30-4.19 (m, 4H), 3.92-3.32 (m, 12H), 3.29-3.20 (m, 4H), 3.11 (t, 2H), 2.18-1.87 (m, 6H). LC/MS (ESI): 544.3 (MH)$^+$.

Example 202

4-{7-[2-(4-Methyl-3-oxo-piperazin-1-yl)-ethoxy]-quinazolin-4-yl}-piperidine-1-carboxylic acid (4-pyrrolidin-1-yl-phenyl)-amide

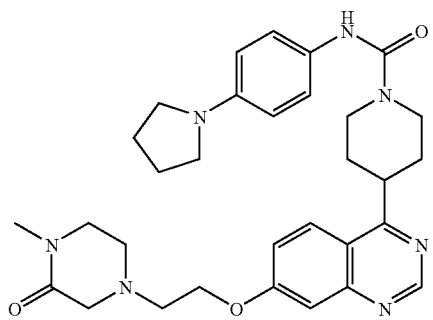

To a solution of 4-[7-(-hydroxy-ethoxy)-quinazolin-4-yl]-piperidine-1-carboxylic acid tert-butyl ester (0.5 mmol), prepared as described in Example 169a, in anhydrous DCM, was added Et$_3$N (1 mmol) and methanesulfonyl chloride (1 mmol) and the mixture was stirred at rt for 2 h. It was then washed with water (3×), dried over anhydrous MgSO$_4$, filtered and concentrated in vacuo to obtain crude 4-[7-(3-methanesulfonyloxy-ethoxy)-quinazolin-4-yl]-piperidine-1-carboxylic acid tert-butyl ester. This (0.1 mmol) was dissolved in anhydrous DMSO together with 1-methyl-piperazin-2-one (0.2 mmol) and the mixture was stirred at 100° C. for 2 h and then diluted with water and extracted with DCM. The DCM extract was washed with water (3×), dried over anhydrous MgSO$_4$, filtered and concentrated in vacuo. To this was added 3M HCl/MeOH (1 mL) and the mixture was stirred at rt for 2 h and then concentrated in vacuo and the residue was dissolved in a 1:1 mixture of DCM:MeOH, neutralized with excess Et$_3$N and treated with (4-pyrrolidin-1-yl-phenyl)-carbamic acid 4-nitrophenyl ester hydrochloride (0.11 mmol), as prepared by the method outlined in Example 74a. The mixture was stirred at rt overnight and then concentrated in vacuo and partitioned between water and DCM. DCM layer was drawn off, washed with water thrice, then dried over anhydrous MgSO$_4$, filtered and concentrated in vacuo. The residue was purified by Preparative TLC (silica gel; DCM:MeOH, 95:5) followed by a further purification by Preparative HPLC to obtain 5.6 mg (6%) of the title compound. $^1$H-NMR (300 MHz, CD$_3$OD): 9.10 (s, 1H), 8.44 (d, 1H), 7.59-7.31 (m, 6H), 4.62 (t, 2H), 4.37 (m, 2H), 4.04-3.93 (m, 4H), 3.78-3.54 (m, 8H), 3.21 (m, 2H), 3.03 (s, 3H), 2.30-2.18 (m, 5H), 2.11-1.91 (m, 4H). LC/MS (ESI): 558.3 (MH)$^+$.

Example 203

4-(6-Methoxy-quinazolin-4-yl)-piperidine-1-carboxylic acid (4-isopropoxy-phenyl)-amide

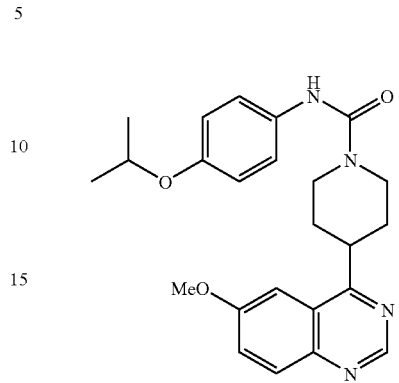

The title compound was prepared from 4-chloro-6-methoxyquinazoline (WO 2001032632 A2, WO 9609294 A1) essentially as described for Example 1, except the methyl ester intermediate was stirred in KOH/MeOH at 100° C. for 3 hr instead of 1 hr. $^1$H-NMR (300 MHz, CDCl$_3$) δ 9.15 (s, 1H), 7.99 (d, 1H), 7.56 (dd, 1H), 7.33 (d, 1H), 7.25 (m, 2H), 6.85 (m, 2H), 6.31 (br s, 1H), 4.49 (heptet, 1H), 4.27 (m, 2H), 4.00 (s, 3H), 3.66 (tt, 1H), 3.17 (td, 2H), 2.22-1.97 (m, 4H), 1.32 (d, 6H). LC/MS (ESI): calcd mass 420.2, found 421.2 (MH)$^+$.

Example 204

4-{7-[3-(1H-Tetrazol-5-yl)-propoxy]-quinazolin-4-yl}-piperidine-1-carboxylic acid (4-isopropoxy-phenyl)-amide

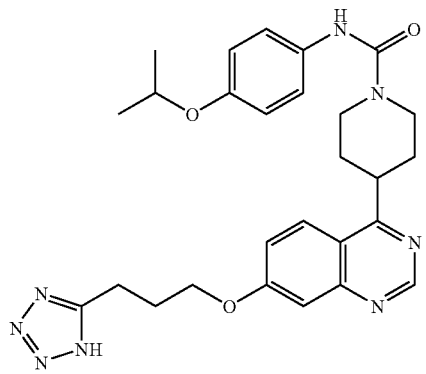

a. 4-[7-(3-Cyano-propoxy)-quinazolin-4-yl]-piperidine-1-carboxylic acid tert-butyl ester

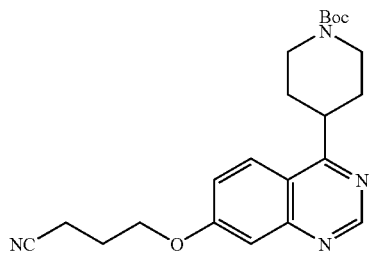

A mixture of 4-hydroxybutyronitrile (24.2 mg, 285 µmol) [*Organometallics* (1996), 15(4), 1236-41], KOtBu (34.8 mg, 311 µmol), and DME was stirred at rt, followed by the addition of 4-(7-Fluoro-quinazolin-4-yl)-piperidine-1-carboxylic acid tert-butyl ester (48.8 mg, 147 µmol) (prepared as described in Example 65b). The resulting homogeneous solution was stirred at rt for 2 hr, and was then directly loaded onto a 5 g Jones silica cartridge pre-equilibrated with 9:1 DCM/acetone, and eluted with 9:1→8:2 DCM/acetone to afford the title intermediate (24.5 mg, 42%) as a colorless oil. LC/MS (ESI) calcd mass 396.2, found 397.1 (MH)$^+$.

b. 4-{7-[3-(1H-Tetrazol-5-yl)-propoxy]-quinazolin-4-yl}-piperidine-1-carboxylic acid tert-butyl ester

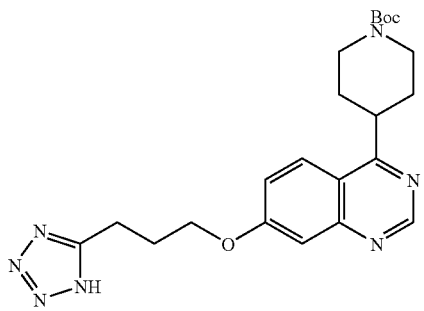

A mixture of 4-[7-(3-Cyano-propoxy)-quinazolin-4-yl]-piperidine-1-carboxylic acid tert-butyl ester (24.5 mg, 62 µmol), as prepared in the preceding step, NaN$_3$ (13.4 mg, 206 µmol), TEA.HCl (25.5 mg, 185 µmol), and toluene (100 µL) was tightly capped and stirred at 100° C. for 6.5 hr. The reaction was then allowed to cool to rt, partitioned with EtOAc (1 mL) and 0.1 M HCl (1 mL). The aqueous layer was then extracted with EtOAc (2×1 mL), the organic layers were combined, dried (Na$_2$SO$_4$), and concentrated. The residue was purified via flash silica chromatography (3:2 EtOAc/acetone) to yield the title intermediate as an off-white solid (12.2 mg, 44%). LC/MS (ESI) calcd mass 439.2, found 440.1 (MH)$^+$.

c. 4-{7-[3-(1H-Tetrazol-5-yl)-propoxy]-quinazolin-4-yl}-piperidine-1-carboxylic acid (4-isopropoxy-phenyl)-amide

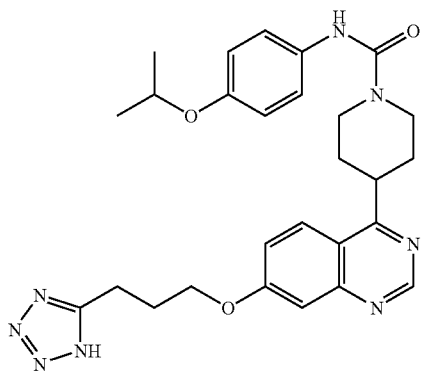

A solution of 4-{7-[3-(1H-Tetrazol-5-yl)-propoxy]-quinazolin-4-yl}-piperidine-1-carboxylic acid tert-butyl ester (6.1 mg, 14 µmol), as prepared in the previous step, in 9:1 TFA/anisole (100 µL) was stirred at 100° C. for 10 min. The solution was then concentrated. Pyridine (100 µL) and (4-isopropoxy-phenyl)-carbamic acid 4-nitro-phenyl ester (5.8 mg, 18 µmol), as prepared in Example 1a, were added, and the solution was stirred at 80° C. for 15 min. The reaction was concentrated, taken up in 1M NaH$_2$PO$_4$ (2 mL), and extracted with 95:5 DCM/MeOH (2×2 mL). The combined organic layers were dried (Na$_2$SO$_4$), concentrated, and purified by flash silica cartridge chromatography (EtOAc→acetone eluent) to provide the title compound (1.0 mg, 14%). $^1$H-NMR (400 MHz, 95:5 CDCl$_3$/CD$_3$OD) δ 9.09 (s, 1H), 8.08 (s, 1H), 7.30-7.21 (m, 4H), 6.85 (m, 2H), 4.49 (septet, 1H), 4.27 (m, 2H), 4.24 (t, 2H), 3.70 (tt, 1H), 3.19 (t, 2H), 3.12 (td, 2H), 2.40 (m, 2H), 2.17-1.92 (m, 4H), 1.32 (d, 6H). LC/MS (ESI) calcd mass 516.3, found 517.2 (MH)$^+$.

Example 205

4-{6-Fluoro-7-[3-(4-methyl-piperazin-1-yl)-propoxy]-quinazolin-4-yl}-piperidine-1-carboxylic acid (4-morpholin-4-yl-phenyl)-amide

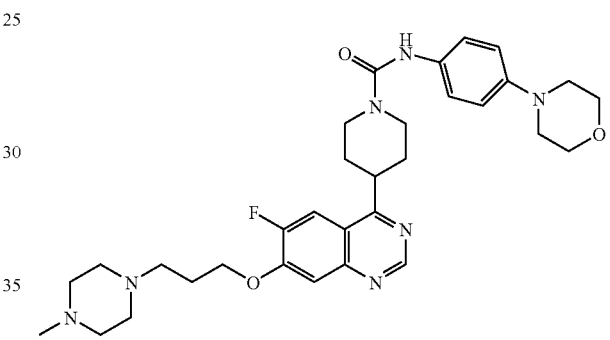

a. 4-Chloro-6,7-difluoro-quinazoline

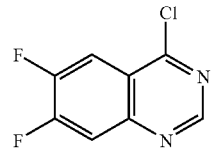

A mixture of 4,5-difluoroanthranilic acid (20.43 g, 118 mmol) and formamidine acetate (13.55 g, 130 mmol) in reagent EtOH was stirred at 120° C. (oil bath) for 3 hr. The reaction was briefly a homogeneous brown solution, and then became an opaque mixture. The reaction was allowed to cool to rt, and the resulting solid was filtered, washed with denatured EtOH (1×10 mL), and allowed to air dry. Powdering with a mortar and pestle provided 4-hydroxy-6,7-difluoro-quinazoline as a beige powder (16.9 g, 79%). 16.6 g of this material (91.1 mmol) was taken up in SOCl$_2$ (66 mL), DCE (66 mL), and DMF (7.05 mL, 91 mmol), and was stirred at 110° C. (oil bath) for 1 hr. The resulting homogeneous amber solution was then concentrated under rotary evaporation, and taken up in toluene (2×100 mL) with repeated rotary evaporation to provide the crude title compound as a beige solid. A portion of this material (8.4 g of 17.7 g total) was taken up in DCM (80 mL) and gently shaken with 2M trisodium citrate (1×40 mL) until a homogeneous clear organic layer resulted. This organic layer was immediately applied (without drying) directly onto a silica flash column (79 mm×6") pre-equilibrated with 1:1 hexanes/EtOAc. Trivial elution with 1:1 hexanes/EtOAc, followed by repeated rotary evaporation from toluene (2×50 mL) of the combined fractions afforded the title compound as a light yellow solid (6.79 g, 78%). ¹H-NMR (400 MHz, CDCl₃) δ 9.05 (s, 1H), 8.05 (dd, 1H), 7.86 (dd, 1H).

b. 4-(6,7-Difluoro-quinazolin-4-yl)-piperidine-1,4-dicarboxylic acid 1-tert-butyl ester 4-methyl ester

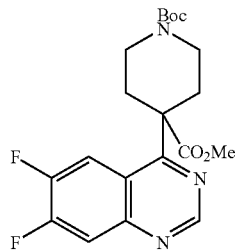

A solution of piperidine-1,4-dicarboxylic acid 1-tert-butyl ester 4-methyl ester (1.27 g, 5.23 mmol) in dry THF (2 mL) was added dropwise over 2 minutes with stirring to 1.01M LiHMDS/THF (5.75 mL, 5.81 mmol) at −78° C. under argon. After 5 min at −78° C., the cold bath was removed and the reaction was allowed to stir at "rt" for 30 min. A portion of this enolate solution (5.1 mL, ~3 mmol enolate) was added dropwise over 2-3 min to a stirred homogeneous solution of 4-chloro-6,7-difluoroquinazoline (600 mg, 2.99 mmol) in dry THF (3 mL) at 0° C. under argon. The reaction was stirred for 30 min at 0° C., and was then quenched with 1M NaH₂PO₄ (50 mL) and extracted with EtOAc (1×50 mL). The organic layer was washed with 4M NaCl (1×50 mL), dried (Na₂SO₄), and concentrated. The residue was purified with silica flash chromatography (3:1 hexanes/EtOAc) to afford the title compound as a yellow oil (451 mg, 37%). LC/MS (ESI): calcd mass 407.2, found 408.2 (MH)⁺.

c. 4-(6,7-Difluoro-quinazolin-4-yl)-piperidine-1-carboxylic acid tert-butyl ester

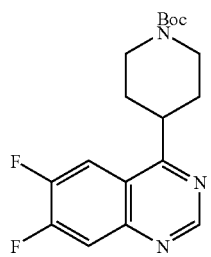

A mixture of 4-(6,7-Difluoro-quinazolin-4-yl)-piperidine-1,4-dicarboxylic acid 1-tert-butyl ester 4-methyl ester (451 mg, 1.11 mmol), as prepared in the previous step, LiCl (89 mg, 2.12 mmol), water (60 μL, 3.3 mmol), and DMSO (430 μL) was stirred at 150° C. for 7.5 hrs with a reflux condenser. The reaction was then allowed to cool to rt, shaken with 1M NaCl (5 mL), and extracted with DCM (1×3 mL) and 9:1 DCM/MeOH (1×3 mL). The organic layers were combined, dried (Na₂SO₄), and concentrated. The residue was purified by silica flash chromatography (3:1 hex/EtOAc→2:1 eluent) to provide the title compound (151.8 mg, 39%). ¹H-NMR (300 MHz, CDCl₃) δ 9.22 (s, 1H), 7.90 (dd, 1H), 7.81 (dd, 1H), 4.33 (br m, 2H), 3.50 (tt, 1H), 2.96 (br t, 2H), 2.11-1.82 (m, 4H), 1.49 (s, 9H). LC/MS (ESI): calcd mass 349.2, found 368.3 (MH.H₂O)⁺.

d. 4-{6-Fluoro-7-[3-(4-methyl-piperazin-1-yl)-propoxy]-quinazolin-4-yl}-piperidine-1-carboxylic acid tert-butyl ester

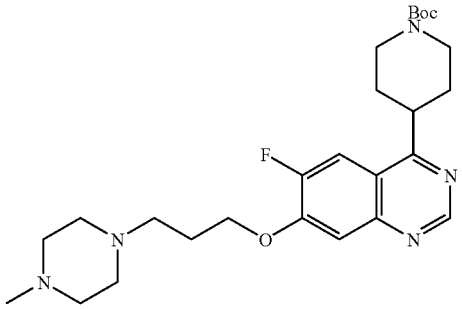

A solution of 1.19M KOtBu in THF (128 μL, 152 μmol) was added dropwise with stirring over 2.5 min to a 0° C. homogeneous solution of 4-(6,7-Difluoro-quinazolin-4-yl)-piperidine-1-carboxylic acid tert-butyl ester (38.1 mg, 109 μmol), as prepared in the previous step, and 3-(4-Methyl-piperazin-1-yl)-propan-1-ol (22.4 mg, 142 μmol) in THF (170 μL). The reaction was stirred at 0° C. for 1.5 hr, and was then partitioned with DCM (2 mL) and 1M NaCl (2 mL). The aq layer was back-extracted with DCM (1×2 mL), and the combined cloudy white organic layers were dried (Na₂SO₄) and concentrated. The residue was purified by silica flash chromatography (1:2 hex/EtOAc/3% DMEA eluent) to yield the title compound as an off-white foam (32.6 mg, 61%). NOe experiments support the assigned regioisomer. Select ¹H-NMR resonances and nOes (300 MHz, CDCl₃) δ 7.73 (d, J=11.4 Hz, 1H), 7.43 (d, J=8.1 Hz, 1H), 3.46 (tt, 1H). Irradiation of the diagnostic methine proton at δ 3.46 generates an nOe to the quinazoline C5 proton at δ 7.73, but not to the quinazoline C8 proton at δ 7.43. The C5 proton has a larger coupling constant than the C8 proton, indicating fluorine substitution at C6 of the quinazoline. LC/MS (ESI): calcd mass 487.3, found 488.3 (MH)⁺.

e. 4-{6-Fluoro-7-[3-(4-methyl-piperazin-1-yl)-propoxy]-quinazolin-4-yl}-piperidine-1-carboxylic acid (4-morpholin-4-yl-phenyl)-amide

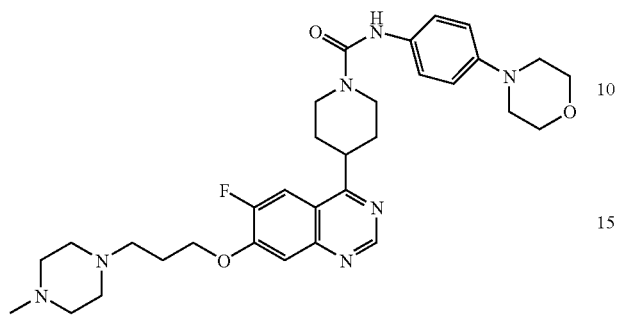

The title compound was prepared from 4-{6-Fluoro-7-[3-(4-methyl-piperazin-1-yl)-propoxy]-quinazolin-4-yl}-piperidine-1-carboxylic acid tert-butyl ester, prepared in the previous step, and (4-morpholin-4-yl-phenyl)-carbamic acid 4-nitro-phenyl ester hydrochloride, prepared as described in Example 66a, using essentially the protocol given for Example 170c. $^1$H-NMR (400 MHz, CDCl$_3$) δ 9.14 (s, 1H), 7.74 (d, 1H), 7.44 (d, 1H), 7.27 (m, 2H), 6.88 (m, 2H), 6.32 (s, 1H), 4.27 (m, 4H), 3.86 (m, 4H), 3.54 (tt, 1H), 3.18-3.08 (m, 6H), 2.58 (t, 2H), 2.64-2.35 (br, 8H), 2.30 (s, 3H), 2.12 (m, 4H), 1.96 (m, 2H). LC/MS (ESI): calcd mass 591.3, found 592.4 (MH)$^+$.

Example 206

4-{6-Fluoro-7-[2-(2-oxo-pyrrolidin-1-yl)-ethoxy]-quinazolin-4-yl}-piperidine-1-carboxylic acid (4-pyrrolidin-1-yl-phenyl)-amide

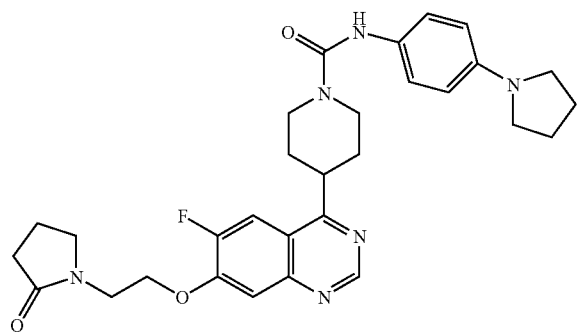

Prepared as for Example 205d-e using 1-(2-Hydroxyethyl)-pyrrolidin-2-one and (4-pyrrolidin-1-yl-phenyl)-carbamic acid 4-nitro-phenyl ester hydrochloride, which was prepared as described in Example 74a. $^1$H-NMR (400 MHz, CDCl$_3$) δ 9.15 (s, 1H), 7.76 (d, 1H), 7.40 (d, 1H), 7.19 (m, 2H), 6.53 (m, 2H), 6.25 (s, 1H), 4.35 (t, 2H), 4.26 (m, 2H), 3.82 (t, 2H), 3.66 (m, 2H), 3.52 (tt, 1H), 3.26 (m, 4H), 3.11 (td, 2H), 2.42 (m, 2H), 2.17-2.02 (m, 4H), 2.02-1.90 (m, 6H). LC/MS (ESI): calcd mass 546.3, found 547.4 (MH)$^+$.

Example 207

4-{6-Methoxy-7-[3-(4-methyl-piperazin-1-yl)-propoxy]-quinazolin-4-yl}-piperidine-1-carboxylic acid (4-morpholin-4-yl-phenyl)-amide

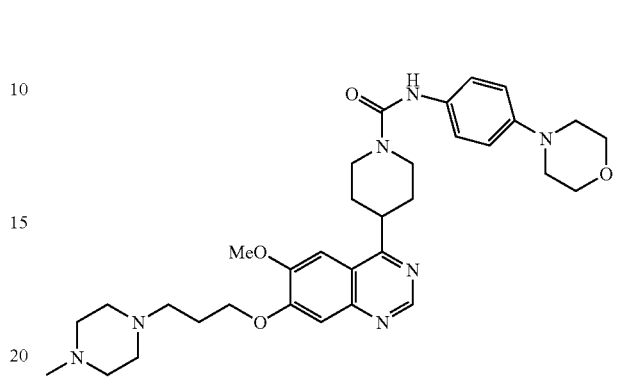

a. 4-{6-Methoxy-7-[3-(4-methyl-piperazin-1-yl)-propoxy]-quinazolin-4-yl}-piperidine-1-carboxylic acid tert-butyl ester

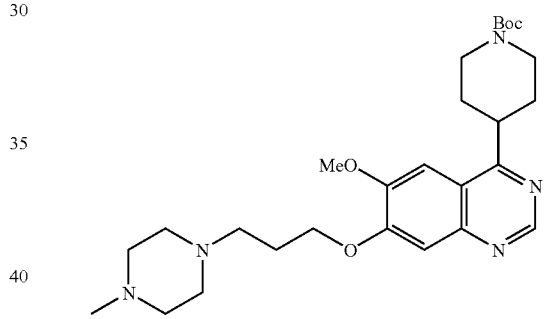

A mixture of 4-{6-Fluoro-7-[3-(4-methyl-piperazin-1-yl)-propoxy]-quinazolin-4-yl}-piperidine-1-carboxylic acid tert-butyl ester (32.6 mg, 66.9 μmol), as prepared in Example 205d, DMSO (50 μL), and 0.31M KOMe/MeOH (270 μL, 83.9 μmol KOMe in 6.4 mmol MeOH) was stirred at 100° C. for 9 hr, and then 110° C. for 2 hr. The resulting pale yellow homogeneous solution was allowed to cool to rt, diluted with DCM (2 mL), and washed with 4M NaCl (1×2 mL). The aq layer was back-extracted with DCM (1×2 mL), and the combined organic layers were dried (Na2SO4) and concentrated. Purification of the residue by silica flash chromatography (1:2 hex/EtOAc→1:2 hex/EtOAc/3% DMEA→9:1 EtOAc/acetone/3% DMEA eluent) afforded the title compound (18.4 mg, 55%). NOe experiments support the assigned regioisomer. Select $^1$H-NMR resonances and nOes (300 MHz, CDCl$_3$) δ 7.34 (s, 1H), 7.24 (s, 1H), 4.04 (s, 3H), 3.51 (m, 1H). Irradiation of the diagnostic methine proton at δ 3.51 generates an nOe to the quinazoline C5 proton at δ 7.24, but not to the quinazoline C8 proton at δ 7.34. Irradiation of the methoxy protons at δ 4.04 generates an nOe to the C5 proton at δ 7.24, but not to the C8 proton at δ 7.34. This indicates methoxy substitution at C6 of the quinazoline. LC/MS (ESI): calcd mass 499.3, found 500.4 (MH)$^+$.

b. 4-{6-Methoxy-7-[3-(4-methyl-piperazin-1-yl)-propoxy]-quinazolin-4-yl}-piperidine-1-carboxylic acid (4-morpholin-4-yl-phenyl)-amide

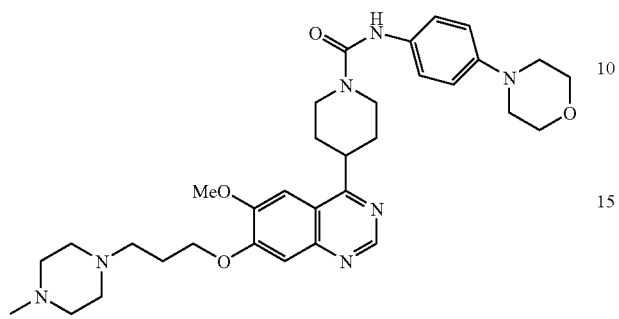

The title compound was prepared from 4-{6-Methoxy-7-[3-(4-methyl-piperazin-1-yl)-propoxy]-quinazolin-4-yl}-piperidine-1-carboxylic acid tert-butyl ester, prepared in the previous step, and (4-morpholin-4-yl-phenyl)-carbamic acid 4-nitro-phenyl ester hydrochloride, prepared as described in Example 66a, using essentially the protocol given for Example 170c. $^1$H-NMR (400 MHz, CDCl$_3$) δ 9.06 (s, 1H), 7.34 (s, 1H), 7.28 (m, 2H), 7.25 (s, 1H), 6.88 (m, 2H), 6.34 (s, 1H), 4.27 (m, 4H), 4.05 (s, 3H), 3.86 (m, 4H), 3.59 (tt, 1H), 3.16 (td, 2H), 3.11 (m, 4H), 2.57 (m, 2H), 2.65-2.34 (br, 8H), 2.30 (s, 3H), 2.21-2.08 (m, 4H), 2.03-1.95 (m, 2H). LC/MS (ESI): calcd mass 603.4, found 604.4 (MH)$^+$.

Example 208

4-{6-Methoxy-7-[3-(4-methyl-piperazin-1-yl)-propoxy]-quinazolin-4-yl}-piperidine-1-carboxylic acid (4-pyrrolidin-1-yl-phenyl)-amide

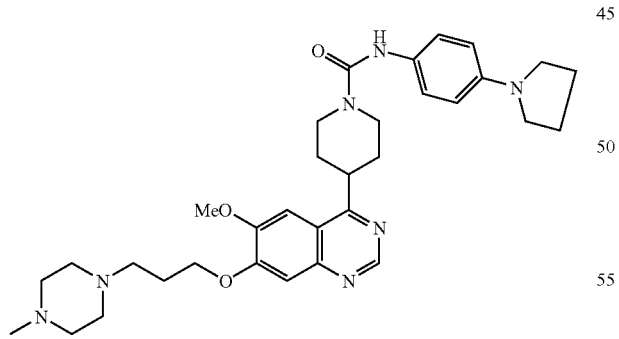

The title compound was prepared from 4-{6-Methoxy-7-[3-(4-methyl-piperazin-1-yl)-propoxy]-quinazolin-4-yl}-piperidine-1-carboxylic acid tert-butyl ester, prepared as described in Example 207a, and (4-pyrrolidin-1-yl-phenyl)-carbamic acid 4-nitro-phenyl ester hydrochloride, prepared as described in Example 74a, using essentially the protocol given for Example 170c. $^1$H-NMR (400 MHz, CDCl$_3$) δ 9.07 (s, 1H), 7.34 (s, 1H), 7.25 (s, 1H), 7.19 (m, 2H), 6.52 (m, 2H), 6.24 (s, 1H), 4.27 (m, 4H), 4.04 (s, 3H), 3.57 (tt, 1H), 3.26 (m, 4H), 3.14 (td, 2H), 2.58 (m, 2H), 2.64-2.35 (br, 8H), 2.30 (s, 3H), 2.20-2.08 (m, 4H), 2.04-1.93 (m, 6H). LC/MS (ESI): calcd mass 587.4, found 588.4 (MH)$^+$.

Example 209

4-{6-Methoxy-7-[2-(2-oxo-pyrrolidin-1-yl)-ethoxy]-quinazolin-4-yl}-piperidine-1-carboxylic acid (4-pyrrolidin-1-yl-phenyl)-amide

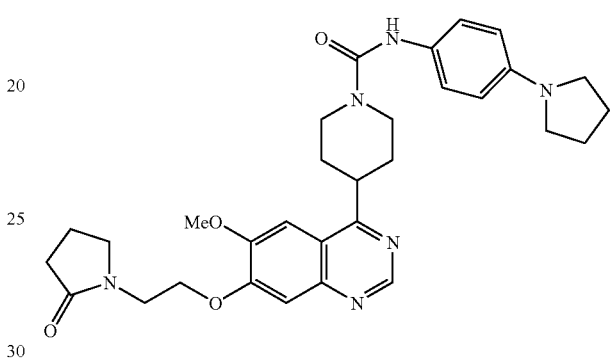

Prepared as for Example 208 using 1-(2-Hydroxy-ethyl)-pyrrolidin-2-one instead of 3-(4-methyl-piperazin-1-yl)-propan-1-ol $^1$H-NMR (400 MHz, CDCl$_3$) δ 9.07 (s, 1H), 7.30 (s, 1H), 7.26 (s, 1H), 7.19 (m, 2H), 6.53 (m, 2H), 6.23 (s, 1H), 4.32 (t, 2H), 4.26 (m, 2H), 4.04 (s, 3H), 3.82 (t, 2H), 3.66 (m, 2H), 3.57 (tt, 1H), 3.26 (m, 4H), 3.14 (td, 2H), 2.41 (m, 2H), 2.22-1.94 (m, 10H). LC/MS (ESI): calcd mass 558.3, found 559.4 (MH)$^+$.

Example 210

4-(6-Fluoro-7-morpholin-4-yl-quinazolin-4-yl)-piperidine-1-carboxylic acid (4-pyrrolidin-1-yl-phenyl)-amide

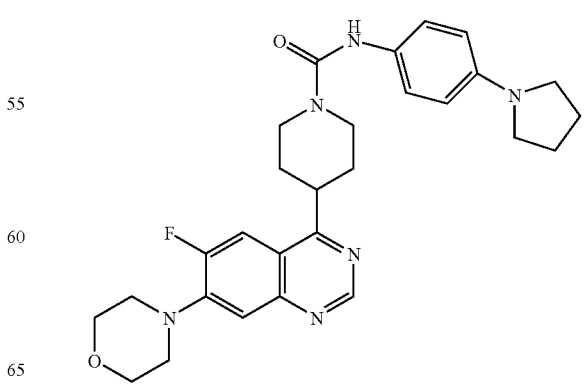

a. 4-(6-Fluoro-7-morpholin-4-yl-quinazolin-4-yl)-piperidine-1-carboxylic acid tert-butyl ester

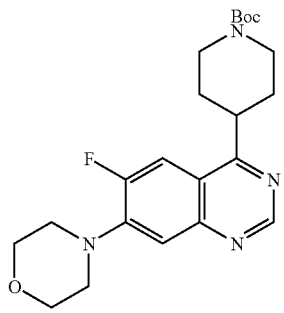

A solution of 4-(6,7-Difluoro-quinazolin-4-yl)-piperidine-1-carboxylic acid tert-butyl ester (37.8 mg, 108 µmol) (preparation in Example 205c) and morpholine (19.8 µL, 227 µmol) in THF (100 µL) and DMSO (50 µL) was heated at 100° C. for 1 hr. The crude reaction was loaded onto a flash silica cartridge (1:1 hexanes/EtOAc eluent) to provide the title compound (40.2 mg, 89%). NOe experiments support the assigned regioisomer. Select $^1$H-NMR resonances and nOes (300 MHz, CDCl$_3$) δ 7.68 (d, J=13.7 Hz, 1H), 7.37 (d, J=8.4 Hz, 1H), 3.45 (tt, 1H), 3.31 (m, 4H). Irradiation of the diagnostic methine proton at δ 3.45 generates an nOe to the quinazoline C5 proton at δ 7.68, but not to the quinazoline C8 proton at δ 7.37. The C5 proton has a larger coupling constant than the C8 proton, indicating fluorine substitution at C6 of the quinazoline. Furthermore, irradiation of the C8 proton at δ 7.37 generates an nOe only to the morpholine C3 protons at δ 3.31, while irradiation of the C5 proton generates an nOe only to the methine proton at δ 3.45. These data indicate morpholine substitution at the quinazoline C7 carbon. LC/MS (ESI): calcd mass 416.2, found 417.3 (MH)$^+$.

b. 4-(6-Fluoro-7-morpholin-4-yl-quinazolin-4-yl)-piperidine-1-carboxylic acid (4-pyrrolidin-1-yl-phenyl)-amide

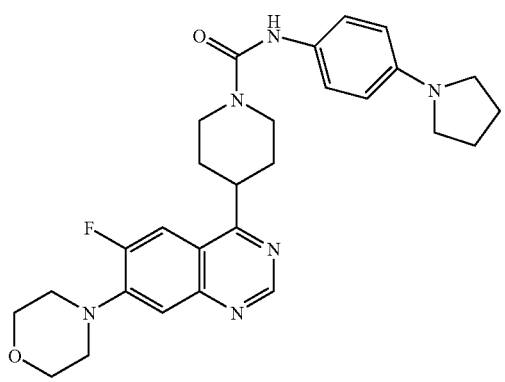

The title compound was prepared from 4-(6-Fluoro-7-morpholin-4-yl-quinazolin-4-yl)-piperidine-1-carboxylic acid tert-butyl ester, prepared as described in Example 210a, and (4-pyrrolidin-1-yl-phenyl)-carbamic acid 4-nitro-phenyl ester hydrochloride, prepared as described in Example 74a, using essentially the protocol given for Example 170c. $^1$H-NMR (400 MHz, CDCl$_3$) δ 9.12 (s, 1H), 7.70 (d, 1H), 7.38 (d, 1H), 7.18 (m, 2H), 6.52 (m, 2H), 6.24 (s, 1H), 4.26 (m, 2H), 3.93 (m, 4H), 3.51 (tt, 1H), 3.31 (m, 4H), 3.26 (m, 4H), 3.11 (td, 2H), 2.17-2.05 (m, 2H), 2.03-1.90 (m, 6H). LC/MS (ESI): calcd mass 504.3, found 505.3.

Example 211

4-(6-Methoxy-7-morpholin-4-yl-quinazolin-4-yl)-piperidine-1-carboxylic acid (4-pyrrolidin-1-yl-phenyl)-amide

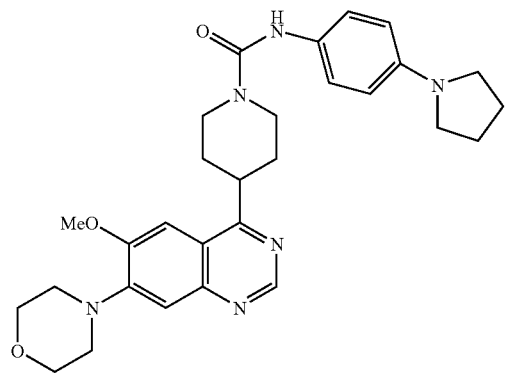

a. 4-(6-Methoxy-7-morpholin-4-yl-quinazolin-4-yl)-piperidine-1-carboxylic acid tert-butyl ester

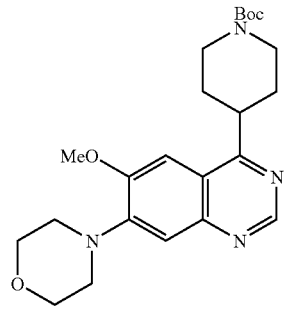

A mixture of 4-(6-Fluoro-7-morpholin-4-yl-quinazolin-4-yl)-piperidine-1-carboxylic acid tert-butyl ester (28.9 mg, 69.5 µmol), as prepared in Example 210a, DMSO (50 µL), and 10M KOMe/MeOH (140 µL, 140 µmol) was stirred in a sealed vial at 100° C. (aluminum block) for 13 hr. The crude reaction was then diluted with toluene and directly loaded onto a silica flash column (1:2 hexanes/EtOAc eluent) to provide the title compound (20.0 mg, 67%). NOe experiments support the assigned regioisomer. Select $^1$H-NMR resonances and nOes (300 MHz, CDCl$_3$) δ 7.36 (s, 1H), 7.25 (s, 1H), 4.05 (s, 3H), 3.51 (m, 1H). Irradiation of the diagnostic methine proton at δ 3.51 generates an nOe to the quinazoline C5 proton at δ 7.25, but not to the quinazoline C8 proton at δ 7.36. Irradiation of the methoxy protons at δ 4.05 generates an nOe to the C5 proton at δ 7.25, but not to the C8 proton at δ 7.36. This indicates methoxy substitution at C6 of the quinazoline. LC/MS (ESI): calcd mass 428.2, found 429.3 (MH)+.

b. 4-(6-Methoxy-7-morpholin-4-yl-quinazolin-4-yl)-piperidine-1-carboxylic acid (4-pyrrolidin-1-yl-phenyl)-amide

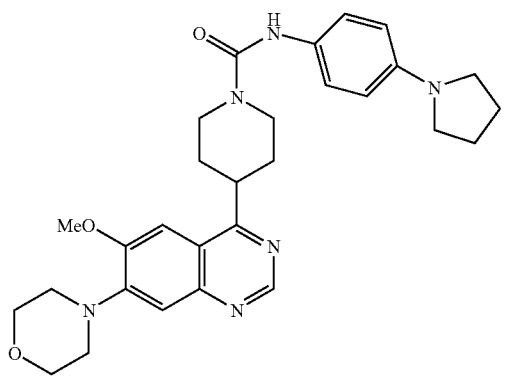

The title compound was prepared from 4-(6-methoxy-7-morpholin-4-yl-quinazolin-4-yl)-piperidine-1-carboxylic acid tert-butyl ester, prepared as described in Example 211a, and (4-pyrrolidin-1-yl-phenyl)-carbamic acid 4-nitro-phenyl ester hydrochloride, prepared as described in Example 74a, using essentially the protocol given for Example 170c. $^1$H-NMR (400 MHz, CDCl$_3$) δ 9.07 (s, 1H), 7.37 (s, 1H), 7.25 (s, 1H), 7.19 (m, 2H), 6.53 (m, 2H), 6.21 (s, 1H), 4.26 (m, 2H), 4.05 (s, 3H), 3.94 (m, 4H), 3.57 (tt, 1H), 3.31-3.24 (m, 8H), 3.15 (td, 2H), 2.20-2.08 (m, 2H), 2.03-1.94 (m, 6H). LC/MS (ESI): calcd mass 516.3, found 517.3 (MH)+.

Example 212

4-(6-Methoxy-7-morpholin-4-yl-quinazolin-4-yl)-piperidine-1-carboxylic acid (4-morpholin-4-yl-phenyl)-amide

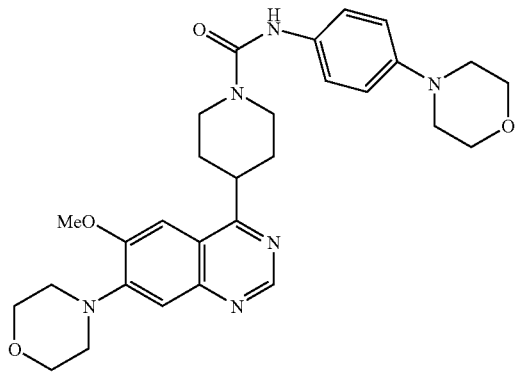

The title compound was prepared from 4-(6-methoxy-7-morpholin-4-yl-quinazolin-4-yl)-piperidine-1-carboxylic acid tert-butyl ester, prepared in Example 211a, and (4-morpholin-4-yl-phenyl)-carbamic acid 4-nitro-phenyl ester hydrochloride, prepared as described in Example 66a, using essentially the protocol given for Example 170c. $^1$H-NMR (400 MHz, CDCl$_3$) δ 9.06 (s, 1H), 7.37 (s, 1H), 7.28 (m, 2H), 7.25 (s, 1H), 6.89 (m, 2H), 6.35 (s, 1H), 4.27 (m, 2H), 4.06 (s, 3H), 3.94 (m, 4H), 3.86 (m, 4H), 3.59 (tt, 1H), 3.29 (m, 4H), 3.16 (td, 2H), 3.11 (m, 4H), 2.21-2.08 (m, 2H), 2.03-1.95 (m, 2H). LC/MS (ESI): calcd mass, 532.3, found 533.3 (MH)+.

Biological Activity
In Vitro Assays

The following representative in vitro assays were performed in determining the biological activities of compounds within the scope of the invention. They are given to illustrate the invention in a non-limiting fashion.

Inhibition of FLT3 enzyme activity, MV4-11 proliferation and Baf3-FLT3 phosphorylation exemplify the specific inhibition of the FLT3 enzyme and cellular processes that are dependent on FLT3 activity. Inhibition of Baf3 cell proliferation is used as a test of FLT3, c-Kit and TrkB independent cytotoxicity of compounds within the scope of the invention. All of the examples herein show significant and specific inhibition of the FLT3 kinase and FLT3-dependent cellular responses. Examples herein also show specific inhibition of the TrkB and c-kit kinase in an enzyme activity assay. The compounds of the present invention are also cell permeable.

FLT3 Fluorescence Polarization Kinase Assay

To determine the activity of the compounds of the present invention in an in vitro kinase assay, inhibition of the isolated kinase domain of the human FLT3 receptor (a.a. 571-993) was performed using the following fluorescence polarization (FP) protocol. The FLT3 FP assay utilizes the fluorescein-labeled phosphopeptide and the anti-phosphotyrosine antibody included in the Panvera Phospho-Tyrosine Kinase Kit (Green) supplied by Invitrogen. When FLT3 phosphorylates polyGlu$_4$Tyr, the fluorescein-labeled phosphopeptide is displaced from the anti-phosphotyrosine antibody by the phosphorylated poly Glu$_4$Tyr, thus decreasing the FP value. The FLT3 kinase reaction is incubated at room temperature for 30 minutes under the following conditions: 10 nM FLT3 571-993, 20 ug/mL poly Glu$_4$Tyr, 150 uM ATP, 5 mM MgCl$_2$, 1% compound in DMSO. The kinase reaction is stopped with the addition of EDTA. The fluorescein-labeled phosphopeptide and the anti-phosphotyrosine antibody are added and incubated for 30 minutes at room temperature.

All data points are an average of triplicate samples. Inhibition and IC$_{50}$ data analysis was done with GraphPad Prism using a non-linear regression fit with a multiparamater, sigmoidal dose-response (variable slope) equation. The IC$_{50}$ for kinase inhibition represents the dose of a compound that results in a 50% inhibition of kinase activity compared to DMSO vehicle control.

c-Kit Fluorescence Polarization Kinase Assay

The compounds of the present invention are also specific inhibitors of c-Kit. Selection of preferred compounds of Formula I for use as c-Kit inhibitors was performed in the following manner using an in vitro kinase assay to measure inhibition of the isolated kinase domain of the human c-kit receptor in a fluorescence polarization (FP) protocol. The c-kit assay utilized the fluorescein-labeled phosphopeptide and the anti-phosphotyrosine antibody included in the Panvera Phospho-Tyrosine Kinase Kit (Green) supplied by Invitrogen. When c-kit phosphorylated the poly Glu$_4$Tyr, the fluorescein-labeled phosphopeptide was displaced from the anti-phosphotyrosine antibody by the phosphorylated poly Glu$_4$Tyr, thus decreasing the FP value. The c-kit kinase reaction was incubated at room temperature for 45 minutes under the following conditions: 1 nM c-kit (ProQinase, lot SP005), 100 ug/mL poly Glu$_4$Tyr, 50 uM ATP, 5 mM MgCl$_2$, 1 mM DTT, 0.01% Tween-20, 1% DMSO or compound in 100 nM Hepes, pH 7.5. The kinase reaction was stopped with the addition of EDTA. The fluorescein-labeled phosphopeptide and the anti-phosphotyrosine antibody were added and incubated for 30 minutes at room temperature and fluorescence polarization was read. Data points were an average of triplicate samples. Inhibition and $IC_{50}$ data analysis were done with GraphPad Prism using a non-linear regression fit with a multiparamater, sigmoidal dose-response (variable slope) equation. The $IC_{50}$ for kinase inhibition represents the dose of a compound that resulted in a 50% inhibition of kinase activity compared to DMSO vehicle control.

Trk B Fluorescence Polarization Kinase Assay (TrkB $IC_{50}$ Data)

The compounds of the present invention are also specific inhibitors of TrkB. Selection of preferred compounds of Formula I for use as TrkB inhibitors was performed in the following manner. The TrkB assay utilized the fluorescein-labeled phosphopeptide and the anti-phosphotyrosine antibody included in the Panvera Phospho-Tyrosine Kinase Kit (Green) supplied by Invitrogen. When TrkB phosphorylated poly $Glu_4Tyr$, the fluorescein-labeled phosphopeptide was displaced from the anti-phosphotyrosine antibody by the phosphorylated poly $Glu_4Tyr$, thus decreasing the FP value. The TrkB kinase reaction was incubated at room temperature for 30 minutes under the following conditions: 50 nM TrkB (Upstate, catalog # 14-507M), 20 ug/mL poly $Glu_4Tyr$, 150 uM ATP, 5 mM $MgCl_2$, 1% compound in DMSO. The kinase reaction was stopped with the addition of EDTA. The fluorescein-labeled phosphopeptide and the anti-phosphotyrosine antibody were added and incubated for 30 minutes at room temperature. Data points were an average of triplicate samples. Inhibition and $IC_{50}$ data analysis were done with GraphPad Prism using a non-linear regression fit with a multiparamater, sigmoidal dose-response (variable slope) equation. The $IC_{50}$ for kinase inhibition represents the dose of a compound that resulted in a 50% inhibition of kinase activity compared to DMSO vehicle control.

Inhibition of MV4-11 and Baf3 Cell Proliferation

To assess the cellular potency of the compounds of the present invention, FLT3 specific growth inhibition was measured in the leukemic cell line MV4-11 (ATCC Number: CRL-9591). MV4-11 cells are derived from a patient with childhood acute myelomonocytic leukemia with an 11q23 translocation resulting in a MLL gene rearrangement and containing an FLT3-ITD mutation (AML subtype M4)(1,2). MV4-11 cells cannot grow and survive without active FLT3ITD.

The IL-3 dependent, murine b-cell lymphoma cell line, Baf3, were used as a control to confirm the selectivity of the compounds of the present invention by measuring non-specific growth inhibition by the compounds of the present invention.

To measure proliferation inhibition by test compounds, the luciferase based CellTiterGlo reagent (Promega), which quantifies total cell number based on total cellular ATP concentration, was used. Cells are plated at 10,000 cells per well in 100 ul of in RPMI media containing penn/strep, 10% FBS and 1 ng/ml GM-CSF or 1 ng/ml IL-3 for MV4-11 and Baf3 cells respectively.

Compound dilutions or 0.1% DMSO (vehicle control) are added to cells and the cells are allowed to grow for 72 hours at standard cell growth conditions (37° C., 5% $CO_2$). For activity measurements in MV4-11 cells grown in 50% plasma, cells were plated at 10,000 cells per well in a 1:1 mixture of growth media and human plasma (final volume of 100 µL). To measure total cell growth an equal volume of CellTiterGlo reagent was added to each well, according to the manufacturer's instructions, and luminescence was quantified. Total cell growth was quantified as the difference in luminescent counts (relative light units, RLU) of cell number at Day 0 compared to total cell number at Day 3 (72 hours of growth and/or compound treatment). One hundred percent inhibition of growth is defined as an RLU equivalent to the Day 0 reading. Zero percent inhibition was defined as the RLU signal for the DMSO vehicle control at Day 3 of growth. All data points are an average of triplicate samples. The $IC_{50}$ for growth inhibition represents the dose of a compound that results in a 50% inhibition of total cell growth at day 3 of the DMSO vehicle control. Inhibition and $IC_{50}$ data analysis was done with GraphPad Prism using a non-linear regression fit with a multiparamater, sigmoidal dose-response (variable slope) equation.

MV4-11 cells express the FLT3 internal tandem duplication mutation, and thus are entirely dependent upon FLT3 activity for growth. Strong activity against the MV4-11 cells is anticipated to be a desirable quality of the invention. In contrast, the Baf3 cell proliferation is driven by the cytokine IL-3 and thus are used as a non-specific toxicity control for test compounds. All compound examples in the present invention showed <50% inhibition at a 3 uM dose (data is not included), suggesting that the compounds are not cytotoxic and have good selectivity for FLT3.

Cell-Based FLT3 Receptor Elisa

Specific cellular inhibition of FLT ligand-induced wild-type FLT3 phosphorylation was measured in the following manner: Baf3 FLT3 cells overexpressing the FLT3 receptor were obtained from Dr. Michael Heinrich (Oregon Health and Sciences University). The Baf3 FLT3 cell lines were created by stable transfection of parental Baf3 cells (a murine B cell lymphoma line dependent on the cytokine IL-3 for growth) with wild-type FLT3. Cells were selected for their ability to grow in the absence of IL-3 and in the presence of FLT3 ligand.

Baf3 cells were maintained in RPMI 1640 with 10% FBS, penn/strep and 10 ng/ml FLT ligand at 37° C., 5% $CO_2$. To measure direct inhibition of the wild-type FLT3 receptor activity and phosphorylation a sandwich ELISA method was developed similar to those developed for other RTKs (3,4). 200 µL of Baf3FLT3 cells ($1\times10^6$/mL) were plated in 96 well dishes in RPMI 1640 with 0.5% serum and 0.01 ng/mL IL-3 for 16 hours prior to 1 hour compound or DMSO vehicle incubation. Cells were treated with 100 ng/mL Flt ligand (R&D Systems Cat# 308-FK) for 10 min. at 37° C. Cells were pelleted, washed and lysed in 100 ul lysis buffer (50 mM Hepes, 150 mM NaCl, 10% Glycerol, 1% Triton-X-100, 10 mM NaF, 1 mM EDTA, 1.5 mM $MgCl_2$, 10 mM NaPyrophosphate) supplemented with phosphatase (Sigma Cat# P2850) and protease inhibitors (Sigma Cat #P8340). Lysates were cleared by centrifugation at 1000×g for 5 minutes at 4° C. Cell lysates were transferred to white wall 96 well microtiter (Costar #9018) plates coated with 50 ng/well anti-FLT3 antibody (Santa Cruz Cat# sc-480) and blocked with SeaBlock reagent (Pierce Cat#37527). Lysates were incubated at 4° C. for 2 hours. Plates were washed 3× with 200 ul/well PBS/0.1% Triton-X-100. Plates were then incubated with 1:8000 dilution of HRP-conjugated anti-phosphotyrosine antibody (Clone 4G10, Upstate Biotechnology Cat#16-105) for 1 hour at room temperature. Plates were washed 3× with 200 ul/well PBS/0.1% Triton-X-100. Signal detection with Super Signal Pico reagent (Pierce Cat#37070) was done according to manufacturer's instruction with a Berthold microplate luminometer. All data points are an average of triplicate samples. The total relative light units (RLU) of Flt ligand stimulated FLT3 phosphorylation in the presence of 0.1% DMSO control was defined as 0% inhibition and 100% inhibition was the total RLU of lysate in the basal state. Inhibition and $IC_{50}$ data analysis was done with GraphPad Prism using a non-linear regression fit with a multiparamater, sigmoidal dose-response (variable slope) equation.

BIOLOGICAL PROCEDURE REFERENCES

1. Drexler H G. *The Leukemia-Lymphoma Cell Line Factsbook.* Academic Pres: San Diego, Calif., 2000.
2. Quentmeier H, Reinhardt J, Zaborski M, Drexler H G. FLT3 mutations in acute myeloid leukemia cell lines. Leukemia. 2003 January; 17:120-124.
3. Sadick, M D, Sliwkowski, M X, Nuijens, A, Bald, L, Chiang, N, Lofgren, J A, Wong W L T. Analysis of Heregulin-Induced ErbB2 Phosphorylation with a High-Throughput Kinase Receptor Activation Enzyme-Linked Immunsorbent Assay, Analytical Biochemistry. 1996; 235:207-214.
4. Baumann C A, Zeng L, Donatelli R R, Maroney A C. Development of a quantitative, high-throughput cell-based enzyme-linked immunosorbent assay for detection of colony-stimulating factor-1 receptor tyrosine kinase inhibitors. J Biochem Biophys Methods. 2004; 60:69-79.

Biological Data

Biological Data for FLT3

The activity of representative compounds of the present invention is presented in the charts below. All activities are in µM and have the following uncertainties: FLT3 kinase: ±10%; MV4-11 and Baf3-FLT3: ±20%.

| | Compound | FLT3 Kinase (uM) | MV4-11 (uM) | BaF3 ELISA (uM) |
|---|---|---|---|---|
| 1 | 4-(6,7-Dimethoxy-quinazolin-4-yl)-piperidine-1-carboxylic acid (4-isopropoxy-phenyl)-amide | 0.046 | 0.088 | 0.017 |
| 2 | 4-(6,7-Dimethoxy-quinazolin-4-yl)-piperidine-1-carboxylic acid (4-iodo-phenyl)-amide | 0.210 | 0.752 | 0.890 |
| 3 | 4-(6,7-Dimethoxy-quinazolin-4-yl)-piperidine-1-carboxylic acid (4-imidazol-1-yl-phenyl)-amide | 3.900 | 0.636 | 0.938 |
| 4 | 4-(6,7-Dimethoxy-quinazolin-4-yl)-piperidine-1-carboxylic acid (4-isopropyl-phenyl)-amide | 0.009 | 0.086 | 0.056 |
| 5 | 4-Quinolin-4-yl-piperidine-1-carboxylic acid (4-isopropyl-phenyl)-amide | 0.094 | 0.290 | nd[1] |
| 6 | 4-Quinolin-4-yl-piperidine-1-carboxylic acid (4-isopropoxy-phenyl)-amide | 0.084 | 0.280 | 0.040 |
| 7 | 4-Quinazolin-4-yl-piperidine-1-carboxylic acid (4-isopropyl-phenyl)-amide | 0.055 | 0.232 | 0.367 |
| 8 | 4-Quinazolin-4-yl-piperidine-1-carboxylic acid (4-isopropoxy-phenyl)-amide | 0.200 | 0.533 | 0.851 |
| 9 | 2-[4-(6,7-Dimethoxy-quinazolin-4-yl)-piperidin-1-yl]-N-(4-isopropyl-phenyl)-acetamide | 0.013 | 0.029 | 0.007 |
| 10 | 2-[4-(6,7-Dimethoxy-quinazolin-4-yl)-piperidin-1-yl]-N-(4-isopropoxy-phenyl)-acetamide | 0.042 | 0.171 | 0.031 |
| 11 | 4-(6-Iodo-quinazolin-4-yl)-piperidine-1-carboxylic acid (4-isopropoxy-phenyl)-amide | 0.046 | 0.460 | 1.400 |
| 12 | 4-[6-(3-Hydroxy-prop-1-ynyl)-quinazolin-4-yl]-piperidine-1-carboxylic acid (4-isopropoxy-phenyl)-amide | 0.032 | 0.149 | 0.036 |
| 13 | 4-[6-(3-Diethylamino-prop-1-ynyl)-quinazolin-4-yl]-piperidine-1-carboxylic acid (4-isopropoxy-phenyl)-amide | 0.072 | 0.059 | 0.027 |
| 14 | 4-[6-(3-Piperidin-1-yl-prop-1-ynyl)-quinazolin-4-yl]-piperidine-1-carboxylic acid (4-isopropoxy-phenyl)-amide | 0.053 | 0.023 | 0.186 |
| 15 | 4-[6-(3-Morpholin-4-yl-prop-1-ynyl)-quinazolin-4-yl]-piperidine-1-carboxylic acid (4-isopropoxy-phenyl)-amide | 0.046 | 0.030 | 0.055 |
| 16 | N-(4-Isopropyl-phenyl)-2-(4-quinazolin-4-yl-piperidin-1-yl)-acetamide | 0.056 | 0.559 | 0.336 |
| 17 | 4-(6,7-Dimethoxy-quinazolin-4-yl)-piperidine-1-carboxylic acid (6-cyclobutoxy-pyridin-3-yl)-amide | 0.016 | 0.031 | 0.292 |
| 18 | 4-(6,7-Dimethoxy-quinazolin-4-yl)-piperidine-1-carboxylic acid (4-morpholin-4-yl-phenyl)-amide | 0.062 | 0.137 | 0.104 |
| 19 | 4-(6,7-Dimethoxy-quinazolin-4-yl)-piperidine-1-carboxylic acid (4-piperidin-1-yl-phenyl)-amide | 0.017 | 0.01 | 0.017 |
| 20 | 4-(6,7-Dimethoxy-quinazolin-4-yl)-piperidine-1-carboxylic acid [4-(4-methyl-piperazin-1-yl)-phenyl]-amide | 6.600 | 1.100 | >3 |
| 21 | 4-(6,7-Dimethoxy-quinazolin-4-yl)-piperidine-1-carboxylic acid (4-cyclohexyl-phenyl)-amide | 0.007 | 0.027 | 0.002 |
| 22 | 4-(6,7-Dimethoxy-quinazolin-4-yl)-piperidine-1-carboxylic acid (4-hydroxymethyl-phenyl)-amide | 4.400 | >10 | 5.1 |
| 23 | 4-(6,7-Dimethoxy-quinazolin-4-yl)-piperidine-1-carboxylic acid (1H-indol-5-yl)-amide | 0.390 | 2.7 | 0.9 |
| 24 | 4-(6,7-Dimethoxy-quinazolin-4-yl)-piperidine-1-carboxylic acid benzothiazol-6-ylamide | 5.500 | 3.7 | 2.6 |
| 25 | 4-(6,7-Dimethoxy-quinazolin-4-yl)-piperidine-1-carboxylic acid (4-acetylamino-phenyl)-amide | 6.100 | >10 | >10 |

-continued

| | Compound | FLT3 Kinase (uM) | MV4-11 (uM) | BaF3 ELISA (uM) |
|---|---|---|---|---|
| 26 | 4-(6,7-Dimethoxy-quinazolin-4-yl)-piperidine-1-carboxylic acid (4-dimethylamino-phenyl)-amide | 0.200 | 0.204 | 0.109 |
| 27 | 4-(6,7-Dimethoxy-quinazolin-4-yl)-piperidine-1-carboxylic acid (2,3-dihydro-benzofuran-5-yl)-amide | 2.000 | 4.1 | nd |
| 28 | 1-[4-(6,7-Dimethoxy-quinazolin-4-yl)-piperidin-1-yl]-2-(4-isopropyl-phenyl)-ethanone | 0.008 | 0.015 | 0.002 |
| 29 | 4-(7-Chloro-quinazolin-4-yl)-piperidine-1-carboxylic acid (4-isopropoxy-phenyl)-amide | 0.150 | 0.315 | 0.050 |
| 30 | 4-(7-Chloro-quinazolin-4-yl)-piperidine-1-carboxylic acid (4-isopropyl-phenyl)-amide | 0.035 | 0.380 | 0.083 |
| 31 | 4-(7-Methoxy-quinazolin-4-yl)-piperidine-1-carboxylic acid (4-isopropoxy-phenyl)-amide | 0.021 | 0.085 | 0.055 |
| 32 | 4-(7-Methoxy-quinazolin-4-yl)-piperidine-1-carboxylic acid (4-isopropyl-phenyl)-amide | 0.011 | 0.235 | 0.035 |
| 33 | 4-[7-(3-Piperidin-1-yl-propoxy)-quinazolin-4-yl]-piperidine-1-carboxylic acid (4-isopropoxy-phenyl)-amide | 0.011 | 0.050 | 0.011 |
| 34 | 4-[7-(2-Piperidin-1-yl-ethoxy)-quinazolin-4-yl]-piperidine-1-carboxylic acid (4-isopropoxy-phenyl)-amide | 0.049 | 0.095 | 0.079 |
| 35 | 4-[7-(2-Diethylamino-ethoxy)-quinazolin-4-yl]-piperidine-1-carboxylic acid (4-isopropoxy-phenyl)-amide | 0.047 | 0.095 | 0.060 |
| 36 | 4-[7-(3-Diethylamino-propoxy)-quinazolin-4-yl]-piperidine-1-carboxylic acid (4-isopropoxy-phenyl)-amide | 0.018 | 0.042 | 0.018 |
| 37 | 4-[7-(2-Morpholin-4-yl-ethoxy)-quinazolin-4-yl]-piperidine-1-carboxylic acid (4-isopropoxy-phenyl)-amide | 0.007 | 0.165 | 0.051 |
| 38 | 4-[7-(3-Morpholin-4-yl-propoxy)-quinazolin-4-yl]-piperidine-1-carboxylic acid (4-isopropoxy-phenyl)-amide | 0.006 | 0.016 | 0.015 |
| 39 | 4-{7-[3-(4-Methyl-piperazin-1-yl)-propoxy]-quinazolin-4-yl}-piperidine-1-carboxylic acid (4-isopropoxy-phenyl)-amide | 0.015 | 0.014 | 0.008 |
| 40 | 4-(6,7-Dimethoxy-quinazolin-4-yl)-piperidine-1-carboxylic acid [4-(2-methoxy-ethoxy)-phenyl]-amide | 0.910 | 2.200 | 1.500 |
| 41 | 4-(6,7-Dimethoxy-quinazolin-4-yl)-piperidine-1-carboxylic acid (4-methoxy-phenyl)-amide | 0.730 | 3.300 | nd |
| 42 | 4-(6,7-Dimethoxy-quinazolin-4-yl)-piperidine-1-carboxylic acid cyclohexylamide | >10 | >10 | nd |
| 43 | 4-(6,7-Dimethoxy-quinazolin-4-yl)-piperidine-1-carboxylic acid (4-butyl-phenyl)-amide | 0.024 | 0.197 | 0.059 |
| 44 | 4-(6,7-Dimethoxy-quinazolin-4-yl)-piperidine-1-carboxylic acid (4-ethoxy-phenyl)-amide | 0.15 | 0.725 | 0.163 |
| 45 | 4-(6,7-Dimethoxy-quinazolin-4-yl)-piperidine-1-carboxylic acid phenylamide | 3.700 | 16.700 | >3 |
| 46 | 4-(6,7-Dimethoxy-quinazolin-4-yl)-piperidine-1-carboxylic acid (4-trifluoromethyl-phenyl)-amide | 0.990 | 2.000 | nd |
| 47 | 4-(6,7-Dimethoxy-quinazolin-4-yl)-piperidine-1-carboxylic acid (4-phenoxy-phenyl)-amide | 0.035 | 0.122 | 0.008 |
| 48 | 4-(6,7-Dimethoxy-quinazolin-4-yl)-piperidine-1-carboxylic acid p-tolylamide | 1.600 | 1.800 | nd |
| 49 | 4-(6,7-Dimethoxy-quinazolin-4-yl)-piperidine-1-carboxylic acid (4-chloro-phenyl)-amide | nd | 7.000 | >3 |
| 50 | 4-(6,7-Dimethoxy-quinazolin-4-yl)-piperidine-1-carboxylic acid (4-trifluoromethoxy-phenyl)-amide | 0.083 | 0.131 | nd |
| 51 | 4-(6,7-Dimethoxy-quinazolin-4-yl)-piperidine-1-carboxylic acid (4-difluoromethoxy-phenyl)-amide | 0.160 | 0.306 | 0.542 |
| 52 | 4-(6,7-Dimethoxy-quinazolin-4-yl)-piperidine-1-carboxylic acid (4-sec-butyl-phenyl)-amide | 0.019 | 0.007 | 0.007 |
| 53 | 4-(6,7-Dimethoxy-quinazolin-4-yl)-piperidine-1-carboxylic acid (4-tert-butyl-phenyl)-amide | 0.015 | 0.048 | 0.005 |
| 54 | 4-(6,7-Dimethoxy-quinazolin-4-yl)-piperidine-1-carboxylic acid (4-tert-butyl-cyclohexyl)-amide | 0.170 | 0.224 | 0.266 |
| 55 | 4-(6,7-Dimethoxy-quinazolin-4-yl)-piperidine-1-carboxylic acid [4-(1-hydroxy-ethyl)-phenyl]-amide | 1.100 | 2.6 | 1 |
| 56 | 4-(6,7-Dimethoxy-quinazolin-4-yl)-piperidine-1-carboxylic acid (6-isopropoxy-pyridin-3-yl)-amide | 0.030 | 0.189 | 0.010 |

-continued

| | Compound | FLT3 Kinase (uM) | MV4-11 (uM) | BaF3 ELISA (uM) |
|---|---|---|---|---|
| 57 | 4-(6,7-Dimethoxy-quinazolin-4-yl)-piperidine-1-carboxylic acid [4-(2-oxo-pyrrolidin-1-yl)-phenyl]-amide | 0.700 | 1.2 | 0.381 |
| 58 | 4-(6,7-Dimethoxy-quinazolin-4-yl)-piperidine-1-carboxylic acid (4-pyrimidin-5-yl-phenyl)-amide | 2.000 | 2 | 0.265 |
| 59 | 4-(6,7-Dimethoxy-quinazolin-4-yl)-piperidine-1-carboxylic acid (4-furan-2-yl-phenyl)-amide | 0.220 | 0.269 | 0.027 |
| 60 | 4-(6,7-Dimethoxy-quinazolin-4-yl)-piperidine-1-carboxylic acid [4-(6-chloro-pyridin-3-yl)-phenyl]-amide | 0.360 | 1.4 | 0.046 |
| 61 | 4-(4-{[4-(6,7-Dimethoxy-quinazolin-4-yl)-piperidine-1-carbonyl]-amino}-phenyl)-3,6-dihydro-2H-pyridine-1-carboxylic acid tert-butyl ester | 8.500 | 6.000 | 1.800 |
| 62 | 4-(6,7-Dimethoxy-quinazolin-4-yl)-piperidine-1-carboxylic acid [4-(1,2,3,6-tetrahydro-pyridin-4-yl)-phenyl]-amide | >10 | 7.500 | 0.976 |
| 63 | 4-(4-{[4-(6,7-Dimethoxy-quinazolin-4-yl)-piperidine-1-carbonyl]-amino}-phenyl)-piperidine-1-carboxylic acid tert-butyl ester | 2.000 | 4.100 | 0.762 |
| 64 | 4-(6,7-Dimethoxy-quinazolin-4-yl)-piperidine-1-carboxylic acid (4-piperidin-4-yl-phenyl)-amide | nd | 0.330 | 0.357 |
| 65 | 4-[7-(3-Methanesulfonylamino-propoxy)-quinazolin-4-yl]-piperidine-1-carboxylic acid (4-isopropoxy-phenyl)-amide | 0.019 | 0.0270 | 0.037 |
| 66 | 4-[7-(3-Methanesulfonylamino-propoxy)-quinazolin-4-yl]-piperidine-1-carboxylic acid (4-morpholin-4-yl-phenyl)-amide | 0.018 | 0.014 | 0.013 |
| 67 | 4-{7-[3-(2-Oxo-pyrrolidin-1-yl)-propoxy]-quinazolin-4-yl}-piperidine-1-carboxylic acid (4-isopropoxy-phenyl)-amide | 0.003 | 0.009 | 0.003 |
| 68 | 4-{7-[3-(2-Oxo-pyrrolidin-1-yl)-propoxy]-quinazolin-4-yl}-piperidine-1-carboxylic acid (4-morpholin-4-yl-phenyl)-amide | 0.037 | 0.030 | 0.029 |
| 69 | 4-(6,7-Dimethoxy-quinazolin-4-yl)-piperidine-1-carboxylic acid (6-cyclopentyloxy-pyridin-3-yl)-amide | 0.076 | 0.059 | 0.029 |
| 70 | 4-(6,7-Dimethoxy-quinazolin-4-yl)-piperidine-1-carboxylic acid (4-azepan-1-yl-phenyl)-amide | 0.027 | 0.008 | nd |
| 71 | 4-(6,7-Dimethoxy-quinazolin-4-yl)-piperidine-1-carboxylic acid (3-chloro-4-piperidin-1-yl-phenyl)-amide | 0.139 | 0.110 | nd |
| 72 | 4-{7-[3-(2-Oxo-pyrrolidin-1-yl)-propoxy]-quinazolin-4-yl}-piperidine-1-carboxylic acid (6-morpholin-4-yl-pyridin-3-yl)-amide | 0.027 | 0.054 | 0.028 |
| 73 | 4-{7-[3-(4-Methyl-piperazin-1-yl)-propoxy]-quinazolin-4-yl}-piperidine-1-carboxylic acid (4-morpholin-4-yl-phenyl)-amide | 0.003 | 0.040 | 0.092 |
| 74 | 4-{7-[2-(2-Oxo-pyrrolidin-1-yl)-ethoxy]-quinazolin-4-yl}-piperidine-1-carboxylic acid (4-pyrrolidin-1-yl-phenyl)-amide | 0.001 | 0.04 | 0.012 |
| 75 | 4-[7-(3-Piperidin-1-yl-propoxy)-quinazolin-4-yl]-piperidine-1-carboxylic acid (4-morpholin-4-yl-phenyl)-amide | 0.049 | 0.07 | 0.084 |
| 76 | 4-{6-[3-(4-Methyl-piperazin-1-yl)-propoxy]-quinazolin-4-yl}-piperidine-1-carboxylic acid (4-isopropoxy-phenyl)-amide | 0.251 | 0.179 | 0.096 |
| 77 | 4-[7-(3-Hydroxy-propoxy)-quinazolin-4-yl]-piperidine-1-carboxylic acid (4-morpholin-4-yl-phenyl)-amide | 0.103 | 0.139 | 0.098 |
| 78 | 4-[7-(3-Methoxy-propoxy)-quinazolin-4-yl]-piperidine-1-carboxylic acid (4-morpholin-4-yl-phenyl)-amide | 0.225 | 0.081 | 0.02 |
| 79 | 4-{7-[2-(2-Oxo-oxazolidin-3-yl)-ethoxy]-quinazolin-4-yl}-piperidine-1-carboxylic acid (4-isopropoxy-phenyl)-amide | 0.058 | 0.044 | 0.017 |
| 80 | 4-{7-[3-(4-Methyl-piperazin-1-yl)-propoxy]-quinazolin-4-yl}-piperidine-1-carboxylic acid (6-morpholin-4-yl-pyridin-3-yl)-amide | 0.004 | 0.052 | 0.019 |
| 81 | 4-{7-[3-(4-Methyl-piperazin-1-yl)-propoxy]-quinazolin-4-yl}-piperidine-1-carboxylic acid (3-fluoro-4-morpholin-4-yl-phenyl)-amide | 0.007 | 0.07 | 0.028 |
| 82 | 4-{7-[3-(4-Methyl-piperazin-1-yl)-propoxy]-quinazolin-4-yl}-piperidine-1-carboxylic acid (6-cyclopentyloxy-pyridin-3-yl)-amide | 0.001 | 0.018 | 0.063 |

-continued

| | Compound | FLT3 Kinase (uM) | MV4-11 (uM) | BaF3 ELISA (uM) |
|---|---|---|---|---|
| 83 | 4-{7-[2-(2-Oxo-pyrrolidin-1-yl)-ethoxy]-quinazolin-4-yl}-piperidine-1-carboxylic acid (6-morpholin-4-yl-pyridin-3-yl)-amide | 0.02 | 0.112 | 0.037 |
| 84 | 4-{7-[2-(2-Oxo-pyrrolidin-1-yl)-ethoxy]-quinazolin-4-yl}-piperidine-1-carboxylic acid (2-pyrrolidin-1-yl-pyrimidin-5-yl)-amide | 0.041 | 0.074 | 0.08 |
| 85 | 4-{7-[2-(2-Oxo-pyrrolidin-1-yl)-ethoxy]-quinazolin-4-yl}-piperidine-1-carboxylic acid (4-morpholin-4-yl-phenyl)-amide | 0.027 | 0.058 | 0.075 |
| 86 | 4-[7-(3-Methanesulfonylamino-propoxy)-quinazolin-4-yl]-piperidine-1-carboxylic acid (6-pyrrolidin-1-yl-pyridin-3-yl)-amide | 0.001 | 0.017 | 0.009 |
| 87 | 4-[7-(3-Methanesulfonylamino-propoxy)-quinazolin-4-yl]-piperidine-1-carboxylic acid (6-morpholin-4-yl-pyridin-3-yl)-amide | 0.032 | 0.069 | 0.023 |
| 88 | 4-[7-(3-Methanesulfonylamino-propoxy)-quinazolin-4-yl]-piperidine-1-carboxylic acid (6-cyclopentyloxy-pyridin-3-yl)-amide | 0.002 | 0.037 | 0.03 |
| 89 | 4-{7-[3-(2-Oxo-pyrrolidin-1-yl)-propoxy]-quinazolin-4-yl}-piperidine-1-carboxylic acid (6-pyrrolidin-1-yl-pyridin-3-yl)-amide | 0.002 | 0.024 | 0.001 |
| 90 | 4-{7-[3-(2-Oxo-pyrrolidin-1-yl)-propoxy]-quinazolin-4-yl}-piperidine-1-carboxylic acid (2-pyrrolidin-1-yl-pyrimidin-5-yl)-amide | 0.073 | 0.187 | 0.279 |
| 91 | 4-{7-[2-(2-Oxo-oxazolidin-3-yl)-ethoxy]-quinazolin-4-yl}-piperidine-1-carboxylic acid (6-morpholin-4-yl-pyridin-3-yl)-amide | 0.003 | 0.098 | 0.006 |
| 92 | 4-{7-[2-(2-Oxo-oxazolidin-3-yl)-ethoxy]-quinazolin-4-yl}-piperidine-1-carboxylic acid (6-pyrrolidin-1-yl-pyridin-3-yl)-amide | 0.0002 | 0.021 | 0.012 |
| 93 | 4-[7-(1-Methyl-piperidin-4-ylmethoxy)-quinazolin-4-yl]-piperidine-1-carboxylic acid (4-isopropoxy-phenyl)-amide | 0.0002 | 0.009 | 0.001 |
| 94 | 4-[7-(1-Methyl-piperidin-4-ylmethoxy)-quinazolin-4-yl]-piperidine-1-carboxylic acid (4-morpholin-4-yl-phenyl)-amide | 0.001 | 0.06 | 0.011 |
| 95 | 4-[7-(2-Morpholin-4-yl-ethoxy)-quinazolin-4-yl]-piperidine-1-carboxylic acid (6-pyrrolidin-1-yl-pyridin-3-yl)-amide | 0.008 | 0.056 | 0.025 |
| 96 | 4-[7-(2-Morpholin-4-yl-ethoxy)-quinazolin-4-yl]-piperidine-1-carboxylic acid (4-morpholin-4-yl-phenyl)-amide | 0.036 | 0.235 | 0.243 |
| 97 | 4-{7-[2-(4-Acetyl-piperazin-1-yl)-ethoxy]-quinazolin-4-yl}-piperidine-1-carboxylic acid (4-morpholin-4-yl-phenyl)-amide | 0.028 | 0.262 | 0.036 |
| 98 | 4-[7-(2-Piperidin-2-yl-ethoxy)-quinazolin-4-yl]-piperidine-1-carboxylic acid (4-morpholin-4-yl-phenyl)-amide | 0.027 | 0.277 | 0.086 |
| 99 | 4-[7-(1-Methyl-piperidin-4-ylmethoxy)-quinazolin-4-yl]-piperidine-1-carboxylic acid (6-pyrrolidin-1-yl-pyridin-3-yl)-amide | 0.001 | 0.058 | 0.014 |
| 100 | 4-(7-Dimethylamino-quinazolin-4-yl)-piperidine-1-carboxylic acid (4-isopropoxy-phenyl)-amide | 0.08 | 0.036 | 0.008 |
| 101 | 4-{6-[3-(2-Oxo-pyrrolidin-1-yl)-propoxy]-quinazolin-4-yl}-piperidine-1-carboxylic acid (4-isopropoxy-phenyl) | 0.0008 | 0.034 | 0.042 |
| 102 | 4-{7-[3-(4-Methyl-piperazin-1-yl)-propylamino]-quinazolin-4-yl}-piperidine-1-carboxylic acid (4-isopropoxy-phenyl)-amide | 0.005 | 0.018 | 0.005 |
| 103 | 4-[7-(4-Methyl-piperazin-1-yl)-quinazolin-4-yl]-piperidine-1-carboxylic acid (4-isopropoxy-phenyl)-amide | 0.001 | 0.025 | 0.013 |
| 104 | 4-{7-[3-(4-Methyl-piperazin-1-yl)-propoxy]-quinazolin-4-yl}-piperidine-1-carboxylic acid (6-pyrrolidin-1-yl-pyridin-3-yl)-amide | 0.011 | 0.012 | 0.016 |
| 105 | 4-{7-[3-(4-Methyl-piperazin-1-yl)-propoxy]-quinazolin-4-yl}-piperidine-1-carboxylic acid (2-pyrrolidin-1-yl-pyrimidin-5-yl)-amide | 0.064 | 0.091 | 0.098 |
| 106 | 4-{7-[3-(4-Methyl-piperazin-1-yl)-propoxy]-quinazolin-4-yl}-piperidine-1-carbothioic acid (6-morpholin-4-yl-pyridin-3-yl)-amide | 2.2 | 1 | nd |
| 107 | 4-[7-(1-Methyl-piperidin-4-ylmethoxy)-quinazolin-4-yl]-piperidine-1-carboxylic acid (6-cyclobutoxy-pyridin-3-yl)-amide | 0.001 | 0.023 | 0.021 |

-continued

| | Compound | FLT3 Kinase (uM) | MV4-11 (uM) | BaF3 ELISA (uM) |
|---|---|---|---|---|
| 108 | 4-[7-(1-Methyl-piperidin-4-ylmethoxy)-quinazolin-4-yl]-piperidine-1-carboxylic acid (6-morpholin-4-yl-pyridin-3-yl)-amide | 0.004 | 0.173 | 0.053 |
| 109 | 4-[7-(1-Methyl-piperidin-4-ylmethoxy)-quinazolin-4-yl]-piperidine-1-carboxylic acid (4-pyrrolidin-1-yl-phenyl)-amide | 0.035 | 0.018 | 0.01 |
| 110 | 4-[7-(3-[1,2,4]Triazol-4-yl-propoxy)-quinazolin-4-yl]-piperidine-1-carboxylic acid (6-morpholin-4-yl-pyridin-3-yl)-amide | 0.028 | 0.893 | nd |
| 111 | 4-{7-[3-(2-Dimethylamino-3,4-dioxo-cyclobut-1-enylamino)-propoxy]-quinazolin-4-yl}-piperidine-1-carboxylic acid (6-pyrrolidin-1-yl-pyridin-3-yl)-amide | 0.019 | 0.625 | nd |
| 112 | Morpholine-4-carboxylic acid (3-{4-[1-(6-pyrrolidin-1-yl-pyridin-3-ylcarbamoyl)-piperidin-4-yl]-quinazolin-7-yloxy}-propyl)-amide | 0.005 | 0.098 | 0.079 |
| 113 | Morpholine-4-carboxylic acid (3-{4-[1-(6-morpholin-4-yl-pyridin-3-ylcarbamoyl)-piperidin-4-yl]-quinazolin-7-yloxy}-propyl)-amide | 0.132 | 0.36 | nd |
| 114 | 4-[7-(3-[1,2,4]Triazol-4-yl-propoxy)-quinazolin-4-yl]-piperidine-1-carboxylic acid (6-pyrrolidin-1-yl-pyridin-3-yl)-amide | 0.009 | 0.178 | nd |
| 115 | 4-{7-[3-(4-Ethyl-piperazin-1-yl)-propoxy]-quinazolin-4-yl}-piperidine-1-carboxylic acid (4-morpholin-4-yl-phenyl)-amide | 0.016 | 0.104 | 0.009 |
| 116 | 4-(7-{3-[4-(2-Hydroxy-ethyl)-piperazin-1-yl]-propoxy}-quinazolin-4-yl)-piperidine-1-carboxylic acid (4-morpholin-4-yl-phenyl)-amide | 0.014 | 0.139 | 0.025 |
| 117 | 4-{7-[3-(4-Acetyl-piperazin-1-yl)-propoxy]-quinazolin-4-yl}-piperidine-1-carboxylic acid (4-morpholin-4-yl-phenyl)-amide | 0.094 | 0.171 | 0.088 |
| 118 | 4-{7-[3-(4-Methanesulfonyl-piperazin-1-yl)-propoxy]-quinazolin-4-yl}-piperidine-1-carboxylic acid (4-morpholin-4-yl-phenyl)-amide | 0.008 | 0.09 | 0.01 |
| 119 | (S)-4-{7-[3-(2-Hydroxymethyl-pyrrolidin-1-yl)-propoxy]-quinazolin-4-yl}-piperidine-1-carboxylic acid (4-morpholin-4-yl-phenyl)-amide | 0.047 | 0.053 | 0.037 |
| 120 | 4-(3-{4-[1-(4-Morpholin-4-yl-phenylcarbamoyl)-piperidin-4-yl]-quinazolin-7-yloxy}-propyl)-piperazine-1-carboxylic acid dimethylamide | 0.036 | 0.22 | 0.023 |
| 121 | Methanesulfonic acid 3-{4-[1-(4-isopropoxy-phenylcarbamoyl)-piperidin-4-yl]-quinazolin-7-yloxy}-propyl ester | 0.003 | 0.027 | 0.117 |
| 122 | Methanesulfonic acid 3-{4-[1-(4-morpholin-4-yl-phenylcarbamoyl)-piperidin-4-yl]-quinazolin-7-yloxy}-propyl ester | 0.023 | 0.136 | 0.11 |
| 123 | 4-[7-(3-Piperazin-1-yl-propoxy)-quinazolin-4-yl]-piperidine-1-carboxylic acid (4-morpholin-4-yl-phenyl)-amide | 0.008 | nd | 0.002 |
| 124 | 4-[7-(3-Pyrrolidin-1-yl-propoxy)-quinazolin-4-yl]-piperidine-1-carboxylic acid (4-morpholin-4-yl-phenyl)-amide | 0.021 | 0.047 | 0.063 |
| 125 | 4-{7-[3-(4-Methyl-[1,4]diazepan-1-yl)-propoxy]-quinazolin-4-yl}-piperidine-1-carboxylic acid (4-morpholin-4-yl-phenyl)-amide | 0.006 | 0.045 | 0.066 |
| 126 | (R)-4-[7-(3-Hydroxy-pyrrolidin-1-yl)-quinazolin-4-yl]-piperidine-1-carboxylic acid (4-morpholin-4-yl-phenyl)-amide | 0.025 | 0.096 | nd |
| 127 | 4-[7-(1-Methyl-piperidin-4-yloxy)-quinazolin-4-yl]-piperidine-1-carboxylic acid (4-morpholin-4-yl-phenyl)-amide | 0.26 | nd | 0.037 |
| 128 | (S)-4-[7-(3-Hydroxy-pyrrolidin-1-yl)-quinazolin-4-yl]-piperidine-1-carboxylic acid (4-morpholin-4-yl-phenyl)-amide | 0.025 | 0.016 | 0.058 |
| 129 | (S)-4-[7-(3-Hydroxy-pyrrolidin-1-yl)-quinazolin-4-yl]-piperidine-1-carboxylic acid (4-pyrrolidin-1-yl-phenyl)-amide | 0.001 | 0.009 | nd |
| 130 | (R)-4-[7-(2-Methoxymethyl-pyrrolidin-1-yl)-quinazolin-4-yl]-piperidine-1-carboxylic acid (4-morpholin-4-yl-phenyl)-amide | 0.626 | nd | 0.586 |
| 131 | 4-[6-(4-Methyl-piperazin-1-yl)-quinazolin-4-yl]-piperidine-1-carboxylic acid (4-isopropoxy-phenyl)-amide | 0.436 | 2.8 | 0.226 |

-continued

| | Compound | FLT3 Kinase (uM) | MV4-11 (uM) | BaF3 ELISA (uM) |
|---|---|---|---|---|
| 132 | (R)-4-[7-(2-Hydroxymethyl-pyrrolidin-1-yl)-quinazolin-4-yl]-piperidine-1-carboxylic acid (4-morpholin-4-yl-phenyl)-amide | 0.067 | 0.033 | 0.027 |
| 133 | 4-[7-(3-Morpholin-4-yl-propoxy)-quinazolin-4-yl]-piperidine-1-carboxylic acid (4-morpholin-4-yl-phenyl)-amide | 0.002 | 0.058 | 0.026 |
| 134 | 4-[7-(3-Diethylamino-propoxy)-quinazolin-4-yl]-piperidine-1-carboxylic acid (4-morpholin-4-yl-phenyl)-amide | 0.002 | 0.043 | 0.031 |
| 135 | 4-[7-(4-Methyl-piperazin-1-yl)-quinazolin-4-yl]-piperidine-1-carboxylic acid (4-morpholin-4-yl-phenyl)-amide | 0.027 | 0.125 | 0.027 |
| 136 | 4-[7-(4-Ethyl-piperazin-1-yl)-quinazolin-4-yl]-piperidine-1-carboxylic acid (4-morpholin-4-yl-phenyl)-amide | 0.025 | 0.163 | 0.036 |
| 137 | 4-{7-[4-(2-Hydroxy-ethyl)-piperazin-1-yl]-quinazolin-4-yl}-piperidine-1-carboxylic acid (4-morpholin-4-yl-phenyl)-amide | 0.012 | 0.074 | 0.041 |
| 138 | 4-[7-(4-Methyl-[1,4]diazepan-1-yl)-quinazolin-4-yl]-piperidine-1-carboxylic acid (4-morpholin-4-yl-phenyl)-amide | 0.028 | 0.22 | 0.107 |
| 139 | (S)-4-[7-(2-Hydroxymethyl-pyrrolidin-1-yl)-quinazolin-4-yl]-piperidine-1-carboxylic acid (4-morpholin-4-yl-phenyl)-amide | 0.033 | 0.387 | 0.211 |
| 140 | 4-(7-Piperazin-1-yl-quinazolin-4-yl)-piperidine-1-carboxylic acid (4-morpholin-4-yl-phenyl)-amide | 0.045 | 0.17 | 0.031 |
| 141 | 4-[7-(4-Acetyl-piperazin-1-yl)-quinazolin-4-yl]-piperidine-1-carboxylic acid (4-morpholin-4-yl-phenyl)-amide | 0.066 | 0.079 | 0.002 |
| 142 | 4-[7-(4-Methanesulfonyl-piperazin-1-yl)-quinazolin-4-yl]-piperidine-1-carboxylic acid (4-morpholin-4-yl-phenyl)-amide | 0.006 | 0.088 | 0.005 |
| 143 | 4-{4-[1-(4-Morpholin-4-yl-phenylcarbamoyl)-piperidin-4-yl]-quinazolin-7-yl}-piperazine-1-carboxylic acid dimethylamide | 0.004 | 0.039 | 0.001 |
| 144 | 4-{7-[4-(2-Dimethylamino-acetyl)-piperazin-1-yl]-quinazolin-4-yl}-piperidine-1-carboxylic acid (4-morpholin-4-yl-phenyl)-amide | 0.013 | 0.117 | 0.17 |
| 145 | 4-(7-Morpholin-4-yl-quinazolin-4-yl)-piperidine-1-carboxylic acid (4-morpholin-4-yl-phenyl)-amide | 0.065 | 0.137 | 0.014 |
| 146 | 4-[7-(2-Methanesulfonyl-ethylamino)-quinazolin-4-yl]-piperidine-1-carboxylic acid (4-morpholin-4-yl-phenyl)-amide | 0.274 | 0.322 | 0.087 |
| 147 | 4-{7-[2-(2-Oxo-oxazolidin-3-yl)-ethoxy]-quinazolin-4-yl}-piperidine-1-carboxylic acid (4-pyrrolidin-1-yl-phenyl)-amide | 0.027 | 0.051 | 0.0002 |
| 148 | 4-{7-[2-(2-Oxo-oxazolidin-3-yl)-ethoxy]-quinazolin-4-yl}-piperidine-1-carboxylic acid (4-morpholin-4-yl-phenyl)-amide | 0.03 | 0.066 | 0.083 |
| 149 | (R)-4-[7-(3-Dimethylamino-pyrrolidin-1-yl)-quinazolin-4-yl]-piperidine-1-carboxylic acid (4-pyrrolidin-1-yl-phenyl)-amide | 0.046 | 0.046 | 0.003 |
| 150 | (R)-4-[7-(3-Dimethylamino-pyrrolidin-1-yl)-quinazolin-4-yl]-piperidine-1-carboxylic acid (4-morpholin-4-yl-phenyl)-amide | 0.014 | 0.269 | 0.019 |
| 151 | (S)-4-[7-(1-Methyl-pyrrolidin-2-ylmethoxy)-quinazolin-4-yl]-piperidine-1-carboxylic acid (4-pyrrolidin-1-yl-phenyl)-amide | 0.062 | 0.193 | 0.045 |
| 152 | (S)-4-{7-[2-(2-Hydroxymethyl-pyrrolidin-1-yl)-ethoxy]-quinazolin-4-yl}-piperidine-1-carboxylic acid (4-pyrrolidin-1-yl-phenyl)-amide | 0.018 | 0.021 | 0.042 |
| 153 | (S)-4-{7-[2-(2-Hydroxymethyl-pyrrolidin-1-yl)-ethoxy]-quinazolin-4-yl}-piperidine-1-carboxylic acid (4-morpholin-4-yl-phenyl)-amide | 0.022 | 0.395 | 0.11 |
| 154 | (R)-4-[7-(1-Acetyl-pyrrolidin-3-yloxy)-quinazolin-4-yl]-piperidine-1-carboxylic acid (4-pyrrolidin-1-yl-phenyl)-amide | 0.015 | 0.063 | 0.002 |
| 155 | 4-[7-(4-Carboxylic acid methylamide-piperidin-1-yl)-quinazolin-4-yl]-piperidine-1-carboxylic acid (4-pyrrolidin-1-yl-phenyl)-amide | 0.008 | 0.013 | 0.0004 |
| 156 | 4-{7-[2-(4-Methyl-piperazin-1-yl)-ethoxy]-quinazolin-4-yl}-piperidine-1-carboxylic acid (4-morpholin-4-yl-phenyl)-amide | 0.006 | 0.074 | 0.032 |

-continued

| | Compound | FLT3 Kinase (uM) | MV4-11 (uM) | BaF3 ELISA (uM) |
|---|---|---|---|---|
| 157 | 4-{7-[2-(4-Methyl-piperazin-1-yl)-ethoxy]-quinazolin-4-yl}-piperidine-1-carboxylic acid (4-pyrrolidin-1-yl-phenyl)-amide | 0.0005 | 0.009 | 0.016 |
| 158 | 4-{7-[3-(4-Methyl-piperazin-1-yl)-propoxy]-quinazolin-4-yl}-piperidine-1-carboxylic acid (4-pyrrolidin-1-yl-phenyl)-amide | 0.008 | 0.011 | 0.0004 |
| 159 | 4-[7-(4-Methyl-piperazin-1-yl)-quinazolin-4-yl]-piperidine-1-carboxylic acid (4-pyrrolidin-1-yl-phenyl)-amide | 0.007 | 0.006 | 0.006 |
| 160 | 4-[7-(4-Methyl-piperazin-1-yl)-quinazolin-4-yl]-piperidine-1-carboxylic acid (6-pyrrolidin-1-yl-pyridin-3-yl)-amide | 0.014 | 0.067 | 0.011 |
| 161 | (S)-4-{7-[3-(2-Hydroxymethyl-pyrrolidin-1-yl)-propoxy]-quinazolin-4-yl}-piperidine-1-carboxylic acid (4-pyrrolidin-1-yl-phenyl)-amide | 0.001 | 0.013 | 0.059 |
| 162 | (S)-4-[7-(1-Acetyl-pyrrolidin-2-ylmethoxy)-quinazolin-4-yl]-piperidine-1-carboxylic acid (4-pyrrolidin-1-yl-phenyl)-amide | 0.032 | 0.046 | 0.01 |
| 163 | 4-[7-(1-Acetyl-piperidin-4-ylmethoxy)-quinazolin-4-yl]-piperidine-1-carboxylic acid (4-pyrrolidin-1-yl-phenyl)-amide | 0.011 | 0.020 | 0.118 |
| 164 | 4-{7-[3-(4-Methanesulfonyl-piperazin-1-yl)-propoxy]-quinazolin-4-yl}-piperidine-1-carboxylic acid (4-pyrrolidin-1-yl-phenyl)-amide | 0.025 | 0.036 | 0.011 |
| 165 | 4-(3-{4-[1-(4-Pyrrolidin-1-yl-phenylcarbamoyl)-piperidin-4-yl]-quinazolin-7-yloxy}-propyl)-piperazine-1-carboxylic acid dimethylamide | 0.015 | 0.018 | 0.004 |
| 166 | 4-[7-(4-Acetyl-piperazin-1-yl)-quinazolin-4-yl]-piperidine-1-carboxylic acid (4-pyrrolidin-1-yl-phenyl)-amide | 0.009 | 0.017 | 0.016 |
| 167 | 4-[7-(4-Methanesulfonyl-piperazin-1-yl)-quinazolin-4-yl]-piperidine-1-carboxylic acid (4-pyrrolidin-1-yl-phenyl)-amide | 0.044 | 0.021 | 0.003 |
| 168 | 4-{4-[1-(4-Pyrrolidin-1-yl-phenylcarbamoyl)-piperidin-4-yl]-quinazolin-7-yl}-piperazine-1-carboxylic acid dimethylamide | 0.003 | 0.017 | nd |
| 169 | 4-[7-(2-Hydroxy-ethoxy)-quinazolin-4-yl]-piperidine-1-carboxylic acid (4-pyrrolidin-1-yl-phenyl)-amide | 0.032 | 0.032 | 0.002 |
| 170 | 4-[7-(1-Acetyl-azetidin-3-yloxy)-quinazolin-4-yl]-piperidine-1-carboxylic acid (4-pyrrolidin-1-yl-phenyl)-amide | 0.29 | 0.097 | 0.004 |
| 171 | 4-[7-(1-Methanesulfonyl-azetidin-3-yloxy)-quinazolin-4-yl]-piperidine-1-carboxylic acid (4-pyrrolidin-1-yl-phenyl)-amide | 0.13 | 0.185 | 0.01 |
| 172 | 4-[7-(2-Morpholin-4-yl-2-oxo-ethoxy)-quinazolin-4-yl]-piperidine-1-carboxylic acid (4-pyrrolidin-1-yl-phenyl)-amide | 0.542 | 0.248 | 0.149 |
| 173 | 4-(7-Azetidin-1-yl-quinazolin-4-yl)-piperidine-1-carboxylic acid (4-pyrrolidin-1-yl-phenyl)-amide | 0.001 | 0.016 | 0.002 |
| 174 | 4-[7-(Pyridin-3-yloxy)-quinazolin-4-yl]-piperidine-1-carboxylic acid (4-pyrrolidin-1-yl-phenyl)-amide | 0.042 | 0.214 | 0.13 |
| 175 | 4-[7-(2-Hydroxy-ethylamino)-quinazolin-4-yl]-piperidine-1-carboxylic acid (4-pyrrolidin-1-yl-phenyl)-amide | 0.001 | 0.018 | 0.006 |
| 176 | 4-[7-(2-Oxo-oxazolidin-3-yl)-quinazolin-4-yl]-piperidine-1-carboxylic acid (4-pyrrolidin-1-yl-phenyl)-amide | 0.102 | 0.008 | 0.007 |
| 177 | (R)-4-[7-(1-Methanesulfonyl-pyrrolidin-3-yloxy)-quinazolin-4-yl]-piperidine-1-carboxylic acid (4-pyrrolidin-1-yl-phenyl)-amide | 0.001 | 0.265 | nd |
| 178 | 4-[7-(2-Oxo-imidazolidin-1-yl)-quinazolin-4-yl]-piperidine-1-carboxylic acid (4-pyrrolidin-1-yl-phenyl)-amide | 0.01 | 0.011 | 0.004 |
| 179 | 4-(7-Pyrrolidin-1-yl-quinazolin-4-yl)-piperidine-1-carboxylic acid (4-pyrrolidin-1-yl-phenyl)-amide | 0.017 | 0.034 | 0.049 |
| 180 | 4-(7-Imidazol-1-yl-quinazolin-4-yl)-piperidine-1-carboxylic acid (4-pyrrolidin-1-yl-phenyl)-amide | 0.006 | 0.02 | 0.01 |
| 181 | 4-(7-Morpholin-4-yl-quinazolin-4-yl)-piperidine-1-carboxylic acid (4-pyrrolidin-1-yl-phenyl)-amide | 0.01 | 0.009 | 0.005 |
| 182 | 4-(7-Thiomorpholin-4-yl-quinazolin-4-yl)-piperidine-1-carboxylic acid (4-pyrrolidin-1-yl-phenyl)-amide | 0.011 | 0.107 | 0.024 |

-continued

| | Compound | FLT3 Kinase (uM) | MV4-11 (uM) | BaF3 ELISA (uM) |
|---|---|---|---|---|
| 183 | 4-[7-(3-Oxo-piperazin-1-yl)-quinazolin-4-yl]-piperidine-1-carboxylic acid (4-pyrrolidin-1-yl-phenyl)-amide | 0.003 | 0.018 | 0.031 |
| 184 | 4-[7-(4-Methyl-3-oxo-piperazin-1-yl)-quinazolin-4-yl]-piperidine-1-carboxylic acid (4-pyrrolidin-1-yl-phenyl)-amide | 0.244 | 0.058 | 0.098 |
| 185 | 4-{7-[4-(2-Hydroxy-ethyl)-piperazin-1-yl]-quinazolin-4-yl}-piperidine-1-carboxylic acid (4-pyrrolidin-1-yl-phenyl)-amide | 0.055 | 0.006 | 0.001 |
| 186 | 4-{7-[4-(2-Methoxy-ethyl)-piperazin-1-yl]-quinazolin-4-yl}-piperidine-1-carboxylic acid (4-pyrrolidin-1-yl-phenyl)-amide | 0.093 | 0.015 | 0.003 |
| 187 | 4-[7-(4-Ethyl-piperazin-1-yl)-quinazolin-4-yl]-piperidine-1-carboxylic acid (4-pyrrolidin-1-yl-phenyl)-amide | 0.146 | 0.021 | 0.012 |
| 188 | 4-[7-(Tetrahydro-pyran-4-ylmethoxy)-quinazolin-4-yl]-piperidine-1-carboxylic acid (4-pyrrolidin-1-yl-phenyl)-amide | 0.386 | 0.067 | 0.093 |
| 189 | 4-[7-(Tetrahydro-pyran-4-yloxy)-quinazolin-4-yl]-piperidine-1-carboxylic acid (4-pyrrolidin-1-yl-phenyl)-amide | 1.13 | 0.286 | 0.104 |
| 190 | (S)-4-[7-(Tetrahydro-furan-3-yloxy)-quinazolin-4-yl]-piperidine-1-carboxylic acid (4-pyrrolidin-1-yl-phenyl)-amide | 0.277 | 0.088 | 0.109 |
| 191 | (R)-4-[7-(Tetrahydro-furan-3-yloxy)-quinazolin-4-yl]-piperidine-1-carboxylic acid (4-pyrrolidin-1-yl-phenyl)-amide | 0.216 | 0.071 | 0.144 |
| 192 | 4-[7-(4-Pyridin-2-yl-piperazin-1-yl)-quinazolin-4-yl]-piperidine-1-carboxylic acid (4-pyrrolidin-1-yl-phenyl)-amide | 0.002 | 0.013 | 0.001 |
| 193 | 4-[7-(4-Pyrimidin-2-yl-piperazin-1-yl)-quinazolin-4-yl]-piperidine-1-carboxylic acid (4-pyrrolidin-1-yl-phenyl)-amide | 0.004 | 0.016 | 0.003 |
| 194 | 4-[7-(4-Pyridin-4-yl-piperazin-1-yl)-quinazolin-4-yl]-piperidine-1-carboxylic acid (4-pyrrolidin-1-yl-phenyl)-amide | 0.02 | 0.0004 | 0.011 |
| 195 | 4-[7-(4-Fluoro-piperidin-1-yl)-quinazolin-4-yl]-piperidine-1-carboxylic acid (4-pyrrolidin-1-yl-phenyl)-amide | 0.163 | 0.017 | 0.081 |
| 196 | 4-[7-(4-Fluoro-piperidin-1-yl)-quinazolin-4-yl]-piperidine-1-carboxylic acid (4-morpholin-4-yl-phenyl)-amide | 0.291 | 0.075 | 0.003 |
| 197 | 4-[7-(2-Oxo-imidazolidin-1-yl)-quinazolin-4-yl]-piperidine-1-carboxylic acid (4-morpholin-4-yl-phenyl)-amide | 1.04 | 0.143 | 0.078 |
| 198 | 4-[6-(4-Methyl-piperazin-1-yl)-quinazolin-4-yl]-piperidine-1-carboxylic acid (4-morpholin-4-yl-phenyl)-amide | 10.2 | 0.227 | nd |
| 199 | 4-{4-[1-(4-Pyrrolidin-1-yl-phenylcarbamoyl)-piperidin-4-yl]-quinazolin-7-yl}-piperazine-1-carboxylic acid ethylamide | 0.028 | 0.003 | 0.040 |
| 200 | 4-{7-[4-(2-Methoxy-acetyl)-piperazin-1-yl]-quinazolin-7-yl}-piperidine-1-carboxylic acid (4-pyrrolidin-1-yl-phenyl)-amide | 0.021 | 0.006 | nd |
| 201 | 4-{7-[4-(2-Hydroxy-acetyl)-piperazin-1-yl]-quinazolin-7-yl}-piperidine-1-carboxylic acid (4-pyrrolidin-1-yl-phenyl)-amide | 0.017 | 0.016 | 0.065 |
| 202 | 4-{7-[2-(4-Methyl-3-oxo-piperazin-1-yl)-ethoxy]-quinazolin-4-yl}-piperidine-1-carboxylic acid (4-pyrrolidin-1-yl-phenyl)-amide | 0.090 | 0.074 | 0.015 |
| 203 | 4-(6-Methoxy-quinazolin-4-yl)-piperidine-1-carboxylic acid (4-isopropoxy-phenyl)-amide | 0.297 | 0.149 | nd |
| 204 | 4-{7-[3-(1H-Tetrazol-5-yl)-propoxy]-quinazolin-4-yl}-piperidine-1-carboxylic acid (4-isopropoxy-phenyl)-amide | 0.306 | >1 | nd |
| 205 | 4-{6-Fluoro-7-[3-(4-methyl-piperazin-1-yl)-propoxy]-quinazolin-4-yl}-piperidine-1-carboxylic acid (4-morpholin-4-yl-phenyl)-amide | 0.063 | 0.078 | 0.006 |
| 206 | 4-{6-Fluoro-7-[2-(2-oxo-pyrrolidin-1-yl)-ethoxy]-quinazolin-4-yl}-piperidine-1-carboxylic acid (4-pyrrolidin-1-yl-phenyl)-amide | 0.028 | 0.061 | 0.022 |
| 207 | 4-{6-Methoxy-7-[3-(4-methyl-piperazin-1-yl)-propoxy]-quinazolin-4-yl}-piperidine-1-carboxylic acid (4-morpholin-4-yl-phenyl)-amide | 0.029 | 0.048 | 0.042 |

-continued

| | Compound | FLT3 Kinase (uM) | MV4-11 (uM) | BaF3 ELISA (uM) |
|---|---|---|---|---|
| 208 | 4-{6-Methoxy-7-[3-(4-methyl-piperazin-1-yl)-propoxy]-quinazolin-4-yl}-piperidine-1-carboxylic acid (4-pyrrolidin-1-yl-phenyl)-amide | 0.002 | 0.003 | nd |
| 209 | 4-{6-Methoxy-7-[2-(2-oxo-pyrrolidin-1-yl)-ethoxy]-quinazolin-4-yl}-piperidine-1-carboxylic acid (4-pyrrolidin-1-yl-phenyl)-amide | 0.017 | 0.026 | 0.037 |
| 210 | 4-(6-Fluoro-7-morpholin-4-yl-quinazolin-4-yl)-piperidine-1-carboxylic acid (4-pyrrolidin-1-yl-phenyl)-amide | 0.021 | 0.102 | 0.025 |
| 211 | 4-(6-Methoxy-7-morpholin-4-yl-quinazolin-4-yl)-piperidine-1-carboxylic acid (4-pyrrolidin-1-yl-phenyl)-amide | 0.008 | 0.020 | 0.001 |
| 212 | 4-(6-Methoxy-7-morpholin-4-yl-quinazolin-4-yl)-piperidine-1-carboxylic acid (4-morpholin-4-yl-phenyl)-amide | 0.239 | 0.367 | 0.093 |

[1]Not determined.

Biological Data for Trk B

The activity of representative compounds of the present invention is presented in the charts below. All activities are in µM and have the following uncertainties: TrkB $IC_{50}$: ±10%.

| Number | Compound Name | TrkB $IC_{50}$ (uM) |
|---|---|---|
| 1 | 4-(6,7-Dimethoxy-quinazolin-4-yl)-piperidine-1-carboxylic acid (4-isopropoxy-phenyl)-amide | 0.22 |
| 2 | 4-(6,7-Dimethoxy-quinazolin-4-yl)-piperidine-1-carboxylic acid (4-iodo-phenyl)-amide | 6.2 |
| 3 | 4-(6,7-Dimethoxy-quinazolin-4-yl)-piperidine-1-carboxylic acid (4-imidazol-1-yl-phenyl)-amide | >42 |
| 4 | 4-(6,7-Dimethoxy-quinazolin-4-yl)-piperidine-1-carboxylic acid (4-isopropyl-phenyl)-amide | nd |
| 5 | 4-Quinolin-4-yl-piperidine-1-carboxylic acid (4-isopropyl-phenyl)-amide | 0.7 |
| 6 | 4-Quinolin-4-yl-piperidine-1-carboxylic acid (4-isopropoxy-phenyl)-amide | 0.8 |
| 7 | 4-Quinazolin-4-yl-piperidine-1-carboxylic acid (4-isopropyl-phenyl)-amide | 3.3 |
| 8 | 4-Quinazolin-4-yl-piperidine-1-carboxylic acid (4-isopropoxy-phenyl)-amide | 2.4 |
| 9 | 2-[4-(6,7-Dimethoxy-quinazolin-4-yl)-piperidin-1-yl]-N-(4-isopropyl-phenyl)-acetamide | 0.5 |
| 10 | 2-[4-(6,7-Dimethoxy-quinazolin-4-yl)-piperidin-1-yl]-N-(4-isopropoxy-phenyl)-acetamide | 1 |
| 11 | 4-(6-Iodo-quinazolin-4-yl)-piperidine-1-carboxylic acid (4-isopropoxy-phenyl)-amide | 0.2 |
| 12 | 4-[6-(3-Hydroxy-prop-1-ynyl)-quinazolin-4-yl]-piperidine-1-carboxylic acid (4-isopropoxy-phenyl)-amide | 0.5 |
| 13 | 4-[6-(3-Diethylamino-prop-1-ynyl)-quinazolin-4-yl]-piperidine-1-carboxylic acid (4-isopropoxy-phenyl)-amide | 1.3 |
| 14 | 4-[6-(3-Piperidin-1-yl-prop-1-ynyl)-quinazolin-4-yl]-piperidine-1-carboxylic acid (4-isopropoxy-phenyl)-amide | 0.3 |
| 15 | 4-[6-(3-Morpholin-4-yl-prop-1-ynyl)-quinazolin-4-yl]-piperidine-1-carboxylic acid (4-isopropoxy-phenyl)-amide | 0.8 |
| 16 | N-(4-Isopropyl-phenyl)-2-(4-quinazolin-4-yl-piperidin-1-yl)-acetamide | 2.6 |
| 17 | 4-(6,7-Dimethoxy-quinazolin-4-yl)-piperidine-1-carboxylic acid (6-cyclobutoxy-pyridin-3-yl)-amide | 0.5 |
| 18 | 4-(6,7-Dimethoxy-quinazolin-4-yl)-piperidine-1-carboxylic acid (4-morpholin-4-yl-phenyl)-amide | 19.2 |
| 19 | 4-(6,7-Dimethoxy-quinazolin-4-yl)-piperidine-1-carboxylic acid (4-piperidin-1-yl-phenyl)-amide | 2.7 |
| 20 | 4-(6,7-Dimethoxy-quinazolin-4-yl)-piperidine-1-carboxylic acid [4-(4-methyl-piperazin-1-yl)-phenyl]-amide | 39.9 |
| 21 | 4-(6,7-Dimethoxy-quinazolin-4-yl)-piperidine-1-carboxylic acid (4-cyclohexyl-phenyl)-amide | 0.6 |
| 22 | 4-(6,7-Dimethoxy-quinazolin-4-yl)-piperidine-1-carboxylic acid (4-hydroxymethyl-phenyl)-amide | 17.7 |
| 23 | 4-(6,7-Dimethoxy-quinazolin-4-yl)-piperidine-1-carboxylic acid (1H-indol-5-yl)-amide | 13.3 |

-continued

| Number | Compound Name | TrkB IC$_{50}$ (uM) |
|---|---|---|
| 24 | 4-(6,7-Dimethoxy-quinazolin-4-yl)-piperidine-1-carboxylic acid benzothiazol-6-ylamide | 35 |
| 25 | 4-(6,7-Dimethoxy-quinazolin-4-yl)-piperidine-1-carboxylic acid (4-acetylamino-phenyl)-amide | >42 |
| 26 | 4-(6,7-Dimethoxy-quinazolin-4-yl)-piperidine-1-carboxylic acid (4-dimethylamino-phenyl)-amide | 9.4 |
| 27 | 4-(6,7-Dimethoxy-quinazolin-4-yl)-piperidine-1-carboxylic acid (2,3-dihydro-benzofuran-5-yl)-amide | 9.4 |
| 28 | 1-[4-(6,7-Dimethoxy-quinazolin-4-yl)-piperidin-1-yl]-2-(4-isopropyl-phenyl)-ethanone | 0.1 |
| 29 | 4-(7-Chloro-quinazolin-4-yl)-piperidine-1-carboxylic acid (4-isopropoxy-phenyl)-amide | 0.5 |
| 30 | 4-(7-Chloro-quinazolin-4-yl)-piperidine-1-carboxylic acid (4-isopropyl-phenyl)-amide | 0.7 |
| 31 | 4-(7-Methoxy-quinazolin-4-yl)-piperidine-1-carboxylic acid (4-isopropoxy-phenyl)-amide | 0.4 |
| 32 | 4-(7-Methoxy-quinazolin-4-yl)-piperidine-1-carboxylic acid (4-isopropyl-phenyl)-amide | 0.5 |
| 33 | 4-[7-(3-Piperidin-1-yl-propoxy)-quinazolin-4-yl]-piperidine-1-carboxylic acid (4-isopropoxy-phenyl)-amide | 0.9 |
| 34 | 4-[7-(2-Piperidin-1-yl-ethoxy)-quinazolin-4-yl]-piperidine-1-carboxylic acid (4-isopropoxy-phenyl)-amide | 2.8 |
| 35 | 4-[7-(2-Diethylamino-ethoxy)-quinazolin-4-yl]-piperidine-1-carboxylic acid (4-isopropoxy-phenyl)-amide | 1.5 |
| 36 | 4-[7-(3-Diethylamino-propoxy)-quinazolin-4-yl]-piperidine-1-carboxylic acid (4-isopropoxy-phenyl)-amide | 0.6 |
| 37 | 4-[7-(2-Morpholin-4-yl-ethoxy)-quinazolin-4-yl]-piperidine-1-carboxylic acid (4-isopropoxy-phenyl)-amide | 0.7 |
| 38 | 4-[7-(3-Morpholin-4-yl-propoxy)-quinazolin-4-yl]-piperidine-1-carboxylic acid (4-isopropoxy-phenyl)-amide | 0.1 |
| 39 | 4-{7-[3-(4-Methyl-piperazin-1-yl)-propoxy]-quinazolin-4-yl}-piperidine-1-carboxylic acid (4-isopropoxy-phenyl)-amide | 0.6 |
| 40 | 4-(6,7-Dimethoxy-quinazolin-4-yl)-piperidine-1-carboxylic acid [4-(2-methoxy-ethoxy)-phenyl]-amide | >42 |
| 41 | 4-(6,7-Dimethoxy-quinazolin-4-yl)-piperidine-1-carboxylic acid (4-methoxy-phenyl)-amide | 11.7 |
| 42 | 4-(6,7-Dimethoxy-quinazolin-4-yl)-piperidine-1-carboxylic acid cyclohexylamide | 28.7 |
| 43 | 4-(6,7-Dimethoxy-quinazolin-4-yl)-piperidine-1-carboxylic acid (4-butyl-phenyl)-amide | 0.8 |
| 44 | 4-(6,7-Dimethoxy-quinazolin-4-yl)-piperidine-1-carboxylic acid (4-ethoxy-phenyl)-amide | 2.2 |
| 45 | 4-(6,7-Dimethoxy-quinazolin-4-yl)-piperidine-1-carboxylic acid phenylamide | 6.5 |
| 46 | 4-(6,7-Dimethoxy-quinazolin-4-yl)-piperidine-1-carboxylic acid (4-trifluoromethyl-phenyl)-amide | 18.3 |
| 47 | 4-(6,7-Dimethoxy-quinazolin-4-yl)-piperidine-1-carboxylic acid (4-phenoxy-phenyl)-amide | 4 |
| 48 | 4-(6,7-Dimethoxy-quinazolin-4-yl)-piperidine-1-carboxylic acid p-tolylamide | 6.6 |
| 49 | 4-(6,7-Dimethoxy-quinazolin-4-yl)-piperidine-1-carboxylic acid (4-chloro-phenyl)-amide | 22.3 |
| 50 | 4-(6,7-Dimethoxy-quinazolin-4-yl)-piperidine-1-carboxylic acid (4-trifluoromethoxy-phenyl)-amide | 0.5 |
| 51 | 4-(6,7-Dimethoxy-quinazolin-4-yl)-piperidine-1-carboxylic acid (4-difluoromethoxy-phenyl)-amide | 4 |
| 52 | 4-(6,7-Dimethoxy-quinazolin-4-yl)-piperidine-1-carboxylic acid (4-sec-butyl-phenyl)-amide | 1.2 |
| 53 | 4-(6,7-Dimethoxy-quinazolin-4-yl)-piperidine-1-carboxylic acid (4-tert-butyl-phenyl)-amide | 1.1 |
| 54 | 4-(6,7-Dimethoxy-quinazolin-4-yl)-piperidine-1-carboxylic acid (4-tert-butyl-cyclohexyl)-amide- | 6.2 |
| 55 | 4-(6,7-Dimethoxy-quinazolin-4-yl)-piperidine-1-carboxylic acid [4-(1-hydroxy-ethyl)-phenyl]-amide | 39.1 |
| 56 | 4-(6,7-Dimethoxy-quinazolin-4-yl)-piperidine-1-carboxylic acid (6-isopropoxy-pyridine-3-yl)-amide | 0.4 |
| 57 | 4-(6,7-Dimethoxy-quinazolin-4-yl)-piperidine-1-carboxylic acid [4-(2-oxo-pyrrolidin-1-yl)-phenyl]-amide | 24.9 |
| 58 | 4-(6,7-Dimethoxy-quinazolin-4-yl)-piperidine-1-carboxylic acid (4-pyrimidin-5-yl-phenyl)-amide | >42 |
| 59 | 4-(6,7-Dimethoxy-quinazolin-4-yl)-piperidine-1-carboxylic acid (4-furan-2-yl-phenyl)-amide | 13.9 |
| 60 | 4-(6,7-Dimethoxy-quinazolin-4-yl)-piperidine-1-carboxylic acid [4-(6-chloro-pyridin-3-yl)-phenyl]-amide | 8.1 |
| 61 | 4-(4-{[4-(6,7-Dimethoxy-quinazolin-4-yl)-piperidine-1-carbonyl]-amino}-phenyl)-3,6-dihydro-2H-pyridine-1-carboxylic acid tert-butyl ester | 40.6 |

-continued

| Number | Compound Name | TrkB IC$_{50}$ (uM) |
|---|---|---|
| 62 | 4-(6,7-Dimethoxy-quinazolin-4-yl)-piperidine-1-carboxylic acid [4-(1,2,3,6-tetrahydro-pyridin-4-yl)-phenyl]-amide | >10 |
| 63 | 4-(4-{[4-(6,7-Dimethoxy-quinazolin-4-yl)-piperidine-1-carbonyl]-amino}-phenyl)-piperidine-1-carboxylic acid tert-butyl ester | >42 |
| 64 | 4-(6,7-Dimethoxy-quinazolin-4-yl)-piperidine-1-carboxylic acid (4-piperidin-4-yl-phenyl)-amide | 37.8 |
| 65 | 4-[7-(3-Methanesulfonylamino-propoxy)-quinazolin-4-yl]-piperidine-1-carboxylic acid (4-isopropoxy-phenyl)-amide | 0.5 |
| 66 | 4-[7-(3-Methanesulfonylamino-propoxy)-quinazolin-4-yl]-piperidine-1-carboxylic acid (4-morpholin-4-yl-phenyl)-amide | >42 |
| 67 | 4-{7-[3-(2-Oxo-pyrrolidin-1-yl)-propoxy]-quinazolin-4-yl}-piperidine-1-carboxylic acid (4-isopropoxy-phenyl)-amide | 0.6 |
| 68 | 4-{7-[3-(2-Oxo-pyrrolidin-1-yl)-propoxy]-quinazolin-4-yl}-piperidine-1-carboxylic acid (4-morpholin-4-yl-phenyl)-amide | >20 |
| 69 | 4-(6,7-Dimethoxy-quinazolin-4-yl)-piperidine-1-carboxylic acid (6-cyclopentyloxy-pyridin-3-yl)-amide | 0.15 |
| 70 | 4-(6,7-Dimethoxy-quinazolin-4-yl)-piperidine-1-carboxylic acid (4-azepan-1-yl-phenyl)-amide | 2.7 |
| 71 | 4-(6,7-Dimethoxy-quinazolin-4-yl)-piperidine-1-carboxylic acid (3-chloro-4-piperidin-1-yl-phenyl)-amide | 6.1 |
| 72 | 4-{7-[3-(2-Oxo-pyrrolidin-1-yl)-propoxy]-quinazolin-4-yl}-piperidine-1-carboxylic acid (6-morpholin-4-yl-pyridin-3-yl)-amide | 2 |
| 73 | 4-{7-[3-(4-Methyl-piperazin-1-yl)-propoxy]-quinazolin-4-yl}-piperidine-1-carboxylic acid (4-morpholin-4-yl-phenyl)-amide | >20 |
| 74 | 4-{7-[2-(2-Oxo-pyrrolidin-1-yl)-ethoxy]-quinazolin-4-yl}-piperidine-1-carboxylic acid (4-pyrrolidin-1-yl-phenyl)-amide | 3.3 |
| 75 | 4-[7-(3-Piperidin-1-yl-propoxy)-quinazolin-4-yl]-piperidine-1-carboxylic acid (4-morpholin-4-yl-phenyl)-amide | >20 |
| 76 | 4-{6-[3-(4-Methyl-piperazin-1-yl)-propoxy]-quinazolin-4-yl}-piperidine-1-carboxylic acid (4-isopropoxy-phenyl)-amide | 7.9 |
| 77 | 4-[7-(3-Hydroxy-propoxy)-quinazolin-4-yl]-piperidine-1-carboxylic acid (4-morpholin-4-yl-phenyl)-amide | >20 |
| 78 | 4-[7-(3-Methoxy-propoxy)-quinazolin-4-yl]-piperidine-1-carboxylic acid (4-morpholin-4-yl-phenyl)-amide | 18.4 |
| 79 | 4-{7-[2-(2-Oxo-oxazolidin-3-yl)-ethoxy]-quinazolin-4-yl}-piperidine-1-carboxylic acid (4-isopropoxy-phenyl)-amide | 0.3 |
| 80 | 4-{7-[3-(4-Methyl-piperazin-1-yl)-propoxy]-quinazolin-4-yl}-piperidine-1-carboxylic acid (6-morpholin-4-yl-pyridin-3-yl)-amide | 9.1 |
| 81 | 4-{7-[3-(4-Methyl-piperazin-1-yl)-propoxy]-quinazolin-4-yl}-piperidine-1-carboxylic acid (3-fluoro-4-morpholin-4-yl-phenyl)-amide | >20 |
| 82 | 4-{7-[3-(4-Methyl-piperazin-1-yl)-propoxy]-quinazolin-4-yl}-piperidine-1-carboxylic acid (6-cyclopentyloxy-pyridin-3-yl)-amide | 0.4 |
| 83 | 4-{7-[2-(2-Oxo-pyrrolidin-1-yl)-ethoxy]-quinazolin-4-yl}-piperidine-1-carboxylic acid (6-morpholin-4-yl-pyridin-3-yl)-amide | 8.5 |
| 84 | 4-{7-[2-(2-Oxo-pyrrolidin-1-yl)-ethoxy]-quinazolin-4-yl}-piperidine-1-carboxylic acid (2-pyrrolidin-1-yl-pyrimidin-5-yl)-amide | 0.8 |
| 85 | 4-{7-[2-(2-Oxo-pyrrolidin-1-yl)-ethoxy]-quinazolin-4-yl}-piperidine-1-carboxylic acid (4-morpholin-4-yl-phenyl)-amide | >20 |
| 86 | 4-[7-(3-Methanesulfonylamino-propoxy)-quinazolin-4-yl]-piperidine-1-carboxylic acid (6-pyrrolidin-1-yl-pyridin-3-yl)-amide | 2 |
| 87 | 4-[7-(3-Methanesulfonylamino-propoxy)-quinazolin-4-yl]-piperidine-1-carboxylic acid (6-morpholin-4-yl-pyridin-3-yl)-amide | 7.2 |
| 88 | 4-[7-(3-Methanesulfonylamino-propoxy)-quinazolin-4-yl]-piperidine-1-carboxylic acid (6-cyclopentyloxy-pyridin-3-yl)-amide | 0.4 |
| 89 | 4-{7-[3-(2-Oxo-pyrrolidin-1-yl)-propoxy]-quinazolin-4-yl}-piperidine-1-carboxylic acid (6-pyrrolidin-1-yl-pyridin-3-yl)-amide | 2.7 |

-continued

| Number | Compound Name | TrkB IC$_{50}$ (uM) |
|---|---|---|
| 90 | 4-{7-[3-(2-Oxo-pyrrolidin-1-yl)-propoxy]-quinazolin-4-yl}-piperidine-1-carboxylic acid (2-pyrrolidin-1-yl-pyrimidin-5-yl)-amide | 0.3 |
| 91 | 4-{7-[2-(2-Oxo-oxazolidin-3-yl)-ethoxy]-quinazolin-4-yl}-piperidine-1-carboxylic acid (6-morpholin-4-yl-pyridin-3-yl)-amide | 1.9 |
| 92 | 4-{7-[2-(2-Oxo-oxazolidin-3-yl)-ethoxy]-quinazolin-4-yl}-piperidine-1-carboxylic acid (6-pyrrolidin-1-yl-pyridin-3-yl)-amide | 1.3 |
| 93 | 4-[7-(1-Methyl-piperidin-4-ylmethoxy)-quinazolin-4-yl]-piperidine-1-carboxylic acid (4-isopropoxy-phenyl)-amide | nd |
| 94 | 4-[7-(1-Methyl-piperidin-4-ylmethoxy)-quinazolin-4-yl]-piperidine-1-carboxylic acid (4-morpholin-4-yl-phenyl)-amide | >42 |
| 95 | 4-[7-(2-Morpholin-4-yl-ethoxy)-quinazolin-4-yl]-piperidine-1-carboxylic acid (6-pyrrolidin-1-yl-pyridin-3-yl)-amide | 3.4 |
| 96 | 4-[7-(2-Morpholin-4-yl-ethoxy)-quinazolin-4-yl]-piperidine-1-carboxylic acid (4-morpholin-4-yl-phenyl)-amide | 27.9 |
| 97 | 4-{7-[2-(4-Acetyl-piperazin-1-yl)-ethoxy]-quinazolin-4-yl}-piperidine-1-carboxylic acid (4-morpholin-4-yl-phenyl)-amide | >20 |
| 98 | 4-[7-(2-Piperidin-2-yl-ethoxy)-quinazolin-4-yl]-piperidine-1-carboxylic acid (4-morpholin-4-yl-phenyl)-amide | >20 |
| 99 | 4-[7-(1-Methyl-piperidin-4-ylmethoxy)-quinazolin-4-yl]-piperidine-1-carboxylic acid (6-pyrrolidin-1-yl-pyridin-3-yl)-amide | 6.41 |
| 100 | 4-(7-Dimethylamino-quinazolin-4-yl)-piperidine-1-carboxylic acid (4-isopropoxy-phenyl)-amide | 0.1 |
| 101 | 4-{6-[3-(2-Oxo-pyrrolidin-1-yl)-propoxy]-quinazolin-4-yl}-piperidine-1-carboxylic acid (4-isopropoxy-phenyl) | 0.3 |
| 102 | 4-{7-[3-(4-Methyl-piperazin-1-yl)-propylamino]-quinazolin-4-yl}-piperidine-1-carboxylic acid (4-isopropoxy-phenyl)-amide | 0.2 |
| 103 | 4-[7-(4-Methyl-piperazin-1-yl)-quinazolin-4-yl]-piperidine-1-carboxylic acid (4-isopropoxy-phenyl)-amide | 0.2 |
| 104 | 4-{7-[3-(4-Methyl-piperazin-1-yl)-propoxy]-quinazolin-4-yl}-piperidine-1-carboxylic acid (6-pyrrolidin-1-yl-pyridin-3-yl)-amide | 0.8 |
| 105 | 4-{7-[3-(4-Methyl-piperazin-1-yl)-propoxy]-quinazolin-4-yl}-piperidine-1-carboxylic acid (2-pyrrolidin-1-yl-pyrimidin-5-yl)-amide | 0.2 |
| 106 | 4-{7-[3-(4-Methyl-piperazin-1-yl)-propoxy]-quinazolin-4-yl}-piperidine-1-carbothioic acid (6-morpholin-4-yl-pyridin-3-yl)-amide | 16.3 |
| 107 | 4-[7-(1-Methyl-piperidin-4-ylmethoxy)-quinazolin-4-yl]-piperidine-1-carboxylic acid (6-cyclobutoxy-pyridin-3-yl)-amide | 0.2 |
| 108 | 4-[7-(1-Methyl-piperidin-4-ylmethoxy)-quinazolin-4-yl]-piperidine-1-carboxylic acid (6-morpholin-4-yl-pyridin-3-yl)-amide | 5.4 |
| 109 | 4-[7-(1-Methyl-piperidin-4-ylmethoxy)-quinazolin-4-yl]-piperidine-1-carboxylic acid (4-pyrrolidin-1-yl-phenyl)-amide | 8.9 |
| 110 | 4-[7-(3-[1,2,4]Triazol-4-yl-propoxy)-quinazolin-4-yl]-piperidine-1-carboxylic acid (6-morpholin-4-yl-pyridin-3-yl)-amide | 15 |
| 111 | 4-{7-[3-(2-Dimethylamino-3,4-dioxo-cyclobut-1-enylamino)-propoxy]-quinazolin-4-yl}-piperidine-1-carboxylic acid (6-pyrrolidin-1-yl-pyridin-3-yl)-amide | >20 |
| 112 | Morpholine-4-carboxylic acid (3-{4-[1-(6-pyrrolidin-1-yl-pyridin-3-ylcarbamoyl)-piperidin-4-yl]-quinazolin-7-yloxy}-propyl)-amide | nd |
| 113 | Morpholine-4-carboxylic acid (3-{4-[1-(6-morpholin-4-yl-pyridin-3-ylcarbamoyl)-piperidin-4-yl]-quinazolin-7-yloxy}-propyl)-amide | 11.5 |
| 114 | 4-[7-(3-[1,2,4]Triazol-4-yl-propoxy)-quinazolin-4-yl]-piperidine-1-carboxylic acid (6-pyrrolidin-1-yl-pyridin-3-yl)-amide | 10 |
| 115 | 4-{7-[3-(4-Ethyl-piperazin-1-yl)-propoxy]-quinazolin-4-yl}-piperidine-1-carboxylic acid (4-morpholin-4-yl-phenyl)-amide | >20 |
| 116 | 4-(7-{3-[4-(2-Hydroxy-ethyl)-piperazin-1-yl]-propoxy}-quinazolin-4-yl)-piperidine-1-carboxylic acid (4-morpholin-4-yl-phenyl)-amide | 20 |

-continued

| Number | Compound Name | TrkB IC$_{50}$ (uM) |
|---|---|---|
| 117 | 4-{7-[3-(4-Acetyl-piperazin-1-yl)-propoxy]-quinazolin-4-yl}-piperidine-1-carboxylic acid (4-morpholin-4-yl-phenyl)-amide | >20 |
| 118 | 4-{7-[3-(4-Methanesulfonyl-piperazin-1-yl)-propoxy]-quinazolin-4-yl}-piperidine-1-carboxylic acid (4-morpholin-4-yl-phenyl)-amide | 14.6 |
| 119 | (S)-4-{7-[3-(2-Hydroxymethyl-pyrrolidin-1-yl)-propoxy]-quinazolin-4-yl}-piperidine-1-carboxylic acid (4-morpholin-4-yl-phenyl)-amide | >20 |
| 120 | 4-(3-{4-[1-(4-Morpholin-4-yl-phenylcarbamoyl)-piperidin-4-yl]-quinazolin-7-yloxy}-propyl)-piperazine-1-carboxylic acid dimethylamide | 16.7 |
| 121 | Methanesulfonic acid 3-{4-[1-(4-isopropoxy-phenylcarbamoyl)-piperidin-4-yl]-quinazolin-7-yloxy}-propyl ester | 0.13 |
| 122 | Methanesulfonic acid 3-{4-[1-(4-morpholin-4-yl-phenylcarbamoyl)-piperidin-4-yl]-quinazolin-7-yloxy}-propyl ester | 18.91 |
| 123 | 4-[7-(3-Piperazin-1-yl-propoxy)-quinazolin-4-yl]-piperidine-1-carboxylic acid (4-morpholin-4-yl-phenyl)-amide | >20 |
| 124 | 4-[7-(3-Pyrrolidin-1-yl-propoxy)-quinazolin-4-yl]-piperidine-1-carboxylic acid (4-morpholin-4-yl-phenyl)-amide | >20 |
| 125 | 4-{7-[3-(4-Methyl-[1,4]diazepan-1-yl)-propoxy]-quinazolin-4-yl}-piperidine-1-carboxylic acid (4-morpholin-4-yl-phenyl)-amide | >20 |
| 126 | (R)-4-[7-(3-Hydroxy-pyrrolidin-1-yl)-quinazolin-4-yl]-piperidine-1-carboxylic acid (4-morpholin-4-yl-phenyl)-amide | 10.2 |
| 127 | 4-[7-(1-Methyl-piperidin-4-yloxy)-quinazolin-4-yl]-piperidine-1-carboxylic acid (4-morpholin-4-yl-phenyl)-amide | 13.62 |
| 128 | (S)-4-[7-(3-Hydroxy-pyrrolidin-1-yl)-quinazolin-4-yl]-piperidine-1-carboxylic acid (4-morpholin-4-yl-phenyl)-amide | >20 |
| 129 | (S)-4-[7-(3-Hydroxy-pyrrolidin-1-yl)-quinazolin-4-yl]-piperidine-1-carboxylic acid (4-pyrrolidin-1-yl-phenyl)-amide | 3.11 |
| 130 | (R)-4-[7-(2-Methoxymethyl-pyrrolidin-1-yl)-quinazolin-4-yl]-piperidine-1-carboxylic acid (4-morpholin-4-yl-phenyl)-amide | >42 |
| 131 | 4-[6-(4-Methyl-piperazin-1-yl)-quinazolin-4-yl]-piperidine-1-carboxylic acid (4-isopropoxy-phenyl)-amide | 5.31 |
| 132 | (R)-4-[7-(2-Hydroxymethyl-pyrrolidin-1-yl)-quinazolin-4-yl]-piperidine-1-carboxylic acid (4-morpholin-4-yl-phenyl)-amide | >42 |
| 133 | 4-[7-(3-Morpholin-4-yl-propoxy)-quinazolin-4-yl]-piperidine-1-carboxylic acid (4-morpholin-4-yl-phenyl)-amide | >42 |
| 134 | 4-[7-(3-Diethylamino-propoxy)-quinazolin-4-yl]-piperidine-1-carboxylic acid (4-morpholin-4-yl-phenyl)-amide | >42 |
| 135 | 4-[7-(4-Methyl-piperazin-1-yl)-quinazolin-4-yl]-piperidine-1-carboxylic acid (4-morpholin-4-yl-phenyl)-amide | >42 |
| 136 | 4-[7-(4-Ethyl-piperazin-1-yl)-quinazolin-4-yl]-piperidine-1-carboxylic acid (4-morpholin-4-yl-phenyl)-amide | >42 |
| 137 | 4-{7-[4-(2-Hydroxy-ethyl)-piperazin-1-yl]-quinazolin-4-yl}-piperidine-1-carboxylic acid (4-morpholin-4-yl-phenyl)-amide | >42 |
| 138 | 4-[7-(4-Methyl-[1,4]diazepan-1-yl)-quinazolin-4-yl]-piperidine-1-carboxylic acid (4-morpholin-4-yl-phenyl)-amide | >42 |
| 139 | (S)-4-[7-(2-Hydroxymethyl-pyrrolidin-1-yl)-quinazolin-4-yl]-piperidine-1-carboxylic acid (4-morpholin-4-yl-phenyl)-amide | 33.82 |
| 140 | 4-(7-Piperazin-1-yl-quinazolin-4-yl)-piperidine-1-carboxylic acid (4-morpholin-4-yl-phenyl)-amide | >42 |
| 141 | 4-[7-(4-Acetyl-piperazin-1-yl)-quinazolin-4-yl]-piperidine-1-carboxylic acid (4-morpholin-4-yl-phenyl)-amide | 15.01 |
| 142 | 4-[7-(4-Methanesulfonyl-piperazin-1-yl)-quinazolin-4-yl]-piperidine-1-carboxylic acid (4-morpholin-4-yl-phenyl)-amide | 17.42 |
| 143 | 4-{4-[1-(4-Morpholin-4-yl-phenylcarbamoyl)-piperidin-4-yl]-quinazolin-7-yl}-piperazine-1-carboxylic acid dimethylamide | 7.6 |

| Number | Compound Name | TrkB IC$_{50}$ (uM) |
|---|---|---|
| 144 | 4-{7-[4-(2-Dimethylamino-acetyl)-piperazin-1-yl]-quinazolin-4-yl}-piperidine-1-carboxylic acid (4-morpholin-4-yl-phenyl)-amide | 14.23 |
| 145 | 4-(7-Morpholin-4-yl-quinazolin-4-yl)-piperidine-1-carboxylic acid (4-morpholin-4-yl-phenyl)-amide | 21.14 |
| 146 | 4-[7-(2-Methanesulfonyl-ethylamino)-quinazolin-4-yl]-piperidine-1-carboxylic acid (4-morpholin-4-yl-phenyl)-amide | >42 |
| 147 | 4-{7-[2-(2-Oxo-oxazolidin-3-yl)-ethoxy]-quinazolin-4-yl}-piperidine-1-carboxylic acid (4-pyrrolidin-1-yl-phenyl)-amide | 2.73 |
| 148 | 4-{7-[2-(2-Oxo-oxazolidin-3-yl)-ethoxy]-quinazolin-4-yl}-piperidine-1-carboxylic acid (4-morpholin-4-yl-phenyl)-amide | 26.67 |
| 149 | (R)-4-[7-(3-Dimethylamino-pyrrolidin-1-yl)-quinazolin-4-yl]-piperidine-1-carboxylic acid (4-pyrrolidin-1-yl-phenyl)-amide | 7.26 |
| 150 | (R)-4-[7-(3-Dimethylamino-pyrrolidin-1-yl)-quinazolin-4-yl]-piperidine-1-carboxylic acid (4-morpholin-4-yl-phenyl)-amide | >42 |
| 151 | (S)-4-[7-(1-Methyl-pyrrolidin-2-ylmethoxy)-quinazolin-4-yl]-piperidine-1-carboxylic acid (4-pyrrolidin-1-yl-phenyl)-amide | >42 |
| 152 | (S)-4-{7-[2-(2-Hydroxymethyl-pyrrolidin-1-yl)-ethoxy]-quinazolin-4-yl}-piperidine-1-carboxylic acid (4-pyrrolidin-1-yl-phenyl)-amide | 32.74 |
| 153 | (S)-4-{7-[2-(2-Hydroxymethyl-pyrrolidin-1-yl)-ethoxy]-quinazolin-4-yl}-piperidine-1-carboxylic acid (4-morpholin-4-yl-phenyl)-amide | >42 |
| 154 | (R)-4-[7-(1-Acetyl-pyrrolidin-3-yloxy)-quinazolin-4-yl]-piperidine-1-carboxylic acid (4-pyrrolidin-1-yl-phenyl)-amide | >42 |
| 155 | 4-[7-(4-Carboxylic acid methylamide-piperidin-1-yl)-quinazolin-4-yl]-piperidine-1-carboxylic acid (4-pyrrolidin-1-yl-phenyl)-amide | 11 |
| 156 | 4-{7-[2-(4-Methyl-piperazin-1-yl)-ethoxy]-quinazolin-4-yl}-piperidine-1-carboxylic acid (4-morpholin-4-yl-phenyl)-amide | >21 |
| 157 | 4-{7-[2-(4-Methyl-piperazin-1-yl)-ethoxy]-quinazolin-4-yl}-piperidine-1-carboxylic acid (4-pyrrolidin-1-yl-phenyl)-amide | 7.05 |
| 158 | 4-{7-[3-(4-Methyl-piperazin-1-yl)-propoxy]-quinazolin-4-yl}-piperidine-1-carboxylic acid (4-pyrrolidin-1-yl-phenyl)-amide | 5 |
| 159 | 4-[7-(4-Methyl-piperazin-1-yl)-quinazolin-4-yl]-piperidine-1-carboxylic acid (4-pyrrolidin-1-yl-phenyl)-amide | 7.86 |
| 160 | 4-[7-(4-Methyl-piperazin-1-yl)-quinazolin-4-yl]-piperidine-1-carboxylic acid (6-pyrrolidin-1-yl-pyridin-3-yl)-amide | 6.45 |
| 161 | (S)-4-{7-[3-(2-Hydroxymethyl-pyrrolidin-1-yl)-propoxy]-quinazolin-4-yl}-piperidine-1-carboxylic acid (4-pyrrolidin-1-yl-phenyl)-amide | 6.48 |
| 162 | (S)-4-[7-(1-Acetyl-pyrrolidin-2-ylmethoxy)-quinazolin-4-yl]-piperidine-1-carboxylic acid (4-pyrrolidin-1-yl-phenyl)-amide | >21 |
| 163 | 4-[7-(1-Acetyl-piperidin-4-ylmethoxy)-quinazolin-4-yl]-piperidine-1-carboxylic acid (4-pyrrolidin-1-yl-phenyl)-amide | 4.12 |

Biological Data for c-Kit

The activity of representative compounds of the present invention is presented in the charts below. All activities are in nM and have the following uncertainties: C-Kit IC$_{50}$: ±10%.

| Number | Compound Name | ckit IC$_{50}$ (nM) |
|---|---|---|
| 1 | 4-(6,7-Dimethoxy-quinazolin-4-yl)-piperidine-1-carboxylic acid (4-isopropoxy-phenyl)-amide | 82.5 |
| 4 | 4-(6,7-Dimethoxy-quinazolin-4-yl)-piperidine-1-carboxylic acid (4-isopropyl-phenyl)-amide | 610 |

-continued

| Number | Compound Name | ckit IC$_{50}$ (nM) |
|---|---|---|
| 17 | 4-(6,7-Dimethoxy-quinazolin-4-yl)-piperidine-1-carboxylic acid (6-cyclobutoxy-pyridin-3-yl)-amide | 77.5 |
| 18 | 4-(6,7-Dimethoxy-quinazolin-4-yl)-piperidine-1-carboxylic acid (4-morpholin-4-yl-phenyl)-amide | 158.0 |
| 39 | 4-{7-[3-(4-Methyl-piperazin-1-yl)-propoxy]-quinazolin-4-yl}-piperidine-1-carboxylic acid (4-isopropoxy-phenyl)-amide | 14 |
| 68 | 4-{7-[3-(2-Oxo-pyrrolidin-1-yl)-propoxy]-quinazolin-4-yl}-piperidine-1-carboxylic acid (4-morpholin-4-yl-phenyl)-amide | 28 |
| 72 | 4-{7-[3-(2-Oxo-pyrrolidin-1-yl)-propoxy]-quinazolin-4-yl}-piperidine-1-carboxylic acid (6-morpholin-4-yl-pyridin-3-yl)-amide | 23 |
| 73 | 4-{7-[3-(4-Methyl-piperazin-1-yl)-propoxy]-quinazolin-4-yl}-piperidine-1-carboxylic acid (4-morpholin-4-yl-phenyl)-amide | 40 |
| 74 | 4-{7-[2-(2-Oxo-pyrrolidin-1-yl)-ethoxy]-quinazolin-4-yl}-piperidine-1-carboxylic acid (4-pyrrolidin-1-yl-phenyl)-amide | 13 |
| 76 | 4-{6-[3-(4-Methyl-piperazin-1-yl)-propoxy]-quinazolin-4-yl}-piperidine-1-carboxylic acid (4-isopropoxy-phenyl)-amide | 282 |
| 80 | 4-{7-[3-(4-Methyl-piperazin-1-yl)-propoxy]-quinazolin-4-yl}-piperidine-1-carboxylic acid (6-morpholin-4-yl-pyridin-3-yl)-amide | 160 |
| 83 | 4-{7-[2-(2-Oxo-pyrrolidin-1-yl)-ethoxy]-quinazolin-4-yl}-piperidine-1-carboxylic acid (6-morpholin-4-yl-pyridin-3-yl)-amide | 25 |
| 88 | 4-[7-(3-Methanesulfonylamino-propoxy)-quinazolin-4-yl]-piperidine-1-carboxylic acid (6-cyclopentyloxy-pyridin-3-yl)-amide | 11 |
| 89 | 4-{7-[3-(2-Oxo-pyrrolidin-1-yl)-propoxy]-quinazolin-4-yl}-piperidine-1-carboxylic acid (6-pyrrolidin-1-yl-pyridin-3-yl)-amide | 13 |

In Vivo Assays

The following representative in vivo assay was performed in determining the biological activities of compounds within the scope of the invention. They are given to illustrate the invention in a non-limiting fashion.

The oral anti-tumor efficacy of a subset of the compounds of the invention was evaluated in vivo using a nude mouse MV4-11 human tumor xenograft regression model.

Female athymic nude mice (CD-1, nu/nu, 9-10 weeks old) were obtained from Charles River Laboratories (Wilmington, Mass.) and were maintained according to NIH standards. All mice were group housed (5 mice/cage) under clean-room conditions in sterile micro-isolator cages on a 12-hour light/dark cycle in a room maintained at 21-22° C. and 40-50% humidity. Mice were fed irradiated standard rodent diet and water ad libitum. All animals were housed in a Laboratory Animal Medicine facility that is fully accredited by the American Association for Assessment and Accreditation of Laboratory Animal Care (AAALAC). All procedures involving animals were conducted in compliance with the NIH *Guide for the Care and Use of Laboratory Animals* and all protocols were approved by an Internal Animal Care and Use Committee (IACUC).

The human leukemic MV4-11 cell line was obtained from the American Type Culture Collection (ATCC Number: CRL-9591) and propagated in RPMI medium containing 10% FBS (fetal bovine serum) and 5 ng/mL GM-CSF (R&D Systems). MV4-11 cells are derived from a patient with childhood acute myelomonocytic leukemia with an 11q23 translocation resulting in a MLL gene rearrangement and containing an FLT3-ITD mutation (AML subtype M4)(1,2). MV4-11 cells express constitutively active phosphorylated FLT3 receptor as a result of a naturally occurring FLT3/ITD mutation. Strong anti-tumor activity against MV4-11 tumor growth in the nude mouse tumor xenograft model is anticipated to be a desirable quality of the invention.

In pilot growth studies, the following conditions were identified as permitting MV4-11 cell growth in nude mice as subcutaneous solid tumor xenografts: Immediately prior to injection, cells were washed in PBS and counted, suspended 1:1 in a mixture of PBS:Matrigel (BD Biosciences) and then loaded into pre-chilled 1 cc syringes equipped with 25 gauge needles. Female athymic nude mice weighing no less than 20-21 grams were inoculated subcutaneously in the left inguinal region of the thigh with $5 \times 10^6$ tumor cells in a delivery volume of 0.2 mL. For regression studies, the tumors were allowed to grow to a pre-determined size prior to initiation of dosing. Approximately 3 weeks after tumor cell inoculation, mice bearing subcutaneous tumors ranging in size from 106 to 439 mm$^3$ (60 mice in this range) were randomly assigned to treatment groups such that all treatment groups had similar starting mean tumor volumes of ~200 mm$^3$. Mice were dosed orally by gavage with vehicle (control group) or compound at various doses twice-daily (b.i.d.) during the week and once-daily (q.d.) on weekends. Dosing was continued for 11 consecutive days, depending on the kinetics of tumor growth and size of tumors in vehicle-treated control mice. If tumors in the control mice reached ~10% of body weight (~2.0 grams), the study was to be terminated. Compounds of the present invention were prepared fresh daily as a clear solution (@ 1, 3 and 10 mg/mL) in 20% HPβCD/2% NMP/10 mM Na Phosphate, pH 3-4 (NMP=Pharmasolve, ISP Technologies, Inc.) or other suitable vehicle and administered orally as described above. During the study, tumor growth was measured three times-a-week (M, W, F) using electronic Vernier calipers. Tumor volume (mm$^3$) was calculated using the formula $(L \times W)^2/2$, where L=length (mm) and W=width (shortest distance in mm) of the tumor. Body weight was measured three times-a-week and a loss of body weight >10% was used as an indication of lack of compound tolerability.

Unacceptable toxicity was defined as body weight loss >20% during the study. Mice were closely examined daily at each dose for overt clinical signs of adverse, drug-related side effects.

On the day of study termination, a final tumor volume and final body weight were obtained on each animal. Mice were euthanized using 100% CO$_2$ and tumors were immediately excised intact and weighed, with final tumor wet weight (grams) serving as a primary efficacy endpoint.

The time course of the inhibitory effects of compounds of the present invention on the growth of MV4-11 tumors is illustrated in FIG. 1. Values represent the mean (±sem) of 15 mice per treatment group. Percent inhibition (% I) of tumor growth was calculated versus tumor growth in the vehicle-treated Control group on the last study day. Statistical significance versus Control was determined by Analysis of Variance (ANOVA) followed by Dunnett's t-test: * $p<0.05$; ** $p<0.01$.

A similar reduction of final tumor weight was noted at study termination. (See FIG. 2). Values represent the mean (±sem) of 15 mice per treatment group, except for the high dose group where only 5 of 15 mice were sacrificed on the day of study termination. Percent Inhibition was calculated versus the mean tumor weight in the vehicle-treated control group. Statistical significance versus Control was determined by ANOVA followed by Dunnett's t-test: ** $p<0.01$.

FIG. 1a: Compound 73 administered orally by gavage at doses of 10, 30 and 100 mg/kg b.i.d. for 11 consecutive days, produced statistically significant, dose-dependent inhibition of growth of MV4-11 tumors grown subcutaneously in nude mice. On the last day of treatment (Day 11), mean tumor volume was dose-dependently decreased by 44%, 84% ($p<0.01$) and 94% ($p<0.01$) at doses of 10, 30 and 100 mg/kg, respectively, compared to the mean tumor volume of the vehicle-treated group. Tumor regression was observed at doses of 30 mg/kg and 100 mg/kg, with statistically significant decreases of 42% and 77%, respectively, versus the starting mean tumor volumes on Day 1. At the lowest dose tested of 10 mg/kg, modest growth delay was observed (44% I vs Control), however this effect did not achieve statistical significance.

FIG. 2a: Following eleven consecutive days of oral dosing, Compound 73 produced statistically significant, dose-dependent reductions of final tumor weight compared to the mean tumor weight of the vehicle-treated group, with 48%, 85% ($p<0.01$) and 99% ($p<0.01$) decreases at 10, 30 and 100 mg/kg doses, respectively. In some mice, at the high dose of Compound 73, final tumors had regressed to non-palpable, non-detectable tumors.

FIG. 1b: Compound 74 administered orally by gavage at doses of 10, 30 and 100 mg/kg b.i.d. for 11 consecutive days, also produced statistically significant, dose-dependent inhibition of growth of MV4-11 tumors grown subcutaneously in nude mice. On the last day of treatment (Day 11), mean tumor volume was dose-dependently decreased by 22%, 54% ($p<0.01$) and 96% ($p<0.01$) at doses of 10, 30 and 100 mg/kg, respectively, compared to the mean tumor volume of the vehicle-treated group. Tumor regression was observed at a dose of 100 mg/kg, with a statistically significant decrease of 79% versus the starting mean tumor volume on Day 1. Significant growth delay was observed at a dose of 30 mg/kg (54% I vs Control) and, at the lowest dose tested of 10 mg/kg, some growth delay was observed (22% I vs Control); however this effect did not achieve statistical significance.

FIG. 2b: Following eleven consecutive days of oral dosing, Compound 74 produced statistically significant, dose-dependent reductions of final tumor weight compared to the mean tumor weight of the vehicle-treated group, with 12%, 43% ($p<0.01$) and 91% ($p<0.01$) decreases at 10, 30 and 100 mg/kg doses, respectively. In some mice, at the high dose of Compound 73, final tumors had regressed to non-palpable, non-detectable tumors.

Mice were weighed three times each week (M, W, F) during the study and were examined daily at the time of dosing for overt clinical signs of any adverse, drug-related side effects. No overt toxicity was noted for either Compound 73 or 74 and no significant adverse effects on body weight were observed during the 11-day treatment period with either Compound 73 or 74 at doses up to 200 mg/kg/day. Overall, across all dose groups for both Compound 73 and 74 the mean loss of body weight was <3% of initial body weight, indicating that the compounds of the present invention were well-tolerated.

To establish further that compounds of the present invention reached the expected target in tumor tissue, the level of FLT3 phosphorylation in tumor tissue obtained from vehicle- and compound-treated mice was measured. Results for Compound 73 and Compound 74 are shown in FIG. 3 and FIG. 4, respectively. For this pharmacodynamic study, a sub-set of 10 mice from the vehicle-treated control group were randomized into two groups of 5 mice each and then treated with another dose of vehicle or compound (100 mg/kg, po). Tumors were harvested 2 hours later and snap frozen for assessment of FLT3 phosphorylation by immunobloting.

Harvested tumors were processed for immunoblot analysis of FLT3 phosphorylation in the following manner: 100 mg of tumor tissue was dounce homogenized in lysis buffer (50 mM Hepes, 150 mM NaCl, 10% Glycerol, 1% Triton-X-100, 10 mM NaF, 1 mM EDTA, 1.5 mM $MgCl_2$, 10 mM NaPyrophosphate) supplemented with phosphatase (Sigma Cat#P2850) and protease inhibitors (Sigma Cat #P8340). Insoluble debris was removed by centrifugation at 1000×g for 5 minutes at 4° C. Cleared lysates (15 mg of total potein at 10 mg/ml in lysis buffer) were incubated with 10 μg of agarose conjugated anti-FLT3 antibody, clone C-20 (Santa Cruz cat # sc-479ac), for 2 hours at 4° C. with gentle agitation. Immunoprecipitated FLT3 from tumor lysates were then washed four times with lysis buffer and separated by SDS-PAGE. The SDS-PAGE gel was transferred to nitrocellulose and immunoblotted with anti-phosphotyrosine antibody (clone-4G10, UBI cat. #05-777), followed by alkaline phosphatase-conjugated goat anti-mouse secondary antibody (Novagen cat. #401212). Detection of protein was done by measuring the fluorescent product of the alkaline phosphatase reaction with the substrate 9H-(1, 3-dichloro-9,9-dimethylacridin-2-one-7-yl)phosphate, diammonium salt (DDAO phosphate) (Molecular Probes cat. # D 6487) using a Molecular Dynamics Typhoon Imaging system (Molecular Dynamics, Sunyvale, Calif.). Blots were then stripped and reprobed with anti-FLT3 antibody for normalization of phosphorylation signals.

As illustrated in FIG. 3 and FIG. 4, a single dose of Compound 73, and Compound 74, respectively, at 100 mg/kg produced a biologically significant reduction in the level of FLT3 phosphorylation in MV4-11 tumors compared to tumors from vehicle-treated mice. (Total FLT3 is shown in the bottom plot.) These results further demonstrate that the compounds of the present invention are in fact interacting with the expected FLT3 target in the tumor.

Methods of Treatment/Prevention

In another aspect of this invention, compounds of the invention can be used to inhibit tyrosine kinase activity, including Flt3 activity, and/or c-kit activity, and/or TrkB activity, or reduce kinase activity, including Flt3 activity, and/or c-kit activity, and/or TrkB activity, in a cell or a subject, or to treat disorders related to FLT3, and/or c-kit and/or TrkB kinase activity or expression in a subject.

In one embodiment to this aspect, the present invention provides a method for reducing or inhibiting the kinase activity of FLT3 and/or c-kit and/or TrkB in a cell comprising the step of contacting the cell with a compound of Formula I. The present invention also provides a method for reducing or inhibiting the kinase activity of FLT3, and/or c-kit and/or TrkB in a subject comprising the step of administering a compound of Formula I to the subject. The present invention further provides a method of inhibiting cell proliferation in a cell comprising the step of contacting the cell with a compound of Formula I.

The kinase activity of FLT3, c-kit or TrkB in a cell or a subject can be determined by procedures well known in the art, such as the FLT3 kinase assay described herein, the c-kit kinase assay described herein, and the TrkB kinase assay described herein.

The term "subject" as used herein, refers to an animal, preferably a mammal, most preferably a human, who has been the object of treatment, observation or experiment.

The term "contacting" as used herein, refers to the addition of compound to cells such that compound is taken up by the cell.

In other embodiments to this aspect, the present invention provides both prophylactic and therapeutic methods for treating a subject at risk of (or susceptible to) developing a cell proliferative disorder or a disorder related to FLT3 and/or c-kit and/or TrkB.

In one example, the invention provides methods for preventing in a subject a cell proliferative disorder or a disorder related to FLT3 and/or c-kit and/or TrkB, comprising administering to the subject a prophylactically effective amount of a pharmaceutical composition comprising the compound of Formula I and a pharmaceutically acceptable carrier. Administration of said prophylactic agent can occur prior to the manifestation of symptoms characteristic of the cell proliferative disorder or disorder related to FLT3 and/or c-kit and/or TrkB, such that a disease or disorder is prevented or, alternatively, delayed in its progression.

In another example, the invention pertains to methods of treating in a subject a cell proliferative disorder or a disorder related to FLT3 and/or c-kit and/or TrkB comprising administering to the subject a therapeutically effective amount of a pharmaceutical composition comprising the compound of Formula I and a pharmaceutically acceptable carrier. Administration of said therapeutic agent can occur concurrently with the manifestation of symptoms characteristic of the disorder, such that said therapeutic agent serves as a therapy to compensate for the cell proliferative disorder or disorders related to FLT3 and/or c-kit and/or TrkB.

The term "prophylactically effective amount" refers to an amount of an active compound or pharmaceutical agent that inhibits or delays in a subject the onset of a disorder as being sought by a researcher, veterinarian, medical doctor or other clinician.

The term "therapeutically effective amount" as used herein, refers to an amount of active compound or pharmaceutical agent that elicits the biological or medicinal response in a subject that is being sought by a researcher, veterinarian, medical doctor or other clinician, which includes alleviation of the symptoms of the disease or disorder being treated.

Methods are known in the art for determining therapeutically and prophylactically effective doses for the instant pharmaceutical composition.

As used herein, the term "composition" is intended to encompass a product comprising the specified ingredients in the specified amounts, as well as any product which results, directly or indirectly, from combinations of the specified ingredients in the specified amounts.

As used herein, the terms "disorders related to FLT3", or "disorders related to FLT3 receptor", or "disorders related to FLT3 receptor tyrosine kinase" shall include diseases associated with or implicating FLT3 activity, for example, the overactivity of FLT3, and conditions that accompany with these diseases. The term "overactivity of FLT3" refers to either 1) FLT3 expression in cells which normally do not express FLT3; 2) FLT3 expression by cells which normally do not express FLT3; 3) increased FLT3 expression leading to unwanted cell proliferation; or 4) mutations leading to constitutive activation of FLT3. Examples of "disorders related to FLT3" include disorders resulting from over stimulation of FLT3 due to abnormally high amount of FLT3 or mutations in FLT3, or disorders resulting from abnormally high amount of FLT3 activity due to abnormally high amount of FLT3 or mutations in FLT3. It is known that overactivity of FLT3 has been implicated in the pathogenesis of a number of diseases, including the cell proliferative disorders, neoplastic disorders and cancers listed below.

The term "cell proliferative disorders" refers to unwanted cell proliferation of one or more subset of cells in a multicellular organism resulting in harm (i.e., discomfort or decreased life expectancy) to the multicellular organisms. Cell proliferative disorders can occur in different types of animals and humans. For example, as used herein "cell proliferative disorders" include neoplastic and other cell proliferative disorders.

As used herein, a "neoplastic disorder" refers to a tumor resulting from abnormal or uncontrolled cellular growth. Examples of neoplastic disorders include, but are not limited to, hematopoietic disorders such as, for instance, the myeloproliferative disorders, such as thrombocythemia, essential thrombocytosis (ET), agnogenic myeloid metaplasia, myelofibrosis (MF), myelofibrosis with myeloid metaplasia (MMM), chronic idiopathic myelofibrosis (IMF), and polycythemia vera (PV), the cytopenias, and pre-malignant myelodysplastic syndromes; cancers such as glioma cancers, lung cancers, breast cancers, colorectal cancers, prostate cancers, gastric cancers, esophageal cancers, colon cancers, pancreatic cancers, ovarian cancers, and hematoglogical malignancies, including myelodysplasia, multiple myeloma, leukemias and lymphomas. Examples of hematological malignancies include, for instance, leukemias, lymphomas (non-Hodgkin's lymphoma), Hodgkin's disease (also called Hodgkin's lymphoma), and myeloma—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma, (MM).

Examples of other cell proliferative disorders, include but are not limited to, atherosclerosis (Libby P, 2003, "Vascular biology of atherosclerosis: overview and state of the art", Am J Cardiol 91(3A):3A-6A) transplantation-induced vasculopathies (Helisch A, Schaper W. 2003, Arteriogenesis: the development and growth of collateral arteries. Microcirculation, 10(1):83-97), macular degeneration (Holz F G et al., 2004, "Pathogenesis of lesions in late age-related macular disease", Am J Ophthalmol. 137(3):504-10), neointima hyperplasia and restenosis (Schiele T M et. al., 2004, "Vascular restenosis—striving for therapy." Expert Opin Pharmacother. 5(11):2221-32), pulmonary fibrosis (Thannickal V J et al., 2003, "Idiopathic pulmonary fibrosis: emerging concepts on pharmacotherapy, Expert Opin Pharmacother. 5(8): 1671-86), glomerulonephritis (Cybulsky A V, 2000, "Growth factor pathways in proliferative glomerulonephritis", Curr Opin Nephrol Hypertens" 9(3):217-23), glomerulosclerosis (Harris R C et al, 1999, "Molecular basis of injury and progression in focal glomerulosclerosis" Nephron 82(4):289-99), renal dysplasia and kidney fibrosis (Woolf A S et al., 2004, "Evolving concepts in human renal dysplasia", J Am Soc Nephrol.15 (4):998-1007), diabetic retinopathy (Grant M B et al., 2004, "The role of growth factors in the pathogenesis of diabetic retinopathy", Expert Opin Investig Drugs 13(10):1275-93) and rheumatoid arthritis (Sweeney S E, Firestein G S, 2004, Rheumatoid arthritis: regulation of synovial inflammation, Int J Biochem Cell Biol. 36(3):372-8).

As used herein, the terms "disorders related to TrkB", or "disorders related to the TrkB receptor", or "disorders related to the TrkB receptor tyrosine kinase" shall include diseases associated with or implicating TrkB activity, for example, the overactivity of TrkB, and conditions that accompany these diseases. The term "overactivity of TrkB" refers to either 1) TrkB expression in cells which normally do not express TrkB; 2) TrkB expression by cells which normally do not express TrkB; 3) increased TrkB expression leading to unwanted cell proliferation; or 4) increased TrkB expression leading to adhesion independent cell survival; 5) mutations leading to constitutive activation of TrkB. Examples of "disorders related to TrkB" include 1) disorders resulting from over stimulation of TrkB due to abnormally high amount of TrkB or mutations in TrkB, or 2) disorders resulting from abnormally high amount of TrkB activity due to abnormally high amount of TrkB or mutations in TrkB.

Disorders related to TrkB include a number of diseases, including cancers, such as, but not limited to, neuroblastoma, wilm's tumor, breast, colon, prostate, and lung. See, e.g., Brodeur G M, (2003) "Neuroblastoma: biological insights into a clinical enigma." Nat RevCancer; 3(3):203-16; Eggerl A et. al. (2001) "Expression of the neurotrophin receptor TrkB is associated with unfavorable outcome in Wilms' tumor" J Clin Oncol. 19(3):689-96; Descamps S et. al. (2001) "Nerve growth factor stimulates proliferation and survival of human breast cancer cells through two distinct signaling pathways." J Biol Chem. 276(21):17864-70; Bardelli A, et. al. (2003) "Mutational analysis of the tyrosine kinome in colorectal cancers." Science 300(5621):949; Weeraratna A T et. al. (2000) "Rational basis for Trk inhibition therapy for prostate cancer." Prostate 45(2):140-8.19(3):689-96; Ricci et. al., (2001) "Neurotrophins and neurotrophin receptors in human lung cancer." Am J Respir Cell Mol Biol. 25(4):439-46.

As used herein, the terms "disorders related to c-kit", or "disorders related to c-kit receptor", or "disorders related to c-kit receptor tyrosine kinase" shall include diseases associated with or implicating c-kit activity, for example, the overactivity of c-kit, and conditions that accompany these diseases. The term "overactivity of c-kit" refers to either 1) c-kit expression in cells which normally do not express c-kit; 2) c-kit expression by cells which normally do not express c-kit; 3) increased c-kit expression leading to unwanted cell proliferation; or 4) mutations leading to constitutive activation of c-kit. Examples of "disorders related to c-kit" include disorders resulting from over stimulation of c-kit due to abnormally high amount of c-kit or mutations in c-kit, or disorders resulting from abnormally high amount of c-kit activity due to abnormally high amount of c-kit or mutations in c-kit.

Disorders related to c-Kit include a number of diseases, such as mastocytosis, mast cell leukemia, gastrointestinal stromal tumour, sinonasal natural killer/T-cell lymphoma, seminoma, dysgerminoma, thyroid carcinoma; small-cell lung carcinoma, malignant melanoma, adenoid cystic carcinoma, ovarian carcinoma, acute myelogenous leukemia, anaplastic large cell lymphoma, angiosarcoma, endometrial carcinoma, pediatric T-cell ALL, lymphoma, breast carcinoma and prostate carcinoma. See Heinrich, Michael C. et al. Review Article: Inhibition of KIT Tyrosine Kinase Activity: A Novel Molecular Approach to the Treatment of KIT-Positive Malignancies.

In a further embodiment to this aspect, the invention encompasses a combination therapy for treating or inhibiting the onset of a cell proliferative disorder or a disorder related to FLT3 and/or c-kit and/or TrkB in a subject. The combination therapy comprises administering to the subject a therapeutically or prophylactically effective amount of a compound of Formula I, and one or more other anti-cell proliferation therapy including chemotherapy, radiation therapy, gene therapy and immunotherapy.

In an embodiment of the present invention, the compound of the present invention may be administered in combination with chemotherapy. As used herein, chemotherapy refers to a therapy involving a chemotherapeutic agent. A variety of chemotherapeutic agents may be used in the combined treatment methods disclosed herein. Chemotherapeutic agents contemplated as exemplary, include, but are not limited to: platinum compounds (e.g., cisplatin, carboplatin, oxaliplatin); taxane compounds (e.g., paclitaxcel, docetaxol); campothothecin compounds (irinotecan, topotecan); vinca alkaloids (e.g., vincristine, vinblastine, vinorelbine); anti-tumor nucleoside derivatives (e.g., 5-fluorouracil, leucovorin, gemcitabine, capecitabine) alkylating agents (e.g., cyclophosphamide, carmustine, lomustine, thiotepa); epipodophyllotoxins/podophyllotoxins (e.g. etoposide, teniposide); aromatase inhibitors (e.g., anastrozole, letrozole, exemestane); anti-estrogen compounds (e.g., tamoxifen, fulvestrant), antifolates (e.g., premetrexed disodium); hypomethylating agents (e.g., azacitidine); biologics (e.g., gemtuzamab, cetuximab, rituximab, pertuzumab, trastuzumab, bevacizumab, erlotinib); antibiotics/anthracyclines (e.g. idarubicin, actinomycin D, bleomycin, daunorubicin, doxorubicin, mitomycin C, dactinomycin, carminomycin, daunomycin); antimetabolites (e.g., aminopterin, clofarabine, cytosine arabinoside, methotrexate); tubulin-binding agents (e.g. combretastatin, colchicine, nocodazole); topoisomerase inhibitors (e.g., camptothecin). Further useful agents include verapamil, a calcium antagonist found to be useful in combination with antineoplastic agents to establish chemosensitivity in tumor cells resistant to accepted chemotherapeutic agents and to potentiate the efficacy of such compounds in drug-sensitive malignancies. See Simpson W G, The calcium channel blocker verapamil and cancer chemotherapy. Cell Calcium. 1985 December; 6(6):449-67. Additionally, yet to emerge chemotherapeutic agents are contemplated as being useful in combination with the compound of the present invention.

In another embodiment of the present invention, the compound of the present invention may be administered in combination with radiation therapy. As used herein, "radiation therapy" refers to a therapy that comprises exposing the subject in need thereof to radiation. Such therapy is known to those skilled in the art. The appropriate scheme of radiation therapy will be similar to those already employed in clinical therapies wherein the radiation therapy is used alone or in combination with other chemotherapeutics.

In another embodiment of the present invention, the compound of the present invention may be administered in combination with a gene therapy. As used herein, "gene therapy" refers to a therapy targeting on particular genes involved in tumor development. Possible gene therapy strategies include the restoration of defective cancer-inhibitory genes, cell transduction or transfection with antisense DNA corresponding to genes coding for growth factors and their receptors, RNA-based strategies such as ribozymes, RNA decoys, antisense messenger RNAs and small interfering RNA (siRNA) molecules and the so-called 'suicide genes'.

In other embodiments of this invention, the compound of the present invention may be administered in combination with an immunotherapy. As used herein, "immunotherapy" refers to a therapy targeting particular protein involved in tumor development via antibodies specific to such protein. For example, monoclonal antibodies against vascular endothelial growth factor have been used in treating cancers.

Where a second pharmaceutical is used in addition to a compound of the present invention, the two pharmaceuticals may be administered simultaneously (e.g. in separate or unitary compositions) sequentially in either order, at approximately the same time, or on separate dosing schedules. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular chemotherapeutic agent being administered in conjunction with the compound of the present invention, their route of administration, the particular tumor being treated and the particular host being treated.

As will be understood by those of ordinary skill in the art, the appropriate doses of chemotherapeutic agents will be generally similar to or less than those already employed in clinical therapies wherein the chemotherapeutics are administered alone or in combination with other chemotherapeutics.

The optimum method and order of administration and the dosage amounts and regime can be readily determined by those skilled in the art using conventional methods and in view of the information set out herein.

By way of example only, platinum compounds are advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment. Cisplatin is not absorbed orally and must therefore be delivered via injection intravenously, subcutaneously, intratumorally or intraperitoneally.

By way of example only, taxane compounds are advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 mg/m per course of treatment.

By way of example only, camptothecin compounds are advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

By way of example only, vinca alkaloids may be advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

By way of example only, anti-tumor nucleoside derivatives may be advantageously administered in a dosage of 200 to 2500 mg per square meter ($mg/m^2$) of body surface area, for example 700 to 1500 $mg/m^2$. 5-fluorouracil (5-FU) is commonly used via intravenous administration with doses ranging from 200 to 500 $mg/m^2$ (preferably from 3 to 15 mg/kg/day). Gemcitabine is advantageously administered in a dosage of about 800 to 1200 $mg/m^2$ and capecitabine is advantageously administered in about 1000 to 2500 $mg/m^2$ per course of treatment.

By way of example only, alkylating agents may be advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg of body weight, for carmustine in a dosage of about 150 to 200 $mg/m^2$, and for lomustine in a dosage of about 100 to 150 $mg/m^2$ per course of treatment.

By way of example only, podophyllotoxin derivatives may be advantageously administered in a dosage of 30 to 300 mg per square meter (mg/m2) of body surface area, for example 50 to 250 $mg/m^2$, particularly for etoposide in a dosage of about 35 to 100 $mg/m^2$ and for teniposide in about 50 to 250 $mg/m^2$ per course of treatment.

By way of example only, anthracycline derivatives may be advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

By way of example only, anti-estrogen compounds may be advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

By way of example only, biologics may be advantageously administered in a dosage of about 1 to 5 mg per square meter ($mg/m^2$) of body surface area, or as known in the art, if different. For example, trastuzumab is advantageously administered in a dosage of 1 to 5 $mg/m^2$ particularly 2 to 4 $mg/m^2$ per course of treatment.

Dosages may be administered, for example once, twice or more per course of treatment, which may be repeated for example every 7, 14, 21 or 28 days.

The compounds of the present invention can be administered to a subject systemically, for example, intravenously, orally, subcutaneously, intramuscular, intradermal, or parenterally. The compounds of the present invention can also be administered to a subject locally. Non-limiting examples of local delivery systems include the use of intraluminal medical devices that include intravascular drug delivery catheters, wires, pharmacological stents and endoluminal paving. The compounds of the present invention can further be administered to a subject in combination with a targeting agent to achieve high local concentration of the compound at the target site. In addition, the compounds of the present invention may be formulated for fast-release or slow-release with the objective of maintaining the drugs or agents in contact with target tissues for a period ranging from hours to weeks.

The present invention also provides a pharmaceutical composition comprising a compound of Formula I in association with a pharmaceutically acceptable carrier. The pharmaceutical composition may contain between about 0.1 mg and 1000 mg, preferably about 100 to 500 mg, of the compound, and may be constituted into any form suitable for the mode of administration selected.

The phrases "pharmaceutically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

The pharmaceutical composition of the present invention also includes a pharmaceutical composition for slow release of a compound of the present invention. The composition includes a slow release carrier (typically, a polymeric carrier) and a compound of the present invention.

Slow release biodegradable carriers are well known in the art. These are materials that may form particles that capture therein an active compound(s) and slowly degrade/dissolve under a suitable environment (e.g., aqueous, acidic, basic, etc) and thereby degrade/dissolve in body fluids and release the active compound(s) therein. The particles are preferably nanoparticles (i.e., in the range of about 1 to 500 nm in diameter, preferably about 50-200 nm in diameter, and most preferably about 100 nm in diameter).

The present invention also provides methods to prepare the pharmaceutical compositions of this invention. The compound of Formula I, as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. In preparation for slow release, a slow release carrier, typically a polymeric carrier, and a compound of the present invention are first dissolved or dispersed in an organic solvent. The obtained organic solution is then added into an aqueous solution to obtain an oil-in-water-type emulsion. Preferably, the aqueous solution includes surface-active agent(s). Subsequently, the organic solvent is evaporated from the oil-in-water-type emulsion to obtain a colloidal suspension of particles containing the slow release carrier and the compound of the present invention.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, from about 0.01 mg to 200 mg/kg of body weight per day. Preferably, the range is from about 0.03 to about 100 mg/kg of body weight per day, most preferably, from about 0.05 to about 10 mg/kg of body weight per day. The compounds may be administered on a regimen of 1 to 5 times per day. The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, acetyl alcohol and cellulose acetate.

The liquid forms in which the compound of Formula I may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Advantageously, compounds of Formula I may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The daily dosage of the products of the present invention may be varied over a wide range from 1 to 5000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 200 mg/kg of body weight per day. Particularly, the range is from about 0.03 to about 15 mg/kg of body weight per day, and more particularly, from about 0.05 to about 10 mg/kg of body weight per day. The compound of the present invention may be administered on a regimen up to four or more times per day, preferably of 1 to 2 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The compounds of the present invention can also be administered in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phosphatidylethanolamines, phophatidylcholines, cardiolipins, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof. They may either contain cholesterol or may be cholesterol-free.

The compounds of the present invention can also be administered locally. Any delivery device, such as intravascular drug delivery catheters, wires, pharmacological stents and endoluminal paving, may be utilized. The delivery system for such a device may comprise a local infusion catheter that delivers the compound at a rate controlled by the administer.

The present invention provides a drug delivery device comprising an intraluminal medical device, preferably a stent, and a therapeutic dosage of a compound of the invention.

The term "stent" refers to any device capable of being delivered by a catheter. A stent is routinely used to prevent vascular closure due to physical anomalies such as unwanted inward growth of vascular tissue due to surgical trauma. It often has a tubular, expanding lattice-type structure appropriate to be left inside the lumen of a duct to relieve an obstruction. The stent has a lumen wall-contacting surface and a lumen-exposed surface. The lumen-wall contacting surface is the outside surface of the tube and the lumen-exposed surface is the inner surface of the tube. The stent can be polymeric, metallic or polymeric and metallic, and it can optionally be biodegradable.

Commonly, stents are inserted into the lumen in a non-expanded form and are then expanded autonomously, or with the aid of a second device in situ. A typical method of expansion occurs through the use of a catheter-mounted angioplastry balloon which is inflated within the stenosed vessel or body passageway in order to shear and disrupt the obstructions associated with the wall components of the vessel and to obtain an enlarged lumen. Self-expanding stents as described in U.S. Pat. No. 6,776,796 (Falotico et al.) may also be utilized. The combination of a stent with drugs, agents or compounds which prevent inflammation and proliferation, may provide the most efficacious treatment for post-angioplastry restenosis.

Compounds of the invention can be incorporated into or affixed to the stent in a number of ways and in utilizing any number of biocompatible materials. In one exemplary embodiment, the compound is directly incorporated into a polymeric matrix, such as the polymer polypyrrole, and subsequently coated onto the outer surface of the stent. The compound elutes from the matrix by diffusion through the polymer. Stents and methods for coating drugs on stents are discussed in detail in the art. In another exemplary embodiment, the stent is first coated with as a base layer comprising a solution of the compound, ethylene-co-vinylacetate, and polybutylmethacrylate. Then, the stent is further coated with an outer layer comprising only polybutylmethacrylate. The outlayer acts as a diffusion barrier to prevent the compound from eluting too quickly and entering the surrounding tissues. The thickness of the outer layer or topcoat determines the rate at which the compound elutes from the matrix. Stents and methods for coating are discussed in detail in WIPO publication WO9632907, U.S. Publication No. 2002/0016625 and references disclosed therein.

The solution of the compound of the invention and the biocompatible materials/polymers may be incorporated into or onto a stent in a number of ways. For example, the solution may be sprayed onto the stent or the stent may be dipped into the solution. In a preferred embodiment, the solution is sprayed onto the stent and then allowed to dry. In another exemplary embodiment, the solution may be electrically charged to one polarity and the stent electrically changed to the opposite polarity. In this manner, the solution and stent will be attracted to one another. In using this type of spraying process, waste may be reduced and more control over the thickness of the coat may be achieved. Compound is preferably only affixed to the outer surface of the stent which makes contact with one tissue. However, for some compounds, the entire stent may be coated. The combination of the dose of compound applied to the stent and the polymer coating that controls the release of the drug is important in the effectiveness of the drug. The compound preferably remains on the stent for at least three days up to approximately six months and more, preferably between seven and thirty days.

Any number of non-erodible biocompatible polymers may be utilized in conjunction with the compound of the invention. It is important to note that different polymers may be utilized for different stents. For example, the above-described ethylene-co-vinylacetate and polybutylmethacrylate matrix works well with stainless steel stents. Other polymers may be utilized more effectively with stents formed from other materials, including materials that exhibit superelastic properties such as alloys of nickel and titanium.

Restensosis is responsible for a significant morbidity and mortality following coronary angioplasty. Restenosis occurs through a combination of four processes including elastic recoil, thrombus formation, intima hyperplasia and extracellular matrix remodeling. Several growth factors have been recently identified to play a part in these processes leading to restenosis (see, Schiele T M et. al., 2004, "Vascular restenosis—striving for therapy." Expert Opin Pharmacother. 5(11): 2221-32.). Of note, TrkB ligands BDNF and neurotrophins as well as TrkB are expressed by vascular smooth muscle cells and endothelial cells (see, Ricci A, et. al. 2003", Neurotrophins and neurotrophin receptors in human pulmonary arteries." J Vasc Res. 37(5):355-63; see also, Kim H, et. al., 2004 "Paracrine and autocrine functions of brain-derived neurotrophic factor (BDNF) and nerve growth factor (NGF) in brain-derived endothelial cells", J Biol Chem. 279(32):33538-46). Additionally, TrkB may play a role in peripheral angiogenesis and intima hyperplasia because of its ability to prevent anoikis and prolong cell survival (see, Douma S, et. al., 2004, "Suppression of anoikis and induction of metastasis by the neurotrophic receptor TrkB", Nature. 430(7003):1034-9.). Therefore, inhibition of TrkB during and following coronary angioplasty using a coated stent presents a viable therapeutic strategy.

Accordingly, the present invention provides a method for the treatment of disorders related to TrkB, including restenosis, intimal hyperplasia or inflammation, in blood vessel walls, in a subject comprising administering to the subject a compound of the invention in a therapeutically effective amounts by the controlled delivery, by release from an intraluminal medical device, such as a stent, of the compound of the invention.

Methods for introducing a stent into a lumen of a body are well known and the compound-coated stents of this invention are preferably introduced using a catheter. As will be appreciated by those of ordinary skill in the art, methods will vary slightly based on the location of stent implantation. For coronary stent implantation, the balloon catheter bearing the stent is inserted into the coronary artery and the stent is positioned at the desired site. The balloon is inflated, expanding the stent. As the stent expands, the stent contacts the lumen wall. Once the stent is positioned, the balloon is deflated and removed. The stent remains in place with the lumen-contacting surface bearing the compound directly contacting the lumen wall surface. Stent implantation may be accompanied by anticoagulation therapy as needed.

Optimum conditions for delivery of the compounds for use in the stent of the invention may vary with the different local delivery systems used, as well as the properties and concentrations of the compounds used. Conditions that may be optimized include, for example, the concentrations of the compounds, the delivery volume, the delivery rate, the depth of penetration of the vessel wall, the proximal inflation pressure, the amount and size of perforations and the fit of the drug delivery catheter balloon. Conditions may be optimized for inhibition of smooth muscle cell proliferation at the site of injury such that significant arterial blockage due to restenosis does not occur, as measured, for example, by the proliferative ability of the smooth muscle cells, or by changes in the vascular resistance or lumen diameter. Optimum conditions can be determined based on data from animal model studies using routine computational methods.

Another alternative method for administering compounds of this invention may be by conjugating the compound to a targeting agent which directs the conjugate to its intended site of action, i.e., to vascular endothelial cells, or to tumor cells. Both antibody and non-antibody targeting agents may be used. Because of the specific interaction between the targeting agent and its corresponding binding partner, a compound of the present invention can be administered with high local concentrations at or near a target site and thus treats the disorder at the target site more effectively.

The antibody targeting agents include antibodies or antigen-binding fragments thereof, that bind to a targetable or accessible component of a tumor cell, tumor vasculature, or tumor stroma. The "targetable or accessible component" of a tumor cell, tumor vasculature or tumor stroma, is preferably a surface-expressed, surface-accessible or surface-localized component. The antibody targeting agents also include antibodies or antigen-binding fragments thereof, that bind to an intracellular component that is released from a necrotic tumor cell. Preferably such antibodies are monoclonal antibodies, or antigen-binding fragments thereof, that bind to insoluble intracellular antigen(s) present in cells that may be induced to be permeable, or in cell ghosts of substantially all neoplastic and normal cells, but are not present or accessible on the exterior of normal living cells of a mammal.

As used herein, the term "antibody" is intended to refer broadly to any immunologic binding agent such as IgG, IgM, IgA, IgE, F(ab')2, a univalent fragment such as Fab', Fab, Dab, as well as engineered antibodies such as recombinant antibodies, humanized antibodies, bispecific antibodies, and the like. The antibody can be either the polyclonal or the monoclonal, although the monoclonal is preferred. There is a very broad array of antibodies known in the art that have immunological specificity for the cell surface of virtually any solid tumor type (see, Summary Table on monoclonal antibodies for solid tumors in U.S. Pat. No. 5,855,866 to Thorpe et al). Methods are known to those skilled in the art to produce and isolate antibodies against tumor (see, U.S. Pat. No. 5,855, 866 to Thorpe et al., and U.S. Pat. No. 6,342,219 to Thorpe et al.).

Techniques for conjugating therapeutic moiety to antibodies are well known. (See, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985)). Similar techniques can also be applied to attach compounds of the invention to non-antibody targeting agents. Those skilled in the art will know, or be able to determine, methods of forming conjugates with non-antibody targeting agents, such as small molecules, oligopeptides, polysaccharides, or other polyanionic compounds.

Although any linking moiety that is reasonably stable in blood, can be used to link the compounds of the present invention to the targeting agent, biologically-releasable bonds and/or selectively cleavable spacers or linkers are preferred. "Biologically-releasable bonds" and "selectively cleavable spacers or linkers" still have reasonable stability in the circulation, but are releasable, cleavable or hydrolyzable only or preferentially under certain conditions, i.e., within a certain environment, or in contact with a particular agent. Such bonds include, for example, disulfide and trisulfide bonds and acid-labile bonds, as described in U.S. Pat. Nos.

5,474,765 and 5,762,918 and enzyme-sensitive bonds, including peptide bonds, esters, amides, phosphodiesters and glycosides as described in U.S. Pat. Nos. 5,474,765 and 5,762,918. Such selective-release design features facilitate sustained release of the compounds from the conjugates at the intended target site.

The present invention provides a pharmaceutical composition comprising an effective amount of a compound of the present invention conjugated to a targeting agent and a pharmaceutically acceptable carrier.

The present invention further provides a method of treating of a disorder related to FLT3 and/or c-kit and/or TrkB, particularly a tumor, comprising administering to a subject a therapeutically effective amount of a compound of Formula I conjugated to a targeting agent.

When proteins such as antibodies or growth factors, or polysaccharides are used as targeting agents, they are preferably administered in the form of injectable compositions. The injectable antibody solution will be administered into a vein, artery or into the spinal fluid over the course of from 2 minutes to about 45 minutes, preferably from 10 to 20 minutes. In certain cases, intradermal and intracavitary administration are advantageous for tumors restricted to areas close to particular regions of the skin and/or to particular body cavities. In addition, intrathecal administrations may be used for tumors located in the brain.

Therapeutically effective dose of the compound of the present invention conjugated to a targeting agent depends on the individual, the disease type, the disease state, the method of administration and other clinical variables. The effective dosages are readily determinable using data from an animal model. Experimental animals bearing solid tumors are frequently used to optimize appropriate therapeutic doses prior to translating to a clinical environment. Such models are known to be very reliable in predicting effective anti-cancer strategies. For example, mice bearing solid tumors, are widely used in pre-clinical testing to determine working ranges of therapeutic agents that give beneficial anti-tumor effects with minimal toxicity.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of Formula I:

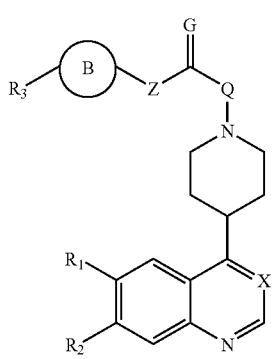

Formula I and N-oxides, pharmaceutically acceptable salts, solvates, and stereochemical isomers thereof, wherein:

Q is $CH_2$ or a direct bond;
G is O or S;
X is N;
Z is NH, N(alkyl), or $CH_2$;
B is phenyl, cycloalkyl, heteroaryl, a nine to ten membered benzo-fused heteroaryl, or a nine to ten membered benzo-fused heterocyclyl;
$R_1$ and $R_2$ are independently selected from:

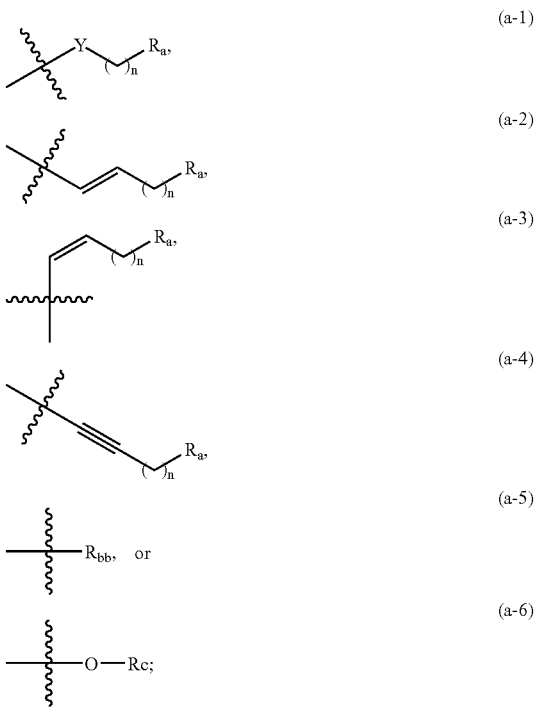

wherein n is 1, 2, 3 or 4;
Y is a direct bond, O, S, NH, or N(alkyl);
$R_a$ is alkoxy, phenoxy, heteroaryl optionally substituted with $R_5$, hydroxyl, alkylamino, dialkylamino, oxazolidinonyl optionally substituted with $R_5$, pyrrolidinonyl optionally substituted with $R_5$, piperidinonyl optionally substituted with $R_5$, piperazinyl-2-one optionally substituted with $R_5$, cyclic heterodionyl optionally substituted with $R_5$, heterocyclyl optionally substituted with $R_5$, squaryl optionally substituted with $R_5$, —$COOR_y$, —$CONR_wR_x$, —$N(R_y)CON(R_w)(R_x)$, —$N(R_w)C(O)OR_x$, —$N(R_w)COR_y$, —$SR_y$, —$SOR_y$, —$SO_2R_y$, —$NR_wSO_2R_y$, —$NR_wSO_2R_x$, —$SO_3R_y$, —$OSO_2NR_wR_x$, or —$SO_2NR_wR_x$;
$R_w$ and $R_x$ are independently selected from: hydrogen, alkyl, alkenyl, aralkyl, or heteroaralkyl, or $R_w$ and $R_x$ may optionally be taken together to form a 5 to 7 membered ring, optionally containing a heteromoiety selected from O, NH, N(alkyl), SO, $SO_2$, or S;
$R_y$ is selected from: hydrogen, alkyl, alkenyl, cycloalkyl, phenyl, aralkyl, heteroaralkyl, or heteroaryl;
$R_5$ is one, two, or three substituents independently selected from: halogen, cyano, trifluoromethyl, amino, hydroxyl, heteroaryl, alkoxy, —C(O)alkyl, —$SO_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_5$ substituent is not present more than once, unless said $R_5$ substituent is halogen, hydroxyl, alkoxy, or alkyl;
$R_{bb}$ is hydrogen, halogen, alkoxy, dialkylamino, phenyl optionally substituted with $R_6$, heteroaryl optionally substituted with $R_6$, piperazinyl-2-one optionally substituted with $R_6$, imidazolidinyl-2-one optionally substituted with $R_6$, oxazolidinyl-2-one optionally substituted with $R_6$, or heterocyclyl optionally substituted with $R_6$;

$R_6$ is one, two, or three substituents independently selected from: halogen, cyano, trifluoromethyl, amino, hydroxyl, heteroaryl, alkoxy, —C(O)alkyl, —SO$_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_6$ substituent is not present more than once, unless said $R_6$ substituent is halogen, hydroxyl, alkoxy, or alkyl;

$R_c$ is heterocyclyl optionally substituted with $R_7$, or heteroaryl; and $R_7$ is one, two, or three substituents independently selected from: halogen, cyano, trifluoromethyl, amino, hydroxyl, heteroaryl, alkoxy, —C(O)alkyl, —SO$_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_7$ substituent is not present more than once, unless said $R_7$ substituent is halogen, hydroxyl, alkoxy, or alkyl;

$R_3$ is one or more substituents independently selected from: hydrogen provided that $R_{bb}$ is not hydrogen, alkyl, alkoxy, halogen, amino optionally substituted with $R_4$, $C_{1-2}$(alkyl)-OH, nitro, cycloalkyl optionally substituted with $R_4$, heteroaryl optionally substituted with $R_4$, alkylamino, heterocyclyl optionally substituted with $R_4$, alkoxyether, —O(cycloalkyl), pyrrolidinonyl optionally substituted with $R_4$, phenoxy optionally substituted with $R_4$, —CN, —OCHF$_2$, —OCF$_3$, —CF$_3$, halogenated alkyl, heteroaryloxy optionally substituted with $R_4$, dialkylamino, —NHSO$_2$alkyl, or —SO$_2$alkyl; wherein $R_4$ is independently selected from: halogen, cyano, trifluoromethyl, amino, hydroxyl, alkoxy, —C(O)alkyl, —CO$_2$alkyl, —SO$_2$alkyl, —C(O)N(alkyl)$_2$, alkyl, or alkylamino.

2. A compound of claim 1, wherein:

$R_w$ and $R_x$ are independently selected from: hydrogen, alkyl, alkenyl, aralkyl, or heteroaralkyl, or $R_w$ and $R_x$ may optionally be taken together to form a ring selected from the group consisting of:

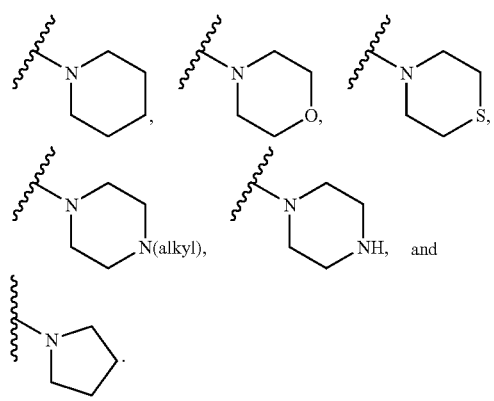

3. A compound of claim 1, wherein:
Z is NH or CH$_2$;
B is phenyl, heteroaryl, or a nine to ten membered benzo-fused heteroaryl.

4. A compound of claim 3, wherein:
G is O;
B is phenyl or heteroaryl;
$R_{bb}$ is hydrogen, halogen, alkoxy, dialkylamino, phenyl, heteroaryl, piperazinyl-2-one optionally substituted with $R_6$, imidazolidinyl-2-one optionally substituted with $R_6$, oxazolidinyl-2-one optionally substituted with $R_6$, or heterocyclyl optionally substituted with $R_6$;

$R_3$ is one or more substituents independently selected from: hydrogen provided that $R_{bb}$ is not hydrogen, alkyl, alkoxy, halogen, amino optionally substituted with $R_4$, $C_{1-2}$(alkyl)-OH, cycloalkyl optionally substituted with $R_4$, heteroaryl optionally substituted with $R_4$, alkylamino, heterocyclyl optionally substituted with $R_4$, alkoxyether, —O(cycloalkyl), pyrrolidinonyl optionally substituted with $R_4$, phenoxy optionally substituted with $R_4$, —CN, —OCHF$_2$, —OCF$_3$, —CF$_3$, halogenated alkyl, dialkylamino and —SO$_2$alkyl.

5. A compound of claim 4, wherein:
Y is a direct bond, O, or NH;
$R_a$ is alkoxy, heteroaryl optionally substituted with $R_5$, hydroxyl, alkylamino, dialkylamino, oxazolidinonyl optionally substituted with $R_5$, pyrrolidinonyl optionally substituted with $R_5$, piperidinonyl optionally substituted with $R_5$, piperazinyl-2-one optionally substituted with $R_5$, cyclic heterodionyl optionally substituted with $R_5$, heterocyclyl optionally substituted with $R_5$, squaryl optionally substituted with $R_5$, —CONR$_w$R$_x$, —N(R$_y$)CON(R$_w$)(R$_x$), —N(R$_w$)C(O)OR$_x$, —N(R$_w$)COR$_y$, —SR$_y$, —SOR$_y$, —SO$_2$R$_y$, or —NR$_w$SO$_2$R$_y$;

$R_{bb}$ is hydrogen, halogen, alkoxy, piperazinyl-2-one optionally substituted with $R_6$, imidazolidinyl-2-one optionally substituted with $R_6$, oxazolidinyl-2-one optionally substituted with $R_6$, or heterocyclyl optionally substituted with $R_6$; and $R_3$ is one or more substituents independently selected from: hydrogen provided that $R_{bb}$ is not hydrogen, alkyl, alkoxy, amino optionally substituted with $R_4$, halogen, $C_{1-2}$(alkyl)-OH, cycloalkyl optionally substituted with $R_4$, heteroaryl optionally substituted with $R_4$, alkylamino, heterocyclyl optionally substituted with $R_4$ alkoxyether, —O(cycloalkyl), pyrrolidinonyl optionally substituted with $R_4$, phenoxy optionally substituted with $R_4$, —OCHF$_2$, —OCF$_3$, —CF$_3$, dialkylamino, or —SO$_2$alkyl; wherein $R_4$ is independently selected from halogen, cyano, trifluoromethyl, amino, hydroxyl, alkoxy, —C(O)alkyl, —CO$_2$alkyl, —SO$_2$alkyl, —C(O)N(alkyl)$_2$, alkyl, or alkylamino.

6. A compound of claim 5, wherein:
$R_1$ and $R_2$ are independently selected from:

(a-1)

(a-4)

(a-5)

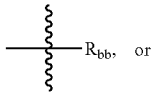
, or

-continued

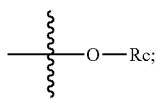
(a-6)

Y is O or NH;

R$_a$ is alkoxy, heteroaryl optionally substituted with R$_5$, hydroxyl, alkylamino, dialkylamino, oxazolidinonyl optionally substituted with R$_5$, pyrrolidinonyl optionally substituted with R$_5$, piperidinonyl optionally substituted with R$_5$, piperazinyl-2-one optionally substituted with R$_5$, heterocyclyl optionally substituted with R$_5$, squaryl optionally substituted with R$_5$, —CONR$_w$R$_x$, —N(R$_y$)CON(R$_w$)(R$_x$), —N(R$_w$)C(O)OR$_x$, —N(R$_w$)COR$_y$, —SO$_2$R$_y$, or —NR$_w$SO$_2$R$_y$;

R$_5$ is one or two substituents selected from: —C(O)alkyl, —SO$_2$alkyl, —C(O)NH(alkyl), —C(O)N(alkyl)$_2$, —C(O)C$_{1-4}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, or —C(O)C$_{(1-4)}$alkyl-OCH$_3$; provided that the same R$_5$ substituent is not present more than once, unless said R$_5$ substituent is alkyl;

R$_6$ is one or two substituents independently selected from: halogen, hydroxyl, heteroaryl, alkoxy, —C(O)alkyl, —SO$_2$alkyl, —C(O)NH(alkyl), —C(O)N(alkyl)$_2$, —C(O)C$_{1-4}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, or —C(O)C$_{(1-4)}$alkyl-OCH$_3$; provided that the same R$_6$ substituent is not present more than once, unless said R$_6$ substituent is halogen, hydroxyl, or alkyl;

R$_c$ is heterocyclyl optionally substituted with R$_7$;

R$_7$ is one substituent selected from: hydroxyl, —C(O)alkyl, —SO$_2$alkyl, alkyl, or —C(O)N(alkyl)$_2$; and R$_3$ is one or more substituents independently selected from: alkyl, alkoxy, halogen, cycloalkyl optionally substituted with R$_4$, heteroaryl optionally substituted with R$_4$, heterocyclyl optionally substituted with R$_4$, alkoxyether, —O(cycloalkyl), phenoxy optionally substituted with R$_4$, dialkylamino, or —SO$_2$alkyl.

7. A compound of claim 6, wherein:
Q is a direct bond;
Z is NH;
B is phenyl, pyrimidinyl, or pyridinyl;
R$_1$ and R$_2$ are independently selected from:

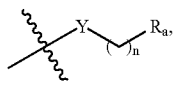
(a-1)

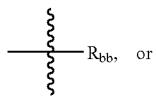
(a-5)

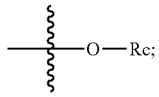
(a-6)

Y is O;

R$_a$ is alkoxy, heteroaryl optionally substituted with R$_5$, hydroxyl, alkylamino, dialkylamino, oxazolidinonyl optionally substituted with R$_5$, pyrrolidinonyl optionally substituted with R$_5$, piperazinyl-2-one optionally substituted with R$_5$, heterocyclyl optionally substituted with R$_5$, —CONR$_w$R$_x$, —N(R$_y$)CON(R$_w$)(R$_x$), —SO$_2$R$_y$, or —NR$_w$SO$_2$R$_y$;

R$_y$ is selected from: hydrogen, alkyl, alkenyl, cycloalkyl, phenyl, aralkyl, heteroaralkyl, or heteroaryl;

R$_5$ is one substituent selected from: —C(O)alkyl, —SO$_2$alkyl, —C(O)NH(alkyl), —C(O)N(alkyl)$_2$, —C(O)C$_{1-4}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, or —C(O)C$_{(1-4)}$alkyl-OCH$_3$;

R$_6$ is one substituent selected from: hydroxyl, alkoxy, —C(O)alkyl, —SO$_2$alkyl, —C(O)NH(alkyl), —C(O)N(alkyl)$_2$, —C(O)C$_{1-4}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, or —C(O)C$_{(1-4)}$alkyl-OCH$_3$;

R$_c$ is heterocyclyl optionally substituted with R$_7$;

R$_7$ is one substituent selected from —C(O)alkyl, —SO$_2$alkyl, or alkyl; and

R$_3$ is one substituent independently selected from: alkyl, alkoxy, cycloalkyl, heterocyclyl, —O(cycloalkyl), or dialkylamino.

8. A compound selected from the group consisting of:

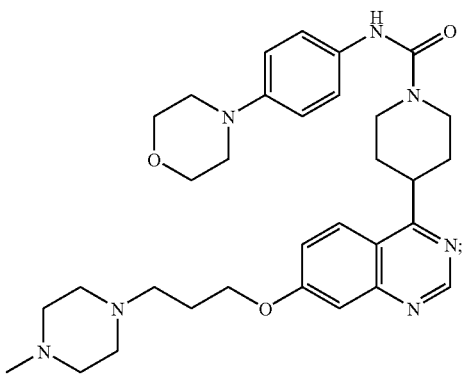

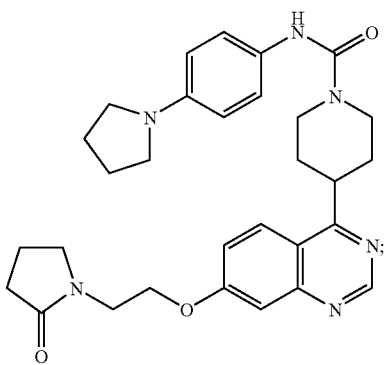

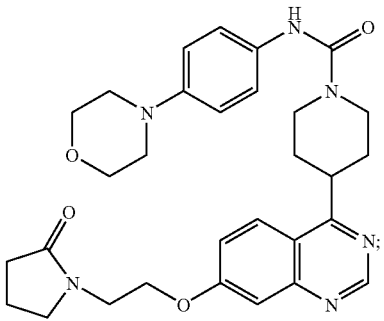

303
-continued
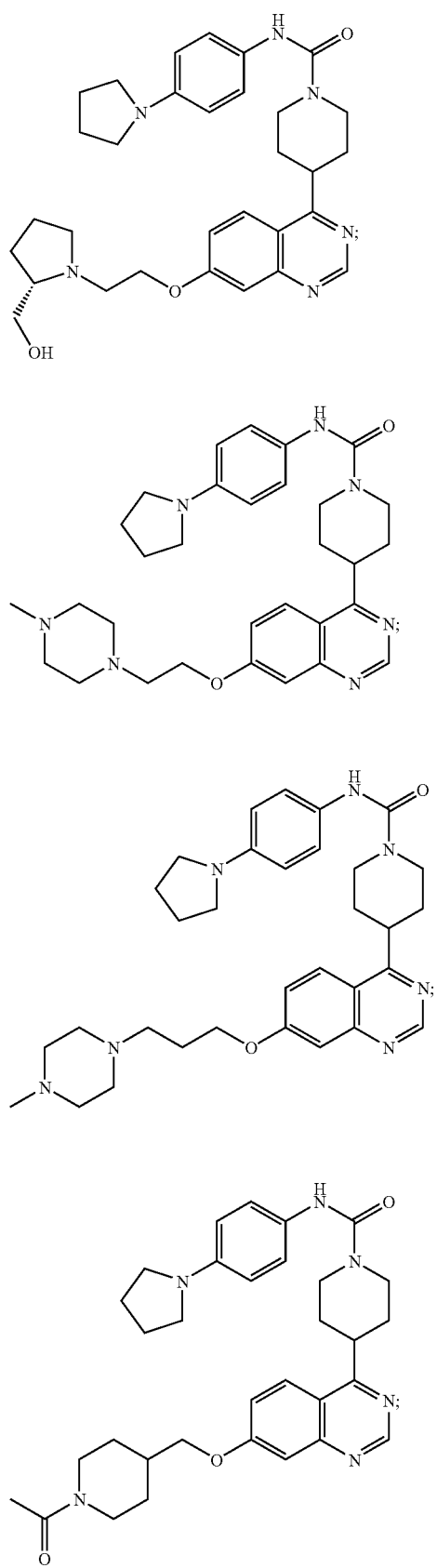
304
-continued
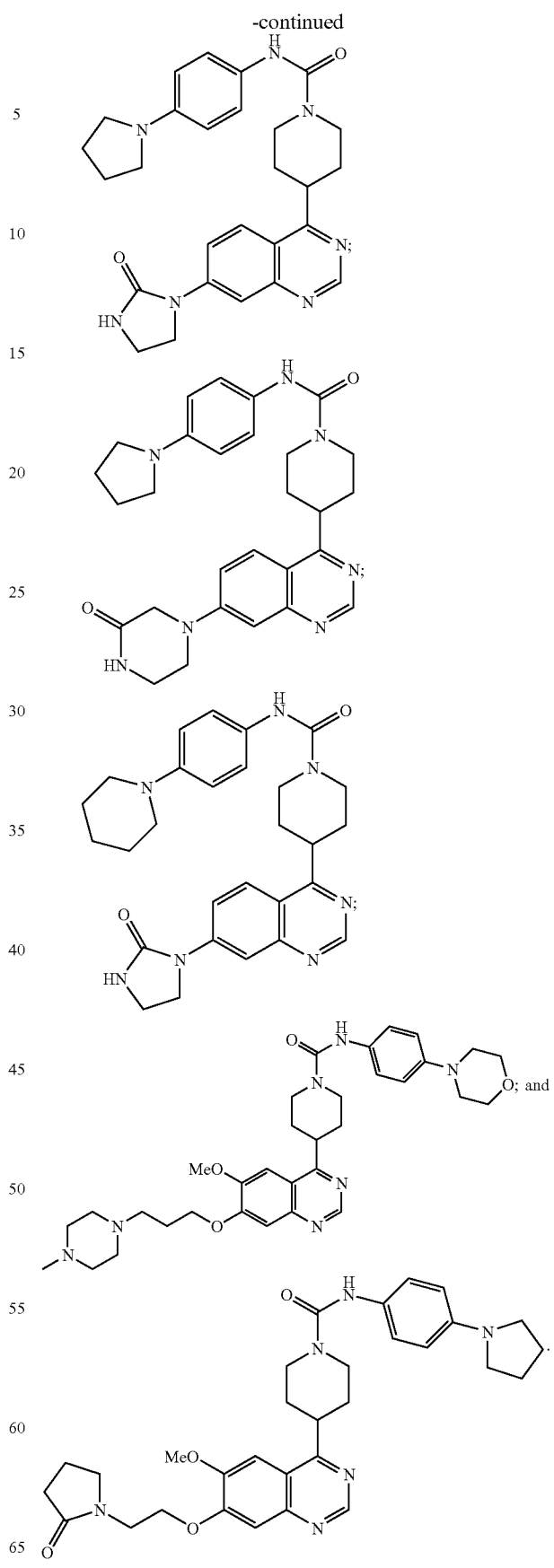

9. A compound selected from the group consisting of:
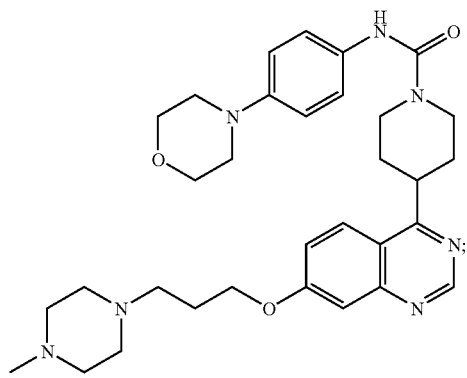
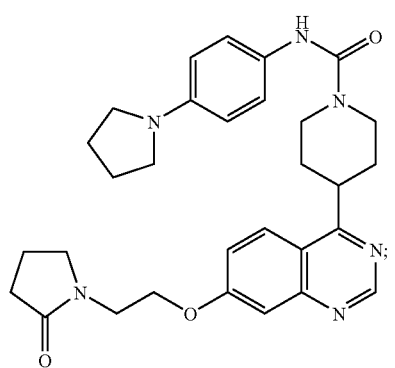
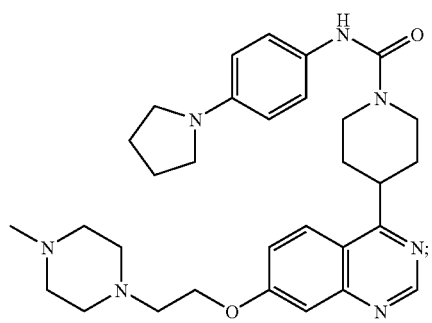
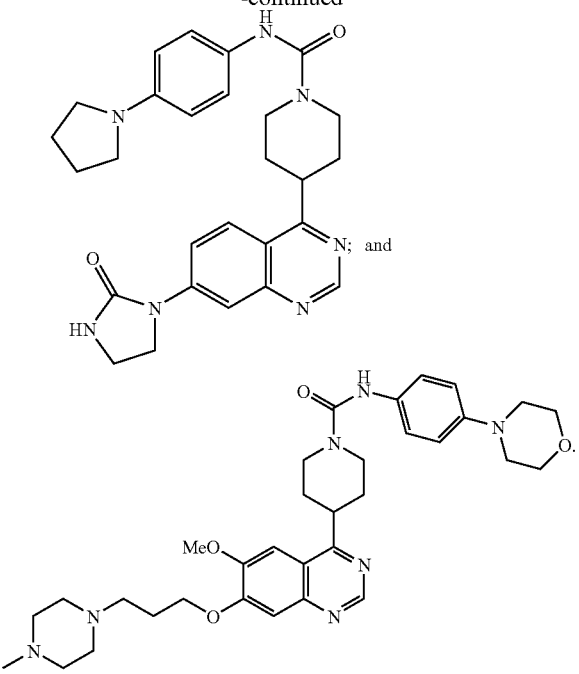
10. A compound that is:
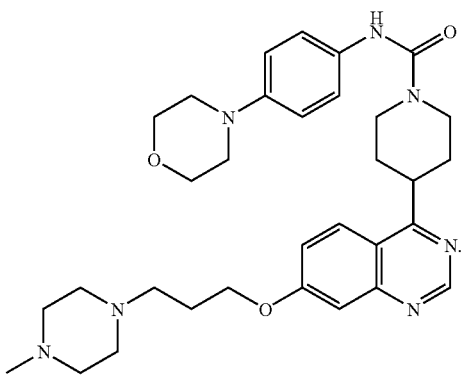
11. A pharmaceutical composition comprising a compound of claim 1 and a pharmaceutically acceptable carrier.
12. A pharmaceutical composition comprising an effective amount of a compound of claim 1 conjugated to a targeting agent and a pharmaceutically acceptable carrier.
* * * * *